United States Patent
Kim et al.

(10) Patent No.: US 12,209,095 B2
(45) Date of Patent: Jan. 28, 2025

(54) COMPOUND AND ORGANIC LIGHT-EMITTING DEVICE COMPRISING SAME

(71) Applicant: LG CHEM, LTD., Seoul (KR)

(72) Inventors: Kyunghee Kim, Daejeon (KR); Wanpyo Hong, Daejeon (KR); Sujeong Geum, Daejeon (KR); Moung Gon Kim, Daejeon (KR); Yonghan Lee, Daejeon (KR)

(73) Assignee: LG Chem, Ltd., Seoul (KR)

(*) Notice: Subject to any disclaimer, the term of this patent is extended or adjusted under 35 U.S.C. 154(b) by 679 days.

(21) Appl. No.: 17/620,255

(22) PCT Filed: Nov. 20, 2020

(86) PCT No.: PCT/KR2020/016425
§ 371 (c)(1),
(2) Date: Dec. 17, 2021

(87) PCT Pub. No.: WO2021/101293
PCT Pub. Date: May 27, 2021

(65) Prior Publication Data
US 2022/0389027 A1 Dec. 8, 2022

(30) Foreign Application Priority Data

Nov. 22, 2019 (KR) .......................... 10-2019-0151322
Nov. 19, 2020 (KR) .......................... 10-2020-0155752

(51) Int. Cl.
*C07D 491/22* (2006.01)
*C07C 15/28* (2006.01)
*C07D 307/91* (2006.01)
*C07D 333/08* (2006.01)
*C07D 333/76* (2006.01)
(Continued)

(52) U.S. Cl.
CPC ............ *C07D 491/22* (2013.01); *C07C 15/28* (2013.01); *C07D 307/91* (2013.01); *C07D 333/08* (2013.01); *C07D 333/76* (2013.01); *C07D 405/10* (2013.01); *C07D 405/14* (2013.01); *C07D 409/10* (2013.01); *C07D 409/14* (2013.01); *C07D 487/06* (2013.01); *C07D 487/16* (2013.01); *C07D 491/16* (2013.01); *C07D 495/16* (2013.01); *C07D 495/22* (2013.01); *C07F 7/0812* (2013.01); *H10K 50/125* (2023.02); *H10K 85/40* (2023.02); *H10K 85/615* (2023.02); *H10K 85/631* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01)

(58) Field of Classification Search
None
See application file for complete search history.

(56) References Cited

U.S. PATENT DOCUMENTS

2010/0051928 A1  3/2010  Fukuzaki
2015/0333273 A1  11/2015  Lee et al.
(Continued)

FOREIGN PATENT DOCUMENTS

KR  10-2015-0126283  11/2015
KR  10-2015-0131564  11/2015
(Continued)

*Primary Examiner* — Robert S Loewe
(74) *Attorney, Agent, or Firm* — Bryan Cave Leighton Paisner LLP

(57) ABSTRACT

Provided is a compound of Formula 1:

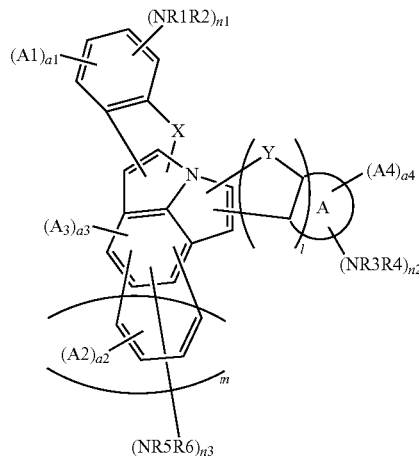

wherein:
X and Y are independently O, S, or $CZ_1Z_2$;
Ring A is a benzene or naphthalene ring;
A1 to A4 are independently hydrogen, deuterium, a halogen group, a cyano group, a nitro group, a hydroxyl group, or a substituted or unsubstituted: alkyl, cycloalkyl, aryl, or heterocyclic group;
R1 to R6, Z1, and Z2 are independently a substituted or unsubstituted: alkyl, aryl, or heterocyclic group;
n1 to n3, m, and l are 0 or 1 and n1+n2+n3 is ≥2;
a1 and a2 are 1 to 4;
a3 is 1 to 3;
a4 is 1 to 6; and
when a1 to a4 are each 2 or higher, structures in the parenthesis are the same or different,
provided that when Ring A is naphthalene, m is 0, and when l is 1, Ring A is a benzene ring,
and an organic light-emitting device comprising the compound.

14 Claims, 1 Drawing Sheet

(51) Int. Cl.
C07D 405/10 (2006.01)
C07D 405/14 (2006.01)
C07D 409/10 (2006.01)
C07D 409/14 (2006.01)
C07D 487/06 (2006.01)
C07D 487/16 (2006.01)
C07D 491/16 (2006.01)
C07D 495/16 (2006.01)
C07D 495/22 (2006.01)
C07F 7/08 (2006.01)
H10K 50/125 (2023.01)
H10K 85/40 (2023.01)
H10K 85/60 (2023.01)

(56) References Cited

U.S. PATENT DOCUMENTS

| | | |
|---|---|---|
| 2015/0340613 A1 | 11/2015 | Parham et al. |
| 2017/0047528 A1 | 2/2017 | Kang et al. |
| 2020/0181165 A1 | 6/2020 | Koo et al. |
| 2021/0057650 A1 | 2/2021 | Kim et al. |
| 2022/0403233 A1* | 12/2022 | Shim ................. C07F 5/027 |
| 2023/0422610 A1* | 12/2023 | Parham ............. H10K 85/633 |

FOREIGN PATENT DOCUMENTS

| | | |
|---|---|---|
| KR | 10-2017-0016135 | 2/2017 |
| KR | 10-2019-0011463 | 2/2019 |
| KR | 10-2019-0013208 | 2/2019 |
| KR | 10-2019-0044561 | 4/2019 |
| KR | 10-2019-0116947 | 10/2019 |

* cited by examiner

[Figure 1]
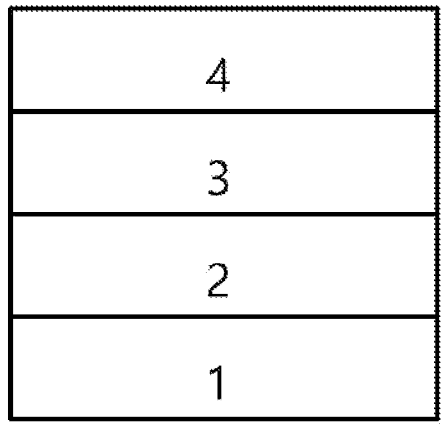
[Figure 2]
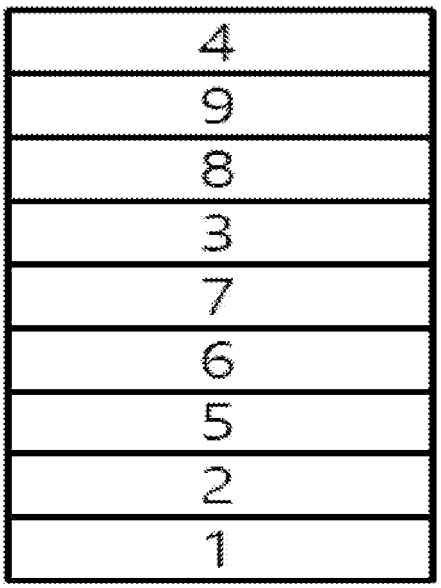

COMPOUND AND ORGANIC LIGHT-EMITTING DEVICE COMPRISING SAME

CROSS-REFERENCE TO RELATED APPLICATION(S)

This application is a National Stage Application of International Application No. PCT/KR2020/016425 filed on Nov. 20, 2020, which claims priority to and the benefit of Korean Patent Application Nos. 10-2019-0151322 and 10-2020-0155752 filed in the Korean Intellectual Property Office on Nov. 22, 2019 and Nov. 19, 2020, respectively, the entire contents of which are incorporated herein by reference.

TECHNICAL FIELD

The present specification relates to a compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a first electrode, a second electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between the two electrodes, holes are injected from the first electrode into the organic material layer and electrons are injected from the second electrode into the organic material layer, and when the injected holes and electrons meet each other, an exciton is formed, and light is emitted when the exciton falls down again to a ground state.

There is a continuous need for developing a new material for the aforementioned organic light emitting device.

BRIEF DESCRIPTION

Technical Problem

The present specification has been made in an effort to provide a compound and an organic light emitting device including the same.

Technical Solution

The present specification provides a compound of the following Formula 1:

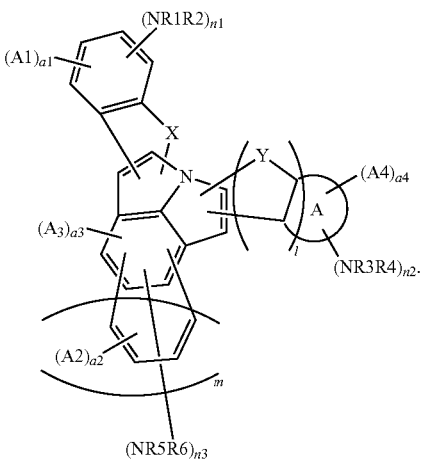

<Formula 1> wherein in Formula 1:
X and Y are the same as or different from each other, and are each independently O, S, or $CZ_1Z_2$;
Ring A is a benzene ring or a naphthalene ring;
A1 to A4 are the same as or different from each other, and are each independently hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group;
R1 to R6, Z1, and Z2 are the same as or different from each other, and each independently a substituted or unsubstituted alkyl group, a substituted or unsubstituted aryl group, or a substituted or unsubstituted heterocyclic group;
n1 to n3, m, and l are each 0 or 1;
a sum of n1 to n3 is 2 or higher;
a1 and a2 are each an integer from 1 to 4;
a3 is an integer from 1 to 3;
a4 is an integer from 1 to 6;
when a1 to a4 are each 2 or higher, structures in the parenthesis are the same as or different from each other;
provided that when Ring A is naphthalene, m is 0; and
when l is 1, Ring A is a benzene ring.

Further, the present specification provides an organic light emitting device including: a first electrode; a second electrode provided to face the first electrode; and an organic material layer having one or more layers provided between the first electrode and the second electrode, in which one or more layers of the organic material layers include the above-described compound.

Advantageous Effects

An organic light emitting device comprising the compound according to an exemplary embodiment of the present application can have a low driving voltage, high light emitting efficiency, or a long service life.

BRIEF DESCRIPTION OF THE DRAWINGS

FIG. 1 illustrates a structure of an organic light emitting device according to an exemplary embodiment.

FIG. 2 illustrates a structure of an organic light emitting device according to another exemplary embodiment.

EXPLANATION OF REFERENCE NUMERALS AND SYMBOLS

1: Substrate
2: First electrode
3: Light emitting layer
4: Second electrode
5: Hole injection layer
6: First hole transport layer
7: Second hole transport layer
8: First electron transport layer
9: Second electron transport layer

DETAILED DESCRIPTION

Hereinafter, the present specification will be described in detail.

The present specification provides the compound of Formula 1.

When one part "includes" one constituent element in the present specification, unless otherwise specifically described, this does not mean that another constituent element is excluded, but means that another constituent element can be further included.

When one member is disposed "on" another member in the present specification, this includes not only a case where the one member is brought into contact with another member, but also a case where still another member is present between the two members.

According to an exemplary embodiment of the present specification, the compound of Formula 1 has a structure in which a benzothiophene, a benzofuran group or a dihydroindene is directly condensed with an indolocarbazole structure to improve the rigidity of the molecule itself, and thus can enhance the stability of the compound. The compound of Formula 1 has an advantage of improving the service life of the device when driving the organic light emitting device. Further, the compound of Formula 1 has two or more amine groups substituted at specific positions, which has an effect of improving the light emitting efficiency in the device by increasing the oscillator strength value compared to the case where there is no amine group or there is an amine group.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium (-D), a halogen group, a nitrile group, a nitro group, a hydroxyl group, an amine group, a silyl group, a boron group, an alkoxy group, an alkyl group, a cycloalkyl group, an aryl group, and a heterocyclic group, being substituted with a substituent to which two or more substituents among the above-exemplified substituents are linked, or having no substituent. For example, "the substituent to which two or more substituents are linked" can be a biphenyl group. That is, the biphenyl group can also be an aryl group, and can be interpreted as a substituent to which two phenyl groups are linked.

Examples of the substituents will be described below, but are not limited thereto.

In the present specification, examples of a halogen group include fluorine (—F), chlorine (—Cl), bromine (—Br) or iodine (—I).

In the present specification, a silyl group can have a formula of —$SiY_aY_bY_c$, and the $Y_a$, $Y_b$, and $Y_c$ can be each hydrogen, a substituted or unsubstituted alkyl group, or a substituted or unsubstituted aryl group. Specific examples of the silyl group include a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group can have a formula of —$BY_dY_e$, and the $Y_d$ and $Y_e$ can be each hydrogen, a substituted or unsubstituted alkyl group, or a substituted or unsubstituted aryl group. Specific examples of the boron group include a trimethylboron group, a triethylboron group, a tert-butyldimethylboron group, a triphenylboron group, a phenylboron group, and the like, but are not limited thereto.

In the present specification, the alkyl group can be straight-chained or branched, and the number of carbon atoms thereof is not particularly limited, but is preferably 1 to 60. According to an exemplary embodiment, the number of carbon atoms of the alkyl group is 1 to 30. According to another exemplary embodiment, the number of carbon atoms of the alkyl group is 1 to 20. According to still another exemplary embodiment, the number of carbon atoms of the alkyl group is 1 to 10. Specific examples of the alkyl group include a methyl group, an ethyl group, a propyl group, an n-propyl group, an isopropyl group, a butyl group, an n-butyl group, an isobutyl group, a tert-butyl group, a pentyl group, an n-pentyl group, a hexyl group, an n-hexyl group, a heptyl group, an n-heptyl group, an octyl group, an n-octyl group, and the like, but are not limited thereto.

In the present specification, the alkoxy group can be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, and the like, but are not limited thereto. Substituents including an alkyl group, an alkoxy group, and other alkyl group moieties described in the present specification include both a straight-chained form and a branched form.

In the present specification, a cycloalkyl group is not particularly limited, but has preferably 3 to 60 carbon atoms, and according to an exemplary embodiment, the number of carbon atoms of the cycloalkyl group is 3 to 30.

According to another exemplary embodiment, the number of carbon atoms of the cycloalkyl group is 3 to 20. According to still another exemplary embodiment, the number of carbon atoms of the cycloalkyl group is 3 to 6. Specific examples thereof include a cyclopropyl group, a cyclobutyl group, a cyclopentyl group, a cyclohexyl group, a cycloheptyl group, a cyclooctyl group, and the like, but are not limited thereto.

In the present specification, an aryl group is not particularly limited, but has preferably 6 to 60 carbon atoms, and can be a monocyclic aryl group or a polycyclic aryl group. According to an exemplary embodiment, the number of carbon atoms of the aryl group is 6 to 39. According to an exemplary embodiment, the number of carbon atoms of the aryl group is 6 to 30. Examples of the monocyclic aryl group include a phenyl group, a biphenyl group, a terphenyl group, a quaterphenyl group, and the like, but are not limited thereto. Examples of the polycyclic aryl group include a naphthyl group, an anthracenyl group, a phenanthrenyl group, a pyrenyl group, a perylenyl group, a chrysenyl group, a fluorenyl group, a triphenylenyl group, and the like, but are not limited thereto.

In the present specification, a fluorene group can be substituted, and two substituents can be bonded to each other to form a spiro structure.

When the fluorene group is substituted, the fluorene group can be a spirofluorene group such as

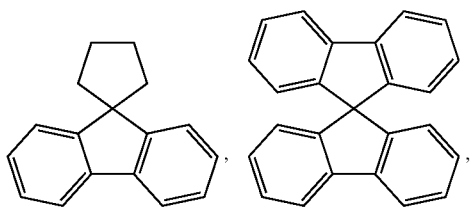

and a substituted fluorene group such as

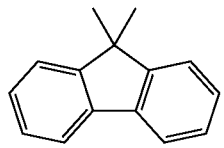

(a 9,9-dimethylfluorene group) and

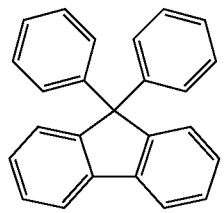 [SMILES: c1ccc(C2(c3ccccc3)c3ccccc3-c3ccccc32)cc1]

(a 9,9-diphenylfluorene group). However, the substituent is not limited thereto.

In the present specification, a heterocyclic group is a cyclic group including one or more of N, O, P, S, Si, and Se as a heteroatom, and the number of carbon atoms thereof is not particularly limited, but is preferably 2 to 60. According to an exemplary embodiment, the number of carbon atoms of the heterocyclic group is 2 to 36. Examples of the heterocyclic group include a pyridine group, a pyrrole group, a pyrimidine group, a quinoline group, a pyridazine group, a furan group, a thiophene group, an imidazole group, a pyrazole group, a dibenzofuran group, a dibenzothiophene group, a carbazole group, a benzocarbazole group, a benzonaphthofuran group, a benzonaphthothiophene group, an indenocarbazole group, an indolocarbazole group, and the like, but are not limited thereto.

In the present specification, the above-described description on the heterocyclic group can be applied to a heteroaryl group except for an aromatic heteroaryl group.

In the present specification, an amine group can be selected from the group consisting of —NH$_2$, an alkylamine group, an N-alkylarylamine group, an arylamine group, an N-arylheteroarylamine group, an N-alkylheteroarylamine group, and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group, an N-phenylnaphthylamine group, an N-biphenyl-naphthylamine group, an N-naphthylfluorenylamine group, an N-phenylphenanthrenylamine group, an N-biphenylphenanthrenylamine group, an N-phenylfluorenylamine group, an N-phenyl terphenylamine group, an N-phenanthrenylfluorenylamine group, an N-biphenyl-fluorenylamine group, and the like, but are not limited thereto.

In the present specification, an N-alkylarylamine group means an amine group in which an alkyl group and an aryl group are substituted with N of the amine group.

In the present specification, an N-arylheteroaryl-amine group means an amine group in which an aryl group and a heteroaryl group are substituted with N of the amine group.

In the present specification, an N-alkylheteroaryl-amine group means an amine group in which an alkyl group and a heteroaryl group are substituted with N of the amine group.

In the present specification, an alkyl group, an aryl group, and a heteroaryl group in an alkylamine group; an N-alkylarylamine group; an arylamine group; an N-arylheteroarylamine group; an N-alkylheteroarylamine group, and a heteroarylamine group are each the same as the above-described examples of the alkyl group, the aryl group, and the heteroaryl group.

In an exemplary embodiment of the present specification, the compound of Formula 1 is any one of the following Formulae 2-1 to 2-8:

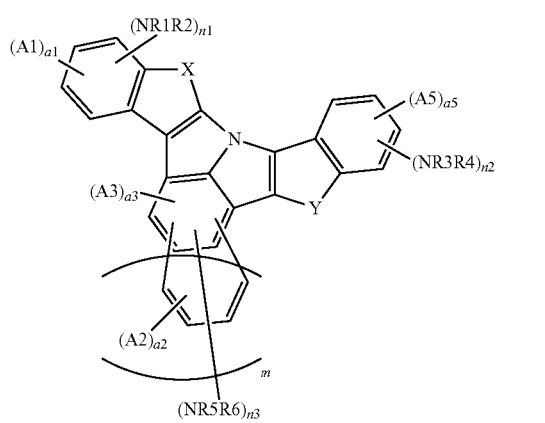

<Formula 2-1>

<Formula 2-2>

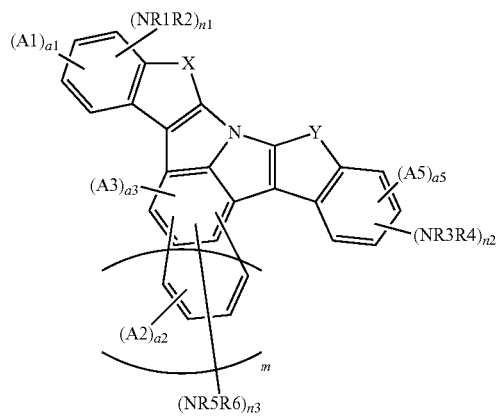

<Formula 2-3>

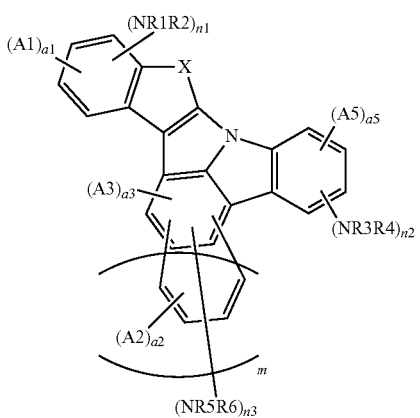

<Formula 2-4>

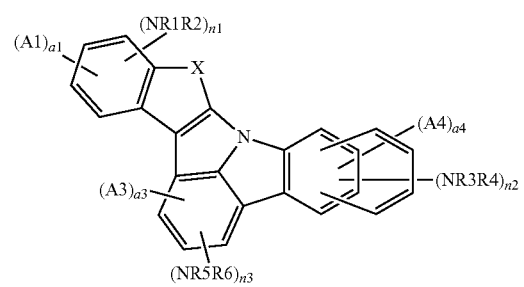

<Formula 2-5>

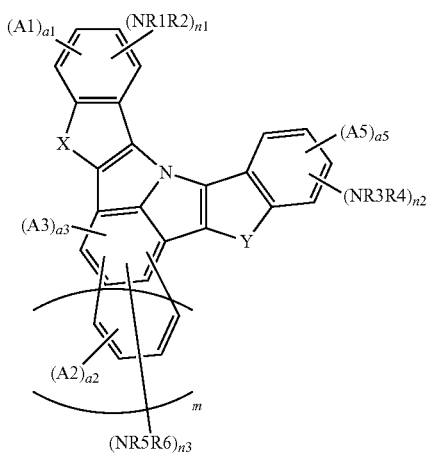

<Formula 2-6>

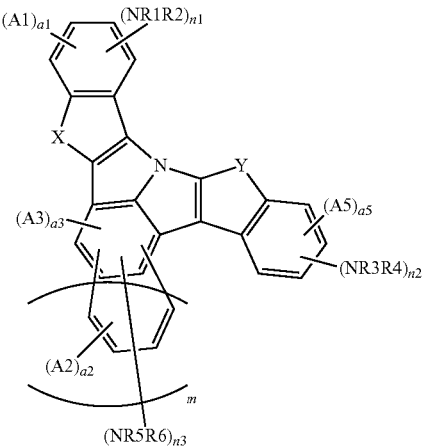

<Formula 2-7>

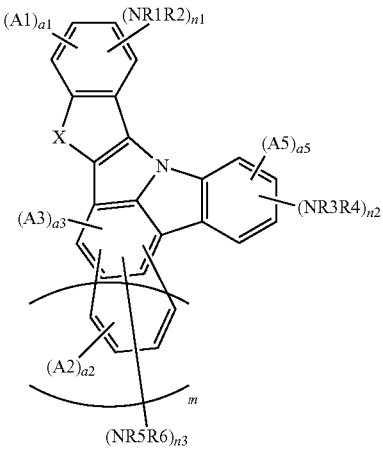

<Formula 2-8>

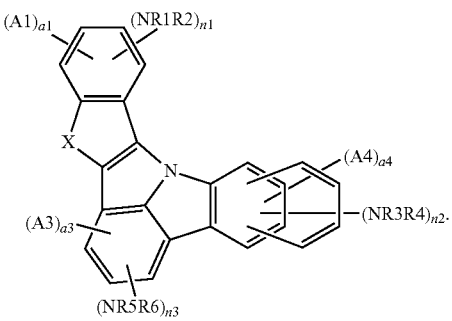

wherein in Formulae 2-1 to 2-8, X, Y, A1 to A4, a1 to a4, R1 to R6, n1 to n3, and m are the same as those defined in Formula 1; A5 is hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group; a5 is an integer from 1 to 4, and when a5 is 2 or higher, structures in the parenthesis are the same as or different from each other.

In an exemplary embodiment of the present specification, X and Y are the same as or different from each other, and are each independently O, S, or CZ1Z2, and Z1 and Z2 are the same as or different from each other, and are each independently a substituted or unsubstituted alkyl group, a substituted or unsubstituted aryl group, or a substituted or unsubstituted heterocyclic group.
In an exemplary embodiment of the present specification, the compound of Formula 1 is any one of the following Formulae 3-1 to 3-12:
<Formula 3-1>
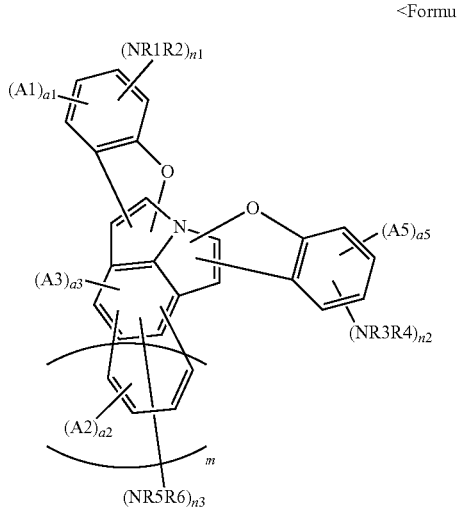
<Formula 3-2>
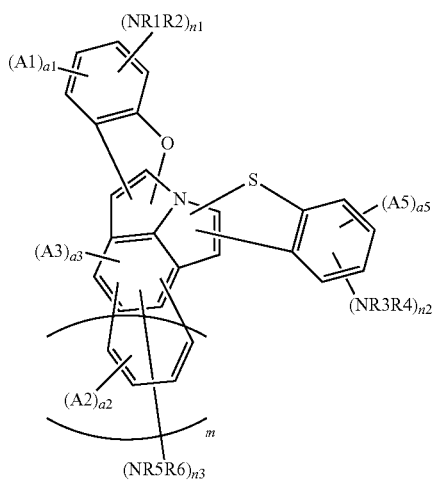
<Formula 3-3>
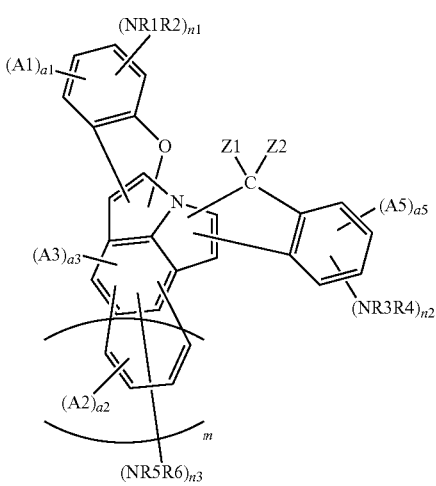
<Formula 3-4>
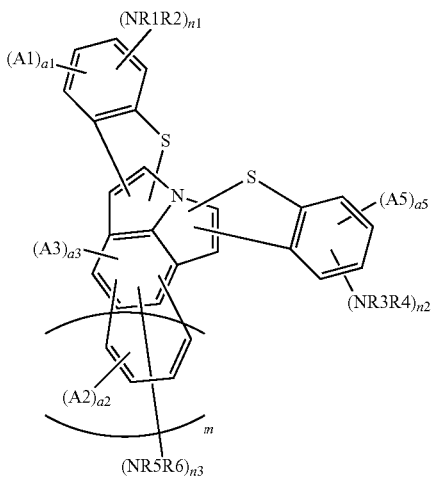
<Formula 3-5>
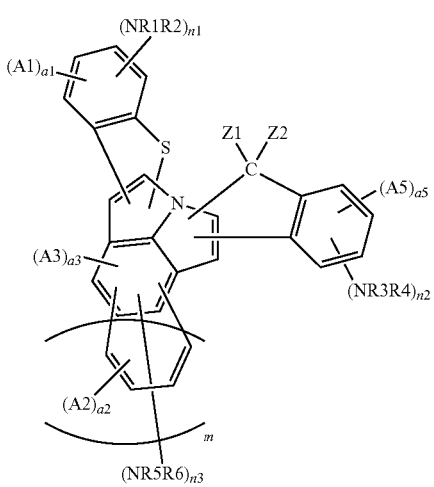
<Formula 3-6>
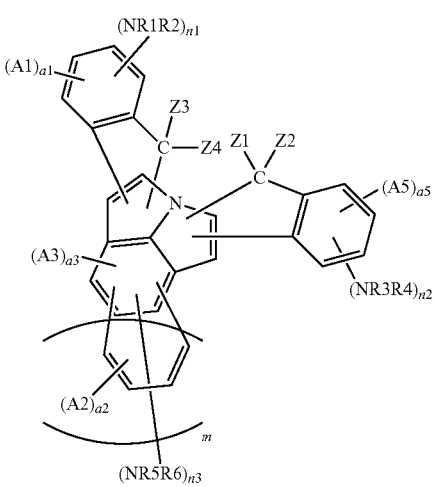

<Formula 3-7>

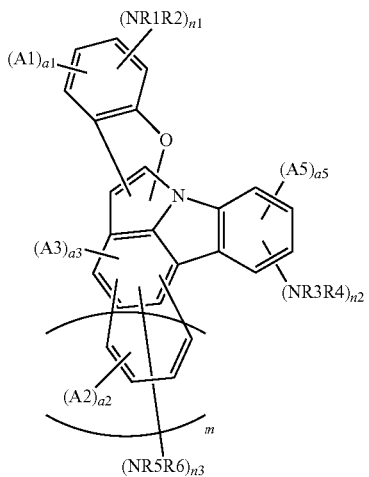

<Formula 3-8>

<Formula 3-9>

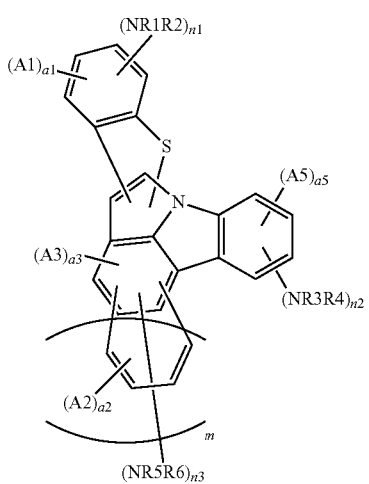

<Formula 3-10>

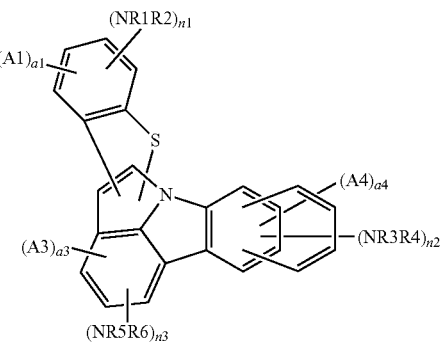

<Formula 3-11>

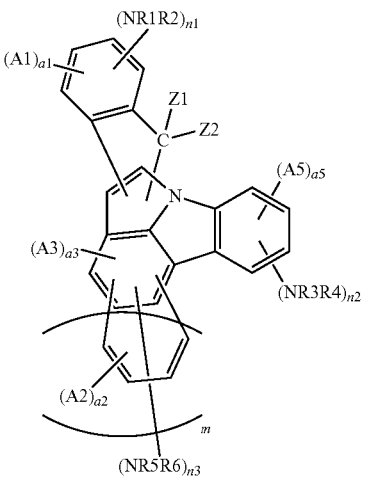

<Formula 3-12>

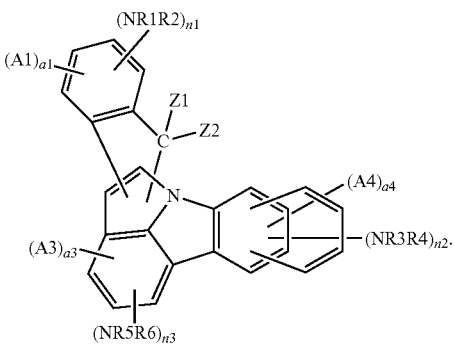

wherein in Formulae 3-1 to 3-12, A1 to A4, a1 to a4, R1 to R6, n1 to n3, m, Z1, and Z2 are the same as those defined in Formula 1; Z3 and Z4 are the same as or different from each other, and are each independently a substituted or unsubstituted alkyl group, a substituted or unsubstituted aryl group, or a substituted or unsubstituted heterocyclic group; A5 is hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group; a5 is an integer from 1 to 4, and when a5 is 2 or higher, structures in the parenthesis are the same as or different from each other.

In an exemplary embodiment of the present specification, the compound of Formula 1 is any one of the following Formulae 4-1 to 4-4:

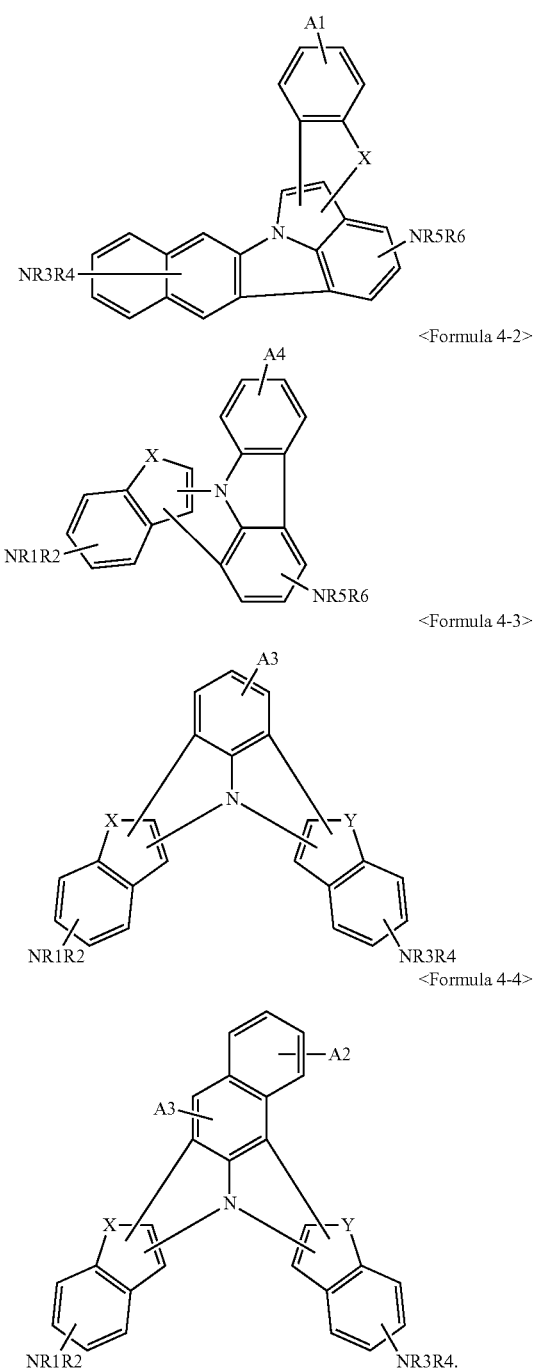

<Formula 4-1>
<Formula 4-2>
<Formula 4-3>
<Formula 4-4> wherein in Formulae 4-1 to 4-4, X, Y, A1 to A4, and R1 to R6 are the same as those defined in Formula 1.

In an exemplary embodiment of the present specification, a sum of n1 to n3 is 2 or higher.

In an exemplary embodiment of the present specification, a sum of n1 to n3 is 2.

In an exemplary embodiment of the present specification, a sum of n1 to n3 is 3.

In an exemplary embodiment of the present specification, A1 to A4 are the same as or different from each other, and are each independently hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group; or a substituted or unsubstituted heterocyclic group.

In an exemplary embodiment of the present specification, A1 to A4 are the same as or different from each other, and are each independently hydrogen, deuterium, a substituted or unsubstituted alkyl group, or a substituted or unsubstituted aryl group.

In an exemplary embodiment of the present specification, A1 to A4 are the same as or different from each other, and are each independently hydrogen, deuterium; a substituted or unsubstituted alkyl group having 1 to 10 carbon atoms, or a substituted or unsubstituted aryl group having 6 to 20 carbon atoms.

In an exemplary embodiment of the present specification, A1 to A4 are the same as or different from each other, and are each independently hydrogen, deuterium, a substituted or unsubstituted straight-chained or branched alkyl group having 1 to 10 carbon atoms, or a substituted or unsubstituted aryl group having 6 to 10 carbon atoms.

In an exemplary embodiment of the present specification, A1 to A4 are the same as or different from each other, and are each independently hydrogen, deuterium, a methyl group, a tert-butyl group, or a phenyl group.

In an exemplary embodiment of the present specification, A1 to A4 are each hydrogen or deuterium.

In an exemplary embodiment of the present specification, R1 to R6 are the same as or different from each other, and are each independently a substituted or unsubstituted alkyl group, a substituted or unsubstituted aryl group, or a substituted or unsubstituted heterocyclic group.

In an exemplary embodiment of the present specification, R1 to R6 are the same as or different from each other, and are each independently a substituted or unsubstituted aryl group or a substituted or unsubstituted heterocyclic group.

In an exemplary embodiment of the present specification, R1 to R6 are the same as or different from each other, and are each independently an aryl group which is unsubstituted or substituted with a group selected from the group consisting of deuterium, an alkyl group, a haloalkyl group, an alkyl group substituted with deuterium, a halogen group, a cyano group, a cycloalkyl group, a silyl group substituted with an alkyl group, and an alkoxy group; or a heterocyclic group which is unsubstituted or substituted with a group selected from the group consisting of deuterium, an alkyl group, a haloalkyl group, an alkyl group substituted with deuterium, a halogen group, an aryl group which is unsubstituted or substituted with deuterium, and a cycloalkyl group.

In an exemplary embodiment of the present specification, R1 to R6 are the same as or different from each other, and are each independently an aryl group which is unsubstituted or substituted with a group selected from the group consisting of deuterium, a methyl group, a tert-butyl group, an iso-propyl group, —$CF_3$, —$CD_3$, F, a cyano group, a cyclohexyl group, a trimethylsilyl group, and a methoxy group; or a heterocyclic group which is unsubstituted or substituted with a group selected from the group consisting of deuterium, a methyl group, a tert-butyl group, an iso-propyl group, —$CF_3$, —$CD_3$, F, a phenyl group which is unsubstituted or substituted with deuterium, and a cyclohexyl group.

In an exemplary embodiment of the present specification, R1 to R6 are the same as or different from each other, and are each independently a phenyl group which is unsubstituted or substituted with a group selected from the group consisting of deuterium, a methyl group, a tert-butyl group, an iso-propyl group, —CF₃, —CD₃, F, a cyano group, a cyclohexyl group, a trimethylsilyl group, and a methoxy group; a biphenyl group which is unsubstituted or substituted with deuterium or a tert-butyl group; a fluorenyl group substituted with a methyl group; a naphthyl group; a phenanthrenyl group; a dibenzofuranyl group which is unsubstituted or substituted with a group selected from the group consisting of a methyl group, an iso-propyl group, a tert-butyl group, —CD₃, a phenyl group which is unsubstituted or substituted with deuterium, and a cyclohexyl group; a dibenzothiophenyl group which is unsubstituted or substituted with a group selected from the group consisting of a methyl group, an iso-propyl group, a tert-butyl group, —CD₃, a phenyl group which is unsubstituted or substituted with deuterium, and a cyclohexyl group; a thiophenyl group which is unsubstituted or substituted with a phenyl group; a quinolinyl group; a benzonaphthofuranyl group; a benzonaphthothiophenyl group; or a benzofluorenyl group substituted with a methyl group.

In an exemplary embodiment of the present specification, the compound of Formula 1 is any one of the following compounds:

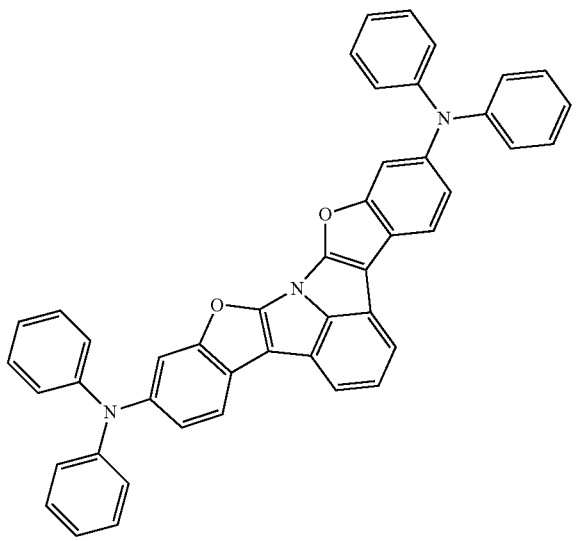

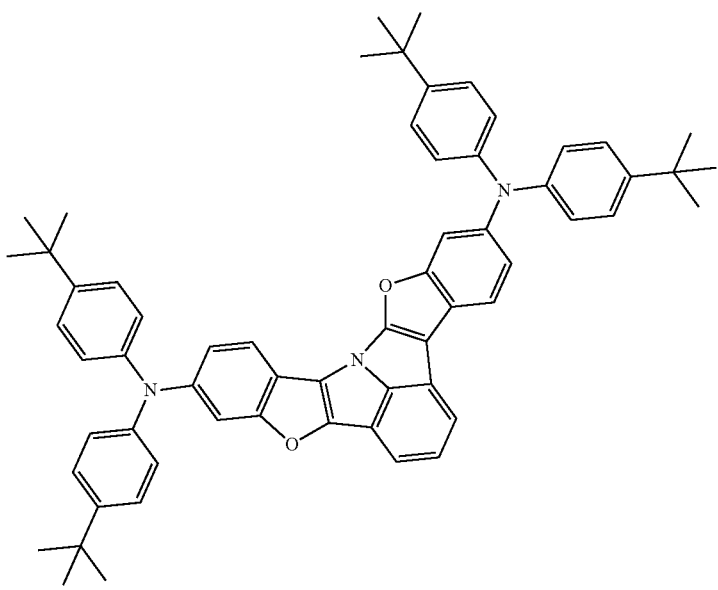

-continued
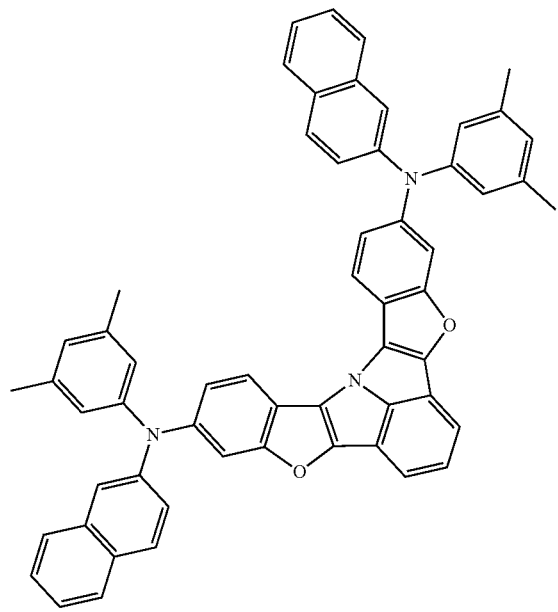
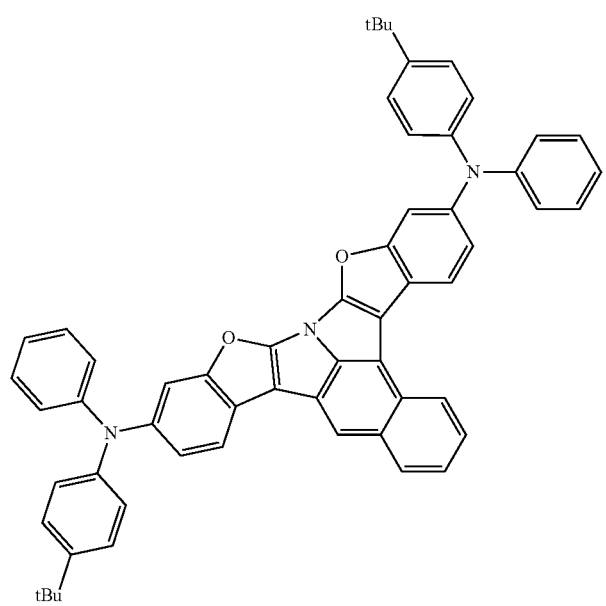

-continued
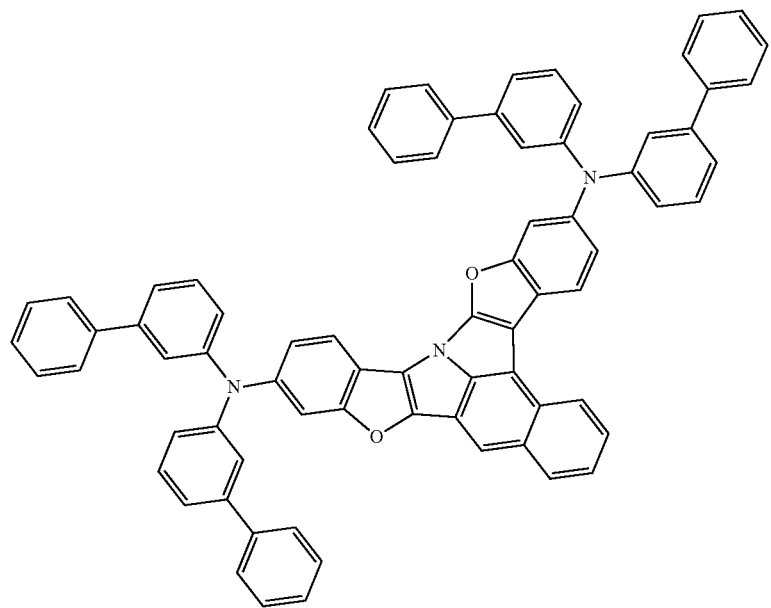
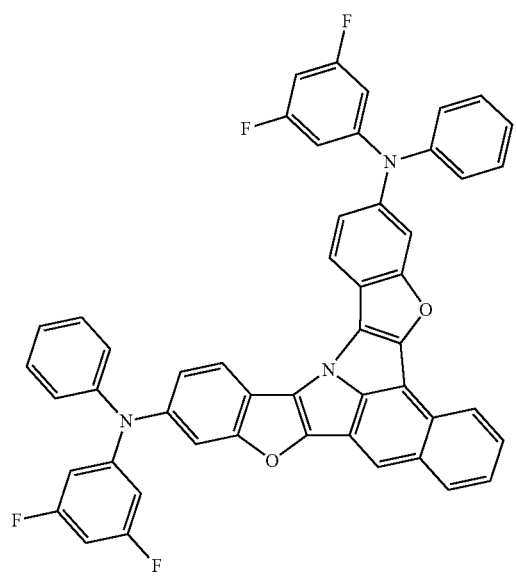

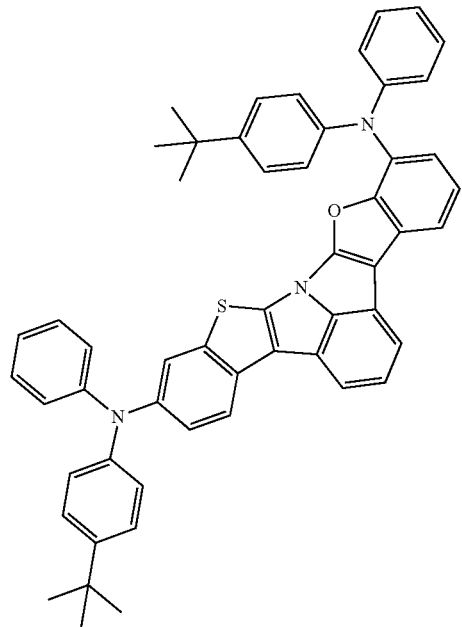
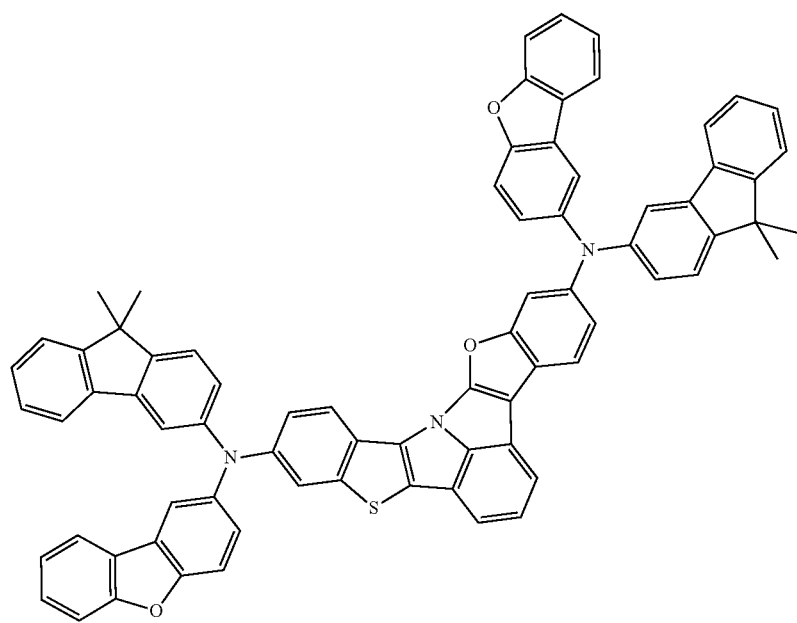

-continued
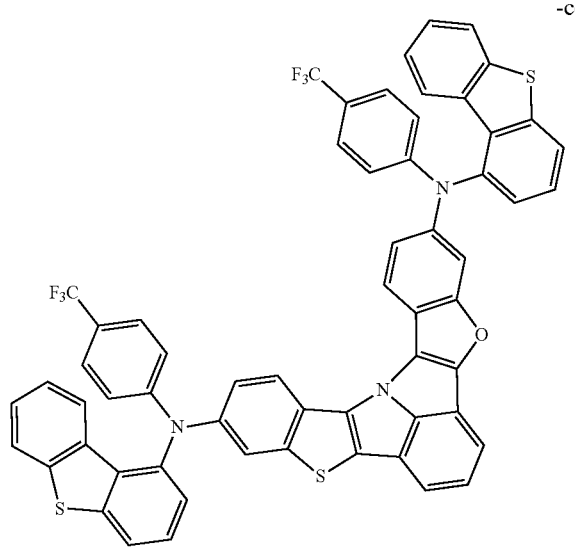
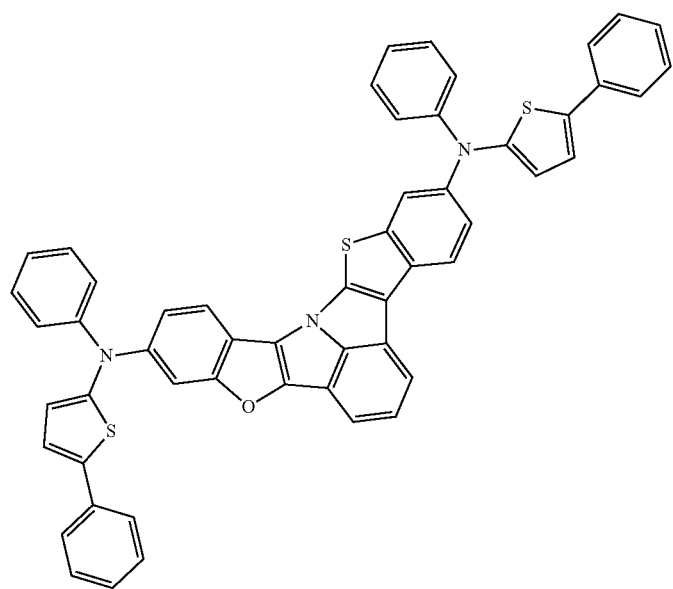

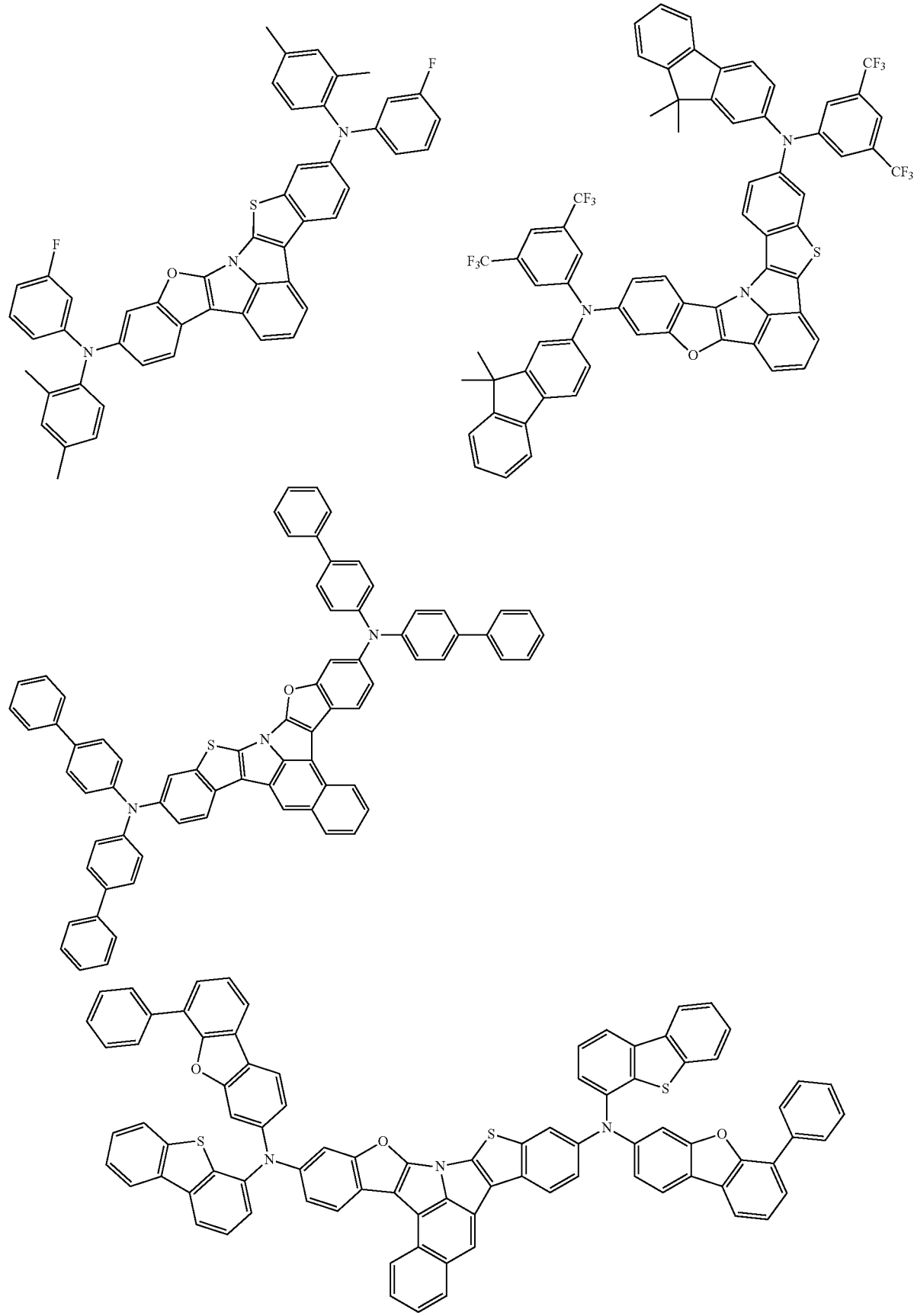

-continued
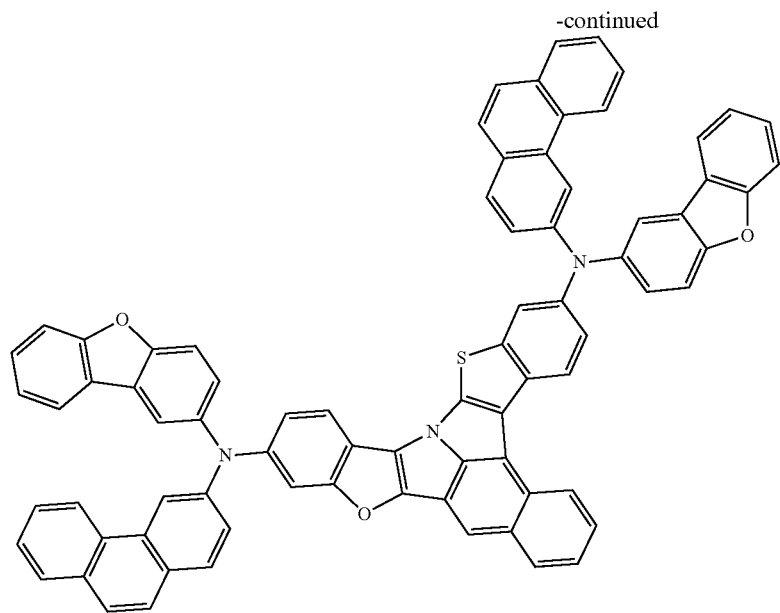
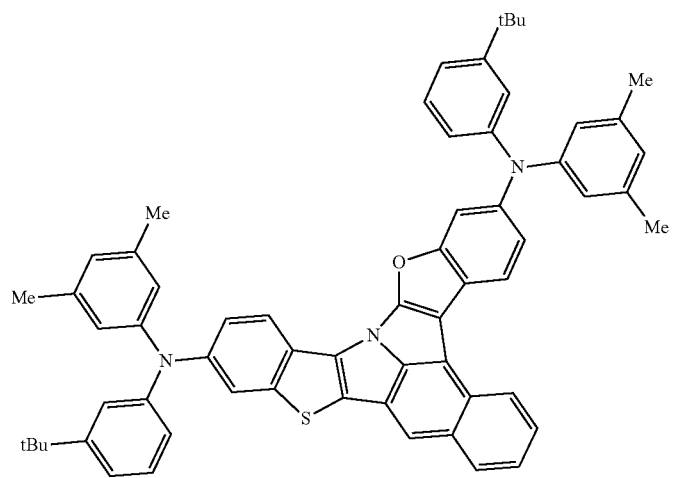
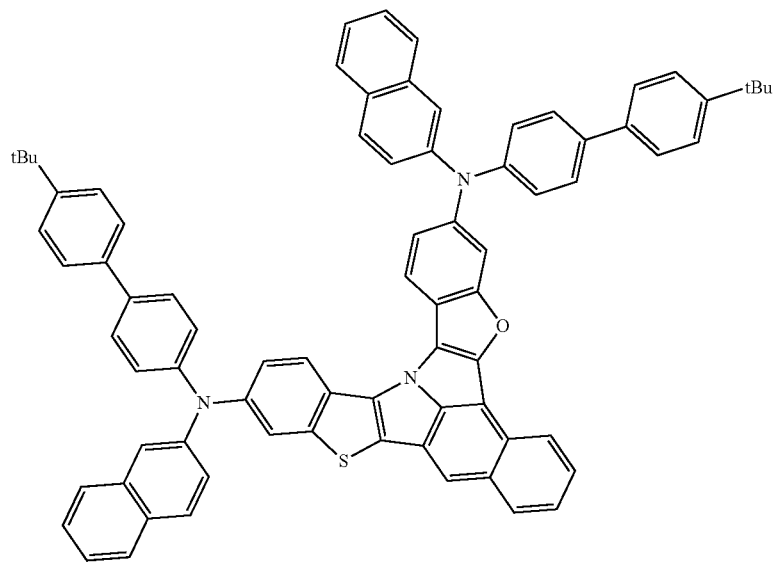

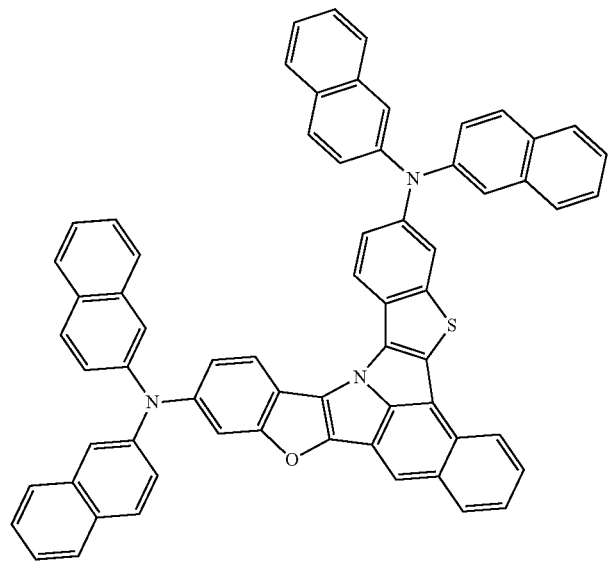
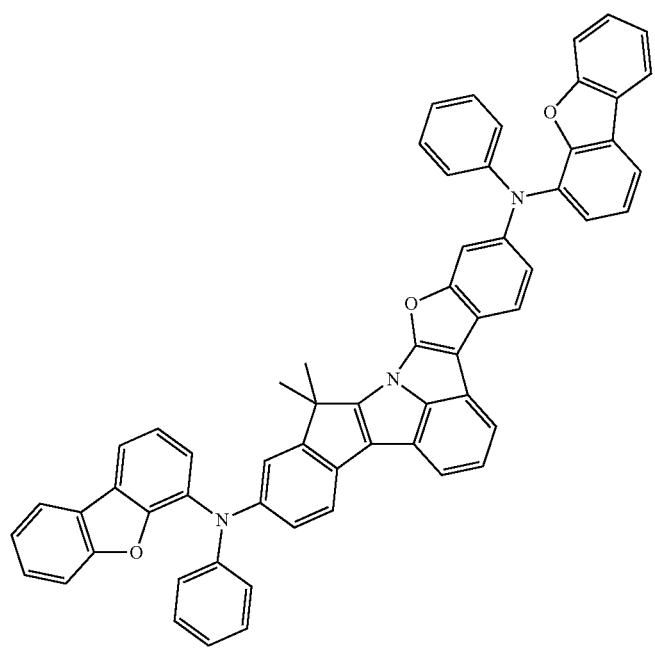

-continued
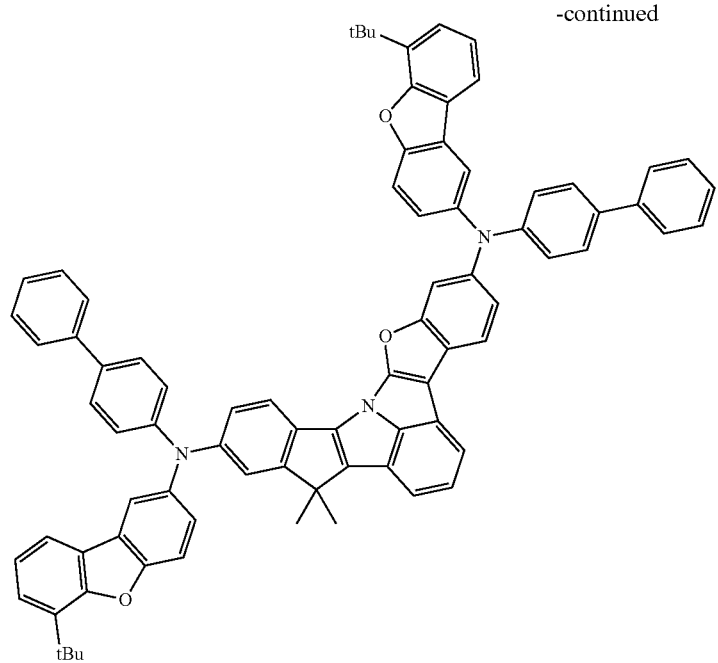
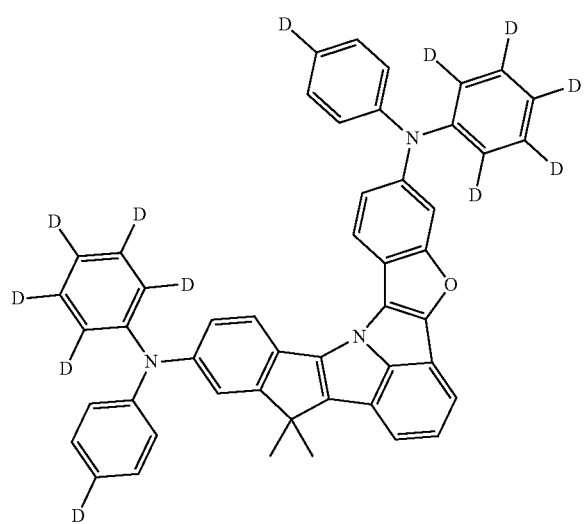

-continued
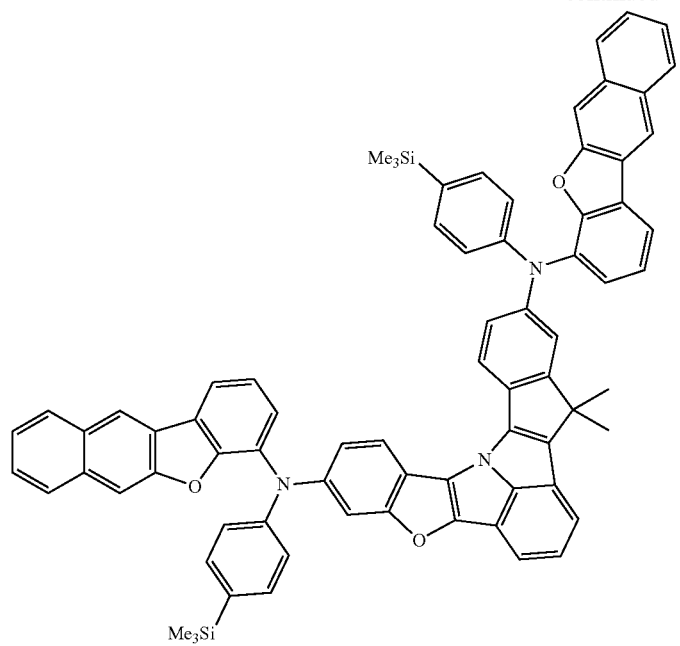
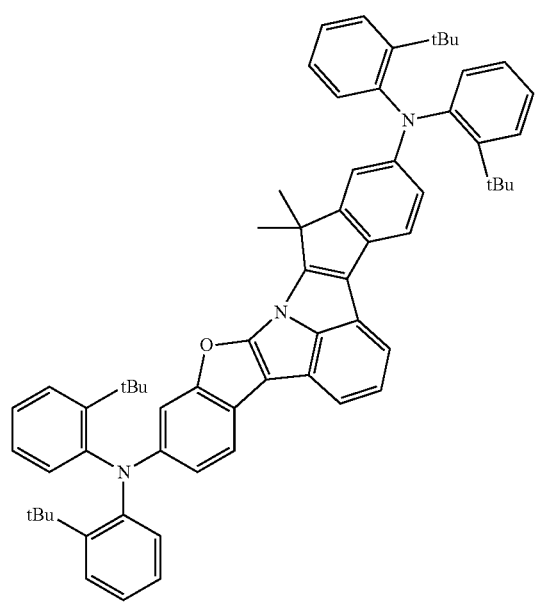

-continued
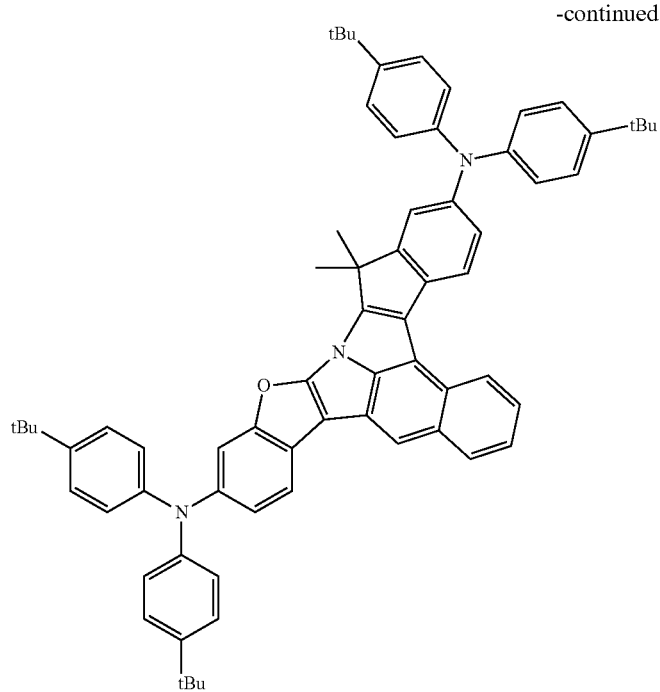
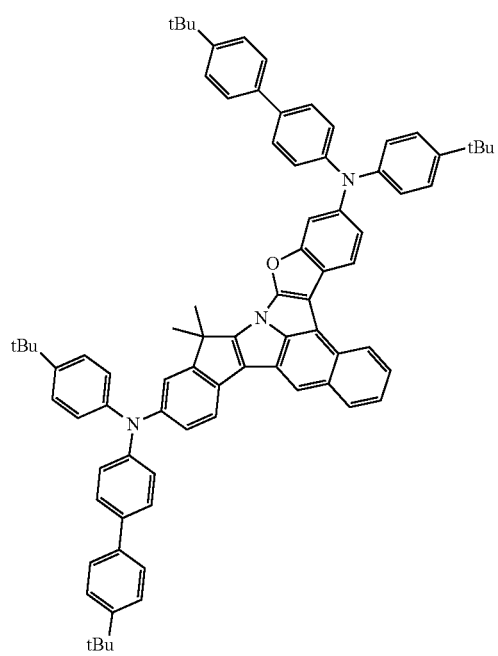

-continued
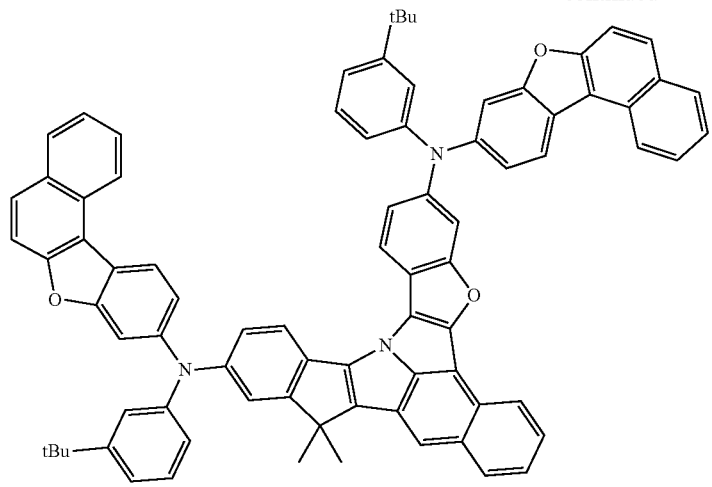
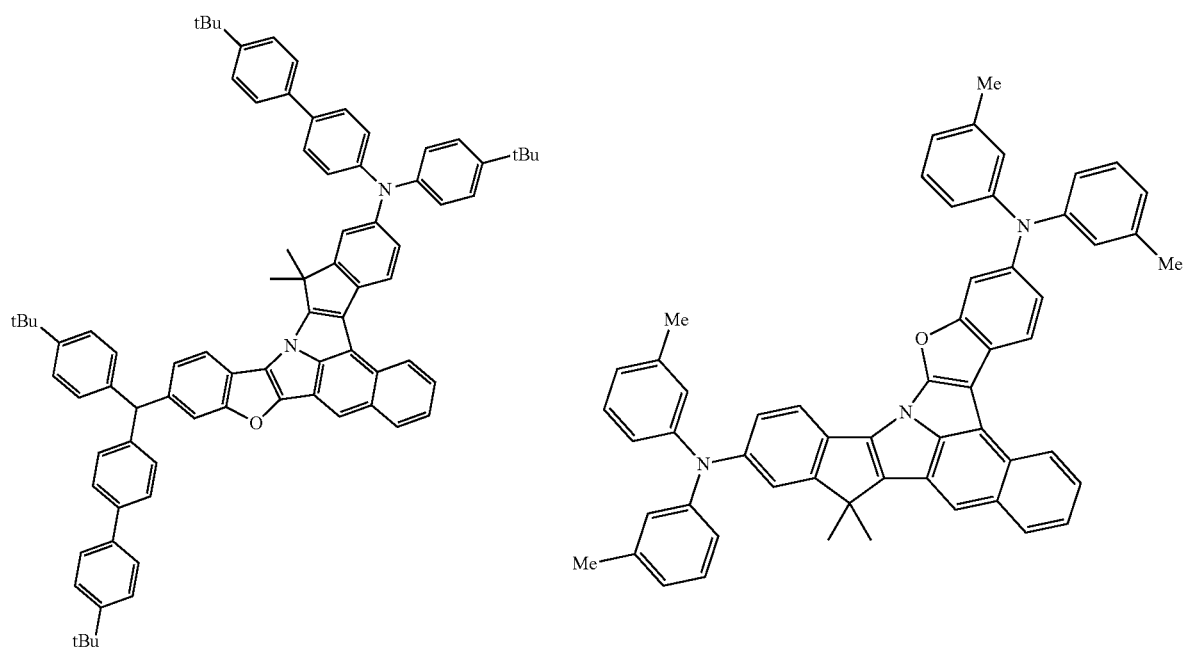
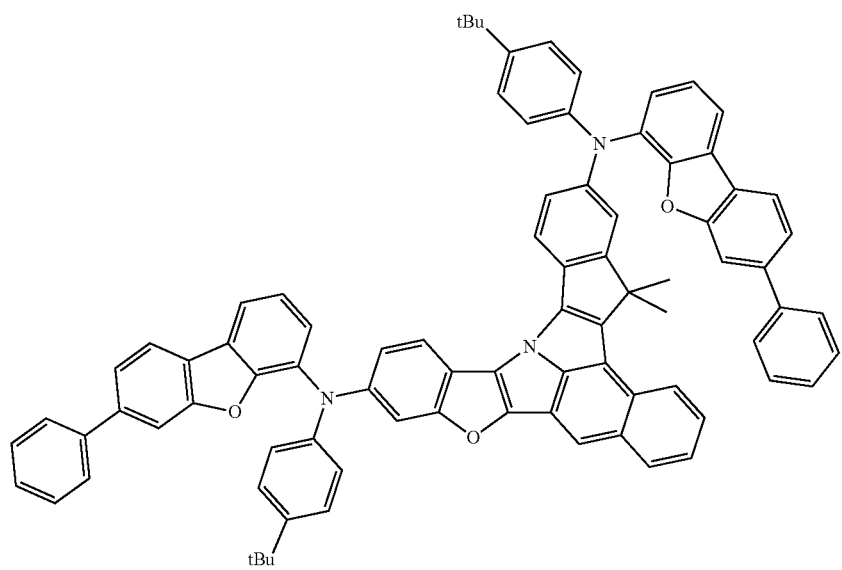

-continued
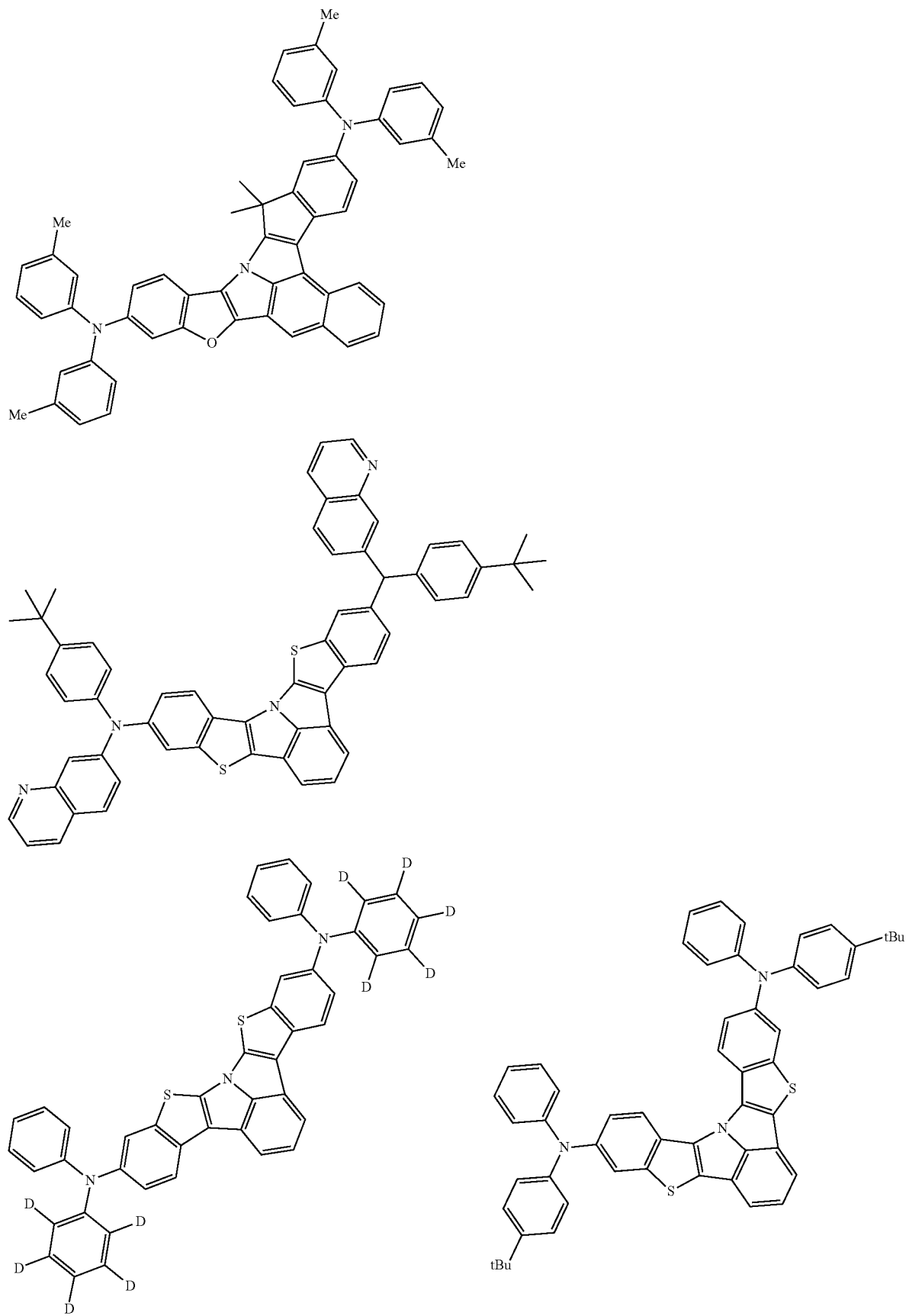

-continued
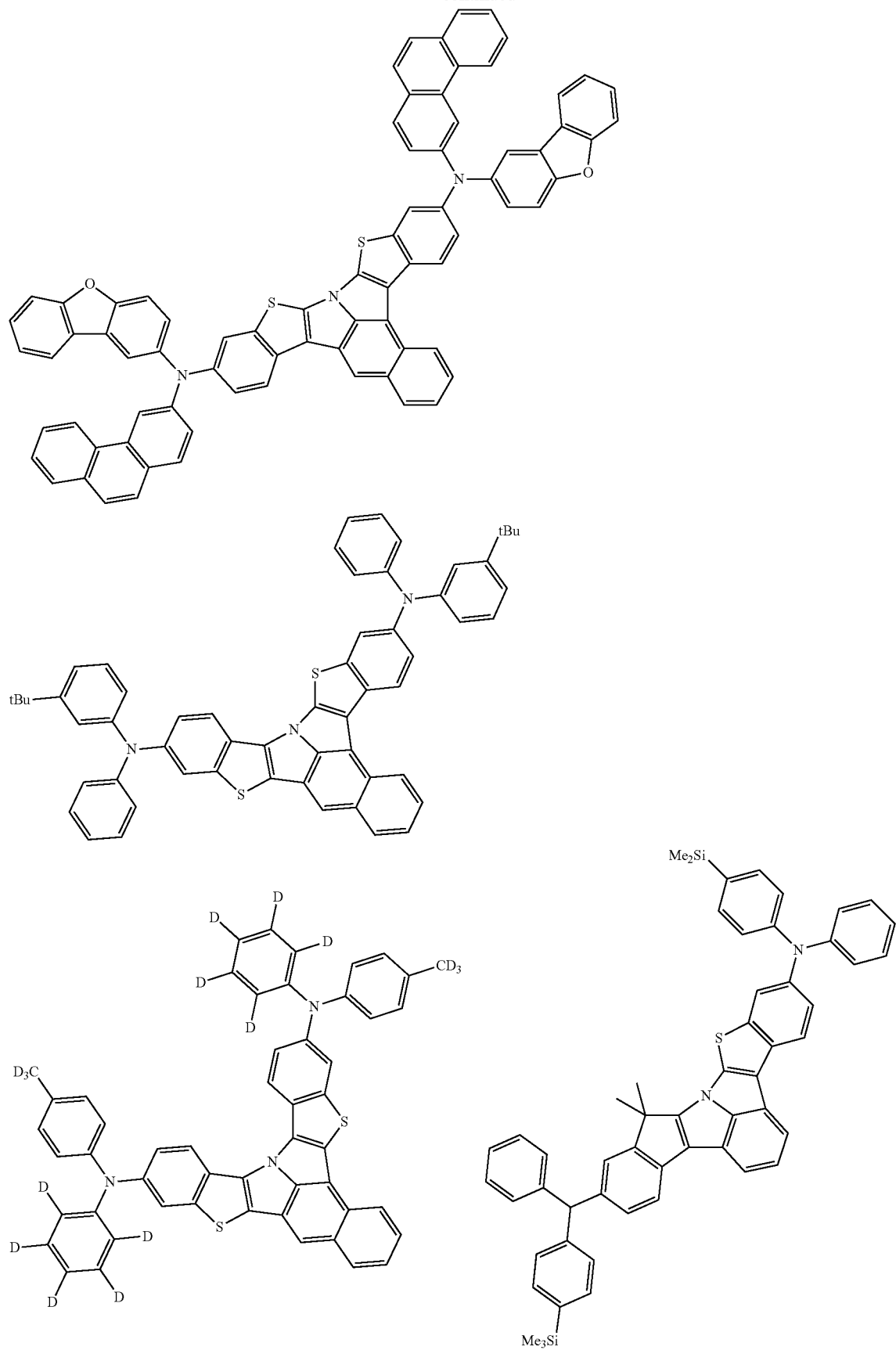

-continued
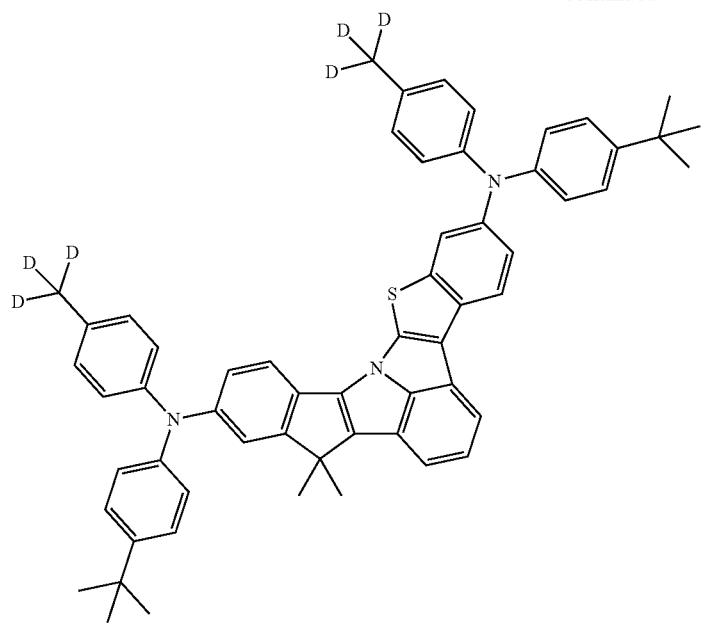
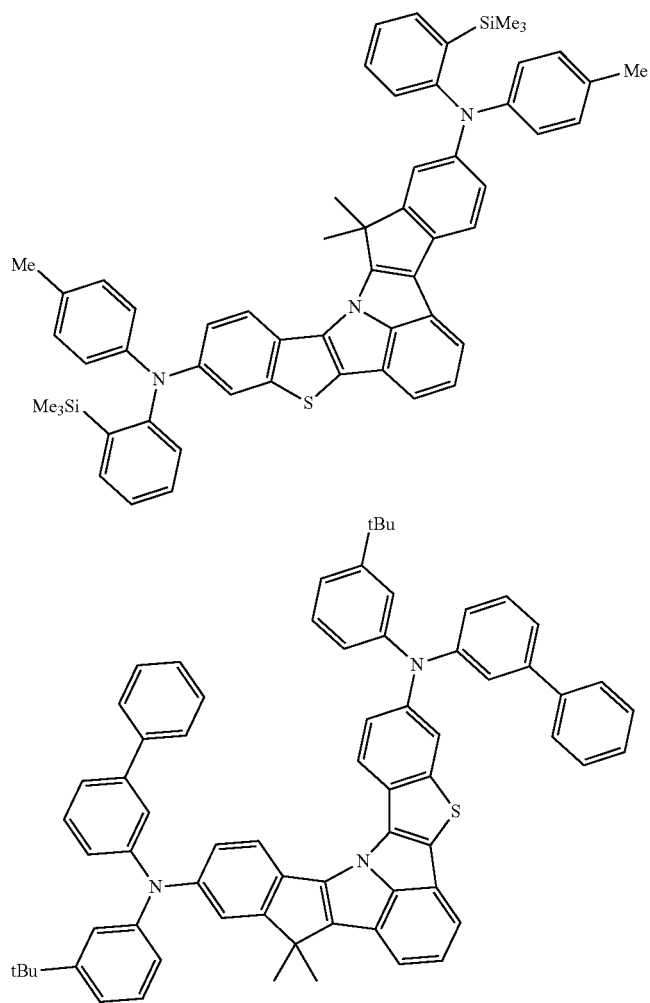

-continued
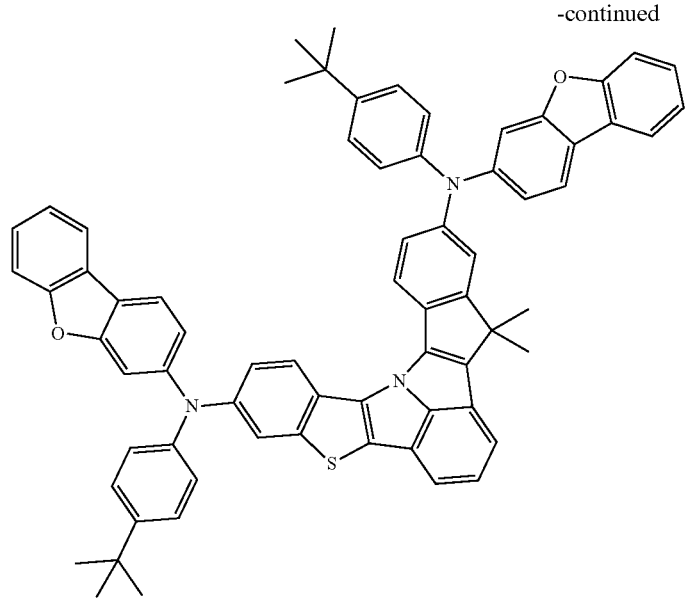
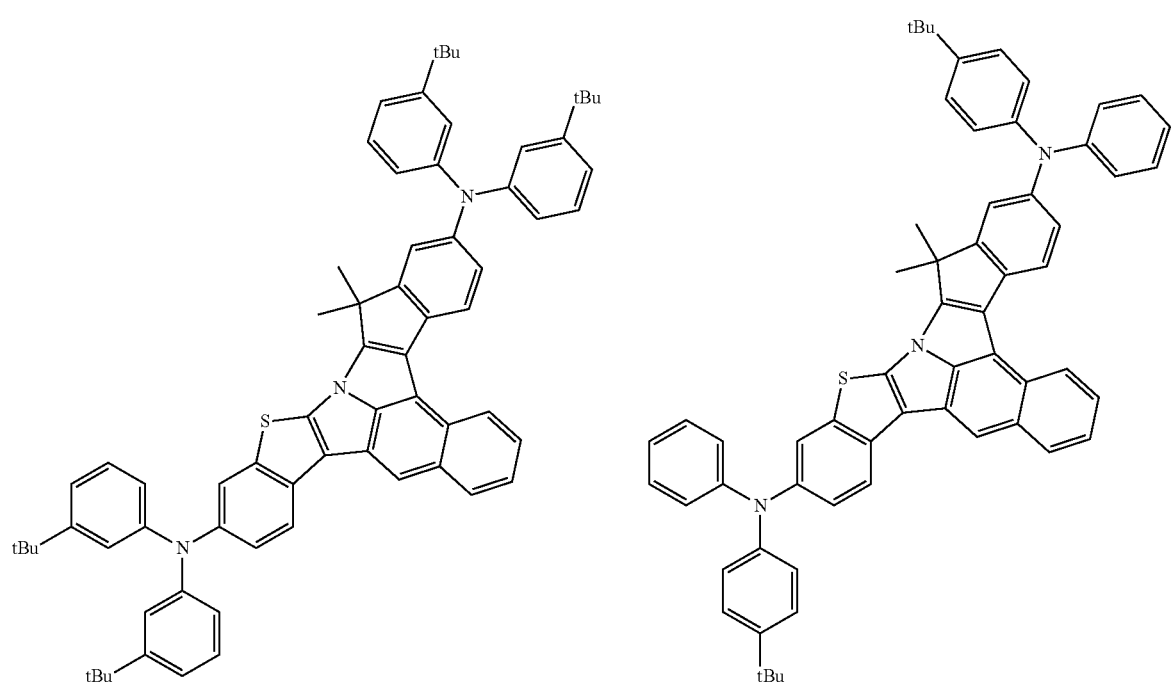

-continued
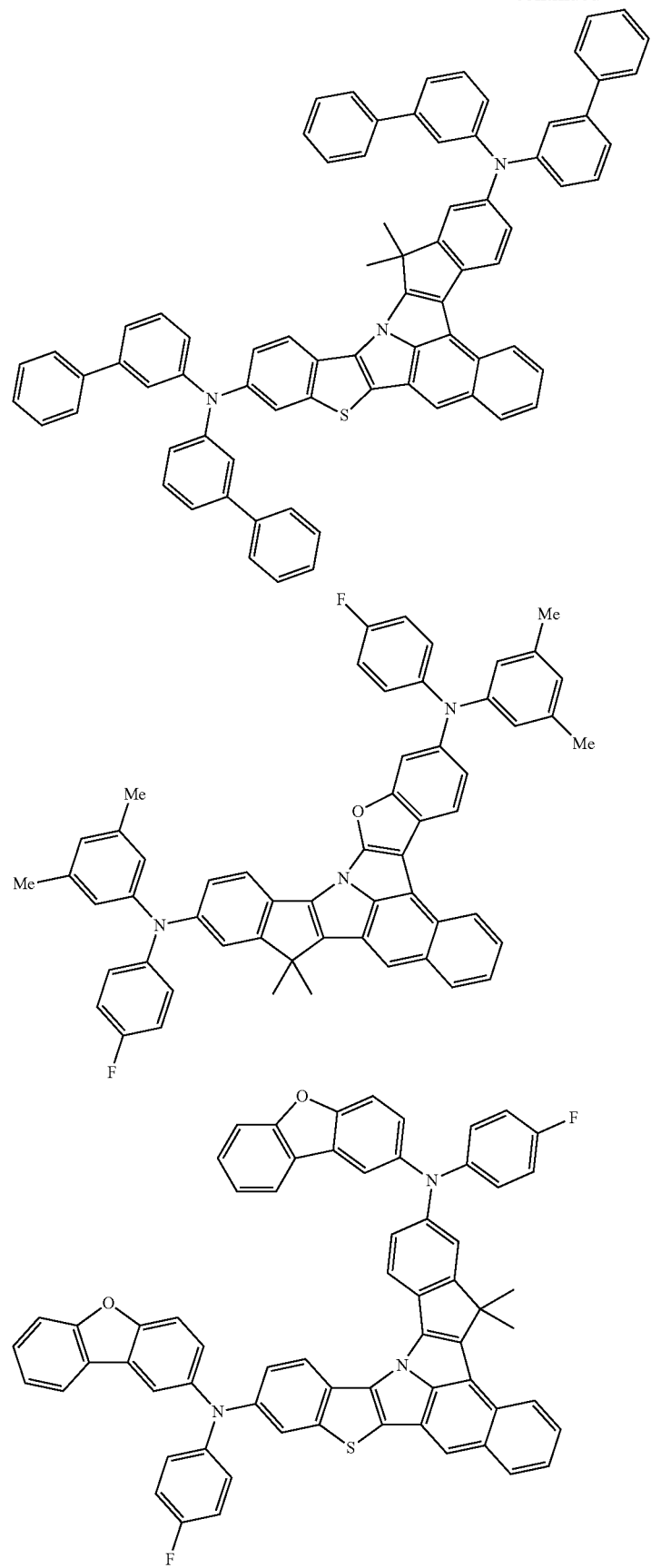

-continued
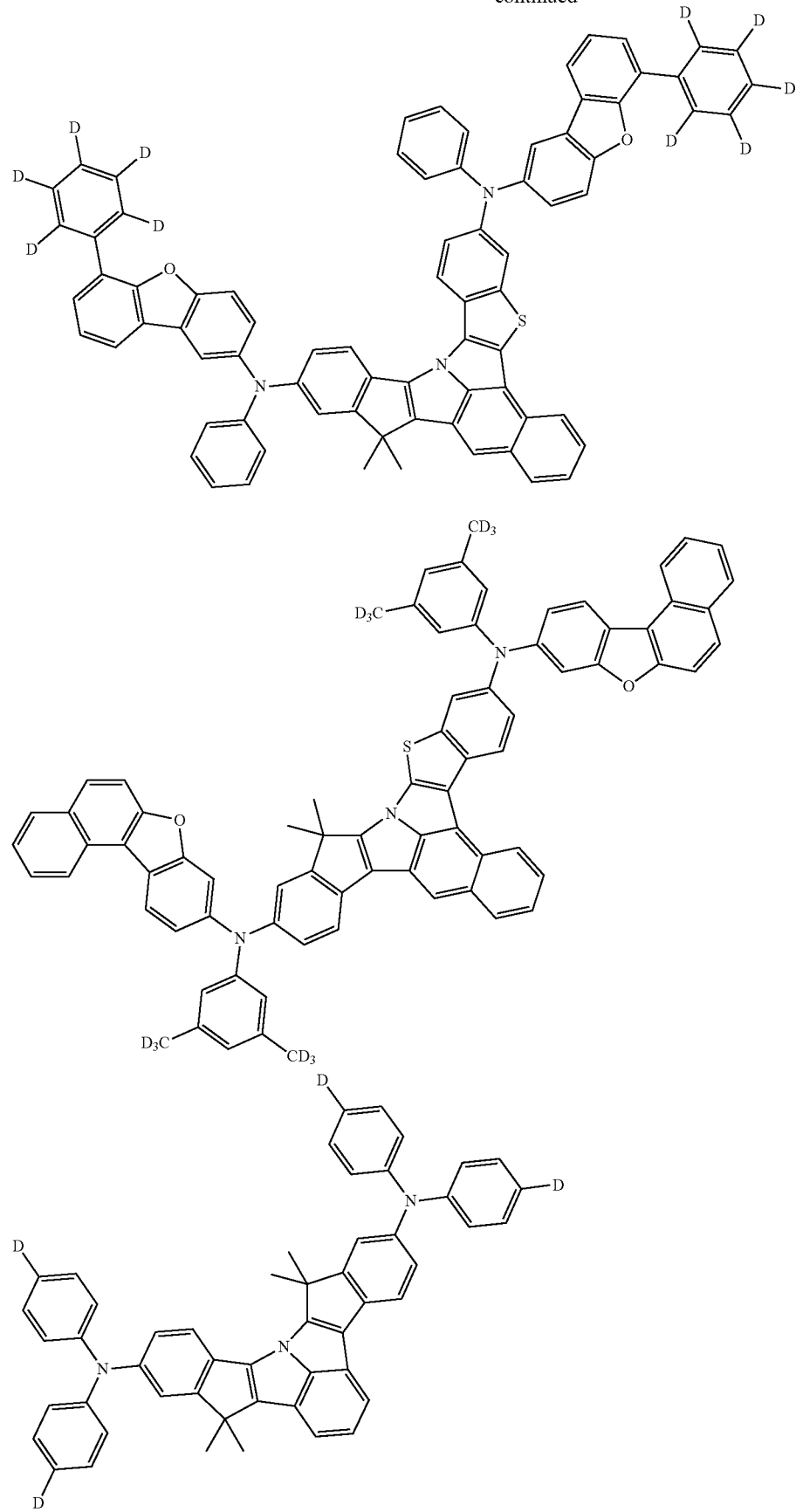

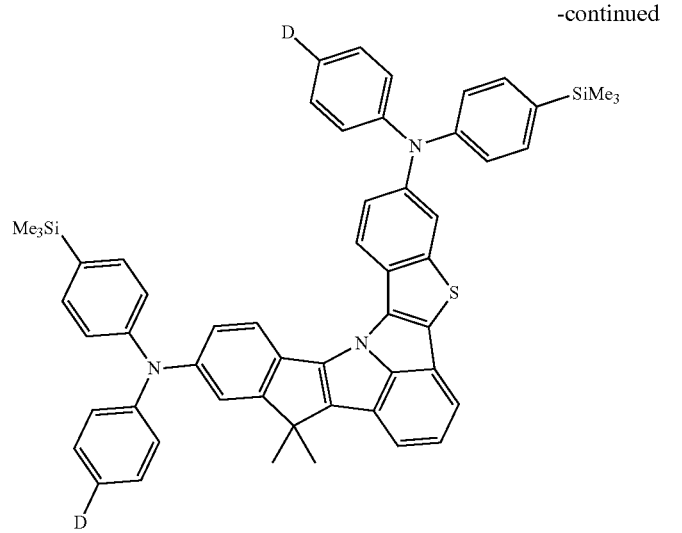
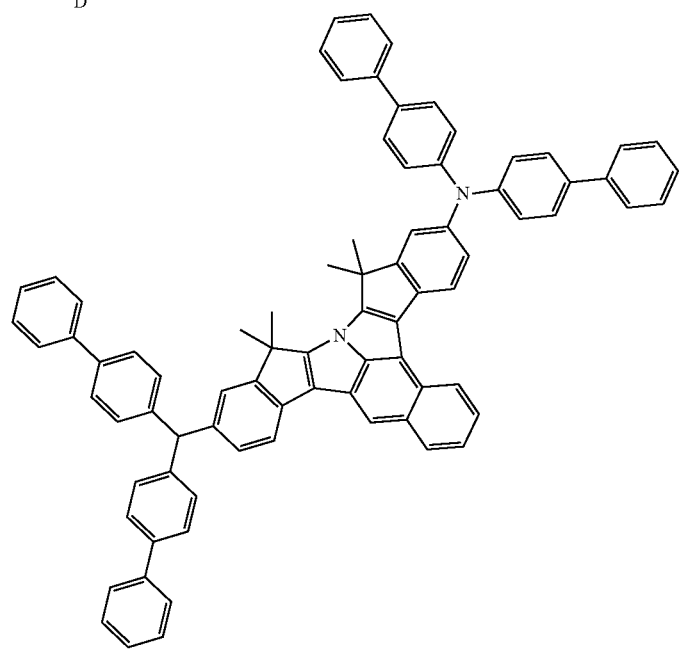
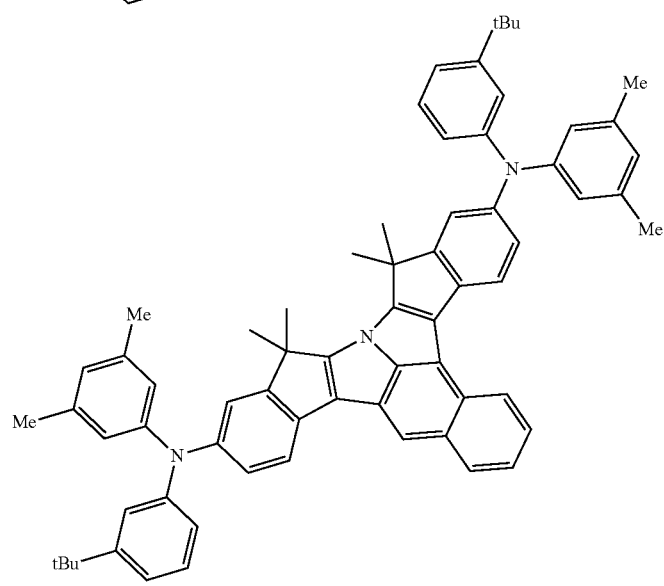

-continued
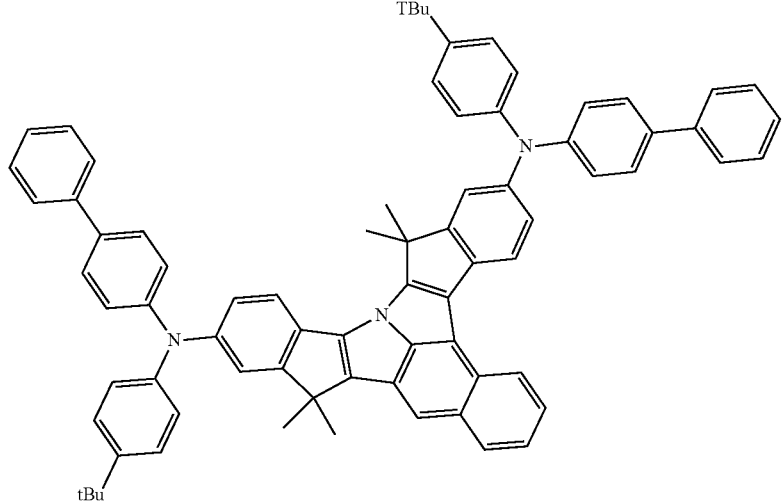
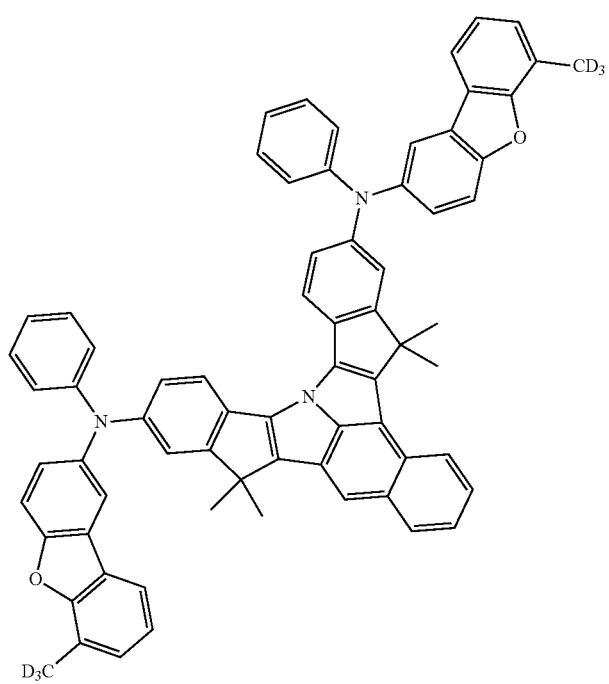

-continued
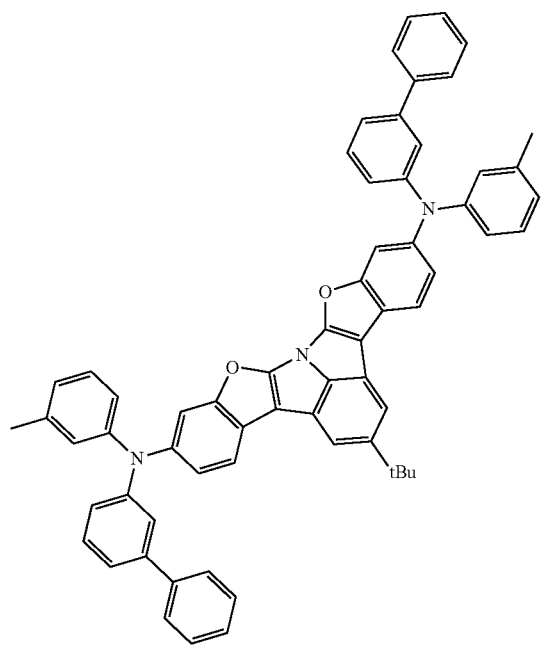
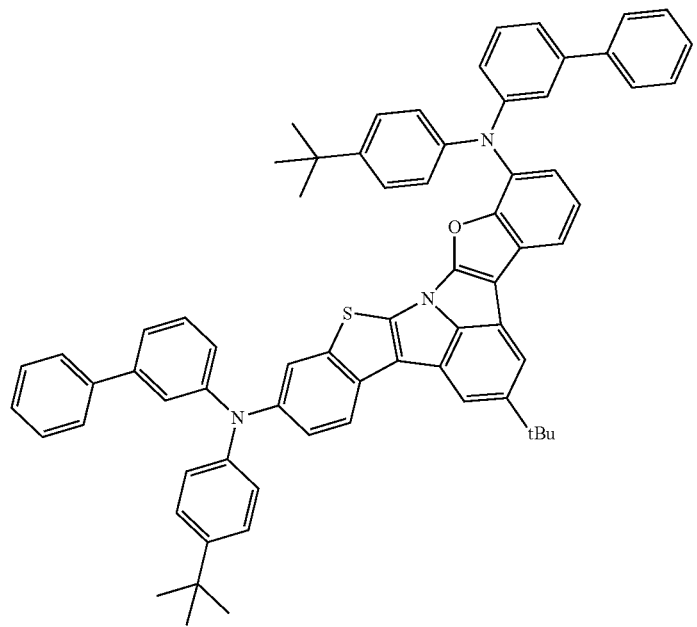

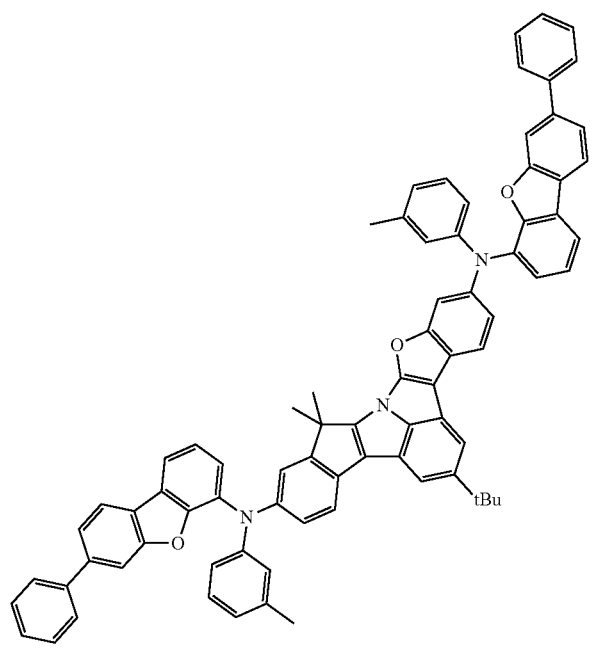
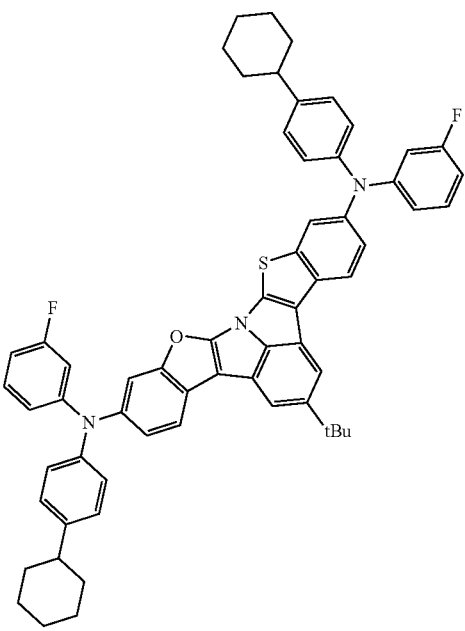
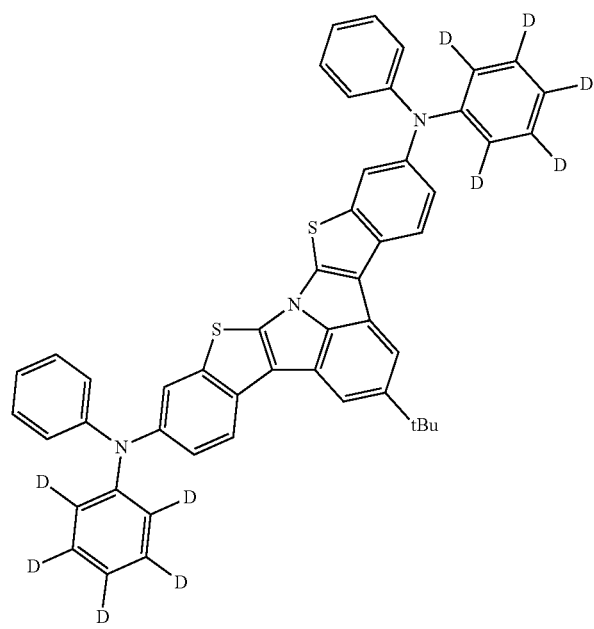

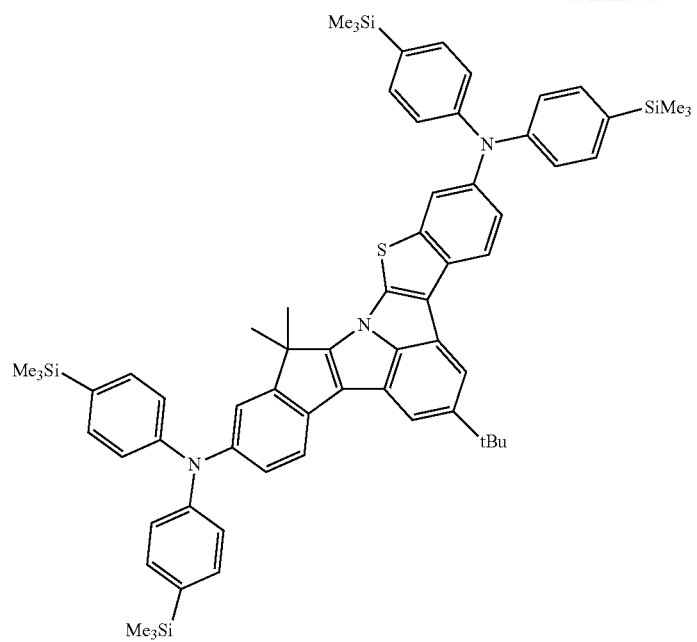
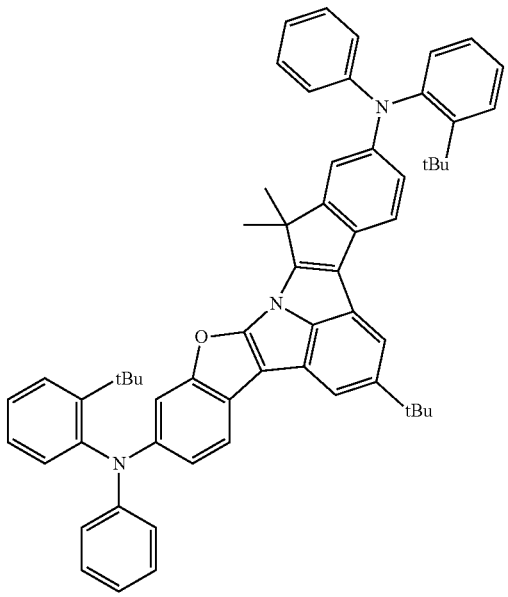
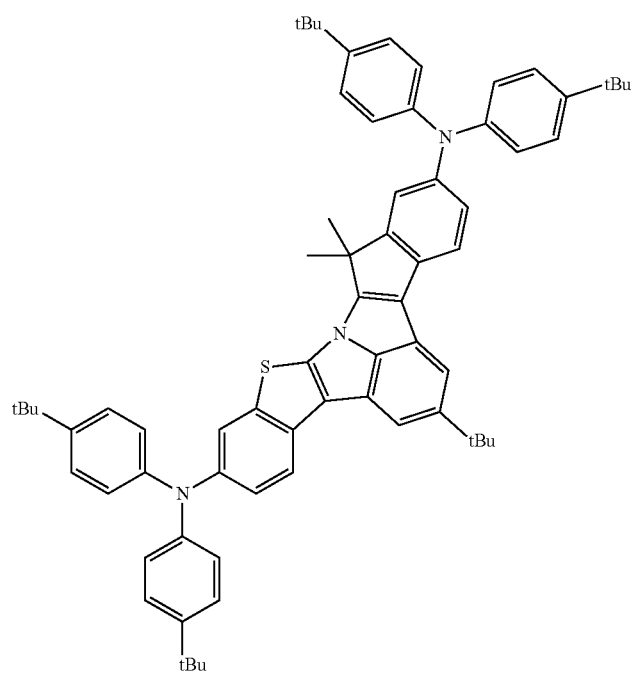

-continued
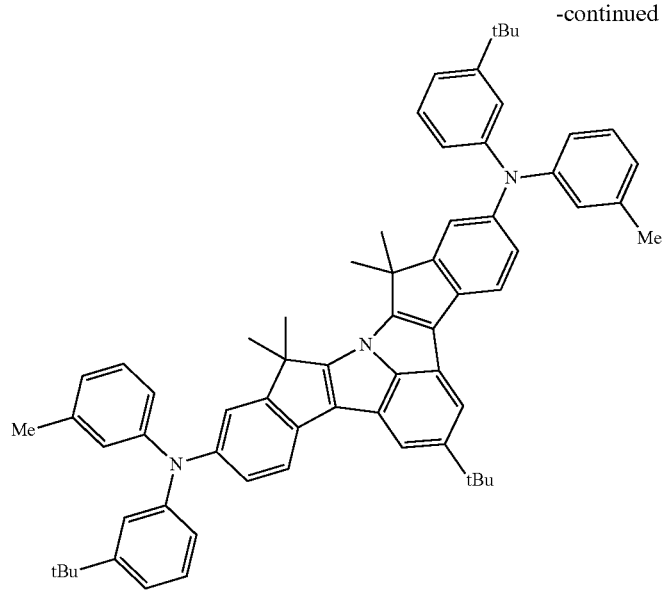
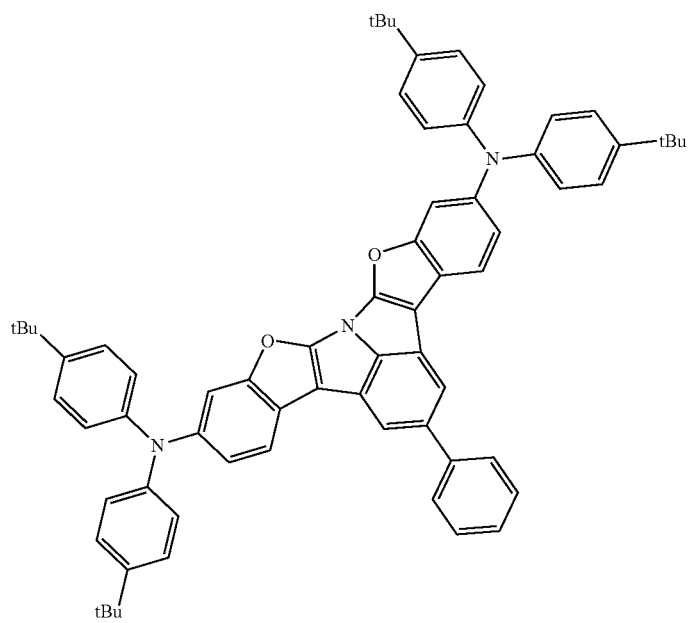
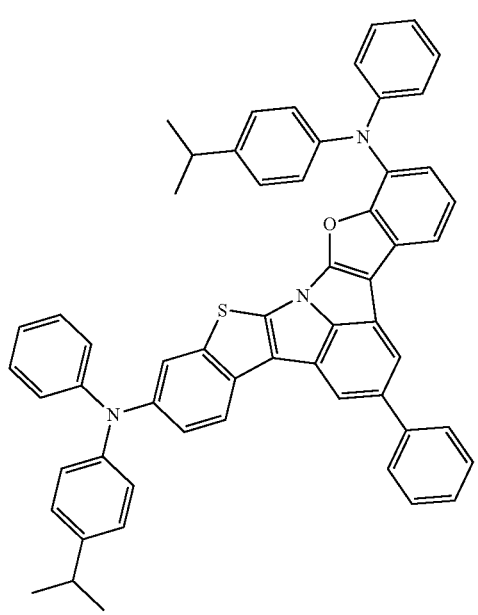

-continued
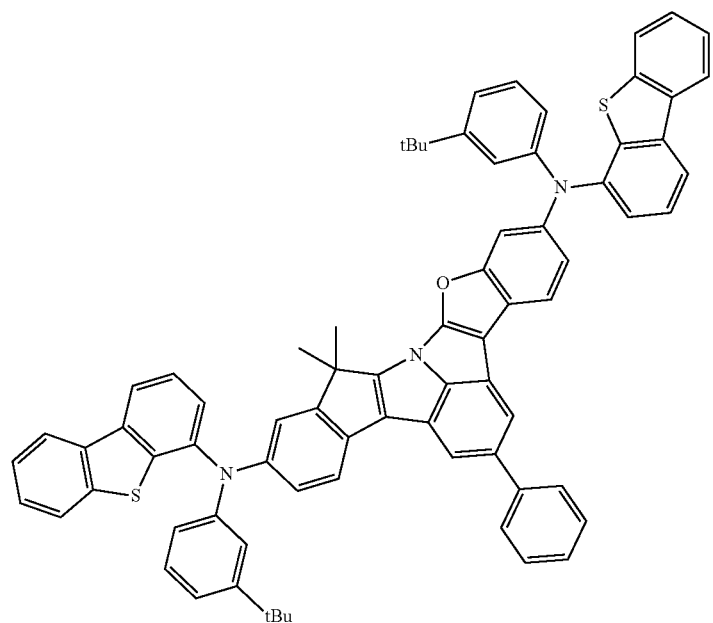
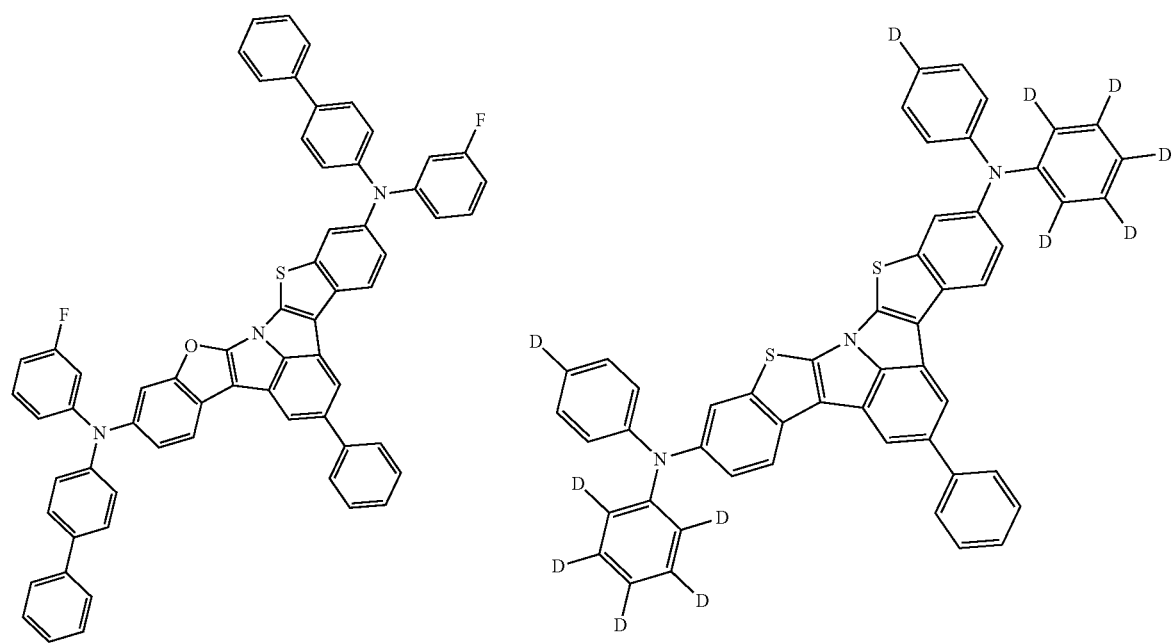

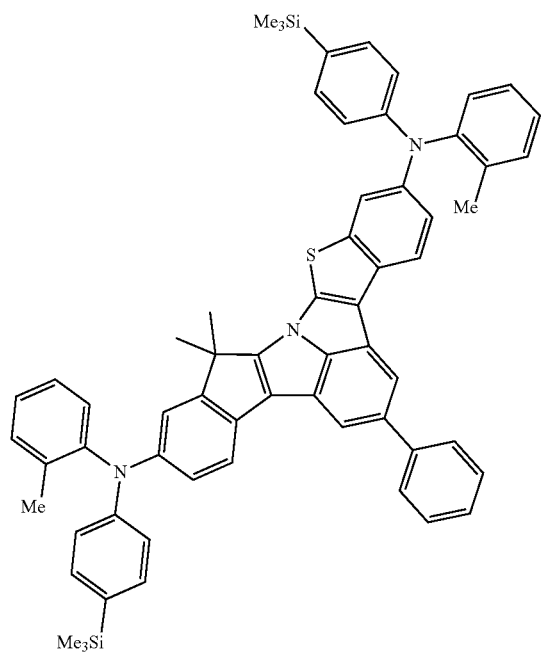 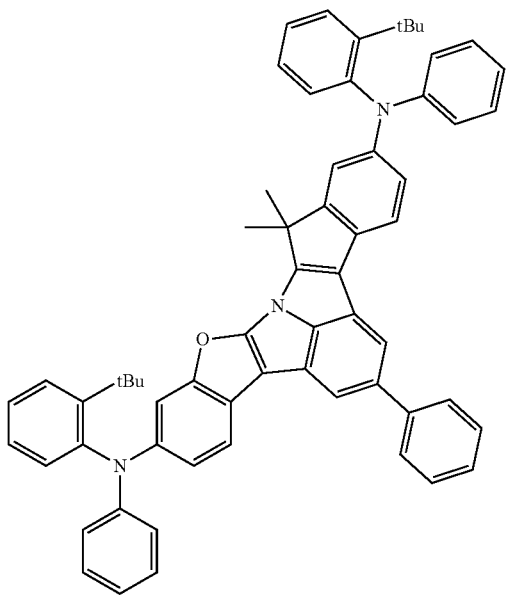 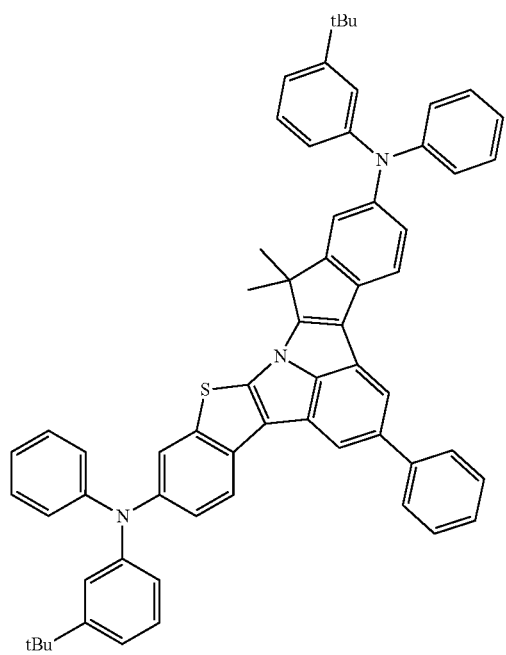

-continued
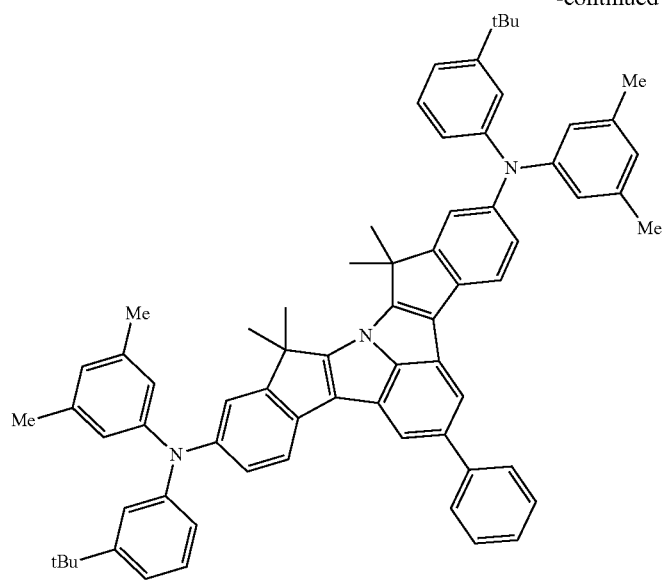
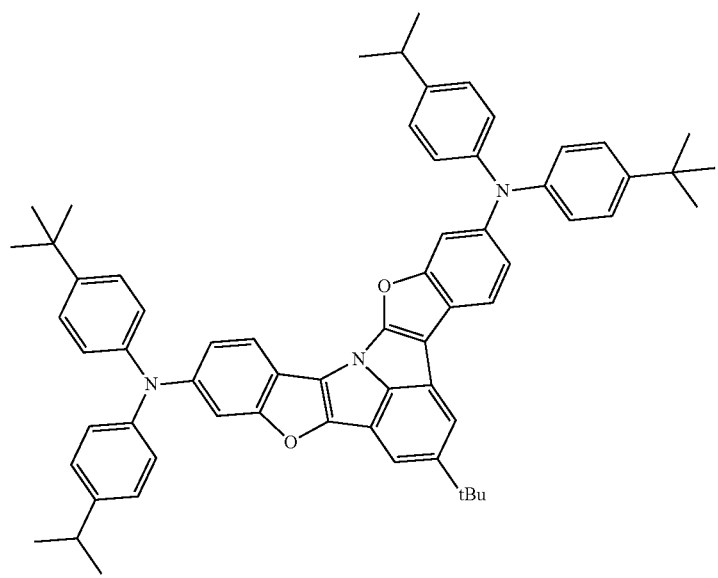

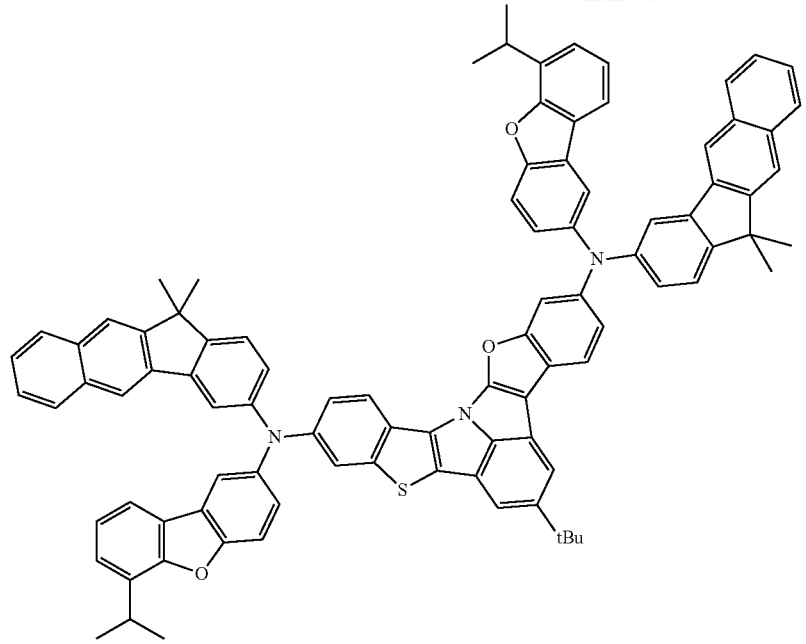
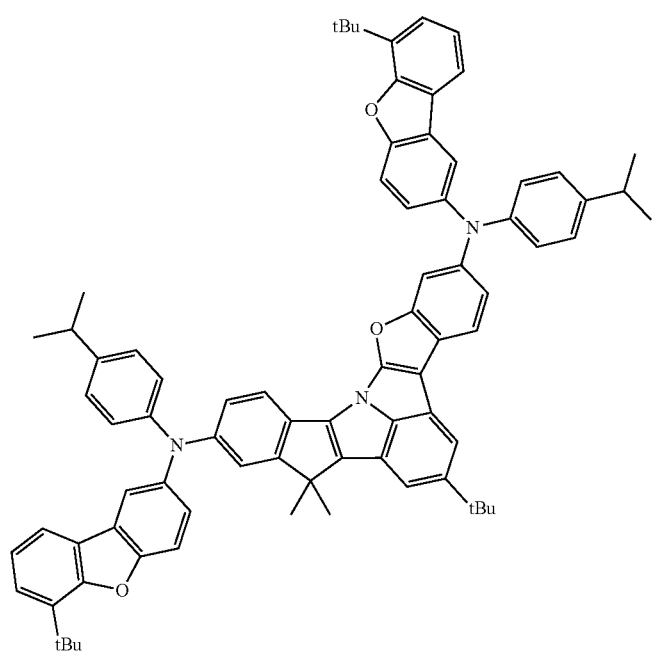

-continued
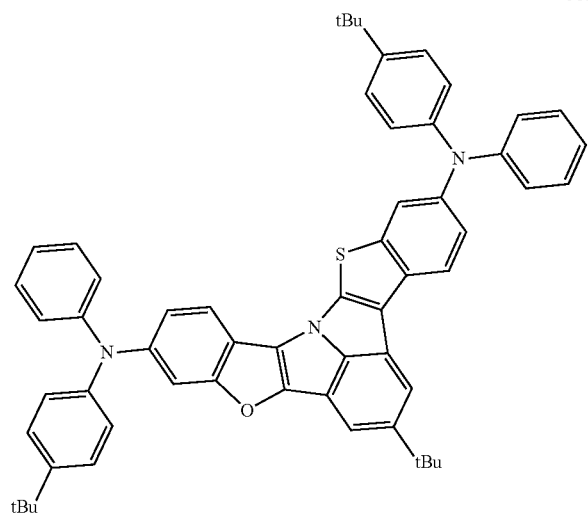
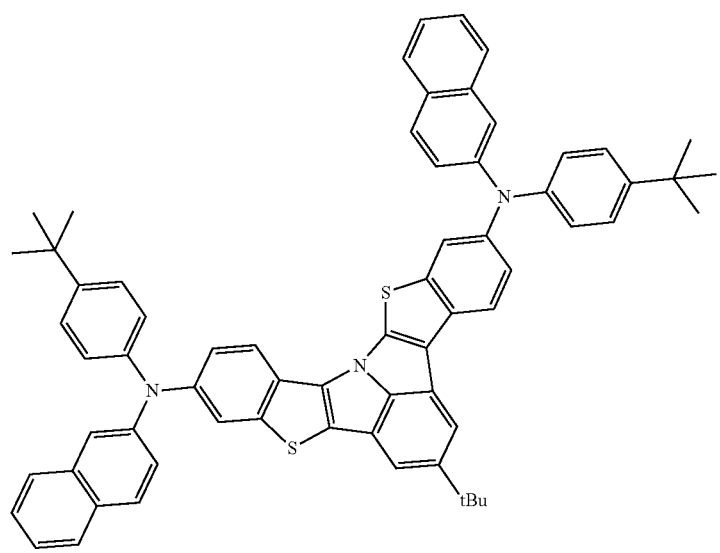
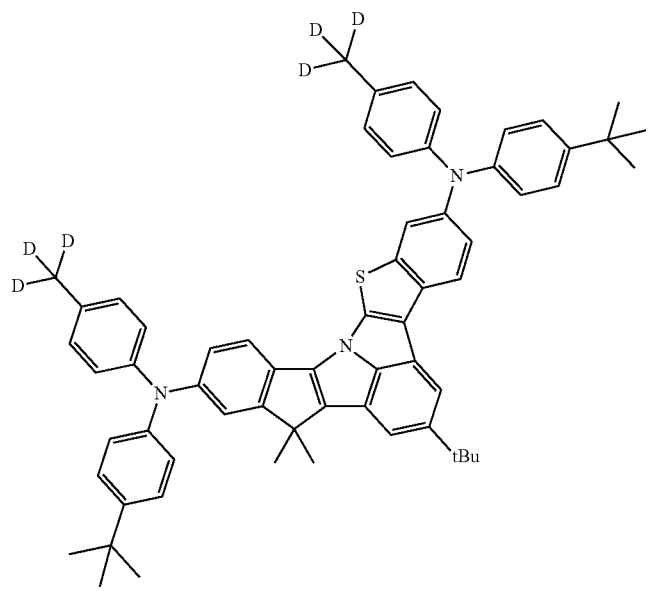

-continued
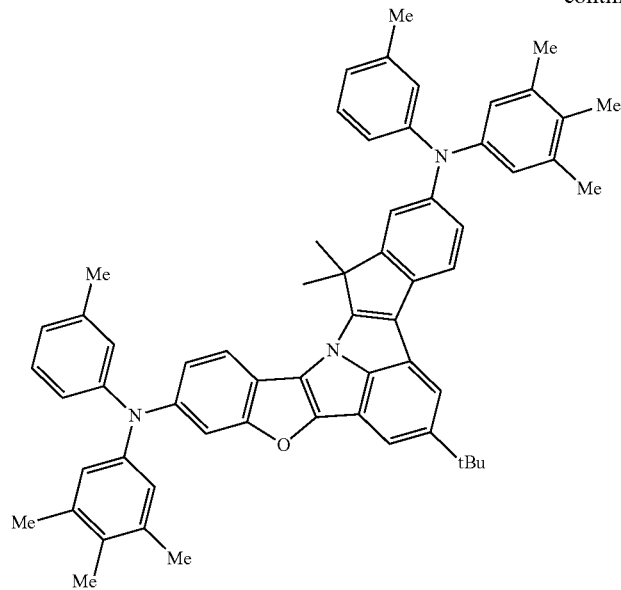
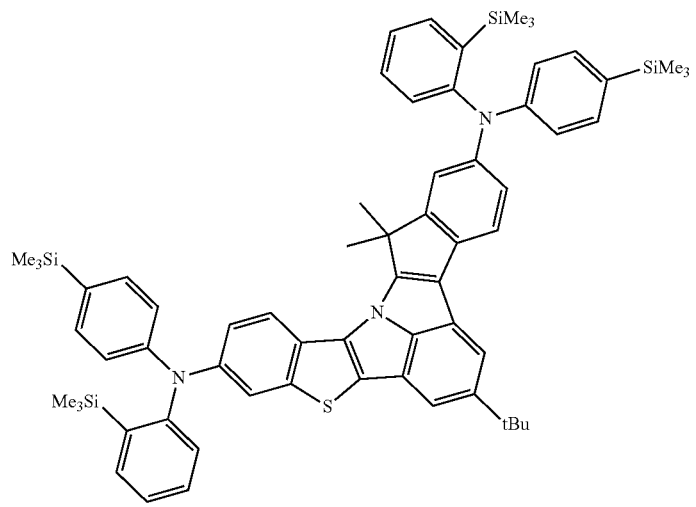
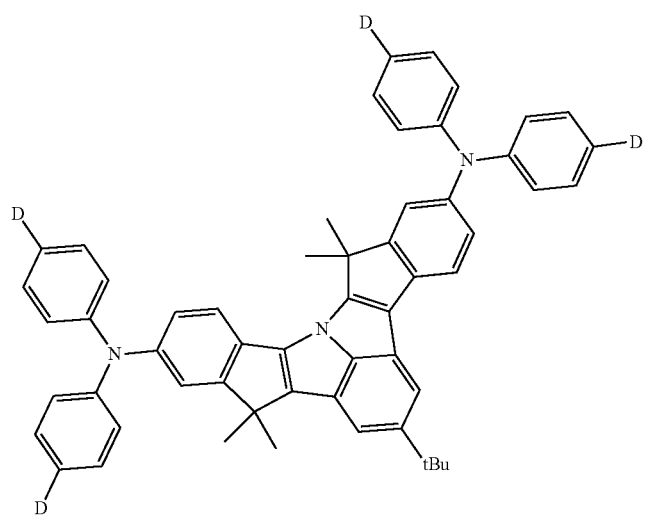

-continued
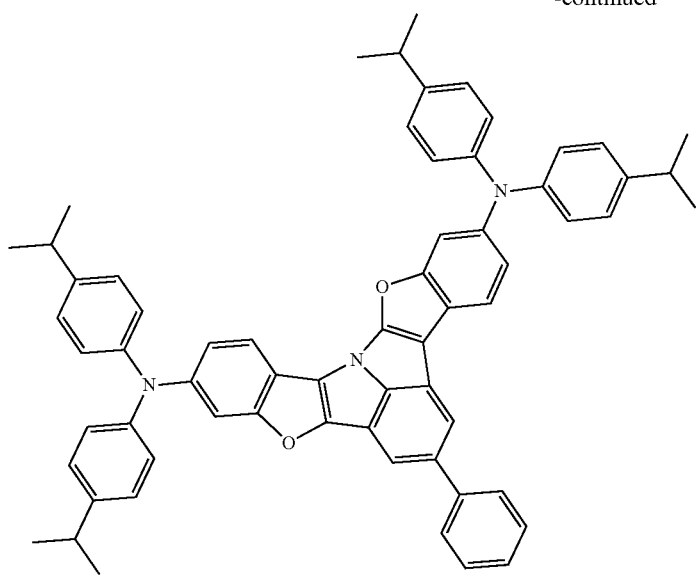
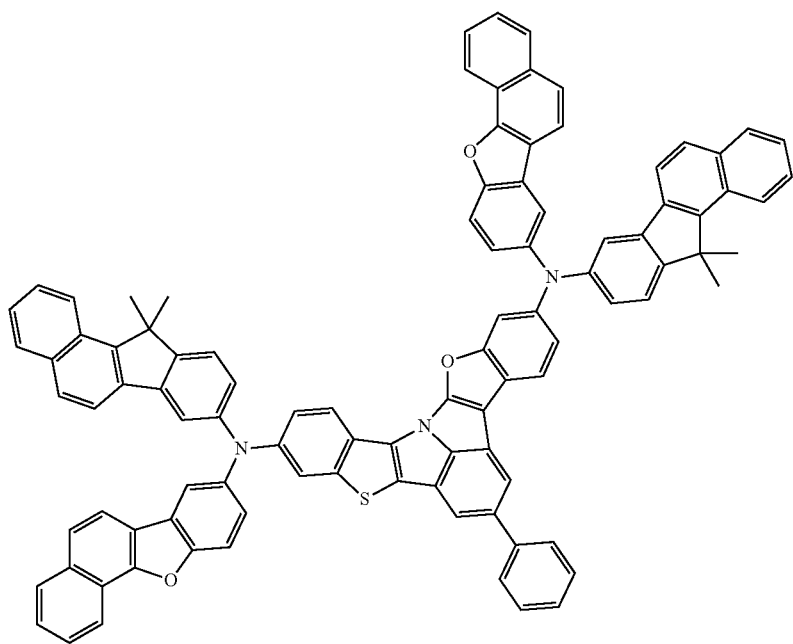

-continued
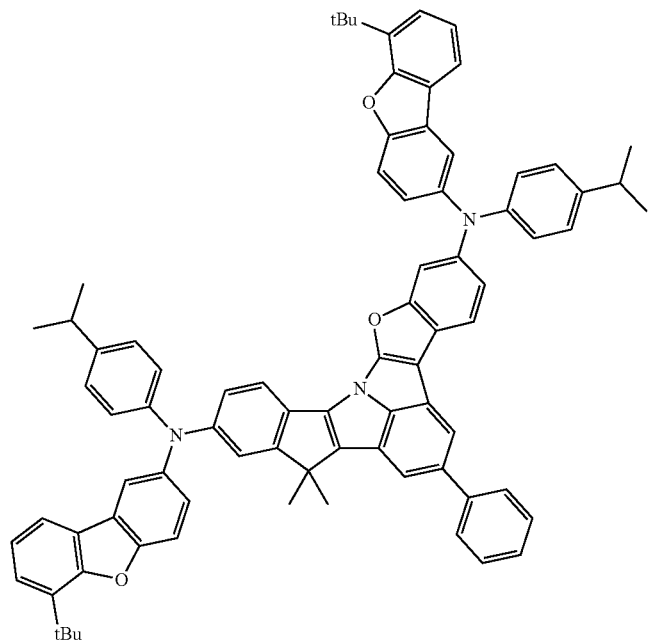
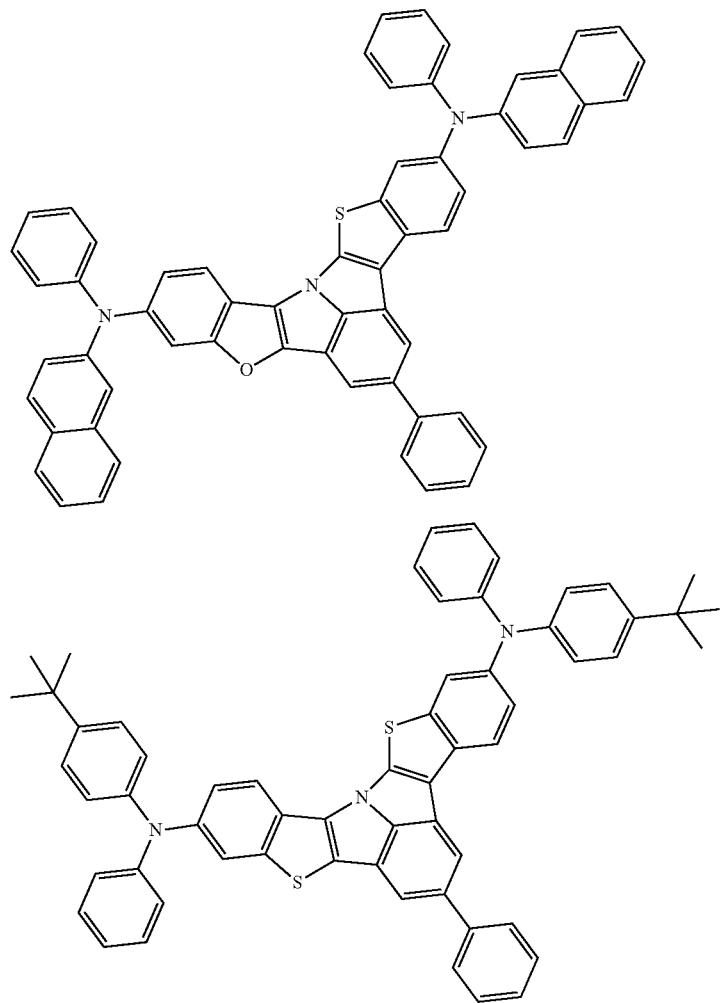

-continued
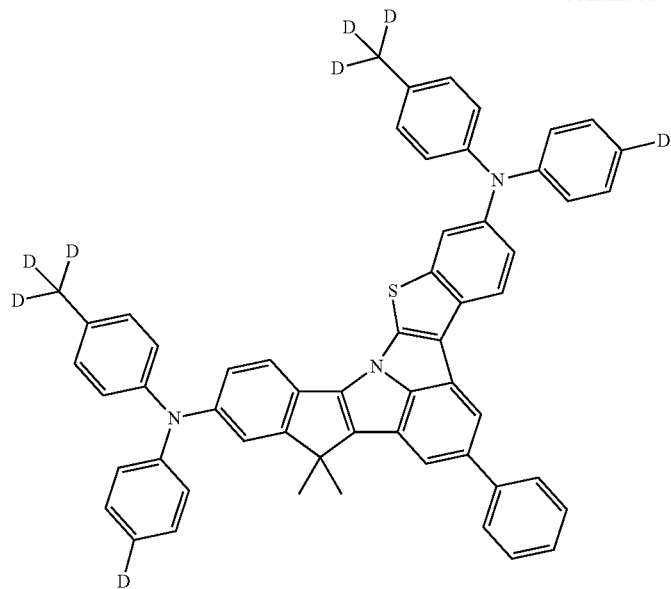
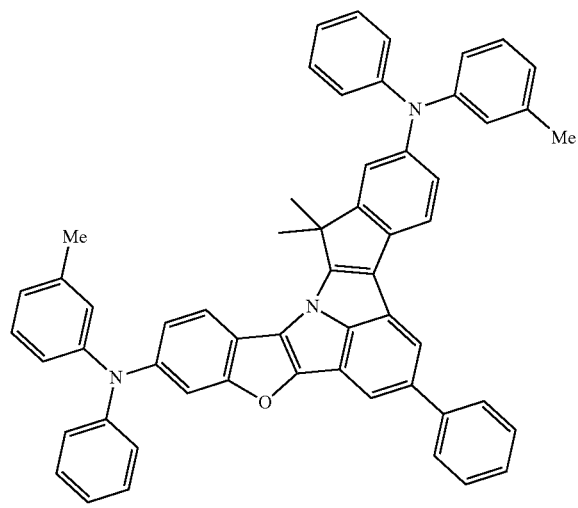
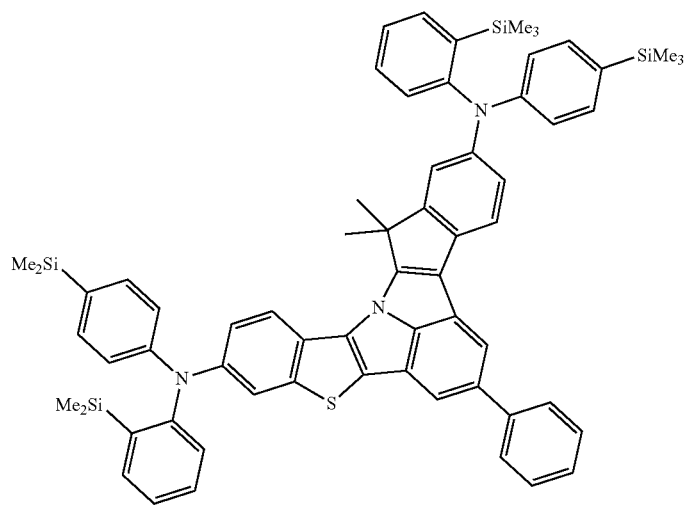

-continued
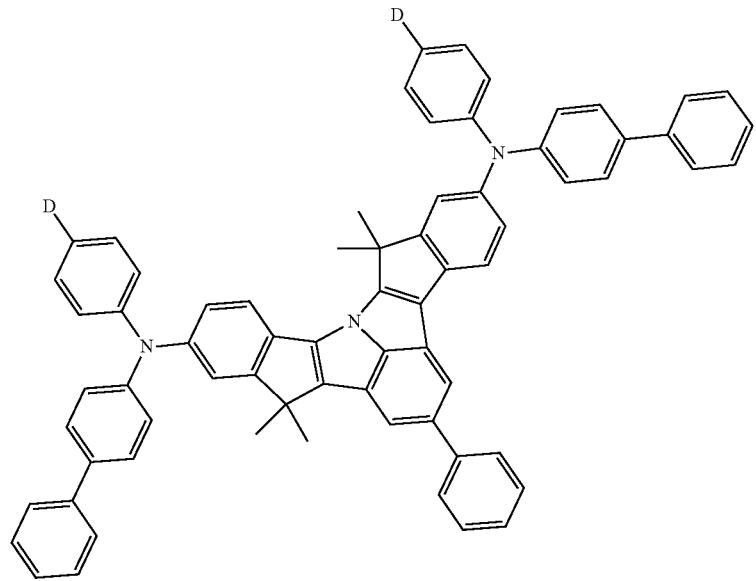
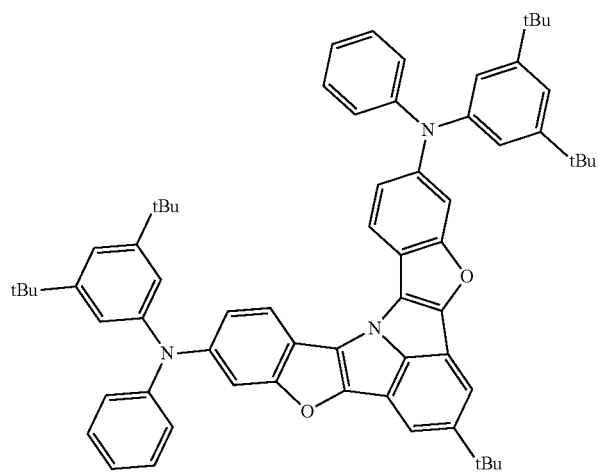
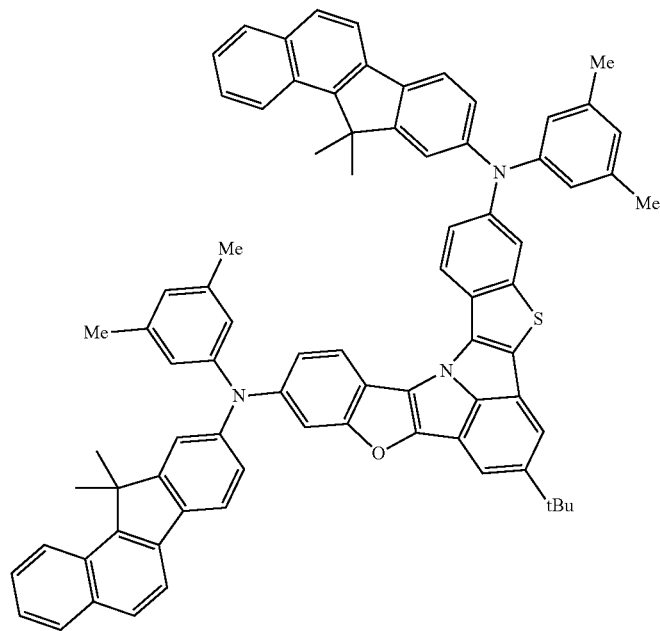

-continued
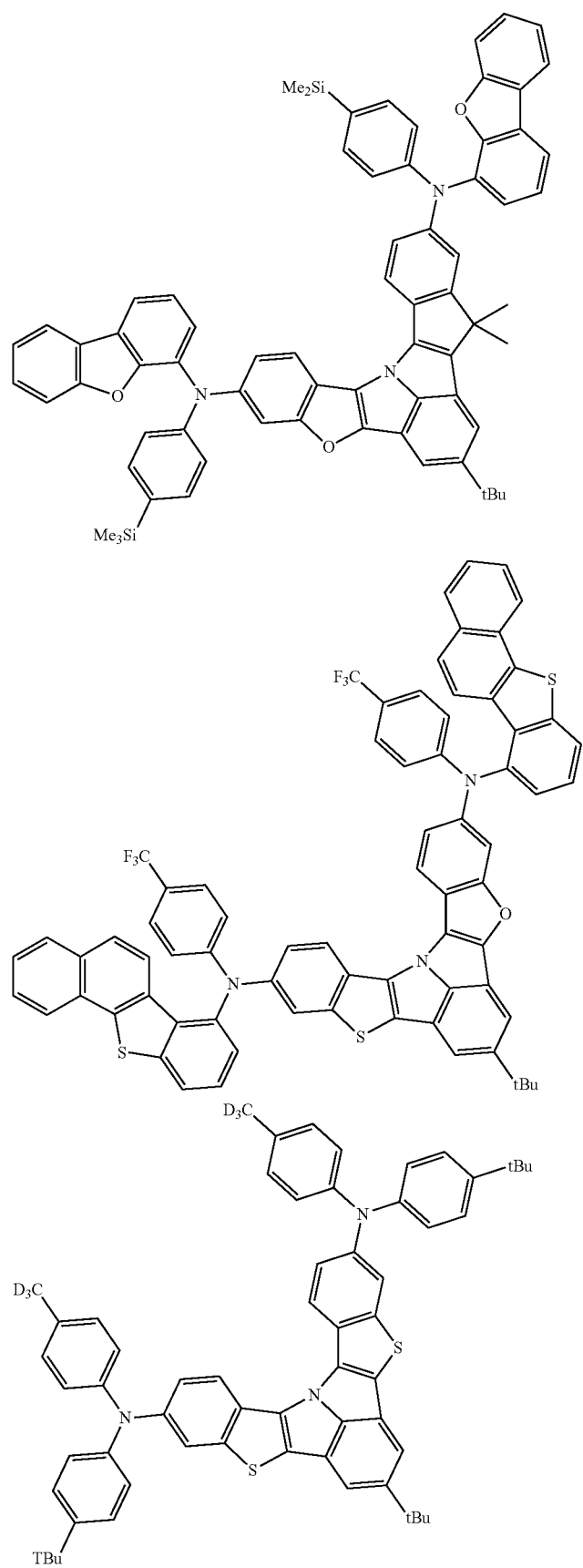

-continued
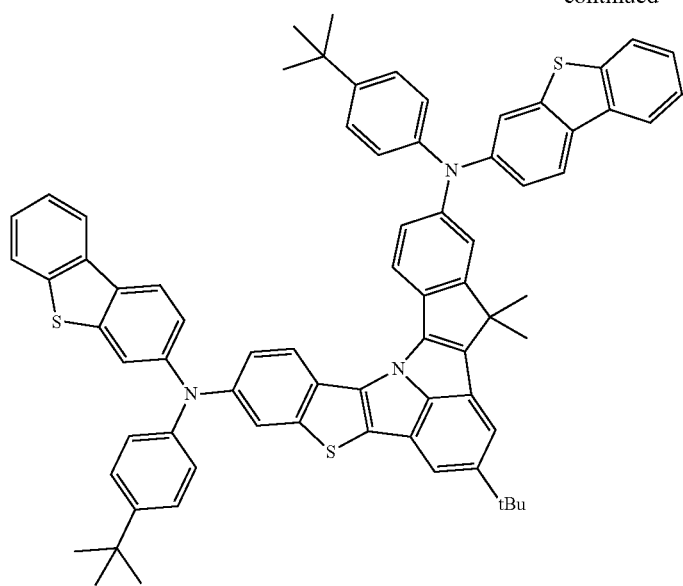
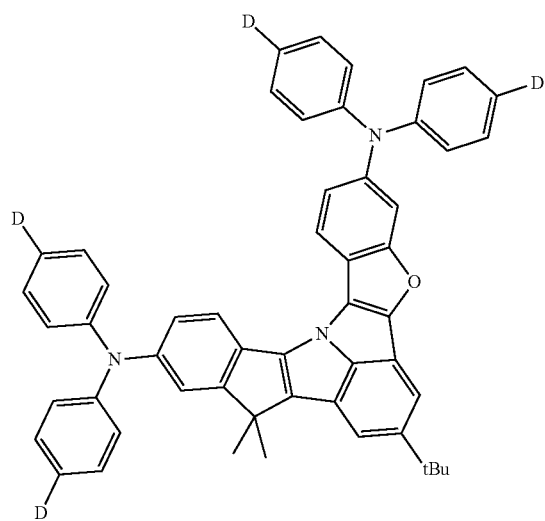
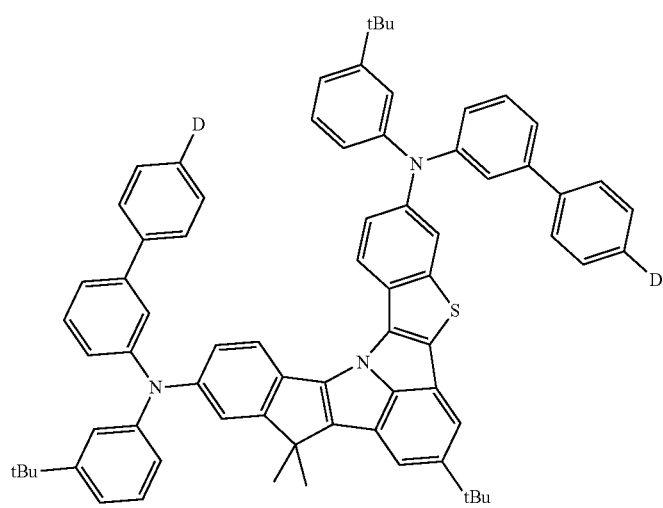

87 88
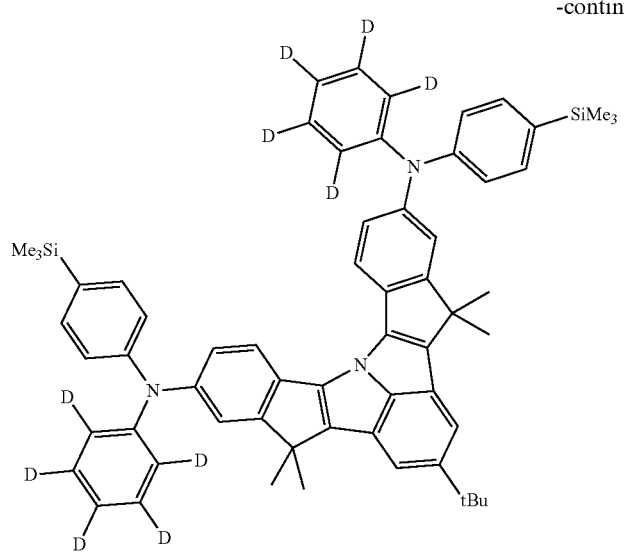
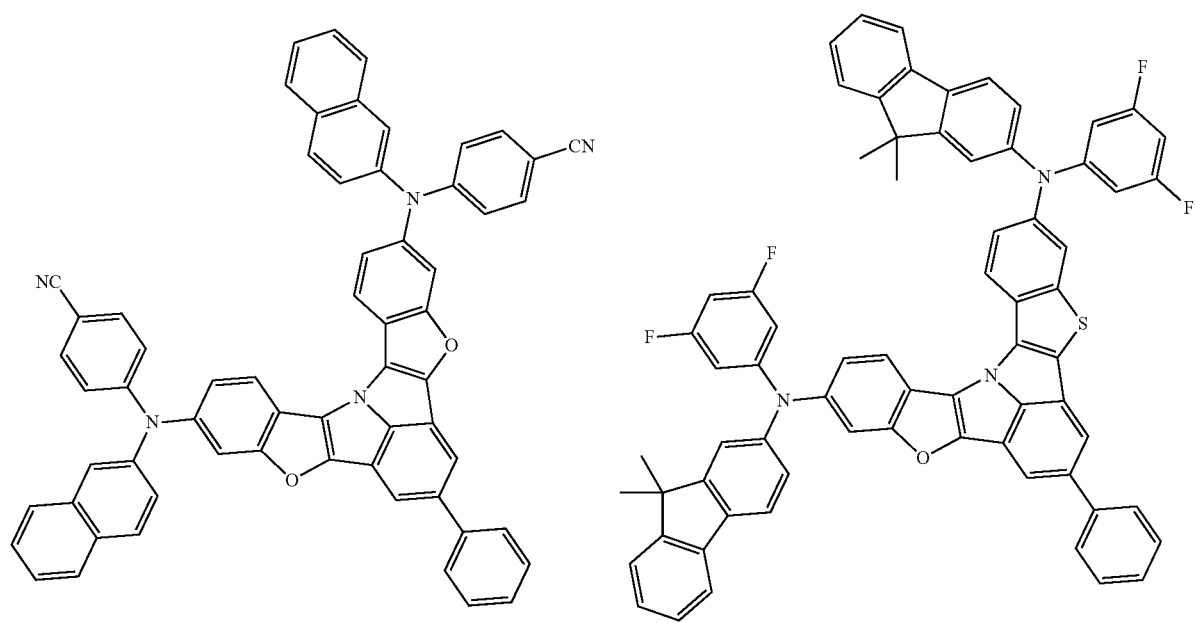

-continued
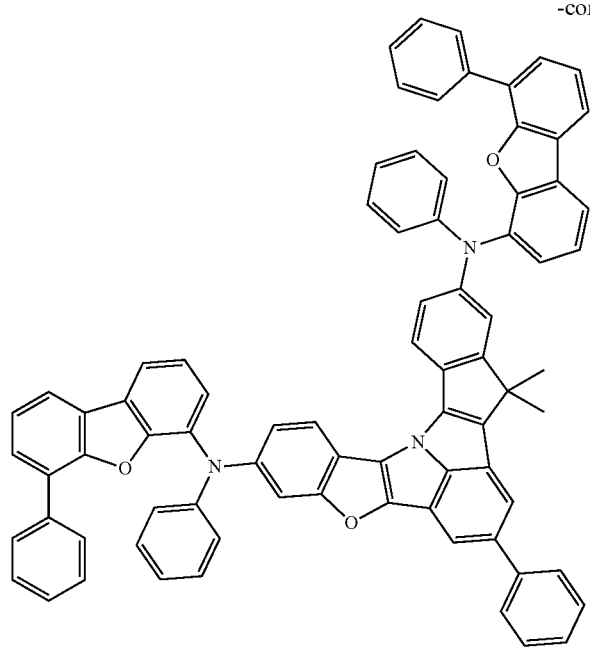
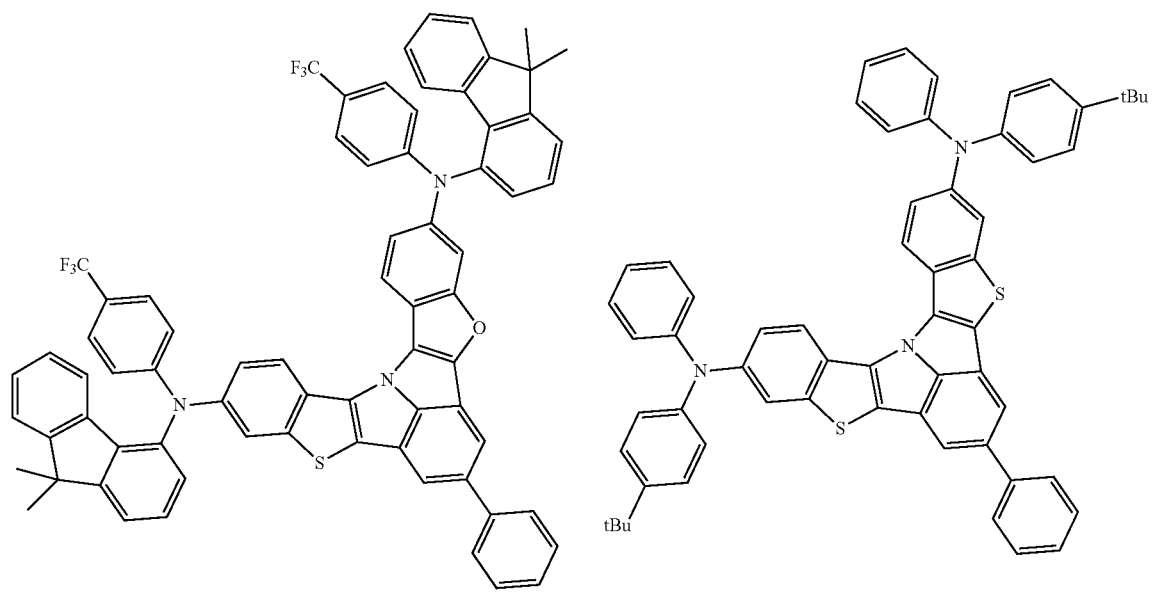

-continued
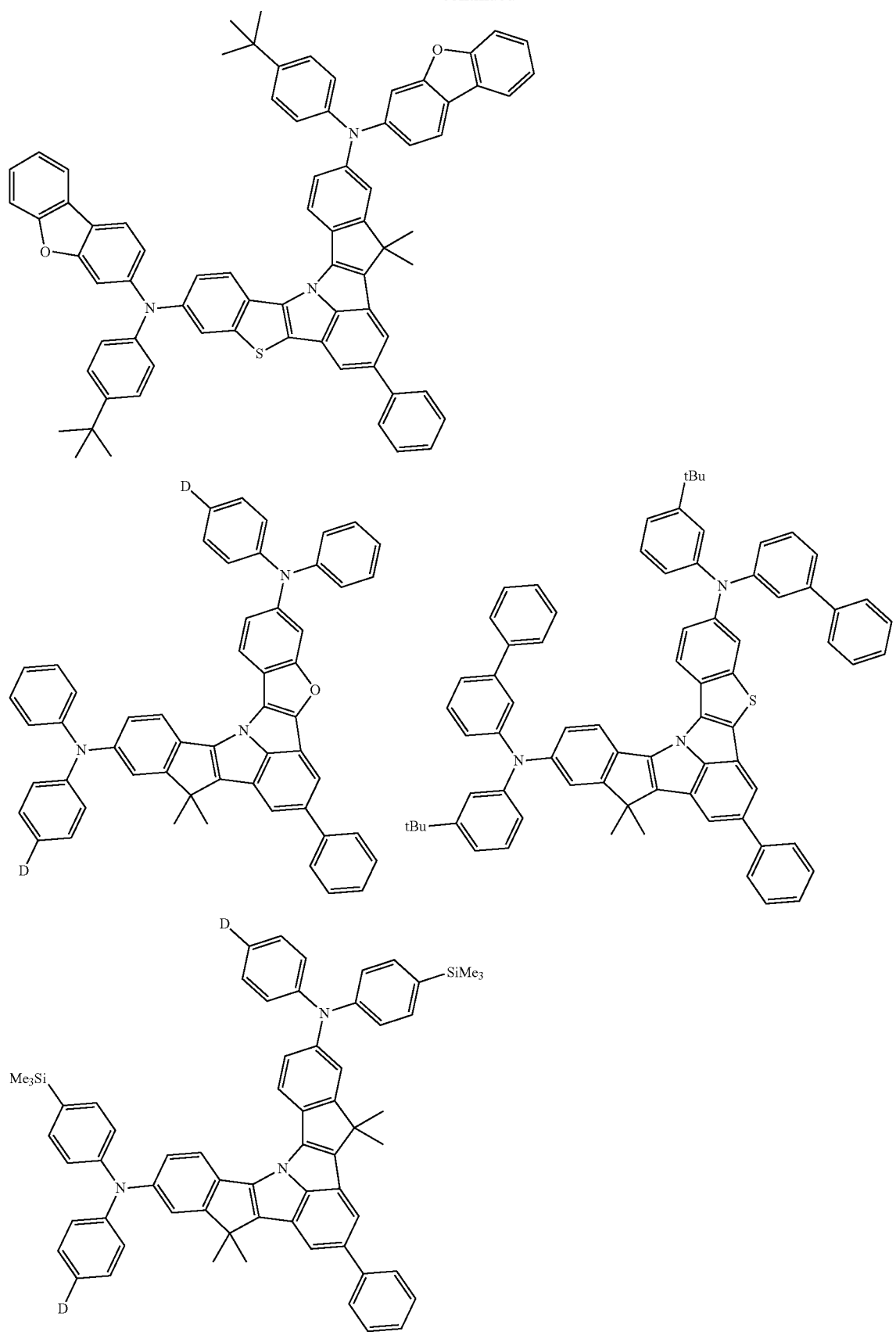

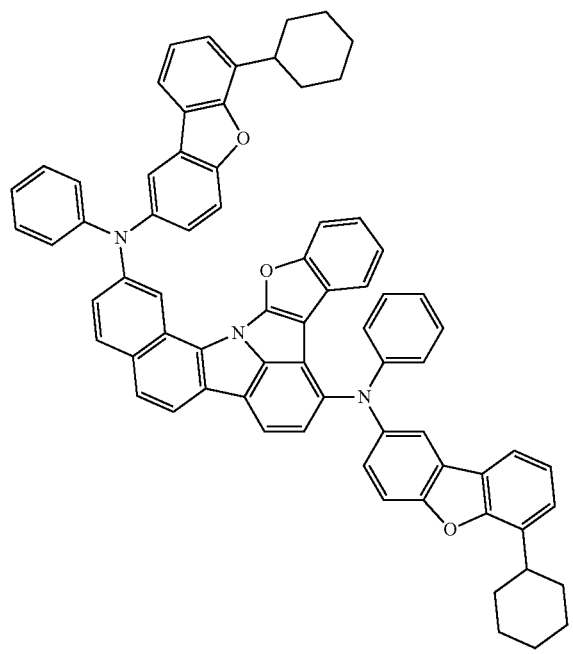
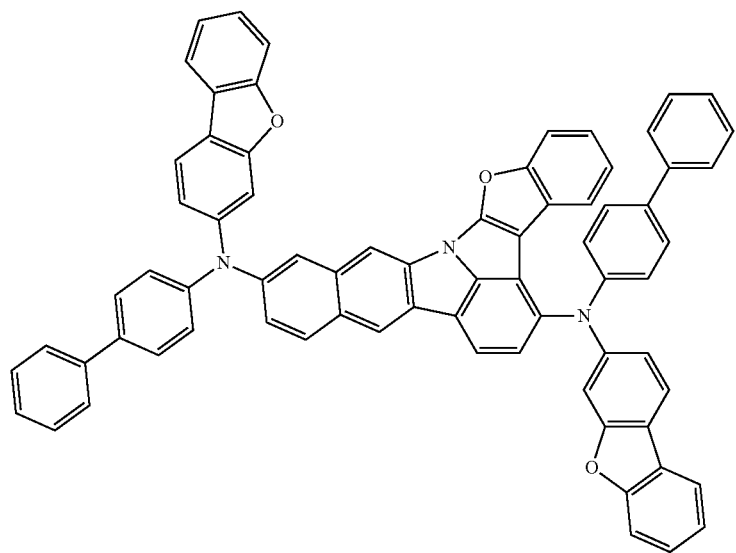

-continued
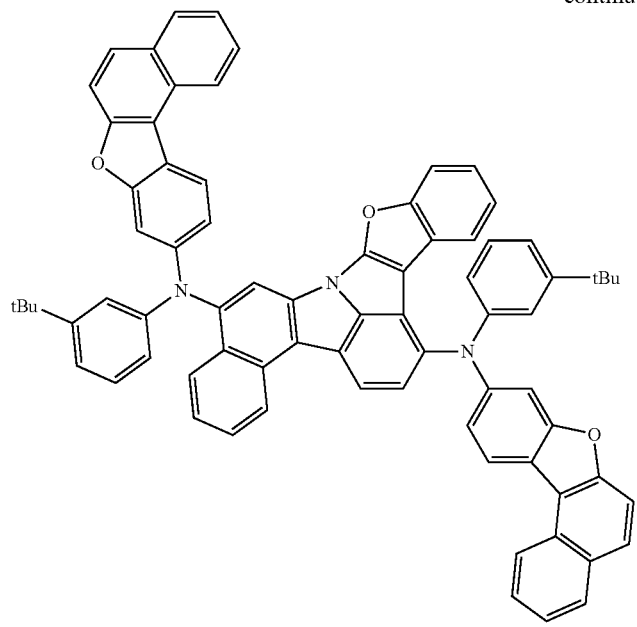
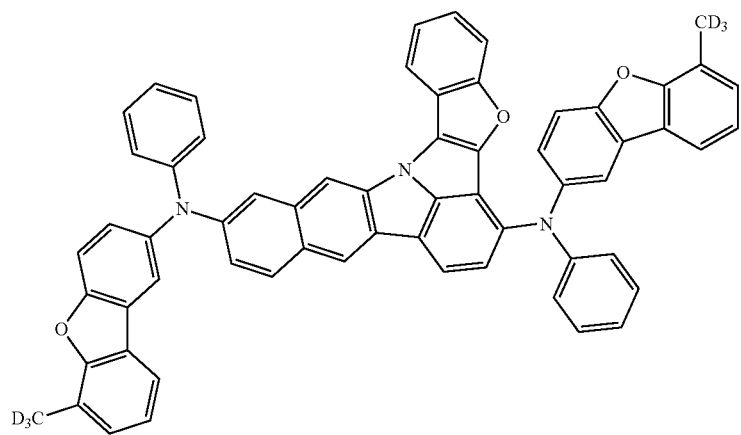
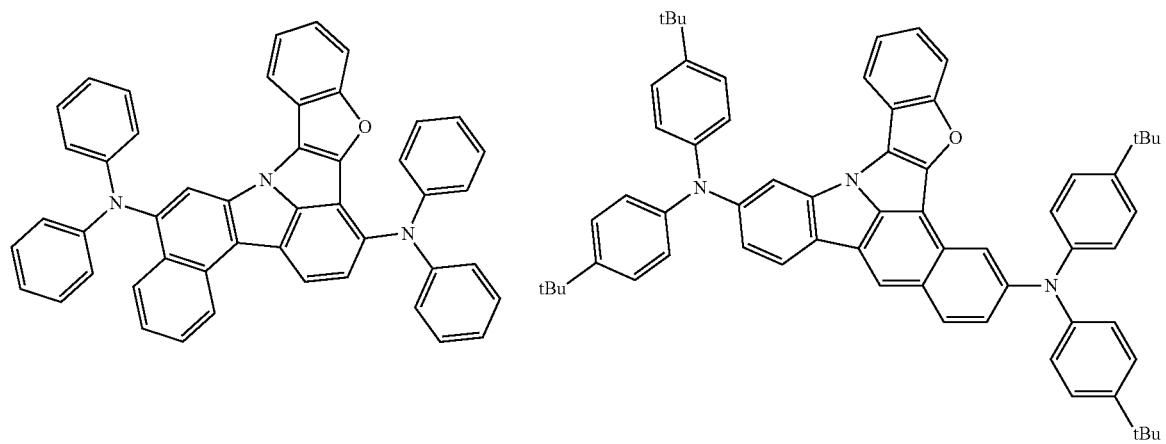

-continued
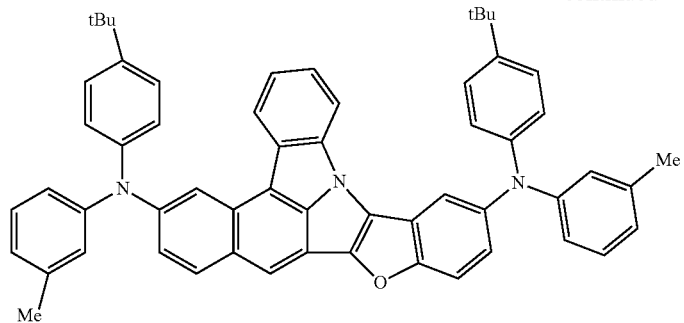
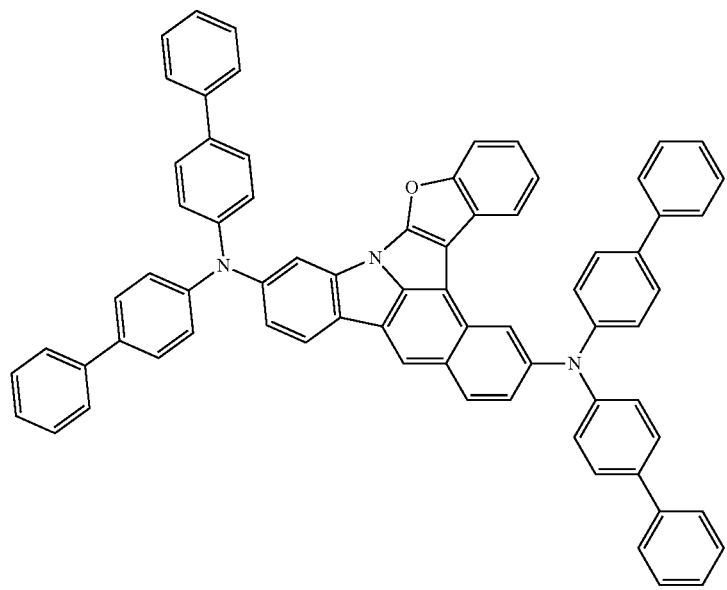
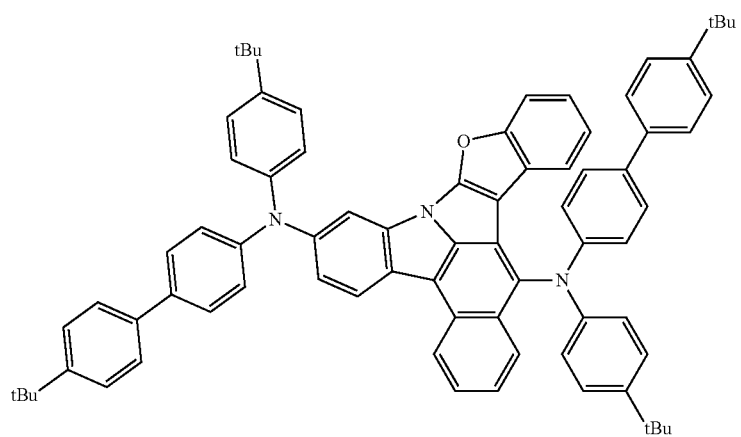

-continued
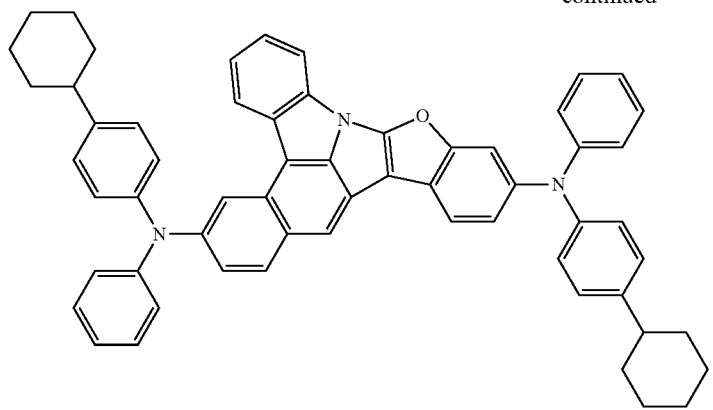
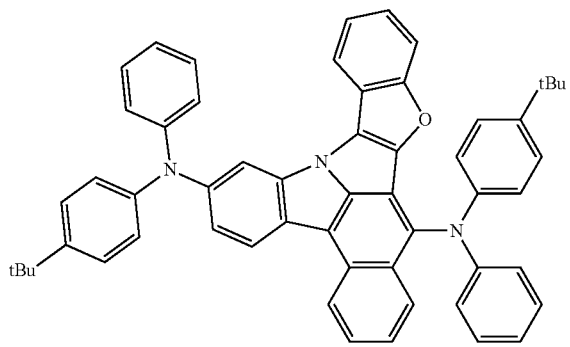
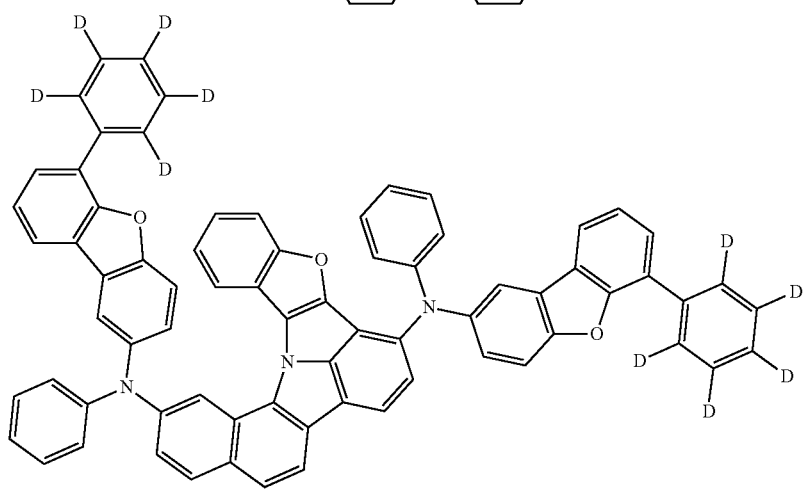
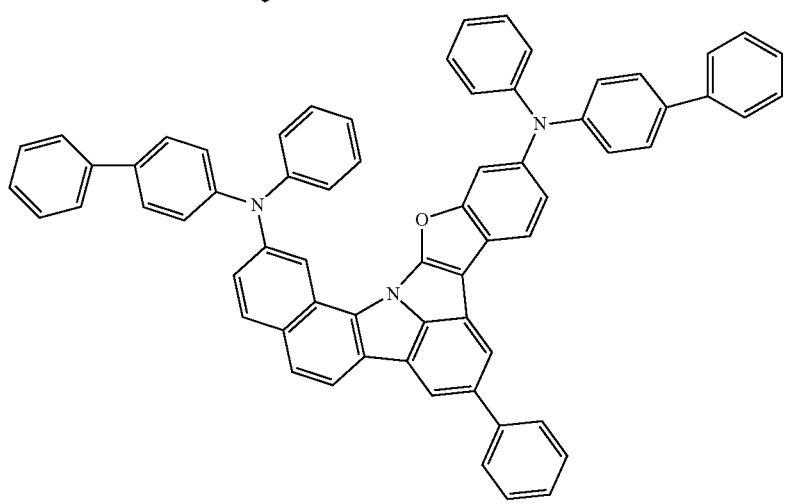

-continued
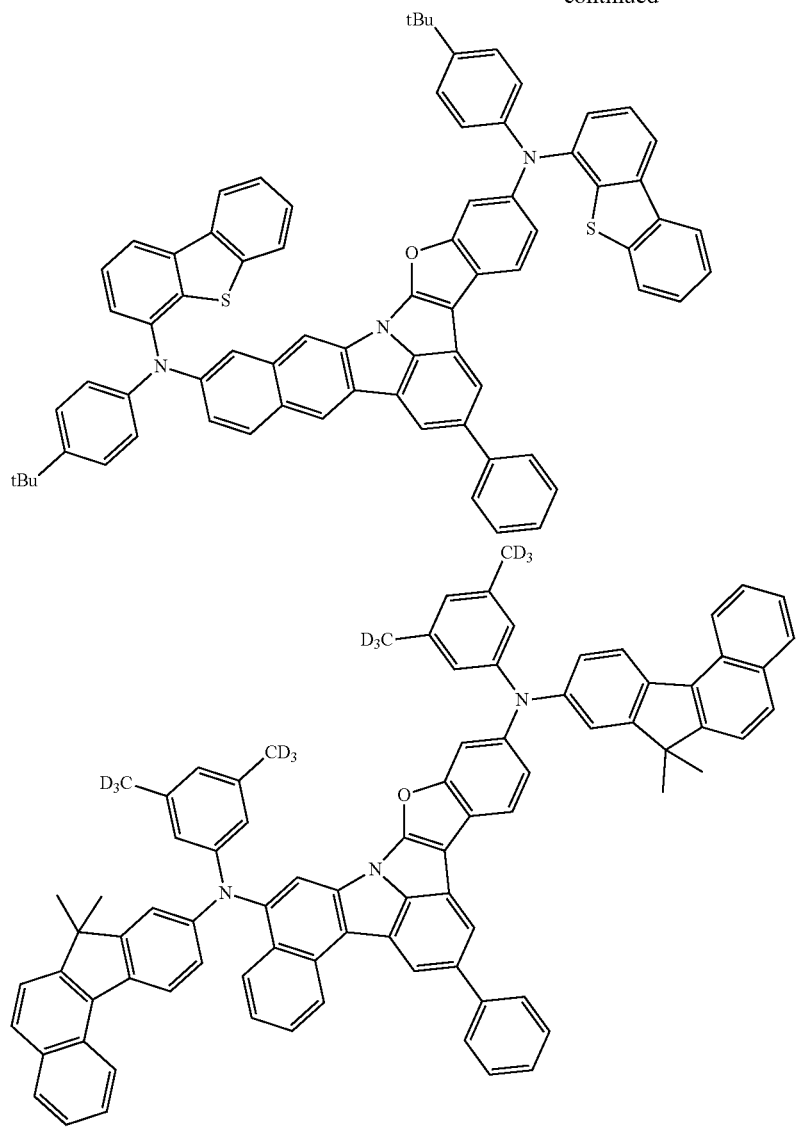
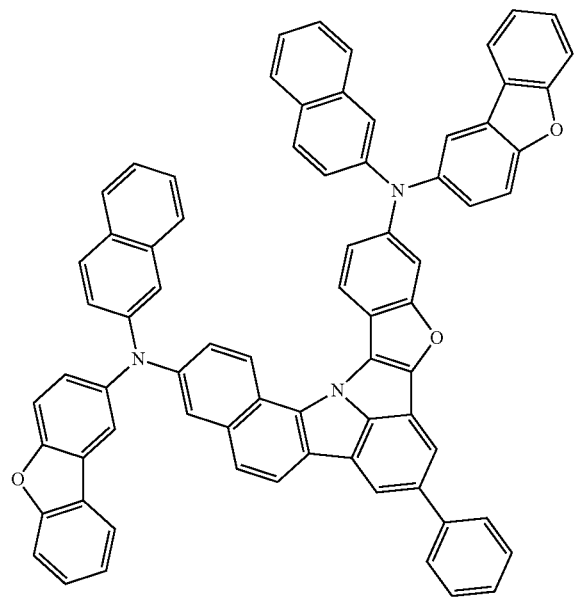
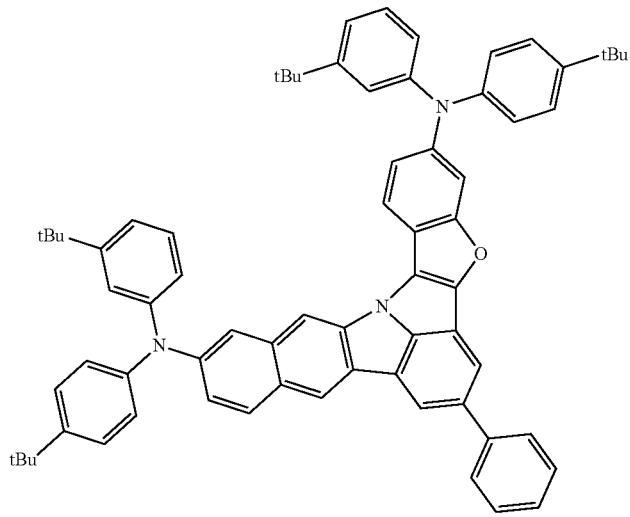

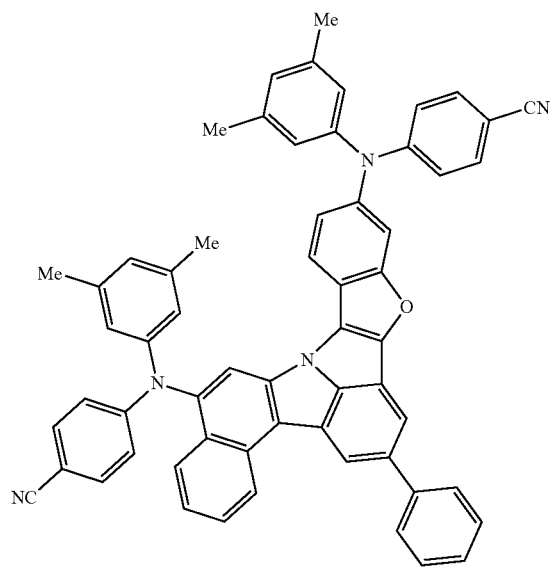
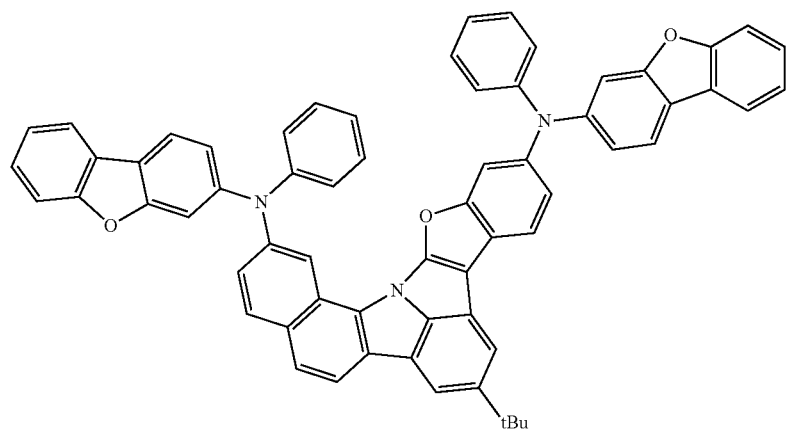
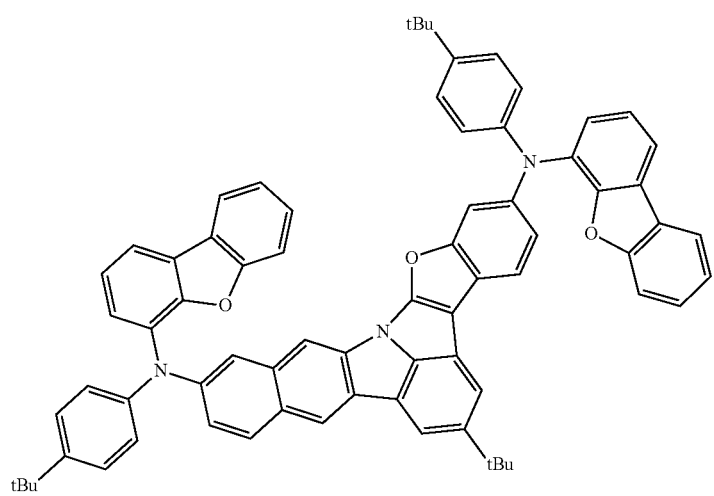

-continued
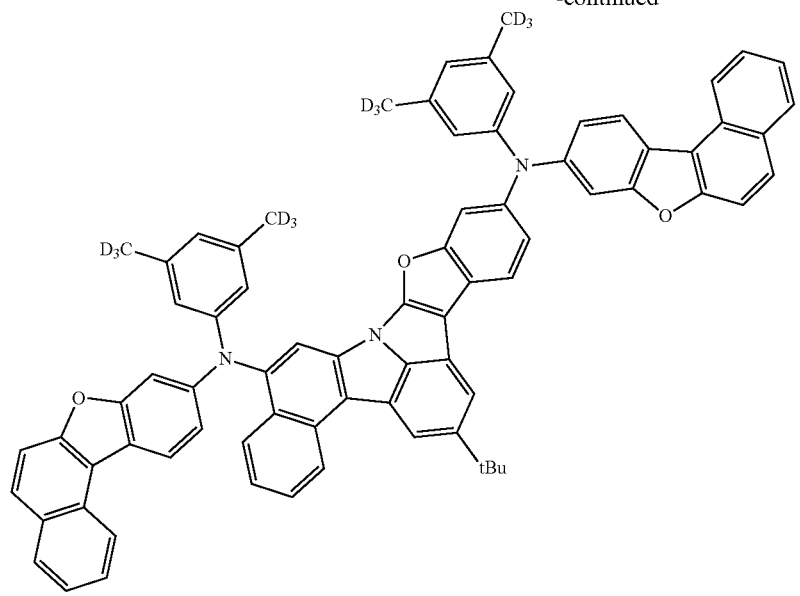
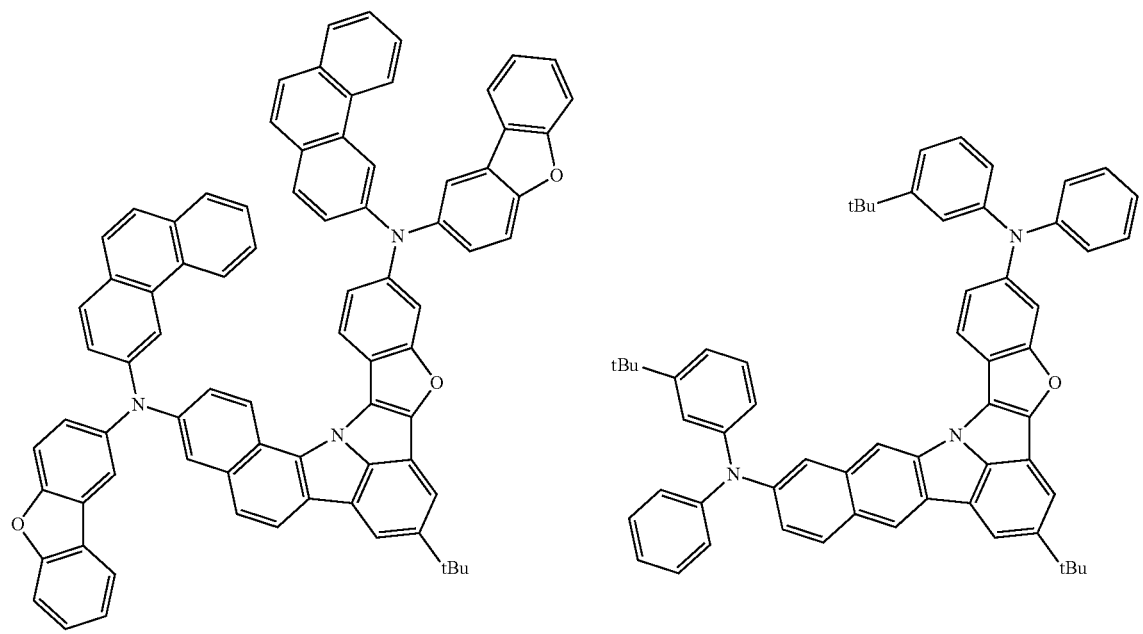

107
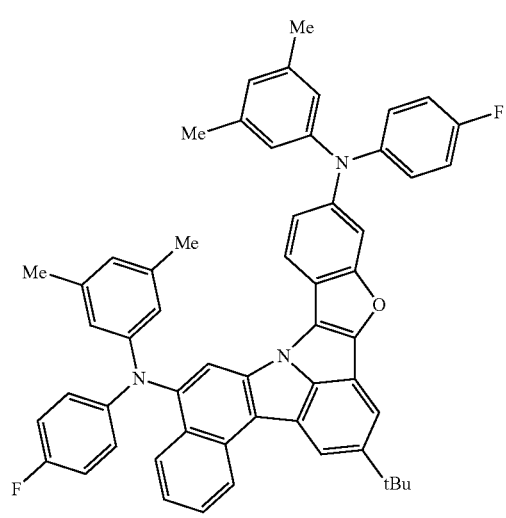
108
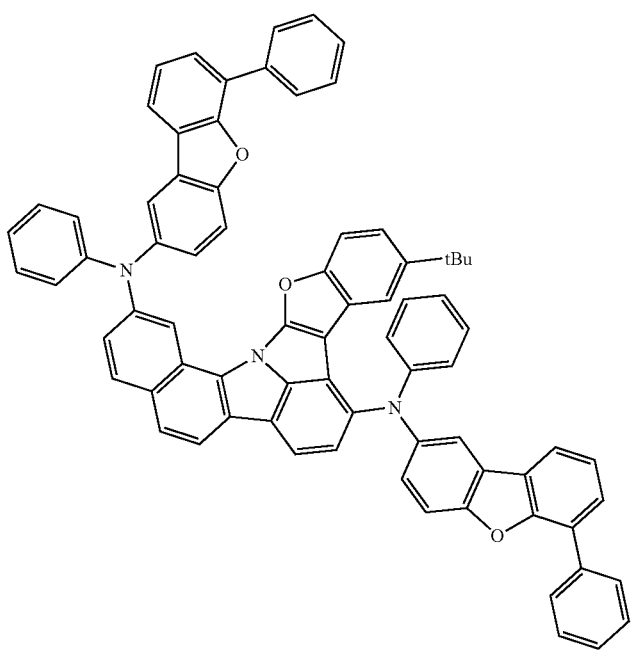
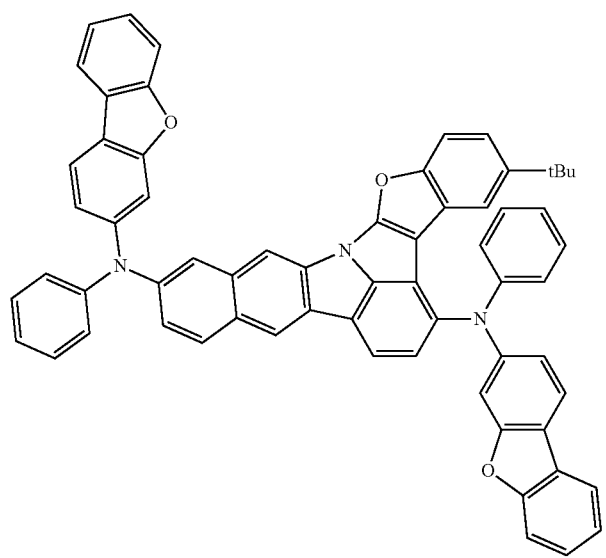

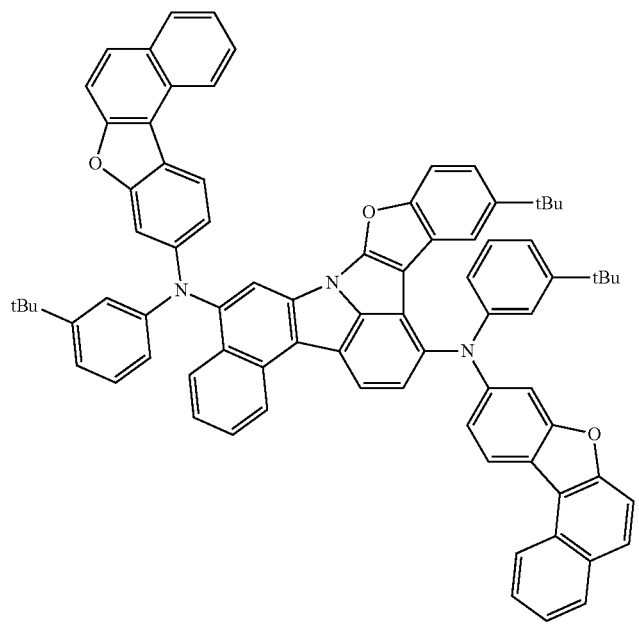
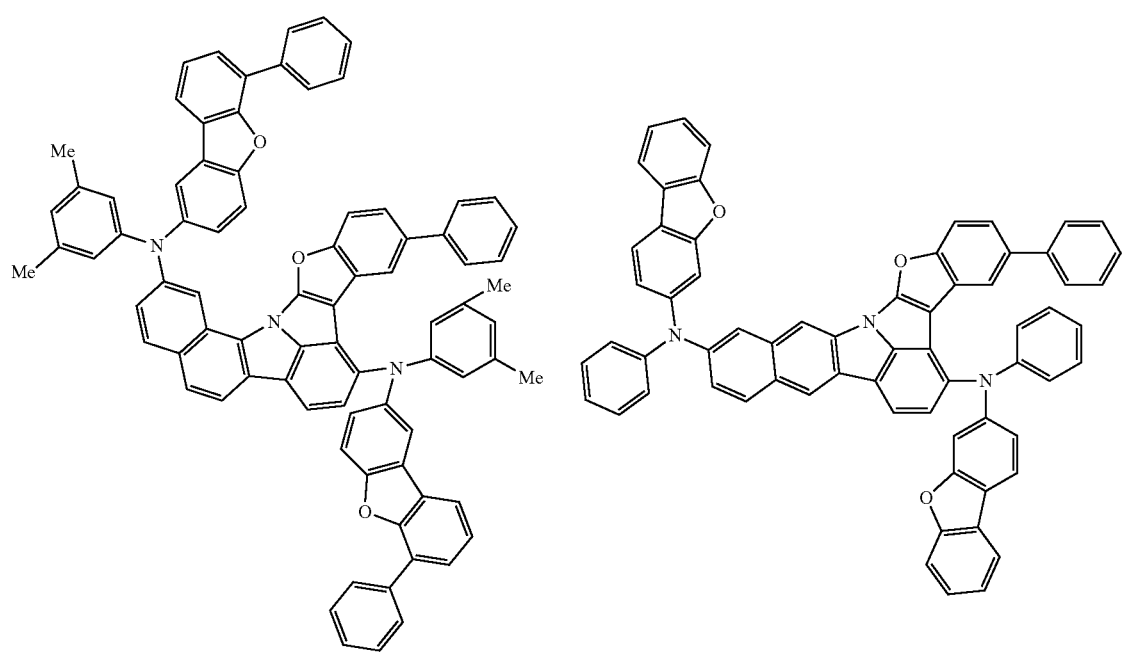

-continued
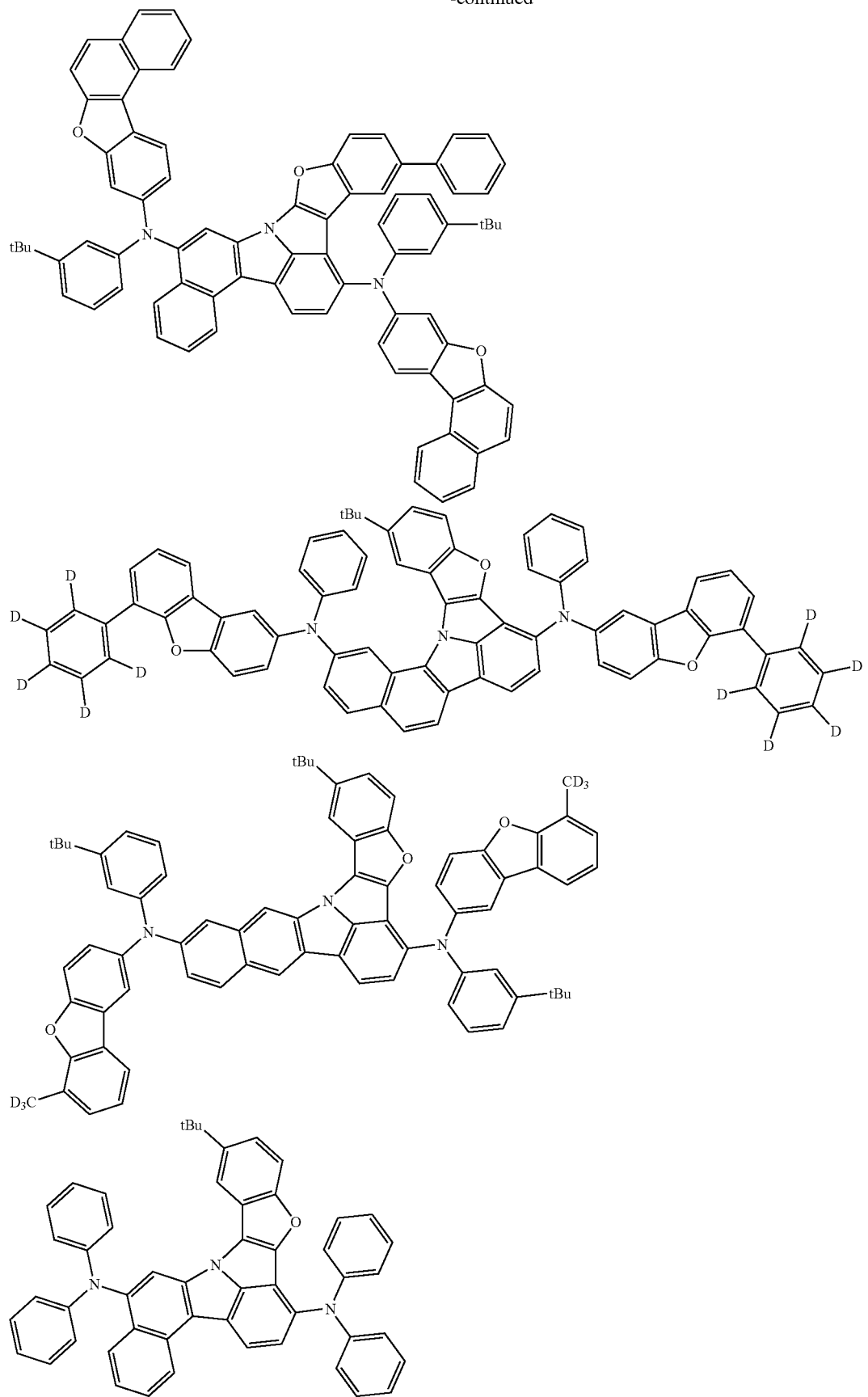

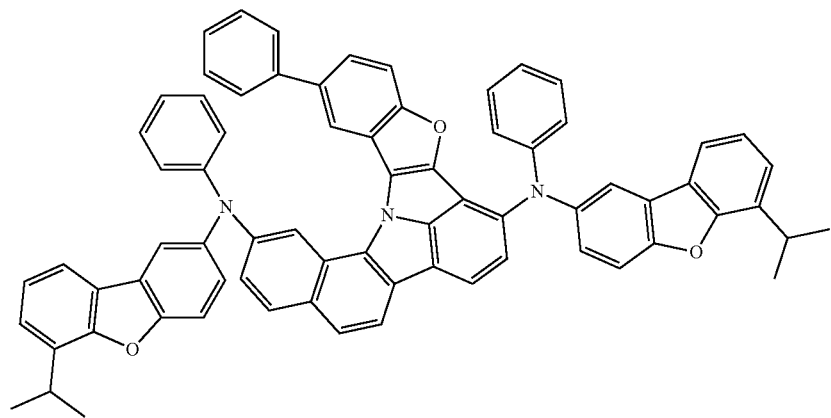
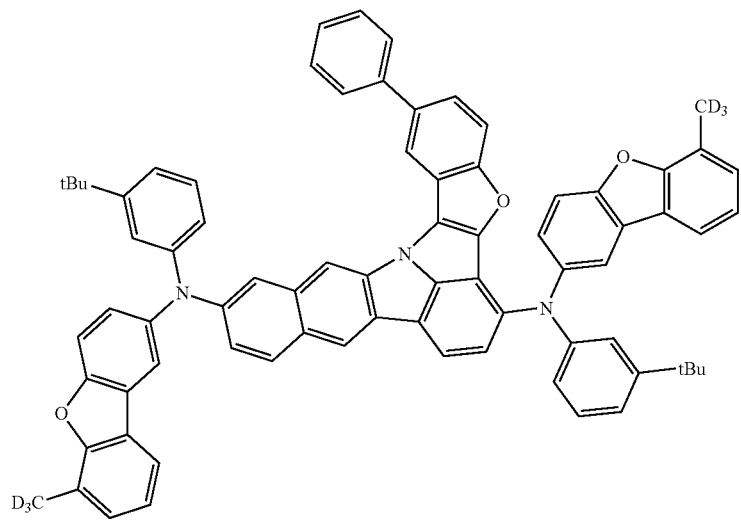
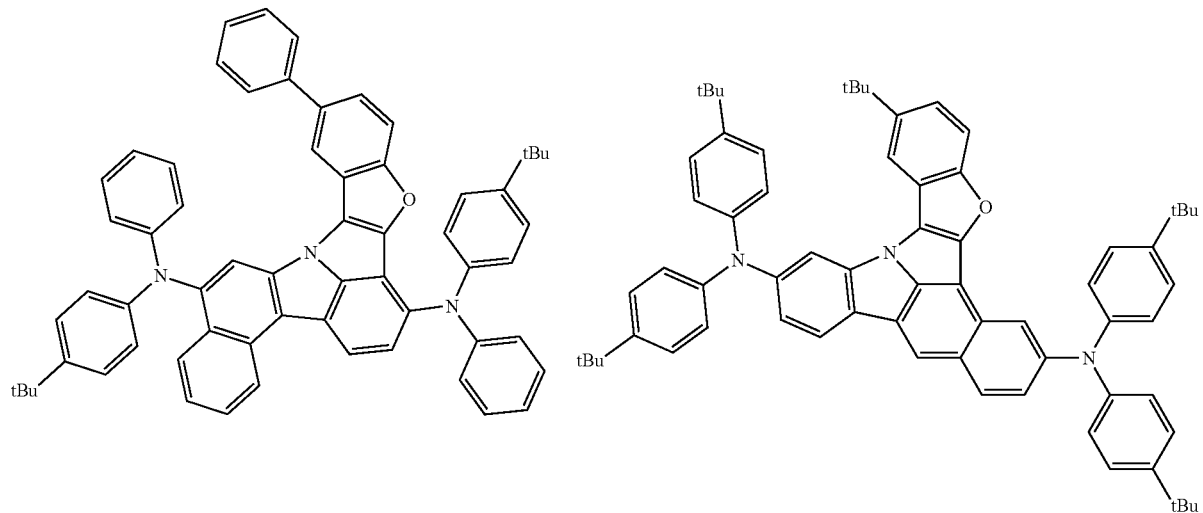

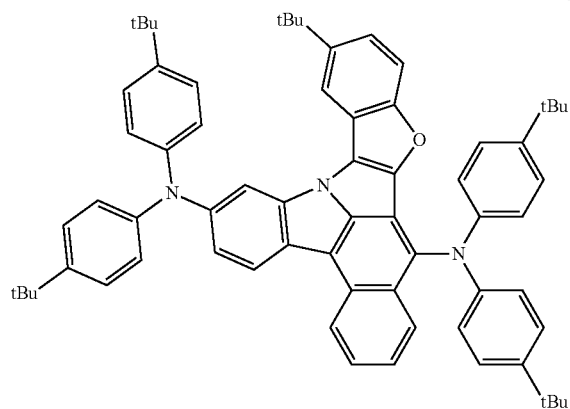
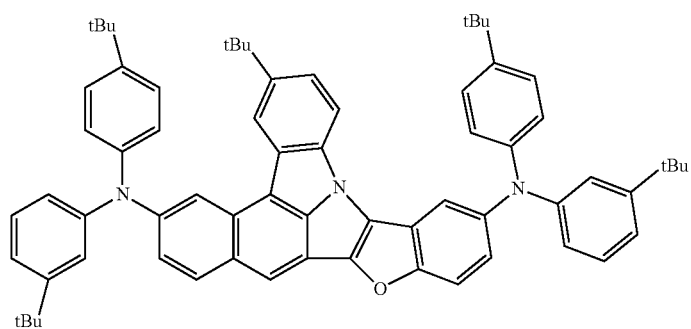
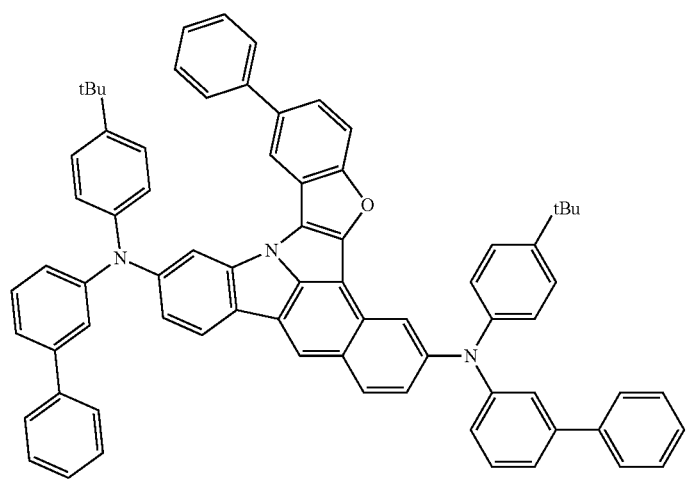
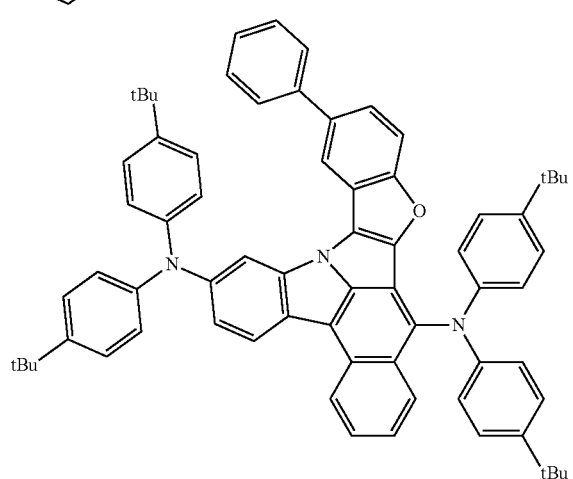

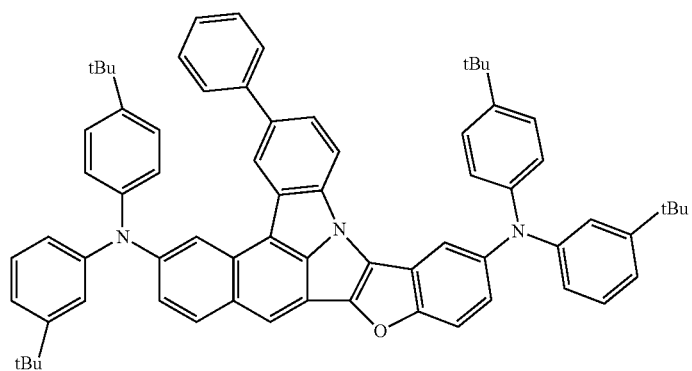
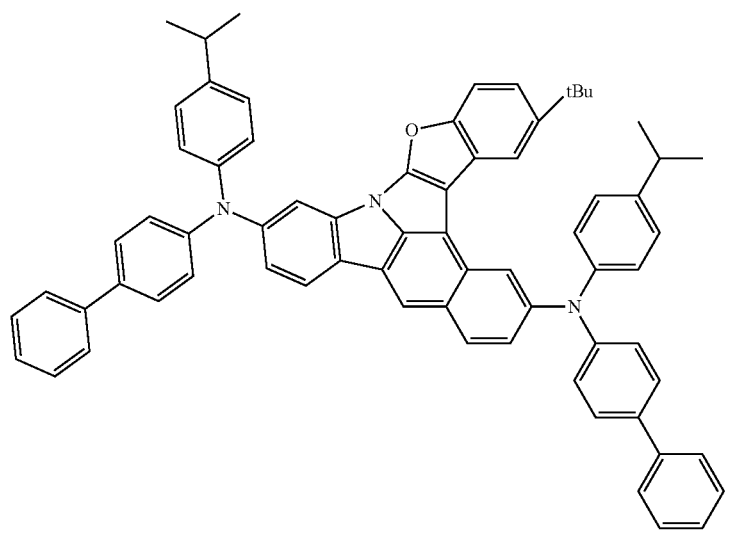
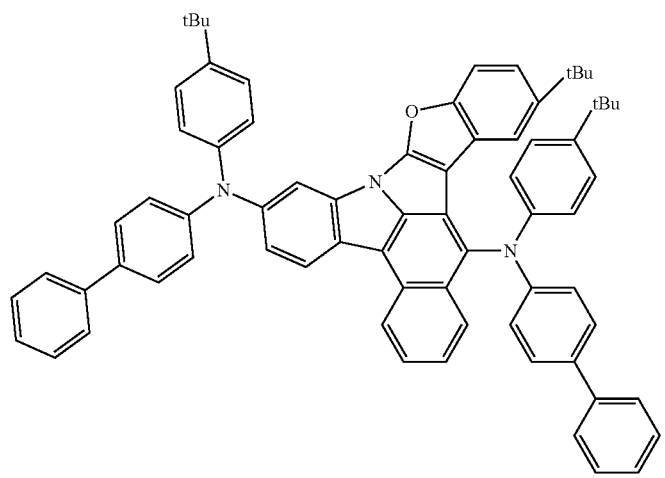

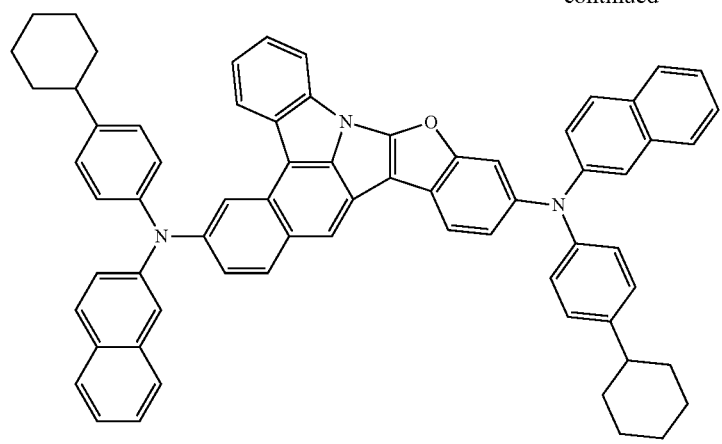
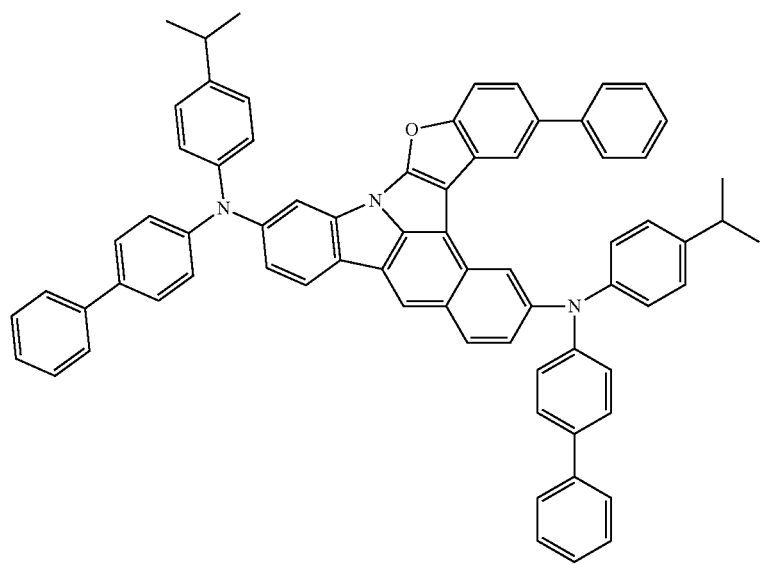
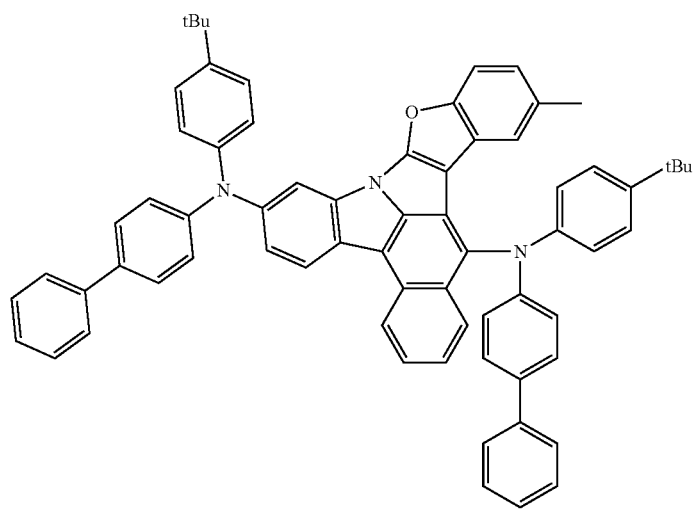

-continued
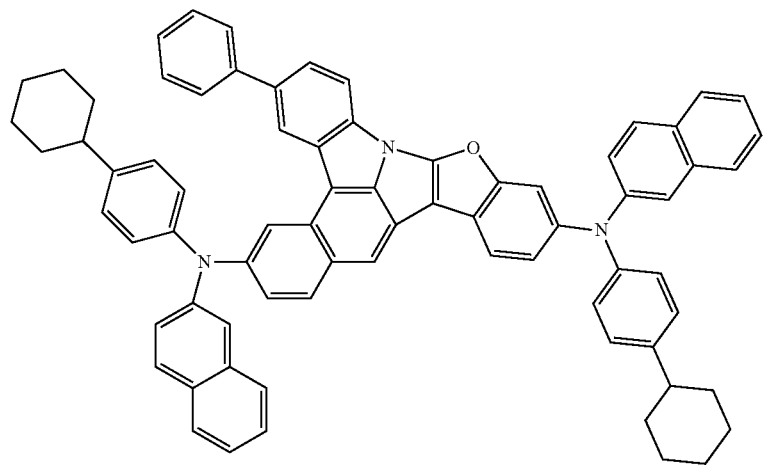
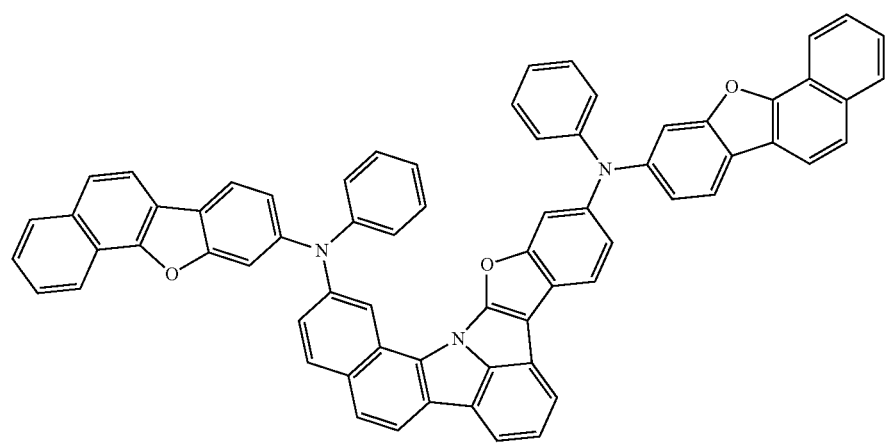
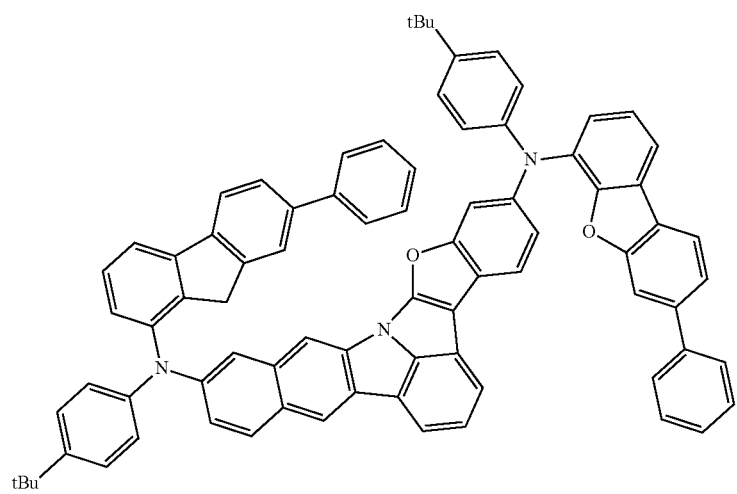

-continued
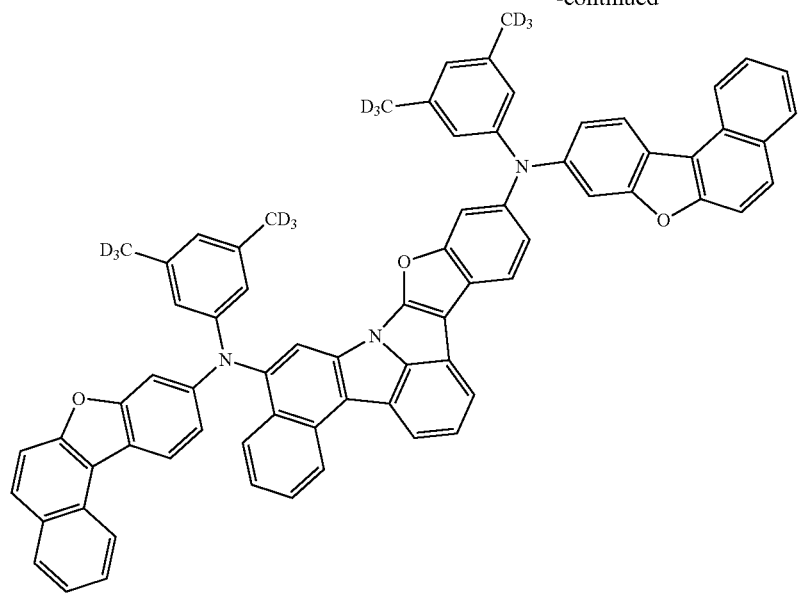
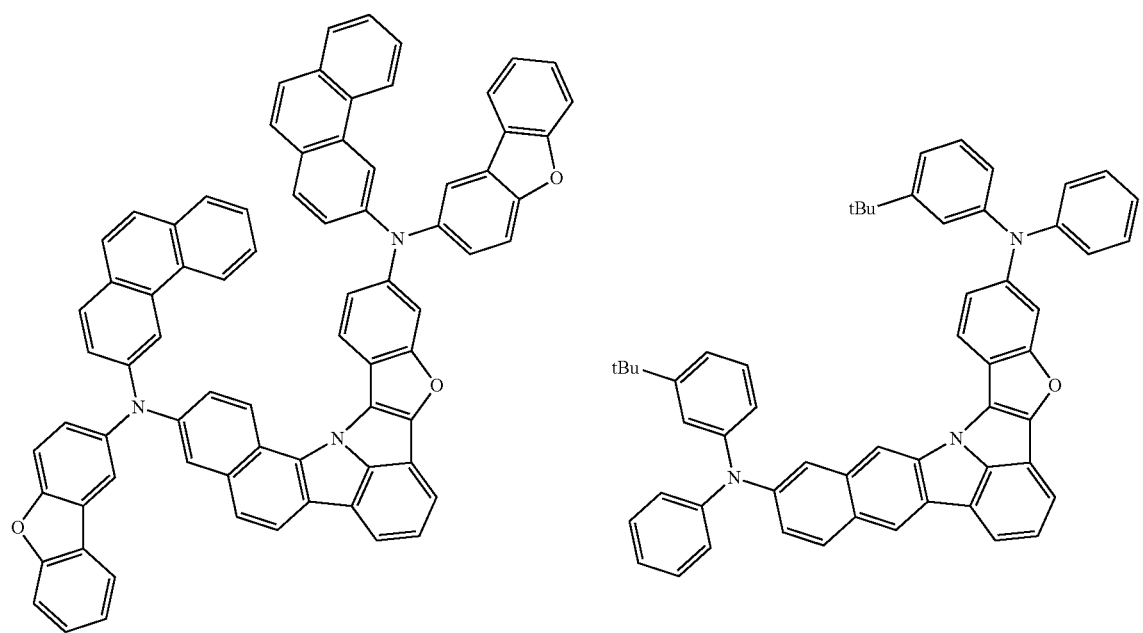

-continued
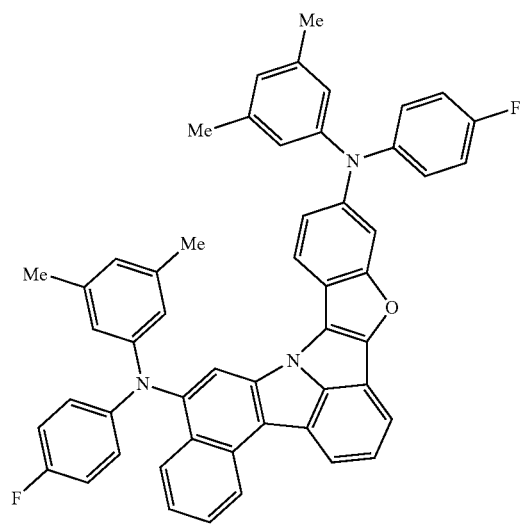
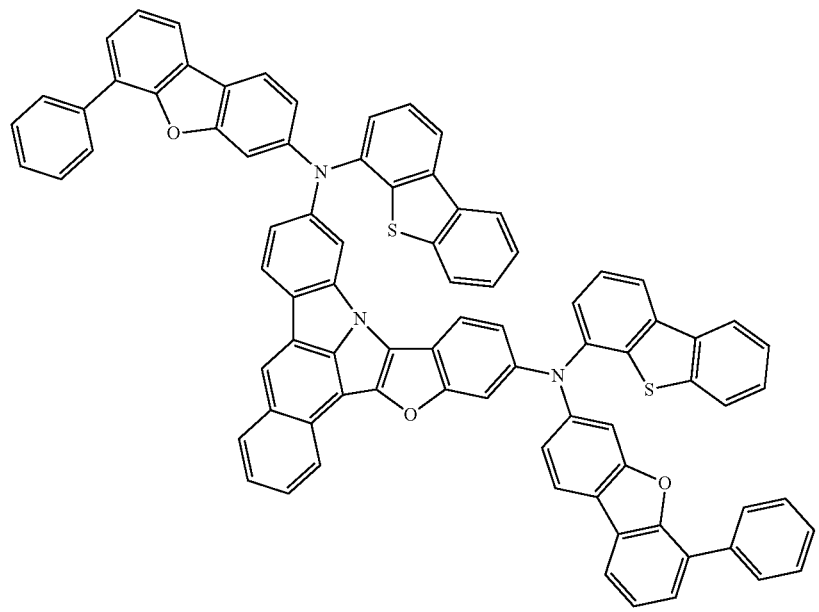
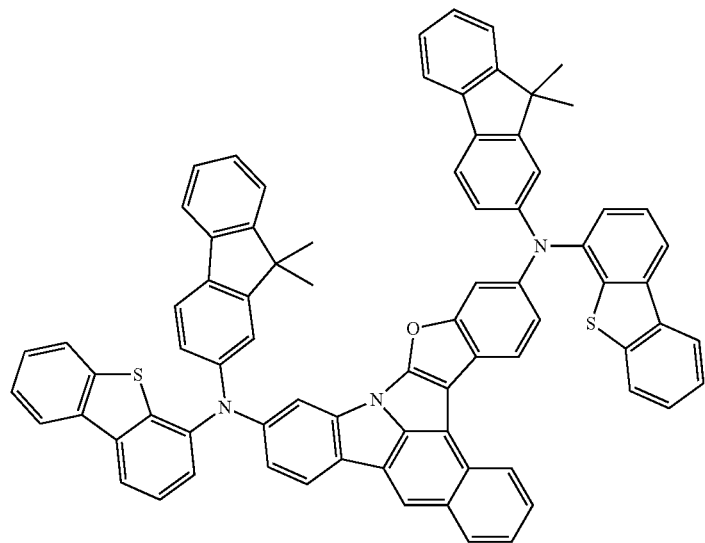

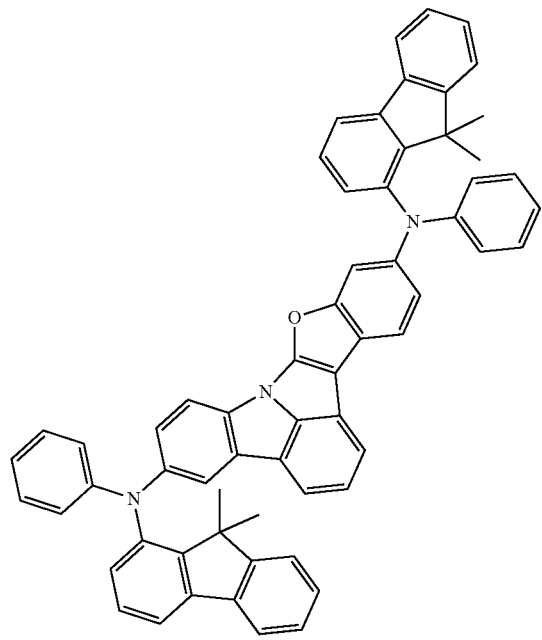 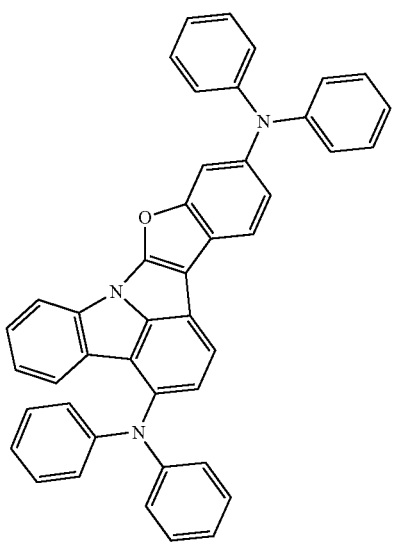
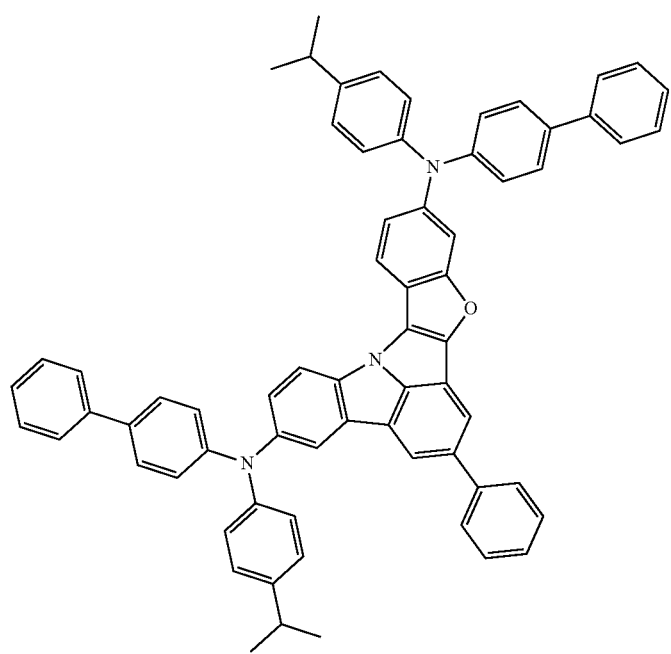

129
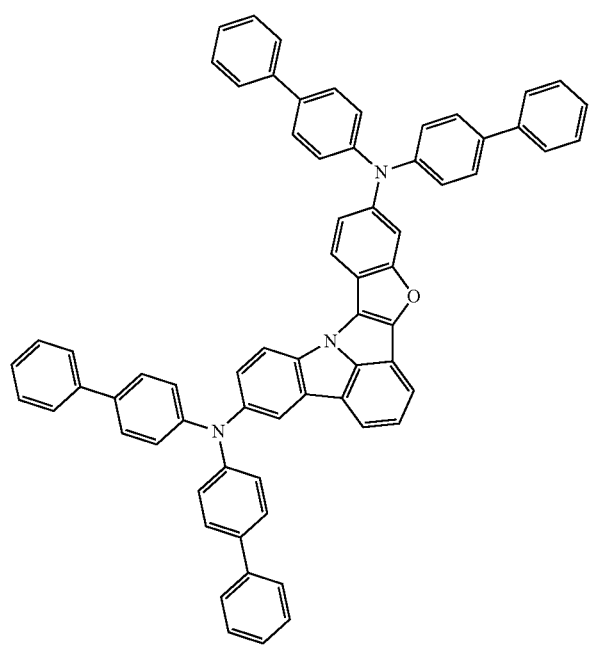
130
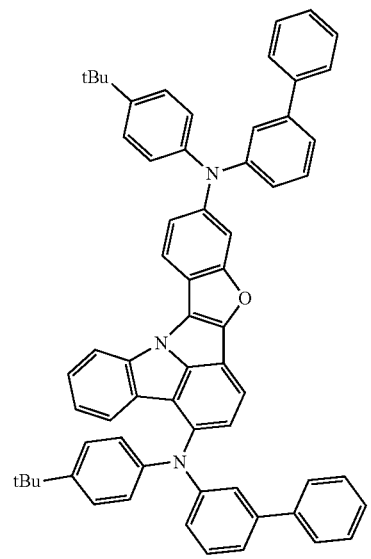
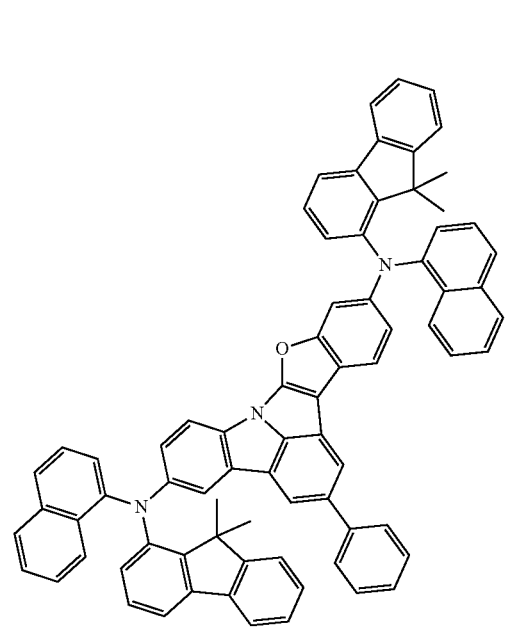
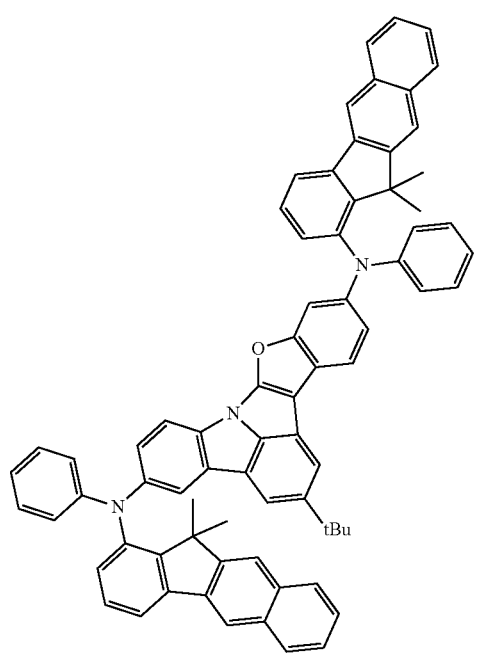

-continued
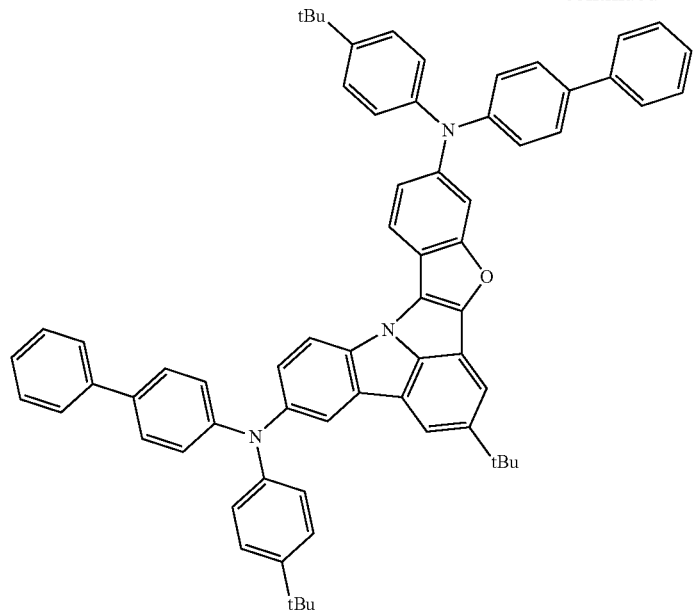
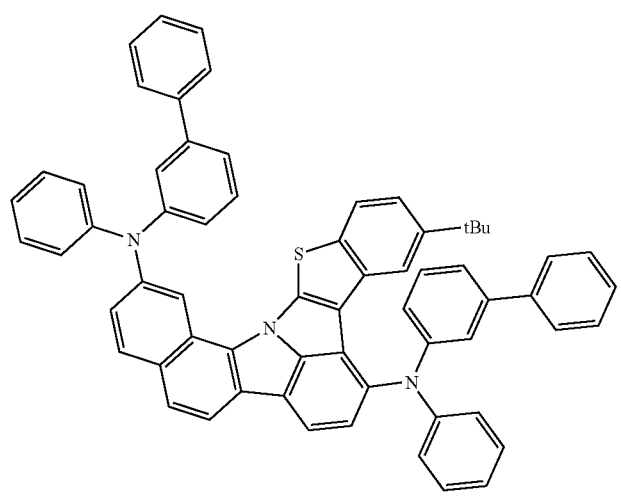
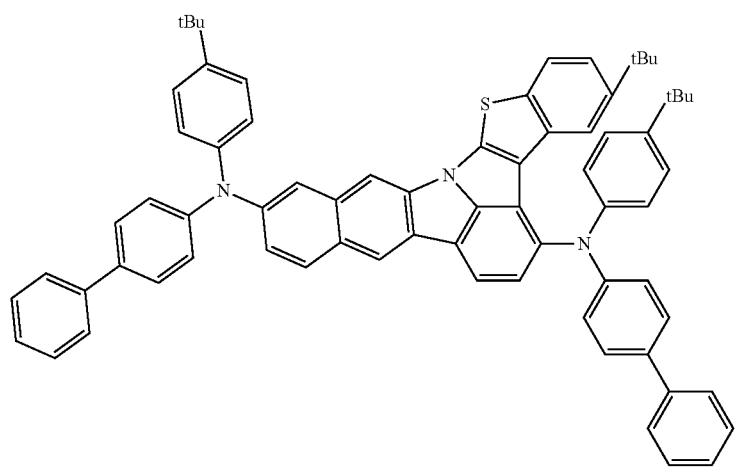

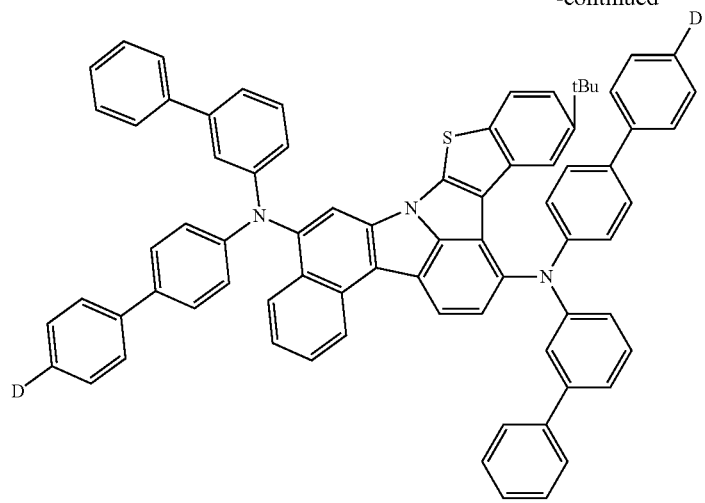
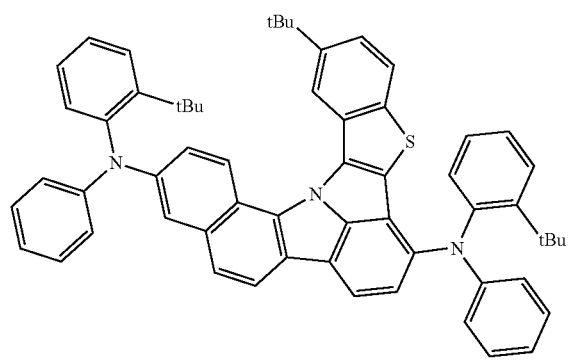
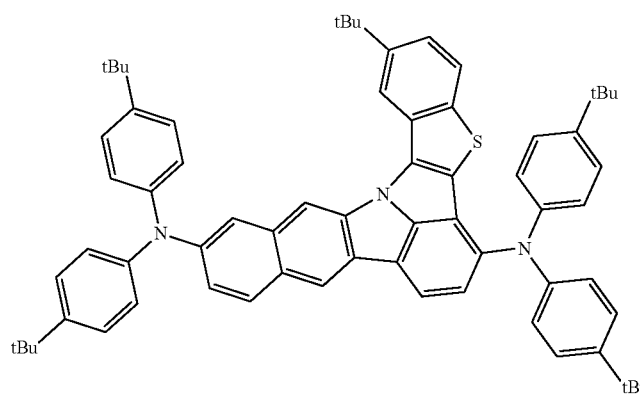
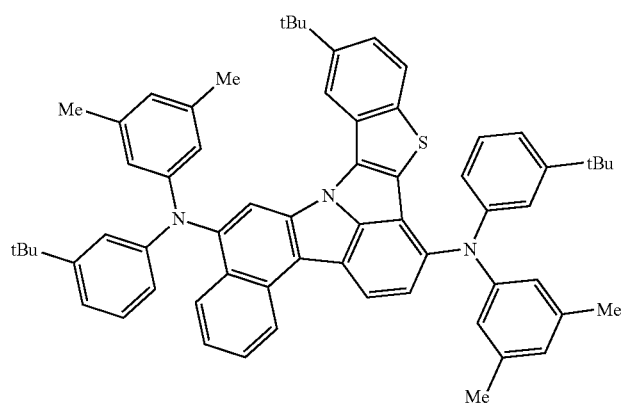

-continued
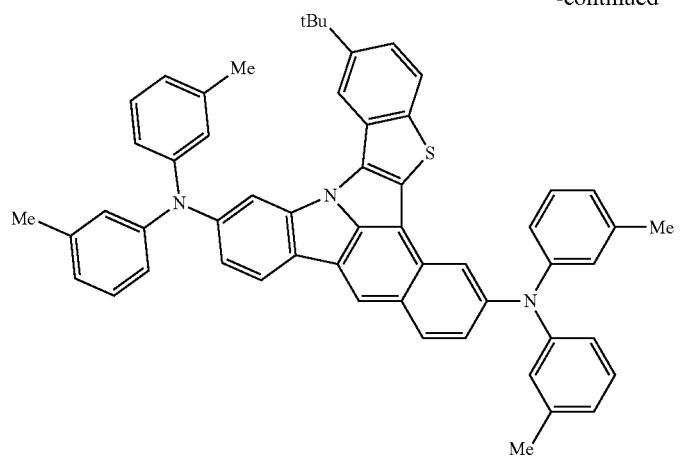
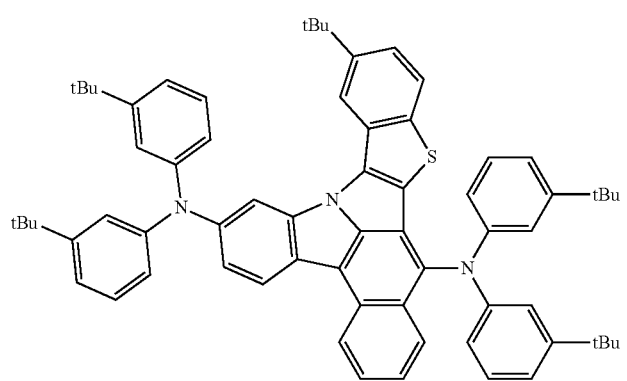
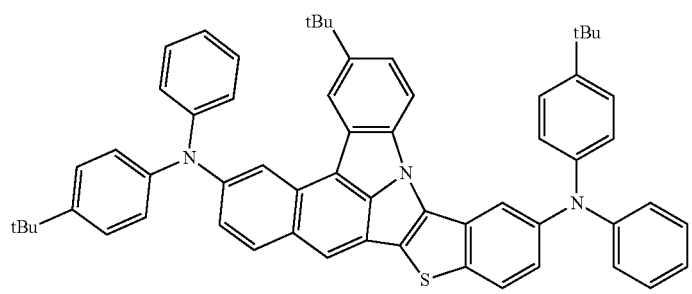
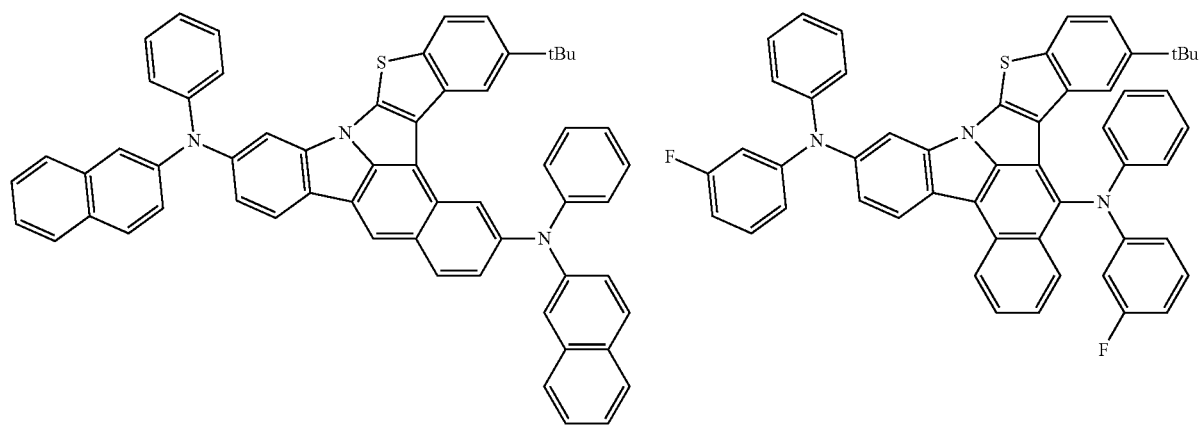

-continued
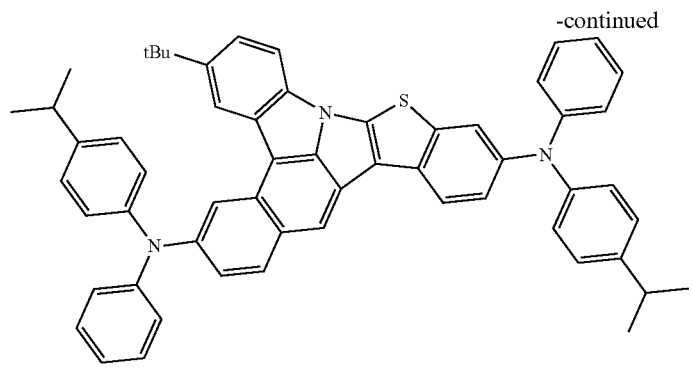
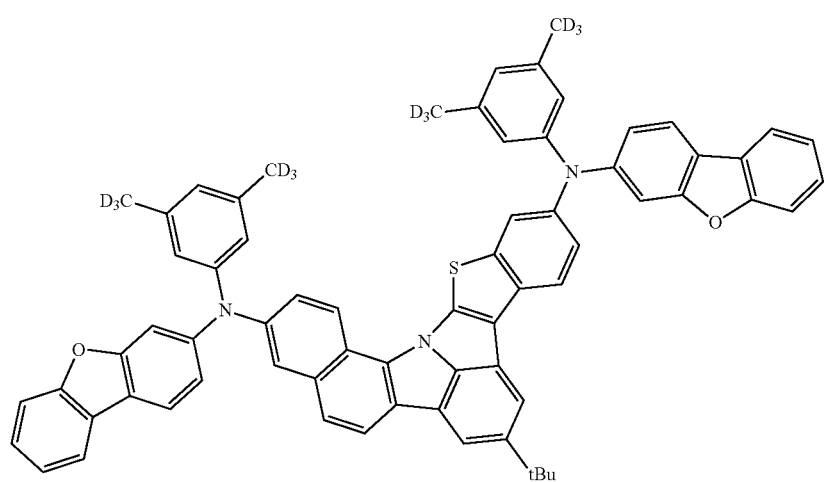
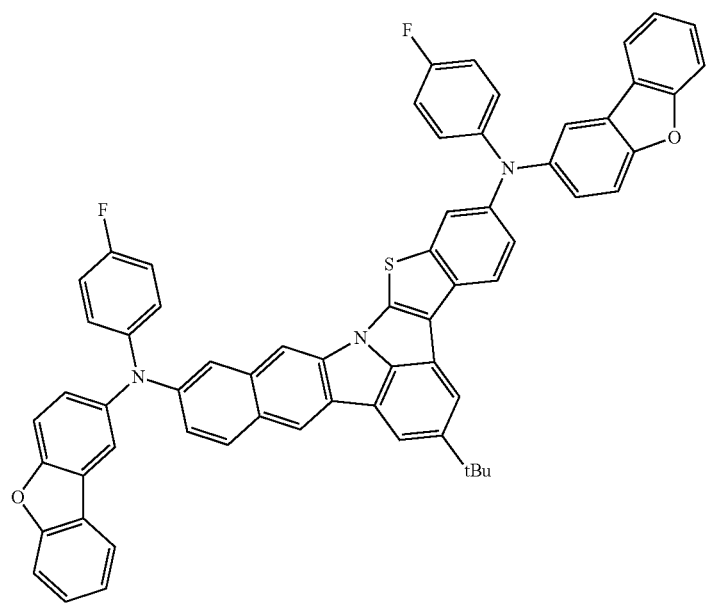

-continued
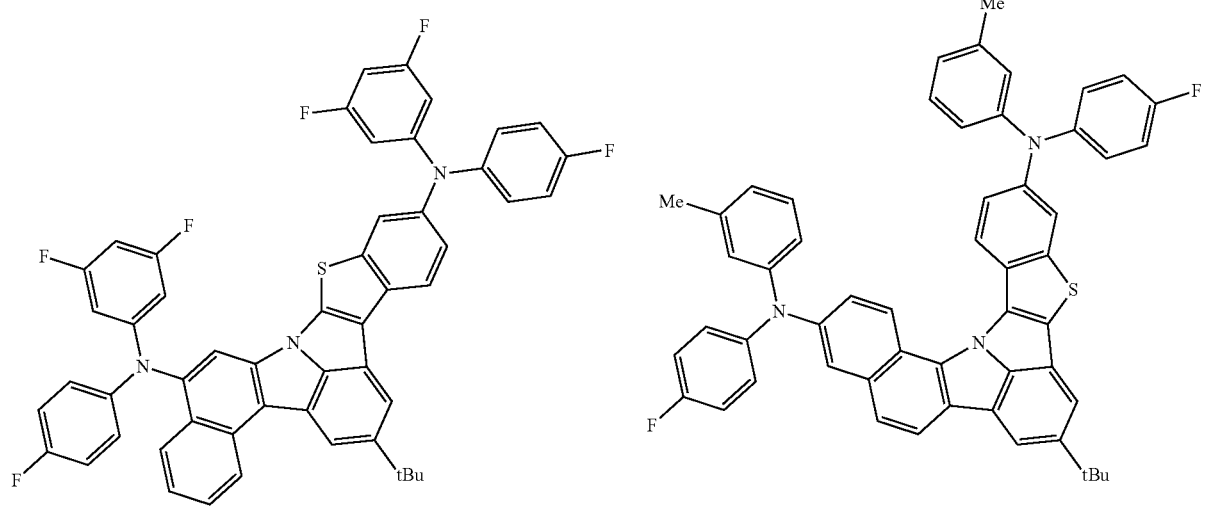
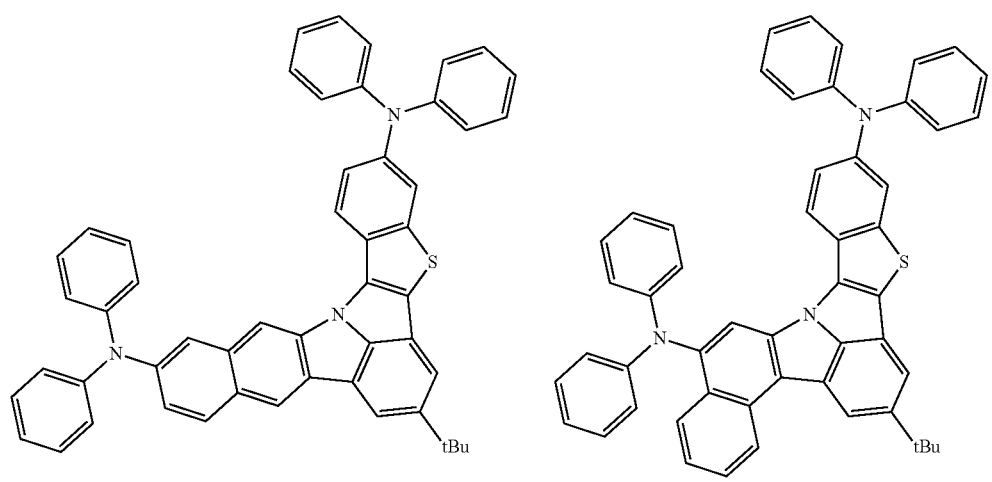
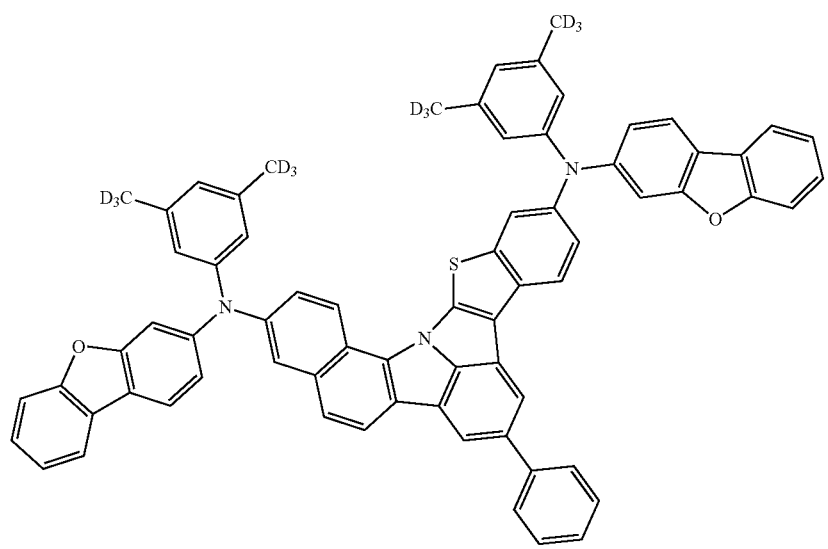

-continued
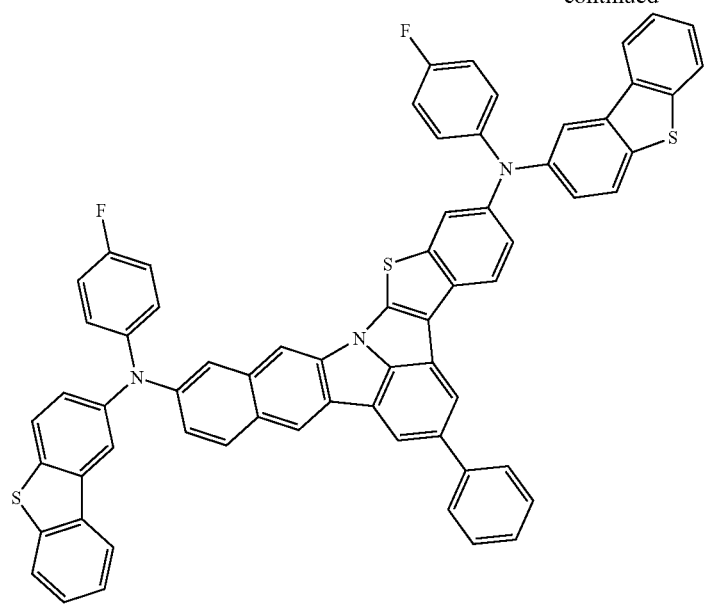
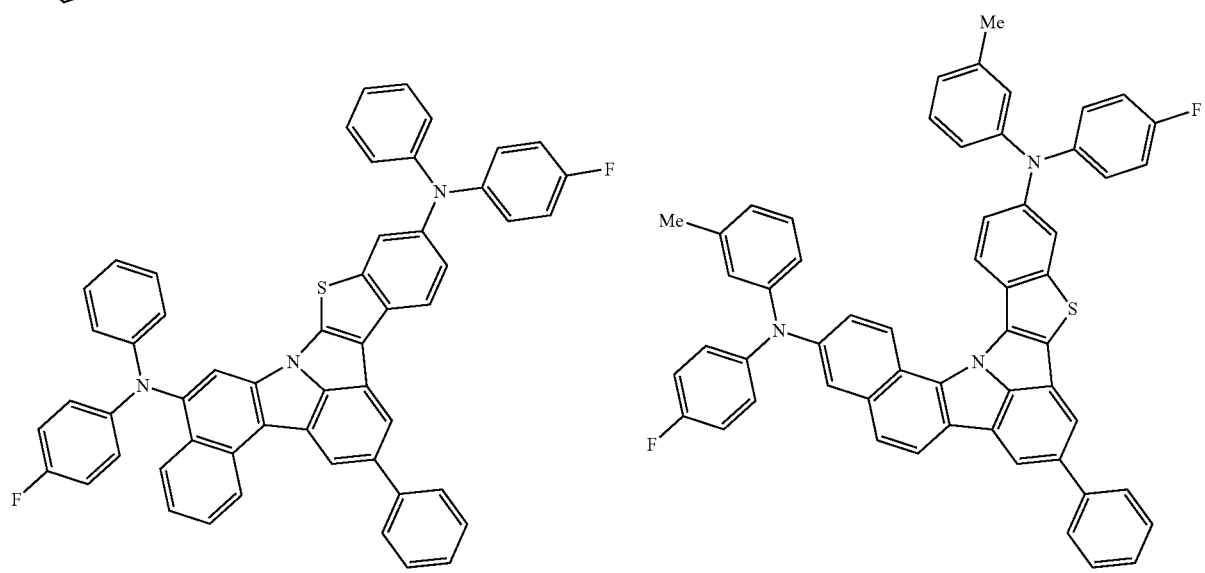
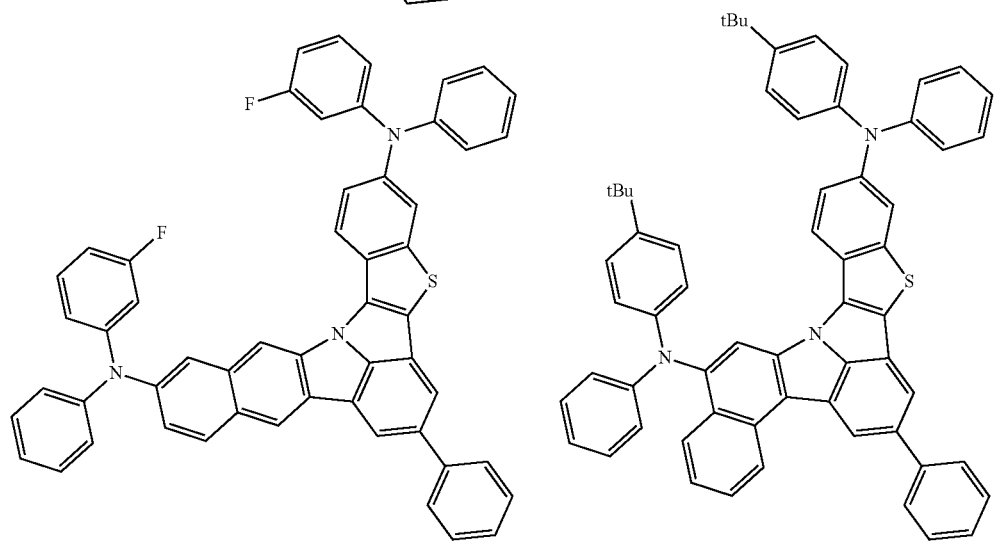

143
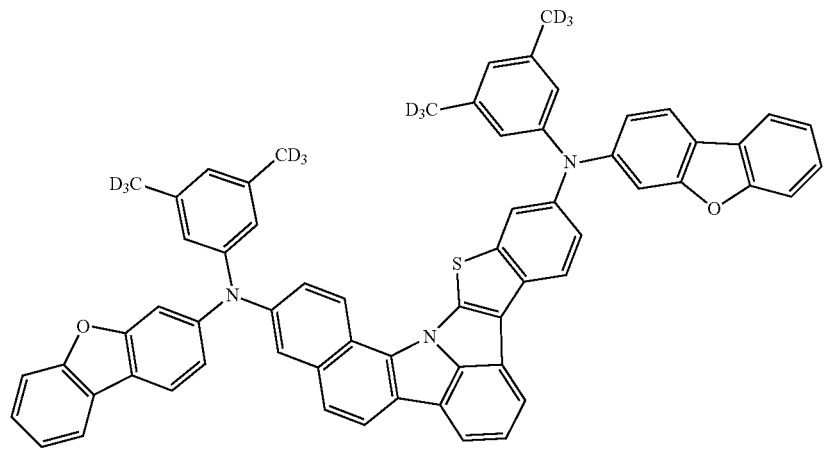
144
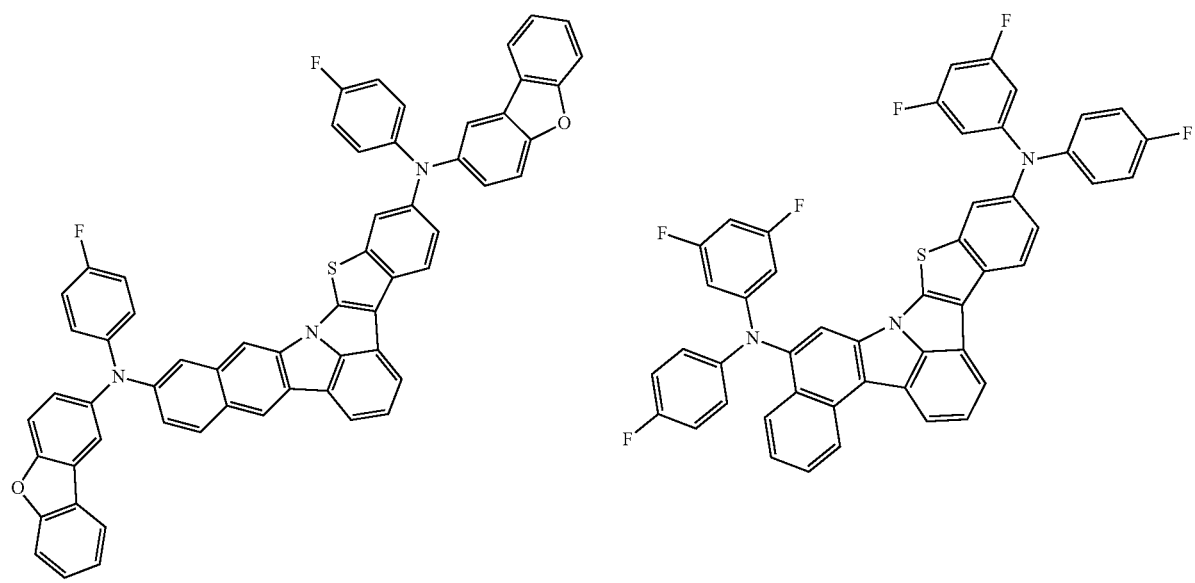
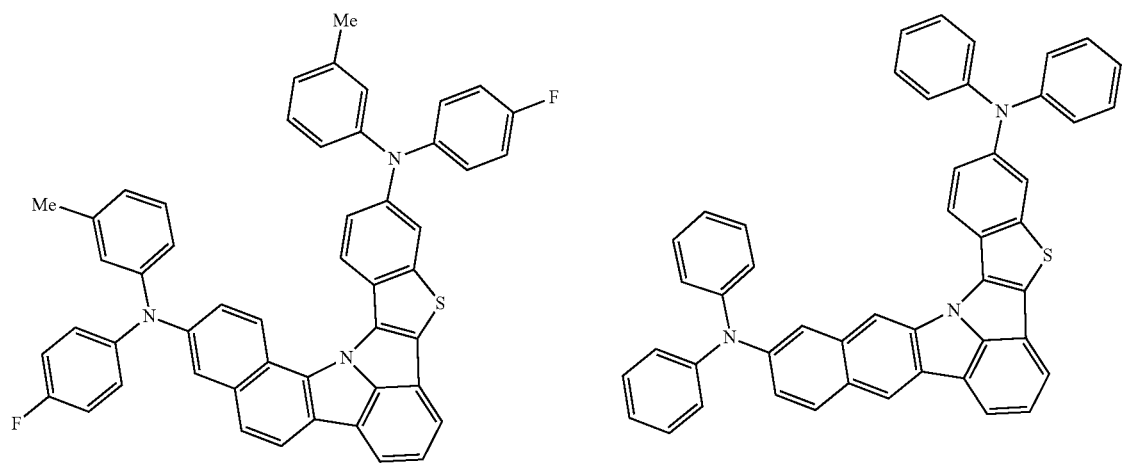

145
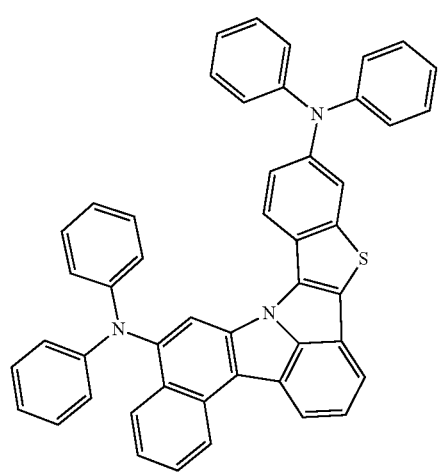
146
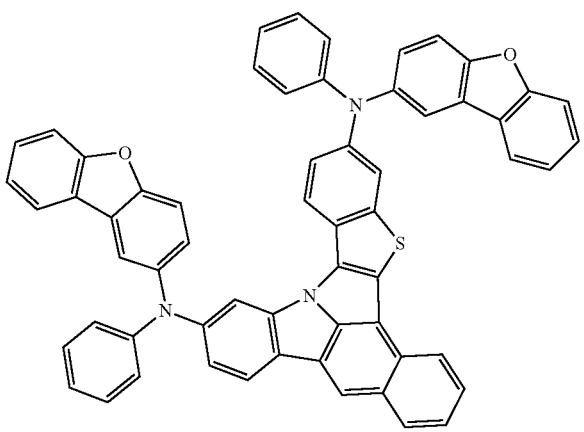
-continued
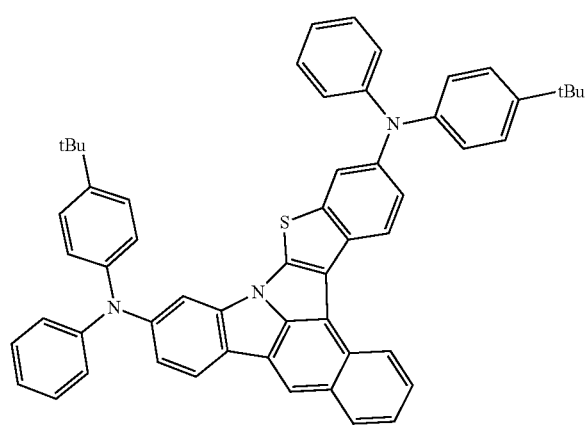
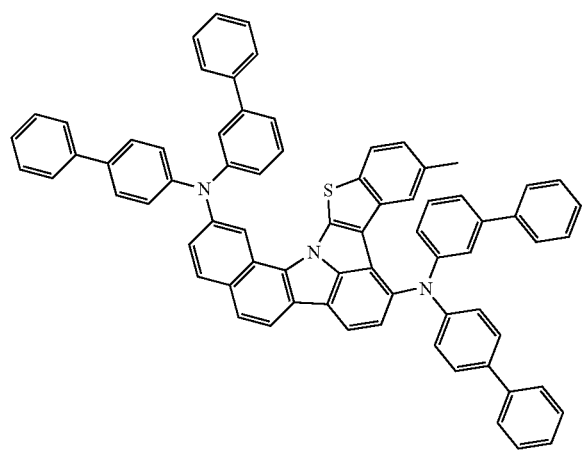
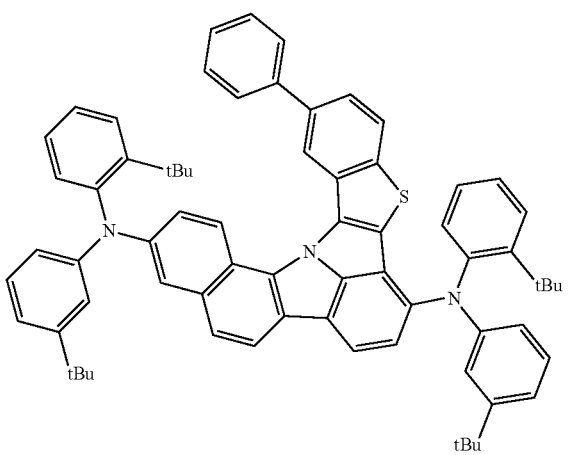

147 148
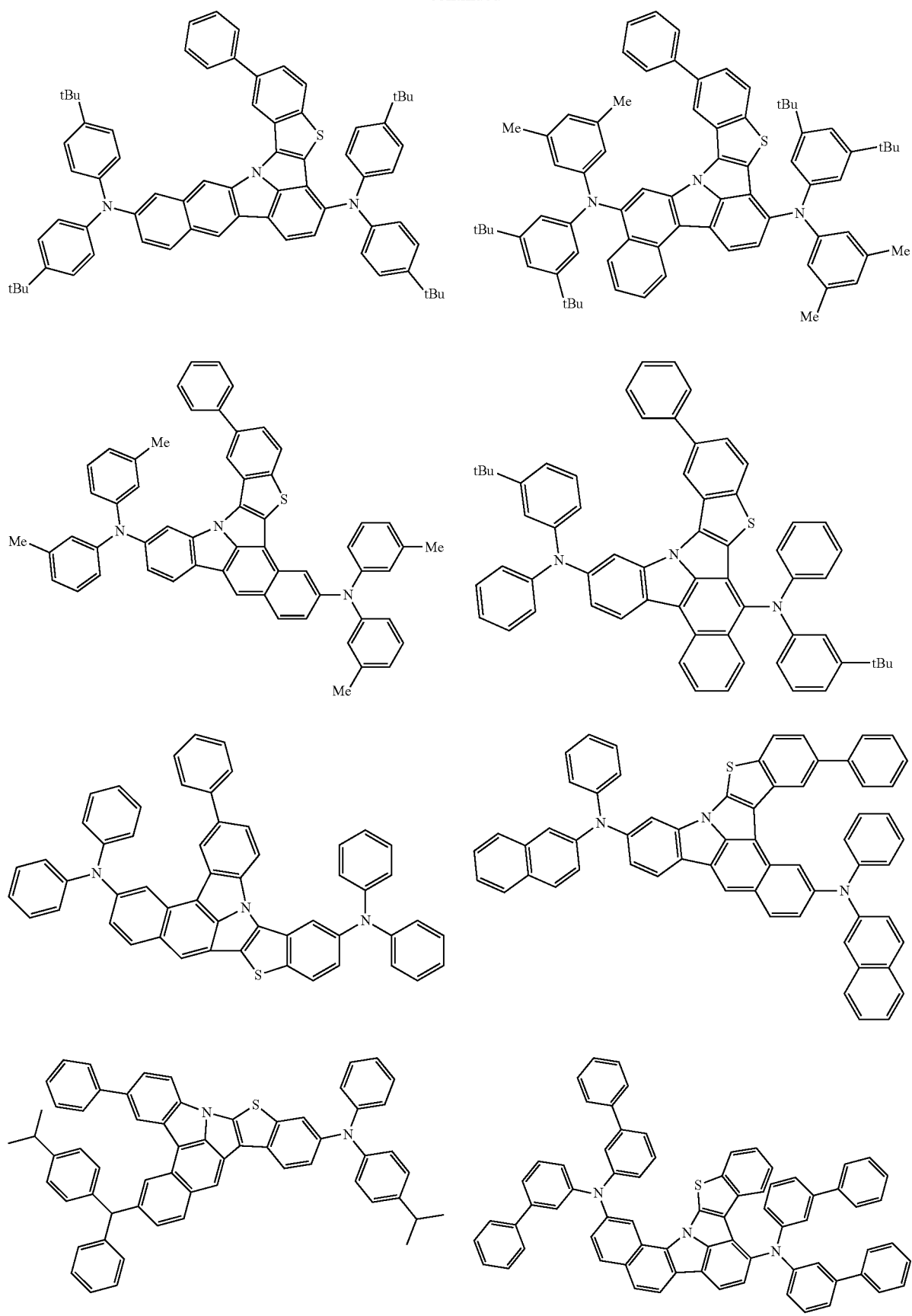

-continued
| 149 | 150 |
|---|---|
| 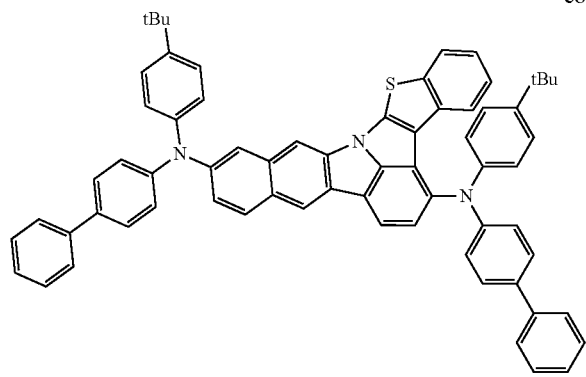 | 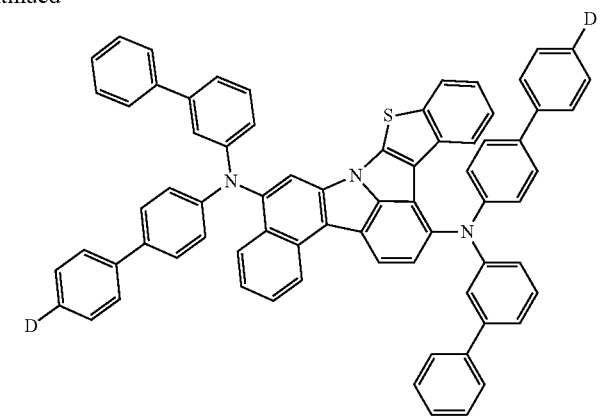 |
| 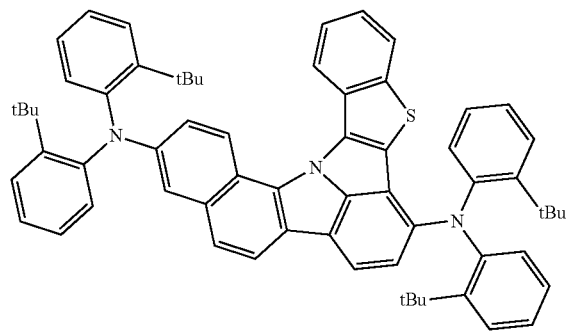 | 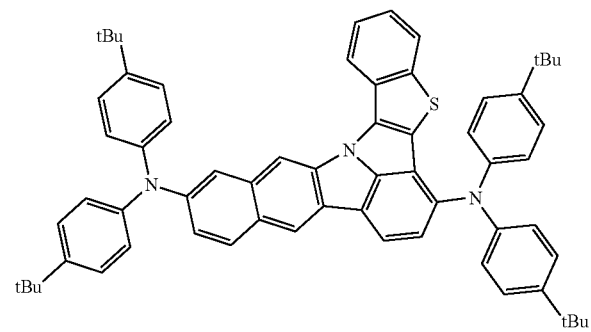 |
| 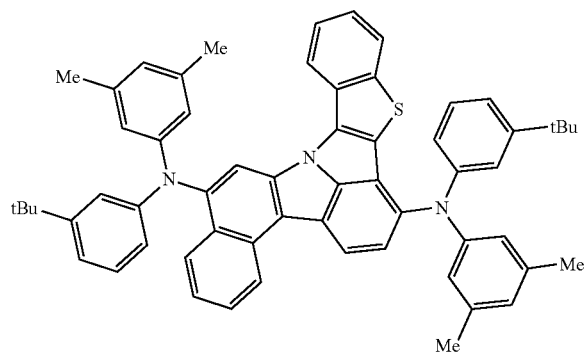 | 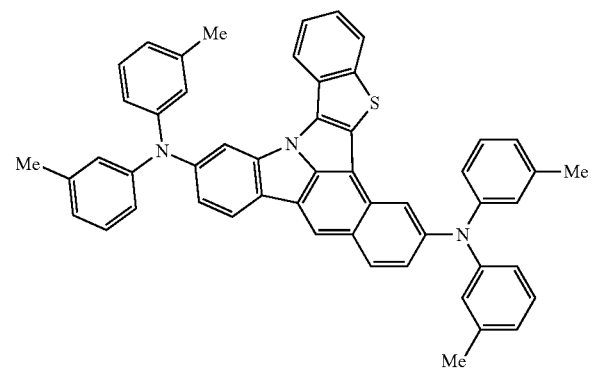 |
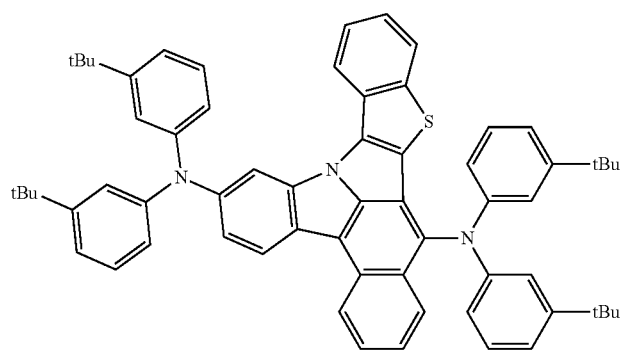

151
152
-continued
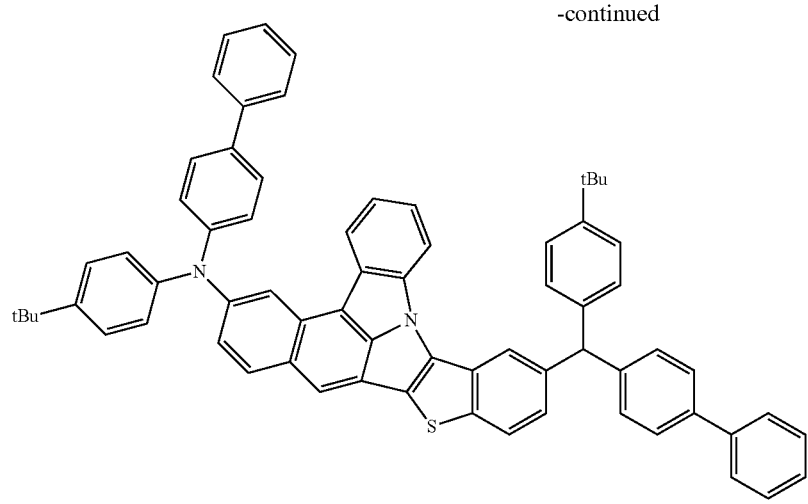
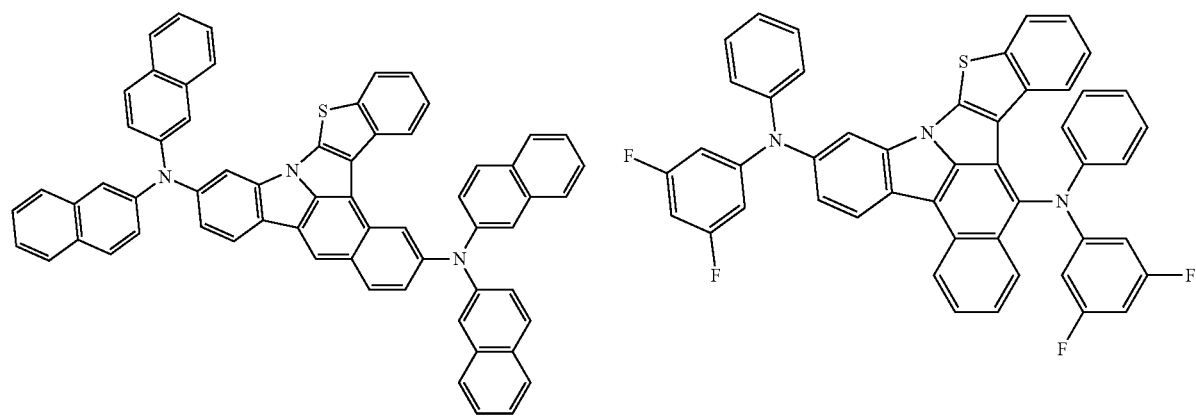
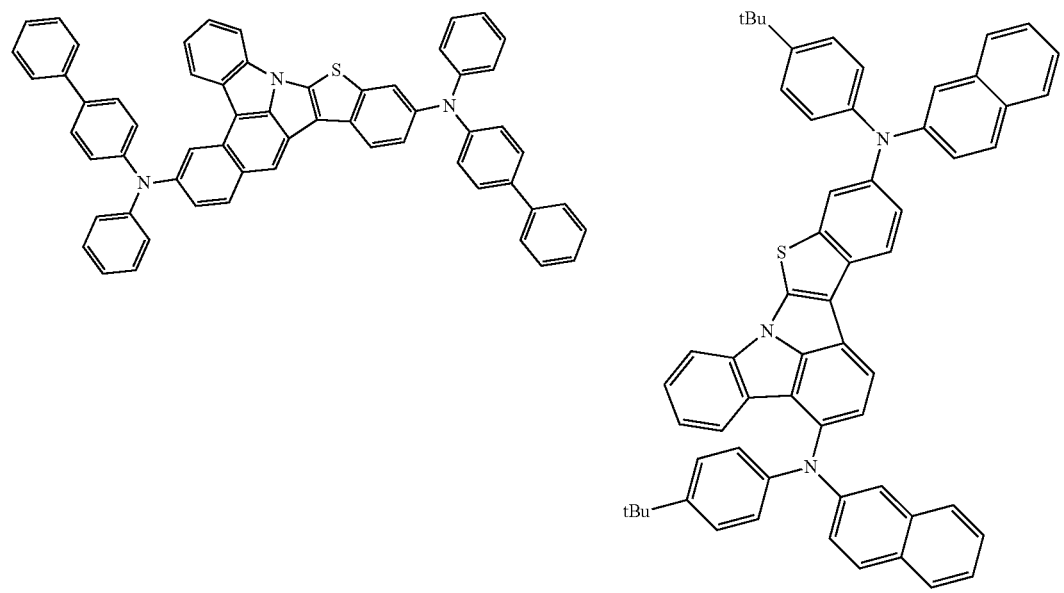

153
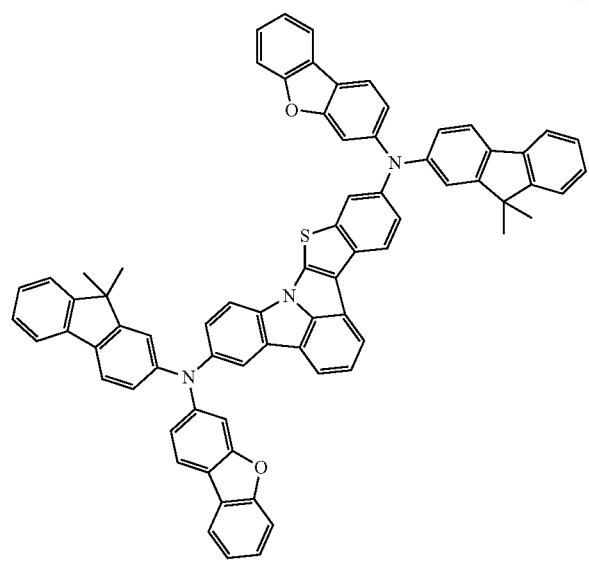
154
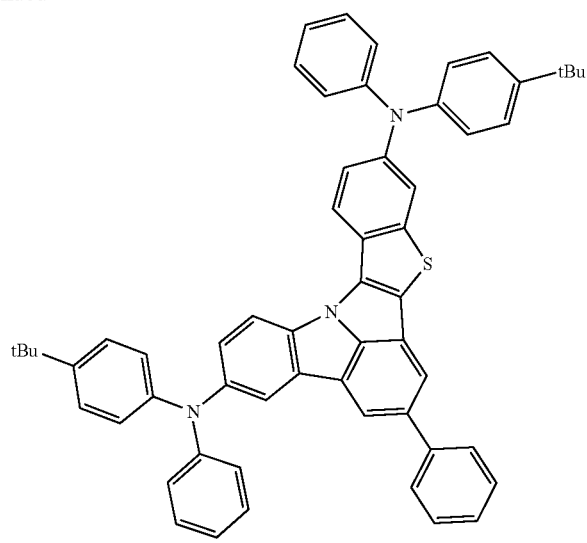
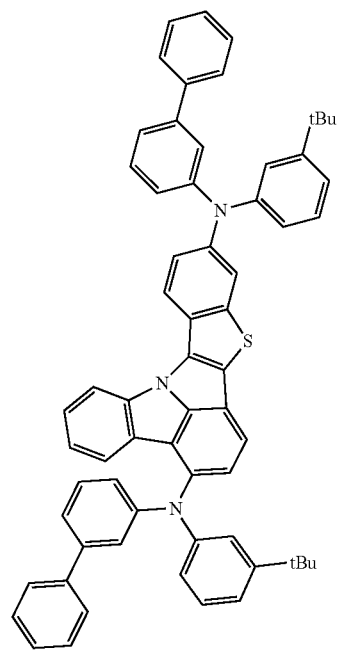
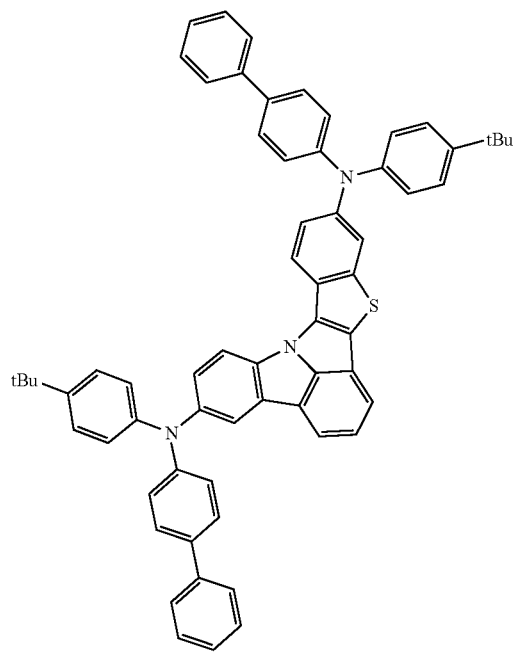

-continued
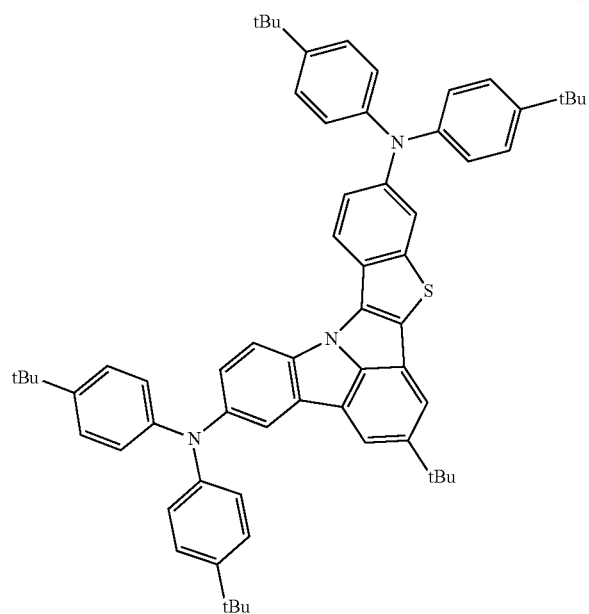
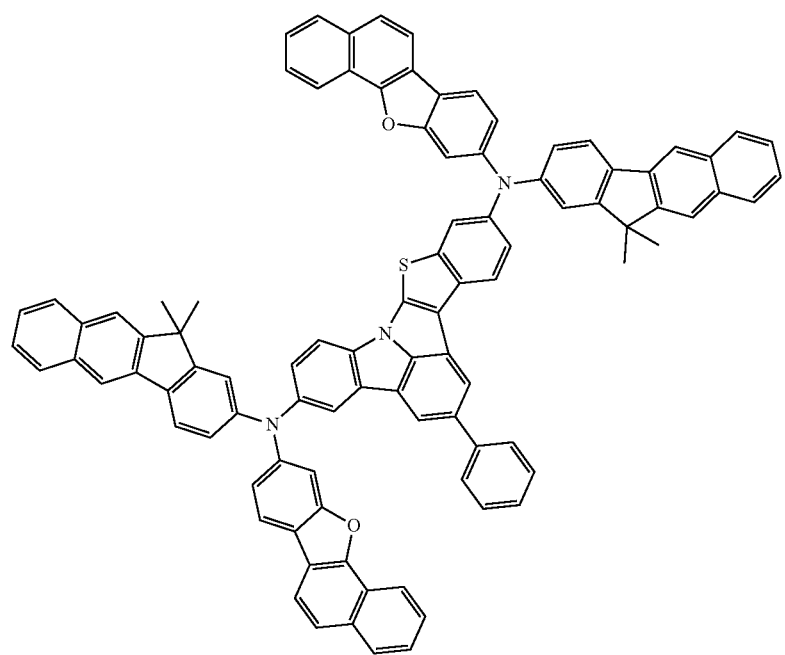

-continued
157
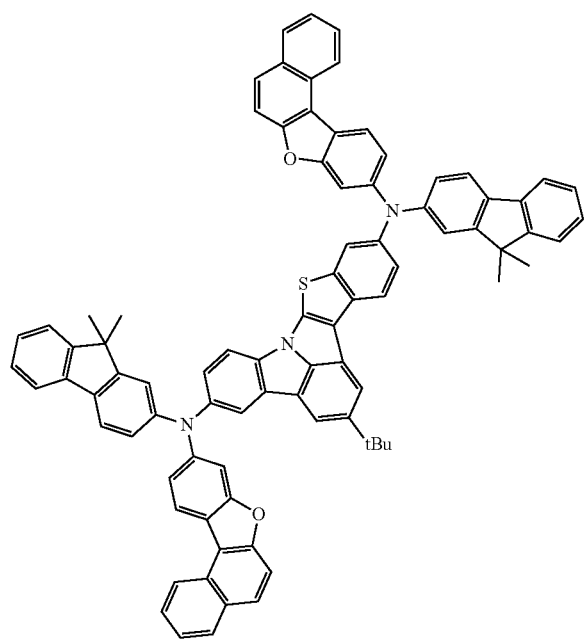
158
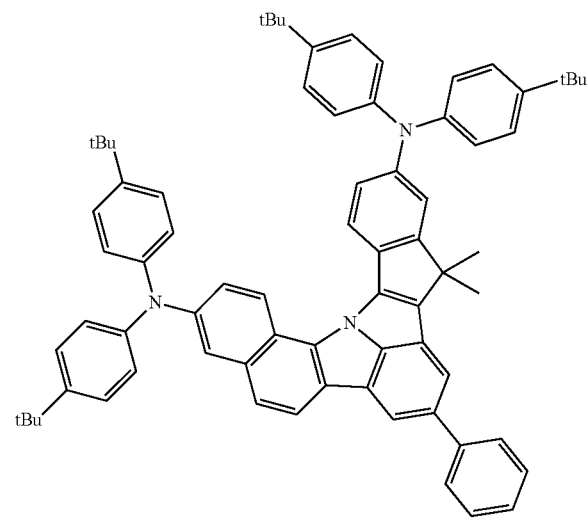
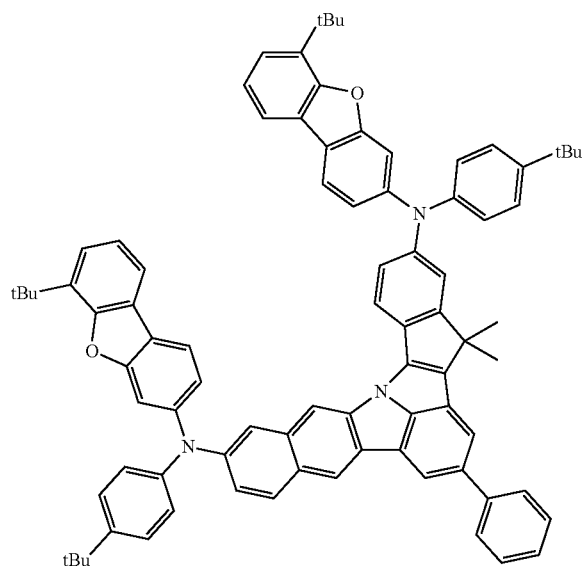
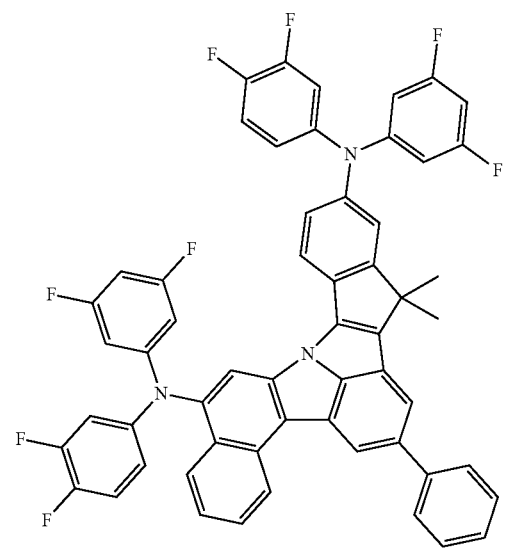

-continued
159
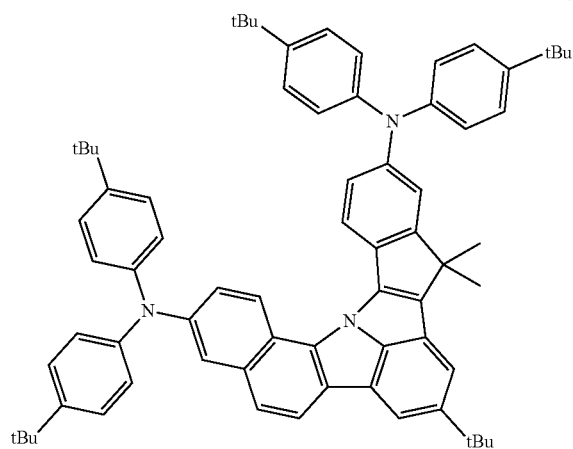
160
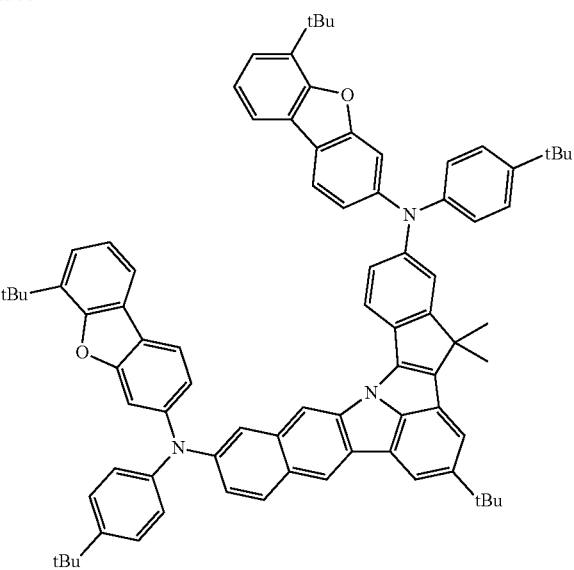
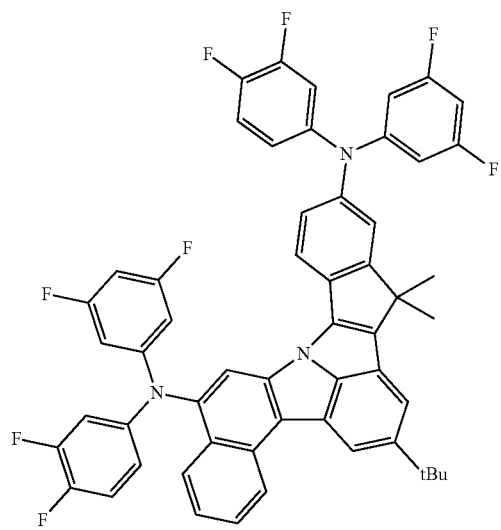
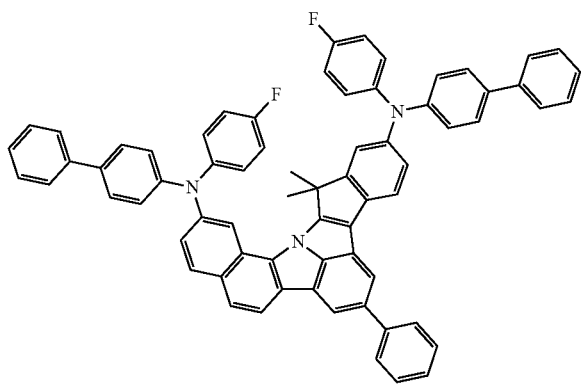
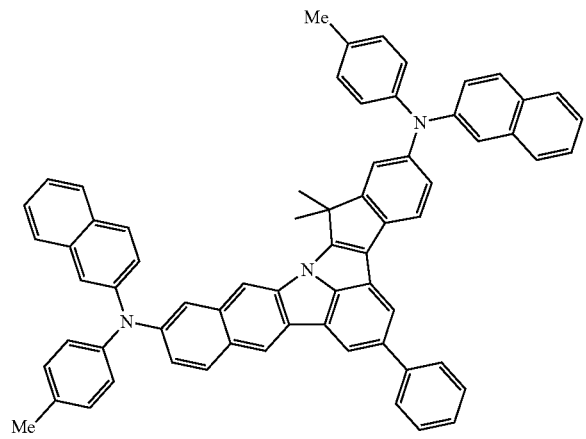
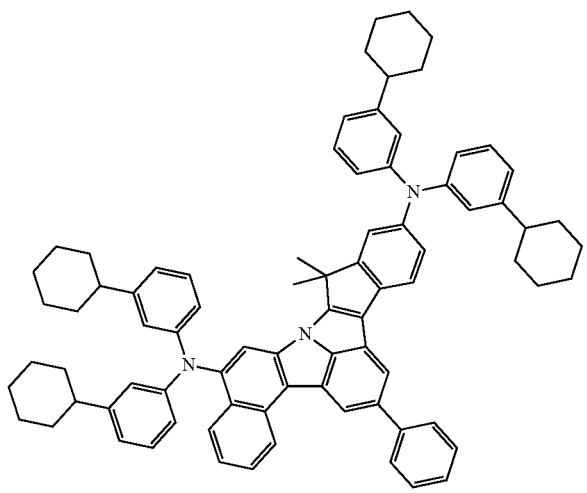

-continued
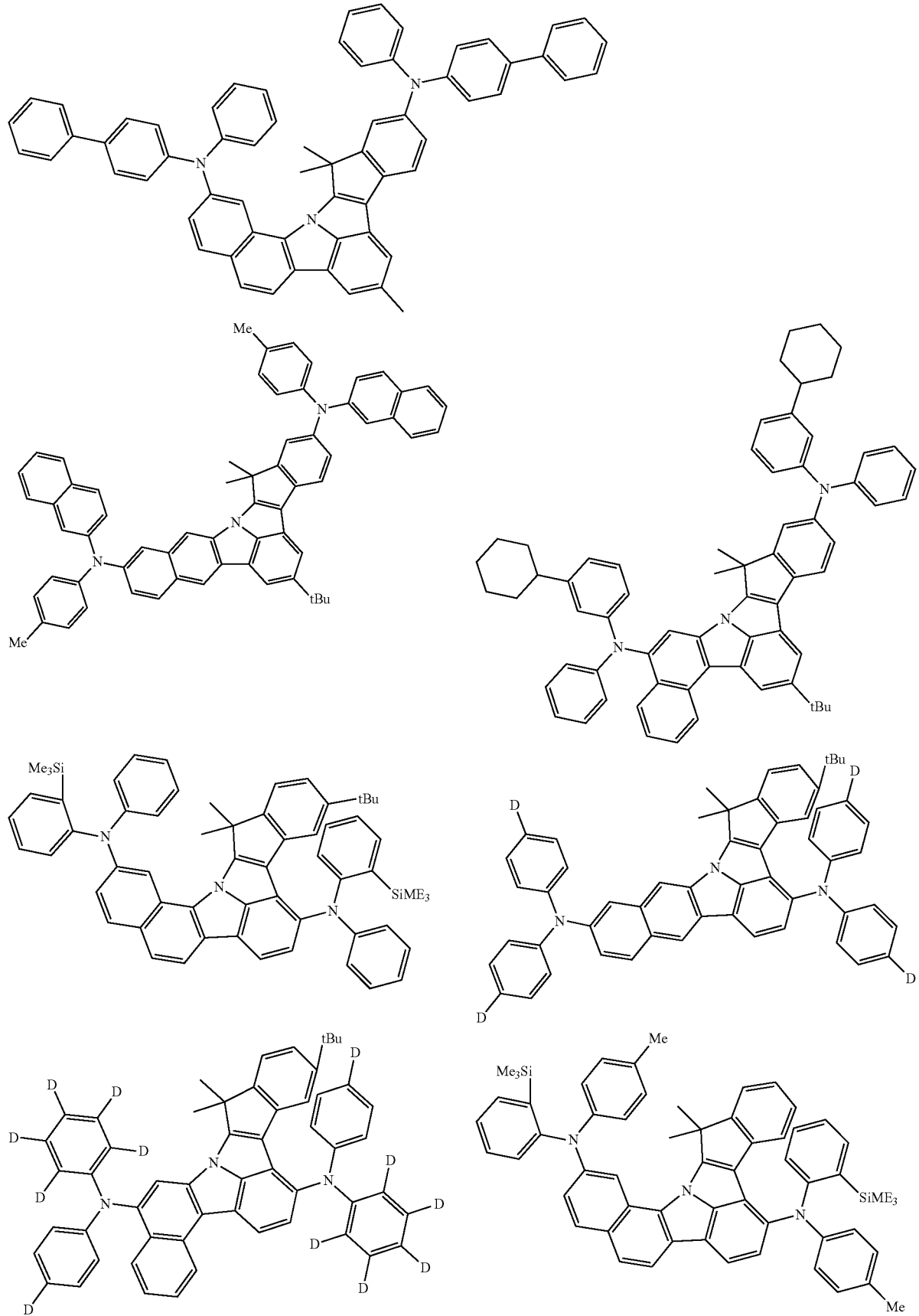

-continued
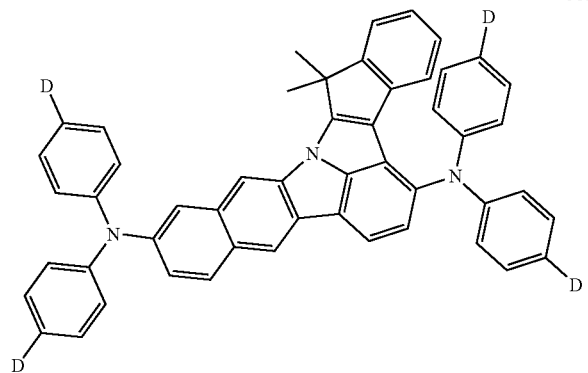
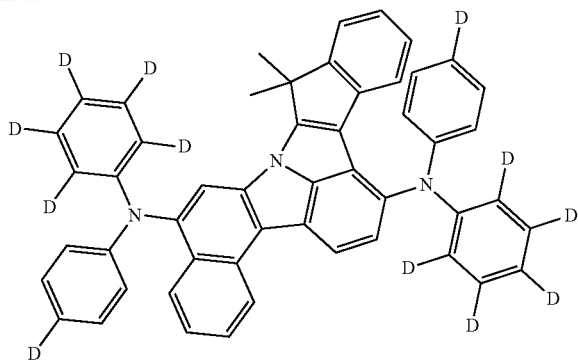
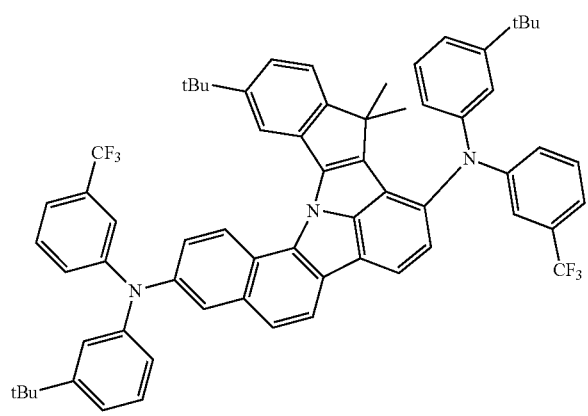
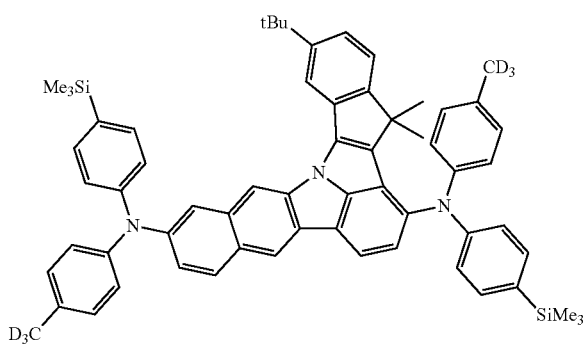
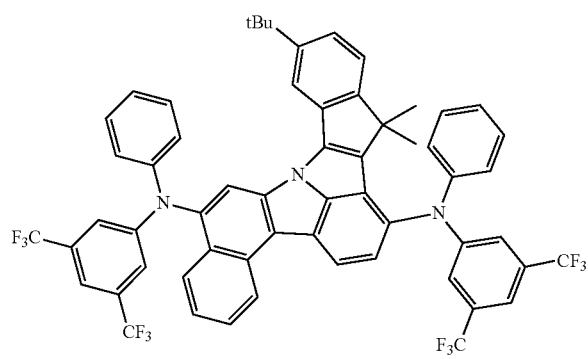
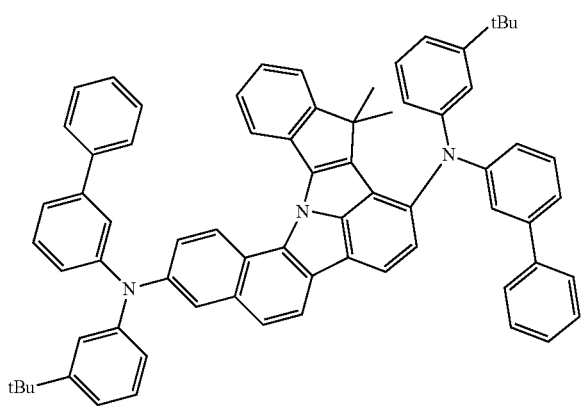
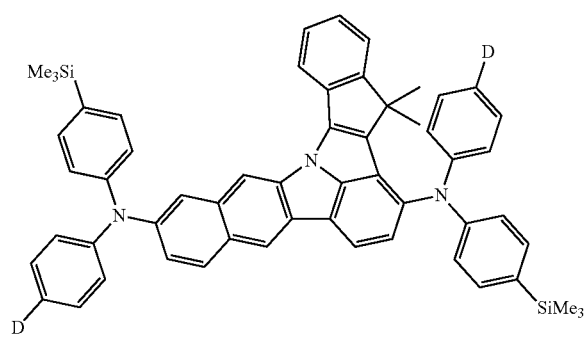
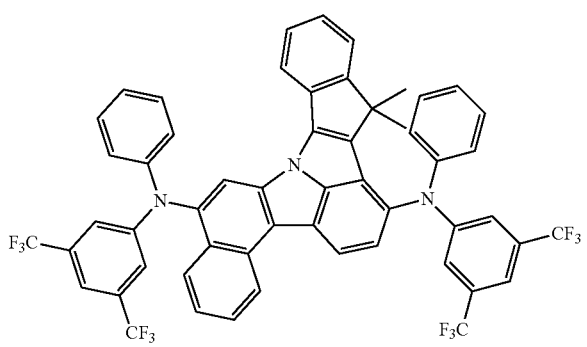

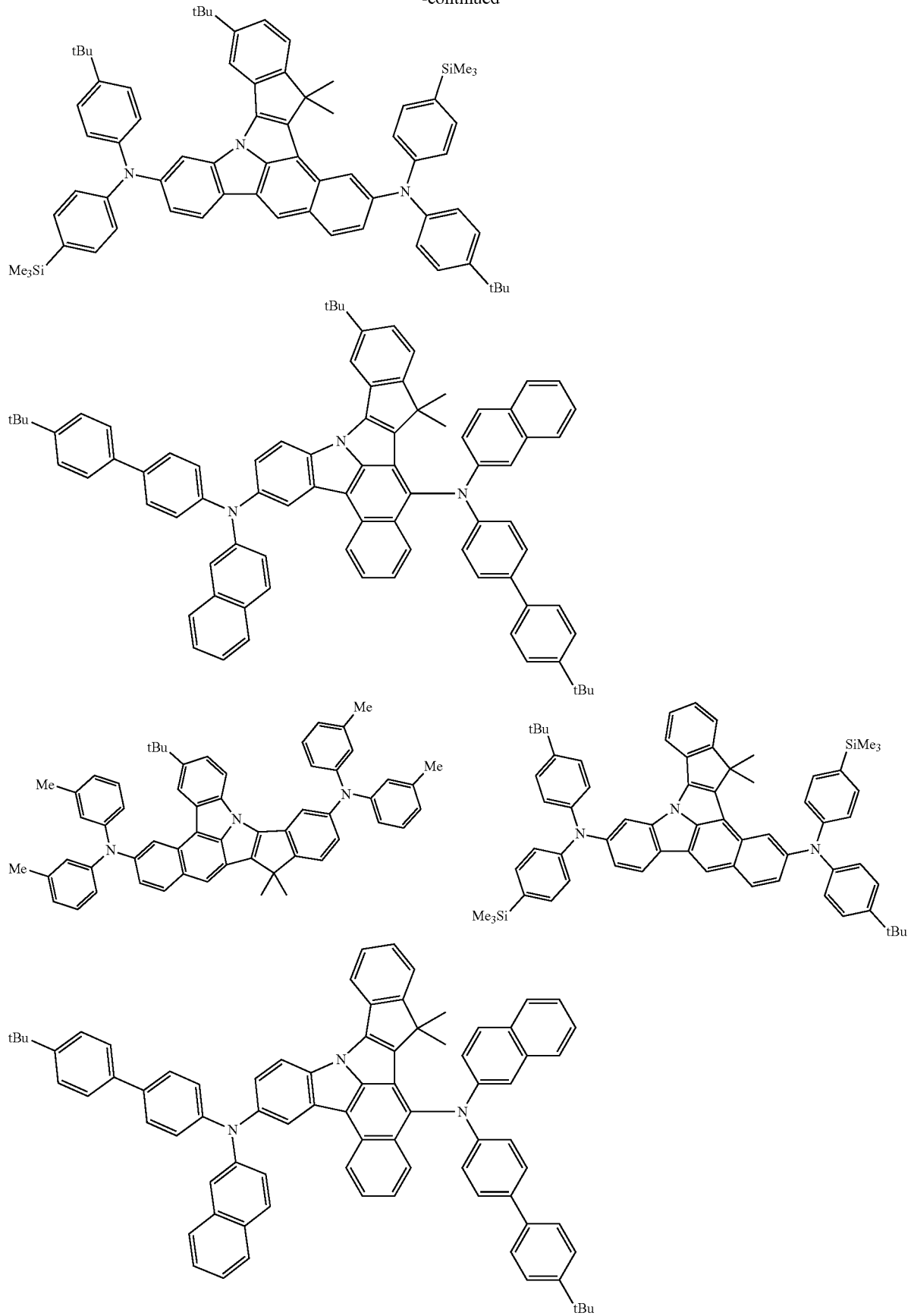

-continued
167
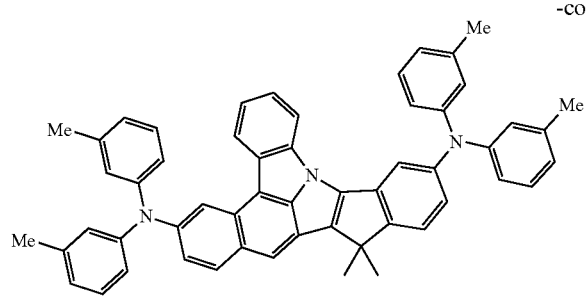
168
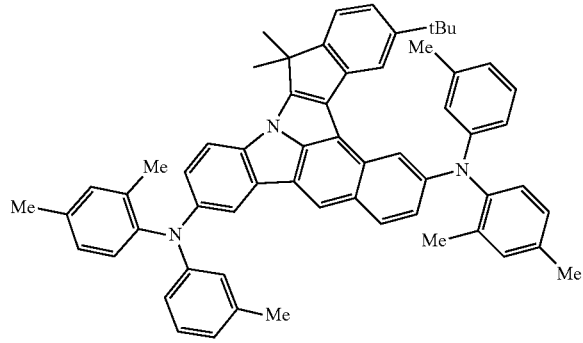
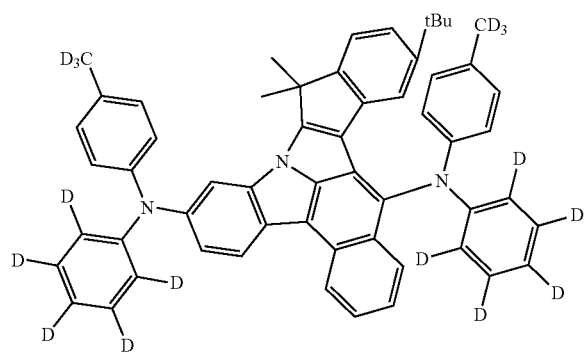
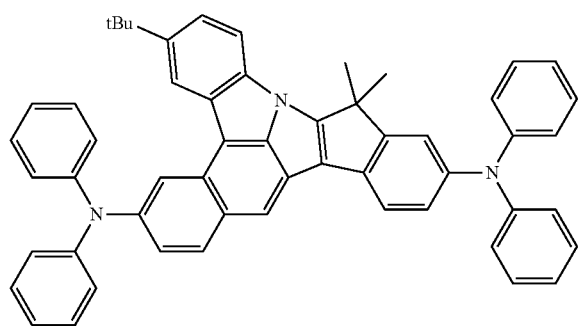
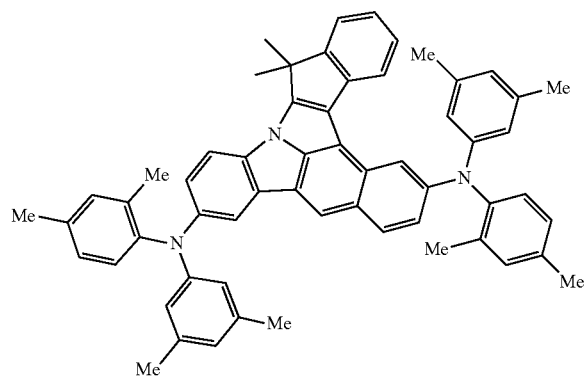
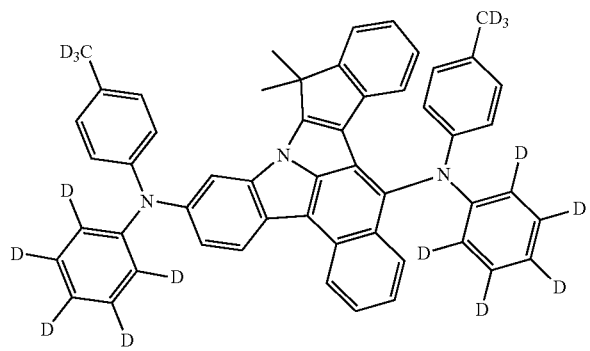
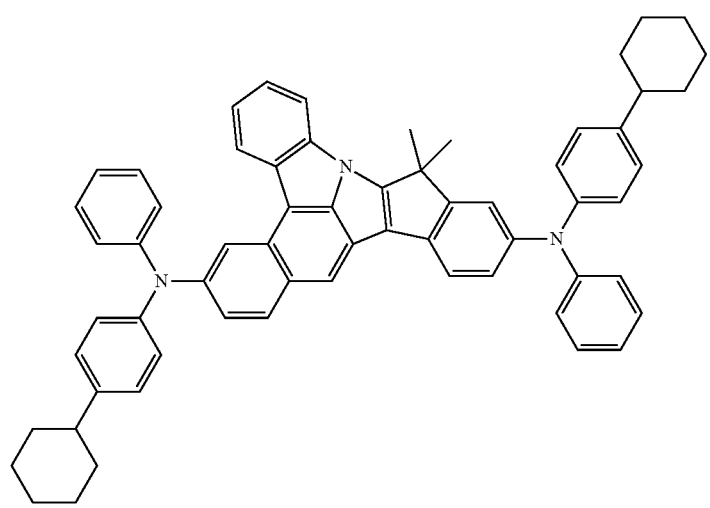

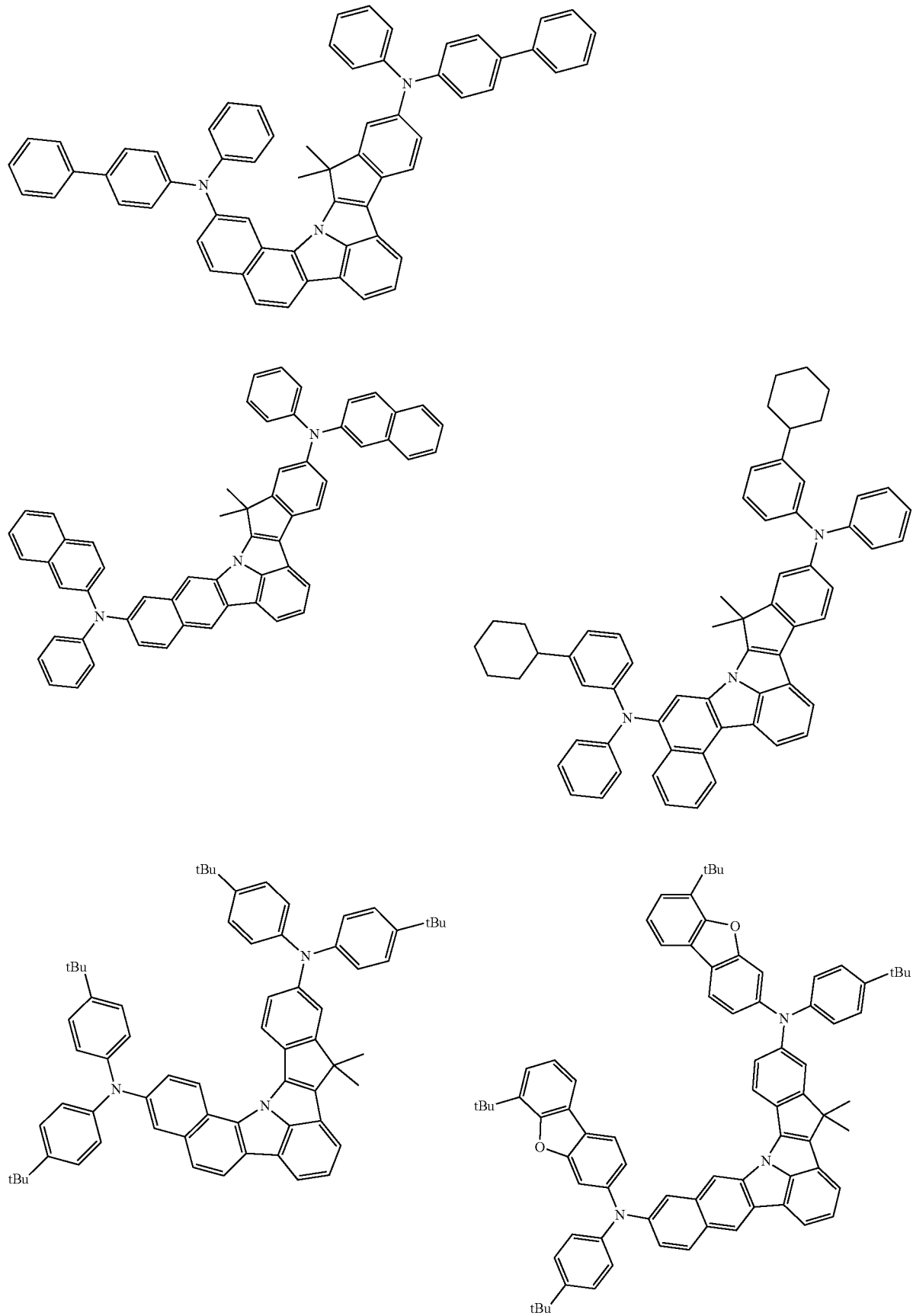

171 172
-continued
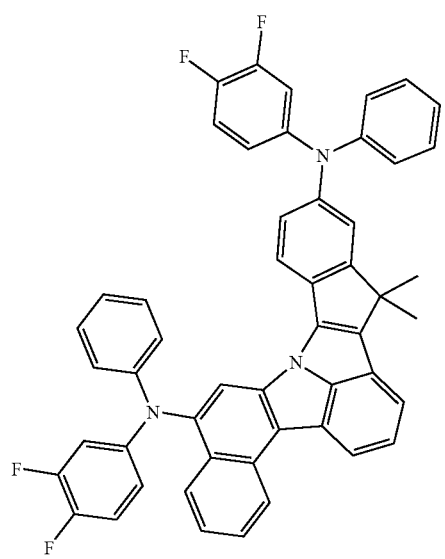
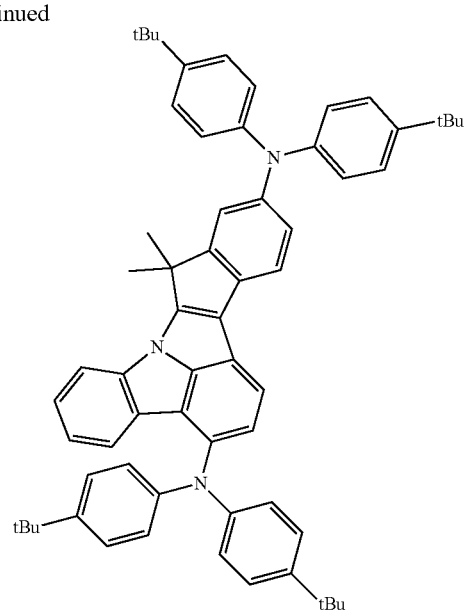
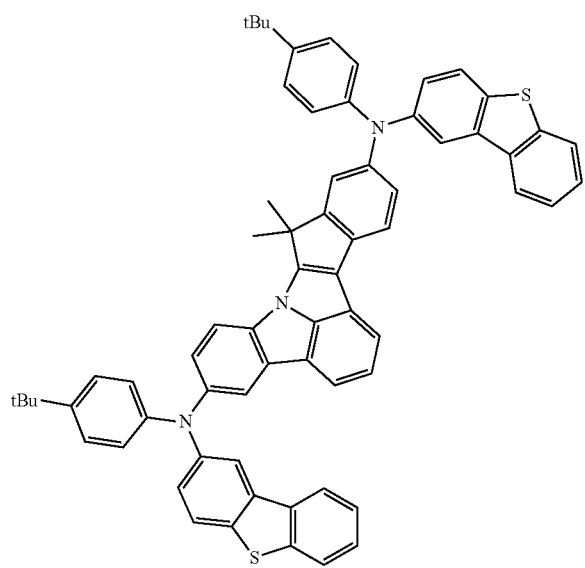
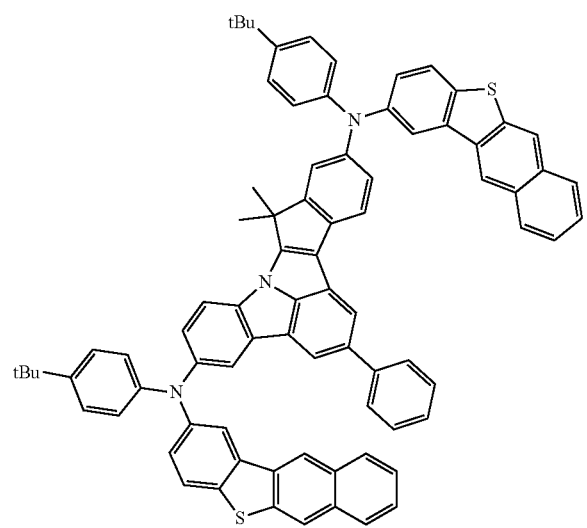

-continued
173
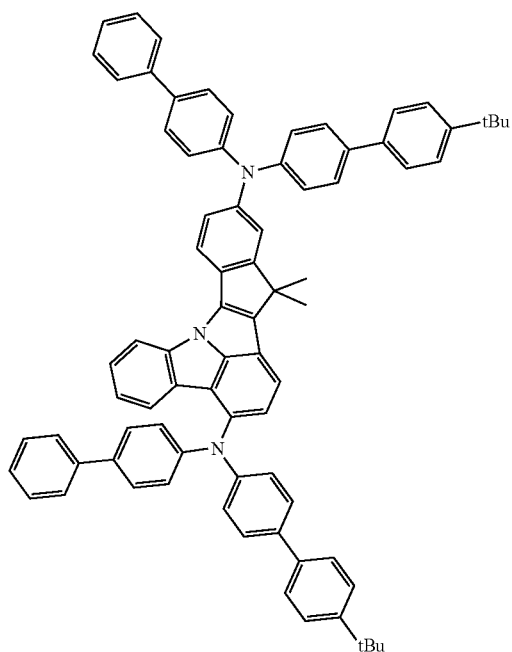
174
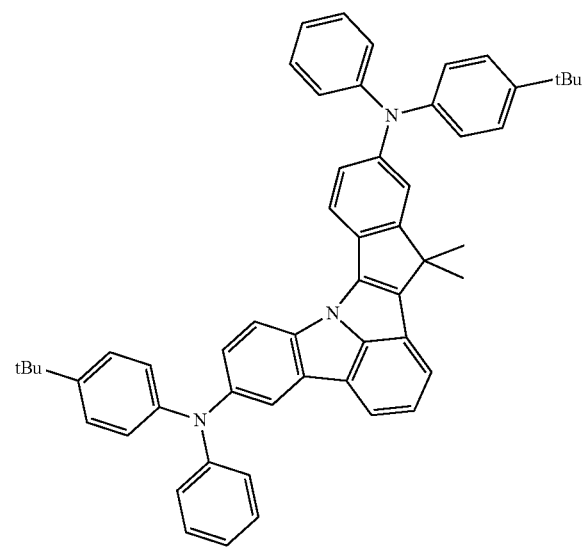
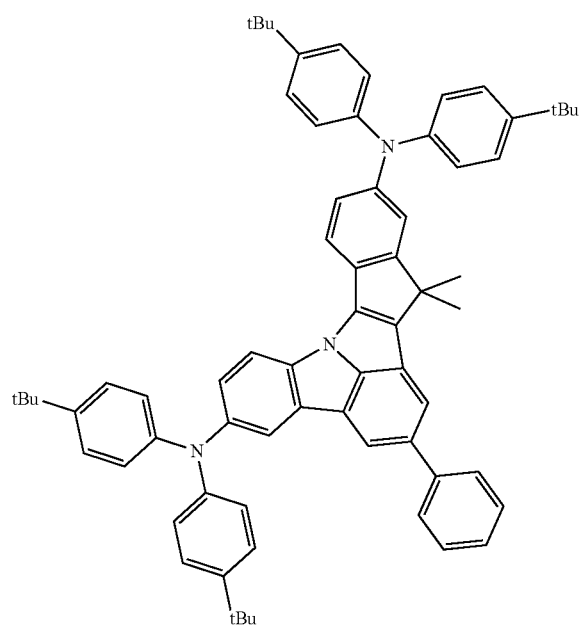
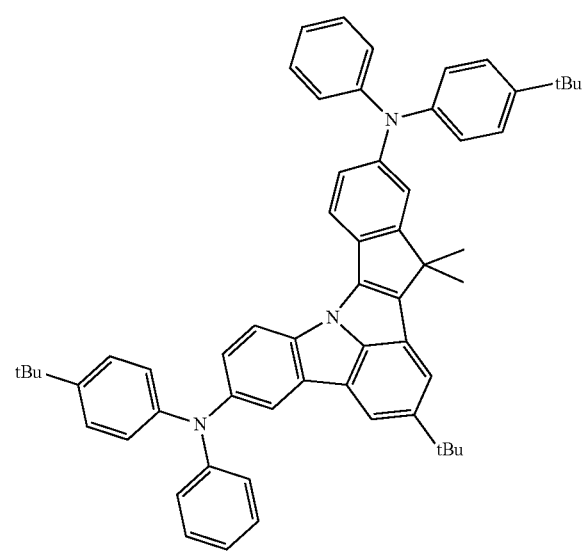

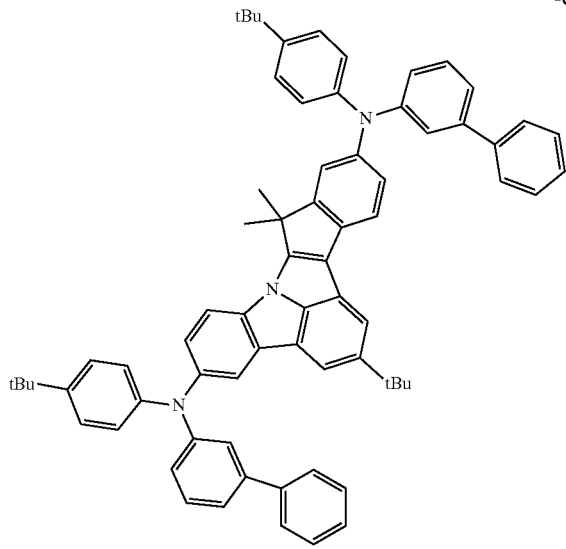

Here, tBu is a tert-butyl group, and Me is a methyl group.

Further, the present specification provides an organic light emitting device including the above-described compound.

An exemplary embodiment of the present specification provides an organic light emitting device including: a first electrode; a second electrode provided to face the first electrode; and an organic material layer having one or more layers provided between the first electrode and the second electrode, in which one or more layers of the organic material layers include the compound.

The organic material layer of the organic light emitting device of the present specification can also be composed of a single-layered structure, but can be composed of a multi-layered structure in which an organic material layer having two or more layers is stacked. For example, the organic light emitting device of the present invention can have a structure including a hole injection layer, a hole transport layer, a light emitting layer, an electron transport layer, an electron injection layer, and the like as organic material layers. However, the structure of the organic light emitting device is not limited thereto, and can include a fewer number of organic layers.

In an exemplary embodiment of the present specification, the organic material layer includes a hole injection layer or a hole transport layer, and the hole injection layer or the hole transport layer includes the compound.

In an exemplary embodiment of the present specification, the organic material layer includes a light emitting layer, and the light emitting layer includes the compound. Specifically, the light emitting layer can include a host and a dopant including the compound.

In an exemplary embodiment of the present specification, the organic material layer includes an electron transport layer or an electron injection layer, and the electron transport layer or the electron injection layer includes the compound.

In an exemplary embodiment of the present specification, the organic material layer includes a light emitting layer, and further includes one or two or more layers selected from the group consisting of a hole injection layer, a hole transport layer, an electron transport layer, an electron injection layer, an electron blocking layer, and a hole blocking layer.

In an exemplary embodiment of the present specification, the organic light emitting device includes: an anode; a cathode provided to face the anode; and an organic material layer having one or more layers provided between the anode and the cathode, the organic material layer includes: a light emitting layer; a hole transport region provided between the light emitting layer and the anode; and an electron transport region provided between the light emitting layer and the cathode, and the light emitting layer includes the compound.

In an exemplary embodiment of the present specification, as the organic material layer in the hole transport region, one or more can be selected from the group consisting of a hole transport layer, a hole injection layer, a layer which simultaneously transports and injects holes, and an electron blocking layer.

In an exemplary embodiment of the present specification, as the organic material layer in the electron transport region, one or more can be selected from the group consisting of an electron transport layer, an electron injection layer, a layer which simultaneously transports and injects electrons, and a hole blocking layer.

In another exemplary embodiment, the organic light emitting device can be a normal type organic light emitting device in which a first electrode, an organic material layer having one or more layers, and a second electrode are sequentially stacked on a substrate.

In still another exemplary embodiment, the organic light emitting device can be an inverted type organic light emitting device in which a second electrode, an organic material layer having one or more layers, and a first electrode are sequentially stacked on a substrate.

The organic light emitting device can have, for example, the stacking structure described below, but the stacking structure is not limited thereto.

(1) Positive electrode/Hole transport layer/Light emitting layer/Negative electrode
(2) Positive electrode/Hole injection layer/Hole transport layer/Light emitting layer/Negative electrode
(3) Positive electrode/Hole injection layer/Hole buffer layer/Hole transport layer/Light emitting layer/Negative electrode
(4) Positive electrode/Hole transport layer/Light emitting layer/Electron transport layer/Negative electrode
(5) Positive electrode/Hole transport layer/Light emitting layer/Electron transport layer/Electron injection layer/Negative electrode (6) Positive electrode/Hole injection layer/Hole transport layer/Light emitting layer/Electron transport layer/Negative electrode
(7) Positive electrode/Hole injection layer/Hole transport layer/Light emitting layer/Electron transport layer/Electron injection layer/Negative electrode
(8) Positive electrode/Hole injection layer/Hole buffer layer/Hole transport layer/Light emitting layer/Electron transport layer/Negative electrode
(9) Positive electrode/Hole injection layer/Hole buffer layer/Hole transport layer/Light emitting layer/Electron transport layer/Electron injection layer/Negative electrode
(10) Positive electrode/Hole transport layer/Electron blocking layer/Light emitting layer/Electron transport layer/Negative electrode
(11) Positive electrode/Hole transport layer/Electron blocking layer/Light emitting layer/Electron transport layer/Electron injection layer/Negative electrode
(12) Positive electrode/Hole injection layer/Hole transport layer/Electron blocking layer/Light emitting layer/Electron transport layer/Negative electrode
(13) Positive electrode/Hole injection layer/Hole transport layer/Electron blocking layer/Light emitting layer/Electron transport layer/Electron injection layer/Negative electrode
(14) Positive electrode/Hole transport layer/Light emitting layer/Hole blocking layer/Electron transport layer/Negative electrode
(15) Positive electrode/Hole transport layer/Light emitting layer/Hole blocking layer/Electron transport layer/Electron injection layer/Negative electrode
(16) Positive electrode/Hole injection layer/Hole transport layer/Light emitting layer/Hole blocking layer/Electron transport layer/Negative electrode
(17) Positive electrode/Hole injection layer/Hole transport layer/Light emitting layer/Hole blocking layer/Electron transport layer/Electron injection layer/Negative electrode
(18) Positive electrode/Hole injection layer/Hole transport layer/Light emitting layer/Layer which simultaneously injects and transports electrons/Negative electrode
(19) Positive electrode/Hole injection layer/Hole transport layer/Electron blocking layer/Light emitting layer/Hole blocking layer/Electron transport layer/Electron injection layer/Negative electrode
(20) Positive electrode/Hole injection layer/Hole transport layer/Electron blocking layer/Light emitting layer/Hole blocking layer/Electron transport layer/Negative electrode
(21) Positive electrode/Hole injection layer/Hole transport layer/Electron blocking layer/Light emitting layer/Hole blocking layer/Layer which simultaneously injects and transports electrons/Negative electrode For example, the structure of the organic light emitting device according to an exemplary embodiment of the present specification is exemplified in FIGS. 1 and 2.

FIG. 1 exemplifies a structure of an organic light emitting device in which a substrate 1, a first electrode 2, a light emitting layer 3, and a second electrode 4 are sequentially stacked.

FIG. 2 exemplifies a structure of an organic light emitting device in which a substrate 1, a first electrode 2, a hole injection layer 5, a hole transport layer 6, an electron transport layer 7, a light emitting layer 3, a first electron transport layer 8, a second electron transport layer 9, and a second electrode 4 are sequentially stacked. In the structure described above, the compound can be included in the light emitting layer 3.

The organic light emitting device of the present specification can be manufactured by the materials and methods known in the art, except that one or more layers of the organic material layer include the compound of the present specification, that is, the compound.

When the organic light emitting device includes a plurality of organic material layers, the organic material layers can be formed of the same material or different materials.

The organic light emitting device of the present specification can be manufactured by the materials and methods known in the art, except that one or more layers of the organic material layer include the compound, that is, the compound of Formula 1.

For example, the organic light emitting device of the present specification can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which can be used as a second electrode, thereon, by using a physical vapor deposition (PVD) method such as sputtering or e-beam evaporation. In addition to the method described above, an organic light emitting device can be made by sequentially depositing a second electrode material, an organic material layer, and a first electrode material on a substrate.

Further, the compound of Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

The positive electrode is an electrode which injects holes, and as a positive electrode material, materials having a high work function are usually preferred so as to facilitate the injection of holes into an organic material layer. Specific examples of the positive electrode material which can be used in the present invention include: a metal, such as vanadium, chromium, copper, zinc, and gold, or an alloy thereof; a metal oxide, such as zinc oxide, indium oxide, indium tin oxide (ITO), and indium zinc oxide (IZO); a combination of a metal and an oxide, such as ZnO:Al or SnO$_2$:Sb; a conductive polymer, such as poly(3-methylthiophene), poly[3,4-(ethylene-1,2-dioxy)thiophene] (PEDOT), polypyrrole, and polyaniline; and the like, but are not limited thereto.

The negative electrode is an electrode which injects electrons, and as a negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al; and the like, but are not limited thereto.

The hole injection layer is a layer which injects holes from an electrode, and a hole injection material is preferably a compound which has a capability of transporting holes and thus has an effect of injecting holes at a first electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the first electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport layer is a layer which accepts holes from a hole injection layer and transports the holes to a light emitting layer, and a hole transport material is suitably a material having high hole mobility which can accept holes from a first electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting layer can include a host material and a dopant material.

Examples of the host material for the light emitting layer include fused aromatic ring derivatives, or hetero ring-containing compounds, and the like. Specifically, examples of the fused aromatic ring derivative include anthracene derivatives, pyrene derivatives, naphthalene derivatives, pentacene derivatives, phenanthrene compounds, fluoranthene compounds, and the like, and examples of the hetero ring-containing compound include carbazole derivatives, dibenzofuran, dibenzofuran derivatives, dibenzothiophene, dibenzothiophene derivatives, ladder-type furan compounds, pyrimidine derivatives, and the like, but the examples thereof are not limited thereto.

In an exemplary embodiment of the present specification, the host includes a compound of the following Formula 5:

<Formula 5>

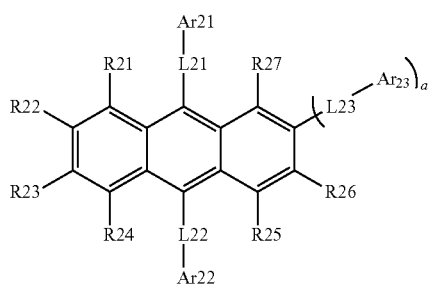

wherein in Formula 5:
L21 to L23 are the same as or different from each other, and are each independently a direct bond, or a substituted or unsubstituted arylene group, or a substituted or unsubstituted heteroarylene group;

R21 to R27 are the same as or different from each other, and are each independently hydrogen, deuterium, a substituted or unsubstituted alkyl group, a substituted or unsubstituted cycloalkyl group, a substituted or unsubstituted silyl group, a substituted or unsubstituted aryl group, or a substituted or unsubstituted heteroaryl group;

Ar21 to Ar23 are the same as or different from each other, and are each independently a substituted or unsubstituted aryl group or a substituted or unsubstituted heteroaryl group; and a is 0 or 1.

In an exemplary embodiment of the present specification, the host includes a compound that is any one of the following compounds:

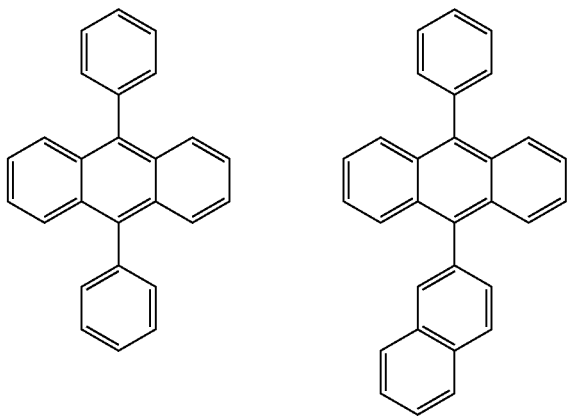

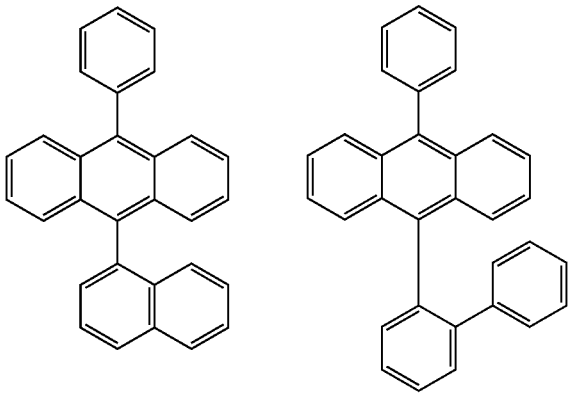

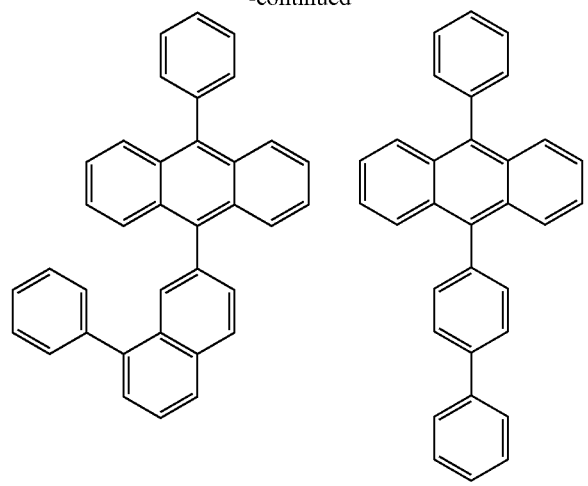
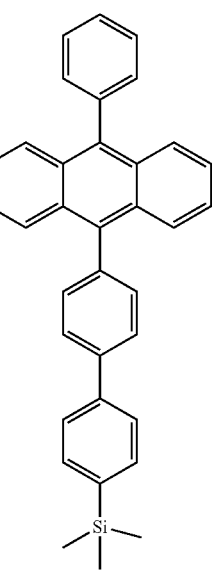
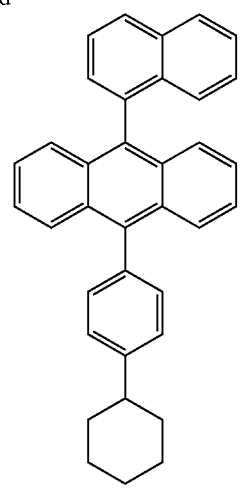
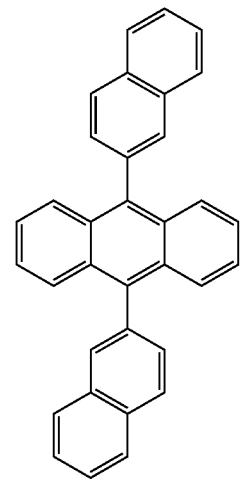
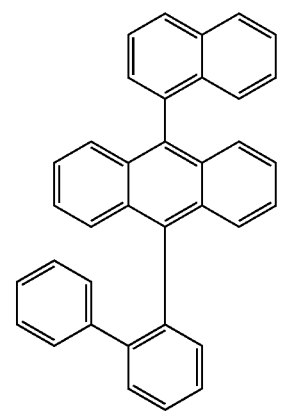
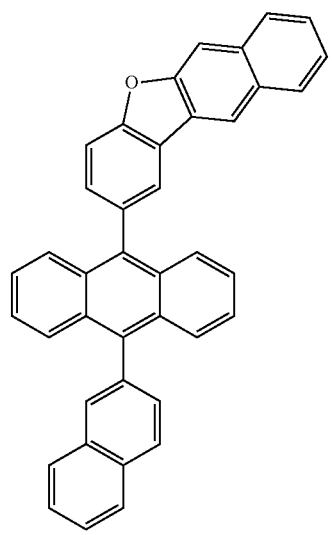
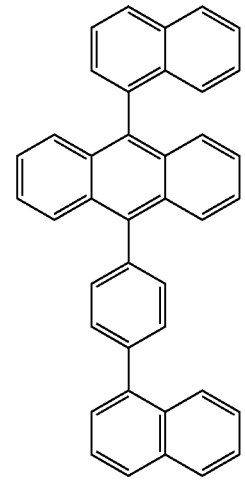
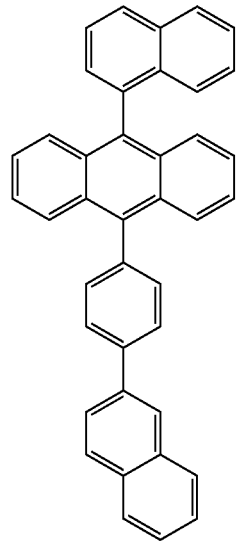
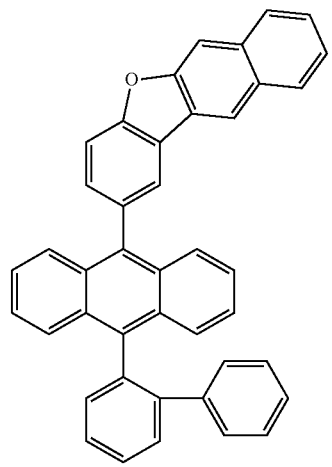

183
-continued
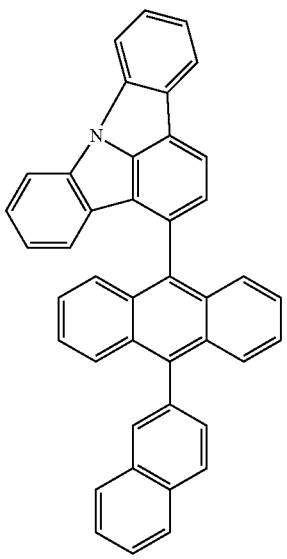
184
-continued
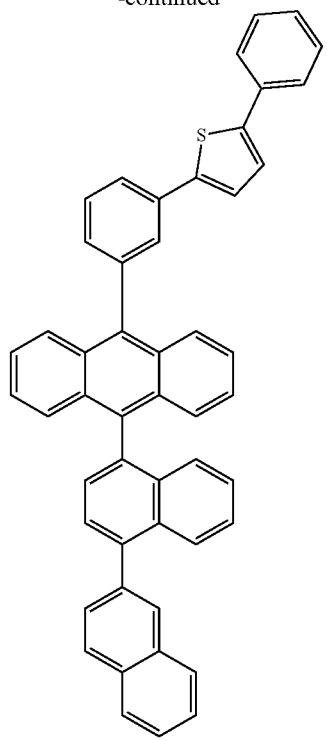
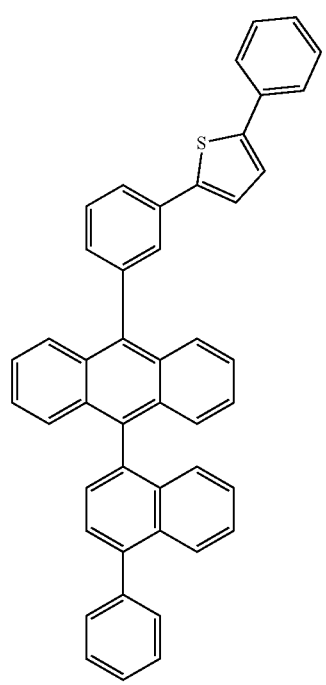

185
-continued
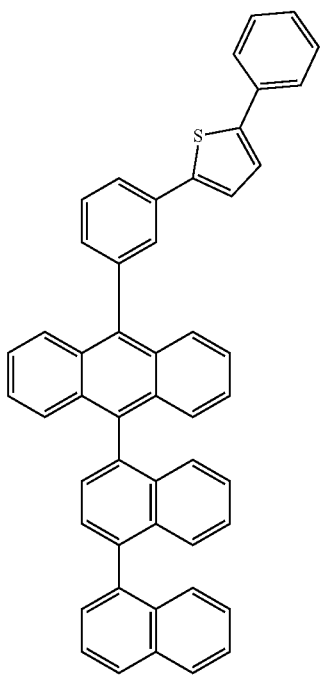
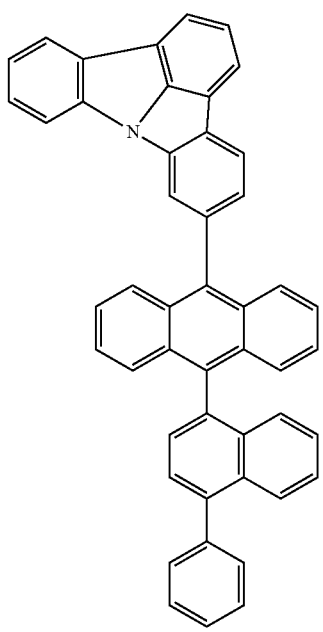
186
-continued
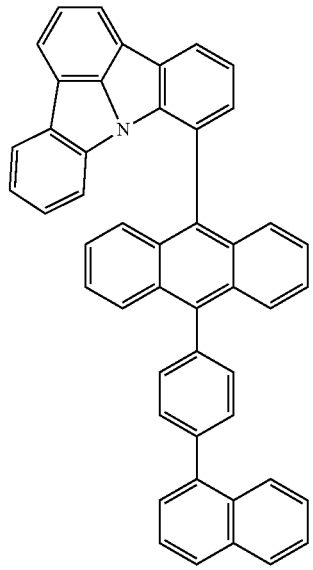
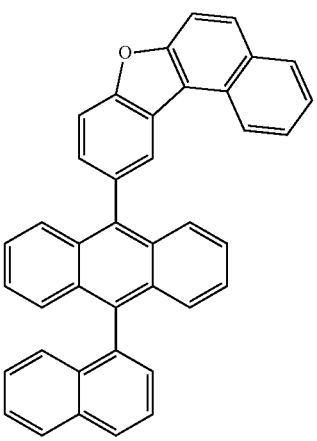
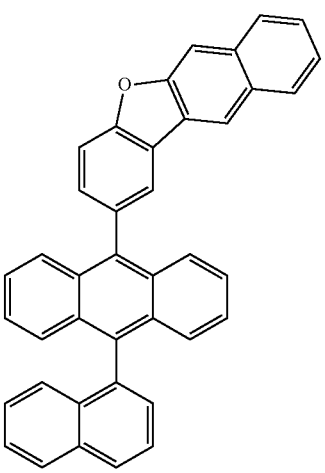

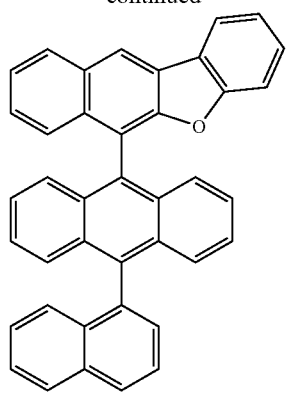
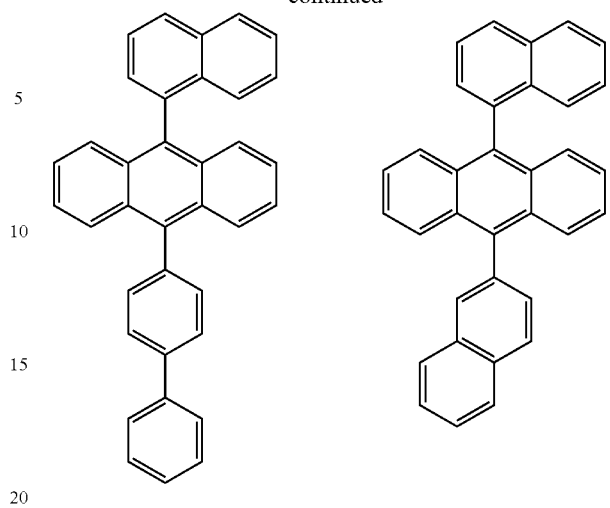
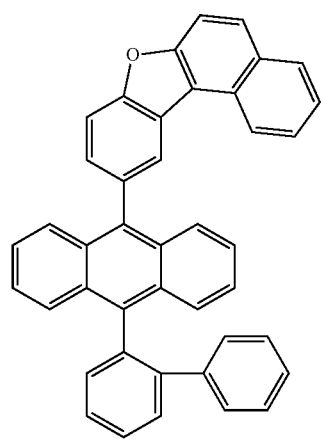
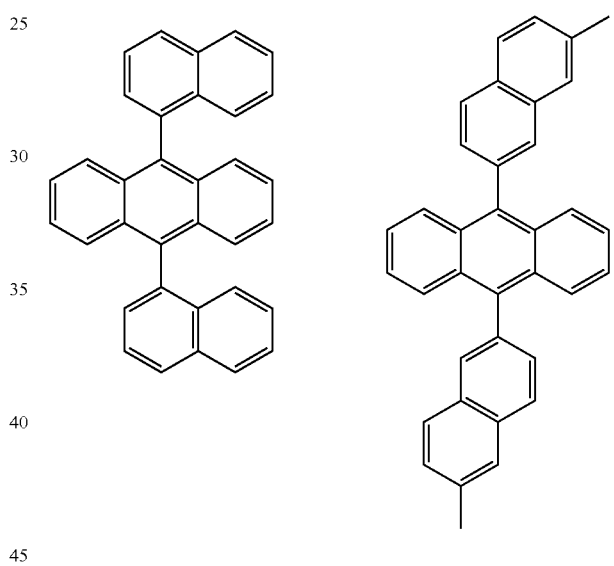
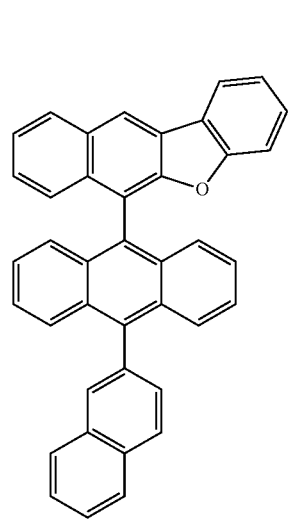
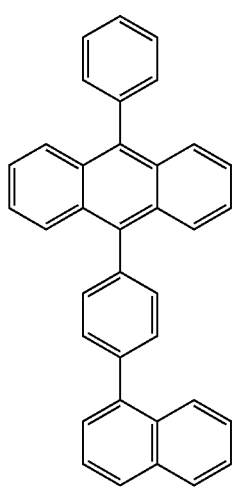
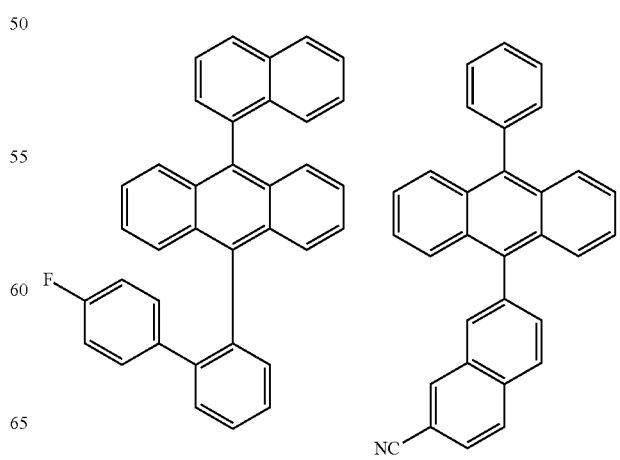

189
-continued
190
-continued
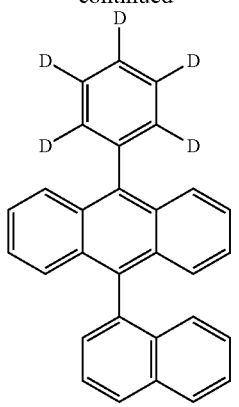
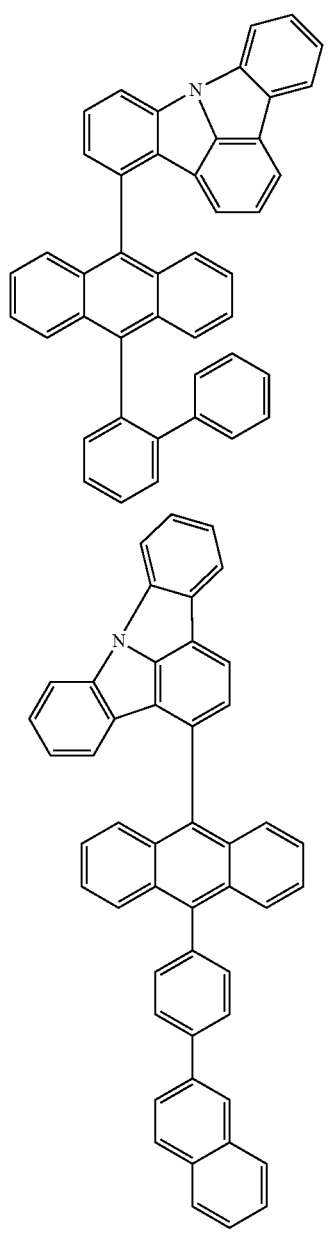
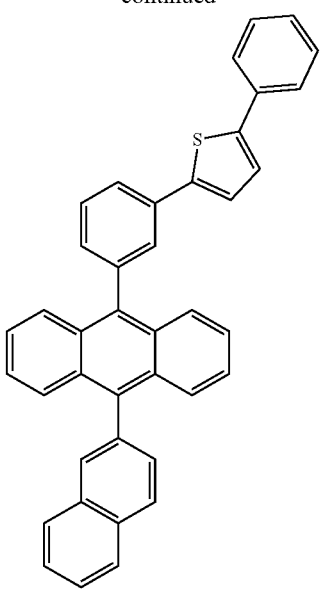
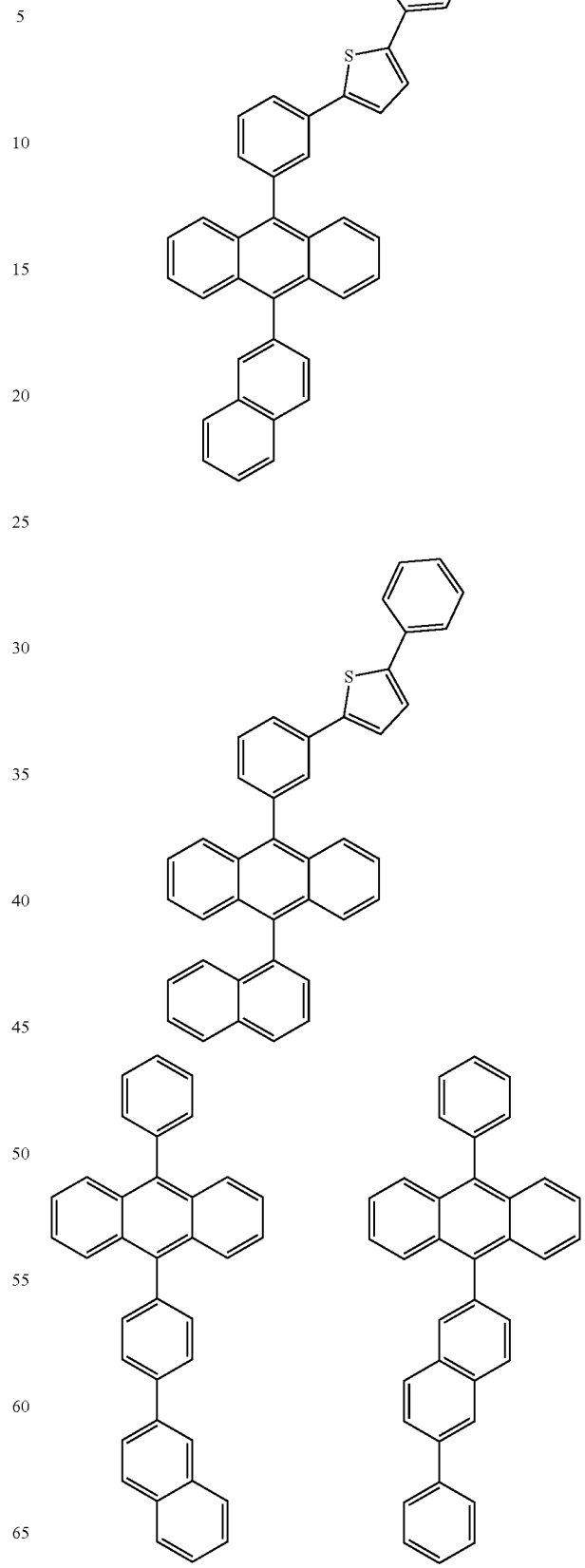

191
-continued
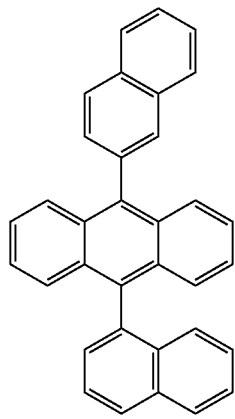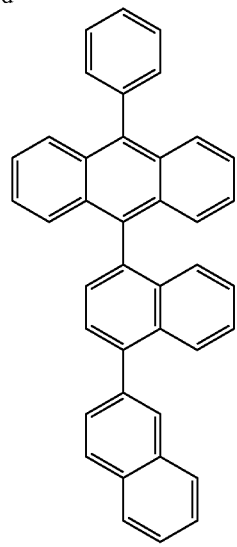
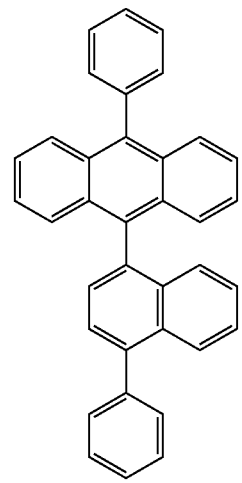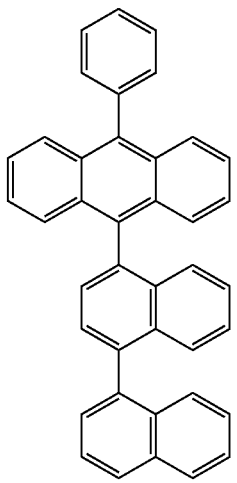
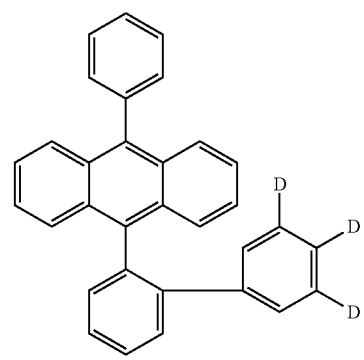
192
-continued
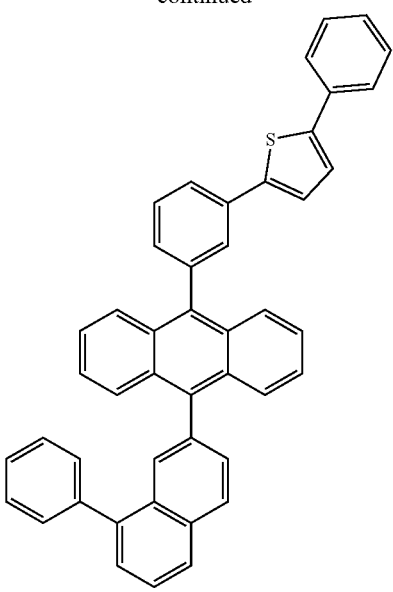
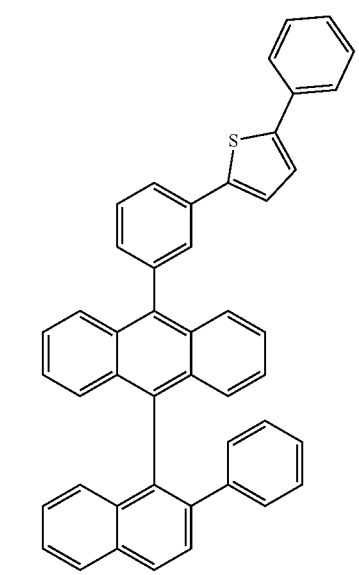
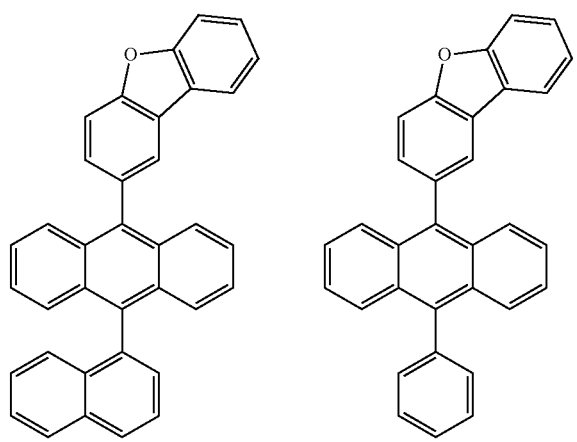

193
-continued
194
-continued
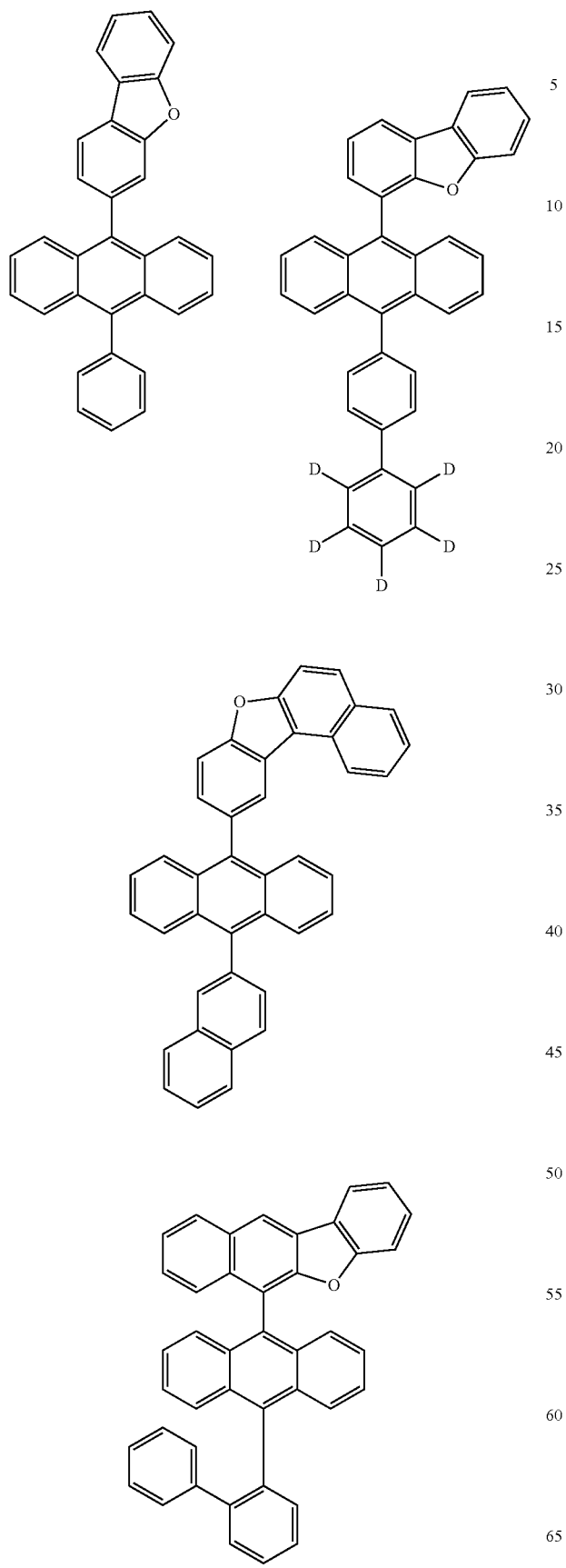
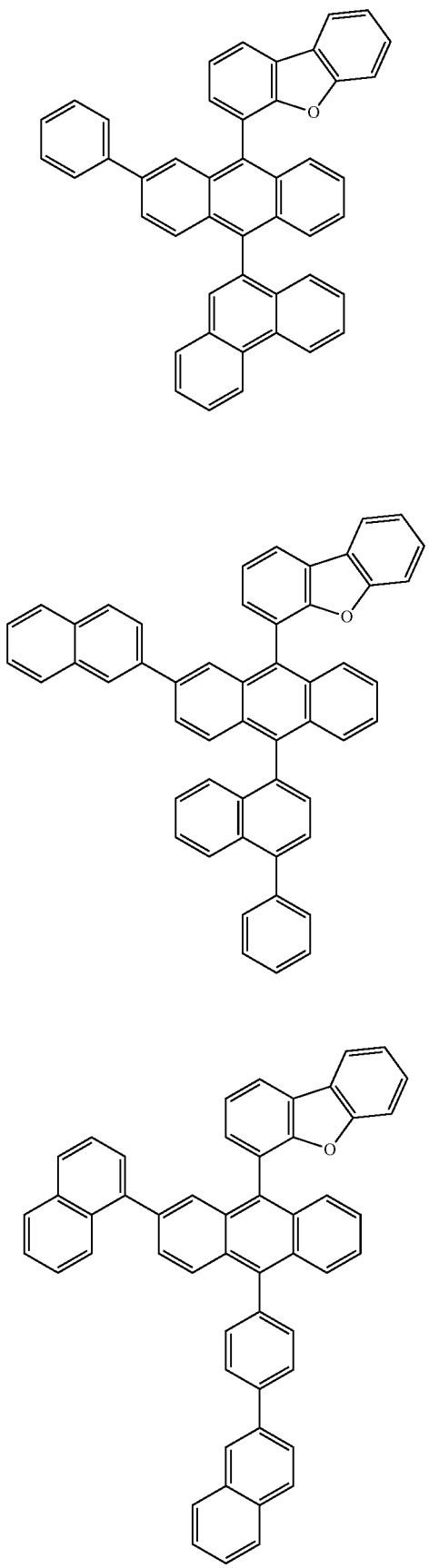

-continued
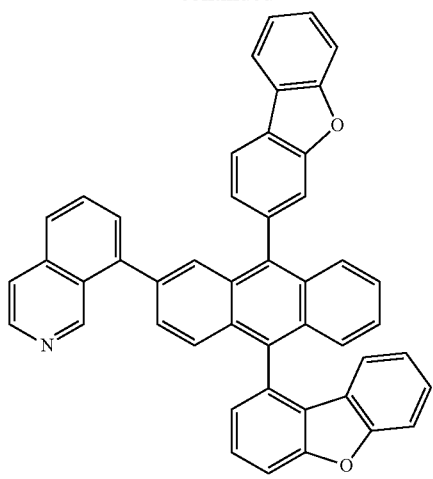
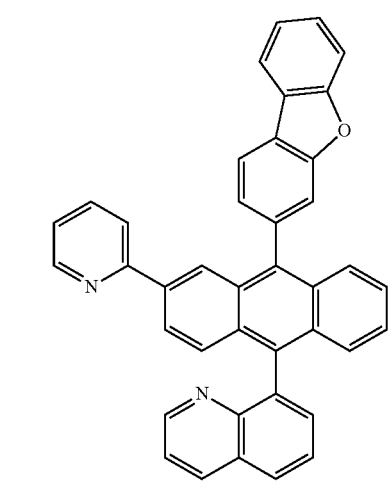
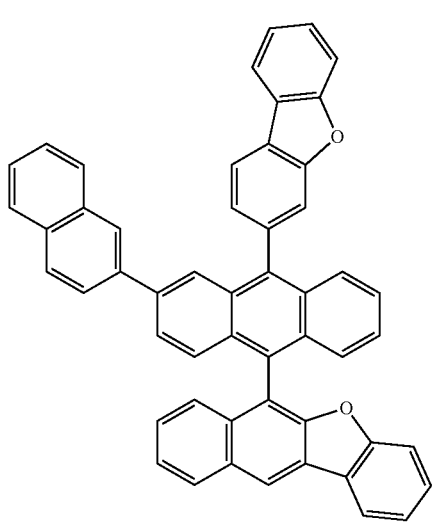
-continued
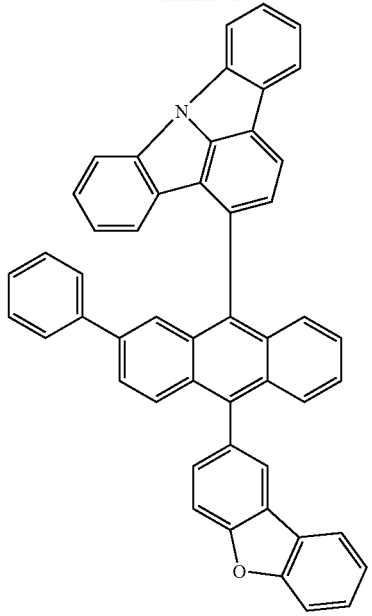
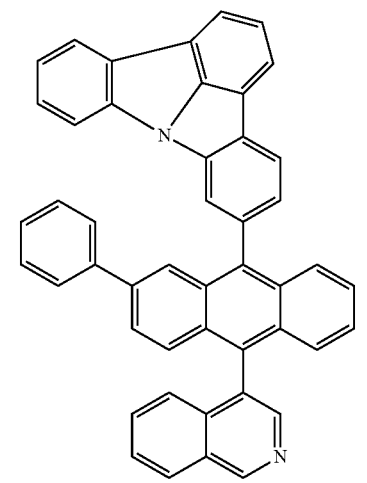

197
-continued
198
-continued
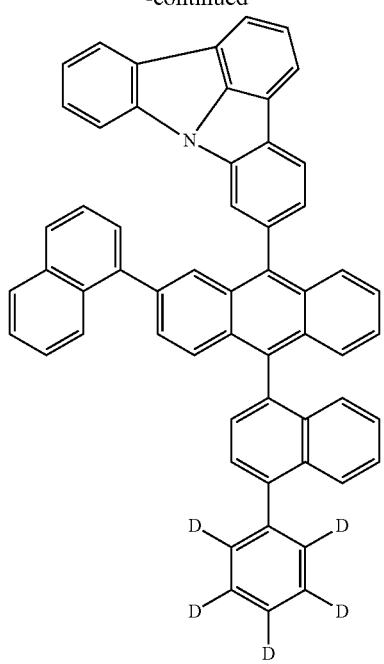
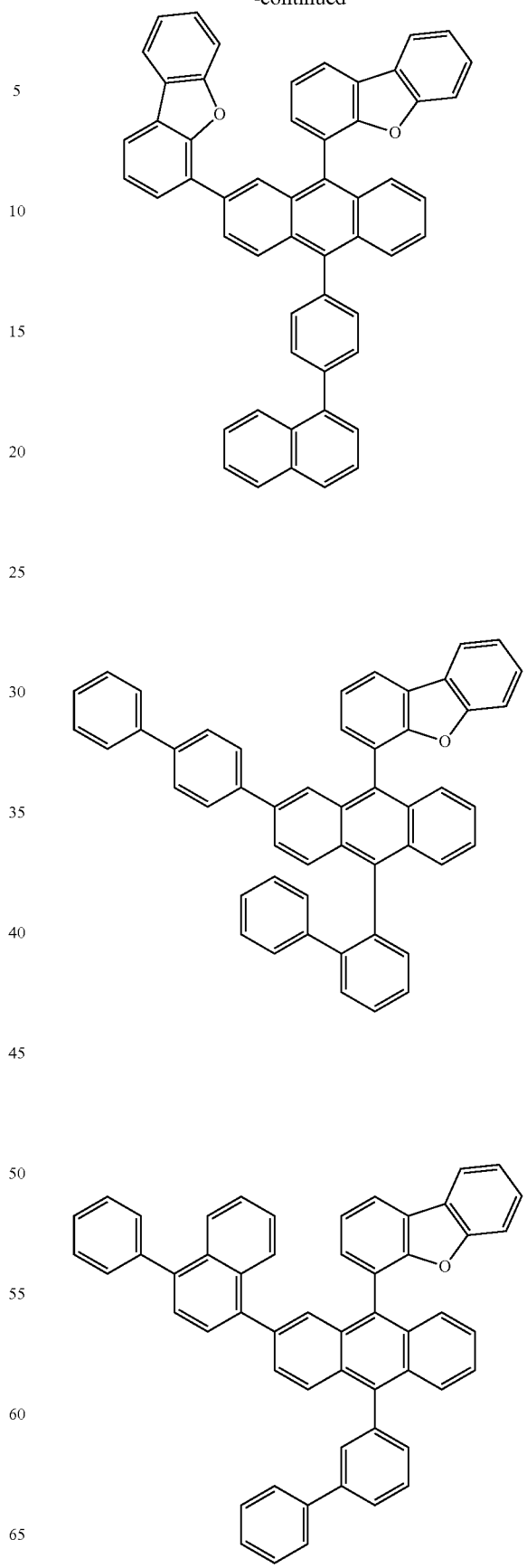

199
-continued
200
-continued
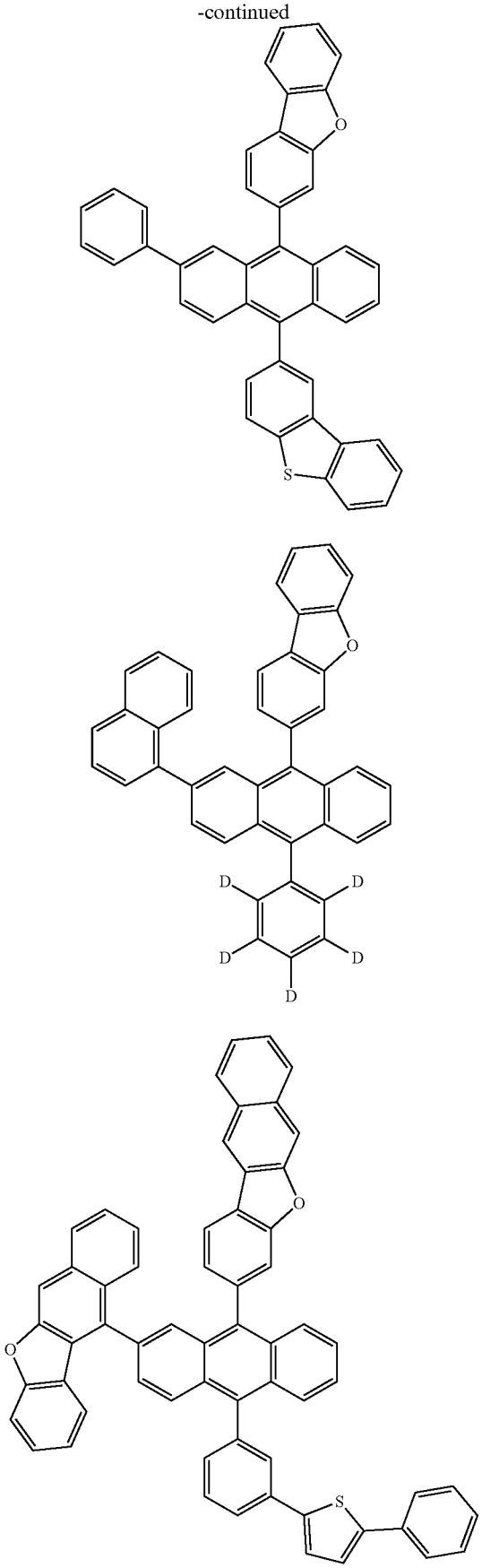
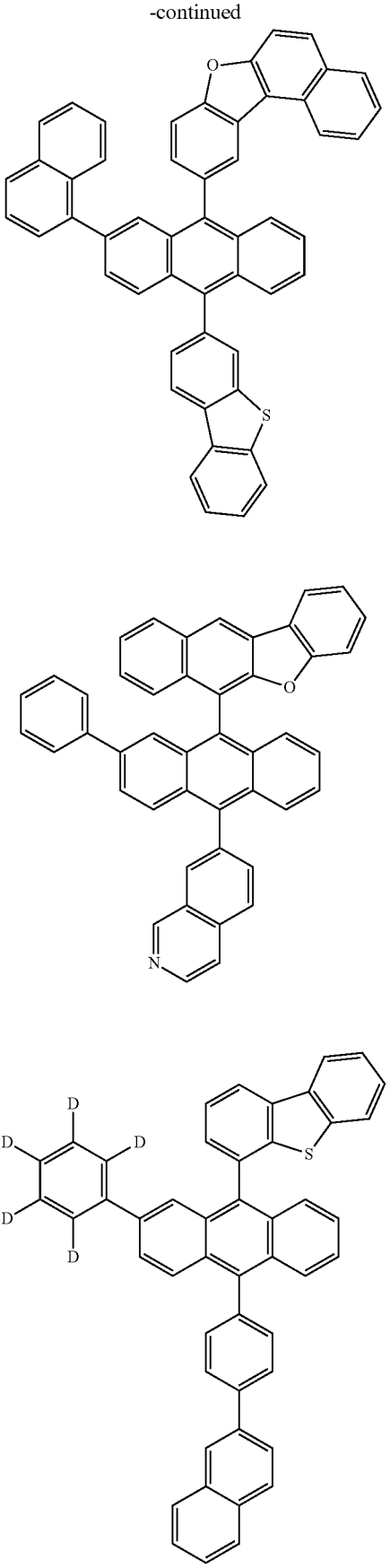

201
-continued
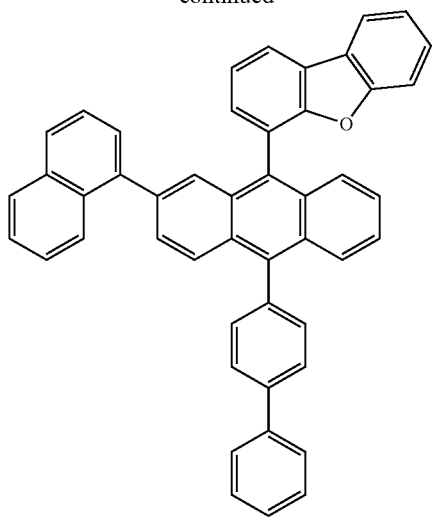
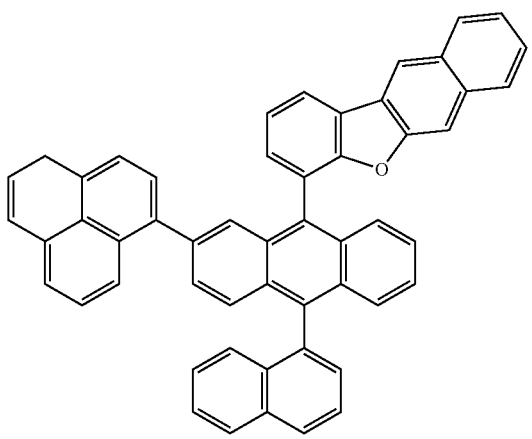
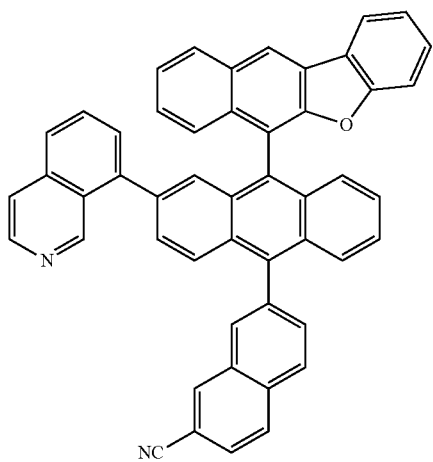
202
-continued
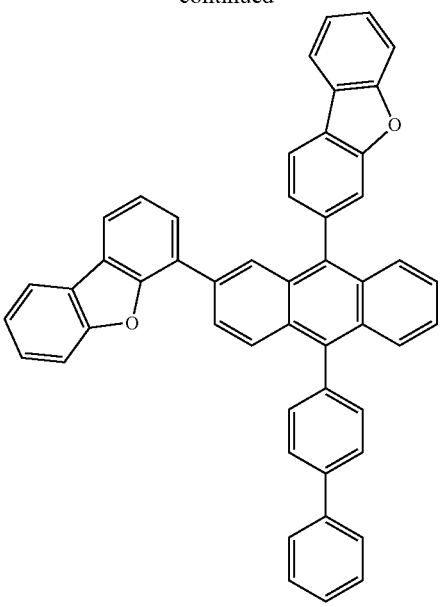
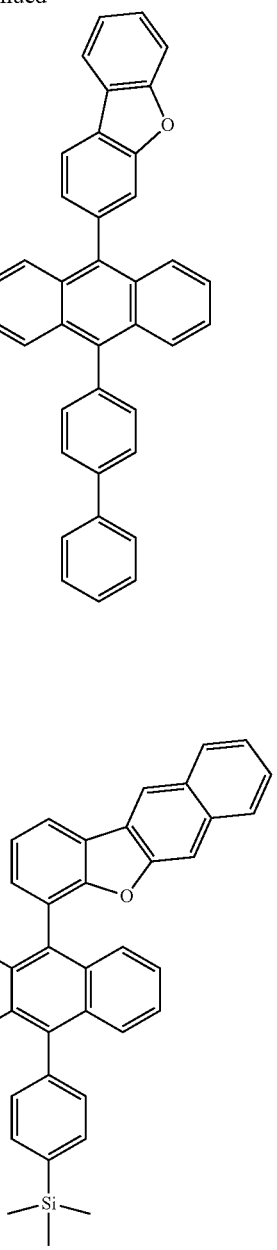

203
-continued
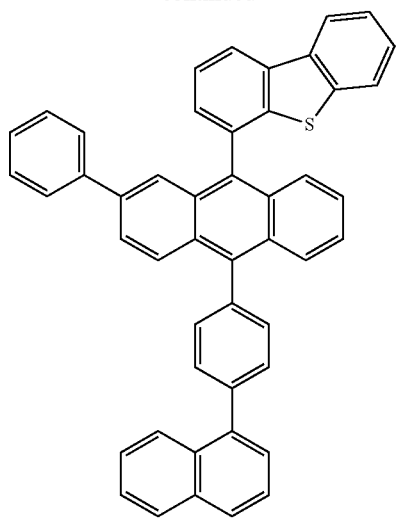
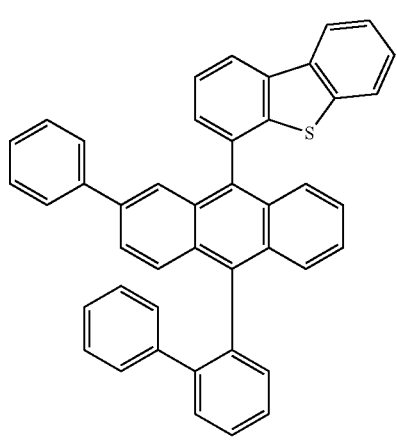
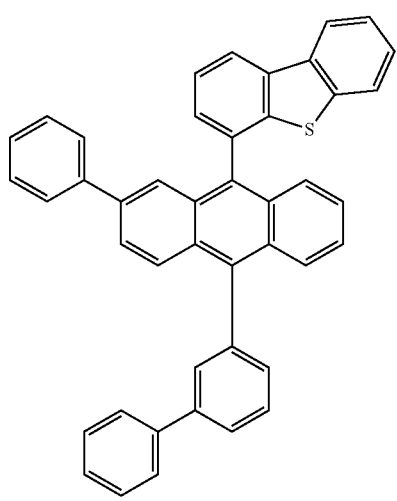
204
-continued
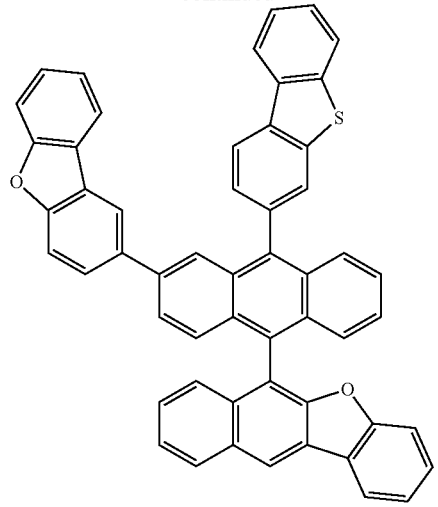
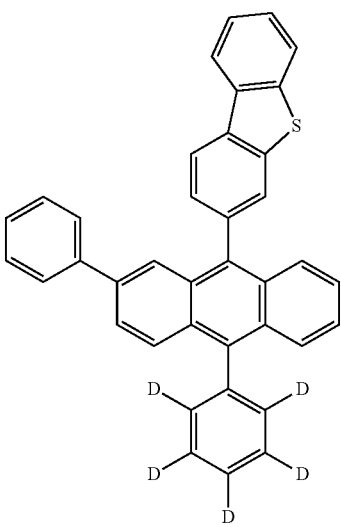
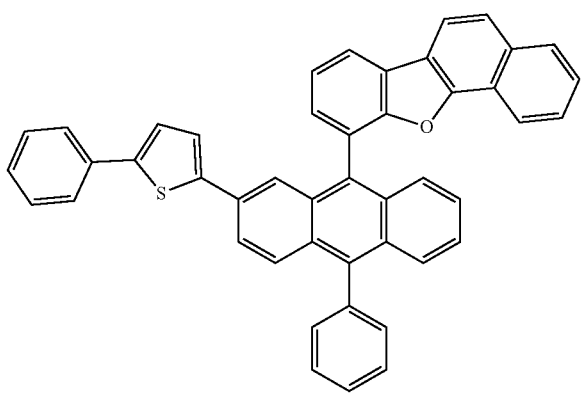

205
-continued
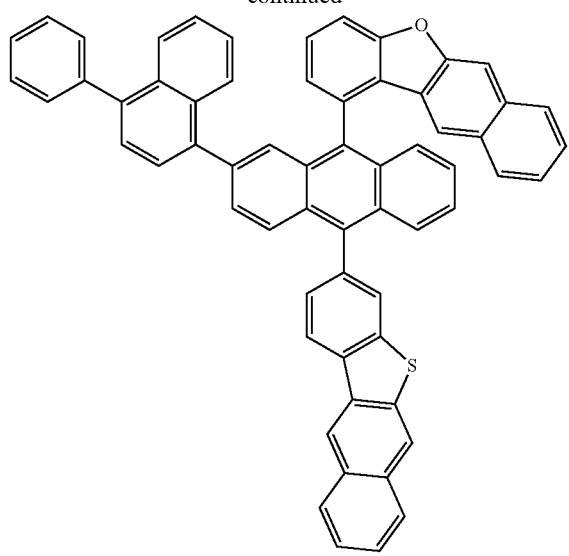
206
-continued
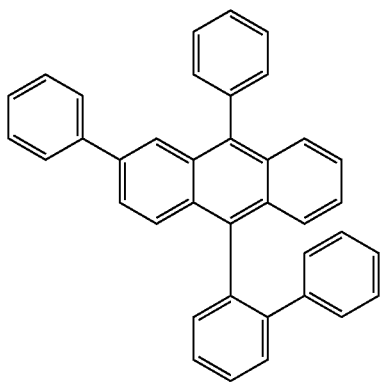
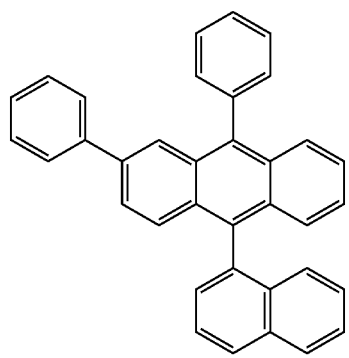
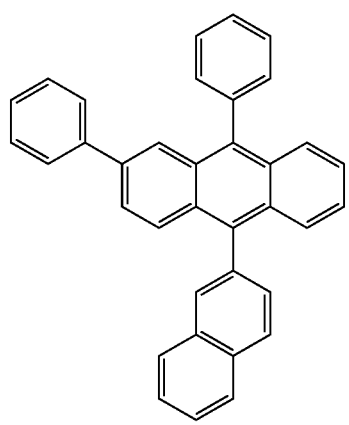
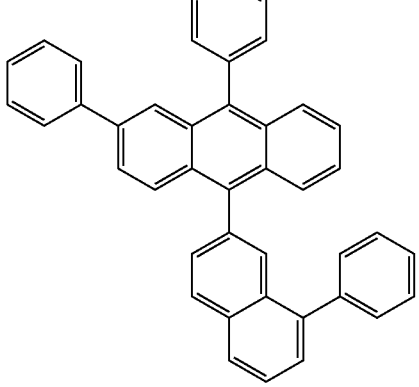

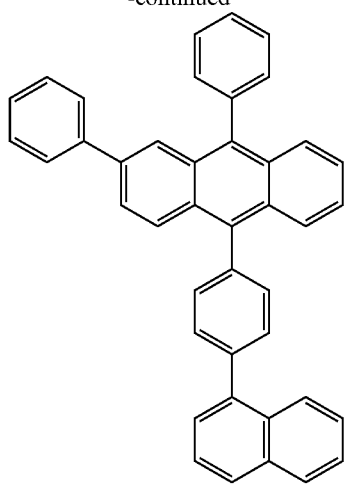
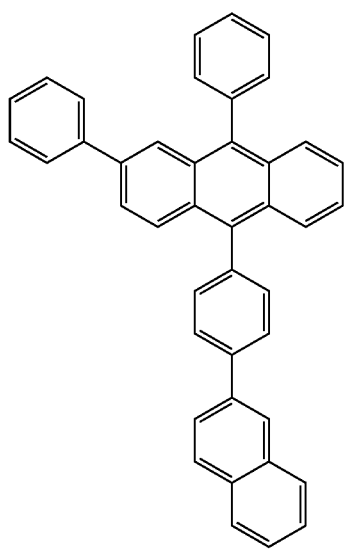
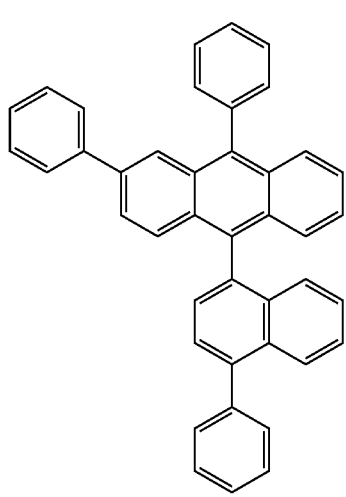
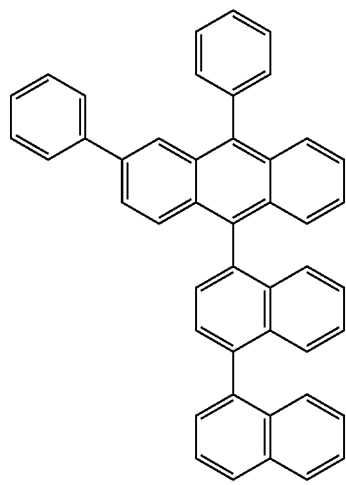
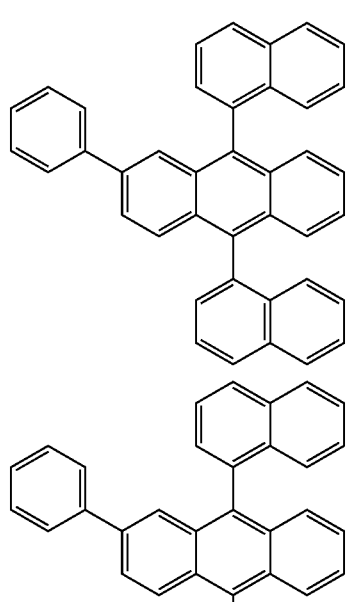
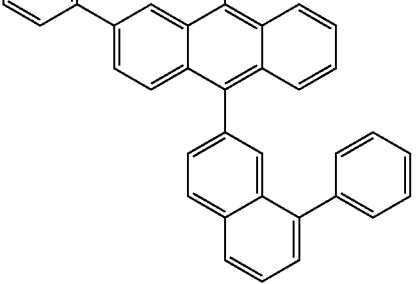

209
-continued
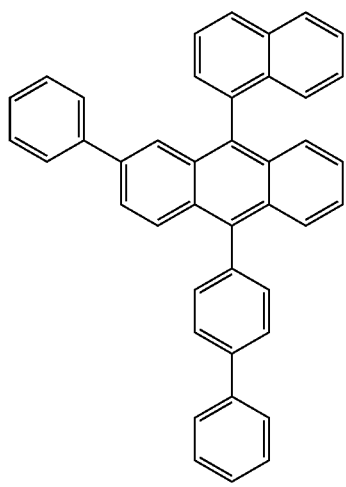
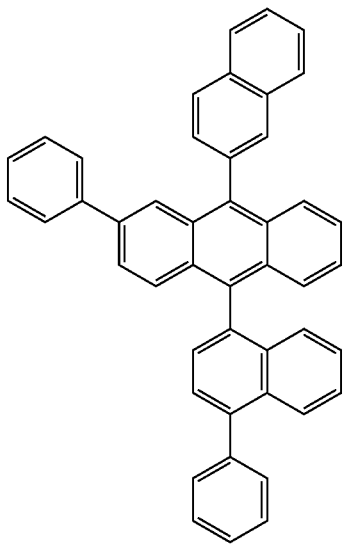
210
-continued
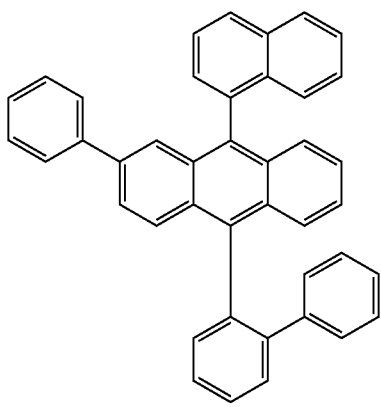
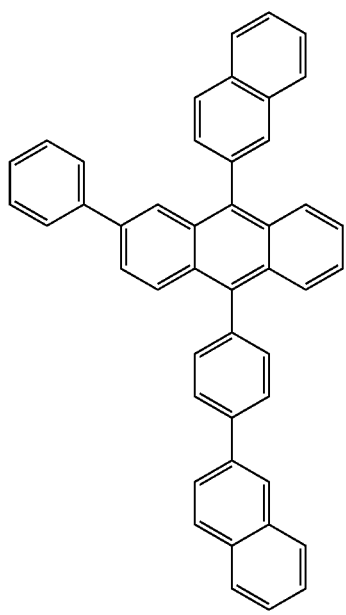

211
-continued
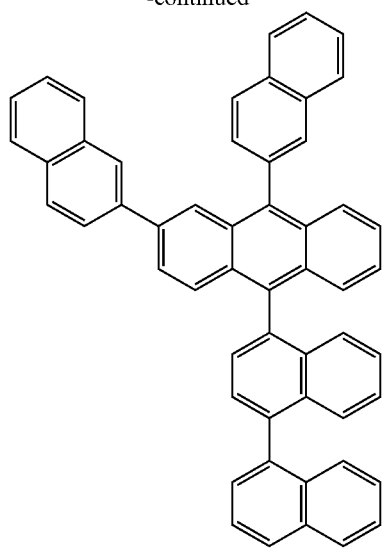
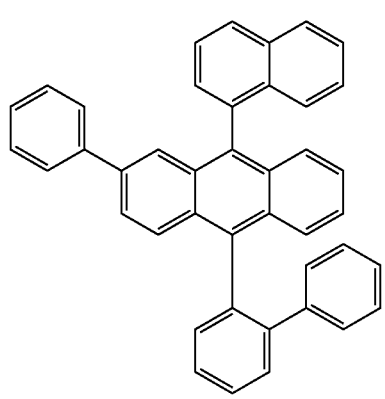
212
-continued
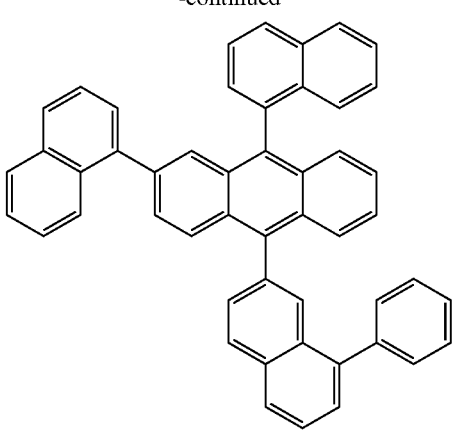
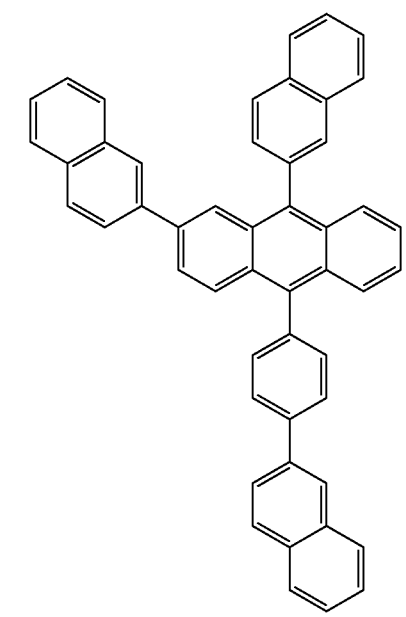
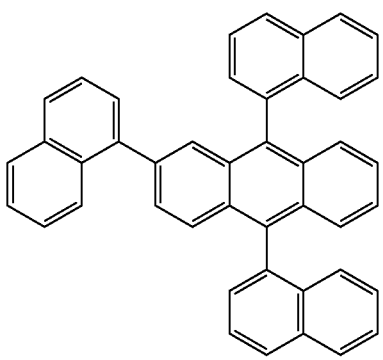

213
-continued
214
-continued
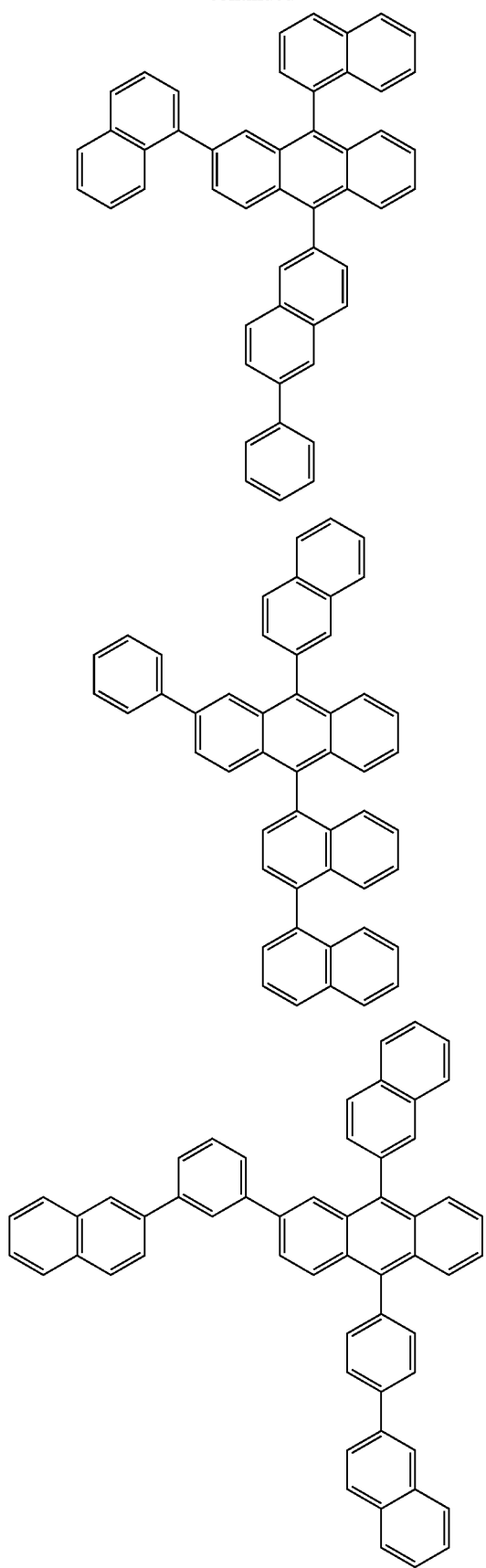
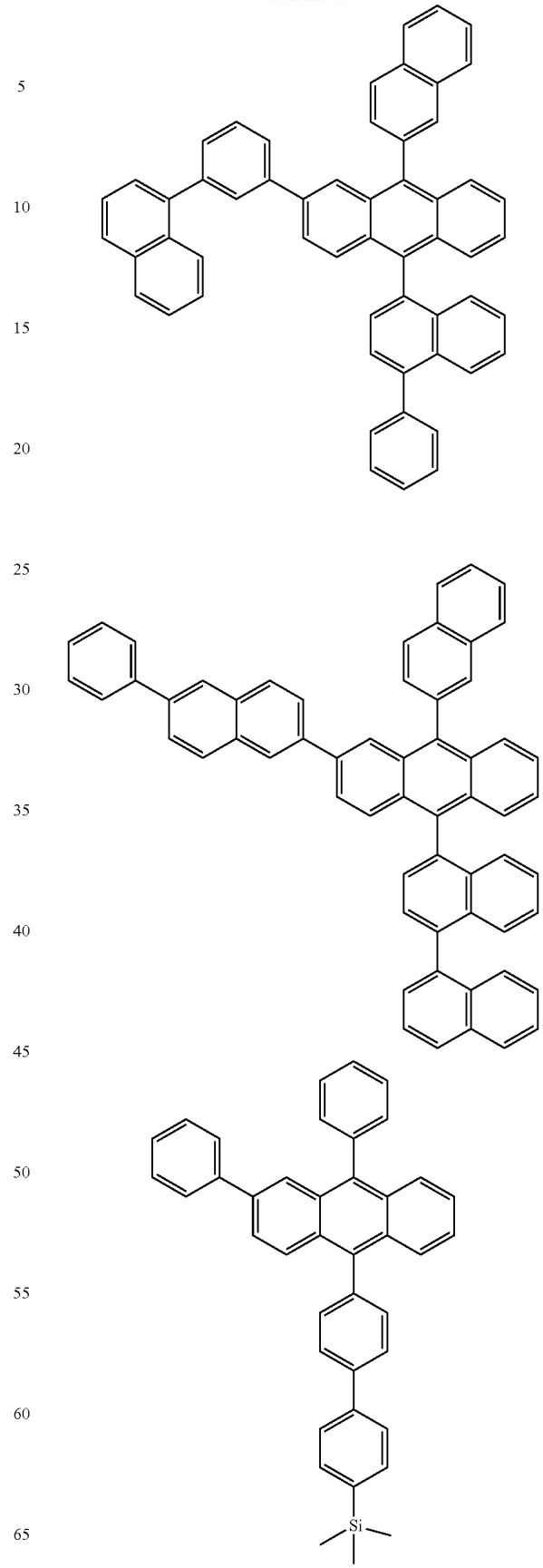

215
-continued
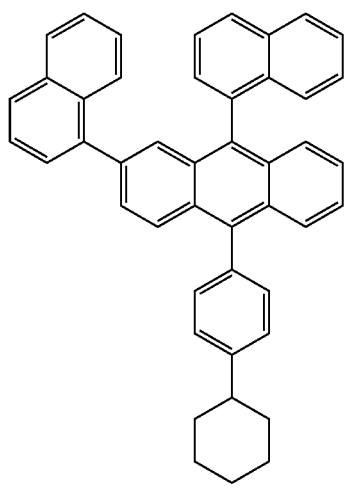
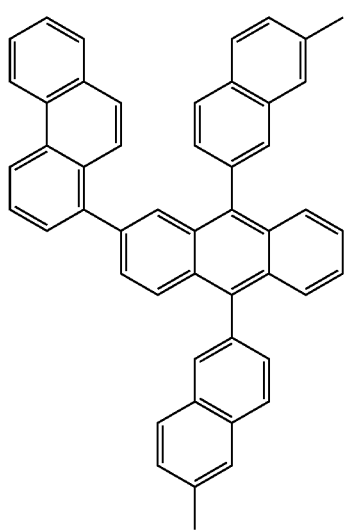
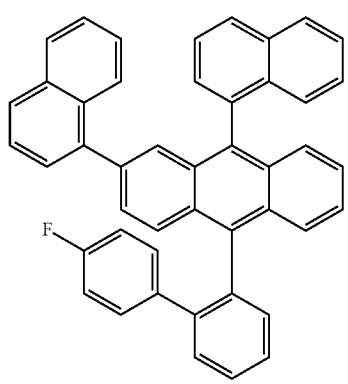
216
-continued
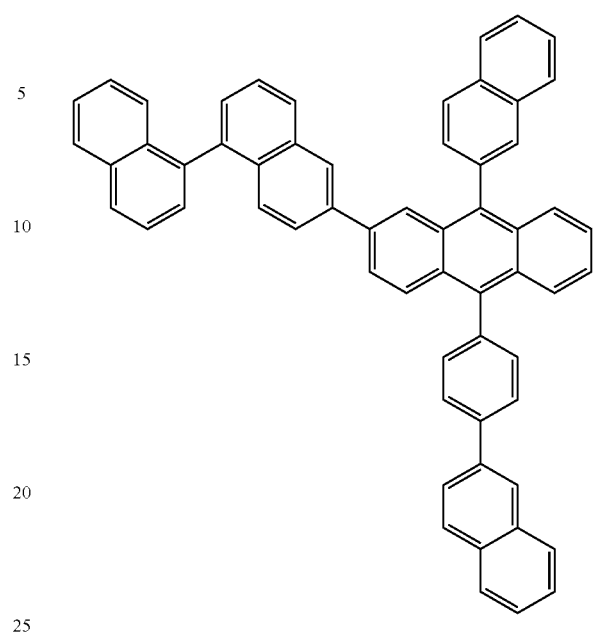

217
-continued
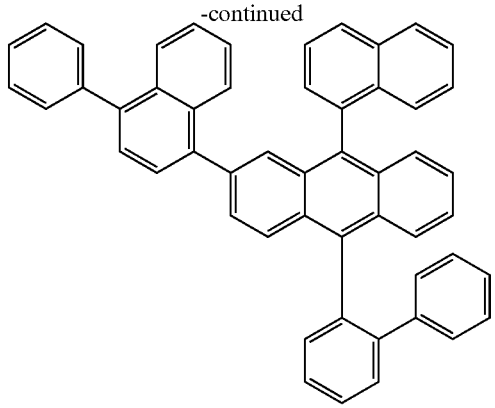
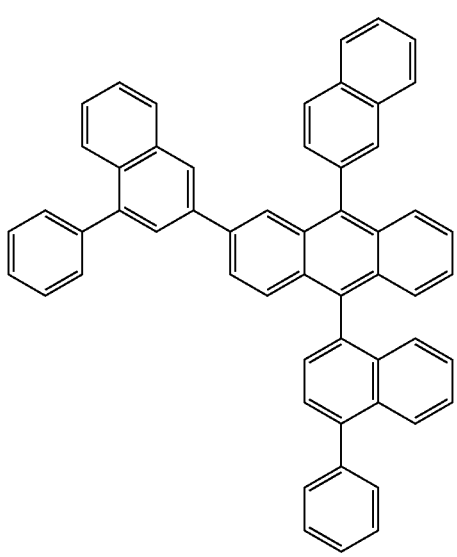
218
-continued
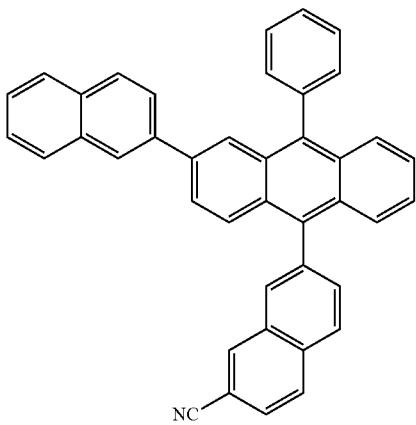
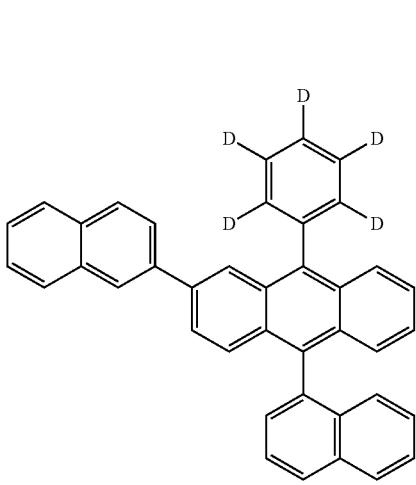
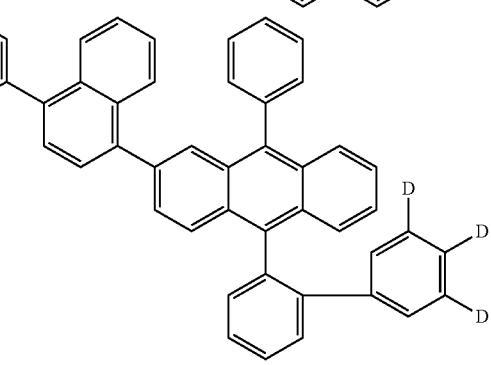
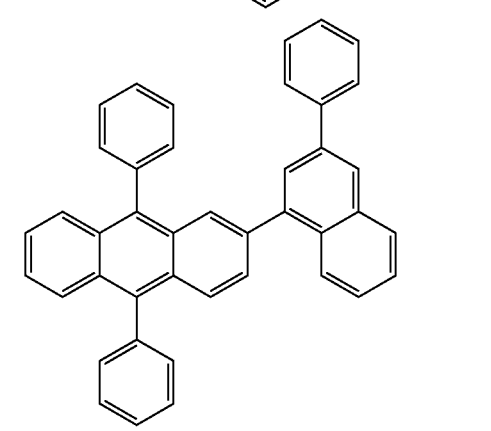

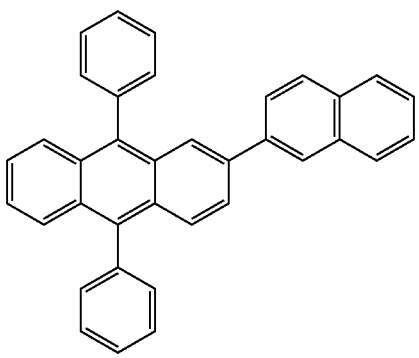
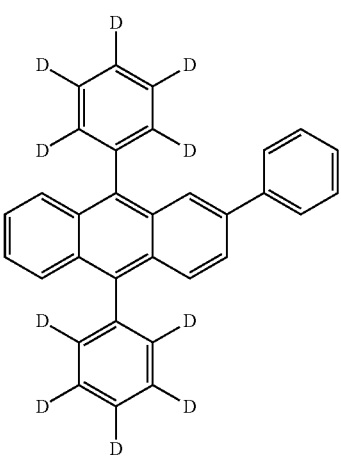
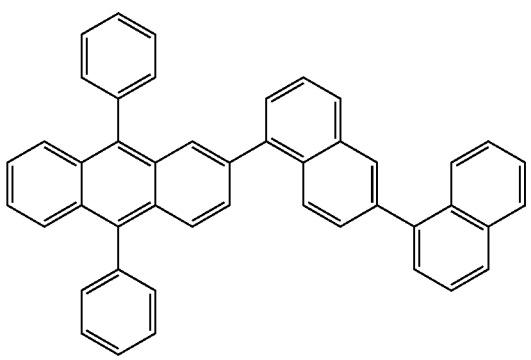
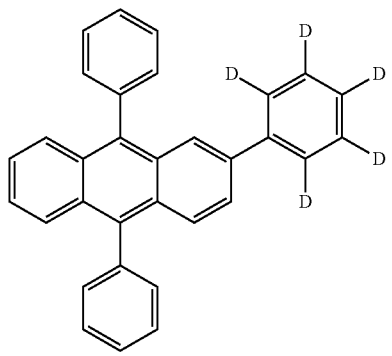
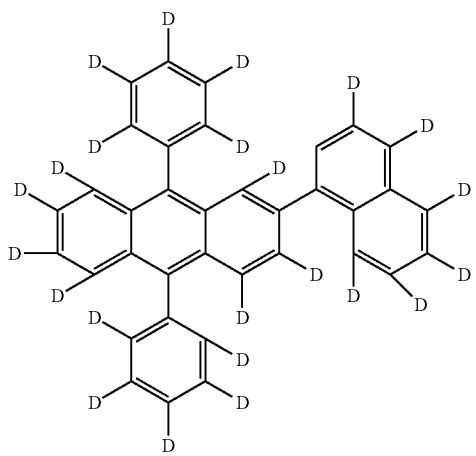
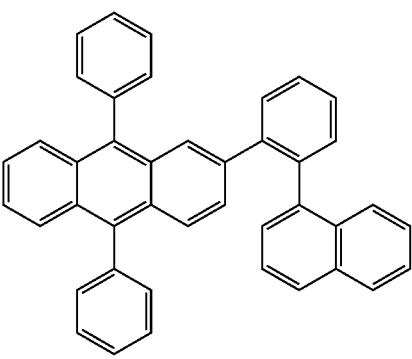
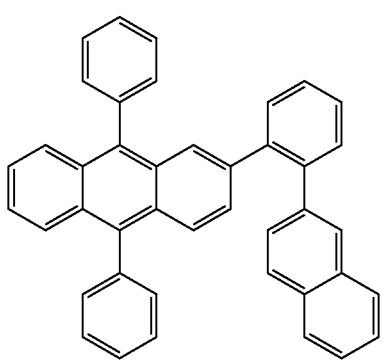
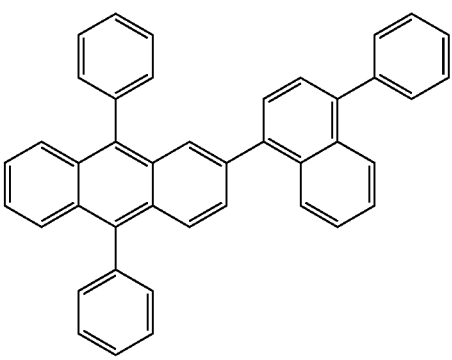

221
-continued
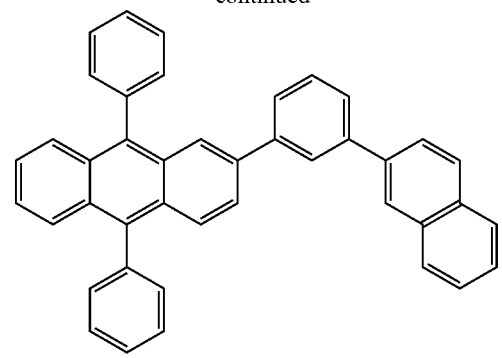
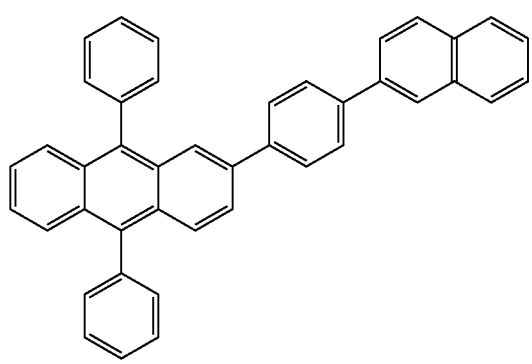
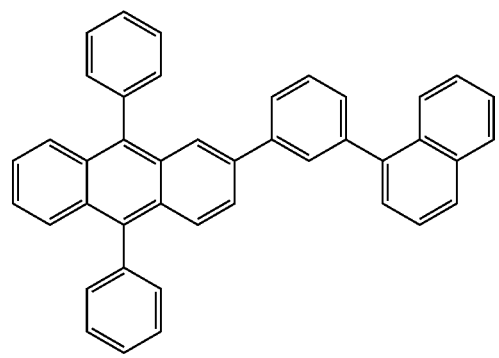
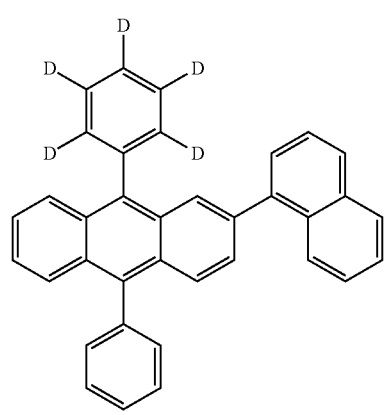
222
-continued
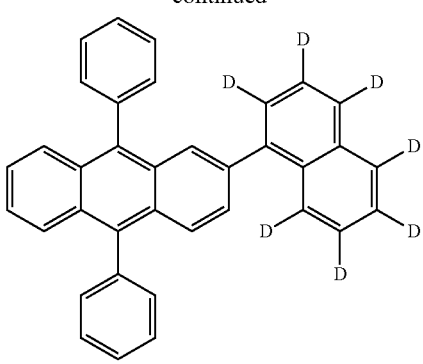
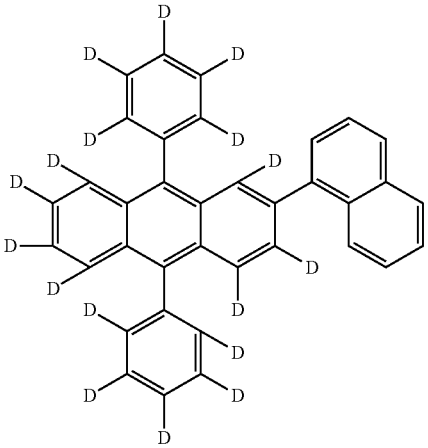
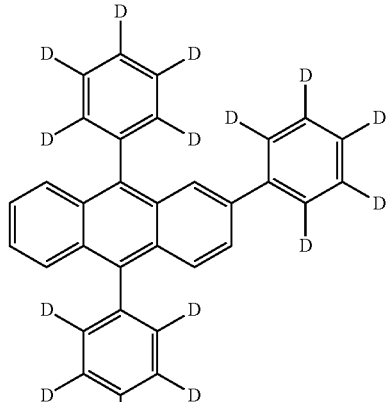
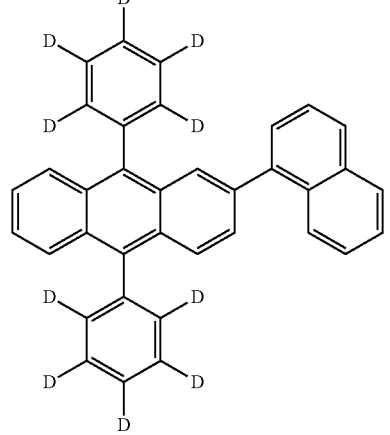

223
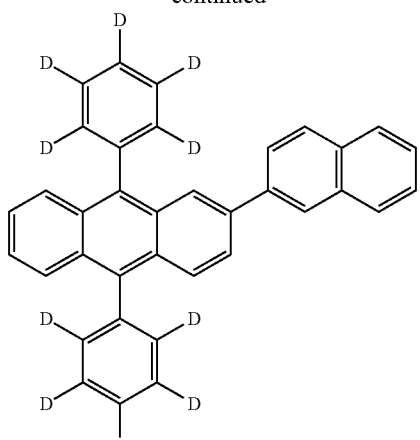
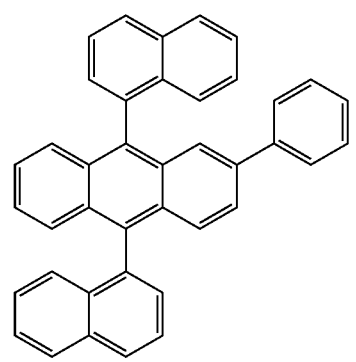
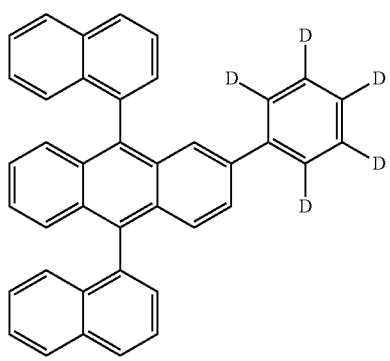
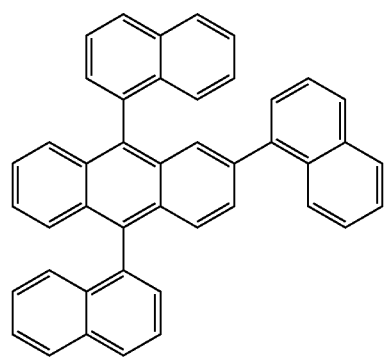
224
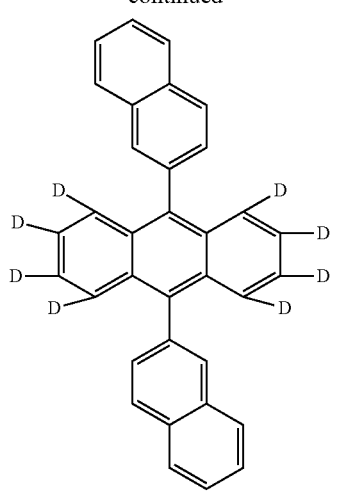
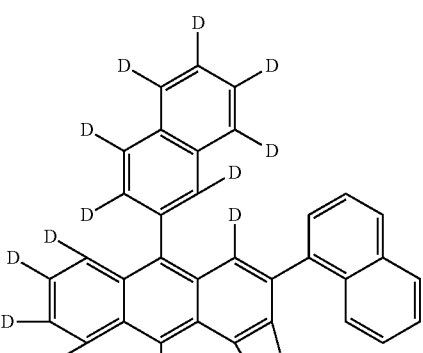
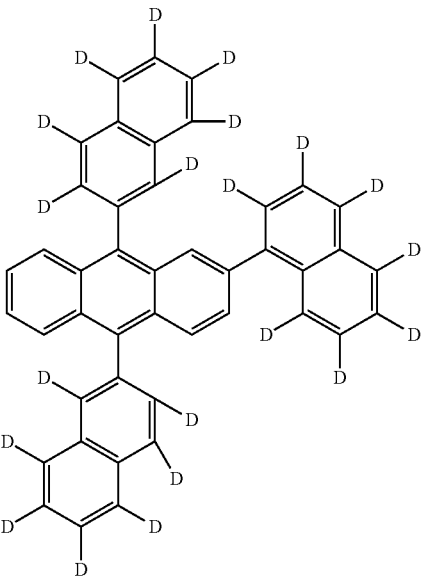

-continued
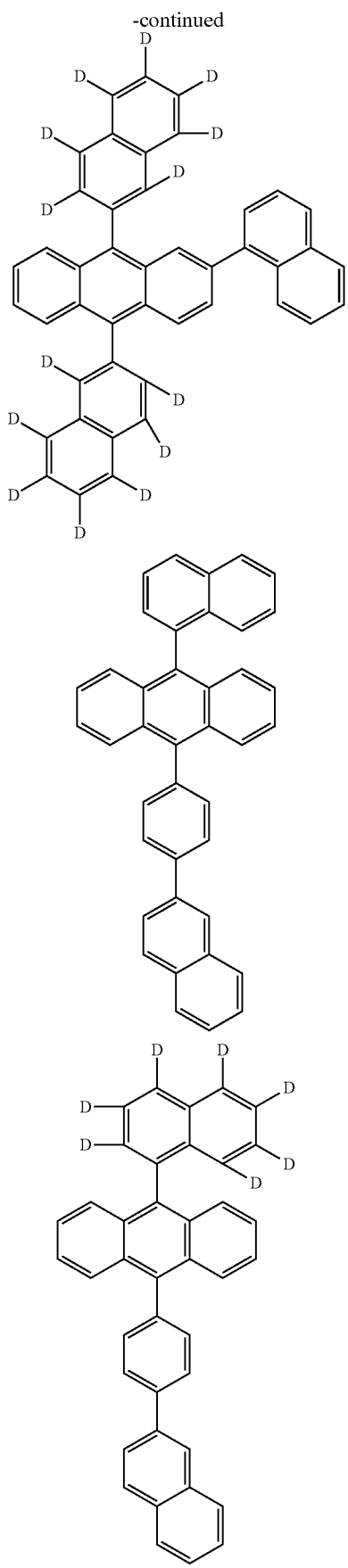
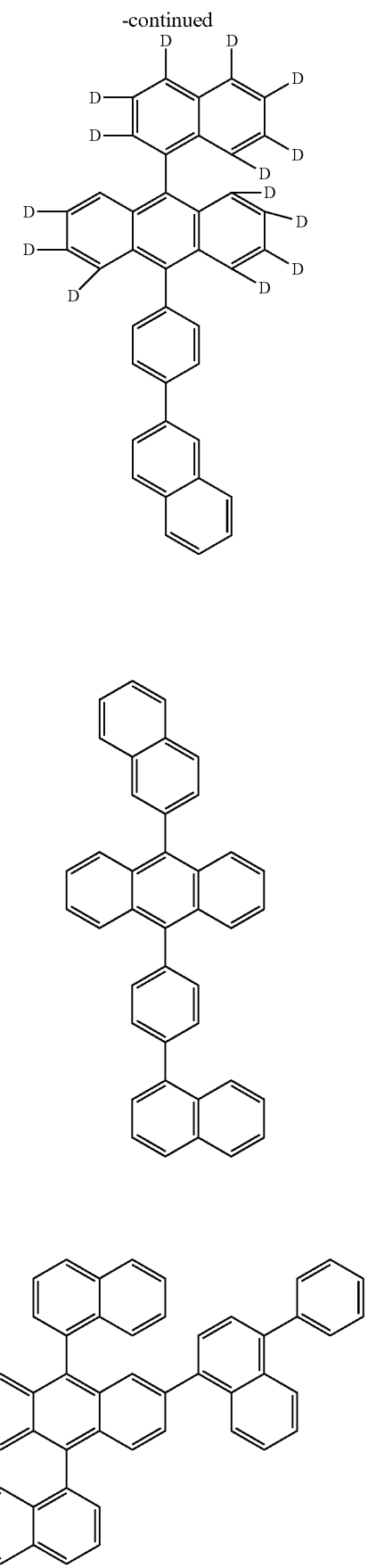

227
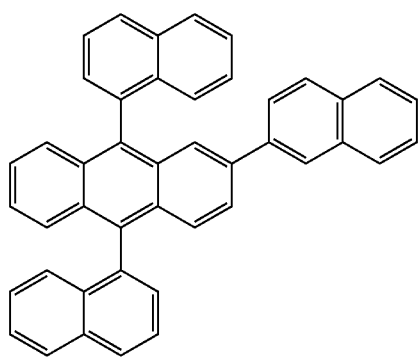
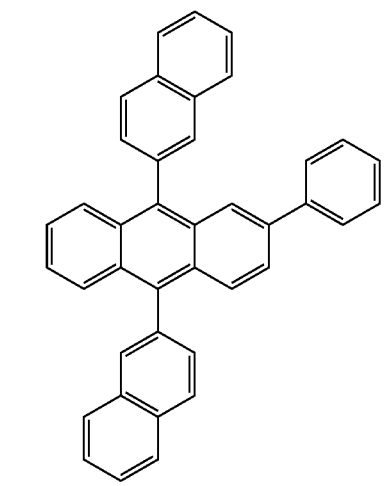
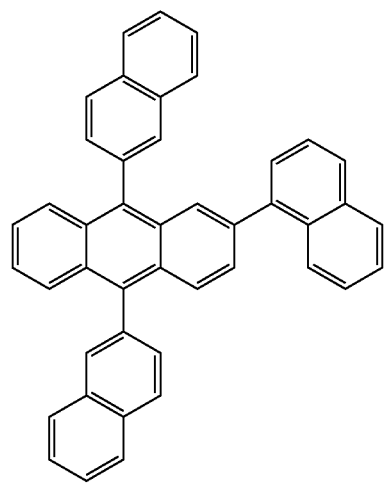
228
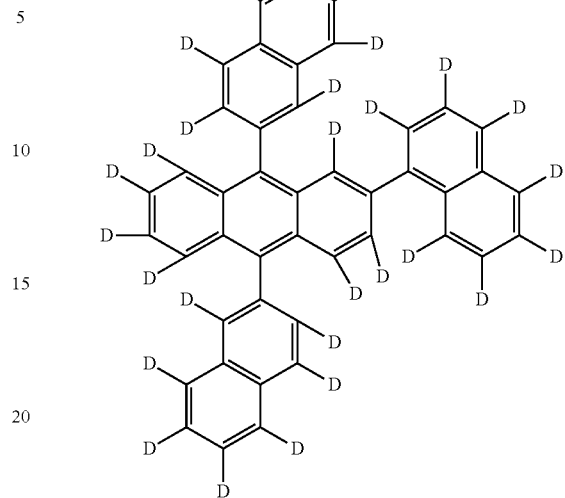
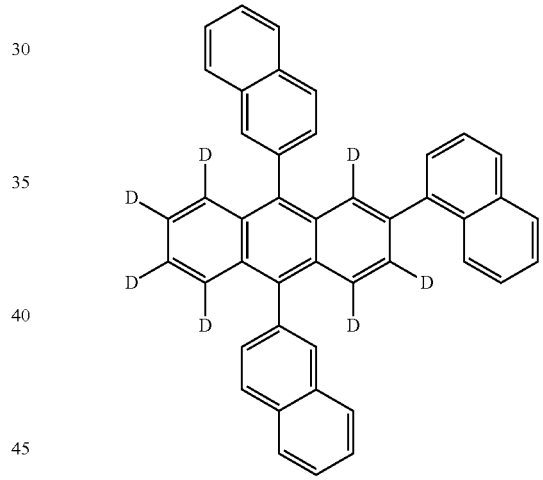
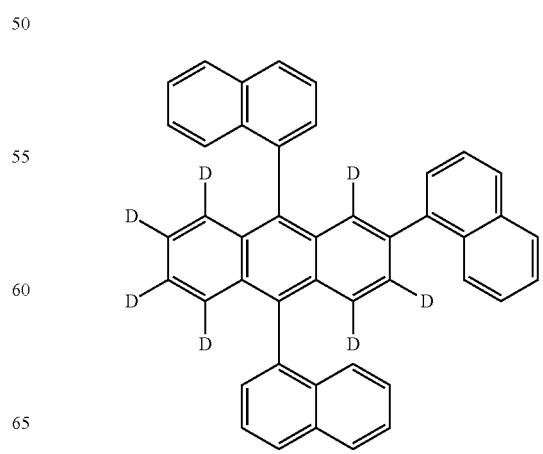

229
-continued
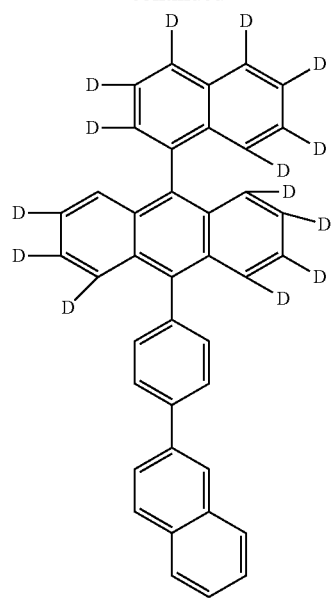
230
-continued
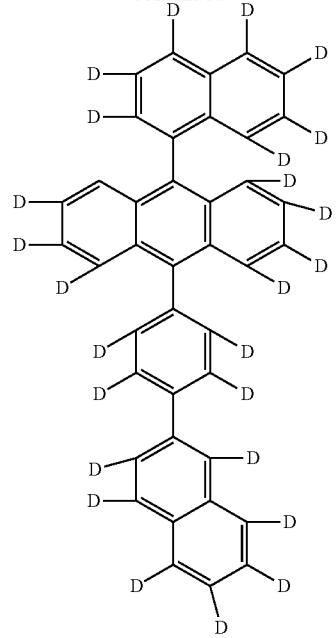
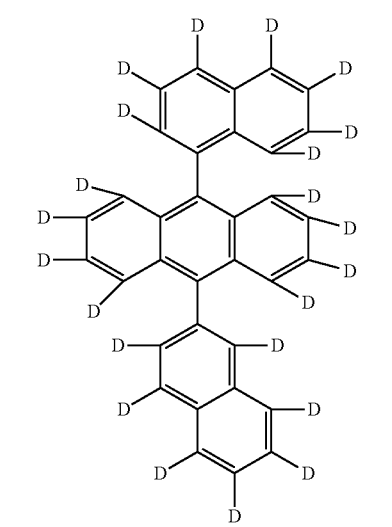
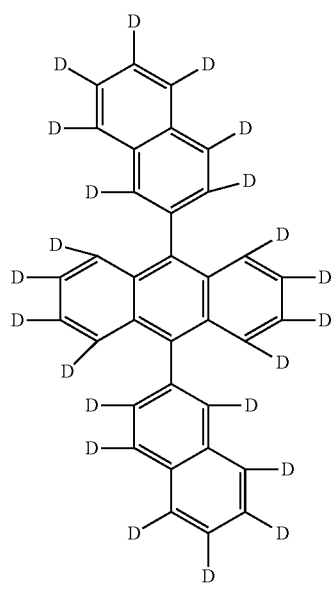
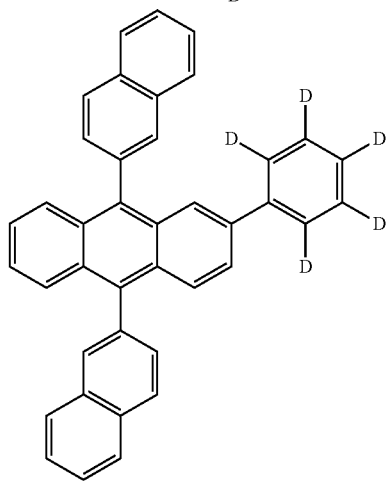

231
-continued
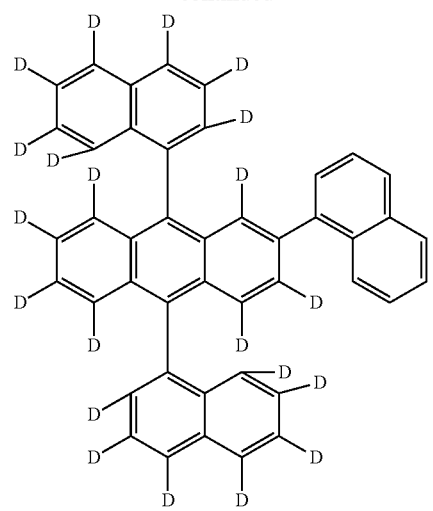
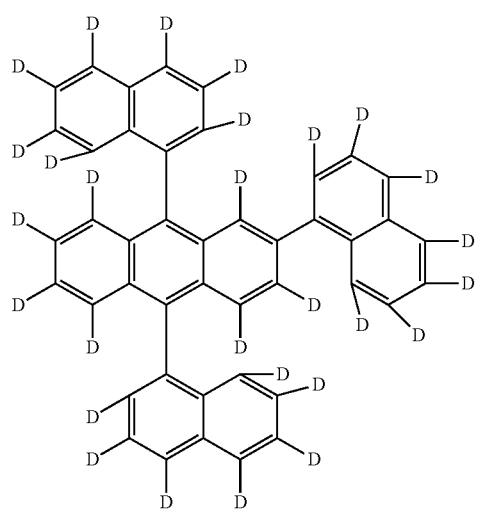
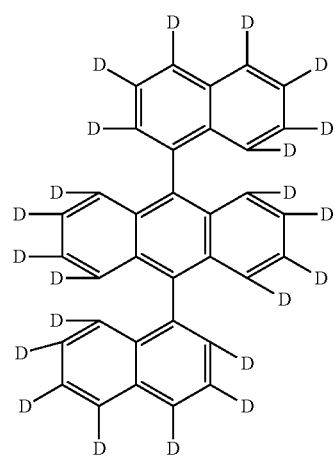
232
-continued
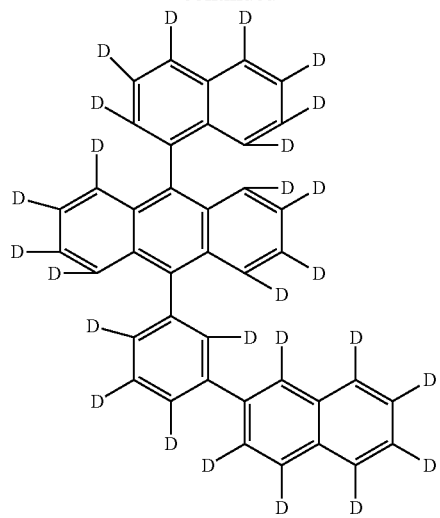
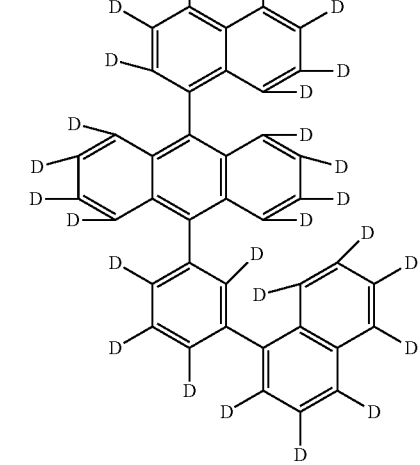
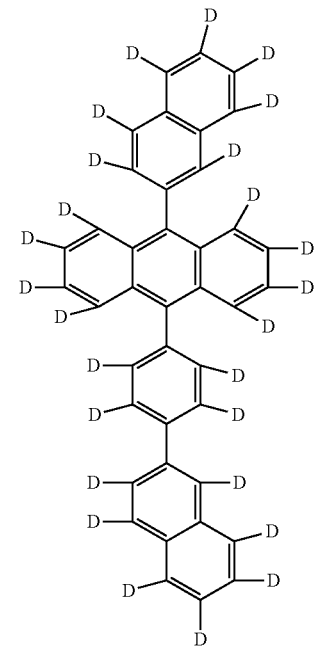

233
-continued
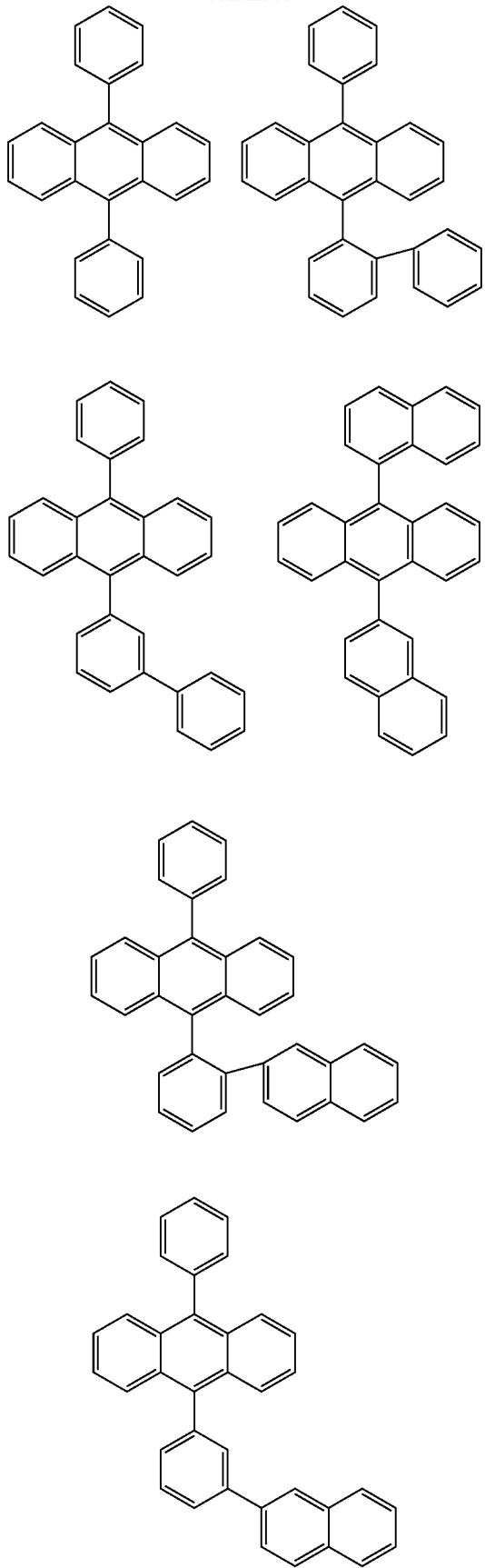
234
-continued
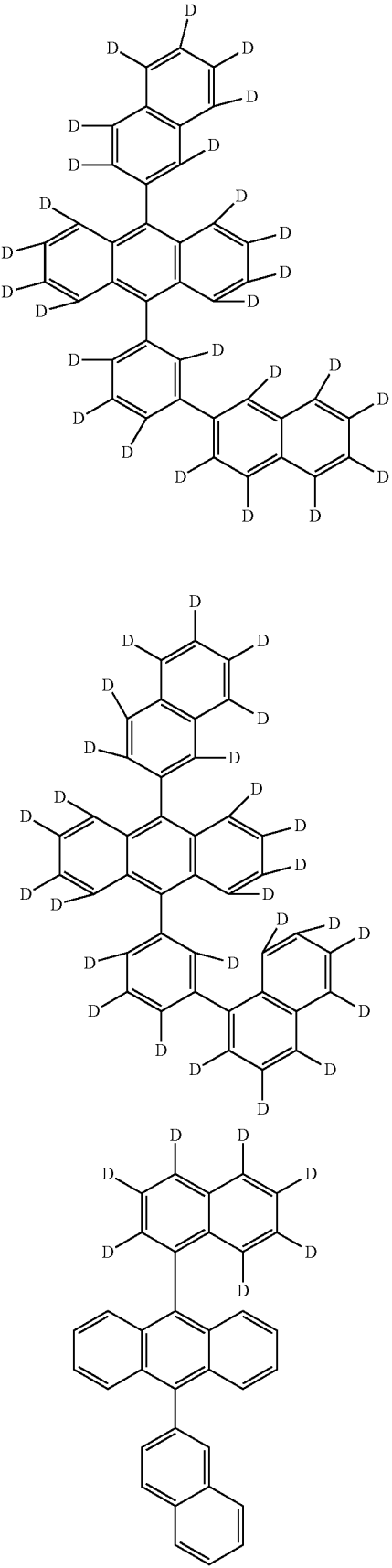

235
-continued
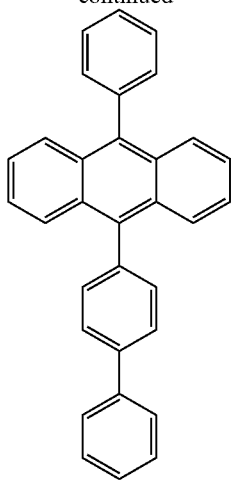
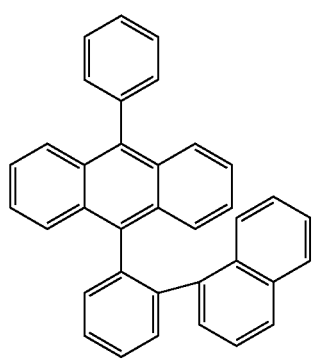
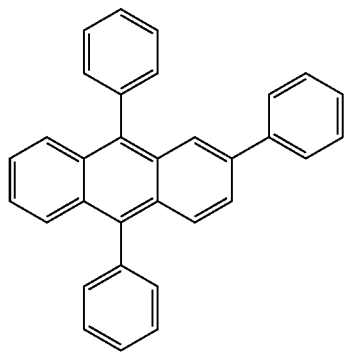
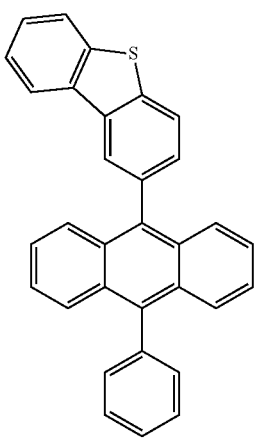
236
-continued
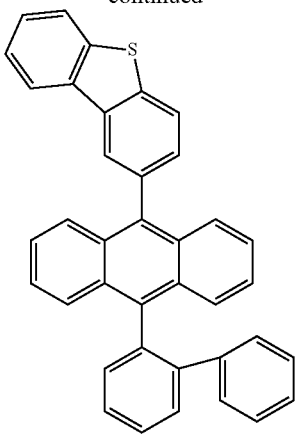
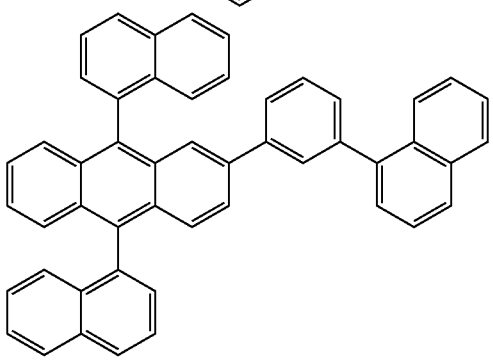
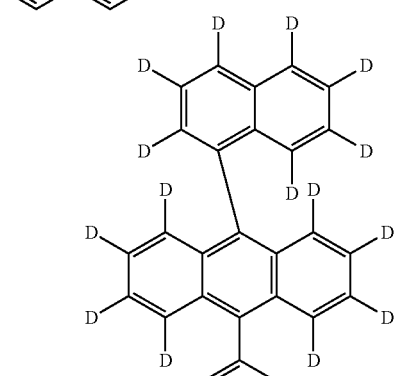
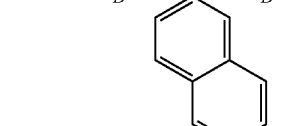
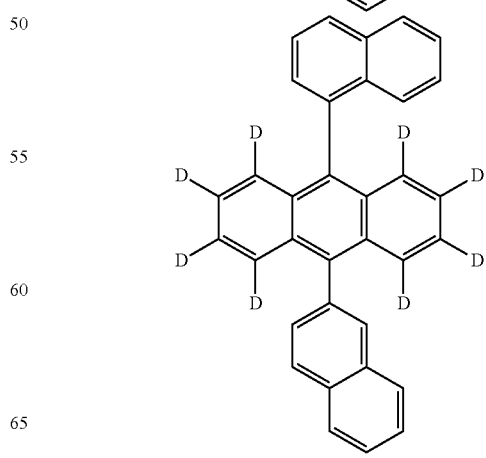

237
-continued
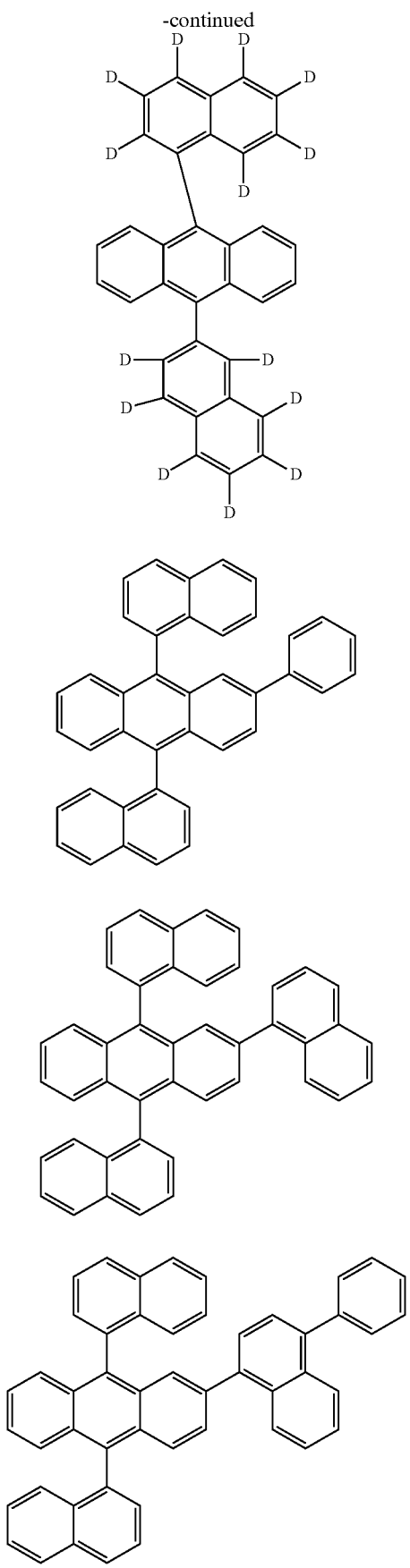
238
-continued
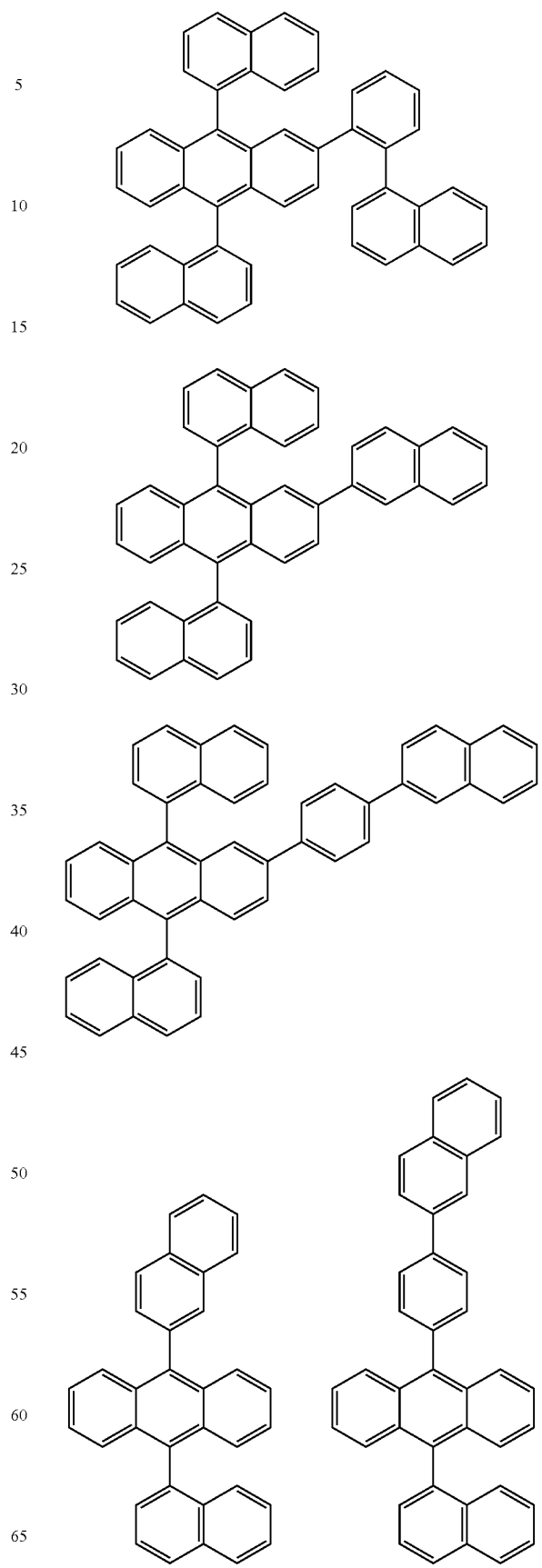

239
-continued
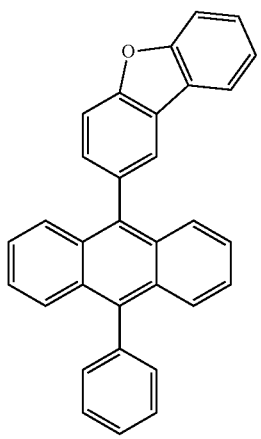
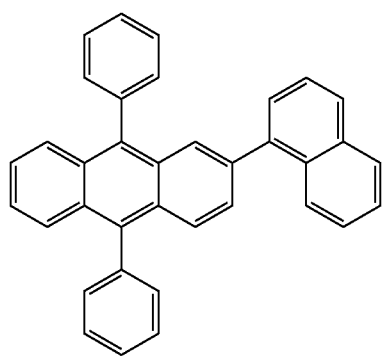
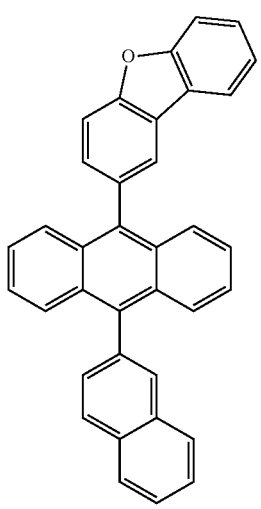
240
-continued
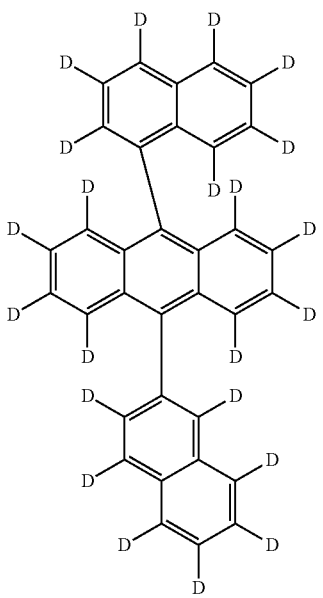
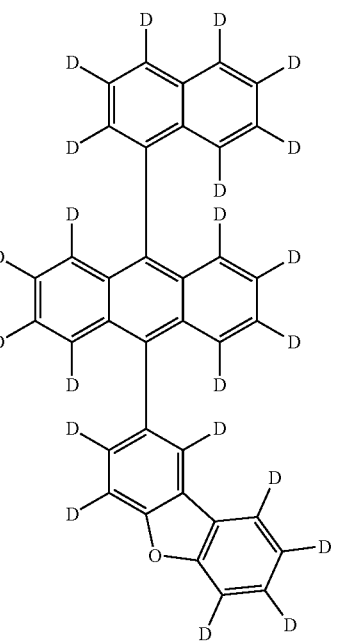

241
-continued
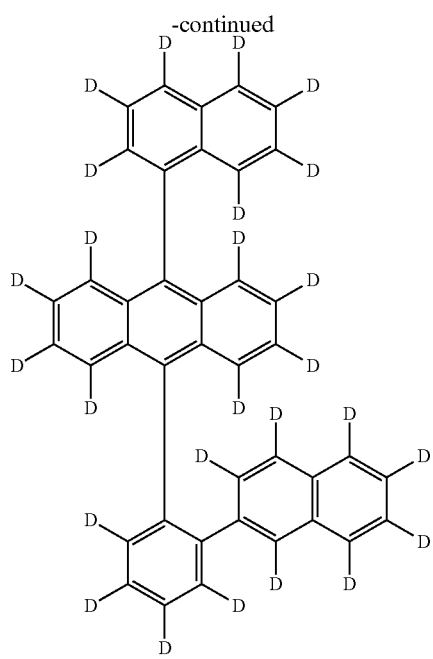
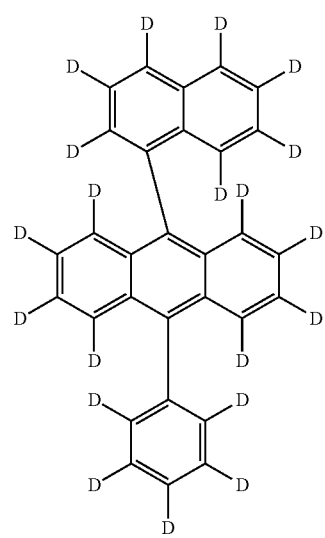
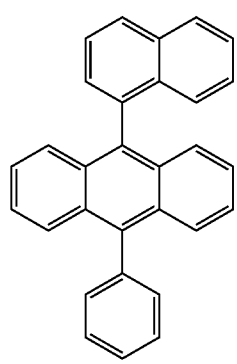
242
-continued
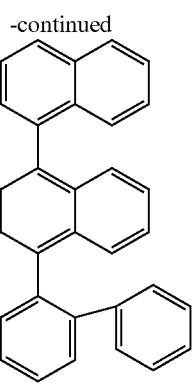
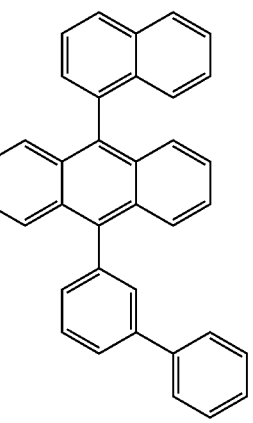
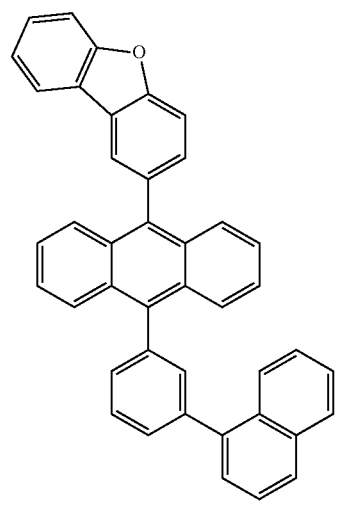

243
-continued
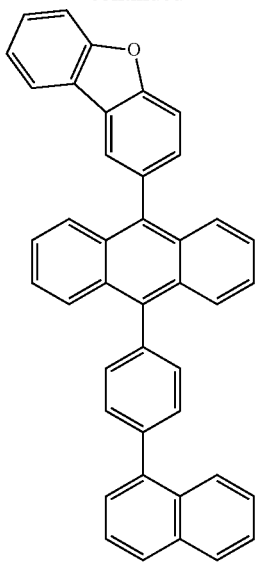
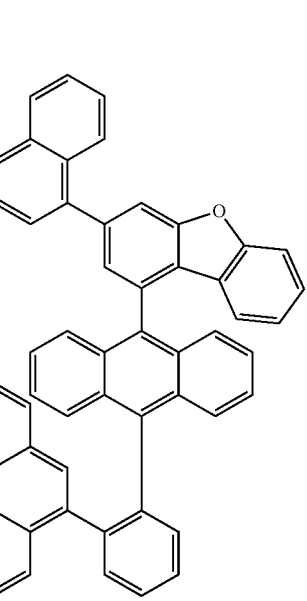
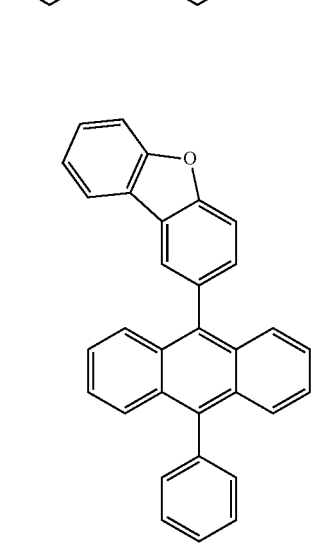
244
-continued
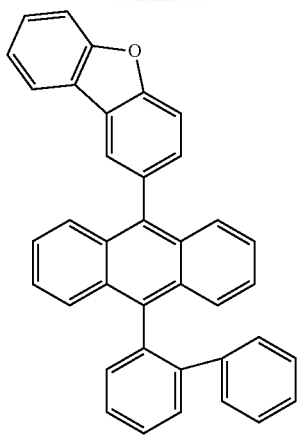
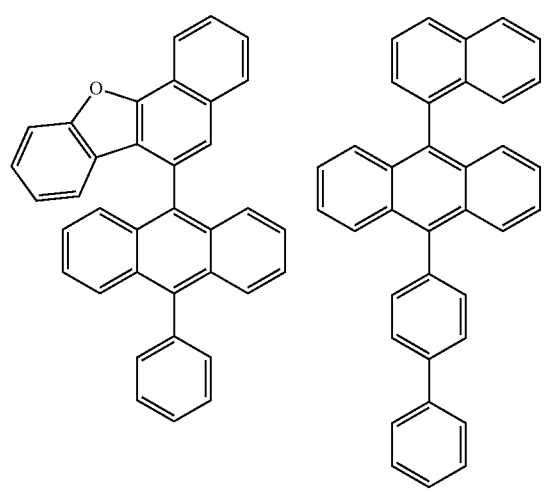
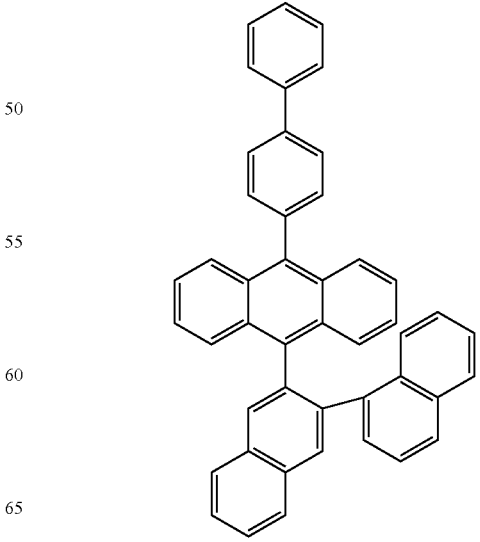

245
-continued
246
-continued
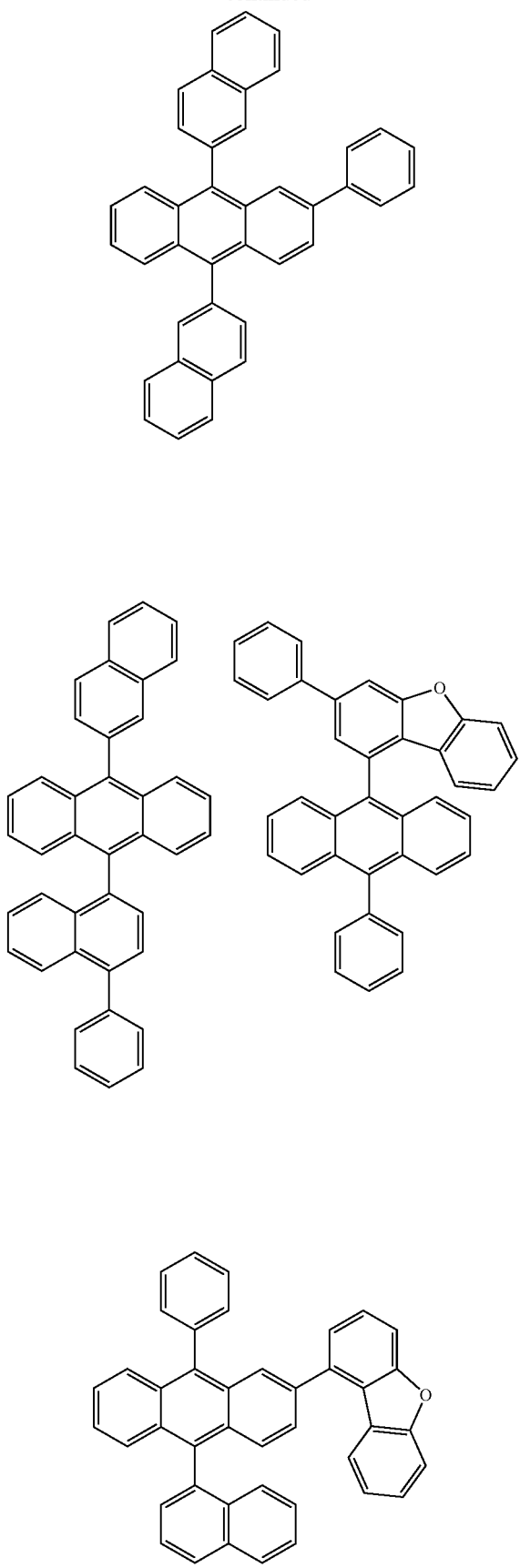
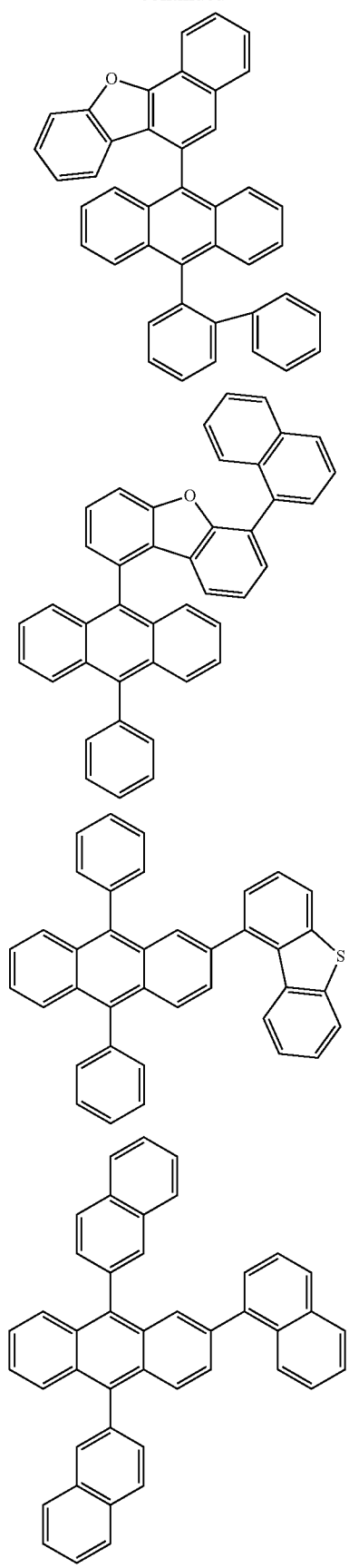

247
-continued
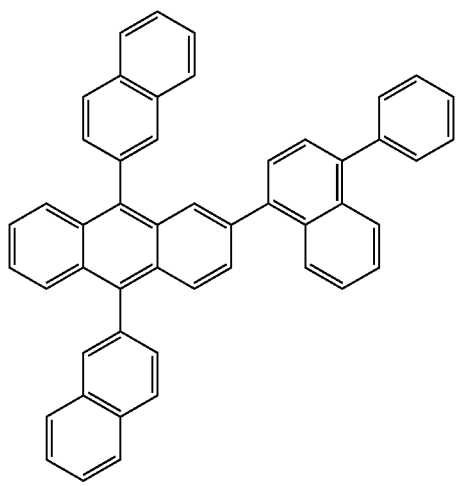
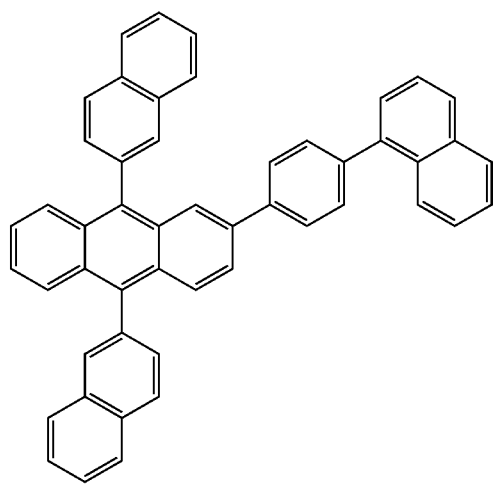
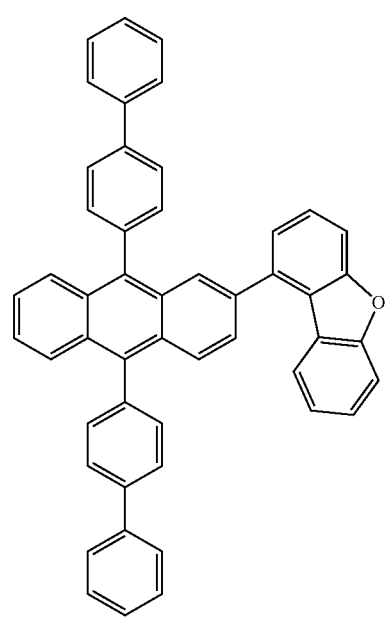
248
-continued
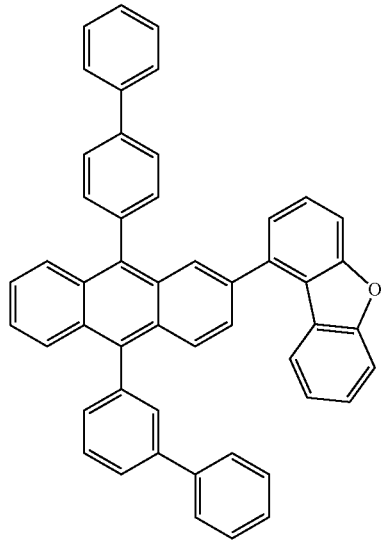
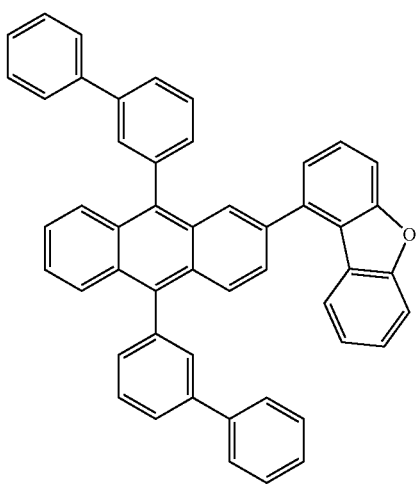
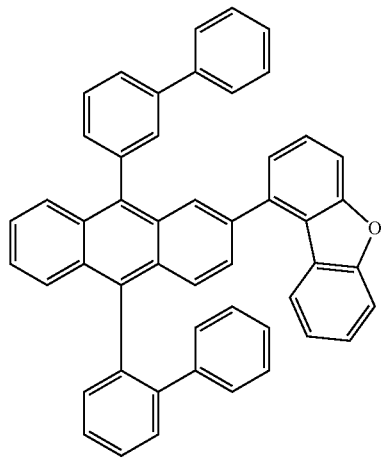

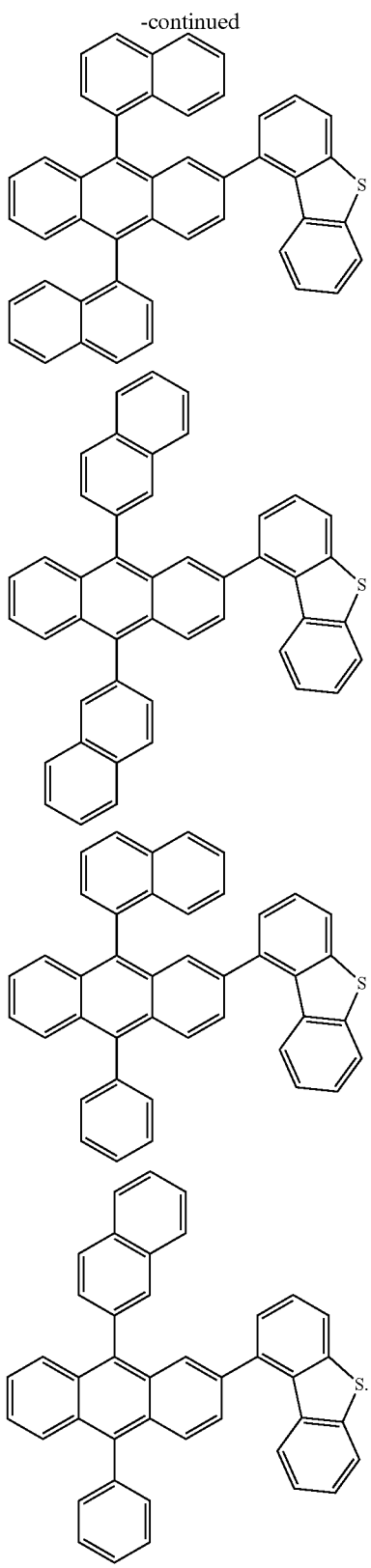

The compound is used as a dopant material for a light emitting layer and can further include an additional dopant.

For the additional dopant, when the light emitting layer emits red light, it is possible to use a phosphorescent material such as bis(1-phenyl-isoquinoline)acetylacetonate iridium (PIQIr(acac)), bis(1-phenylquinoline)acetylacetonate iridium (PQIr(acac)), tris(1-phenylquinoline)iridium (PQIr), or octaethylporphyrin platinum (PtOEP), or a fluorescent material such as tris(8-hydroxyquinolino)aluminum ($Alq_3$) as a light emitting dopant, but the light emitting dopant is not limited thereto. When the light emitting layer emits green light, it is possible to use a phosphorescent material such as fac-tris(2-phenyl-pyridine)iridium ($Ir(ppy)_3$), or a fluorescent material such as tris(8-hydroxyquinolino)aluminum ($Alq_3$), as the light emitting dopant, but the light emitting dopant is not limited thereto. When the additional light emitting layer emits blue light, it is possible to use a phosphorescent material such as $(4,6-F2ppy)_2Irpic$, or a fluorescent material such as spiro-DPVBi, spiro-6P, distyryl benzene (DSB), distyryl arylene (DSA), a PFO-based polymer or a PPV-based polymer as the light emitting dopant, but the light emitting dopant is not limited thereto.

In an exemplary embodiment of the present specification, the compound is a dopant, specifically a fluorescent dopant, and more specifically a blue fluorescent dopant.

In an exemplary embodiment of the present specification, a maximum light emission peak of the compound of Formula 1 is 420 nm to 480 nm.

In an exemplary embodiment of the present specification, the light emitting layer includes a host and a dopant at a mass ratio of 99:1 to 1:99.

In an exemplary embodiment of the present specification, the light emitting layer includes a host and a dopant at a mass ratio of 99:1 to 10:90.

In an exemplary embodiment of the present specification, the light emitting layer includes a host and a dopant at a mass ratio of 99:1 to 50:50.

In an exemplary embodiment of the present specification, the dopant of the light emitting layer includes the compound of Formula 1, and when the host of the light emitting layer includes the compound of Formula 5, the content of the compound of Formula 1 can be 0.01 part by weight to 30 parts by weight, specifically 0.1 part by weight to 20 parts by weight, and more specifically 0.5 part by weight to 10 parts by weight, when the weight of the compound of Formula 5 is set to 100 parts by weight.

The electron transport layer is a layer which accepts electrons from an electron injection layer and transports the electrons to a light emitting layer, and an electron transport material is suitably a material having high electron mobility which can proficiently accept electrons from a second electrode and transfer the electrons to a light emitting layer. Specific examples thereof include: Al complexes of 8-hydroxyquinoline, complexes including Alq3, organic radical compounds, hydroxyflavone-metal complexes, and the like, but are not limited thereto. The electron transport layer can be used with any desired cathode material, as used according to the related art. In particular, examples of an appropriate cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a second electrode, and an excellent effect of injecting electrons into a light emitting layer or a light emitting material, prevents excitons produced from a light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxy-quinolinato) manganese, tris(8-hydroxyquinolinato) aluminum, tris (2-methyl-8-hydroxyquinolinato) aluminum, tris(8-hydroxyquinolinato) gallium, bis(10-hydroxy-benzo[h] quinolinato) beryllium, bis(10-hydroxybenzo[h]-quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a negative electrode, and can be generally formed under the same conditions as those of the hole injection layer. Specific examples thereof include an oxadiazole derivative or a triazole derivative, a phenanthroline derivative, BCP, an aluminum complex, and the like, but are not limited thereto.

An electron blocking layer can be provided between the hole transport layer and the light emitting layer. For the electron blocking layer, materials known in the art can be used.

The organic light emitting device according to the present specification can be a top emission type, a bottom emission type, or a dual emission type according to the materials to be used.

A core structure can be prepared, as in the following reaction schemes, from the compound of Formula 1 of the present specification. The substituent can be bonded by a method known in the art, and the type and position of the substituent and the number of substituents can be changed according to the technology known in the art.

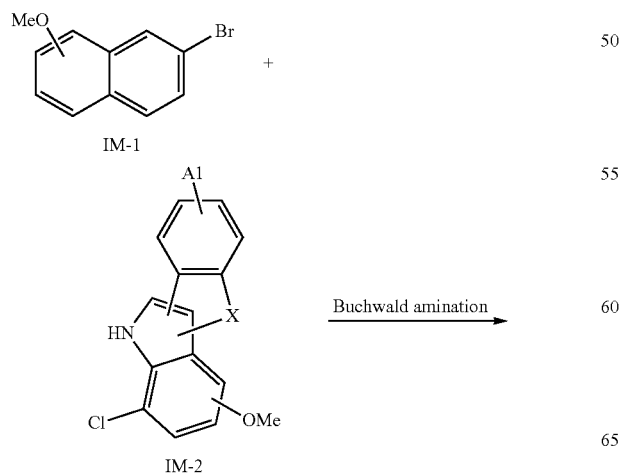

In Reaction Scheme 1, X, A1, and R3 to R6 are the same as those defined in Formula 1;
—OSO$_2$R is a substituent including a sulfone group produced as a result of a sulfonylation reaction, and is a leaving group which is desorbed by the Buchwald amination reaction; and
Me is a methyl group.

Intermediate IM-3 can be synthesized by Buchwald amination reaction of Intermediate IM-1 and Intermediate IM-2, and Intermediate IM-4 can be obtained by the Heck reaction. Intermediate IM-5 including a sulfone group can be obtained by a demethylation reaction and a sulfonylation reaction from Intermediate IM-4. Formula 4-1 can be obtained by the Buchwald amination reaction from Intermediate IM-5.

253

<Reaction Scheme 2> Synthesis of Formula 4-2

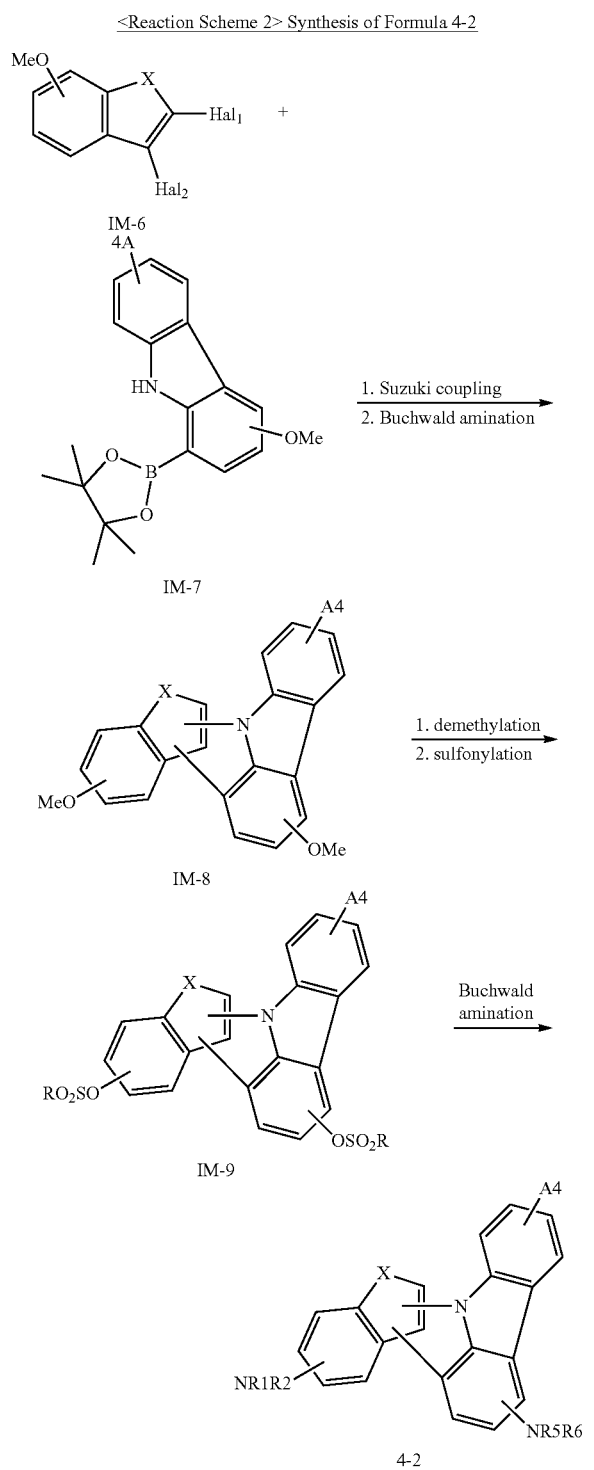

In Reaction Scheme 2, X, A4, R1, R2, R5, and R6 are the same as those defined in Formula 1;

—OSO₂R is a substituent including a sulfone group produced as a result of a sulfonylation reaction, and is a living group which is desorbed by the Buchwald amination; and Me is a methyl group, and Hal₁ and Hal₂ are different from each other, and are each independently a halogen group.

254

Intermediate IM-8 can be synthesized by the Suzuki coupling reaction and Buchwald amination reaction of Intermediate IM-6 and Intermediate IM-7, which are substituted with each different halogen, and Intermediate IM-9 including a sulfone group can be obtained by a demethylation reaction and a sulfonylation reaction from Intermediate IM-8. Formula 4-2 can be obtained by the Buchwald amination reaction from Intermediate IM-9.

<Reaction Scheme 3> Synthesis of Formula 4-3

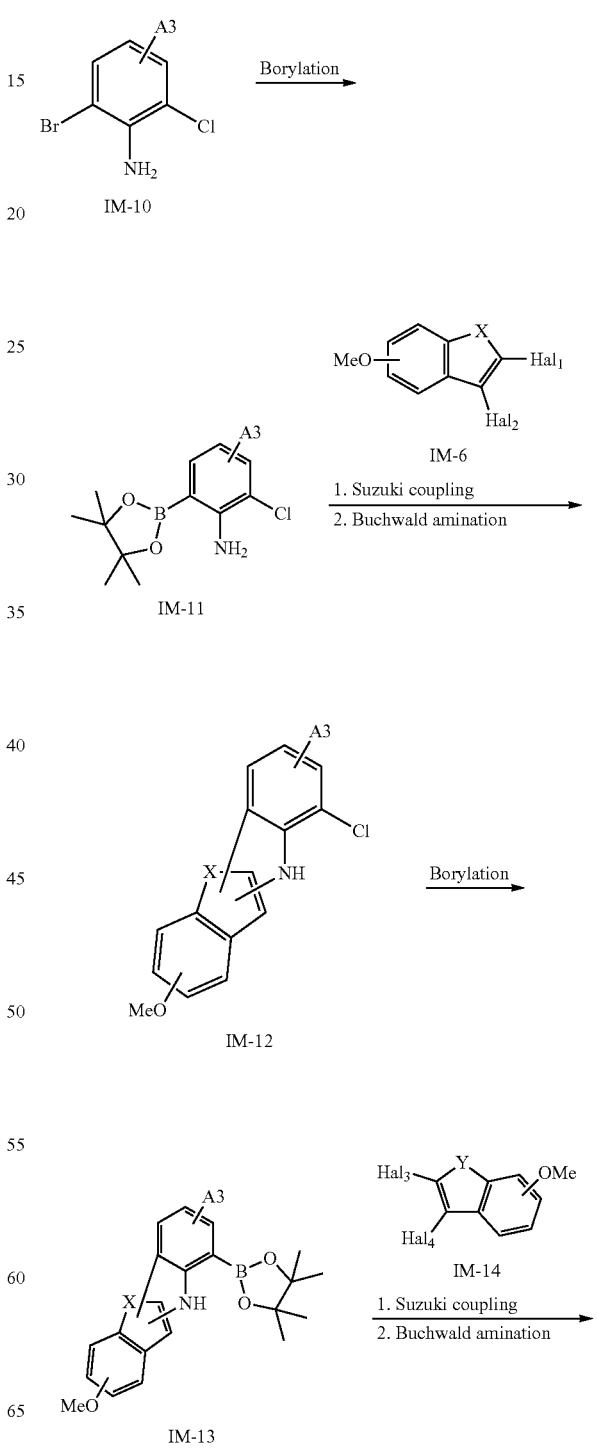

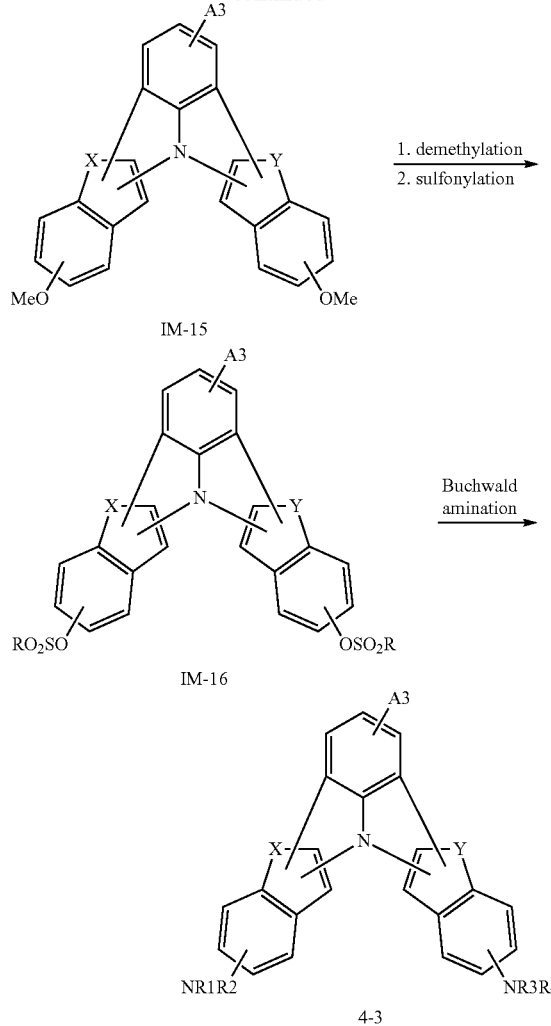

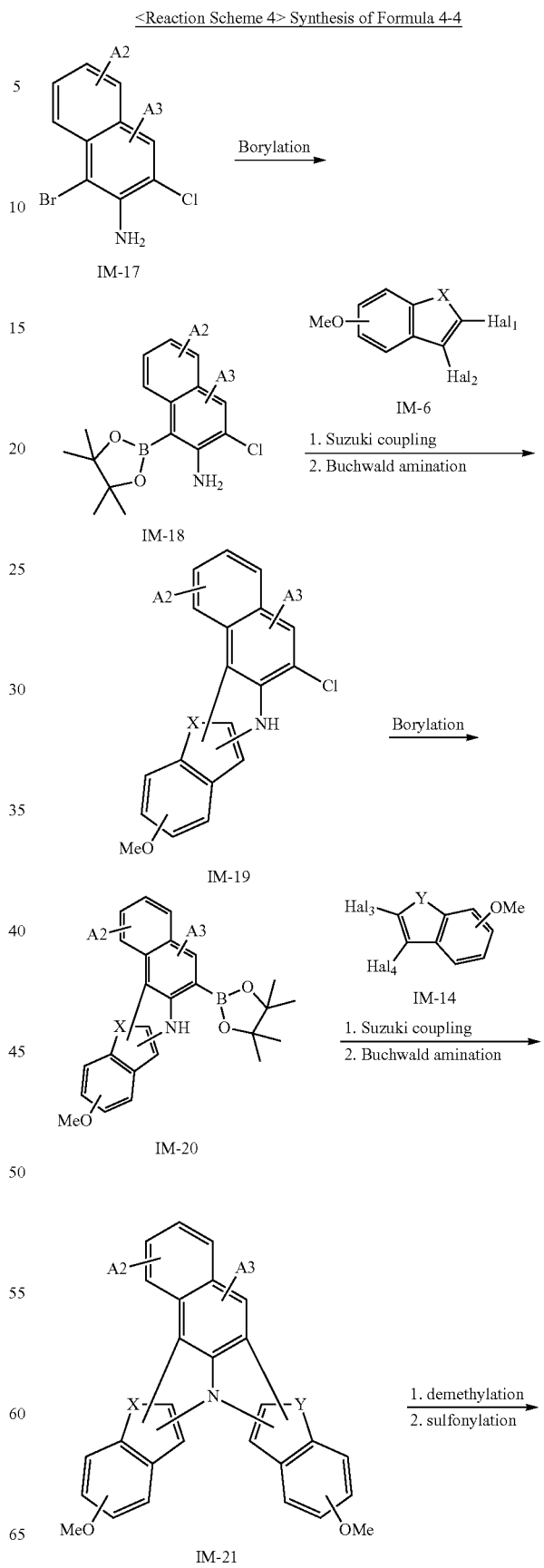

<Reaction Scheme 4> Synthesis of Formula 4-4

In Reaction Scheme 3, X, A3, Y, and R1 to R4 are the same as those defined in Formula 1;

—$OSO_2R$ is a substituent including a sulfone group produced as a result of a sulfonylation reaction, and is a leaving group which is desorbed by the Buchwald amination reaction;

Me is a methyl group;

$Hal_1$ and $Hal_2$ are different from each other, and are each independently a halogen group; and $Hal_3$ and $Hal_4$ are different from each other, and are each independently a halogen group.

Intermediate IM-11 can be synthesized by a borylation reaction of Intermediate IM-10, and Intermediate IM-12 can be obtained by the Suzuki coupling reaction and Buchwald amination reaction with Intermediate IM-6. Intermediate IM-13 can be again synthesized by the borylation reaction from Intermediate IM-12, and Intermediate IM-15 can be obtained by the Suzuki coupling reaction and Buchwald amination reaction with Intermediate IM-14. Intermediate IM-16 including a sulfone group can be obtained by a demethylation reaction and a sulfonylation reaction from Intermediate IM-15. Finally, Formula 4-3 can be obtained by the Buchwald amination reaction from Intermediate IM-16.

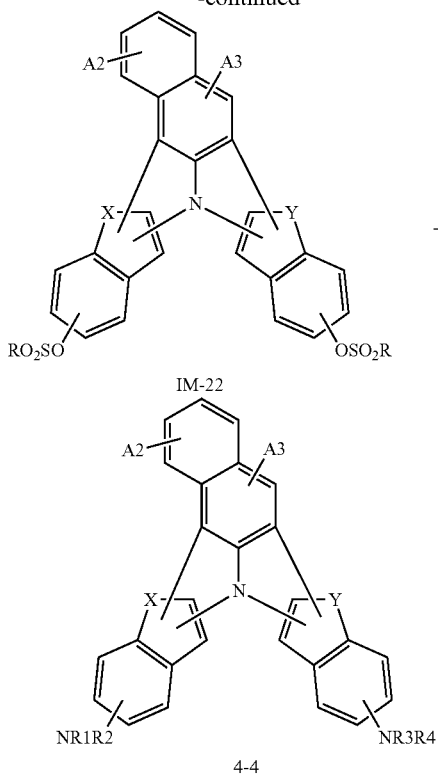

IM-22

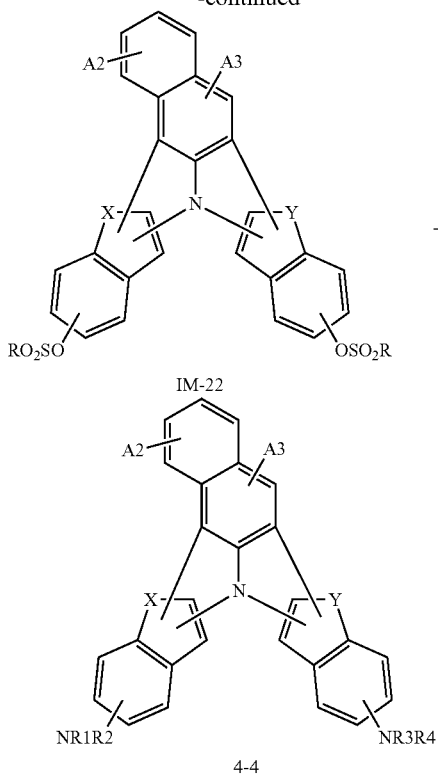

4-4

In Reaction Scheme 4, X, Y, A2, A3, and R1 to R4 are the same as those defined in Formula 1;

—OSO$_2$R is a substituent including a sulfone group produced as a result of a sulfonylation reaction, and is a living group which is desorbed by the Buchwald amination;

Me is a methyl group;

Hal$_1$ and Hal$_2$ are different from each other, and are each independently a halogen group; and Hal$_3$ and Hal$_4$ are different from each other, and are each independently a halogen group.

Intermediate IM-18 can be synthesized by a borylation reaction of Intermediate IM-17, and Intermediate IM-19 can be obtained by the Suzuki coupling reaction and Buchwald amination reaction with Intermediate 6 (IM-6). Intermediate IM-20 can be again synthesized by a borylation reaction from Intermediate IM-19, and Intermediate IM-21 can be obtained by the Suzuki coupling reaction and Buchwald amination reaction with Intermediate IM-14. Intermediate IM-22 including a sulfone group can be obtained by a demethylation reaction and a sulfonylation reaction from Intermediate IM-21. Finally, Formula 4-4 can be obtained by the Buchwald amination reaction from Intermediate IM-22.

When any one of Reaction Schemes 1 to 4 of the present specification and the intermediates are appropriately combined based on a typical technology common sense, the compounds of Formula 1 described in the present specification can be all prepared.

EXAMPLES

Hereinafter, the present specification will be described in more detail through Examples. However, the following Examples are provided only for exemplifying the present specification, but are not intended to limit the present specification.

Synthesis Example 1. Synthesis of Compound 1

A. Synthesis of Intermediate 1

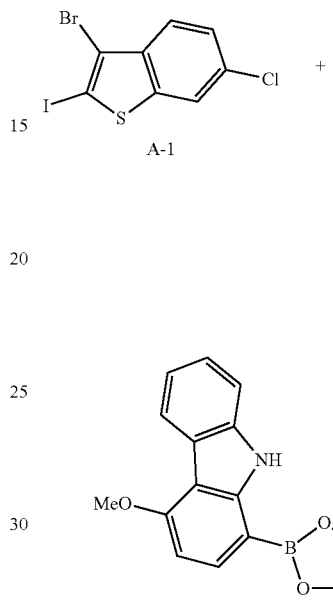

A-1

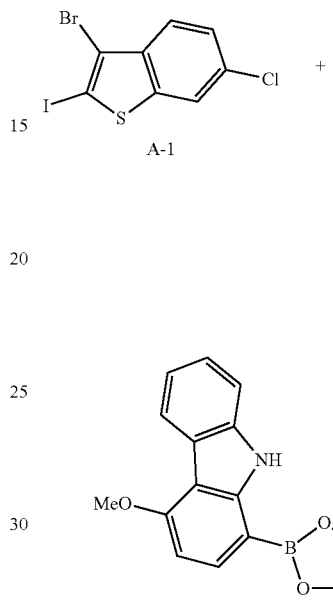

B-1

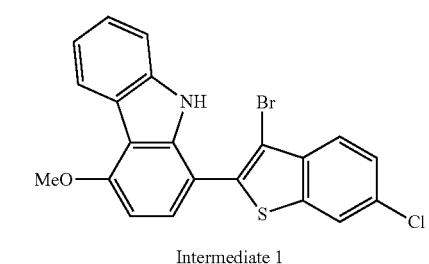

Intermediate 1

After 20 g of a starting material A-1, 12 g of a boronic ester B-1, 11 g of potassium carbonate, 400 mL of tetrahydrofuran (THF), and 40 mL of water were put into a container under a nitrogen atmosphere, 1.2 g of [tetrakis (triphenylphosphine)palladium(0), (TTP), Pd(PPh$_3$)$_4$] was added thereto, and then the resulting mixture was heated at 120° C. and stirred for 4 hours. After the reaction was terminated, the reaction solution was cooled to room temperature, aliquoted by adding water and ethyl acetate thereto, and then filtered by treatment with MgSO$_4$ (anhydrous). The filtered solution was distilled off under reduced pressure and purified with recrystallization (ethyl acetate/hexane) to obtain Intermediate 1 (18 g). (Yield 76%, Mass [M+]=443)

B. Synthesis of Intermediate 2

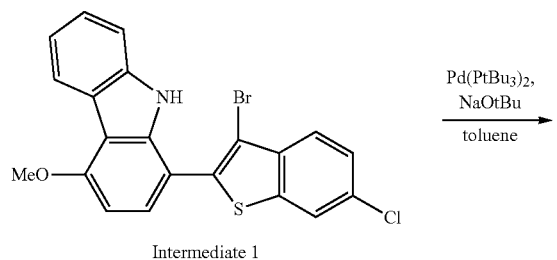

Intermediate 1

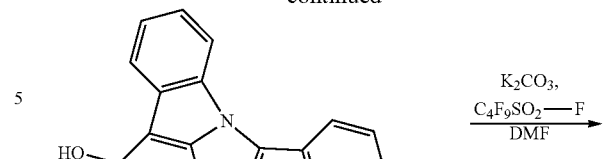

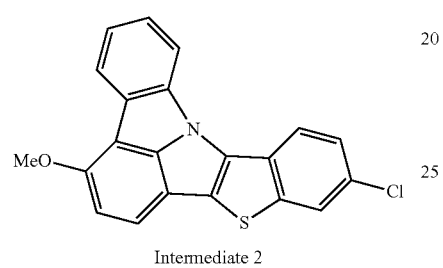

Intermediate 2

After 18 g of Intermediate 1, 7.8 g of sodium t-butoxide (NaOtBu), and 0.4 g of [bis(tri(tert-butyl)-phosphine)palladium(0)] Pd(PtBu$_3$)$_2$ were put into 200 mL of toluene under a nitrogen atmosphere, the resulting mixture was heated at 140° C. and stirred for 6 hours. After the reaction was terminated, the reaction solution was cooled to room temperature, aliquoted by adding water and aq. NH$_4$Cl thereto, and then filtered by treatment with MgSO$_4$ (anhydrous). The filtered solution was distilled off under reduced pressure and purified with recrystallization to obtain Intermediate 2 (8.5 g). (Yield 58%, Mass [M+]=362)

C. Synthesis of Intermediates 3 and 4

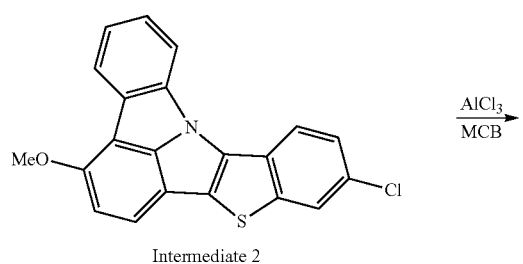

Intermediate 2

-continued

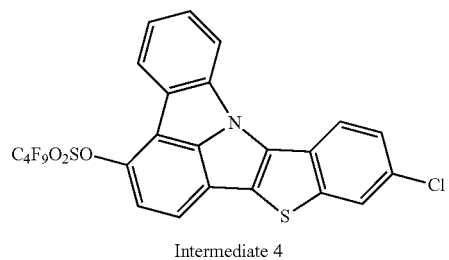

Intermediate 4

After 8.5 g of Intermediate 2 and 4.7 g of aluminum chloride were put into 200 mL of chlorobenzene (MCB) under a nitrogen atmosphere, the resulting mixture was heated at 130° C. and stirred for 4 hours. After the reaction was terminated, the reaction solution was cooled to room temperature, aliquoted by adding water and ethyl acetate thereto, and then filtered by treatment with MgSO$_4$ (anhydrous). The filtered solution was distilled off under reduced pressure and purified with recrystallization (ethyl acetate/hexane) to obtain Intermediate 3 (6.7 g). (Yield 82%, Mass [M+]=348)

After 150 mL of dimethylformamide (DMF) was put into 6.7 g of Intermediate 3 and 5.3 g of potassium carbonate, 3.8 mL of nonafluorobutanesulfonyl fluoride was added dropwise thereto at room temperature. After the reaction was terminated by stirring the resulting mixture for 5 hours, the reaction solution was filtered. The filtered solution was aliquoted by adding water and ethyl acetate thereto, and then filtered with a treatment with MgSO$_4$ (anhydrous). The filtered solution was distilled off under reduced pressure and purified with recrystallization (toluene/hexane) to obtain Intermediate 4 (9.4 g). (Yield 77%, Mass [M+]=630)

D. Synthesis of Compound 1

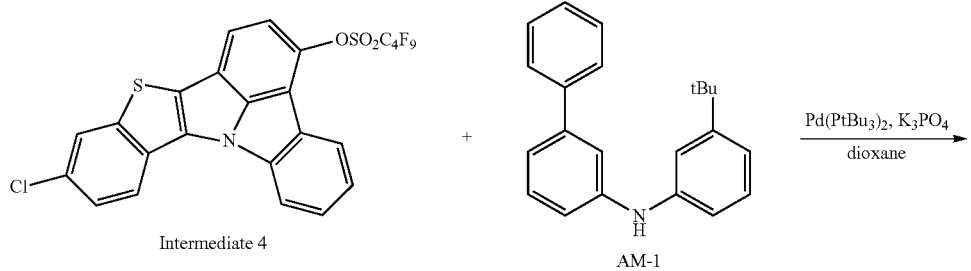

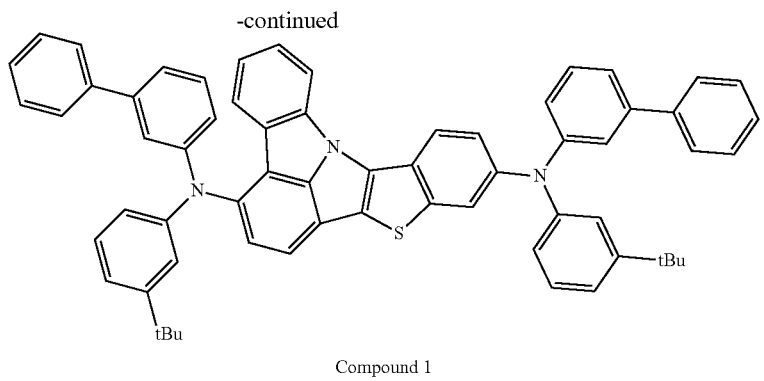

Compound 1

After 3.0 g of Intermediate 4, 2.9 g of amine AM-1, 2.5 g of potassium phosphate, and 0.05 g of [bis(tri(tert-butyl)phosphine)palladium(0), Pd(PtBu$_3$)$_2$] were put into 40 mL of dioxane under a nitrogen atmosphere, the resulting mixture was heated at 100° C. and stirred for 28 hours. After the reaction was terminated, the reaction solution was cooled to room temperature, aliquoted by adding water and NaCl thereto, and then filtered by treatment with MgSO$_4$ (anhydrous). The filtered solution was distilled off under reduced pressure and purified with recrystallization (toluene/hexane) to obtain Compound 1 (3.1 g). (Yield 73%, Mass [M+]=897)

Synthesis Example 2. Synthesis of Compound 2

A. Synthesis of Intermediate 5

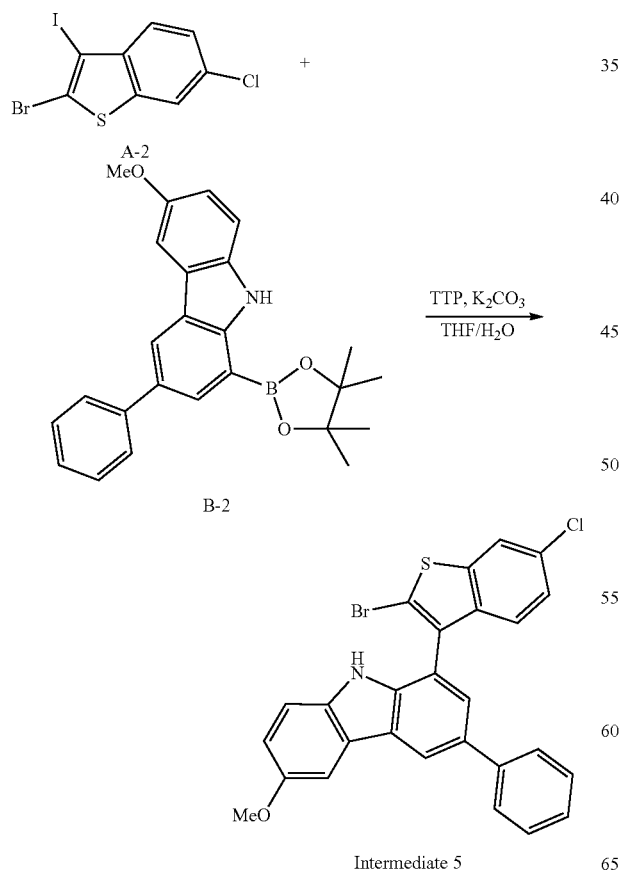

Intermediate 5

Intermediate 5 (10 g) was obtained by preparation in the same manner as in the synthesis method of Intermediate 1, except that A-2 (10 g) and B-2 (10.8 g) were used instead of the starting material A-1 and the boronic ester B-1, respectively, in the synthesis of Intermediate 1 in Synthesis Example 1. (Yield 72%, Mass [M+]=519)

B. Synthesis of Intermediate 6

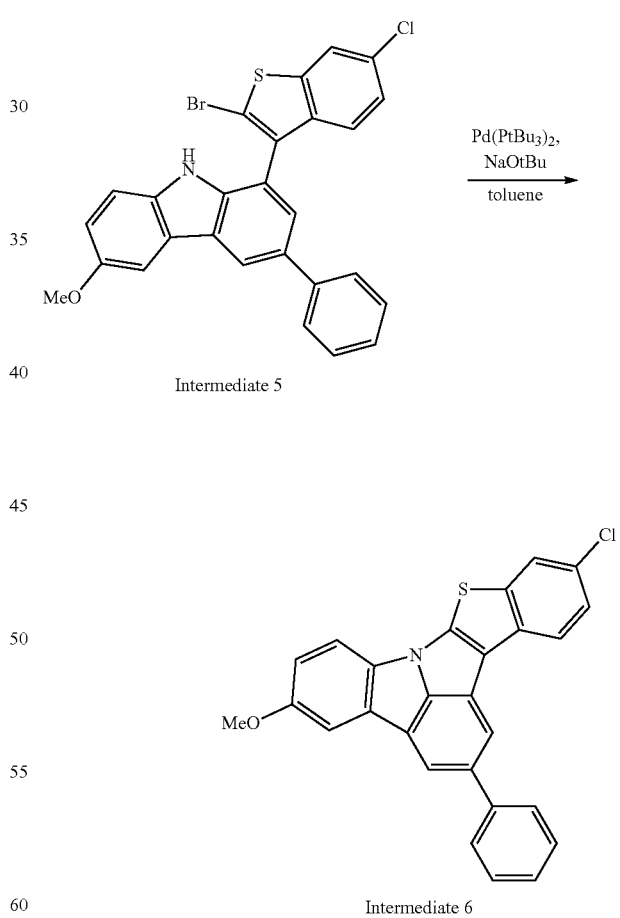

Intermediate 6

Intermediate 6 (5.3 g) was obtained by preparation in the same manner as in the synthesis method of Intermediate 2, except that Intermediate 5 (10 g) was used instead of Intermediate 1 in the synthesis of Intermediate 2 in Synthesis Example 1. (Yield 63%, Mass [M+]=438)

C. Synthesis of Intermediates 7 and 8

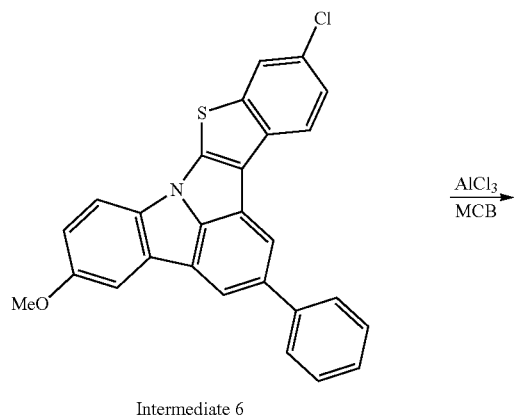

Intermediate 6

AlCl₃ / MCB →

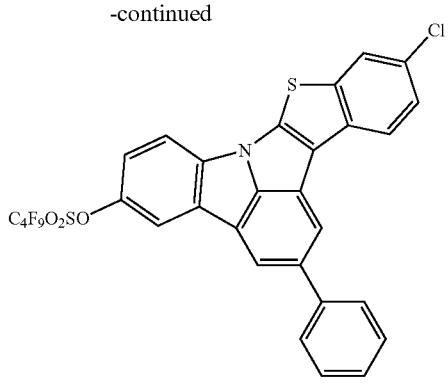

Intermediate 8

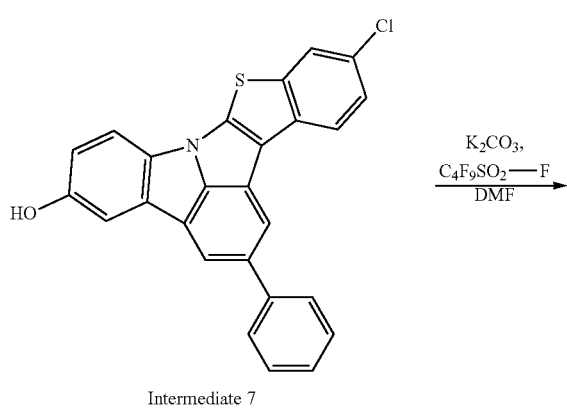

Intermediate 7

K₂CO₃, C₄F₉SO₂—F / DMF →

Intermediate 7 (3.8 g) was obtained by preparation in the same manner as in the synthesis method of Intermediate 3, except that Intermediate 6 (5.3 g) was used instead of Intermediate 2 in the synthesis of Intermediate 3 in Synthesis Example 1. (Yield 74%, Mass [M+]=424)

Intermediate 8 (4.5 g) was obtained by preparation in the same manner as in the synthesis method of Intermediate 4, except that Intermediate 7 (3.8 g) was used instead of Intermediate 3 in the synthesis of Intermediate 4 in Synthesis Example 1. (Yield 71%, Mass [M+]=706)

D. Synthesis of Compound 2

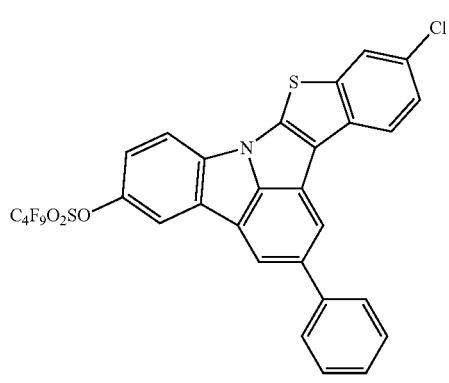

Intermediate 8

+

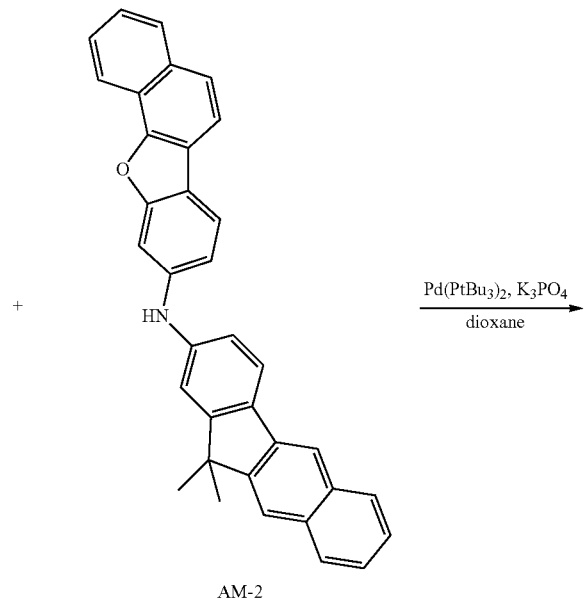

AM-2

Pd(PtBu₃)₂, K₃PO₄ / dioxane →

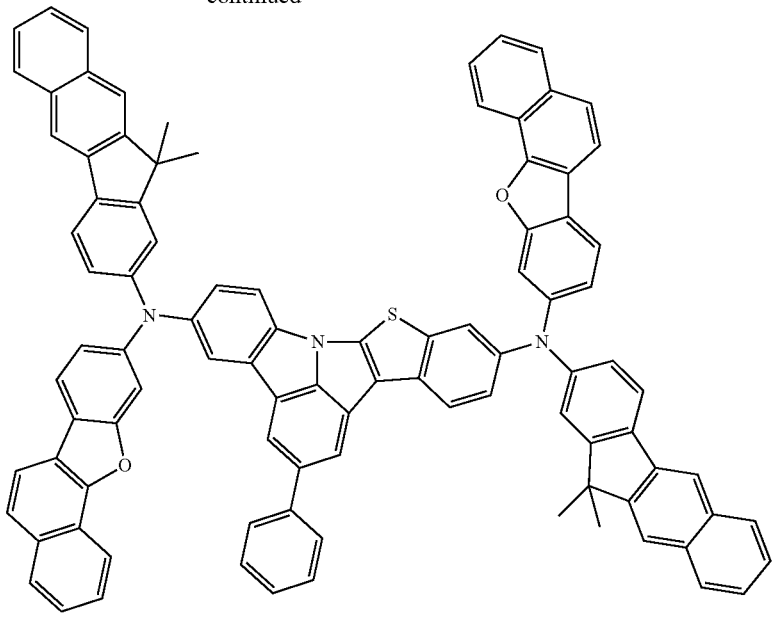

Compound2

Compound 2 (3.5 g) was obtained by preparation in the same manner as in the synthesis method of Compound 1, except that Intermediate 8 (3.0 g) and AM-2 (4.0 g) were used instead of Intermediate 4 and AM-1 as an amine, respectively, in the synthesis of Compound 1 in Synthesis Example 1. (Yield 62%, Mass [M+]=1321)

Synthesis Example 3. Synthesis of Compound 3

A. Synthesis of Intermediate 9

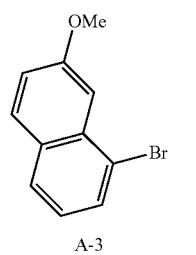

A-3

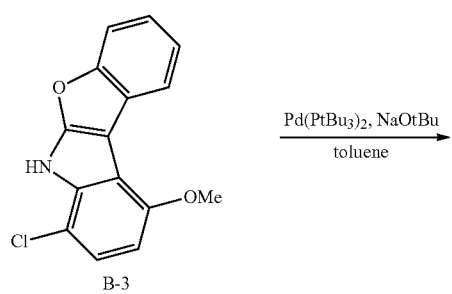

B-3

Pd(PtBu₃)₂, NaOtBu
toluene

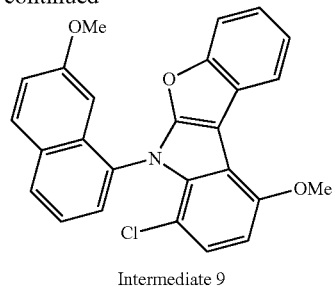

Intermediate 9

After 10 g of a starting material A-3, 11.6 g of benzofuroindole B-3, 6.0 g of sodium t-butoxide, and 0.4 g of [bis(tri(tert-butyl)phosphine)palladium(0), Pd(PtBu₃)₂] were put into 350 mL of toluene under a nitrogen atmosphere, the resulting mixture was heated at 140° C. and stirred for 5 hours. After the reaction was terminated, the reaction solution was cooled to room temperature, aliquoted by adding water and aq. NH₄Cl thereto, and then filtered by treatment with MgSO₄ (anhydrous). The filtered solution was distilled off under reduced pressure and purified with recrystallization to obtain Intermediate 9 (13.6 g). (Yield 75%, Mass [M+]=428)

B. Synthesis of Intermediate 10

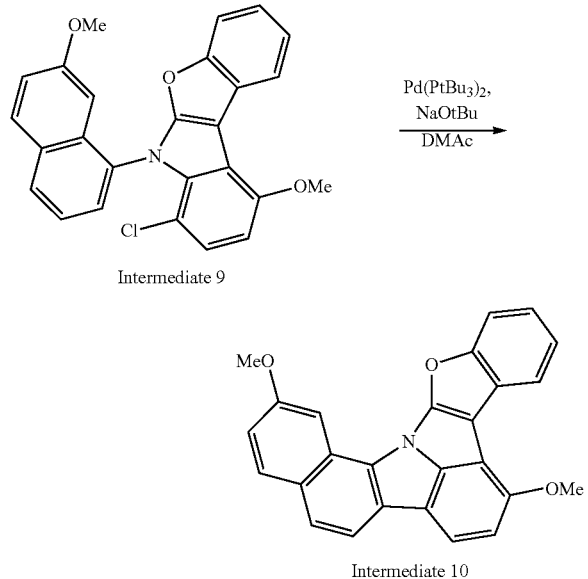

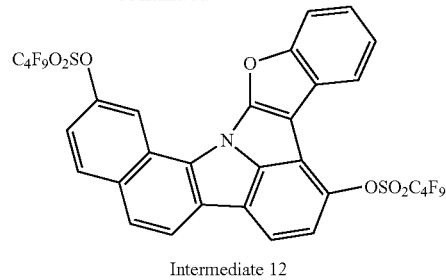

Intermediate 12

Intermediate 11 (5.0 g) was obtained by preparation in the same manner as in the synthesis method of Intermediate 3, except that Intermediate 10 (7.9 g) was used instead of Intermediate 2 in the synthesis of Intermediate 3 in Synthesis Example 1. (Yield 68%, Mass [M+]=364)

Intermediate 12 (8.1 g) was obtained by preparation in the same manner as in the synthesis method of Intermediate 4, except that Intermediate 11 (5.0 g) was used instead of Intermediate 3 in the synthesis of Intermediate 4 in Synthesis Example 1. (Yield 63%, Mass [M+]=928)

D. Synthesis of Compound 3

After 13.6 g of Intermediate 9, 6.1 g of sodium tert-butoxide, and 0.3 g of [bis(tri(tert-butyl)-phosphine)palladium (0), Pd(PtBu₃)₂] were put into 160 mL of dimethylacetamide under a nitrogen atmosphere, the resulting mixture was heated at 120° C. and stirred for 10 hours. After the reaction was terminated, the reaction solution was cooled to room temperature, aliquoted by adding water and aq. NH₄Cl thereto, and then filtered by treatment with MgSO₄ (anhydrous). The filtered solution was distilled off under reduced pressure and purified with recrystallization (toluene/hexane) to obtain Intermediate 10 (7.9 g). (Yield 63%, Mass [M+]=392)

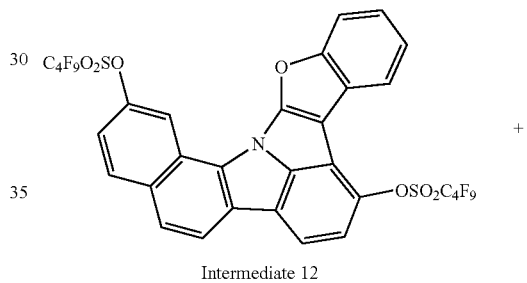

Intermediate 12

C. Synthesis of Intermediates 11 and 12

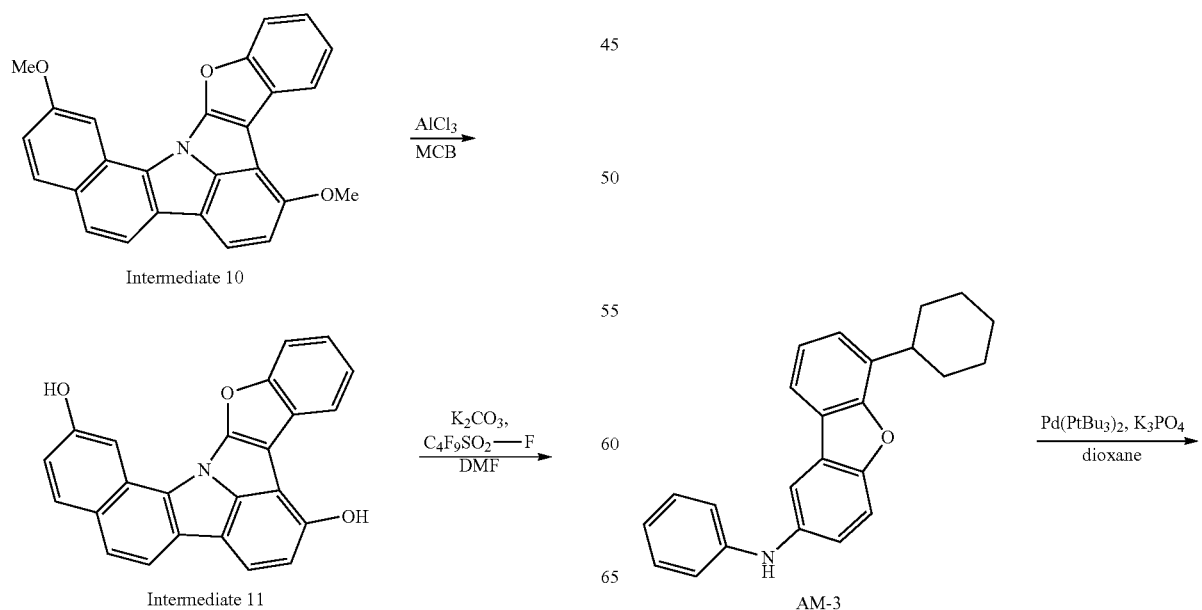

-continued

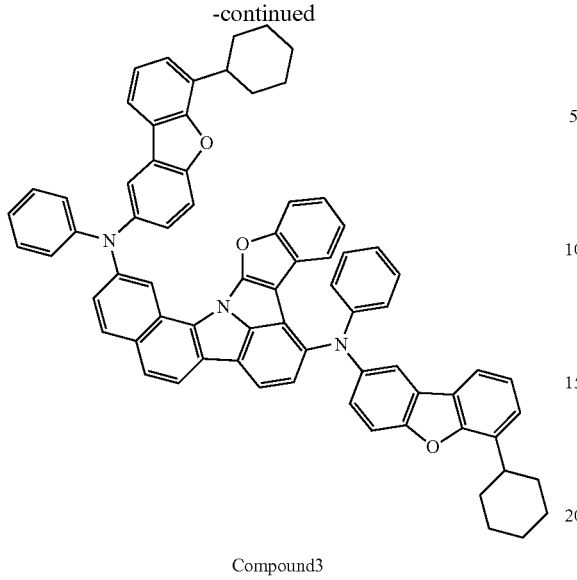

Compound3

Compound 3 (2.5 g) was obtained by preparation in the same manner as in the synthesis method of Compound 1, except that Intermediate 12 (3.0 g) and AM-3 (2.2 g) were used instead of Intermediate 4 and AM-1 as an amine, respectively, in the synthesis of Compound 1 in Synthesis Example 1. (Yield 77%, Mass [M+]=1011)

Synthesis Example 4. Synthesis of Compound 4

A. Synthesis of Intermediate 13

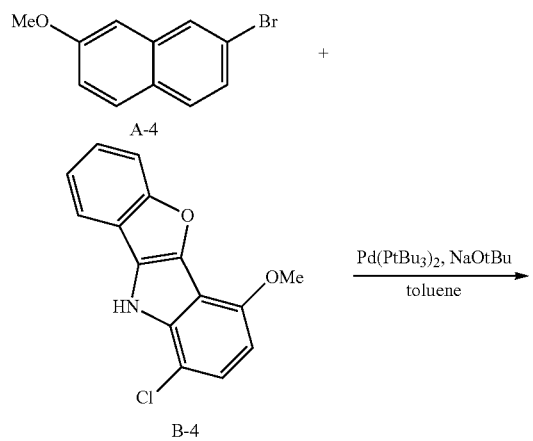

Intermediate 13 (6.8 g) was obtained by preparation in the same manner as in the synthesis method of Intermediate 9, except that A-4 (5.0 g) and B-4 (5.8 g) were used instead of the starting material A-3 and the benzofuroindole B-3, respectively, in the synthesis of Intermediate 9 in Synthesis Example 3. (Yield 75%, Mass [M+]=428)

B. Synthesis of Intermediate 14

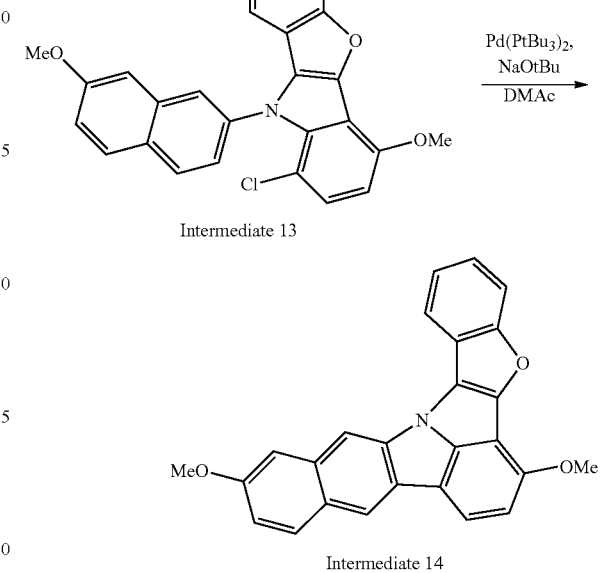

Intermediate 14 (3.8 g) was obtained by preparation in the same manner as in the synthesis method of Intermediate 10, except that Intermediate 13 (6.8 g) was used instead of Intermediate 9 in the synthesis of Intermediate 10 in Synthesis Example 3. (Yield 61%, Mass [M+]=392)

C. Synthesis of Intermediates 15 and 16

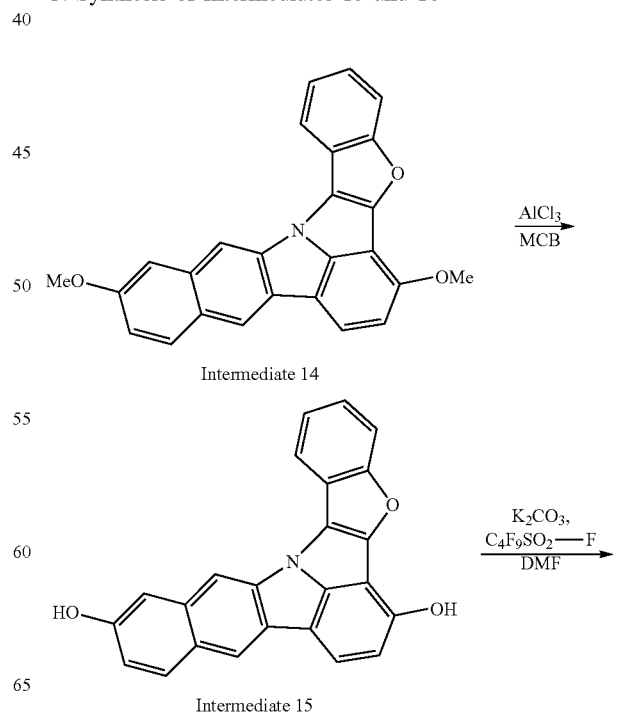

-continued

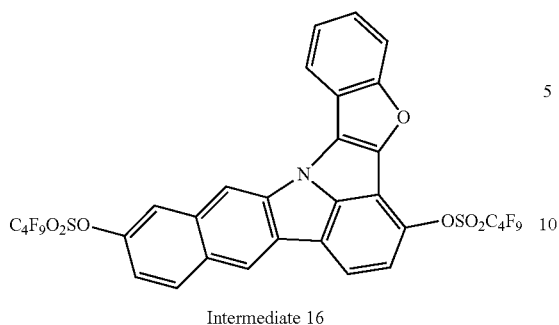

Intermediate 16

Intermediate 15 (2.7 g) was obtained by preparation in the same manner as in the synthesis method of Intermediate 3, except that Intermediate 14 (3.8 g) was used instead of Intermediate 2 in the synthesis of Intermediate 3 in Synthesis Example 1. (Yield 77%, Mass [M+]=364)

Intermediate 16 (4.3 g) was obtained by preparation in the same manner as in the synthesis method of Intermediate 4, except that Intermediate 15 (2.7 g) was used instead of Intermediate 3 in the synthesis of Intermediate 4 in Synthesis Example 1. (Yield 62%, Mass [M+]=928)

D. Synthesis of Compound 4

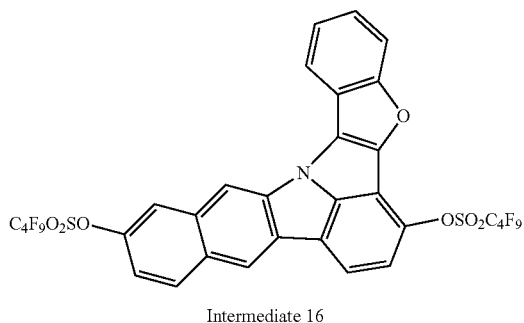

Intermediate 16

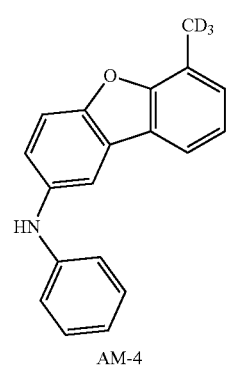

AM-4

-continued

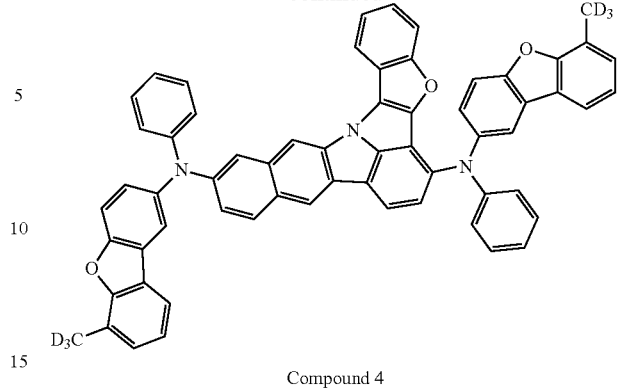

Compound 4

Compound 4 (2.1 g) was obtained by preparation in the same manner as in the synthesis method of Compound 1, except that Intermediate 16 (3.0 g) and AM-4 (1.8 g) were used instead of Intermediate 4 and AM-1 as an amine, respectively, in the synthesis of Compound 1 in Synthesis Example 1. (Yield 74%, Mass [M+]=881)

Synthesis Example 5. Synthesis of Compound 5

A. Synthesis of Intermediate 17

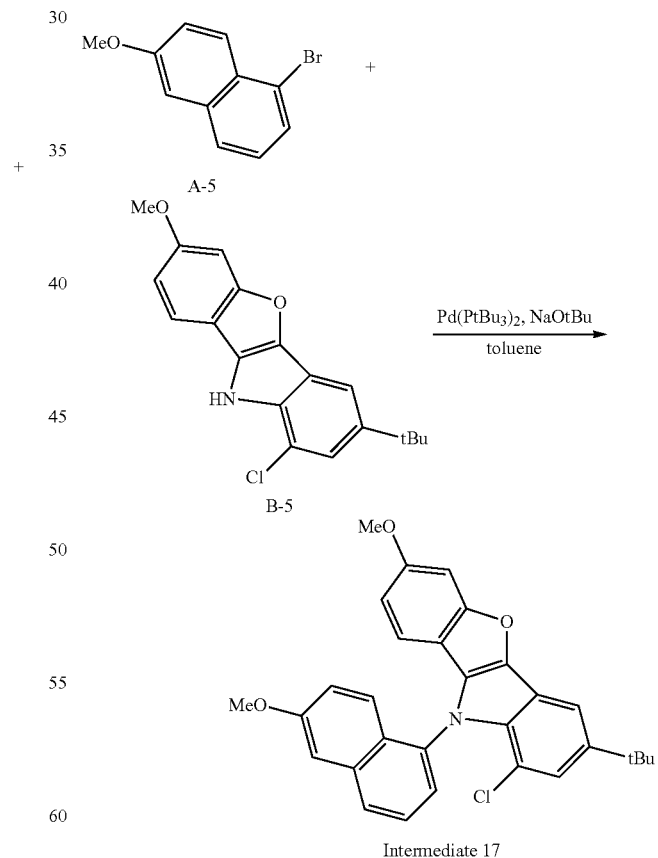

Intermediate 17

Intermediate 17 (6.8 g) was obtained by preparation in the same manner as in the synthesis method of Intermediate 9, except that A-5 (5.0 g) and B-5 (7.0 g) were used instead of the staring material A-3 and the benzofuroindole B-3, respectively, in the synthesis of Intermediate 9 in Synthesis Example 3. (Yield 73%, Mass [M+]=439)

B. Synthesis of Intermediate 18

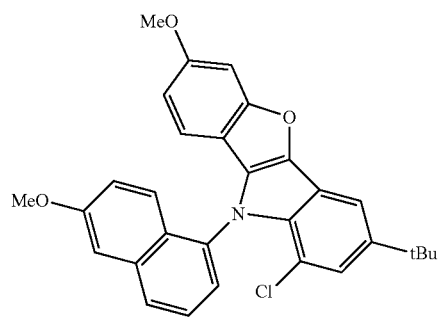

Intermediate 17

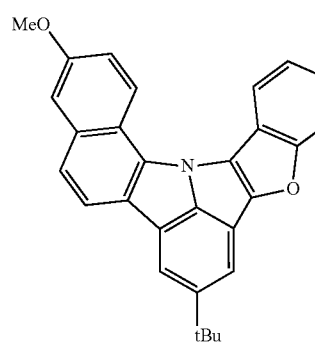

Intermediate 18

Intermediate 18 (4.6 g) was obtained by preparation in the same manner as in the synthesis method of Intermediate 10, except that Intermediate 17 (6.8 g) was used instead of Intermediate 9 in the synthesis of Intermediate 10 in Synthesis Example 3. (Yield 66%, Mass [M+]=448)

C. Synthesis of Intermediates 19 and 20

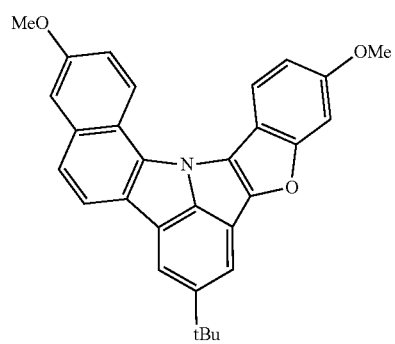

Intermediate 18

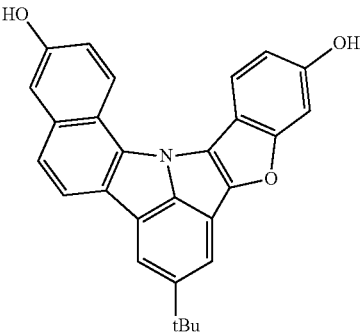

Intermediate 19

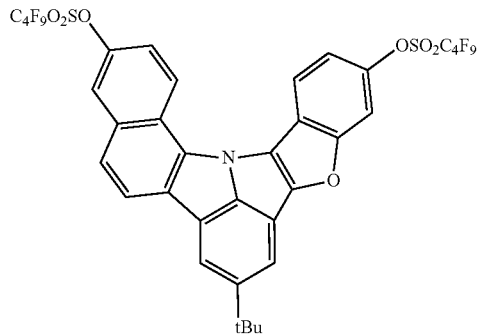

Intermediate 20

Intermediate 19 (3.4 g) was obtained by preparation in the same manner as in the synthesis method of Intermediate 3, except that Intermediate 18 (4.6 g) was used instead of Intermediate 2 in the synthesis of Intermediate 3 in Synthesis Example 1. (Yield 79%, Mass [M+]=420)

Intermediate 20 (6.1 g) was obtained by preparation in the same manner as in the synthesis method of Intermediate 4, except that Intermediate 19 (3.4 g) was used instead of Intermediate 3 in the synthesis of Intermediate 4 in Synthesis Example 1. (Yield 77%, Mass [M+]=984)

D. Synthesis of Compound 5

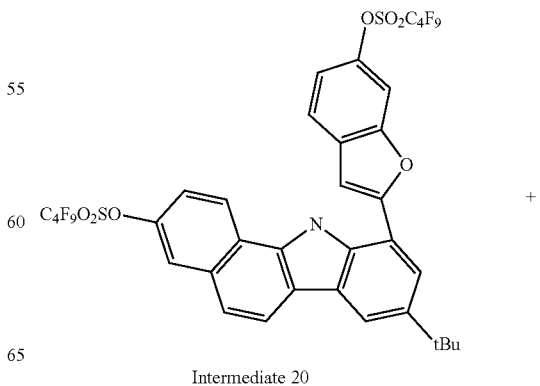

Intermediate 20

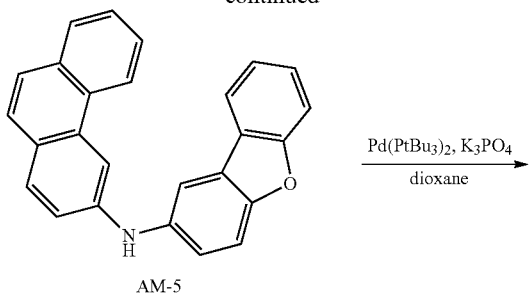

AM-5

Pd(PtBu₃)₂, K₃PO₄
──────────────→
dioxane

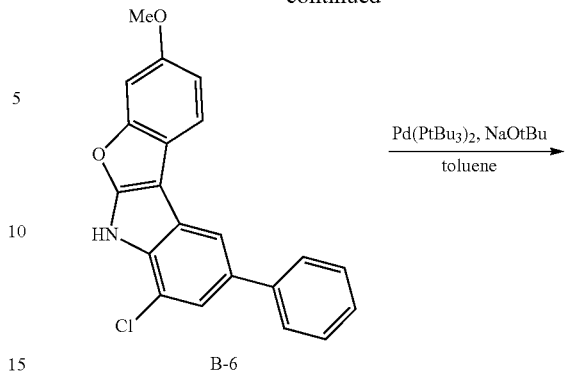

B-6

Pd(PtBu₃)₂, NaOtBu
──────────────→
toluene

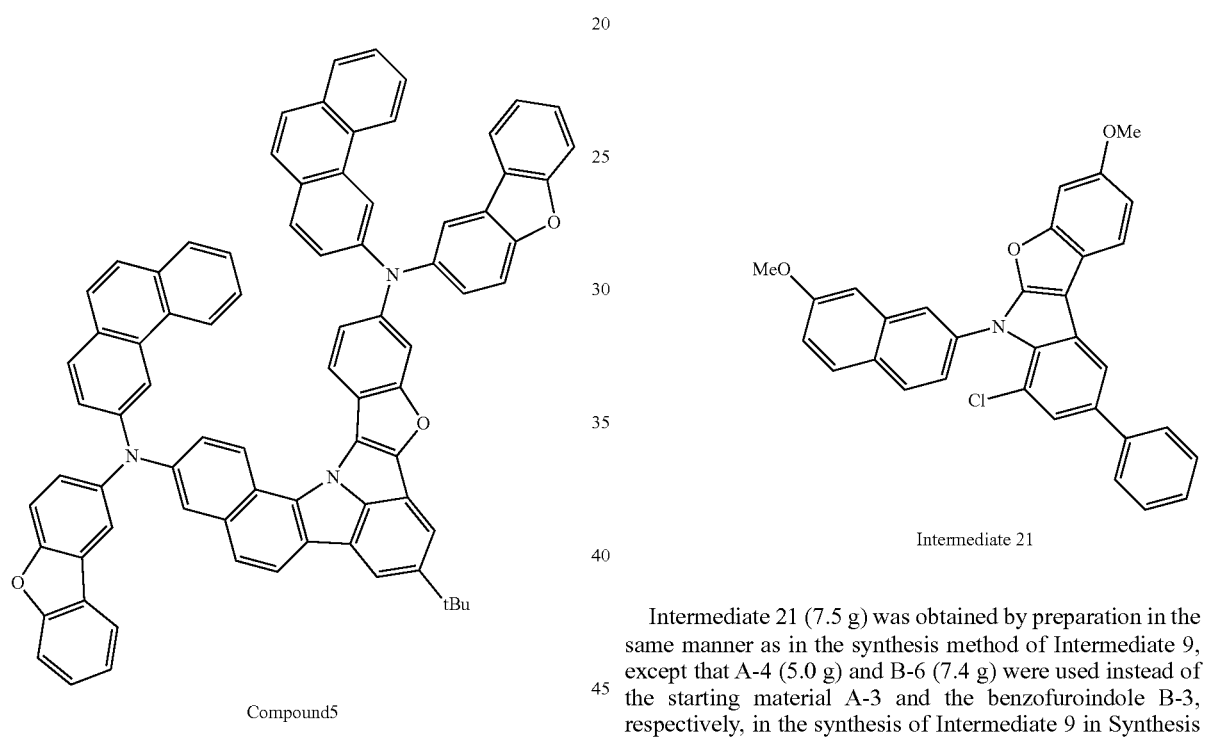

Compound5

Compound 5 (2.5 g) was obtained by preparation in the same manner as in the synthesis method of Compound 1, except that Intermediate 20 (3.0 g) and AM-5 (2.2 g) were used instead of Intermediate 4 and AM-1 as an amine, respectively, in the synthesis of Compound 1 in Synthesis Example 1. (Yield 74%, Mass [M+]=1103)

Synthesis Example 6. Synthesis of Compound 6

A. Synthesis of Intermediate 21

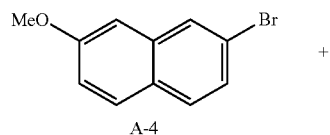

A-4

+

Intermediate 21

Intermediate 21 (7.5 g) was obtained by preparation in the same manner as in the synthesis method of Intermediate 9, except that A-4 (5.0 g) and B-6 (7.4 g) were used instead of the starting material A-3 and the benzofuroindole B-3, respectively, in the synthesis of Intermediate 9 in Synthesis Example 3. (Yield 71%, Mass [M+]=504)

B. Synthesis of Intermediate 22

Intermediate 21

Pd(PtBu₃)₂, NaOtBu
──────────────→
DMAc

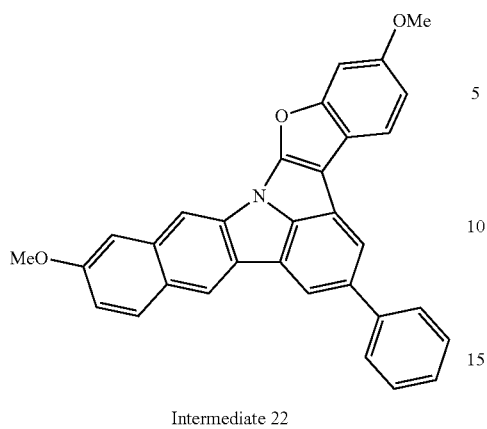

Intermediate 22

Intermediate 22 (4.6 g) was obtained by preparation in the same manner as in the synthesis method of Intermediate 10, except that Intermediate 21 (7.5 g) was used instead of Intermediate 9 in the synthesis of Intermediate 10 in Synthesis Example 3. (Yield 66%, Mass [M+]=468)

C. Synthesis of Intermediates 23 and 24

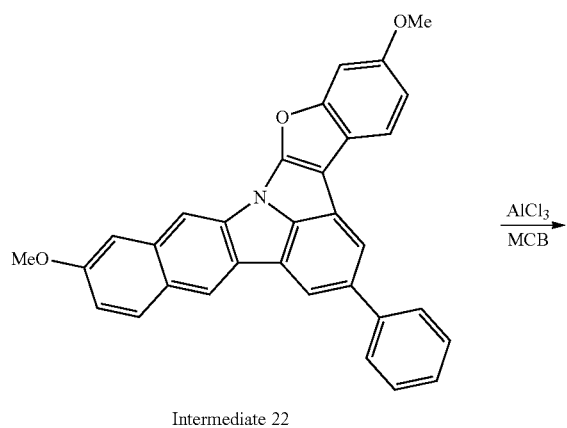

Intermediate 22

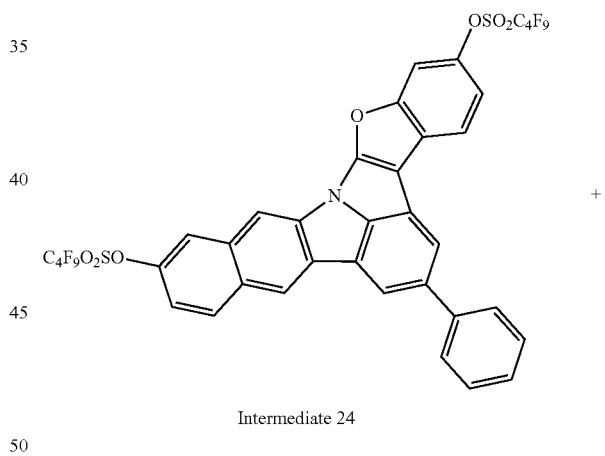

Intermediate 24

Intermediate 23 (3.2 g) was obtained by preparation in the same manner as in the synthesis method of Intermediate 3, except that Intermediate 22 (4.6 g) was used instead of Intermediate 2 in the synthesis of Intermediate 3 in Synthesis Example 1. (Yield 74%, Mass [M+]=440)

Intermediate 24 (5.3 g) was obtained by preparation in the same manner as in the synthesis method of Intermediate 4, except that Intermediate 23 (3.2 g) was used instead of Intermediate 3 in the synthesis of Intermediate 4 in Synthesis Example 1. (Yield 73%, Mass [M+]=1004)

D. Synthesis of Compound 6

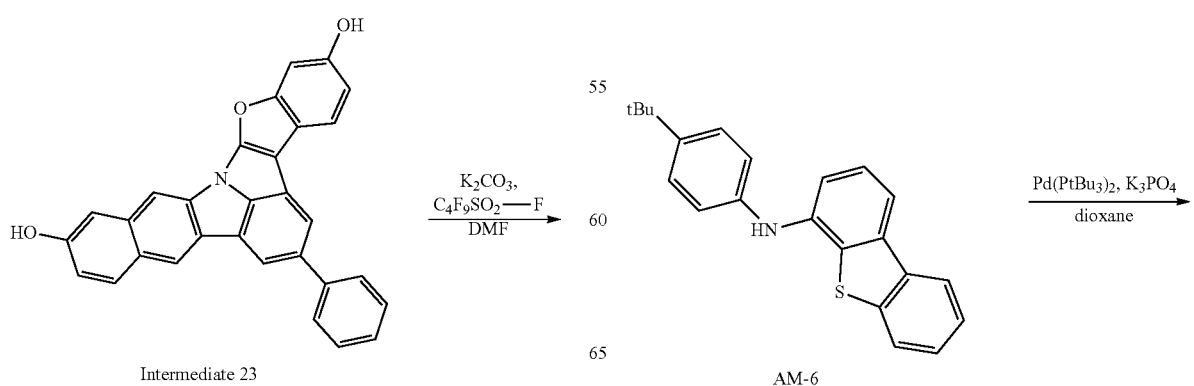

Intermediate 23

AM-6

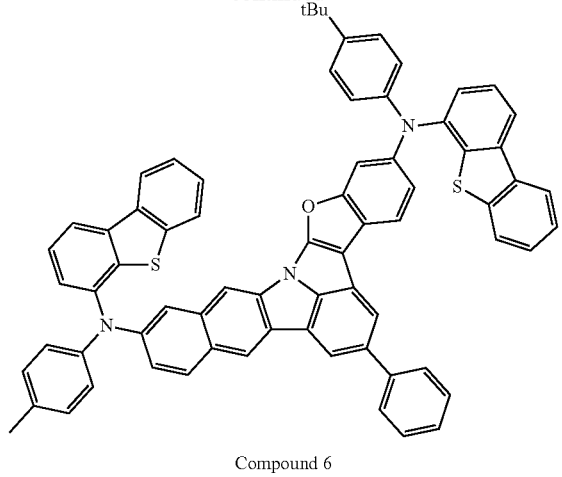

Compound 6

Compound 6 (2.3 g) was obtained by preparation in the same manner as in the synthesis method of Compound 1, except that Intermediate 24 (3.0 g) and AM-6 (2.0 g) were used instead of Intermediate 4 and AM-1 as an amine, respectively, in the synthesis of Compound 1 in Synthesis Example 1. (Yield 72%, Mass [M+]=1067)

Synthesis Example 7. Synthesis of Compound 7

A. Synthesis of Intermediate 25

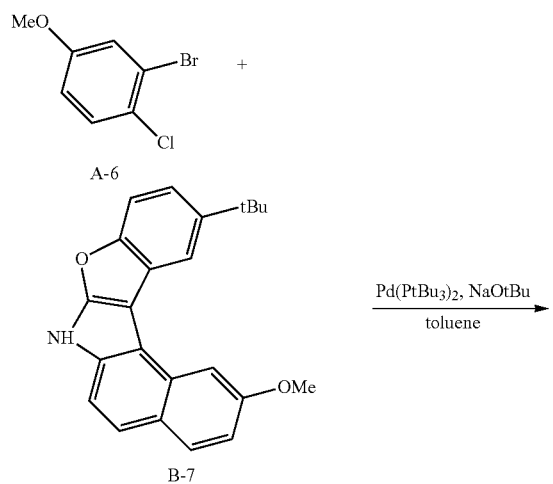

Intermediate 25 (7.6 g) was obtained by preparation in the same manner as in the synthesis method of Intermediate 9, except that A-6 (5.0 g) and B-7 (8.2 g) were used instead of the starting material A-3 and the benzofuroindole B-3, respectively, in the synthesis of Intermediate 9 in Synthesis Example 3. (Yield 66%, Mass [M+]=484)

B. Synthesis of Intermediate 26

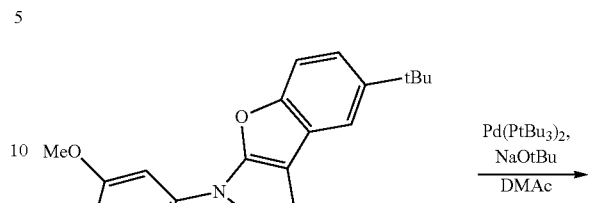

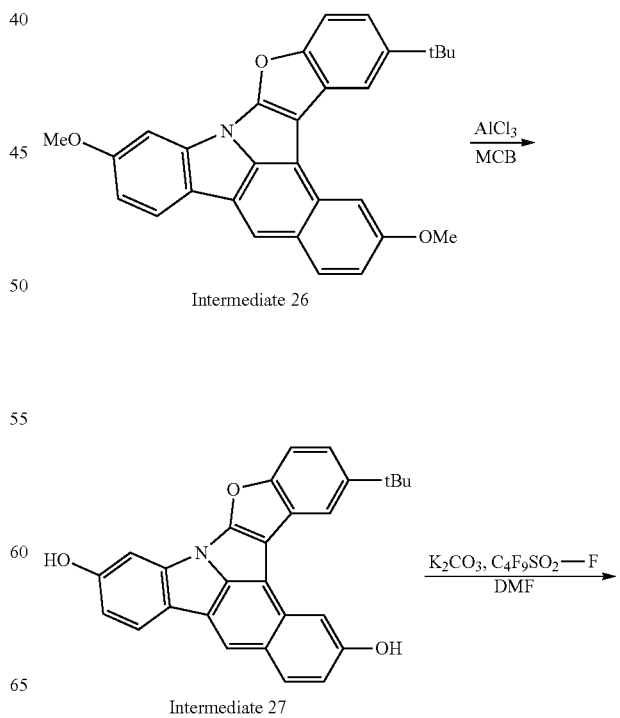

Intermediate 26 (4.3 g) was obtained by preparation in the same manner as in the synthesis method of Intermediate 10, except that Intermediate 25 (7.6 g) was used instead of Intermediate 9 in the synthesis of Intermediate 10 in Synthesis Example 3. (Yield 61%, Mass [M+]=448)

C. Synthesis of Intermediates 27 and 28

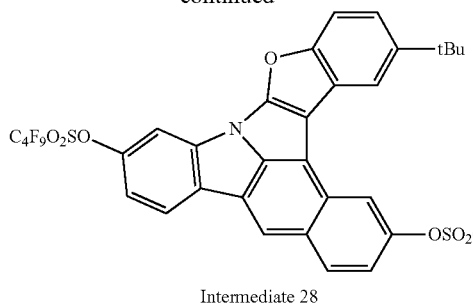

Intermediate 28

Intermediate 27 (3.0 g) was obtained by preparation in the same manner as in the synthesis method of Intermediate 3, except that Intermediate 26 (4.3 g) was used instead of Intermediate 2 in the synthesis of Intermediate 3 in Synthesis Example 1. (Yield 74%, Mass [M+]=420)

Intermediate 28 (4.8 g) was obtained by preparation in the same manner as in the synthesis method of Intermediate 4, except that Intermediate 27 (3.0 g) was used instead of Intermediate 3 in the synthesis of Intermediate 4 in Synthesis Example 1. (Yield 68%, Mass [M+]=984)

D. Synthesis of Compound 7

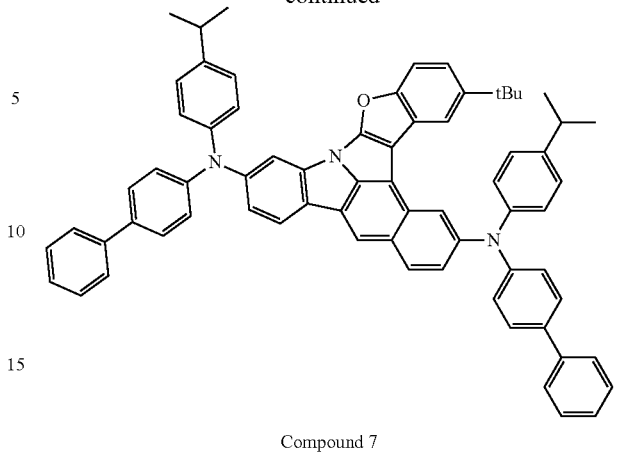

Compound 7

Compound 7 (1.9 g) was obtained by preparation in the same manner as in the synthesis method of Compound 1, except that Intermediate 28 (3.0 g) and AM-7 (1.8 g) were used instead of Intermediate 4 and AM-1 as an amine, respectively, in the synthesis of Compound 1 in Synthesis Example 1. (Yield 65%, Mass [M+]=959)

Synthesis Example 8. Synthesis of Compound 8

A. Synthesis of Intermediate 29

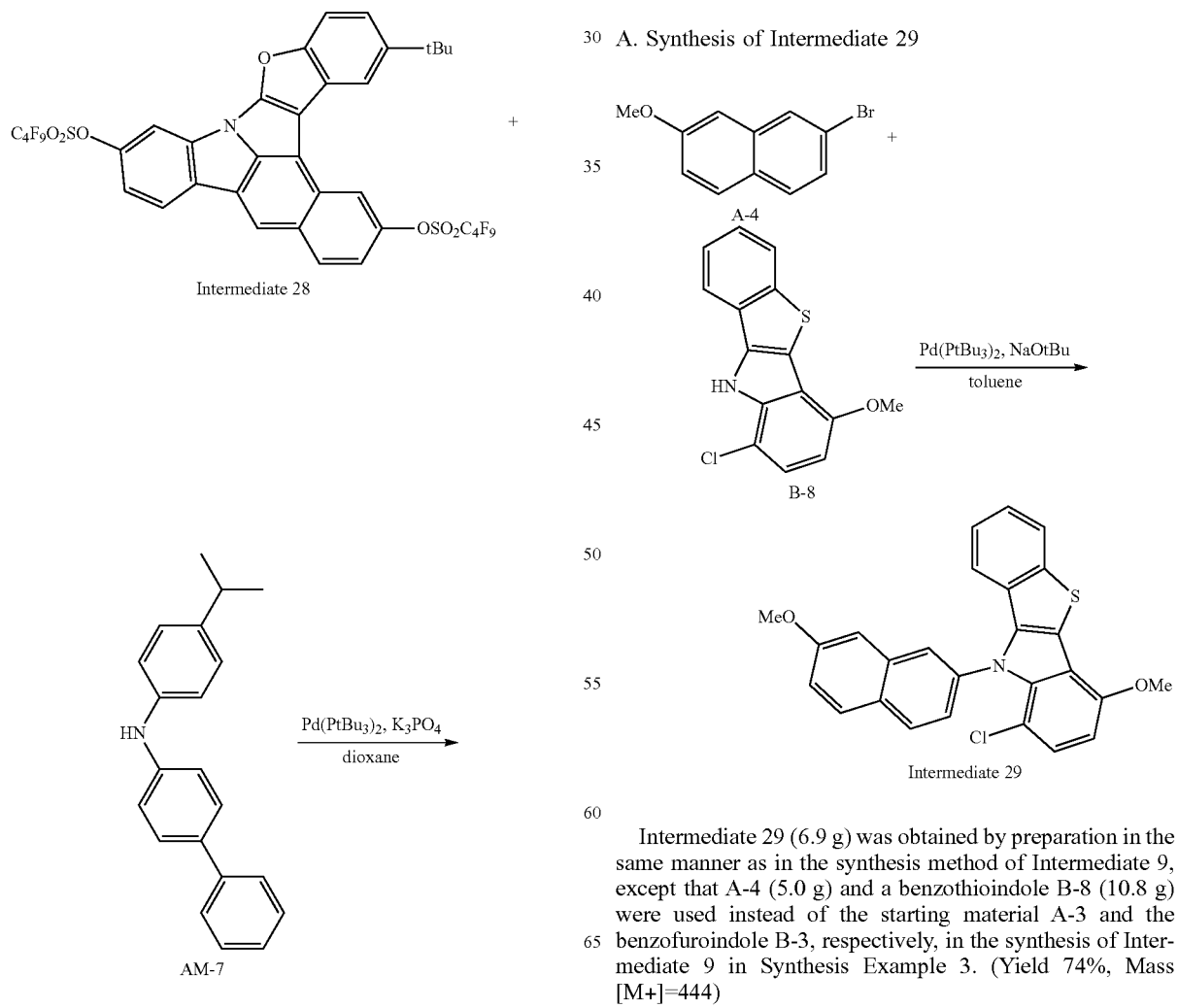

Intermediate 29 (6.9 g) was obtained by preparation in the same manner as in the synthesis method of Intermediate 9, except that A-4 (5.0 g) and a benzothioindole B-8 (10.8 g) were used instead of the starting material A-3 and the benzofuroindole B-3, respectively, in the synthesis of Intermediate 9 in Synthesis Example 3. (Yield 74%, Mass [M+]=444)

B. Synthesis of Intermediate 30

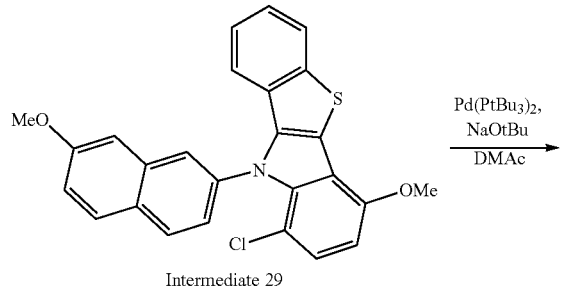
Intermediate 29

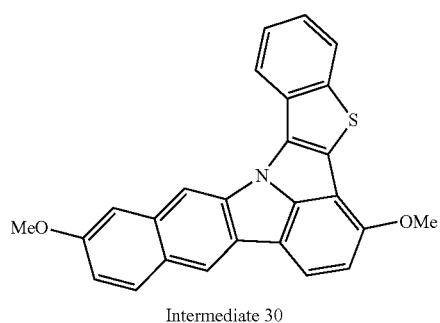
Intermediate 30

Intermediate 30 (4.1 g) was obtained by preparation in the same manner as in the synthesis method of Intermediate 10, except that Intermediate 29 (6.9 g) was used instead of Intermediate 9 in the synthesis of Intermediate 10 in Synthesis Example 3. (Yield 65%, Mass [M+]=408)

C. Synthesis of Intermediates 31 and 32

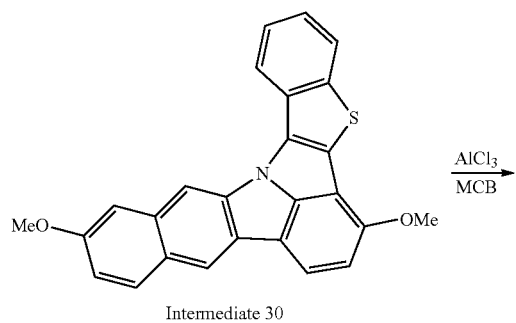
Intermediate 30

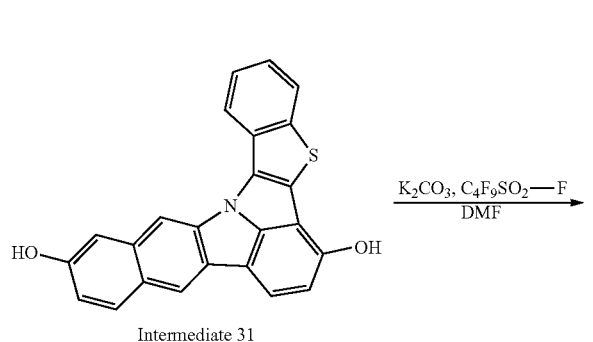
Intermediate 31

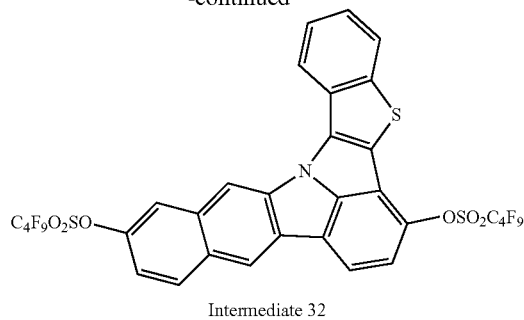
Intermediate 32

Intermediate 31 (3.0 g) was obtained by preparation in the same manner as in the synthesis method of Intermediate 3, except that Intermediate 30 (4.1 g) was used instead of Intermediate 2 in the synthesis of Intermediate 3 in Synthesis Example 1. (Yield 79%, Mass [M+]=380)

Intermediate 32 (5.3 g) was obtained by preparation in the same manner as in the synthesis method of Intermediate 4, except that Intermediate 31 (3.0 g) was used instead of Intermediate 3 in the synthesis of Intermediate 4 in Synthesis Example 1. (Yield 71%, Mass [M+]=944)

D. Synthesis of Compound 8

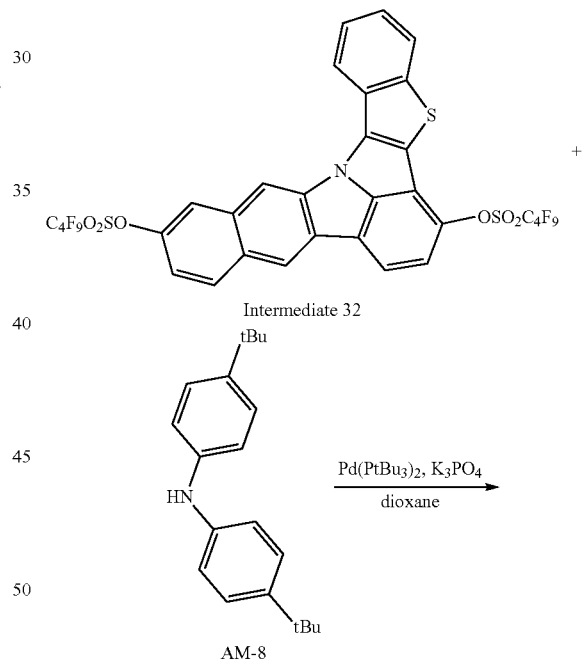

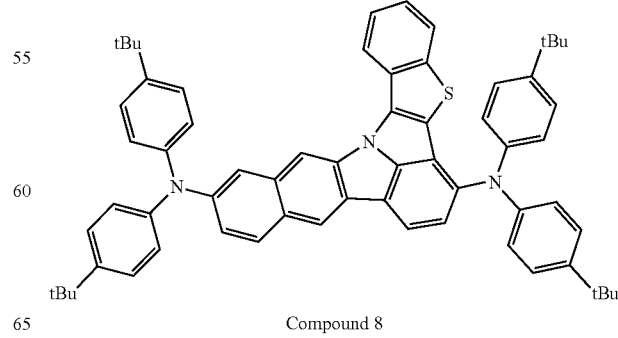
Compound 8

Compound 8 (2.0 g) was obtained by preparation in the same manner as in the synthesis method of Compound 1, except that Intermediate 32 (3.0 g) and AM-8 (1.8 g) were used instead of Intermediate 4 and AM-1 as an amine, respectively, in the synthesis of Compound 1 in Synthesis Example 1. (Yield 69%, Mass [M+]=907)

Synthesis Example 9. Synthesis of Compound 9

A. Synthesis of Intermediate 33

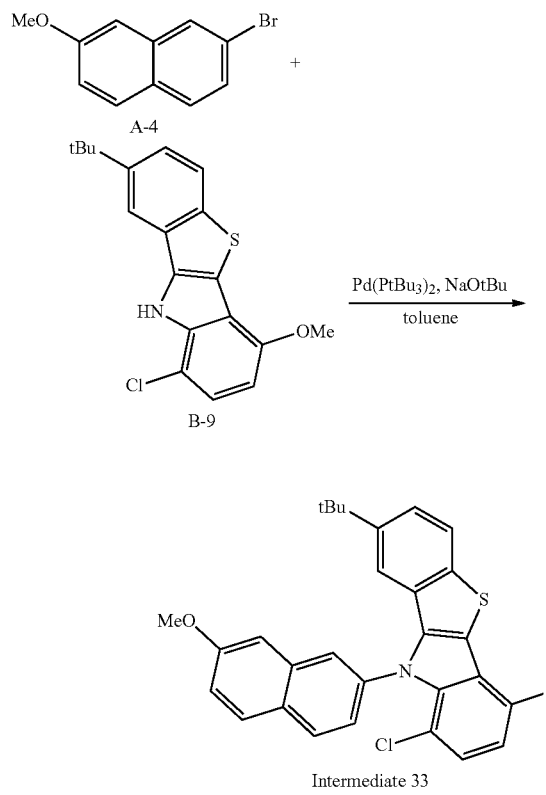

Intermediate 33 (7.1 g) was obtained by preparation in the same manner as in the synthesis method of Intermediate 9, except that A-4 (5.0 g) and a benzothioindole B-9 (7.3 g) were used instead of the staring material A-3 and the benzofuroindole B-3, respectively, in the synthesis of Intermediate 9 in Synthesis Example 3. (Yield 67%, Mass [M+]=501)

B. Synthesis of Intermediate 34

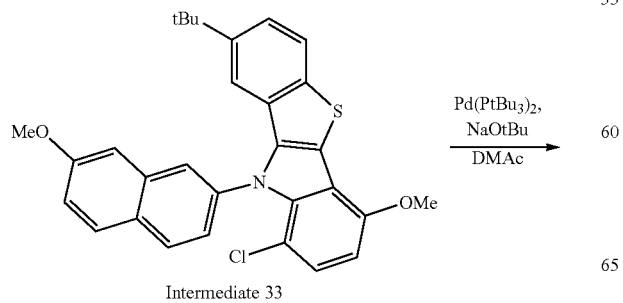

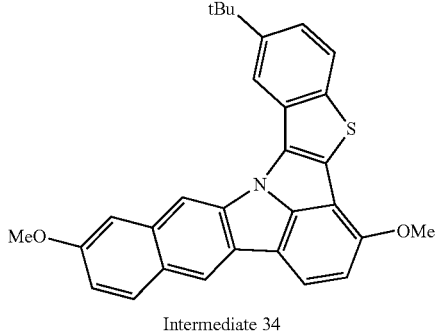

Intermediate 34

Intermediate 34 (3.9 g) was obtained by preparation in the same manner as in the synthesis method of Intermediate 10, except that Intermediate 33 (7.1 g) was used instead of Intermediate 9 in the synthesis of Intermediate 10 in Synthesis Example 3. (Yield 59%, Mass [M+]=464)

C. Synthesis of Intermediates 35 and 36

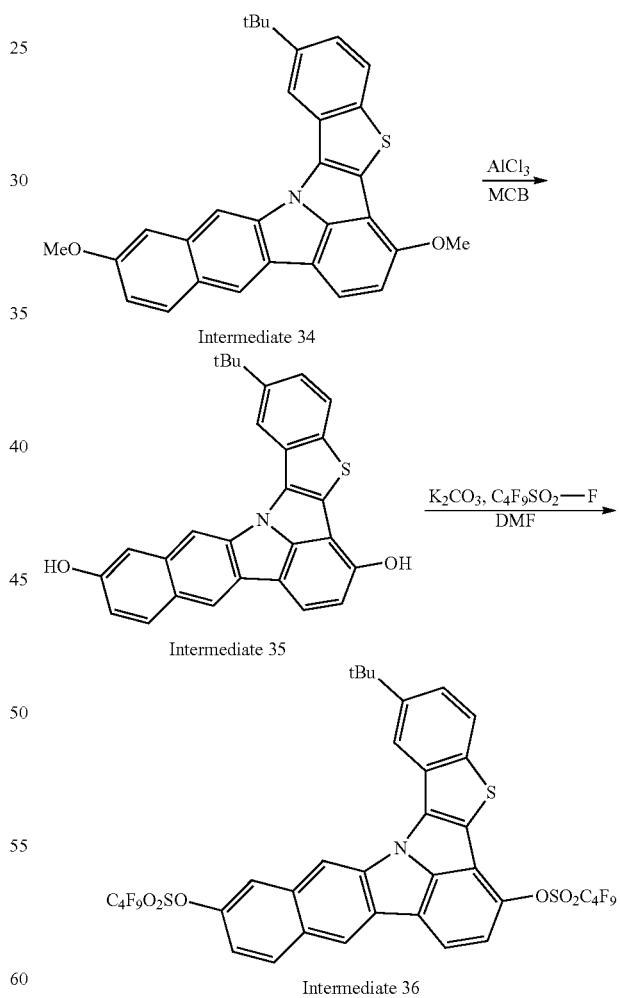

Intermediate 35 (2.7 g) was obtained by preparation in the same manner as in the synthesis method of Intermediate 3, except that Intermediate 34 (3.9 g) was used instead of Intermediate 2 in the synthesis of Intermediate 3 in Synthesis Example 1. (Yield 74%, Mass [M+]=436)

Intermediate 36 (4.6 g) was obtained by preparation in the same manner as in the synthesis method of Intermediate 4, except that Intermediate 35 (2.7 g) was used instead of Intermediate 3 in the synthesis of Intermediate 4 in Synthesis Example 1. (Yield 74%, Mass [M+]=1000)

D. Synthesis of Compound 9

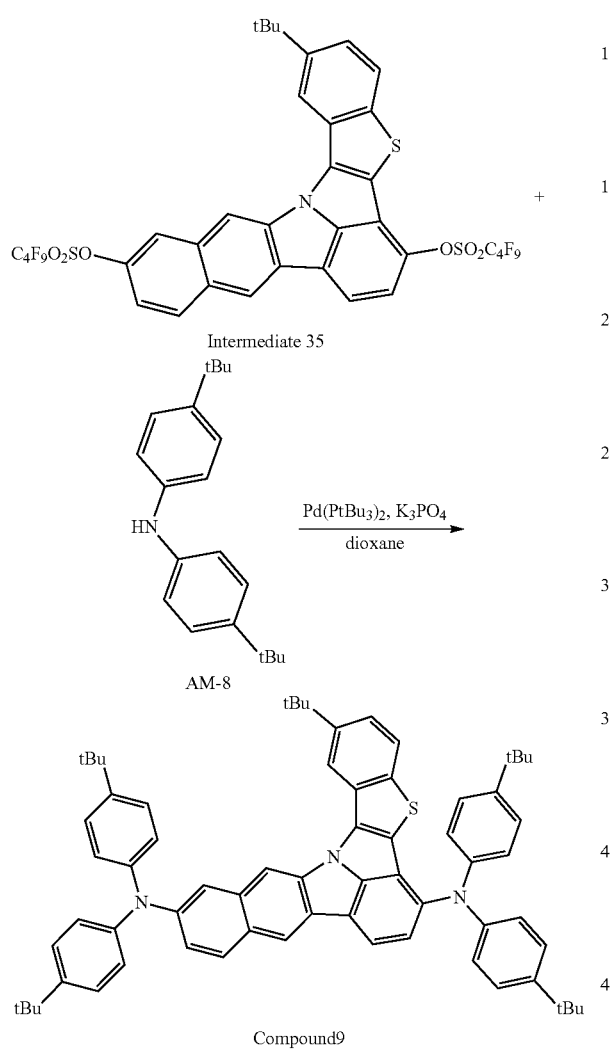

Compound 9 (2.1 g) was obtained by preparation in the same manner as in the synthesis method of Compound 1, except that Intermediate 36 (3.0 g) and AM-8 (1.7 g) were used instead of Intermediate 4 and AM-1 as an amine, respectively, in the synthesis of Compound 1 in Synthesis Example 1. (Yield 73%, Mass [M+]=963)

Synthesis Example 10. Synthesis of Compound 10

A. Synthesis of Intermediate 37

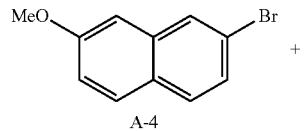

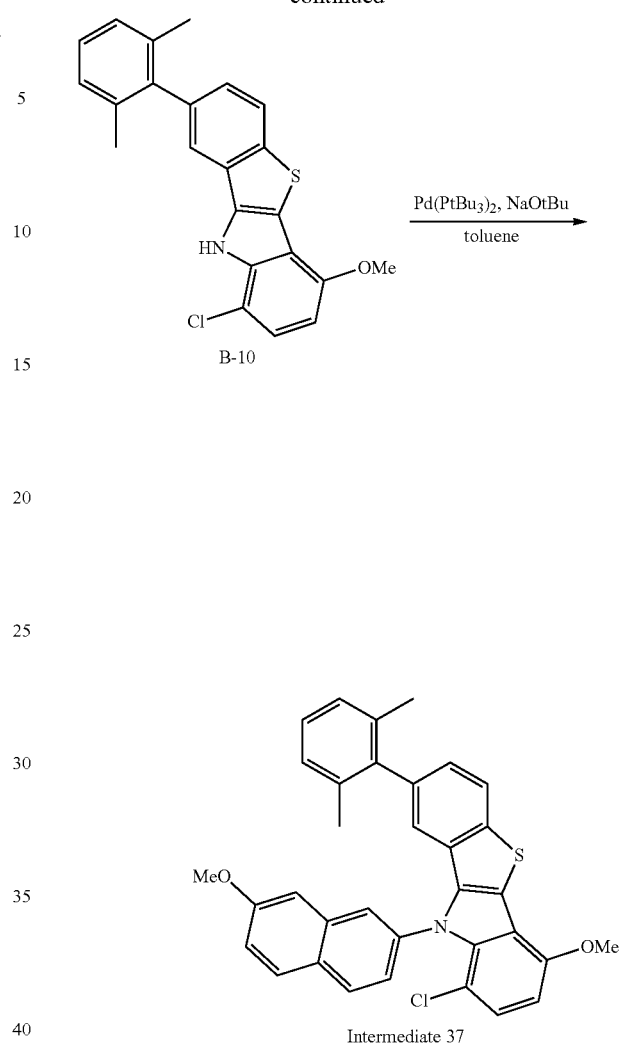

Intermediate 37 (7.0 g) was obtained by preparation in the same manner as in the synthesis method of Intermediate 9, except that A-4 (5.0 g) and a benzothioindole B-10 (8.3 g) were used instead of the staring material A-3 and the benzofuroindole B-3, respectively, in the synthesis of Intermediate 9 in Synthesis Example 3. (Yield 61%, Mass [M+]=549)

B. Synthesis of Intermediate 38

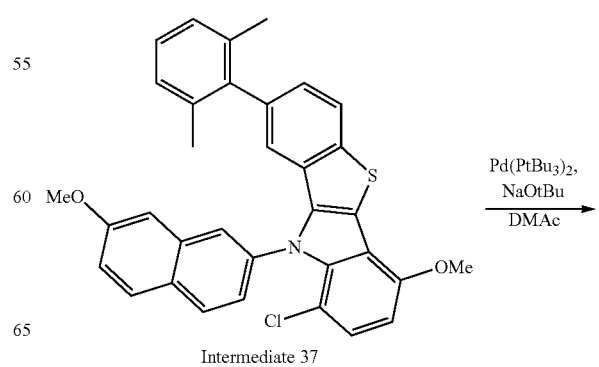

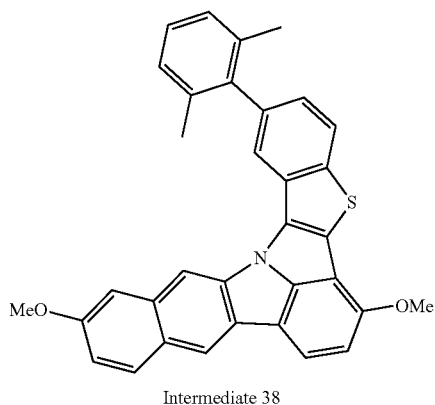

Intermediate 38

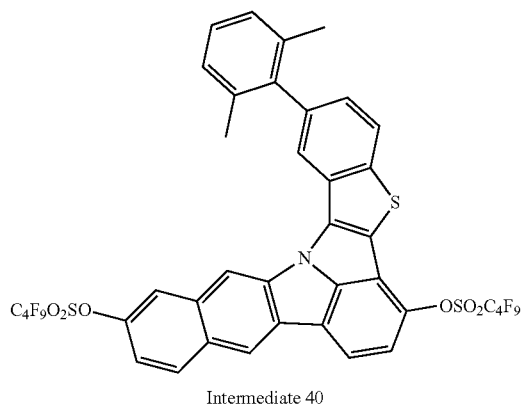

Intermediate 40

Intermediate 38 (4.3 g) was obtained by preparation in the same manner as in the synthesis method of Intermediate 10, except that Intermediate 37 (7.0 g) was used instead of Intermediate 9 in the synthesis of Intermediate 10 in Synthesis Example 3. (Yield 66%, Mass [M+]=512)

C. Synthesis of Intermediates 39 and 40

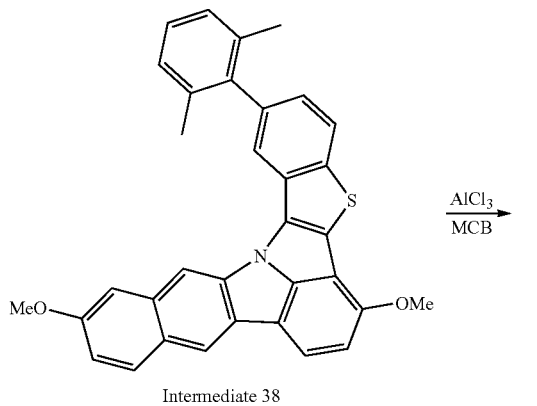

Intermediate 38

Intermediate 39 (3.3 g) was obtained by preparation in the same manner as in the synthesis method of Intermediate 3, except that Intermediate 38 (4.3 g) was used instead of Intermediate 2 in the synthesis of Intermediate 3 in Synthesis Example 1. (Yield 81%, Mass [M+]=484)

Intermediate 40 (5.5 g) was obtained by preparation in the same manner as in the synthesis method of Intermediate 4, except that Intermediate 39 (3.3 g) was used instead of Intermediate 3 in the synthesis of Intermediate 4 in Synthesis Example 1. (Yield 77%, Mass [M+]=1048)

D. Synthesis of Compound 10

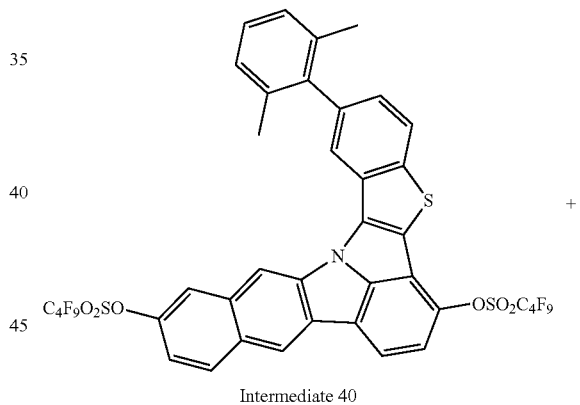

Intermediate 40

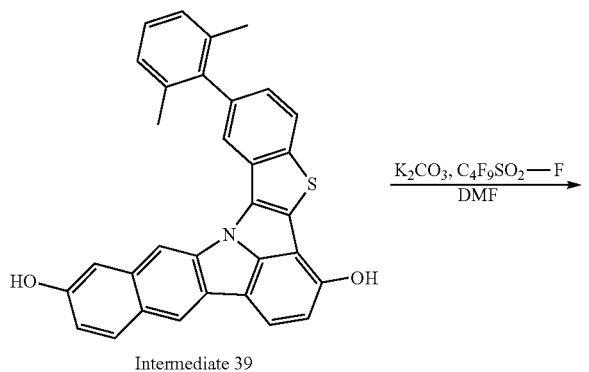

Intermediate 39

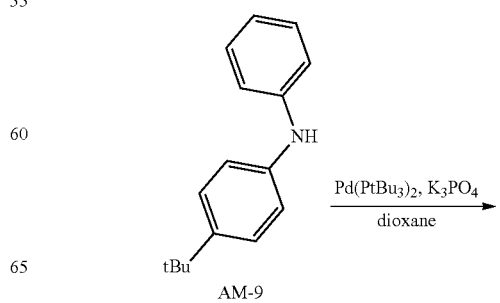

AM-9

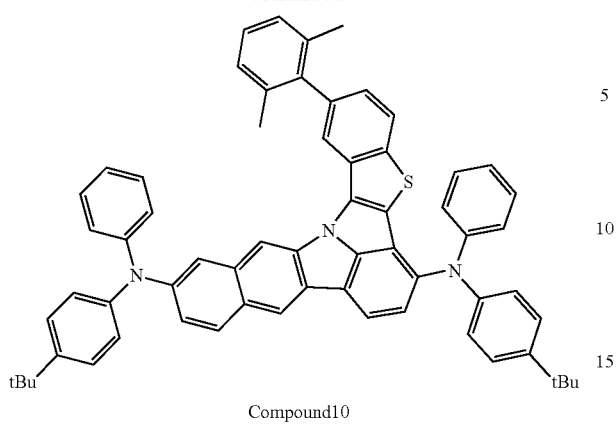

Compound10

Compound 10 (108 g) was obtained by preparation in the same manner as in the synthesis method of Compound 1, except that Intermediate 40 (3.0 g) and AM-9 (1.3 g) were used instead of Intermediate 4 and AM-1 as an amine, respectively, in the synthesis of Compound 1 in Synthesis Example 1. (Yield 70%, Mass [M+]=899)

Synthesis Example 11. Synthesis of Compound 11

A. Synthesis of Intermediate 41

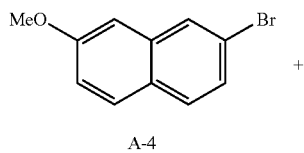

A-4

+

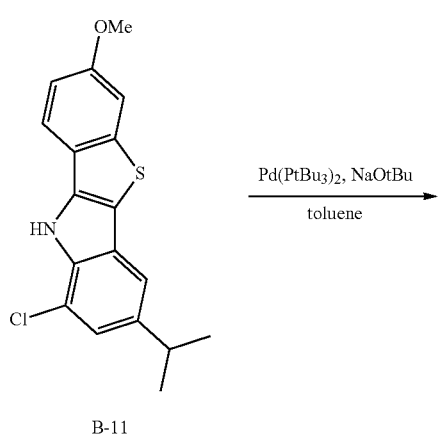

B-11

Pd(PtBu$_3$)$_2$, NaOtBu
toluene

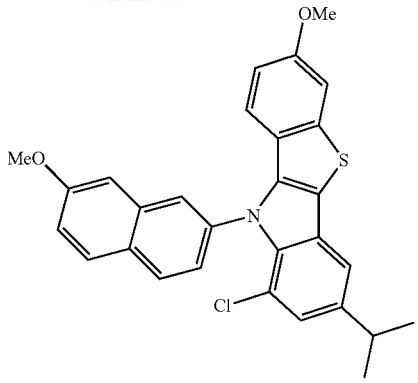

Intermediate 41

Intermediate 41 (7.4 g) was obtained by preparation in the same manner as in the synthesis method of Intermediate 9, except that A-4 (5.0 g) and a benzothioindole B-11 (7.0 g) were used instead of the staring material A-3 and the benzofuroindole B-3, respectively, in the synthesis of Intermediate 9 in Synthesis Example 3. (Yield 72%, Mass [M+]=487)

B. Synthesis of Intermediate 42

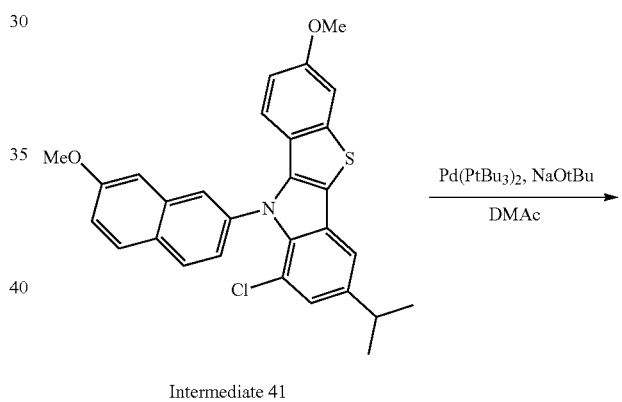

Intermediate 42 (3.8 g) was obtained by preparation in the same manner as in the synthesis method of Intermediate 10, except that Intermediate 41 (7.4 g) was used instead of Intermediate 9 in the synthesis of Intermediate 10 in Synthesis Example 3. (Yield 56%, Mass [M+]=450)

C. Synthesis of Intermediates 43 and 44

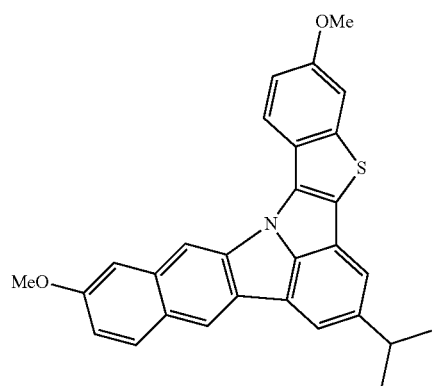

Intermediate 42

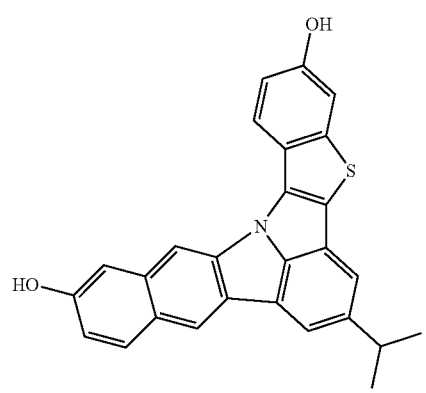

Intermediate 43

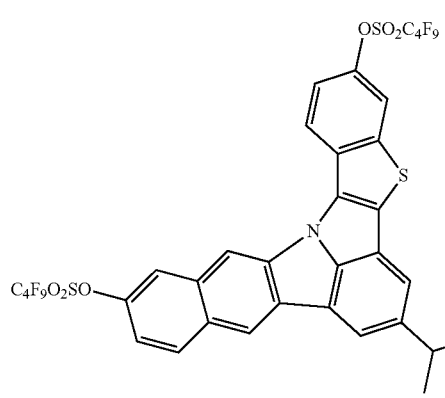

Intermediate 44

Intermediate 43 (2.6 g) was obtained by preparation in the same manner as in the synthesis method of Intermediate 3, except that Intermediate 42 (3.8 g) was used instead of Intermediate 2 in the synthesis of Intermediate 3 in Synthesis Example 1. (Yield 73%, Mass [M+]=422)

Intermediate 44 (4.1 g) was obtained by preparation in the same manner as in the synthesis method of Intermediate 4, except that Intermediate 43 (2.6 g) was used instead of Intermediate 3 in the synthesis of Intermediate 4 in Synthesis Example 1. (Yield 67%, Mass [M+]=986)

D. Synthesis of Compound 11

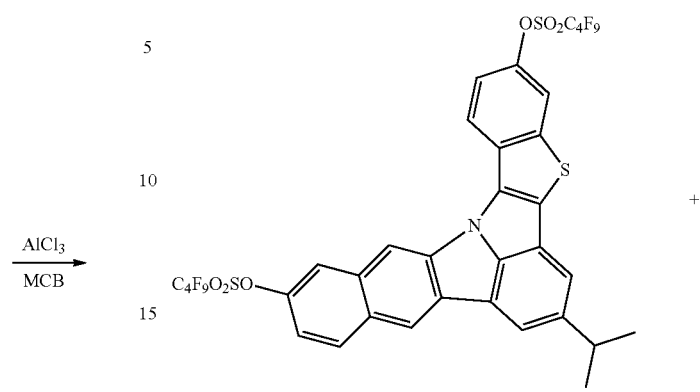

Intermediate 44

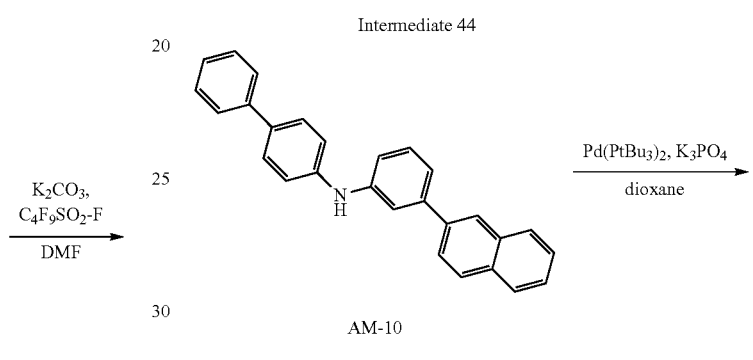

AM-10

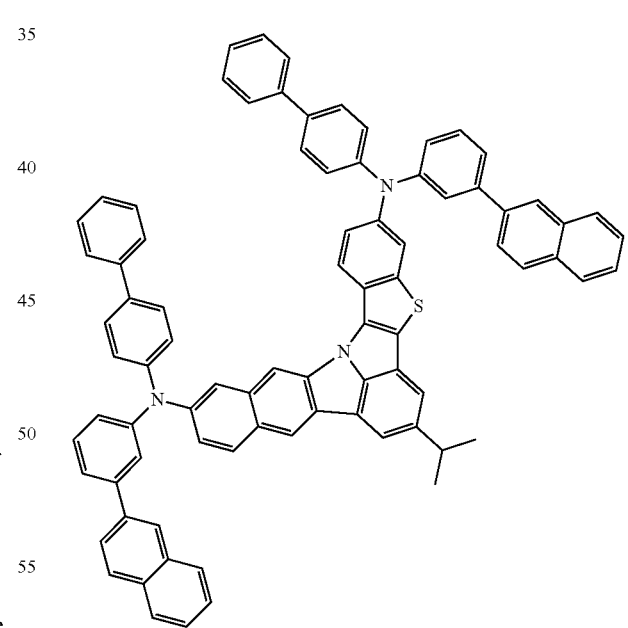

Compound 11

Compound 11 (2.4 g) was obtained by preparation in the same manner as in the synthesis method of Compound 1, except that Intermediate 44 (3.0 g) and AM-10 (2.3 g) were used instead of Intermediate 4 and AM-1 as an amine, respectively, in the synthesis of Compound 1 in Synthesis Example 1. (Yield 70%, Mass [M+]=1129)

Synthesis Example 12. Synthesis of Compound 12

A. Synthesis of Intermediate 45

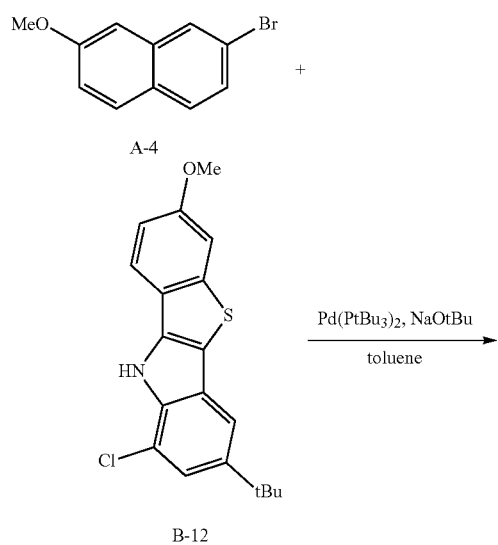

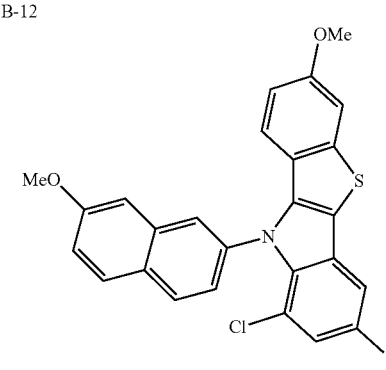

Intermediate 45

Intermediate 45 (6.5 g) was obtained by preparation in the same manner as in the synthesis method of Intermediate 9, except that A-4 (5.0 g) and a benzothioindole B-12 (7.3 g) were used instead of the staring material A-3 and the benzofuroindole B-3, respectively, in the synthesis of Intermediate 9 in Synthesis Example 3. (Yield 62%, Mass [M+]=501)

B. Synthesis of Intermediate 46

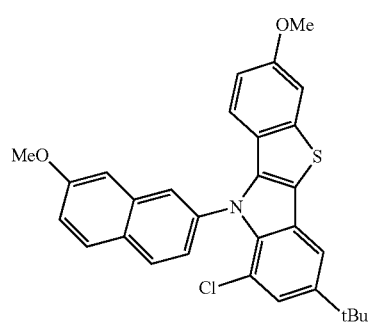

Intermediate 45

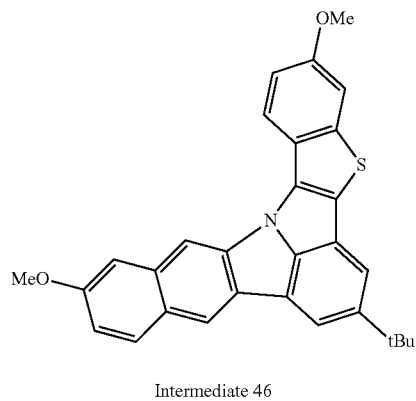

Intermediate 46

Intermediate 46 (3.7 g) was obtained by preparation in the same manner as in the synthesis method of Intermediate 10, except that Intermediate 45 (6.5 g) was used instead of Intermediate 9 in the synthesis of Intermediate 10 in Synthesis Example 3. (Yield 61%, Mass [M+]=464)

C. Synthesis of Intermediates 47 and 48

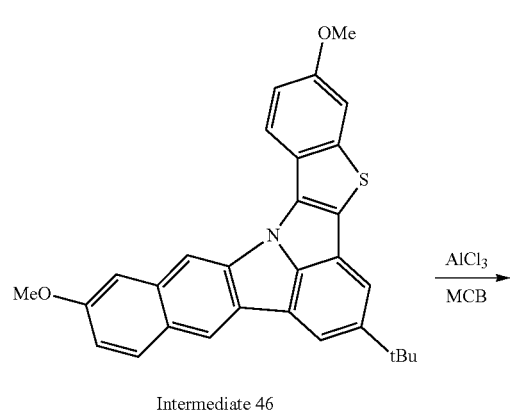

Intermediate 46

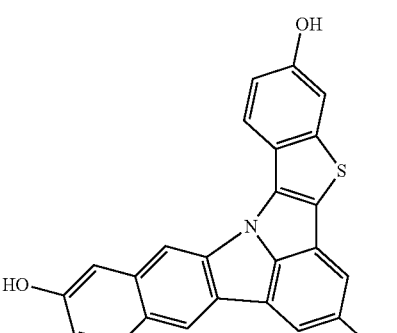

Intermediate 47

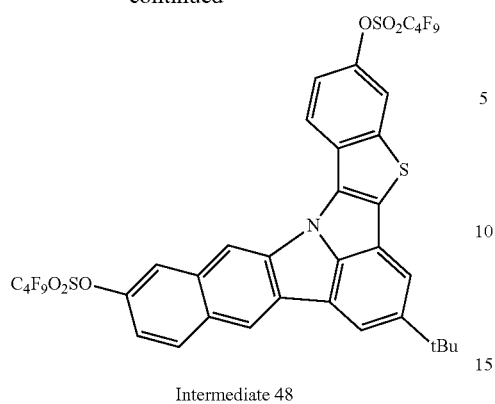

Intermediate 48

Intermediate 47 (2.6 g) was obtained by preparation in the same manner as in the synthesis method of Intermediate 3, except that Intermediate 46 (3.7 g) was used instead of Intermediate 2 in the synthesis of Intermediate 3 in Synthesis Example 1. (Yield 75%, Mass [M+]=436)

Intermediate 48 (4.2 g) was obtained by preparation in the same manner as in the synthesis method of Intermediate 4, except that Intermediate 47 (2.6 g) was used instead of Intermediate 3 in the synthesis of Intermediate 4 in Synthesis Example 1. (Yield 70%, Mass [M+]=1000)

D. Synthesis of Compound 12

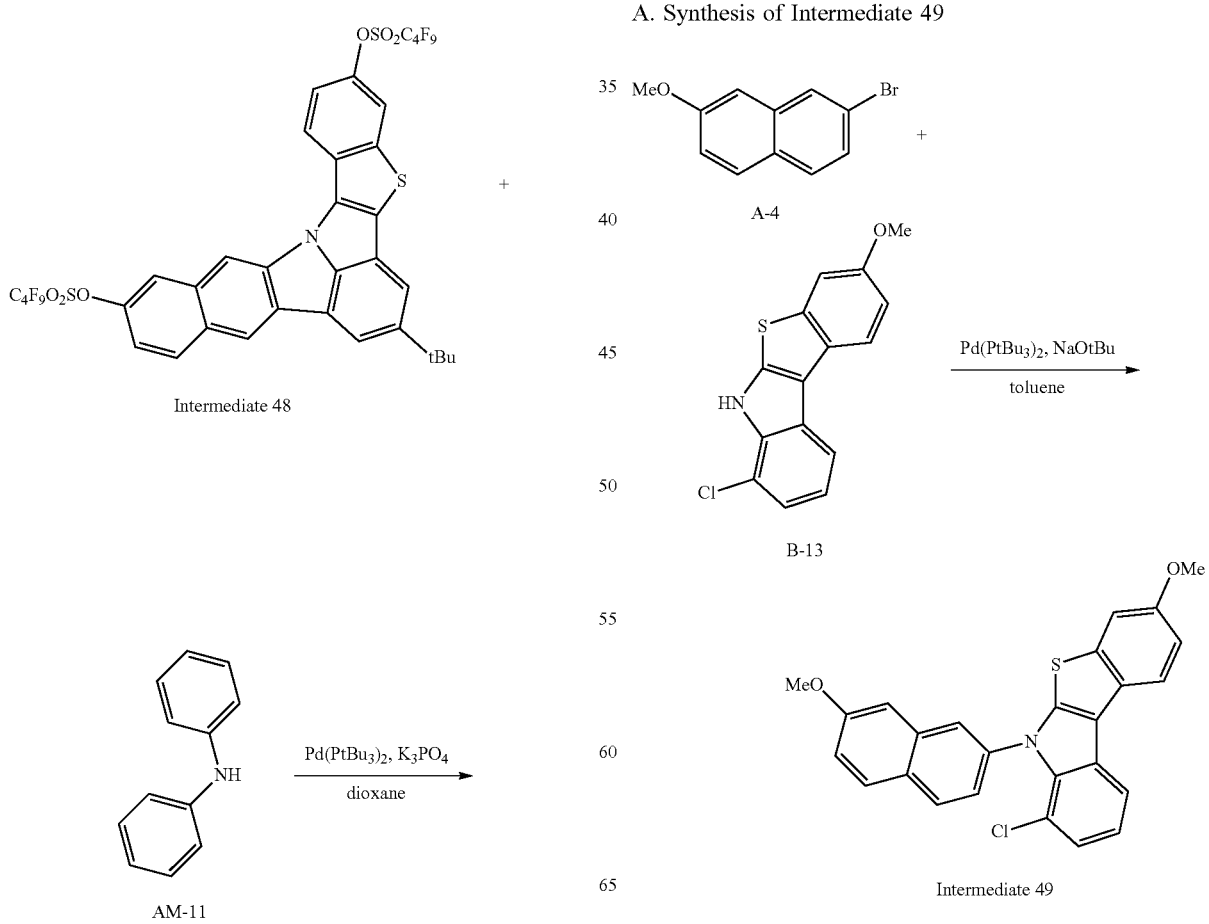

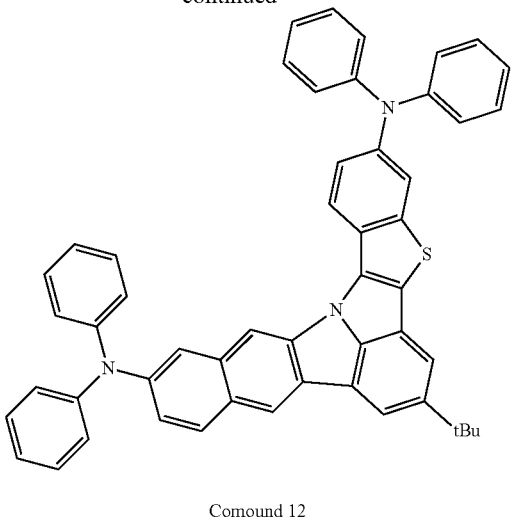

Compound 12

Compound 12 (1.6 g) was obtained by preparation in the same manner as in the synthesis method of Compound 1, except that Intermediate 48 (3.0 g) and AM-11 (1.0 g) were used instead of Intermediate 4 and AM-1 as an amine, respectively, in the synthesis of Compound 1 in Synthesis Example 1. (Yield 72%, Mass [M+]=738)

Synthesis Example 13. Synthesis of Compound 13

A. Synthesis of Intermediate 49

Intermediate 49 (6.5 g) was obtained by preparation in the same manner as in the synthesis method of Intermediate 9, except that A-4 (5.0 g) and a benzothioindole B-13 (10.8 g) were used instead of the staring material A-3 and the benzofuroindole B-3, respectively, in the synthesis of Intermediate 9 in Synthesis Example 3. (Yield 69%, Mass [M+]=444)

B. Synthesis of Intermediate 50

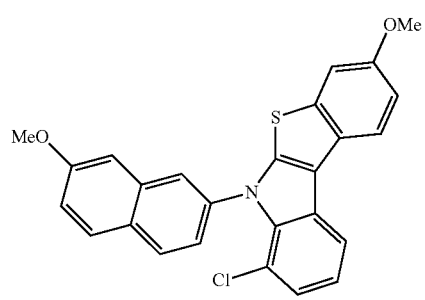

Intermediate 49

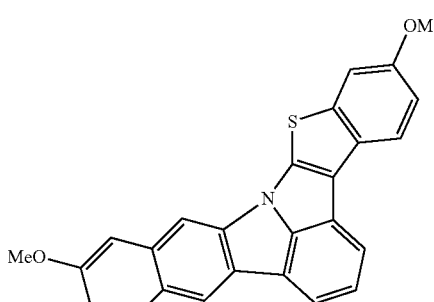

Intermediate 50

Intermediate 50 (3.6 g) was obtained by preparation in the same manner as in the synthesis method of Intermediate 10, except that Intermediate 49 (6.5 g) was used instead of Intermediate 9 in the synthesis of Intermediate 10 in Synthesis Example 3. (Yield 60%, Mass [M+]=408)

C. Synthesis of Intermediates 51 and 52

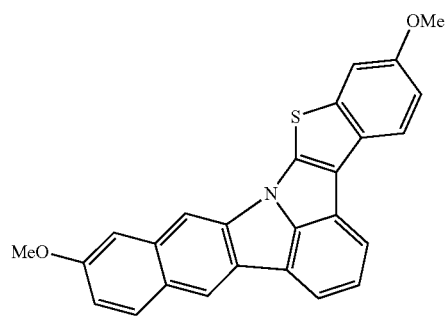

Intermediate 50

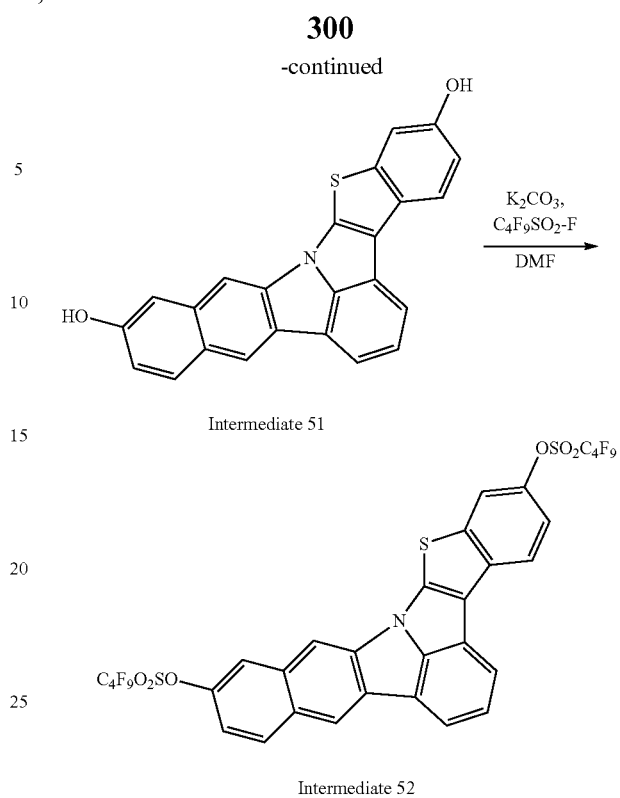

Intermediate 51

Intermediate 52

Intermediate 51 (2.5 g) was obtained by preparation in the same manner as in the synthesis method of Intermediate 3, except that Intermediate 50 (3.6 g) was used instead of Intermediate 2 in the synthesis of Intermediate 3 in Synthesis Example 1. (Yield 75%, Mass [M+]=380)

Intermediate 52 (4.3 g) was obtained by preparation in the same manner as in the synthesis method of Intermediate 4, except that Intermediate 51 (2.5 g) was used instead of Intermediate 3 in the synthesis of Intermediate 4 in Synthesis Example 1. (Yield 70%, Mass [M+]=944)

D. Synthesis of Compound 13

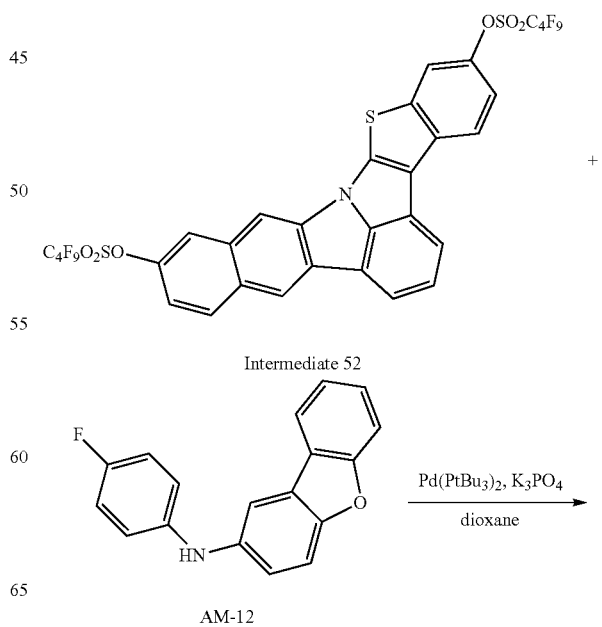

Intermediate 52

AM-12

-continued

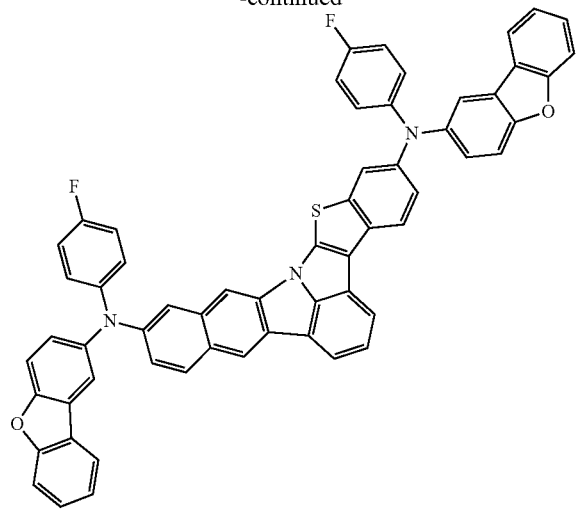

Compound 13

Compound 13 (2.1 g) was obtained by preparation in the same manner as in the synthesis method of Compound 1, except that Intermediate 52 (3.0 g) and AM-12 (1.8 g) were used instead of Intermediate 4 and AM-1 as an amine, respectively, in the synthesis of Compound 1 in Synthesis Example 1. (Yield 74%, Mass [M+]=899)

Synthesis Example 14. Synthesis of Compound 14

A. Synthesis of Intermediate 53

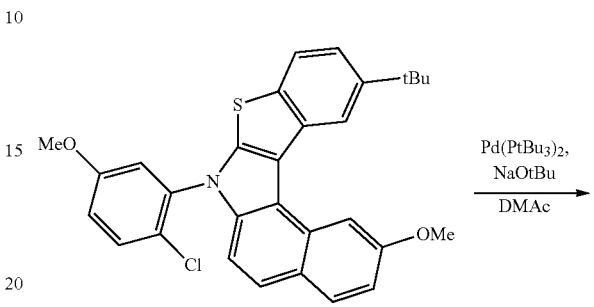

A-6

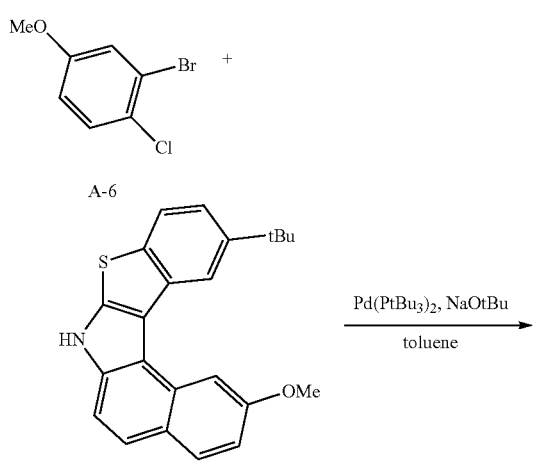

B-14

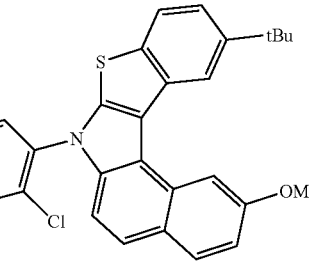

Intermediate 53

Intermediate 53 (7.3 g) was obtained by preparation in the same manner as in the synthesis method of Intermediate 9, except that A-6 (5.0 g) and a benzothioindole B-14 (8.2 g) were used instead of the staring material A-3 and the benzofuroindole B-3, respectively, in the synthesis of Intermediate 9 in Synthesis Example 3. (Yield 65%, Mass [M+]=501)

B. Synthesis of Intermediate 53

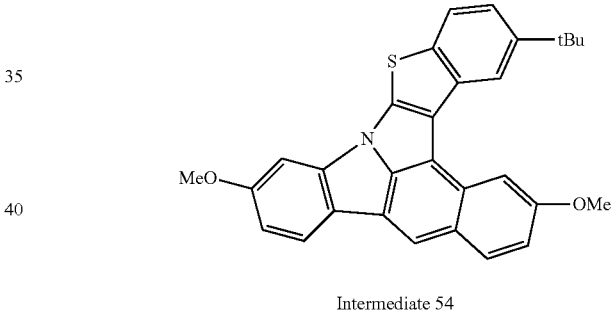

Intermediate 53

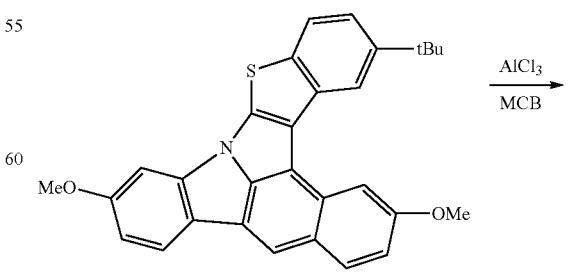

Intermediate 54

Intermediate 54 (4.2 g) was obtained by preparation in the same manner as in the synthesis method of Intermediate 10, except that Intermediate 53 (7.3 g) was used instead of Intermediate 9 in the synthesis of Intermediate 10 in Synthesis Example 3. (Yield 62%, Mass [M+]=464)

C. Synthesis of Intermediates 55 and 56

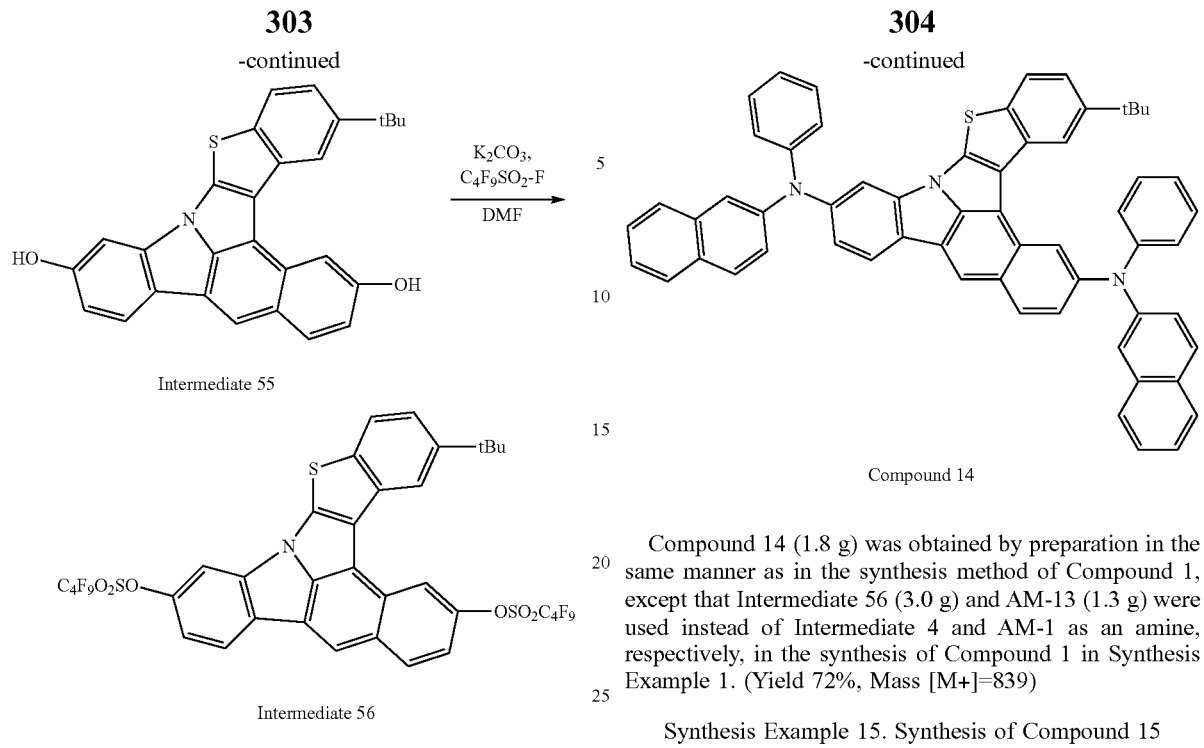

Intermediate 55 (2.8 g) was obtained by preparation in the same manner as in the synthesis method of Intermediate 3, except that Intermediate 54 (4.2 g) was used instead of Intermediate 2 in the synthesis of Intermediate 3 in Synthesis Example 1. (Yield 71%, Mass [M+]=436)

Intermediate 56 (4.2 g) was obtained by preparation in the same manner as in the synthesis method of Intermediate 4, except that Intermediate 55 (2.8 g) was used instead of Intermediate 3 in the synthesis of Intermediate 4 in Synthesis Example 1. (Yield 65%, Mass [M+]=1000)

D. Synthesis of Compound 14

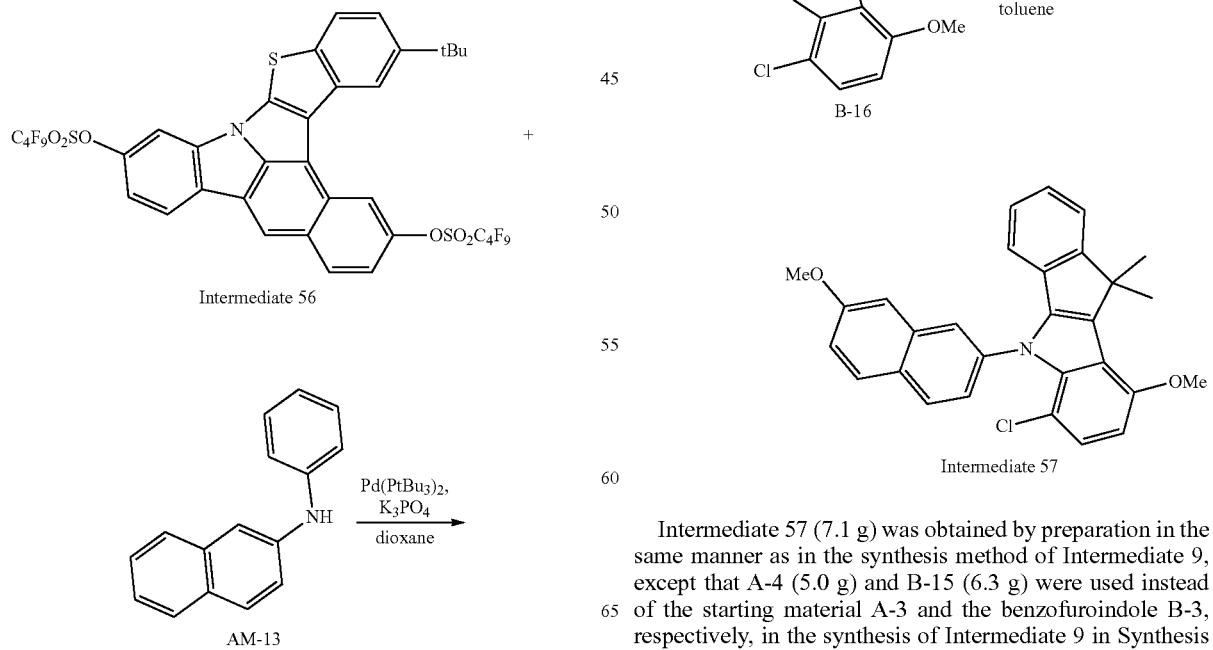

Compound 14 (1.8 g) was obtained by preparation in the same manner as in the synthesis method of Compound 1, except that Intermediate 56 (3.0 g) and AM-13 (1.3 g) were used instead of Intermediate 4 and AM-1 as an amine, respectively, in the synthesis of Compound 1 in Synthesis Example 1. (Yield 72%, Mass [M+]=839)

Synthesis Example 15. Synthesis of Compound 15

A. Synthesis of Intermediate 57

Intermediate 57 (7.1 g) was obtained by preparation in the same manner as in the synthesis method of Intermediate 9, except that A-4 (5.0 g) and B-15 (6.3 g) were used instead of the starting material A-3 and the benzofuroindole B-3, respectively, in the synthesis of Intermediate 9 in Synthesis Example 3. (Yield 74%, Mass [M+]=454)

B. Synthesis of Intermediate 58

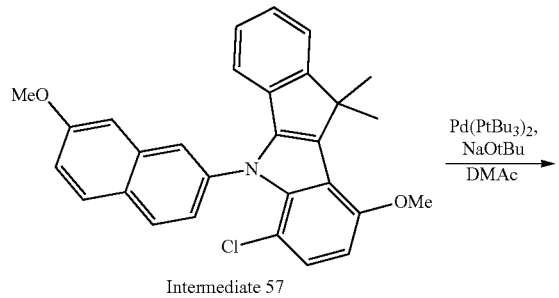

Intermediate 57

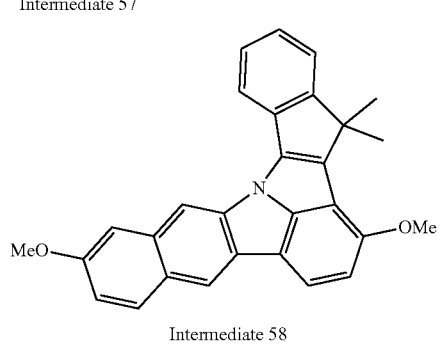

Intermediate 58

Intermediate 58 (3.9 g) was obtained by preparation in the same manner as in the synthesis method of Intermediate 10, except that Intermediate 57 (7.1 g) was used instead of Intermediate 9 in the synthesis of Intermediate 10 in Synthesis Example 3. (Yield 60%, Mass [M+]=418)

C. Synthesis of Intermediates 59 and 60

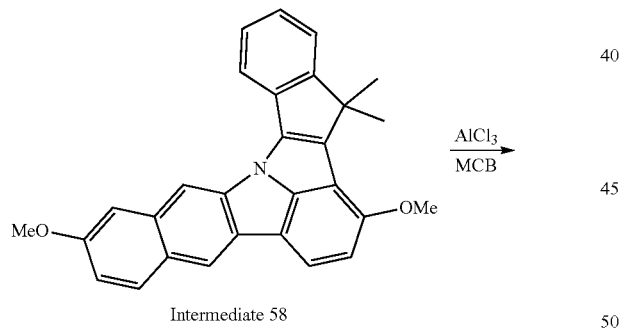

Intermediate 59

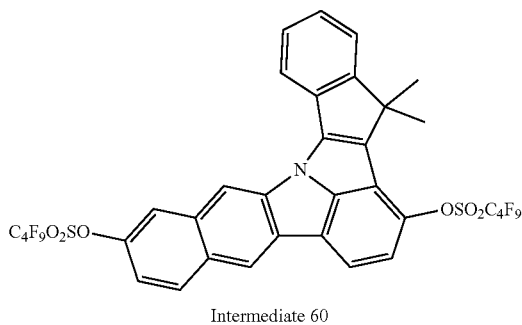

Intermediate 60

Intermediate 59 (2.6 g) was obtained by preparation in the same manner as in the synthesis method of Intermediate 3, except that Intermediate 58 (3.9 g) was used instead of Intermediate 2 in the synthesis of Intermediate 3 in Synthesis Example 1. (Yield 71%, Mass [M+]=390)

Intermediate 60 (3.9 g) was obtained by preparation in the same manner as in the synthesis method of Intermediate 4, except that Intermediate 59 (2.6 g) was used instead of Intermediate 3 in the synthesis of Intermediate 4 in Synthesis Example 1. (Yield 61%, Mass [M+]=954)

D. Synthesis of Compound 15

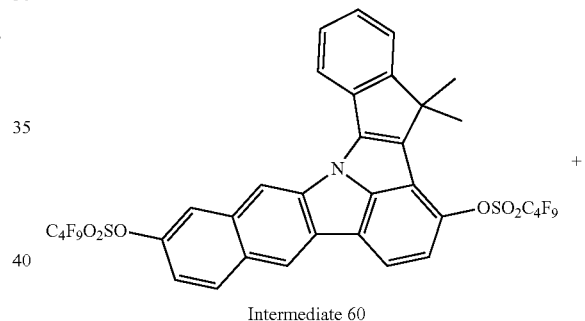

Intermediate 60

+

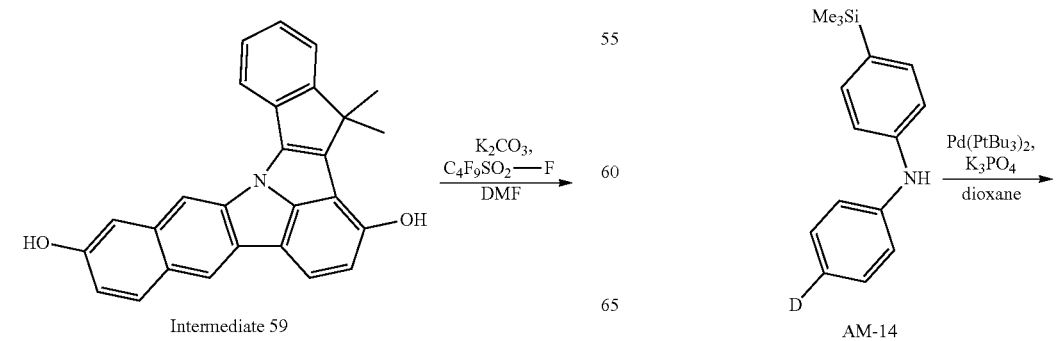

AM-14

307
-continued

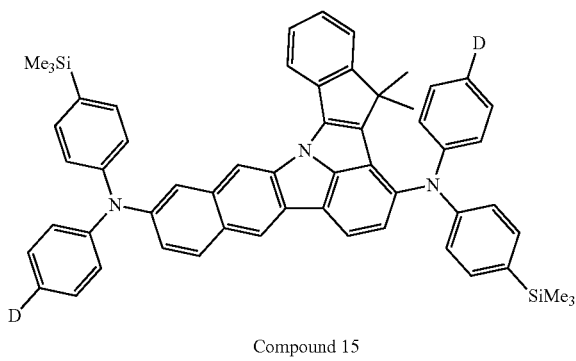

Compound 15

Compound 15 (2.1 g) was obtained by preparation in the same manner as in the synthesis method of Compound 1, except that Intermediate 60 (3.0 g) and AM-14 (1.5 g) were used instead of Intermediate 4 and AM-1 as an amine, respectively, in the synthesis of Compound 1 in Synthesis Example 1. (Yield 80%, Mass [M+]=839)

Synthesis Example 16. Synthesis of Compound 16

A. Synthesis of Intermediate 61

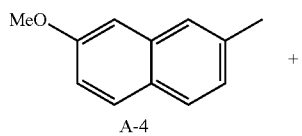

A-4

+

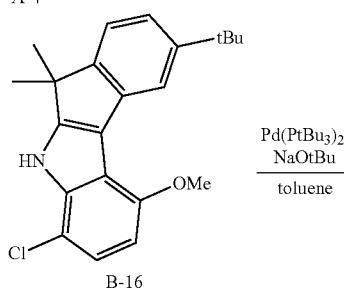

B-16

$\xrightarrow{\text{Pd(PtBu}_3)_2,\ \text{NaOtBu}}_{\text{toluene}}$

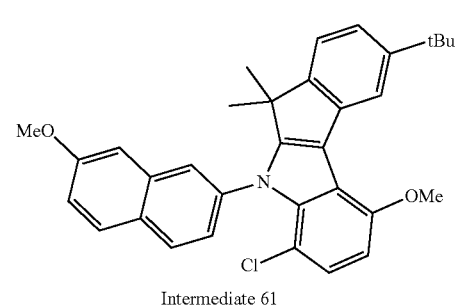

Intermediate 61

Intermediate 61 (7.6 g) was obtained by preparation in the same manner as in the synthesis method of Intermediate 9, except that A-4 (5.0 g) and B-16 (7.5 g) were used instead of the starting material A-3 and the benzofuroindole B-3, respectively, in the synthesis of Intermediate 9 in Synthesis Example 3. (Yield 71%, Mass [M+]=511)

308
B. Synthesis of Intermediate 62

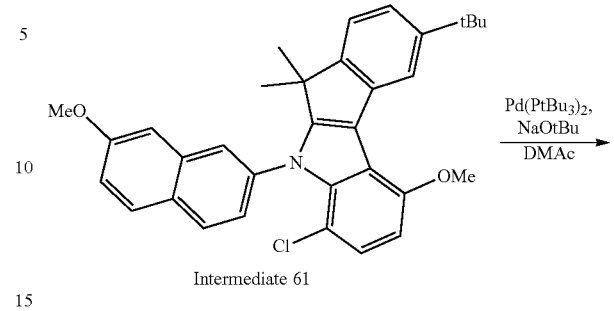

Intermediate 61

$\xrightarrow{\text{Pd(PtBu}_3)_2,\ \text{NaOtBu}}_{\text{DMAc}}$

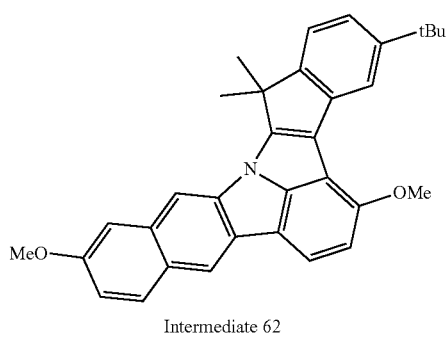

Intermediate 62

Intermediate 62 (4.4 g) was obtained by preparation in the same manner as in the synthesis method of Intermediate 10, except that Intermediate 61 (7.6 g) was used instead of Intermediate 9 in the synthesis of Intermediate 10 in Synthesis Example 3. (Yield 62%, Mass [M+]=474)

C. Synthesis of Intermediates 63 and 64

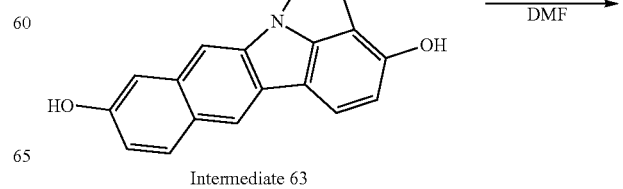

Intermediate 62 $\xrightarrow{\text{AlCl}_3}_{\text{MCB}}$

Intermediate 63 $\xrightarrow{\text{K}_2\text{CO}_3,\ \text{C}_4\text{F}_9\text{SO}_2\text{—F}}_{\text{DMF}}$

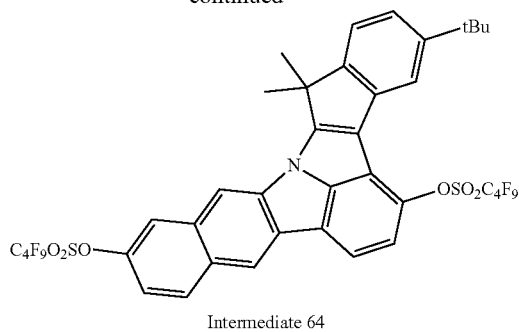

Intermediate 64

Intermediate 63 (3.0 g) was obtained by preparation in the same manner as in the synthesis method of Intermediate 3, except that Intermediate 62 (4.4 g) was used instead of Intermediate 2 in the synthesis of Intermediate 3 in Synthesis Example 1. (Yield 72%, Mass [M+]=446)

Intermediate 64 (5.1 g) was obtained by preparation in the same manner as in the synthesis method of Intermediate 4, except that Intermediate 63 (3.0 g) was used instead of Intermediate 3 in the synthesis of Intermediate 4 in Synthesis Example 1. (Yield 75%, Mass [M+]=1010)

D. Synthesis of Compound 16

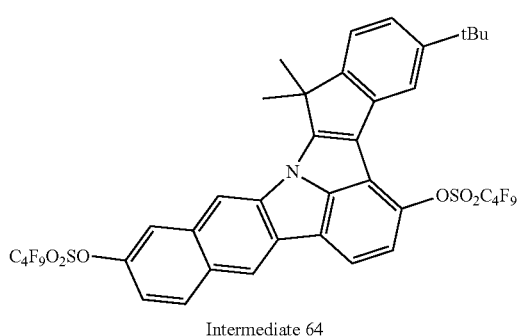

Intermediate 64

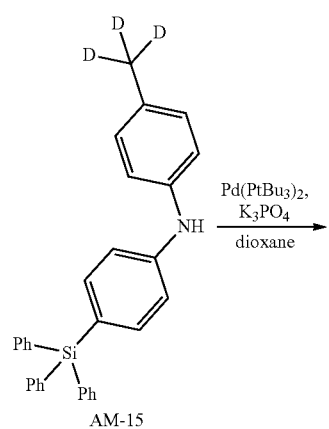

AM-15

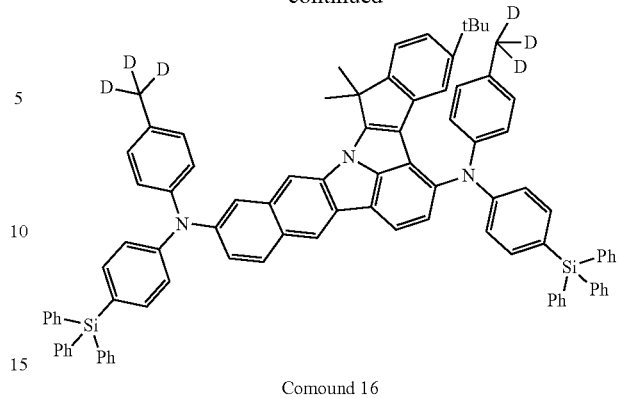

Comound 16

Compound 16 (2.9 g) was obtained by preparation in the same manner as in the synthesis method of Compound 1, except that Intermediate 64 (3.0 g) and AM-15 (2.6 g) were used instead of Intermediate 4 and AM-1 as an amine, respectively, in the synthesis of Compound 1 in Synthesis Example 1. (Yield 75%, Mass [M+]=1299)

Synthesis Example 17. Synthesis of Compound 17

C. Synthesis of Intermediates 65 and 66

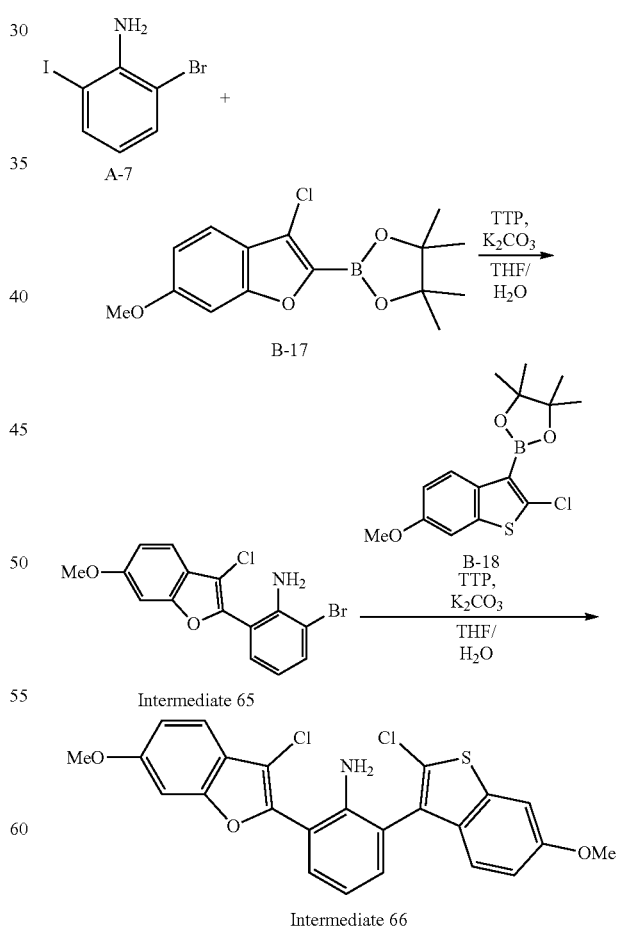

Intermediate 65

Intermediate 66

After 5.0 g of a starting material A-7, 5.2 g of a boronic ester B-17, 3.5 g of potassium carbonate, 130 mL of tetrahydrofuran, and 13 mL of water were put into a container under a nitrogen atmosphere, 0.4 g of [tetrakis(triphenylphosphine) palladium (0)] (Pd(PPh$_3$)$_4$) was added thereto, and then the resulting mixture was heated at 120° C. and stirred for 2 hours. After the starting material disappeared and Intermediate 65 was confirmed, 5.5 g of a boronic ester B-18 and 2.3 g of potassium carbonate were added thereto, and then the resulting mixture was additionally stirred for 4 hours. After the reaction was terminated, the reaction solution was cooled to room temperature, aliquoted by adding water and ethyl acetate thereto, and then filtered by treatment with MgSO$_4$ (anhydrous). The filtered solution was distilled off under reduced pressure and purified with recrystallization (ethyl acetate/hexane) to obtain Intermediate 66 (6.2 g). (Yield 79%, Mass [M+]=471)

B. Synthesis of Intermediate 67

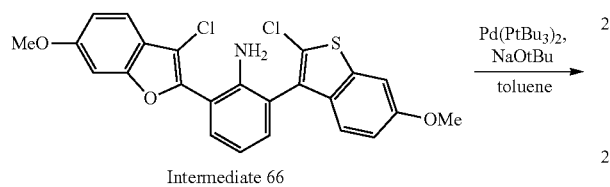

Intermediate 66

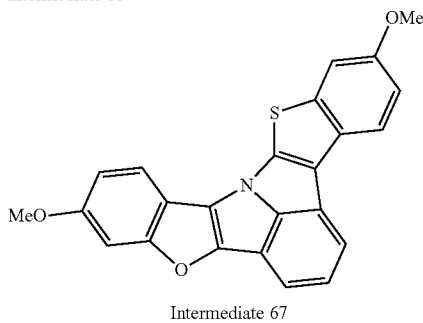

Intermediate 67

After 6.2 g of Intermediate 66, 3.8 g of sodium t-butoxide, and 0.13 g of [bis(tri(tert-butyl)phosphine)-palladium(0), Pd(PtBu$_3$)$_2$] were put into 65 mL of toluene under a nitrogen atmosphere, the resulting mixture was heated at 140° C. and stirred for 6 hours. After the reaction was terminated, the reaction solution was cooled to room temperature, aliquoted by adding water and aq. NH$_4$Cl thereto, and then filtered by treatment with MgSO$_4$ (anhydrous). The filtered solution was distilled off under reduced pressure and purified with recrystallization to obtain Intermediate 67 (4.1 g). (Yield 78%, Mass [M+]=398)

C. Synthesis of Intermediates 68 and 69

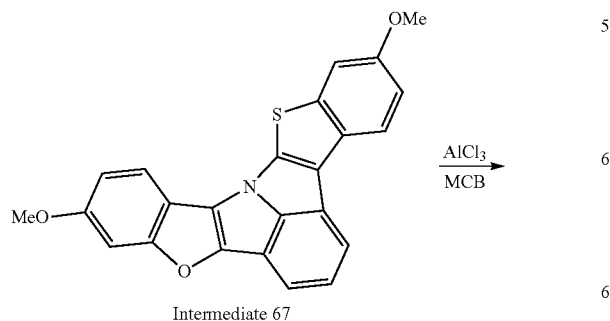

Intermediate 67

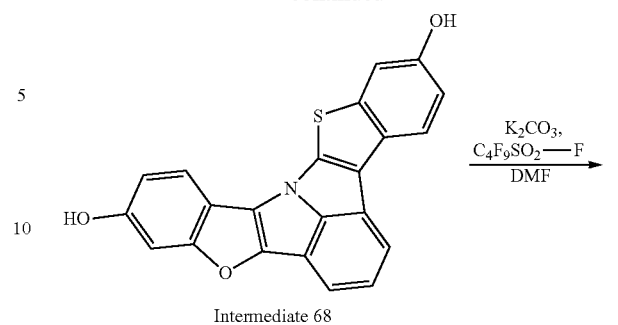

Intermediate 68

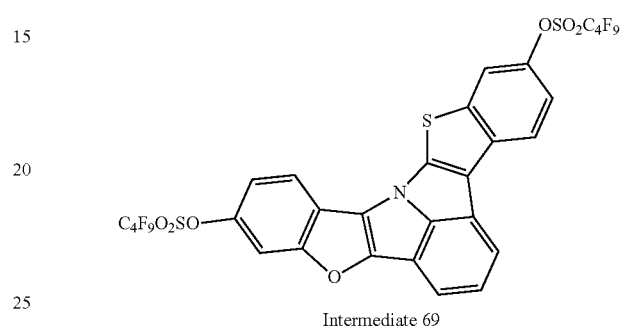

Intermediate 69

Intermediate 68 (2.8 g) was obtained by preparation in the same manner as in the synthesis method of Intermediate 3, except that Intermediate 67 (4.1 g) was used instead of Intermediate 2 in the synthesis of Intermediate 3 in Synthesis Example 1. (Yield 73%, Mass [M+]=370)

Intermediate 69 (5.1 g) was obtained by preparation in the same manner as in the synthesis method of Intermediate 4, except that Intermediate 68 (2.8 g) was used instead of Intermediate 3 in the synthesis of Intermediate 4 in Synthesis Example 1. (Yield 72%, Mass [M+]=934)

D. Synthesis of Compound 17

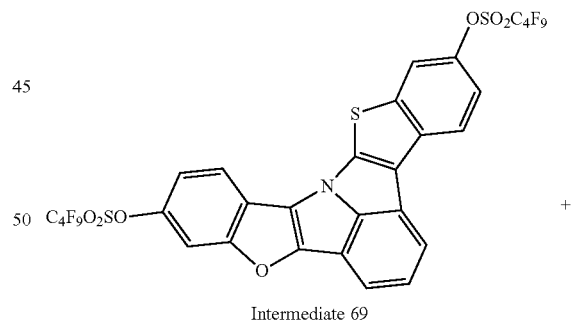

Intermediate 69

+

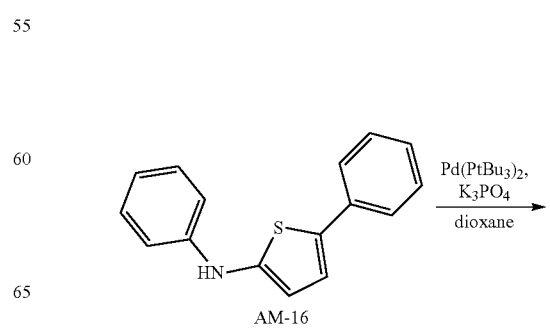

AM-16

-continued

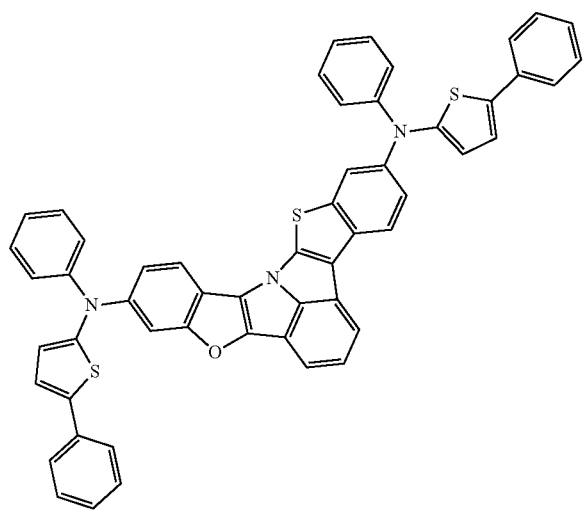

Compound 17

Compound 17 (2.0 g) was obtained by preparation in the same manner as in the synthesis method of Compound 1, except that Intermediate 69 (3.0 g) and AM-16 (1.6 g) were used instead of Intermediate 4 and AM-1 as an amine, respectively, in the synthesis of Compound 1 in Synthesis Example 1. (Yield 74%, Mass [M+]=837)

Synthesis Example 18. Synthesis of Compound 18

C. Synthesis of Intermediates 70 and 71

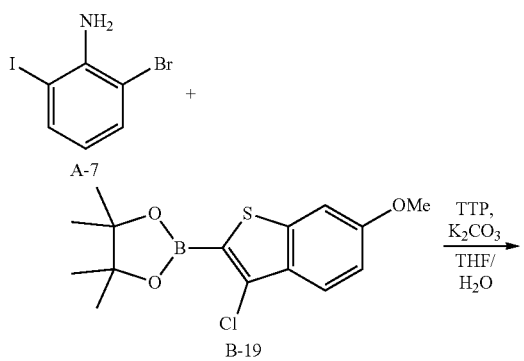

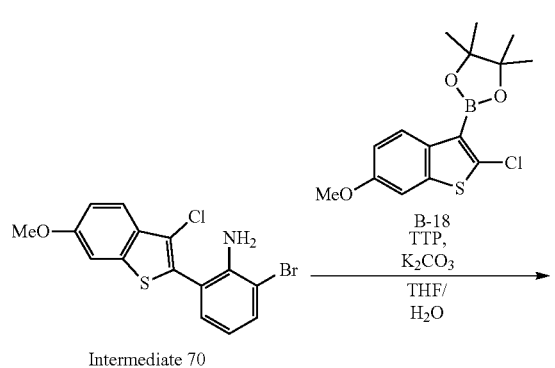

Intermediate 70

-continued

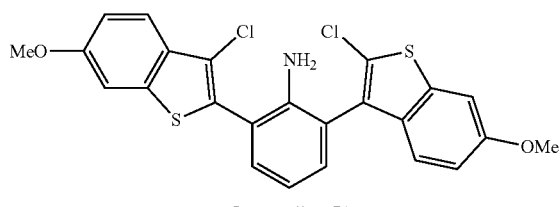

Intermediate 71

After Intermediate 70 was confirmed by preparation in the same manner as in the synthesis method of Intermediate 65, except that B-19 (5.5 g) was used instead of the boronic ester B-17 in the synthesis of Intermediate 65 in Synthesis Example 17, Intermediate 71 (6.5 g) was subsequently obtained by preparation in the same manner as in the synthesis method of Intermediate 66, except that Intermediate 70 (5.5 g) was used instead of Intermediate 65 in the synthesis of Intermediate 66. (Yield 80%, Mass [M+]=487)

B. Synthesis of Intermediate 72

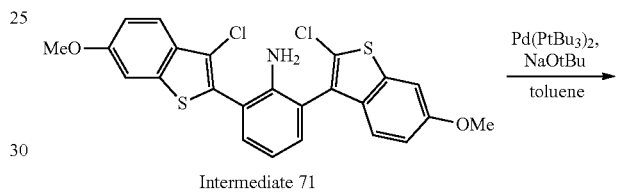

Intermediate 71

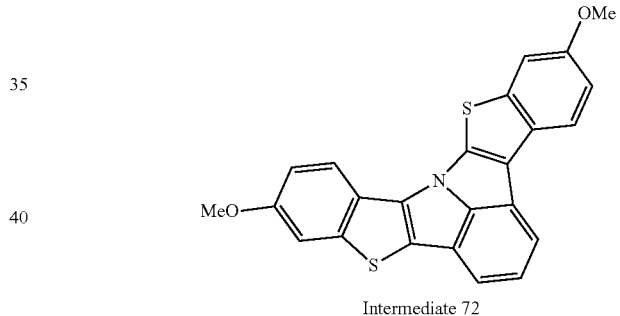

Intermediate 72

Intermediate 72 (4.1 g) was obtained by preparation in the same manner as in the synthesis method of Intermediate 67, except that Intermediate 71 (6.5 g) was used instead of Intermediate 66 in the synthesis of Intermediate 67 in Synthesis Example 17. (Yield 74%, Mass [M+]=414)

C. Synthesis of Intermediates 73 and 74

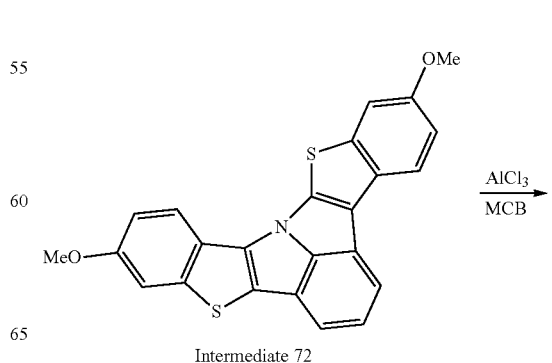

Intermediate 72

-continued

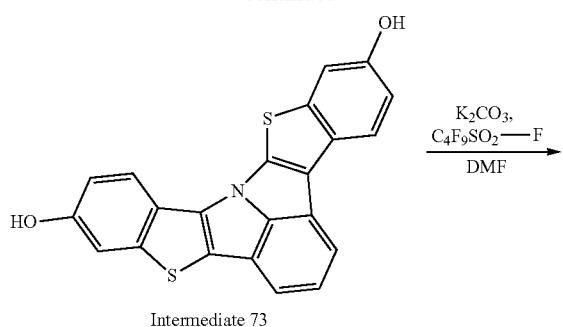
Intermediate 73

K₂CO₃,
C₄F₉SO₂—F
————————→
DMF

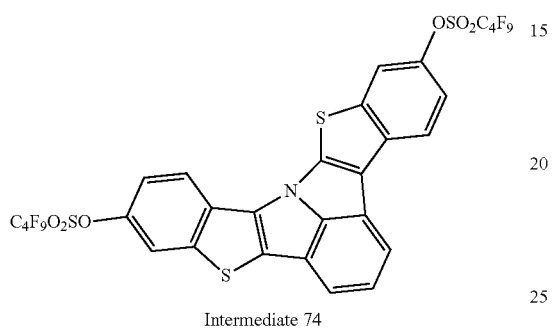
Intermediate 74

Intermediate 73 (3.0 g) was obtained by preparation in the same manner as in the synthesis method of Intermediate 3, except that Intermediate 72 (4.1 g) was used instead of Intermediate 2 in the synthesis of Intermediate 3 in Synthesis Example 1. (Yield 78%, Mass [M+]=386)

Intermediate 74 (5.1 g) was obtained by preparation in the same manner as in the synthesis method of Intermediate 4, except that Intermediate 73 (3.0 g) was used instead of Intermediate 3 in the synthesis of Intermediate 4 in Synthesis Example 1. (Yield 69%, Mass [M+]=950)

D. Synthesis of Compound 18

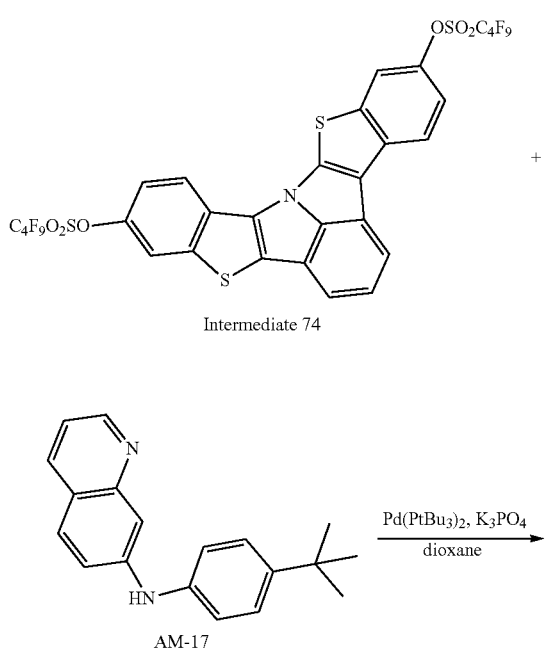
Intermediate 74

+

AM-17

Pd(PtBu₃)₂, K₃PO₄
————————→
dioxane

-continued

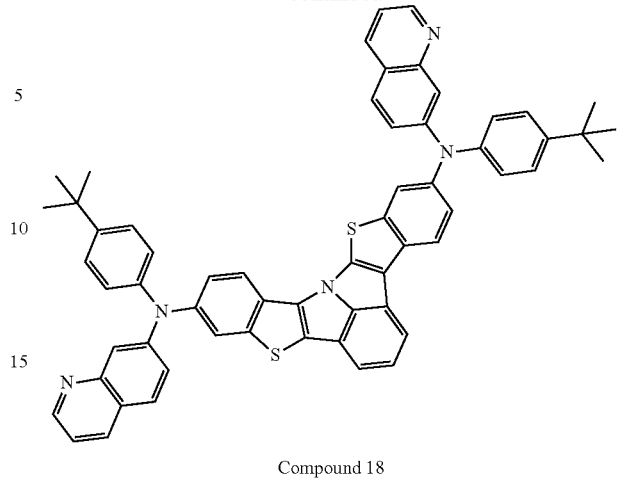
Compound 18

Compound 18 (2.1 g) was obtained by preparation in the same manner as in the synthesis method of Compound 1, except that Intermediate 74 (3.0 g) and AM-17 (1.7 g) were used instead of Intermediate 4 and AM-1 as an amine, respectively, in the synthesis of Compound 1 in Synthesis Example 1. (Yield 74%, Mass [M+]=903)

Synthesis Example 19. Synthesis of Compound 19

C. Synthesis of Intermediates 75 and 76

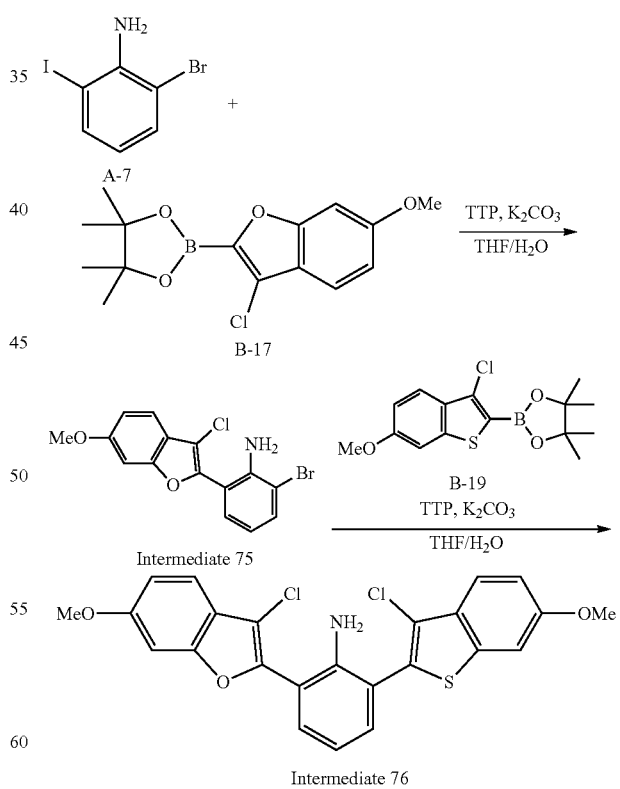

After Intermediate 75 was confirmed by preparation in the same manner as in the synthesis method of Intermediate 65 using a starting material A-7 (5.0 g) and a boronic ester B-17 (5.2 g) in the synthesis of Intermediate 65 in Synthesis Example 17, Intermediate 76 (6.1 g) was subsequently obtained by preparation in the same manner as in the synthesis method of Intermediate 66, except that Intermediate 75 (5.5 g) was used instead of Intermediate 65 in the synthesis of Intermediate 66. (Yield 77%, Mass [M+]=471)

B. Synthesis of Intermediate 77

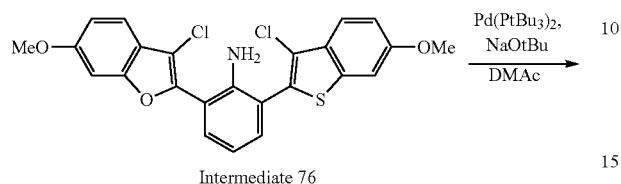

Intermediate 76

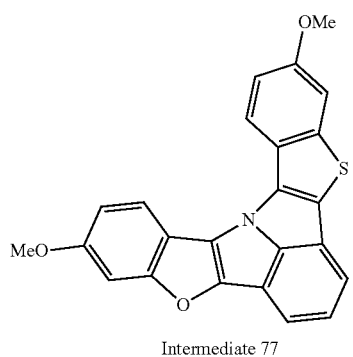

Intermediate 77

Intermediate 77 (3.9 g) was obtained by preparation in the same manner as in the synthesis method of Intermediate 67, except that Intermediate 76 (6.1 g) was used instead of Intermediate 66 in the synthesis of Intermediate 67 in Synthesis Example 17. (Yield 76%, Mass [M+]=398)

C. Synthesis of Intermediates 78 and 79

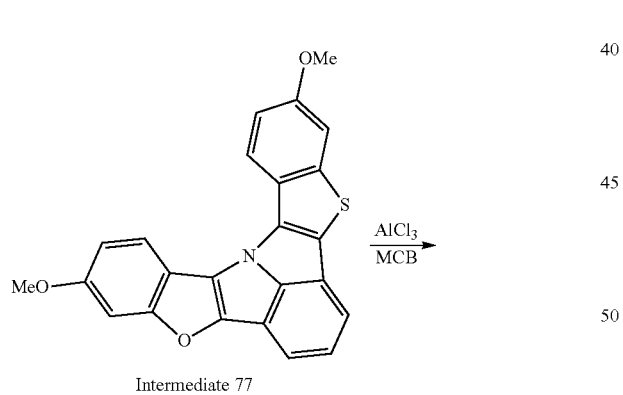

Intermediate 77

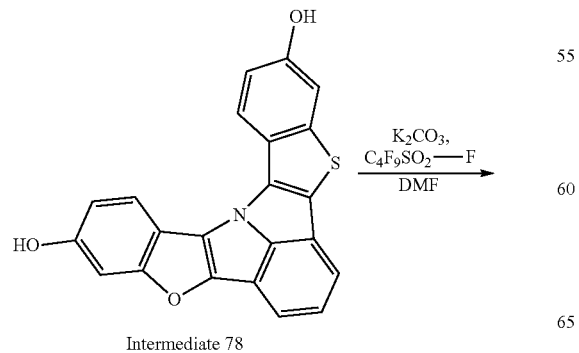

Intermediate 78

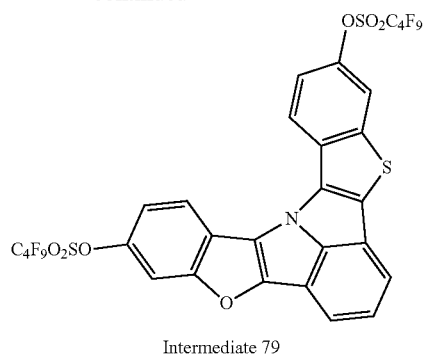

Intermediate 79

Intermediate 78 (2.6 g) was obtained by preparation in the same manner as in the synthesis method of Intermediate 3, except that Intermediate 77 (3.9 g) was used instead of Intermediate 2 in the synthesis of Intermediate 3 in Synthesis Example 1. (Yield 72%, Mass [M+]=370)

Intermediate 79 (4.6 g) was obtained by preparation in the same manner as in the synthesis method of Intermediate 4, except that Intermediate 78 (2.6 g) was used instead of Intermediate 3 in the synthesis of Intermediate 4 in Synthesis Example 1. (Yield 70%, Mass [M+]=934)

D. Synthesis of Compound 19

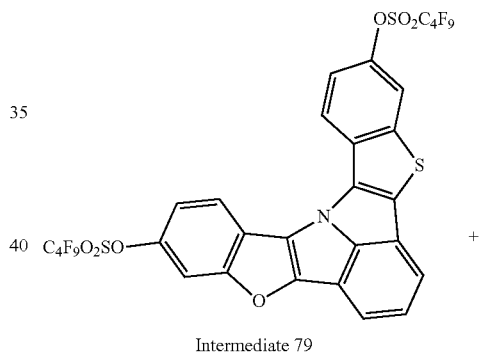

Intermediate 79

+

AM-18

-continued

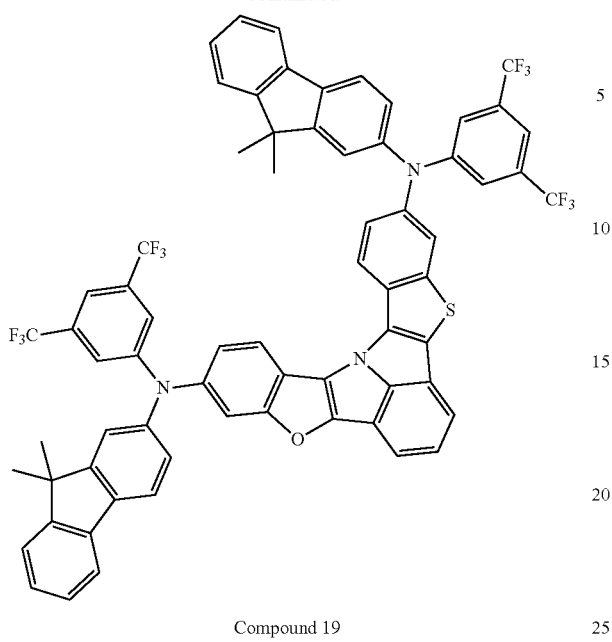

Compound 19

Compound 19 (2.7 g) was obtained by preparation in the same manner as in the synthesis method of Compound 1, except that Intermediate 79 (3.0 g) and AM-18 (2.7 g) were used instead of Intermediate 4 and AM-1 as an amine, respectively, in the synthesis of Compound 1 in Synthesis Example 1. (Yield 71%, Mass [M+]=1177)

Synthesis Example 20. Synthesis of Compound 20

A. Synthesis of Intermediate 80

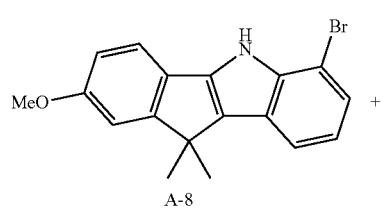

A-8

+

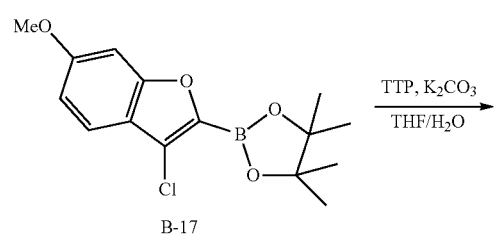

B-17

TTP, K₂CO₃
THF/H₂O
→

-continued

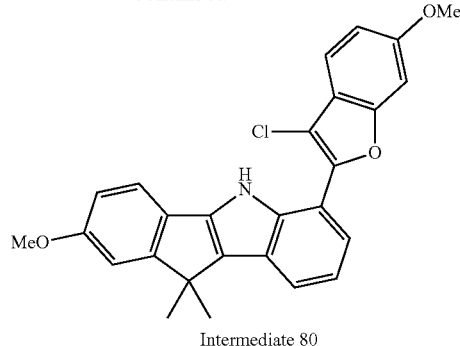

Intermediate 80

Intermediate 80 (4.6 g) was obtained by preparation in the same manner as in the synthesis method of Intermediate 1, except that A-8 (5.0 g) and B-17 (4.6 g) were used instead of the starting material A-1 and the boronic ester B-1, respectively, in the synthesis of Intermediate 1 in Synthesis Example 1. (Yield 71%, Mass [M+]=444)

B. Synthesis of Intermediate 81

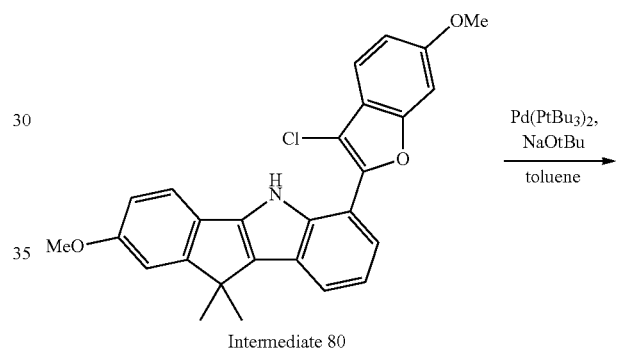

Intermediate 80

Pd(PtBu₃)₂,
NaOtBu
────────→
toluene

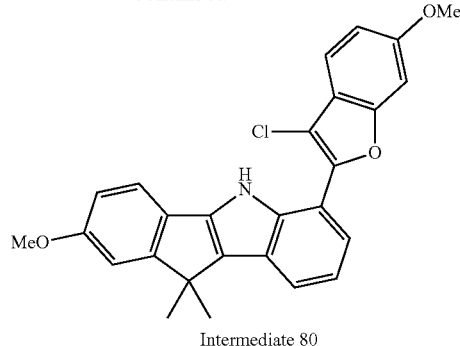

Intermediate 81

Intermediate 81 (3.0 g) was obtained by preparation in the same manner as in the synthesis method of Intermediate 2, except that Intermediate 80 (4.6 g) was used instead of Intermediate 1 in the synthesis of Intermediate 2 in Synthesis Example 1. (Yield 71%, Mass [M+]=408)

C. Synthesis of Intermediates 82 and 83

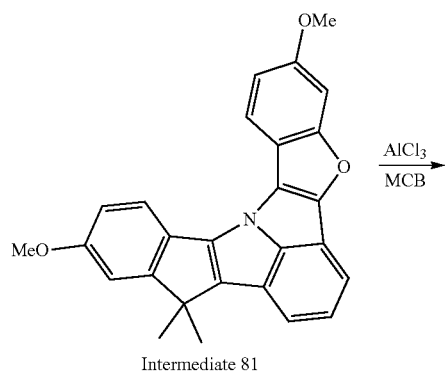
Intermediate 81

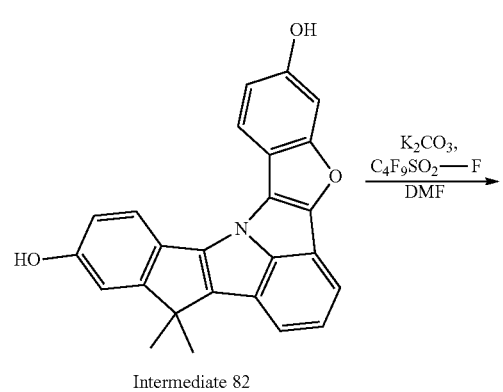
Intermediate 82

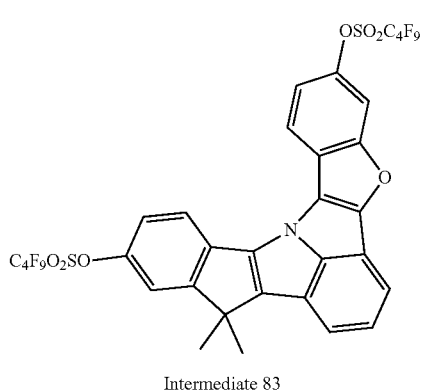
Intermediate 83

Intermediate 82 (2.1 g) was obtained by preparation in the same manner as in the synthesis method of Intermediate 3, except that Intermediate 81 (3.0 g) was used instead of Intermediate 2 in the synthesis of Intermediate 3 in Synthesis Example 1. (Yield 75%, Mass [M+]=380)

Intermediate 83 (4.2 g) was obtained by preparation in the same manner as in the synthesis method of Intermediate 4, except that Intermediate 82 (2.1 g) was used instead of Intermediate 3 in the synthesis of Intermediate 4 in Synthesis Example 1. (Yield 80%, Mass [M+]=944)

D. Synthesis of Compound 20

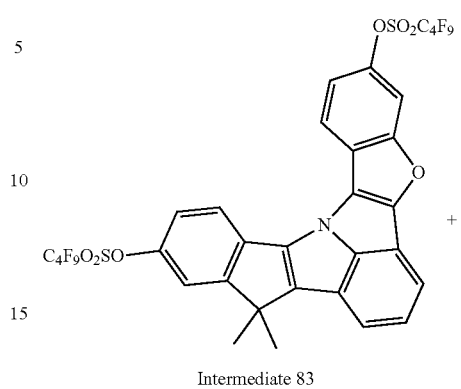
Intermediate 83

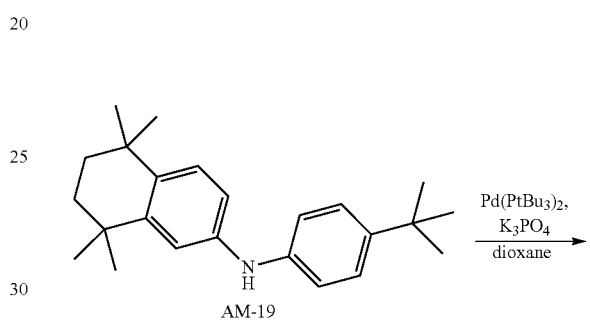
AM-19

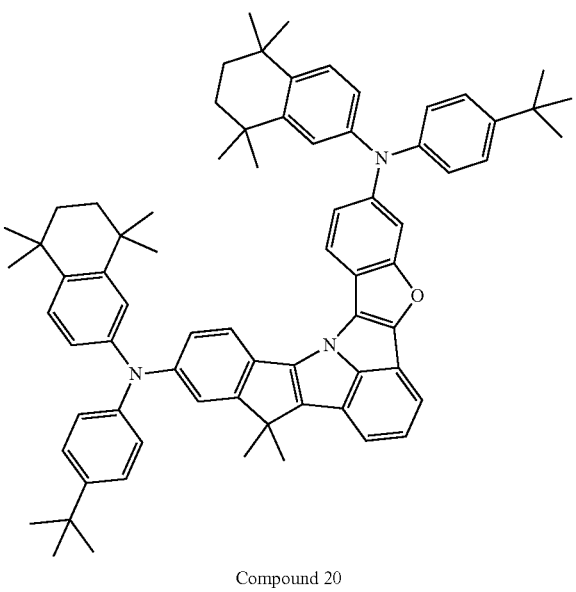
Compound 20

Compound 20 (2.4 g) was obtained by preparation in the same manner as in the synthesis method of Compound 1, except that Intermediate 83 (3.0 g) and AM-19 (2.1 g) were used instead of Intermediate 4 and AM-1 as an amine, respectively, in the synthesis of Compound 1 in Synthesis Example 1. (Yield 74%, Mass [M+]=1015)

Synthesis Example 21. Synthesis of Compound 21

A. Synthesis of Intermediate 84

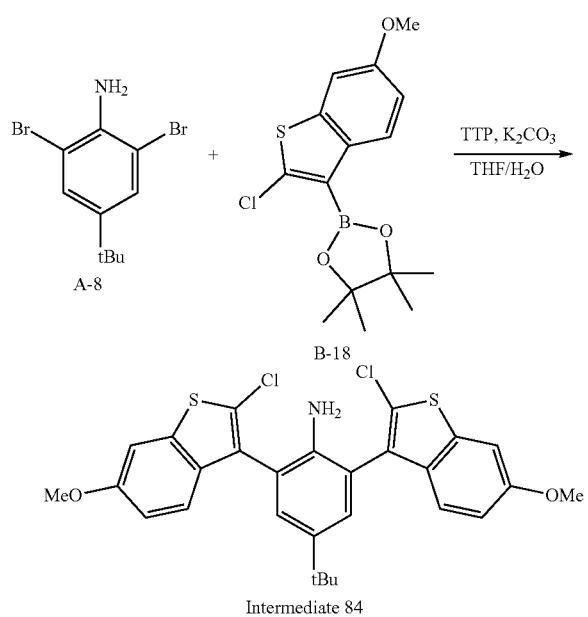

Intermediate 84

After 5.0 g of a starting material A-8, 11 g of a boronic ester B-18, 6.8 g of potassium carbonate, 120 mL of tetrahydrofuran, and 12 mL of water were put into a container under a nitrogen atmosphere, 0.4 g of [tetrakis(triphenylphosphine)palladium(0)] (Pd(PPh$_3$)$_4$) was added thereto, and then the resulting mixture was heated at 120° C. and stirred for 4 hours. After the reaction was terminated, the reaction solution was cooled to room temperature, aliquoted by adding water and ethyl acetate thereto, and then filtered by treatment with MgSO$_4$ (anhydrous). The filtered solution was distilled off under reduced pressure and purified with recrystallization (ethyl acetate/hexane) to obtain Intermediate 84 (7.0 g). (Yield 79%, Mass [M+]=543)

B. Synthesis of Intermediate 85

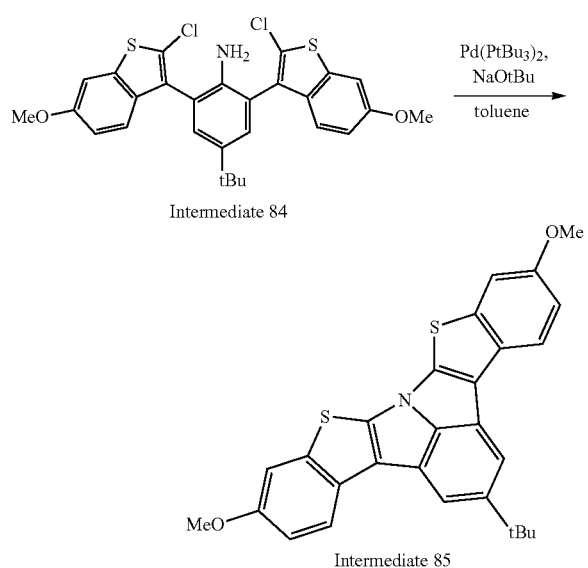

Intermediate 85

Intermediate 85 (4.5 g) was obtained by preparation in the same manner as in the synthesis method of Intermediate 67, except that Intermediate 84 (7.0 g) was used instead of Intermediate 66 in the synthesis of Intermediate 67 in Synthesis Example 17. (Yield 74%, Mass [M+]=470)

C. Synthesis of Intermediates 86 and 87

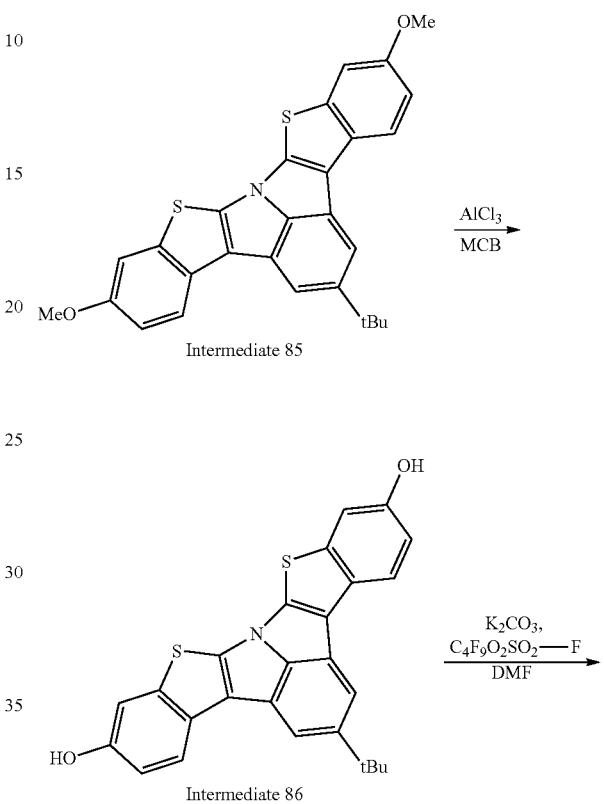

Intermediate 86

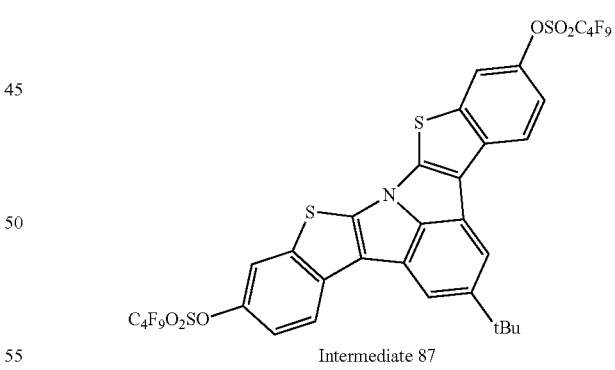

Intermediate 87

Intermediate 86 (3.2 g) was obtained by preparation in the same manner as in the synthesis method of Intermediate 3, except that Intermediate 85 (4.5 g) was used instead of Intermediate 2 in the synthesis of Intermediate 3 in Synthesis Example 1. (Yield 76%, Mass [M+]=442)

Intermediate 87 (5.5 g) was obtained by preparation in the same manner as in the synthesis method of Intermediate 4, except that Intermediate 86 (3.2 g) was used instead of Intermediate 3 in the synthesis of Intermediate 4 in Synthesis Example 1. (Yield 75%, Mass [M+]=1006)

D. Synthesis of Compound 21

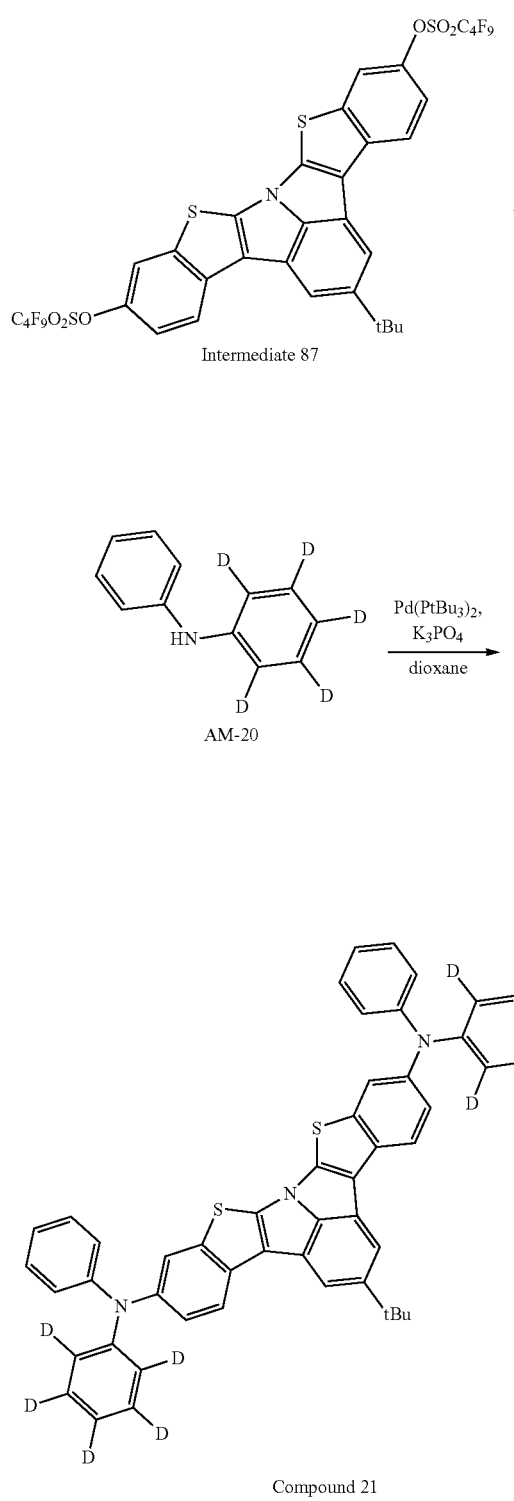

Intermediate 87

AM-20

Compound 21

Compound 21 (1.6 g) was obtained by preparation in the same manner as in the synthesis method of Compound 1, except that Intermediate 87 (3.0 g) and AM-20 (1.0 g) were used instead of Intermediate 4 and AM-1 as an amine, respectively, in the synthesis of Compound 1 in Synthesis Example 1. (Yield 71%, Mass [M+]=755)

Synthesis Example 22. Synthesis of Compound 22

A. Synthesis of Intermediates 88 and 89

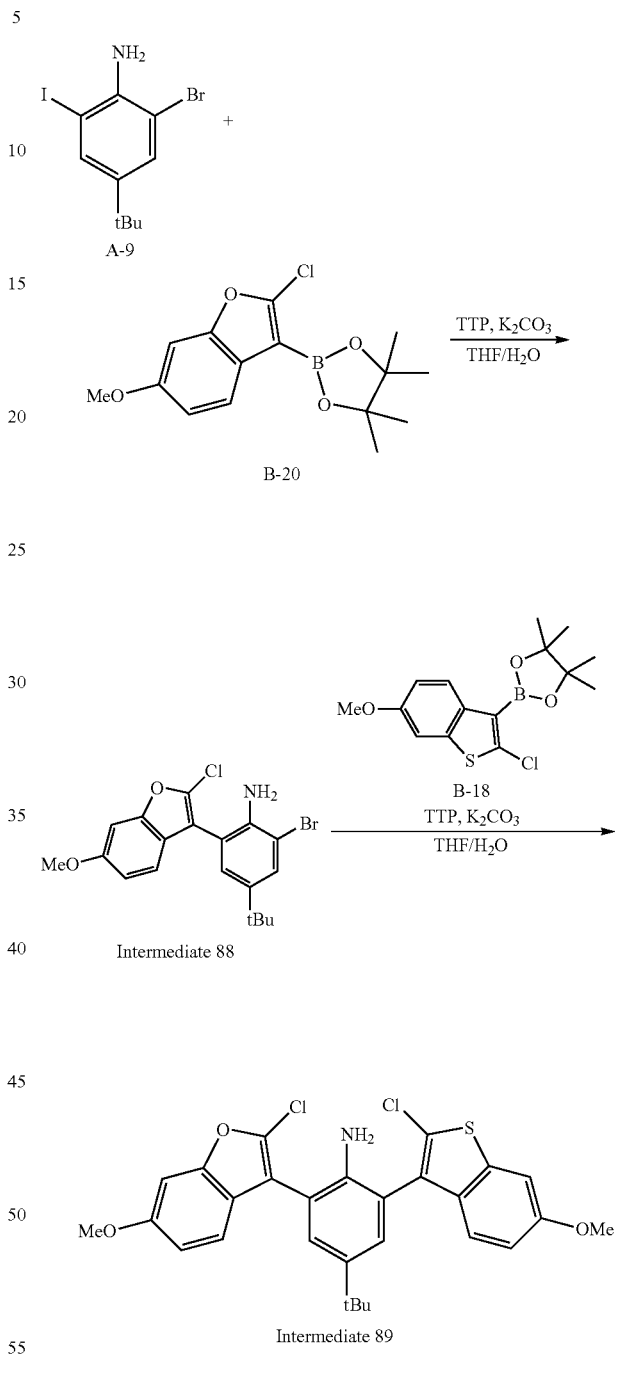

A-9

B-20

Intermediate 88

B-18

Intermediate 89

After Intermediate 88 was confirmed by preparation in the same manner as in the synthesis method of Intermediate 65, except that A-9 (5.0 g) and B-20 (4.4 g) were used instead of the starting material A-7 and the boronic ester B-17, respectively, in the synthesis of Intermediate 65 in Synthesis Example 17, Intermediate 89 (6.0 g) was subsequently obtained by preparation in the same manner as in the synthesis method of Intermediate 66, except that Intermediate 88 (4.4 g) was used instead of Intermediate 65 in the synthesis of Intermediate 66. (Yield 81%, Mass [M+]=527)

B. Synthesis of Intermediate 90

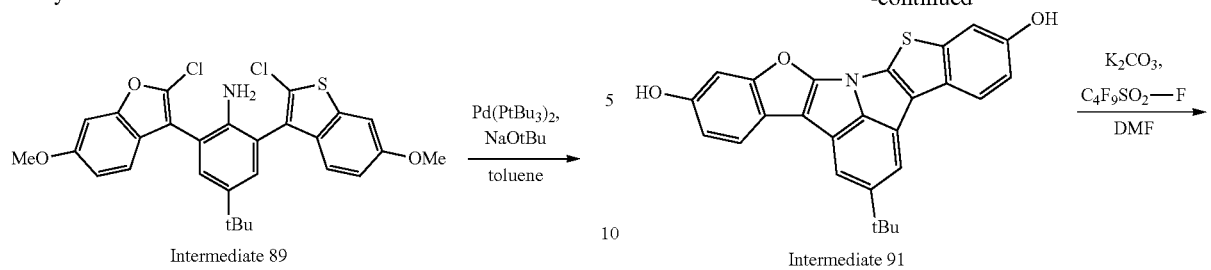

Intermediate 90 (3.9 g) was obtained by preparation in the same manner as in the synthesis method of Intermediate 67, except that Intermediate 89 (6.0 g) was used instead of Intermediate 66 in the synthesis of Intermediate 67 in Synthesis Example 17. (Yield 75%, Mass [M+]=454)

C. Synthesis of Intermediates 91 and 92

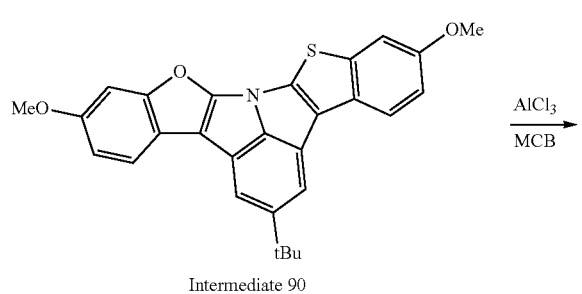

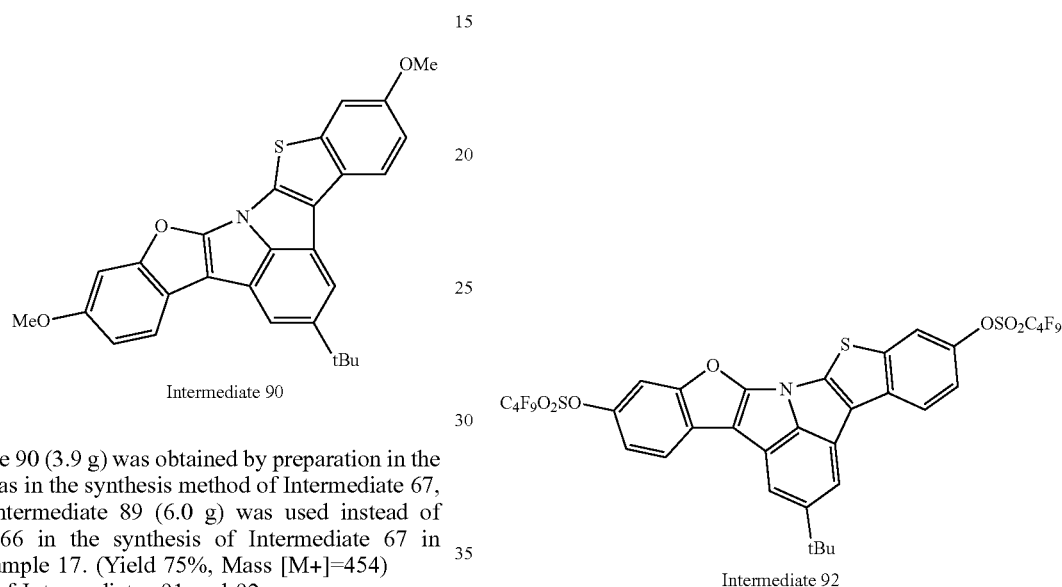

Intermediate 91 (2.6 g) was obtained by preparation in the same manner as in the synthesis method of Intermediate 3, except that Intermediate 90 (3.9 g) was used instead of Intermediate 2 in the synthesis of Intermediate 3 in Synthesis Example 1. (Yield 71%, Mass [M+]=426)

Intermediate 92 (4.3 g) was obtained by preparation in the same manner as in the synthesis method of Intermediate 4, except that Intermediate 91 (2.6 g) was used instead of Intermediate 3 in the synthesis of Intermediate 4 in Synthesis Example 1. (Yield 71%, Mass [M+]=990)

D. Synthesis of Compound 22

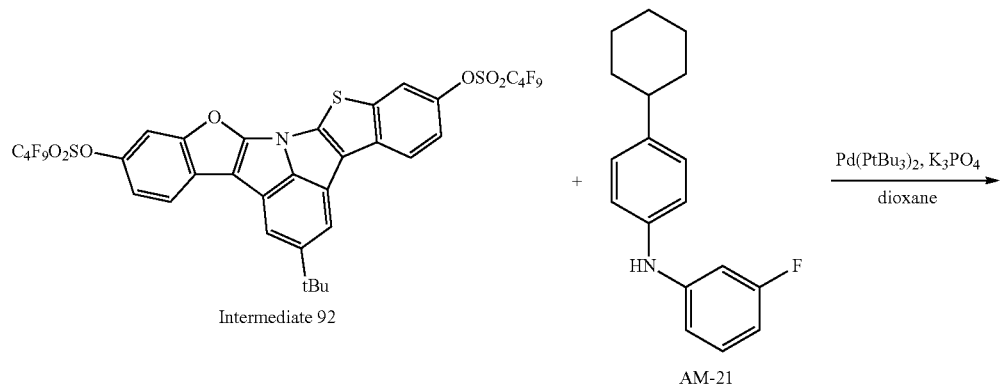

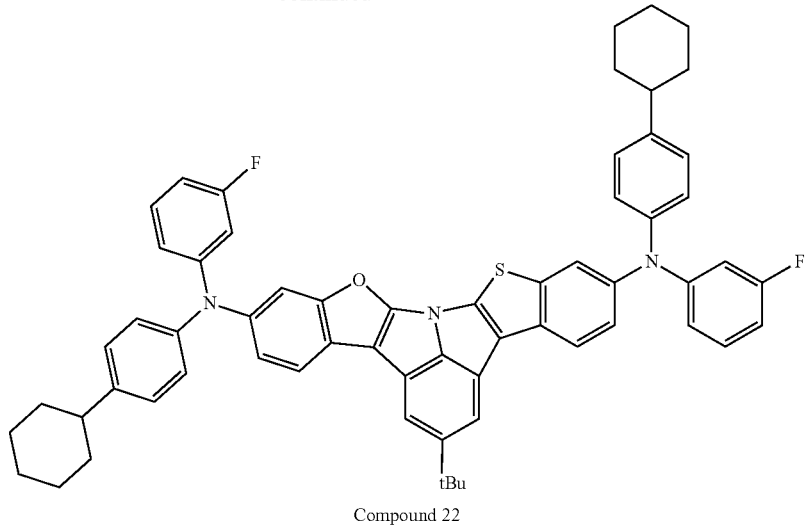

Compound 22

Compound 22 (2.2 g) was obtained by preparation in the same manner as in the synthesis method of Compound 1, except that Intermediate 92 (3.0 g) and AM-21 (1.6 g) were used instead of Intermediate 4 and AM-1 as an amine, respectively, in the synthesis of Compound 1 in Synthesis Example 1. (Yield 78%, Mass [M+]=929)

Synthesis Example 23. Synthesis of Compound 23

A. Synthesis of Intermediate 93

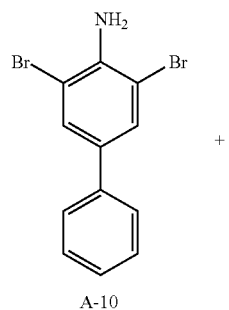

A-10

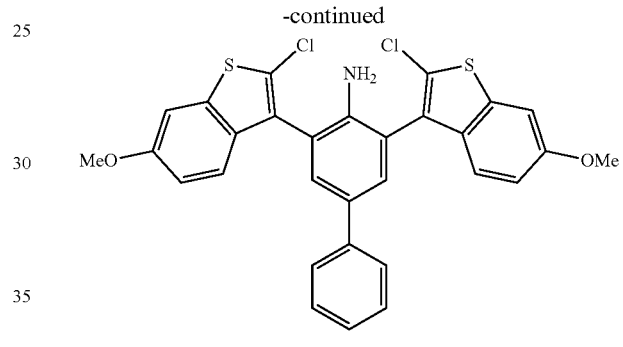

Intermediate 93

Intermediate 93 (7.1 g) was obtained by preparation in the same manner as in the synthesis method of Intermediate 84, except that A-10 (5.0 g) was used instead of the starting material A-8 in the synthesis of Intermediate 84 in Synthesis Example 21. (Yield 83%, Mass [M+]=563)

B. Synthesis of Intermediate 94

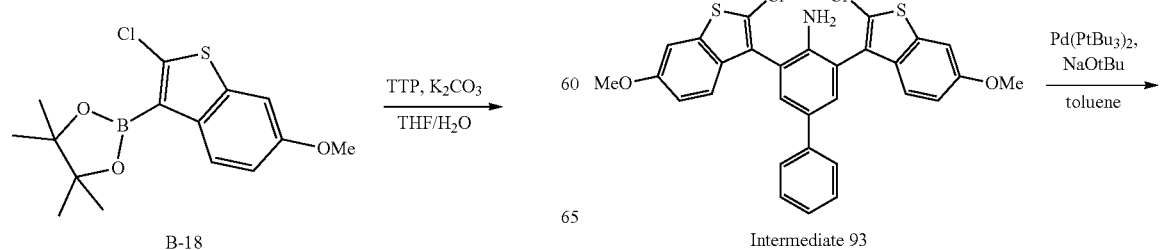

B-18   Intermediate 93

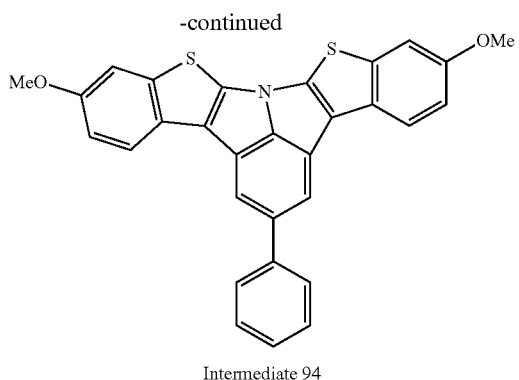

Intermediate 94

Intermediate 94 (4.2 g) was obtained by preparation in the same manner as in the synthesis method of Intermediate 67, except that Intermediate 93 (7.1 g) was used instead of Intermediate 66 in the synthesis of Intermediate 67 in Synthesis Example 17. (Yield 68%, Mass [M+]=490)

C. Synthesis of Intermediates 95 and 96

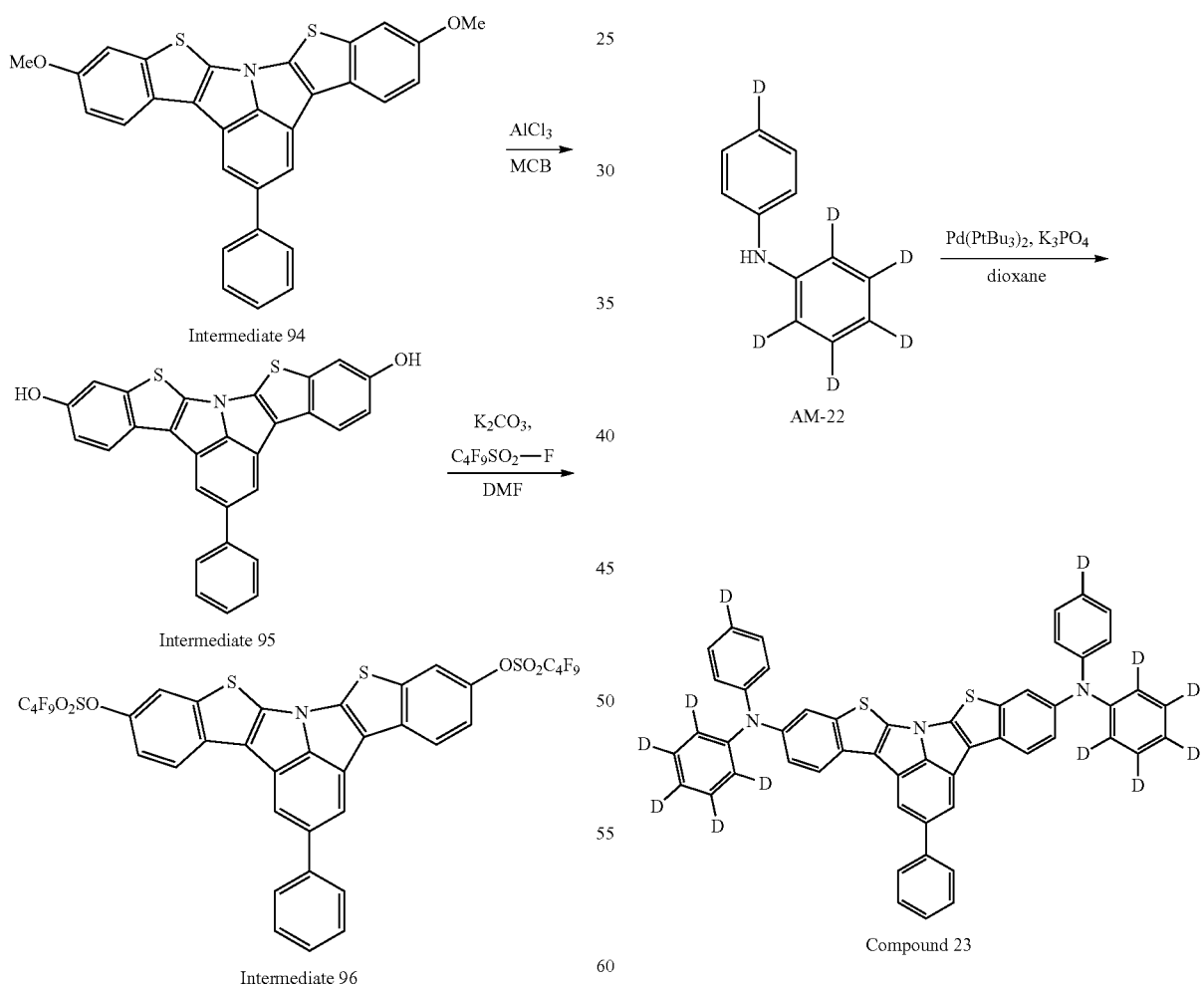

Intermediate 95 (3.1 g) was obtained by preparation in the same manner as in the synthesis method of Intermediate 3, except that Intermediate 94 (4.2 g) was used instead of Intermediate 2 in the synthesis of Intermediate 3 in Synthesis Example 1. (Yield 78%, Mass [M+]=462)

Intermediate 96 (5.6 g) was obtained by preparation in the same manner as in the synthesis method of Intermediate 4, except that Intermediate 95 (3.1 g) was used instead of Intermediate 3 in the synthesis of Intermediate 4 in Synthesis Example 1. (Yield 81%, Mass [M+]=1026)

D. Synthesis of Compound 23

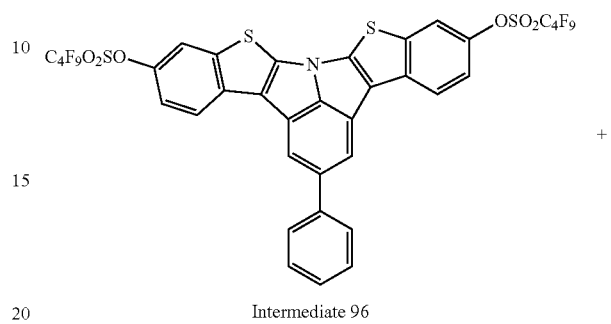

Compound 23 (1.6 g) was obtained by preparation in the same manner as in the synthesis method of Compound 1, except that Intermediate 96 (3.0 g) and AM-22 (1.0 g) were used instead of Intermediate 4 and AM-1 as an amine, respectively, in the synthesis of Compound 1 in Synthesis Example 1. (Yield 70%, Mass [M+]=777)

Synthesis Example 24. Synthesis of Compound 24

A. Synthesis of Intermediate 97

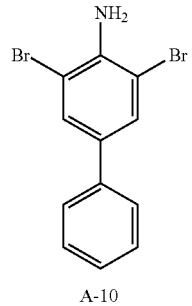

A-10

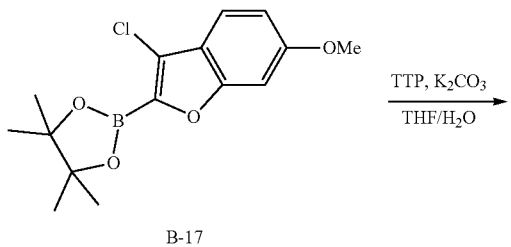

B-17

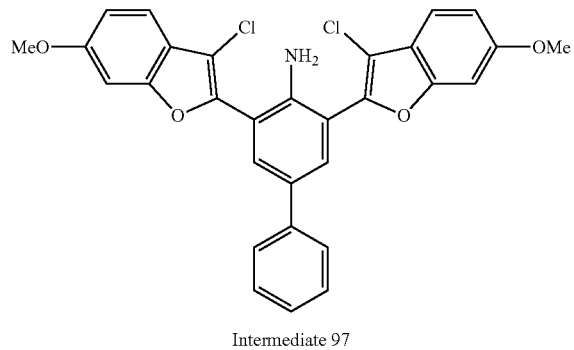

Intermediate 97

Intermediate 97 (6.5 g) was obtained by preparation in the same manner as in the synthesis method of Intermediate 84, except that A-10 (5.0 g) and B-17 (9.9 g) were used instead of the starting material A-8 and the boronic ester B-18, respectively, in the synthesis of Intermediate 84 in Synthesis Example 21. (Yield 80%, Mass [M+]=531)

B. Synthesis of Intermediate 98

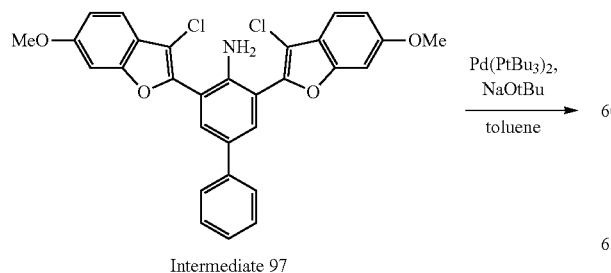

Intermediate 97

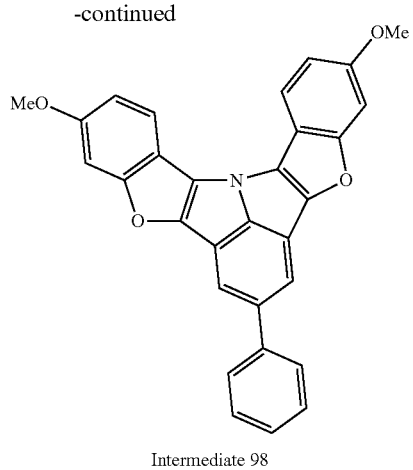

Intermediate 98

Intermediate 98 (4.3 g) was obtained by preparation in the same manner as in the synthesis method of Intermediate 67, except that Intermediate 97 (6.5 g) was used instead of Intermediate 66 in the synthesis of Intermediate 67 in Synthesis Example 17. (Yield 77%, Mass [M+]=458)

C. Synthesis of Intermediates 99 and 100

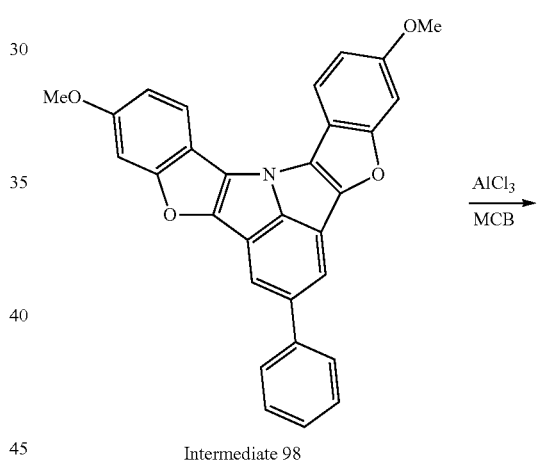

Intermediate 98

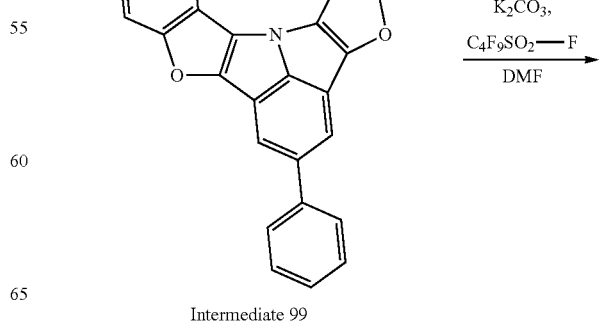

Intermediate 99

-continued

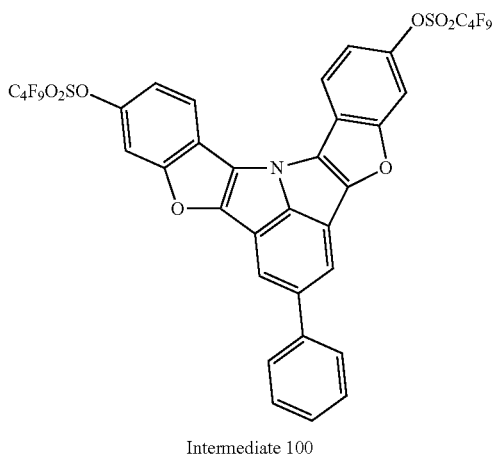

Intermediate 100

Intermediate 99 (3.1 g) was obtained by preparation in the same manner as in the synthesis method of Intermediate 3, except that Intermediate 98 (4.3 g) was used instead of Intermediate 2 in the synthesis of Intermediate 3 in Synthesis Example 1. (Yield 76%, Mass [M+]=430)

Intermediate 100 (5.7 g) was obtained by preparation in the same manner as in the synthesis method of Intermediate 4, except that Intermediate 99 (3.1 g) was used instead of Intermediate 3 in the synthesis of Intermediate 4 in Synthesis Example 1. (Yield 79%, Mass [M+]=994)

D. Synthesis of Compound 24

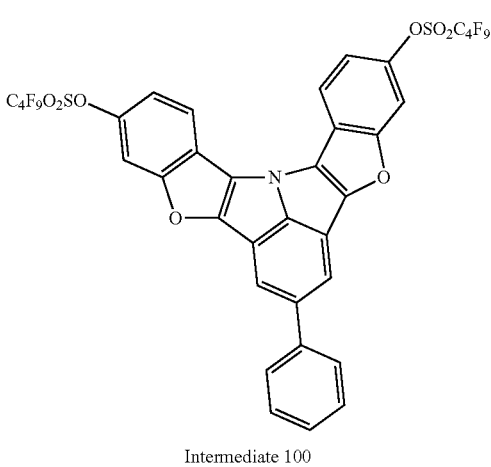

Intermediate 100

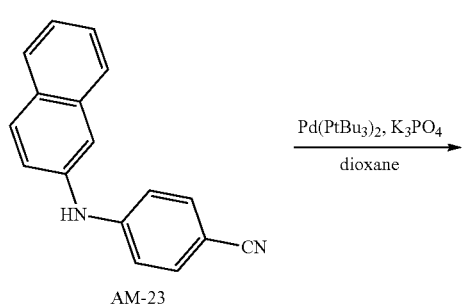

AM-23

Pd(PtBu₃)₂, K₃PO₄
────────────→
dioxane

-continued

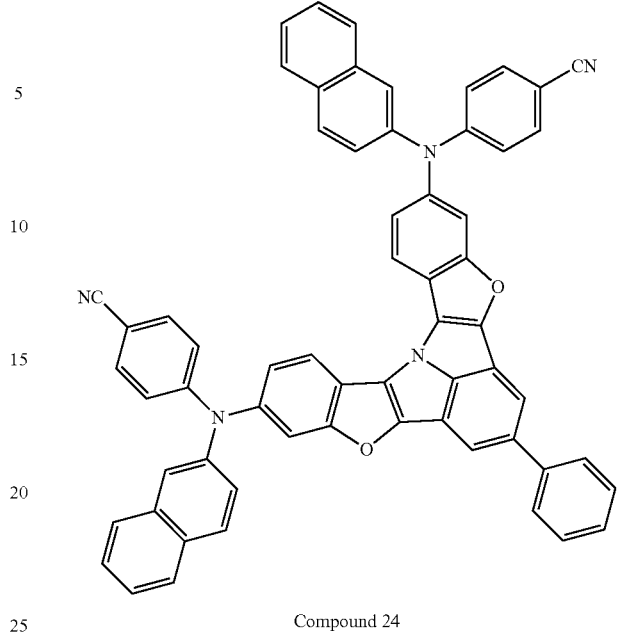

Compound 24

Compound 24 (2.1 g) was obtained by preparation in the same manner as in the synthesis method of Compound 1, except that Intermediate 100 (3.0 g) and AM-23 (1.5 g) were used instead of Intermediate 4 and AM-1 as an amine, respectively, in the synthesis of Compound 1 in Synthesis Example 1. (Yield 79%, Mass [M+]=883)

Synthesis Example 25. Synthesis of Compound 25

A. Synthesis of Intermediate 101

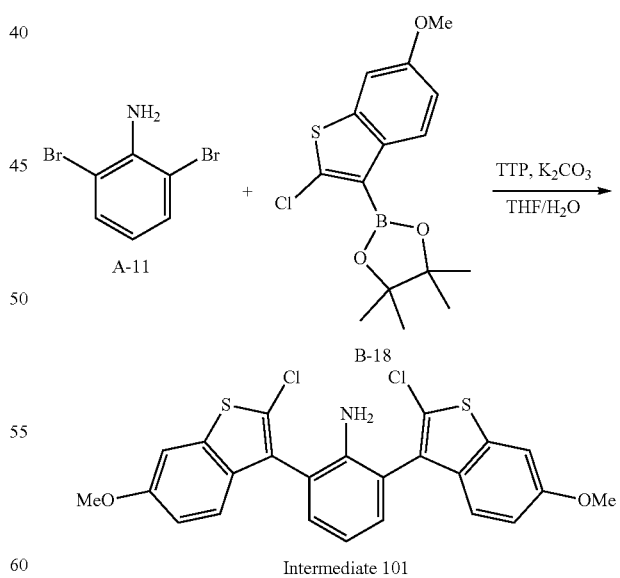

Intermediate 101

Intermediate 101 (7.4 g) was obtained by preparation in the same manner as in the synthesis method of Intermediate 84, except that A-11 (5.0 g) was used instead of the starting material A-8 in the synthesis of Intermediate 84 in Synthesis Example 21. (Yield 76%, Mass [M+]=487)

B. Synthesis of Intermediate 102

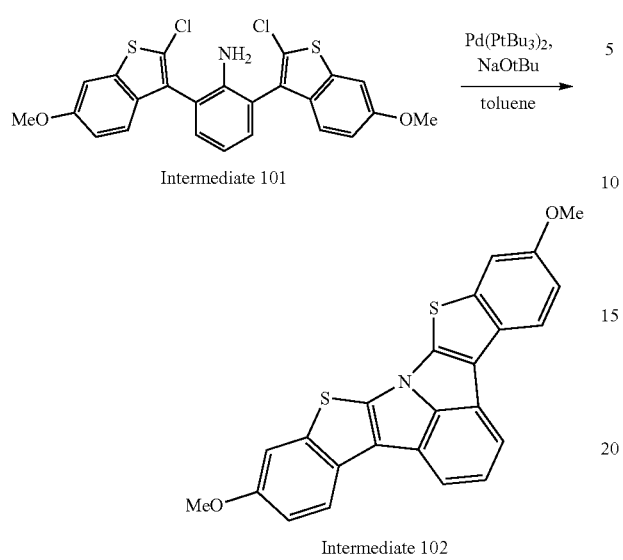

Intermediate 101

Intermediate 102

Intermediate 102 (4.7 g) was obtained by preparation in the same manner as in the synthesis method of Intermediate 67, except that Intermediate 101 (7.4 g) was used instead of Intermediate 66 in the synthesis of Intermediate 67 in Synthesis Example 17. (Yield 75%, Mass [M+]=414)

C. Synthesis of Intermediates 103 and 104

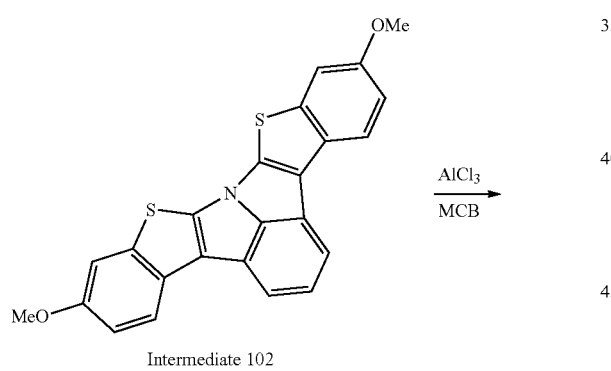

Intermediate 102

Intermediate 103

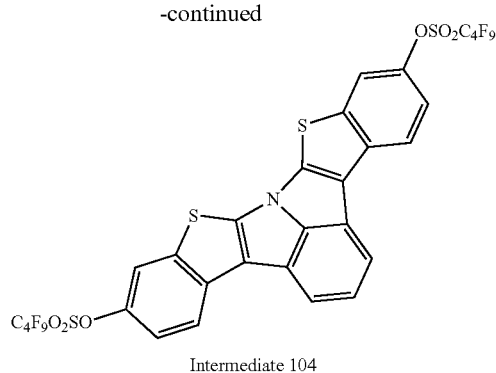

Intermediate 104

Intermediate 103 (3.6 g) was obtained by preparation in the same manner as in the synthesis method of Intermediate 3, except that Intermediate 102 (4.7 g) was used instead of Intermediate 2 in the synthesis of Intermediate 3 in Synthesis Example 1. (Yield 82%, Mass [M+]=386)

Intermediate 104 (7.1 g) was obtained by preparation in the same manner as in the synthesis method of Intermediate 4, except that Intermediate 103 (3.6 g) was used instead of Intermediate 3 in the synthesis of Intermediate 4 in Synthesis Example 1. (Yield 80%, Mass [M+]=950)

D. Synthesis of Compound 25

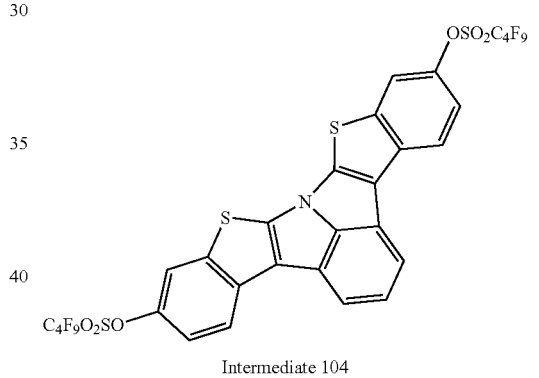

Intermediate 104

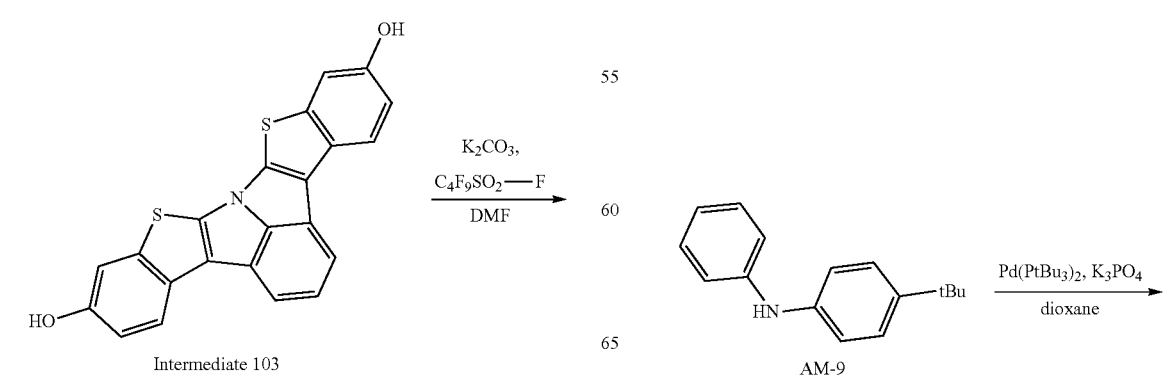

AM-9

-continued

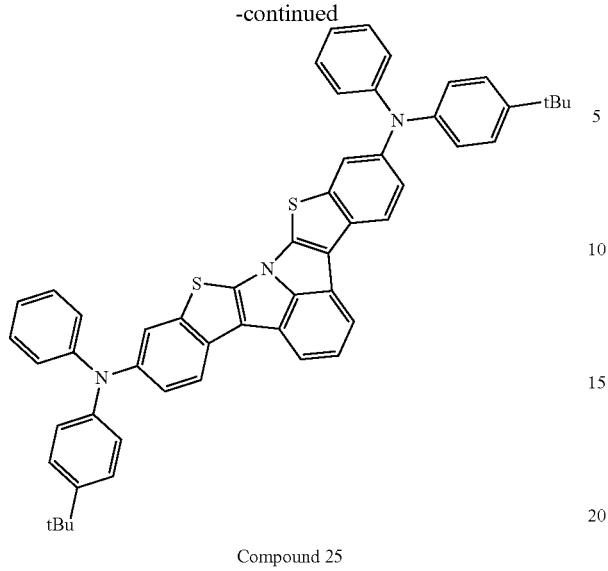

Compound 25

Compound 25 (1.8 g) was obtained by preparation in the same manner as in the synthesis method of Compound 1, except that Intermediate 104 (3.0 g) and AM-9 (1.4 g) were used instead of Intermediate 4 and AM-1 as an amine, respectively, in the synthesis of Compound 1 in Synthesis Example 1. (Yield 71%, Mass [M+]=801)

Example 1

A glass substrate thinly coated with indium tin oxide (ITO) to have a thickness of 1,500 Å was put into distilled water in which a detergent was dissolved, and ultrasonically washed. In this case, a product manufactured by Fischer Co., was used as the detergent, and distilled water, which had been filtered twice with a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted by using isopropyl alcohol, acetone, and methanol solvents, and the resulting product was dried and then transported to a plasma washing machine. The substrate was cleaned by using oxygen plasma for 5 minutes, and then was transported to a vacuum deposition machine.

The following Compound HAT was thermally vacuum deposited to have a thickness of 50 Å on the transparent ITO electrode, which was prepared as described above, thereby forming a hole injection layer. The following Compound HT-A was vacuum deposited on the hole injection layer, thereby forming a first hole transport layer having a thickness of 1100 Å, and the following Compound HT-B was subsequently vacuum deposited thereon, thereby forming a second hole transport layer having a thickness of 100 Å. The following Compound BH-A as a light emitting host and Compound 1 as a dopant were vacuum deposited at a weight ratio of 97:3 on the second hole transport layer, thereby forming a light emitting layer having a thickness of 200 Å.

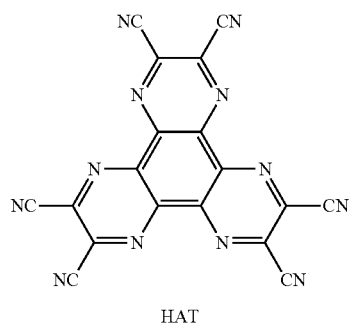

HAT

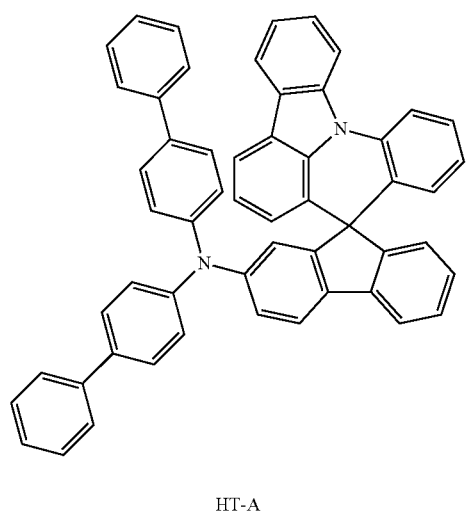

HT-A

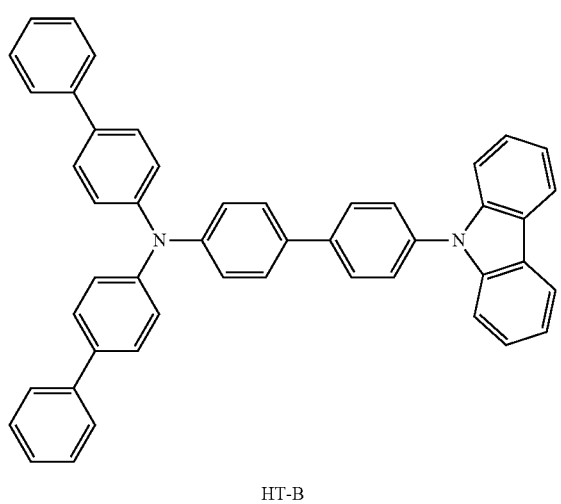

HT-B

-continued

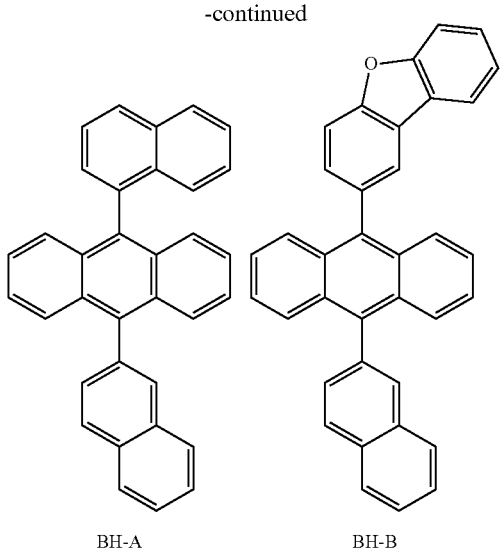

BH-A     BH-B

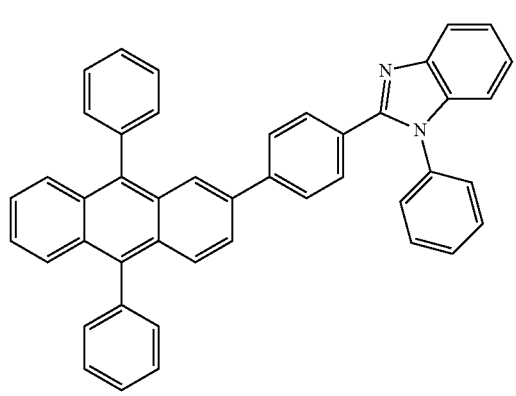

ET-A

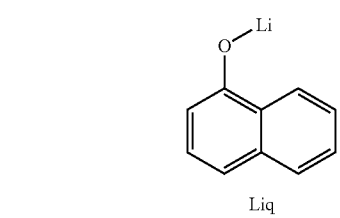

Liq

The Compounds ET-A and LiQ above were vacuum deposited at a weight ratio of 1:1 on the light emitting layer, thereby forming a first electron transport layer having a thickness of 200 Å. [LiF] was vacuum deposited on the first electron transport layer, thereby forming a second electron transport layer having a thickness of 100 Å. Aluminum was deposited to a thickness of 1000 Å on the second electron transport layer, thereby forming a negative electrode.

In the aforementioned procedure, the deposition rates of the organic materials were maintained at 1.0 Å/sec, the deposition rates of lithium fluoride and aluminum of the negative electrode were maintained at 0.3 Å/sec and at 2.0 to 5.0 Å/sec, respectively, and the degree of vacuum during the deposition was maintained at $5 \times 10^{-8}$ to $1 \times 10^{-7}$ torr, thereby manufacturing an organic light emitting device.

Examples 2 to 25 and Comparative Examples 1 to 9

Organic light emitting devices were manufactured in the same manner as in Example 1, except that the dopants in the following Table 1 were used instead of Compound 1 in the light emitting layer.

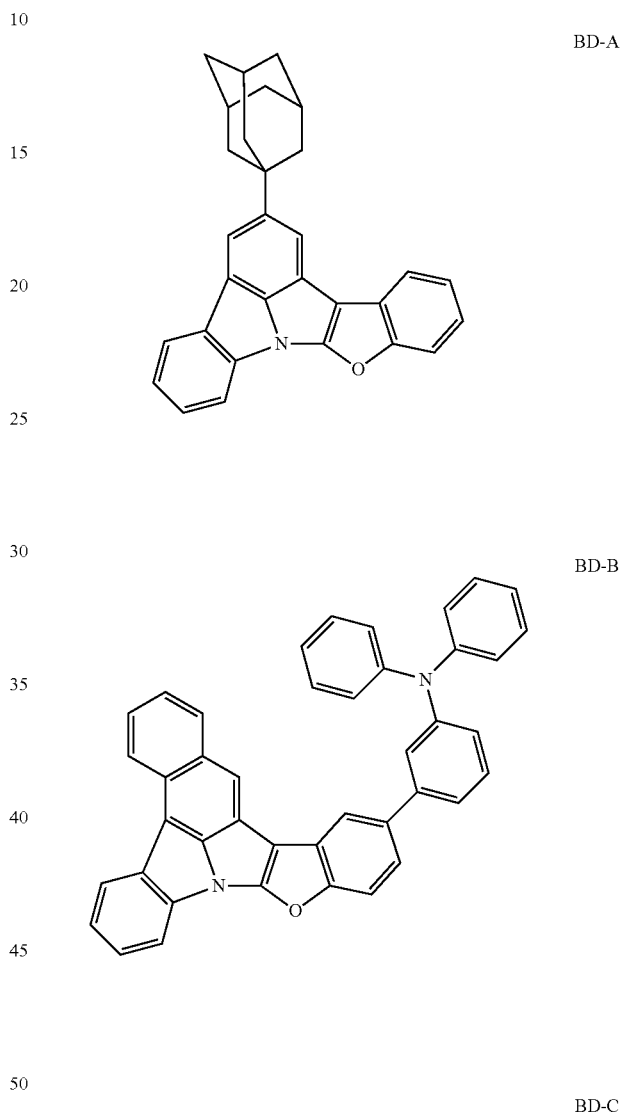

BD-A

BD-B

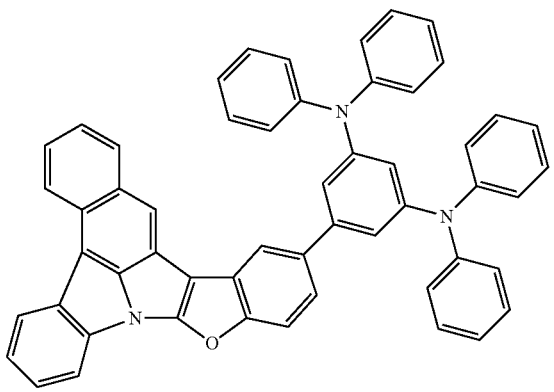

BD-C

BD-D
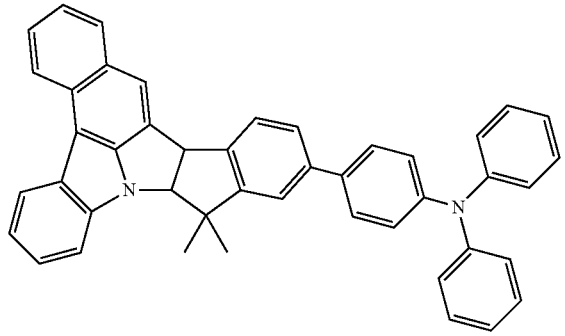

BD-H
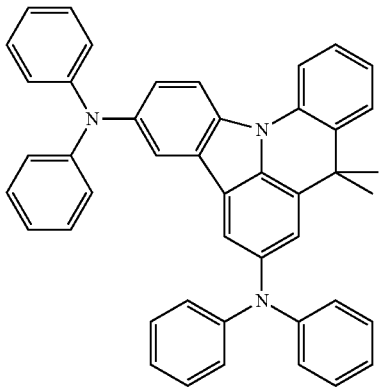

BD-E
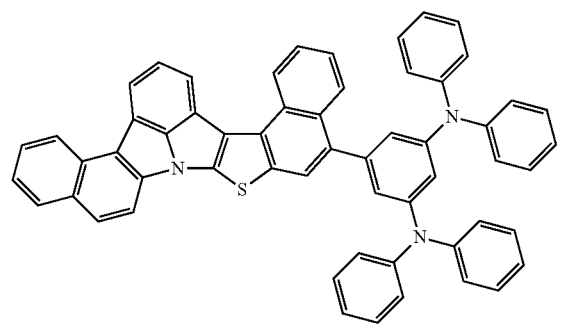

BD-I
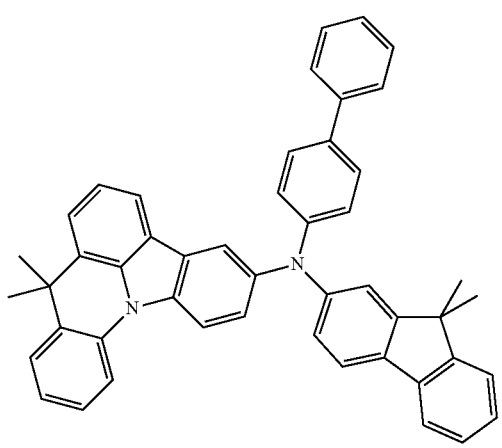

BD-F
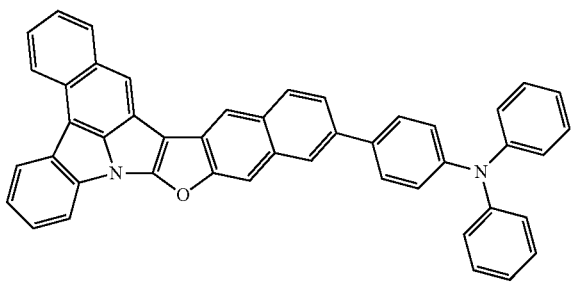

Experimental Examples

Voltages and efficiencies when a current density of 10 mA/cm² was applied to the organic light emitting devices manufactured in Examples 1 to 25 and Comparative Examples 1 to 9 and service lives ($T_{97}$) when a current density of 20 mA/cm² was applied to the devices were measured, and the results are shown in the following Table 1. In this case, $T_{97}$ means time taken for the luminance to decrease to 97% when the initial luminance at the current density of 20 mA/cm² is set to 100%.

BD-G
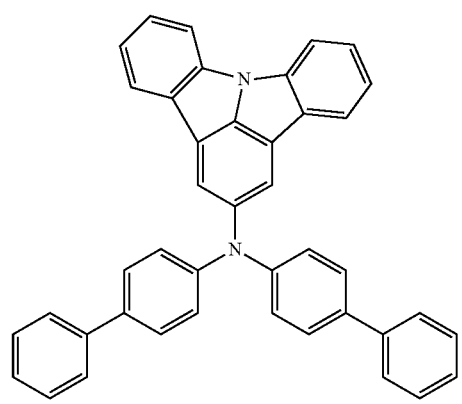

TABLE 1

| | Host | Dopant | Light emitting efficiency (Cd/A) | Service life, $T_{97}$ (h) |
|---|---|---|---|---|
| Example 1 | BH-A | Compound 1 | 4.06 | 70 |
| Example 2 | BH-A | Compound 2 | 4.03 | 68 |
| Example 3 | BH-A | Compound 3 | 4.06 | 71 |
| Example 4 | BH-A | Compound 4 | 4.27 | 72 |
| Example 5 | BH-A | Compound 5 | 4.17 | 72 |
| Example 6 | BH-A | Compound 6 | 4.10 | 69 |
| Example 7 | BH-A | Compound 7 | 4.20 | 73 |
| Example 8 | BH-A | Compound 8 | 4.24 | 75 |
| Example 9 | BH-A | Compound 9 | 4.30 | 73 |
| Example 10 | BH-A | Compound 10 | 4.38 | 71 |
| Example 11 | BH-A | Compound 11 | 4.20 | 74 |
| Example 12 | BH-A | Compound 12 | 4.38 | 72 |
| Example 13 | BH-A | Compound 13 | 4.10 | 49 |
| Example 14 | BH-A | Compound 14 | 4.03 | 71 |
| Example 15 | BH-A | Compound 15 | 4.20 | 70 |

TABLE 1-continued

| | Host | Dopant | Light emitting efficiency (Cd/A) | Service life, $T_{97}$ (h) |
|---|---|---|---|---|
| Example 16 | BH-A | Compound 16 | 4.06 | 72 |
| Comparative Example 1 | BH-A | BD-A | 2.10 | 56 |
| Comparative Example 2 | BH-A | BD-B | 2.52 | 60 |
| Comparative Example 3 | BH-A | BD-C | 2.87 | 59 |
| Comparative Example 4 | BH-A | BD-F | 2.45 | 57 |
| Comparative Example 5 | BH-A | BD-I | 2.98 | 51 |
| Example 17 | BH-B | Compound 17 | 4.31 | 68 |
| Example 18 | BH-B | Compound 18 | 4.34 | 70 |
| Example 19 | BH-B | Compound 19 | 4.27 | 68 |
| Example 20 | BH-B | Compound 20 | 4.31 | 72 |
| Example 21 | BH-B | Compound 21 | 4.41 | 76 |
| Example 22 | BH-B | Compound 22 | 4.31 | 71 |
| Example 23 | BH-B | Compound 23 | 4.48 | 76 |
| Example 24 | BH-B | Compound 24 | 4.30 | 71 |
| Example 25 | BH-B | Compound 25 | 4.36 | 74 |
| Comparative Example 6 | BH-B | BD-D | 2.45 | 56 |
| Comparative Example 7 | BH-B | BD-E | 2.80 | 58 |
| Comparative Example 8 | BH-B | BD-G | 3.08 | 54 |
| Comparative Example 9 | BH-B | BD-H | 3.50 | 53 |

From Table 1, it can be confirmed that Examples 1 to 25 where compounds, which have a structure in which a benzothiophene, a benzofuran group, or a dihydroindene is directly condensed with the indolocarbazole structure of Formula 1 of the present specification and have a core substituted with two or more amine groups, are applied to a dopant of a light emitting layer of an organic light emitting device, have results of inducing better light emitting efficiencies and service lives than the compounds of Comparative Examples 1 to 9 in which a compound, which is not directly condensed with the indolocarbazole structure or whose core is not substituted with an amine group, is applied to a dopant of a light emitting layer of an organic light emitting device.

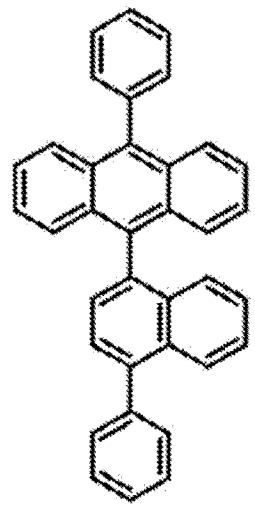

The invention claimed is:

1. A compound of Formula 1:

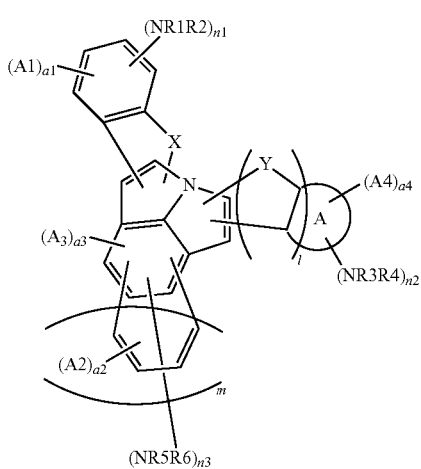

<Formula 1> wherein in Formula 1:

X and Y are the same as or different from each other, and are each independently O, S, or CZ1Z2;

Ring A is a benzene ring or a naphthalene ring;

A1 to A4 are the same as or different from each other, and are each independently hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group;

R1 to R6, Z1, and Z2 are the same as or different from each other, and each independently a substituted or unsubstituted alkyl group, a substituted or unsubstituted aryl group, or a substituted or unsubstituted heterocyclic group;

n1 to n3, m, and l are each 0 or 1;

a sum of n1 to n3 is 2 or 3;

a1 and a2 are each an integer from 1 to 4;

a3 is an integer from 1 to 3;

a4 is an integer from 1 to 6; and when a1 and a2 are each 2 to 4, when a3 is 2 or 3, or when a4 is 2 to 6, structures in the parenthesis are the same as or different from each other, provided that when Ring A is naphthalene, m is 0, and when l is 1, Ring A is a benzene ring.

2. The compound of claim 1, wherein the compound of Formula 1 is any one of the following Formulae 2-1 to 2-8:

<Formula 2-1>

<Formula 2-2>

347
-continued

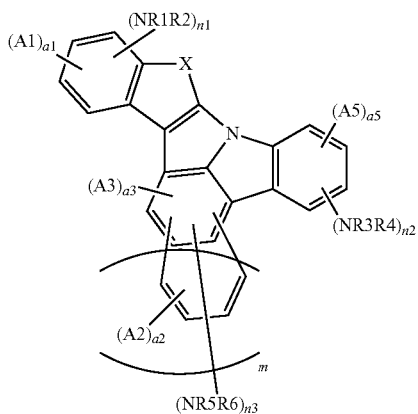

<Formula 2-3>

<Formula 2-4>

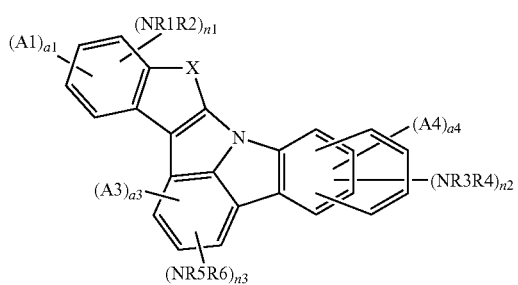

<Formula 2-5>

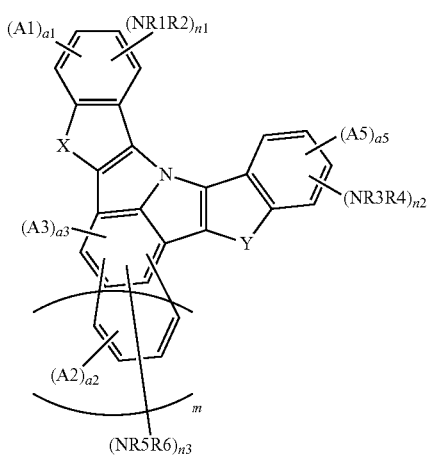

348
-continued

<Formula 2-6>

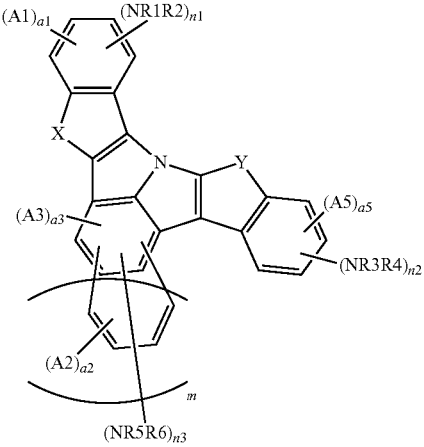

<Formula 2-7>

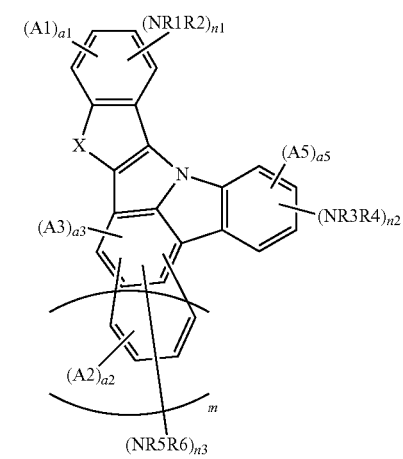

<Formula 2-8>

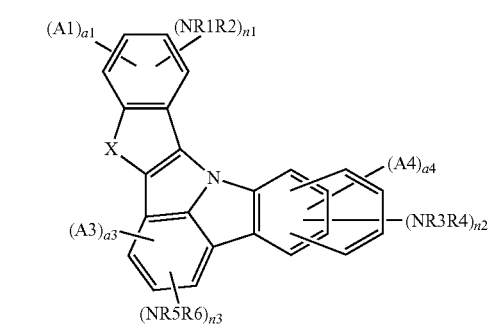

wherein in Formulae 2-1 to 2-8:

X, Y, A1 to A4, a1 to a4, R1 to R6, n1 to n3, and m are the same as those defined in Formula 1;

A5 is hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group;

a5 is an integer from 1 to 4; and when a5 is 2 to 4, structures in the parenthesis are the same as or different from each other.

3. The compound of claim 1, wherein the compound of Formula 1 is any one of the following Formulae 3-1 to 3-12:

<Formula 3-1>
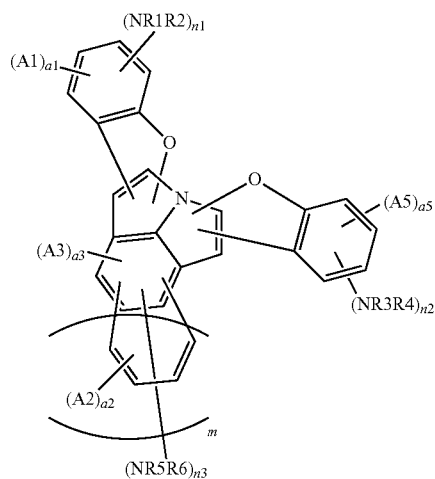
<Formula 3-2>
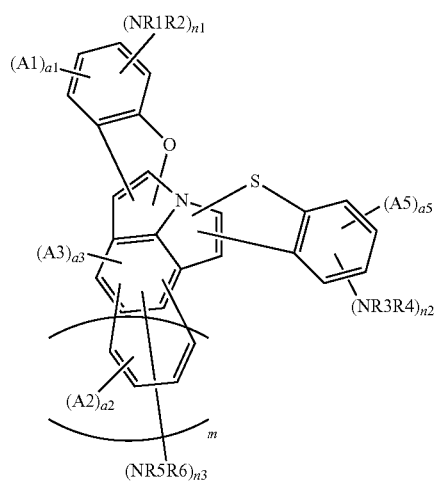
<Formula 3-3>
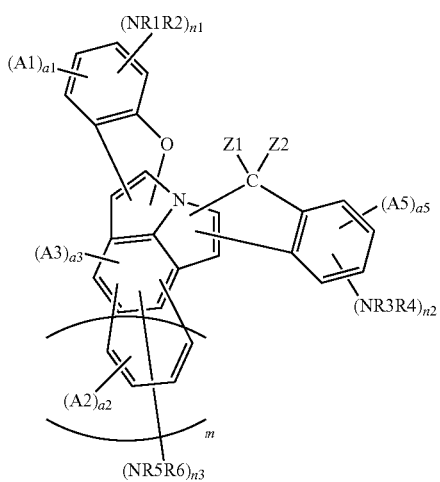
<Formula 3-4>
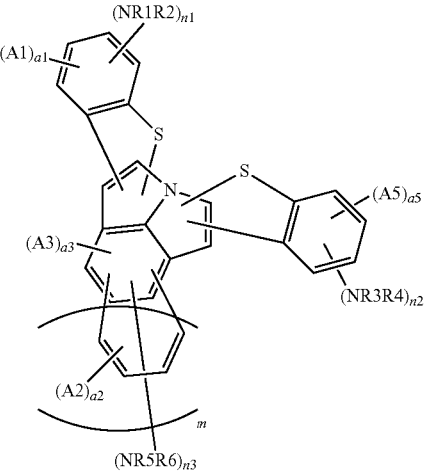
<Formula 3-5>
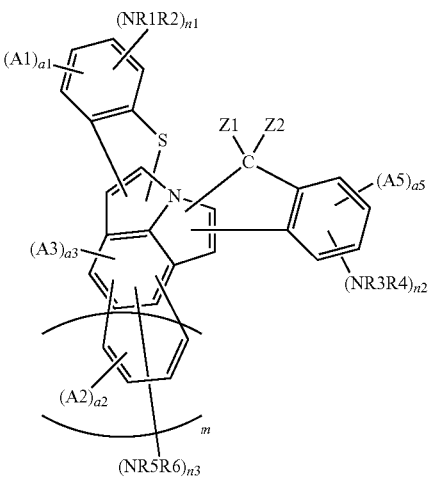
<Formula 3-6>
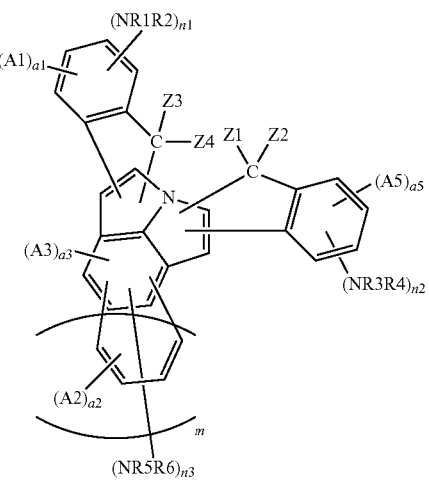

<Formula 3-7>

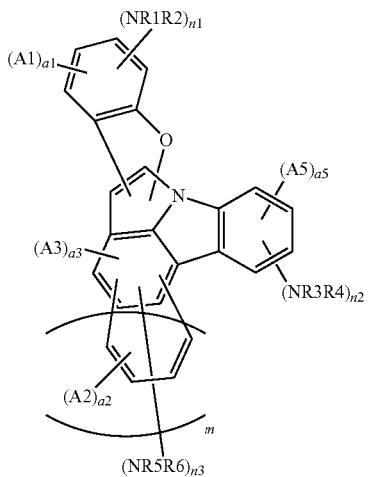

<Formula 3-8>

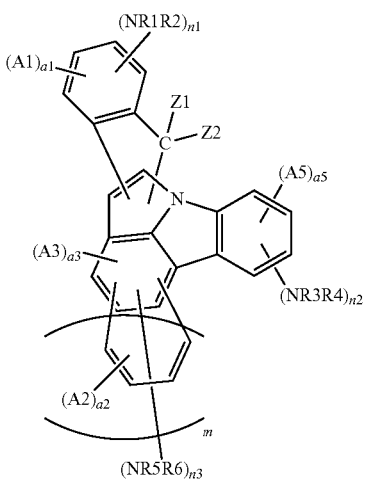

<Formula 3-9>

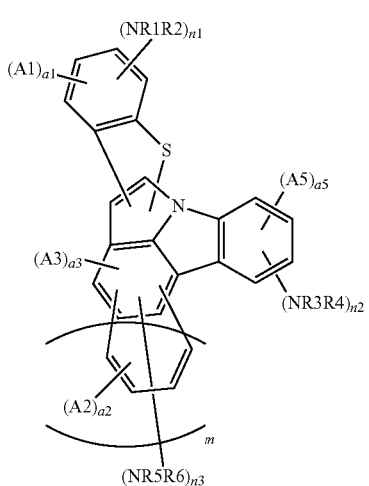

<Formula 3-10>

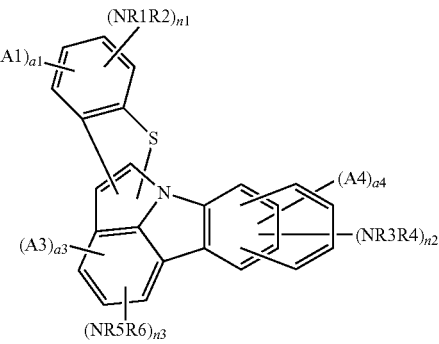

<Formula 3-11>

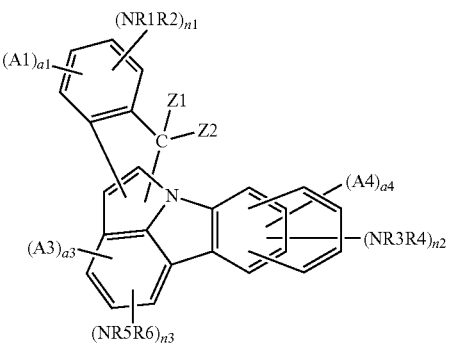

<Formula 3-12> wherein in Formulae 3-1 to 3-12:
A1 to A4, a1 to a4, R1 to R6, n1 to n3, m, Z1, and Z2 are the same as those defined in Formula 1;
Z3 and Z4 are the same as or different from each other, and are each independently a substituted or unsubstituted alkyl group, a substituted or unsubstituted aryl group, or a substituted or unsubstituted heterocyclic group;
A5 is hydrogen, deuterium, a halogen group, a cyano group, a nitro group, a hydroxyl group, a substituted or unsubstituted alkyl group, a substituted or unsubstituted cycloalkyl group, a substituted or unsubstituted aryl group, or a substituted or unsubstituted heterocyclic group;
a5 is an integer from 1 to 4; and
when a5 is 2 to 4, structures in the parenthesis are the same as or different from each other.

4. The compound of claim 1, wherein a sum of n1 to n3 is 2.

5. The compound of claim 1, wherein A1 to A4 are the same as or different from each other, and are each independently hydrogen, deuterium, a substituted or unsubstituted alkyl group, or a substituted or unsubstituted aryl group.

6. The compound of claim 1, wherein R1 to R6 are the same as or different from each other, and are each independently a substituted or unsubstituted aryl group or a substituted or unsubstituted heterocyclic group.

7. The compound of claim 1, wherein a maximum light emission peak of the compound of Formula 1 is 420 nm to 480 nm.

8. The compound of claim 1, wherein the compound of Formula 1 is any one compound of the following compounds:

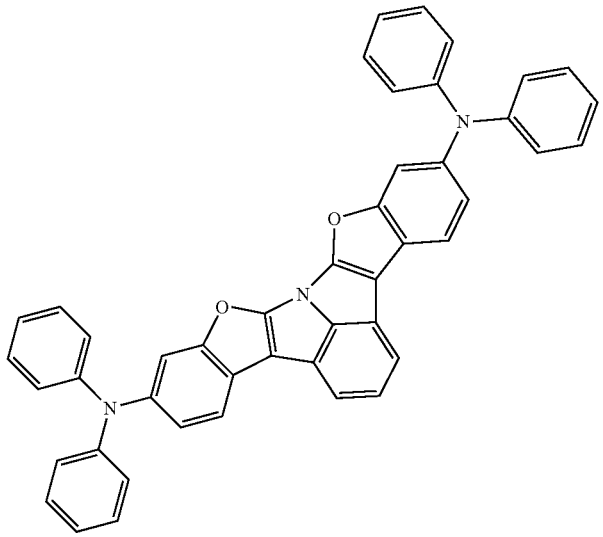

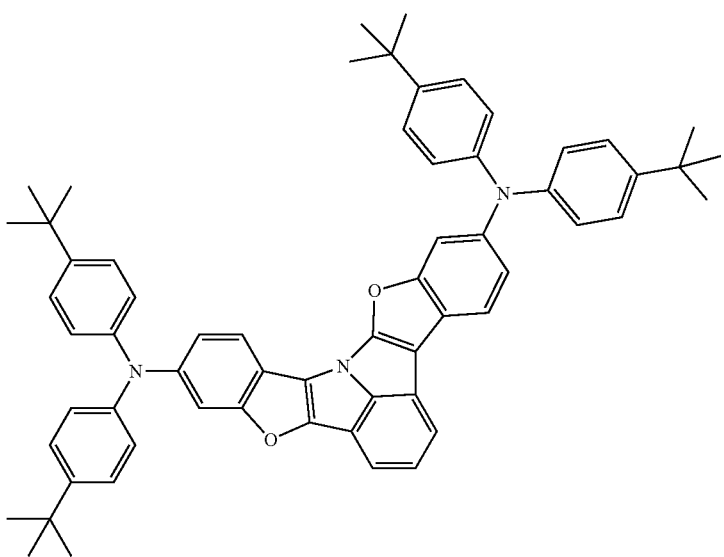

-continued
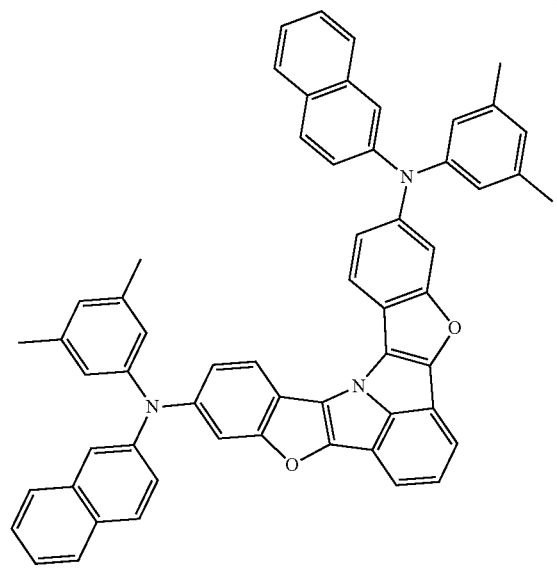
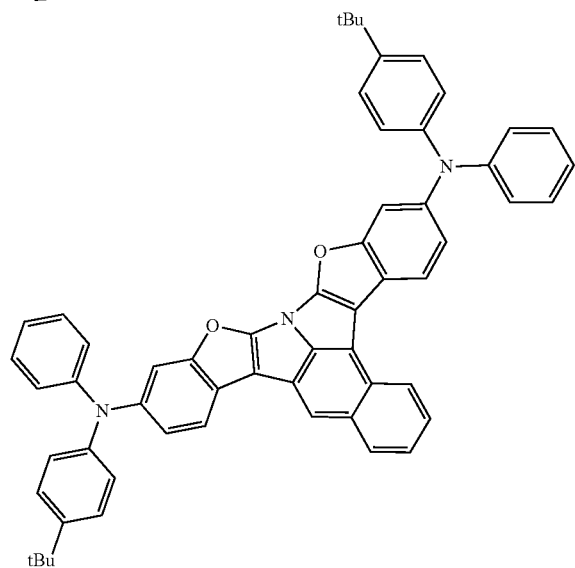
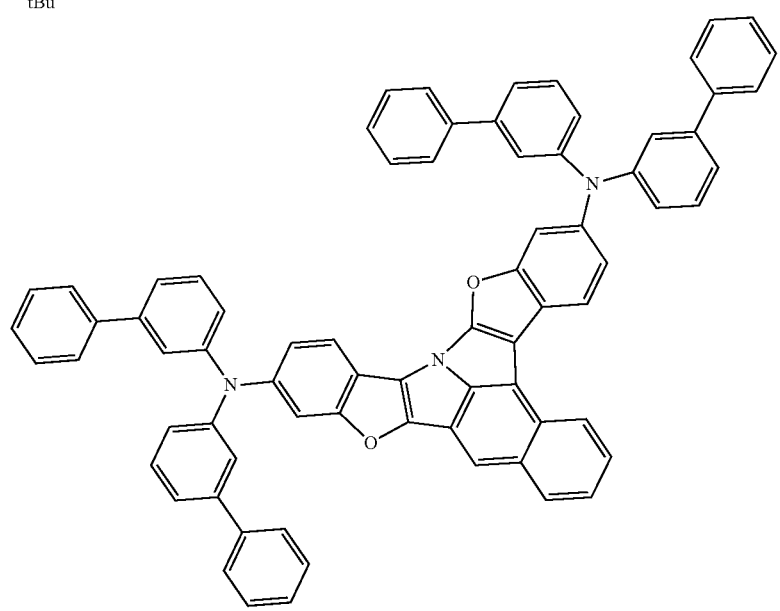

-continued
357
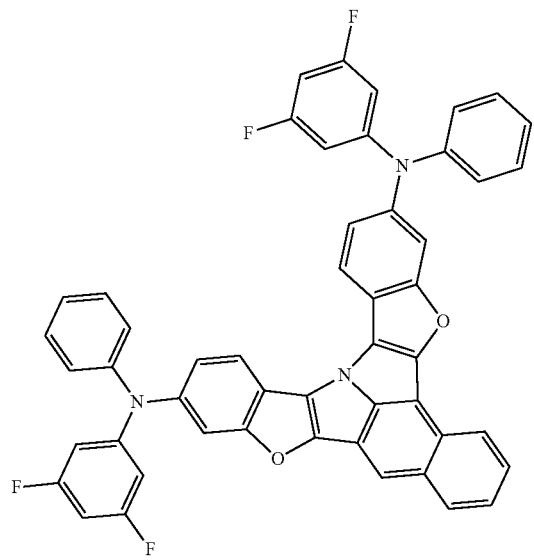
358
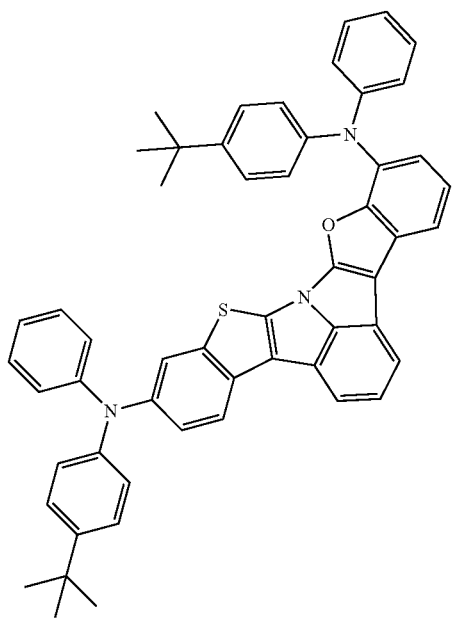
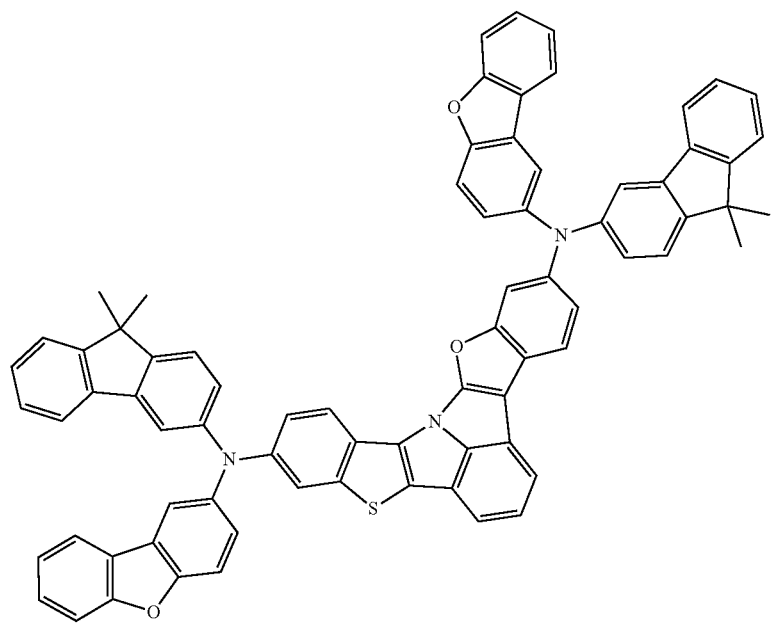

-continued
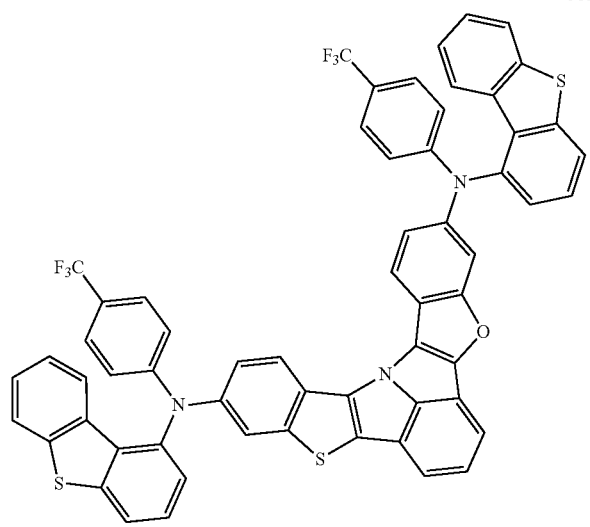
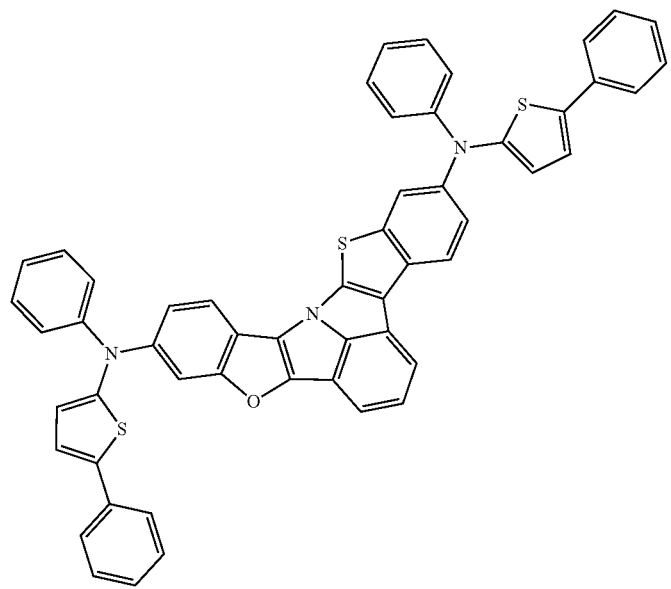

-continued
361
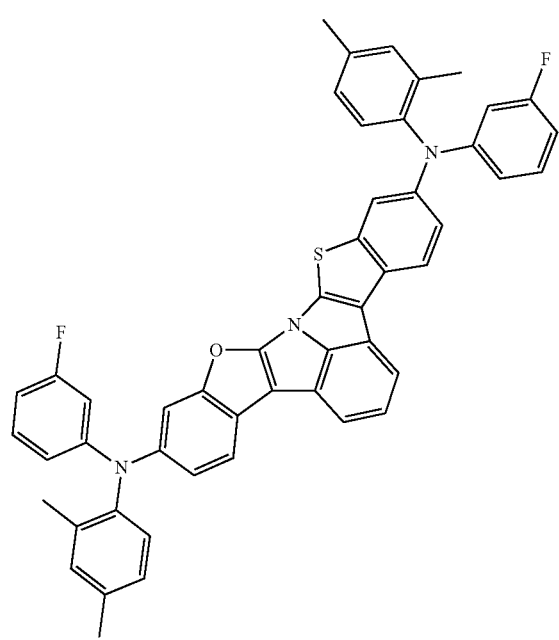
362
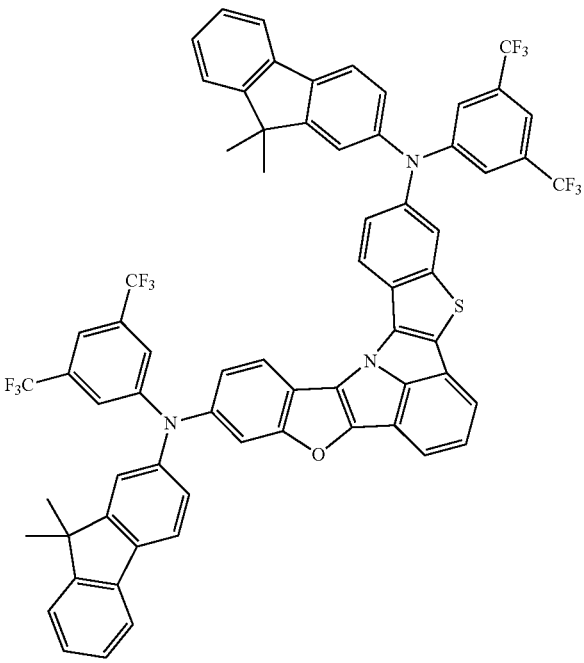
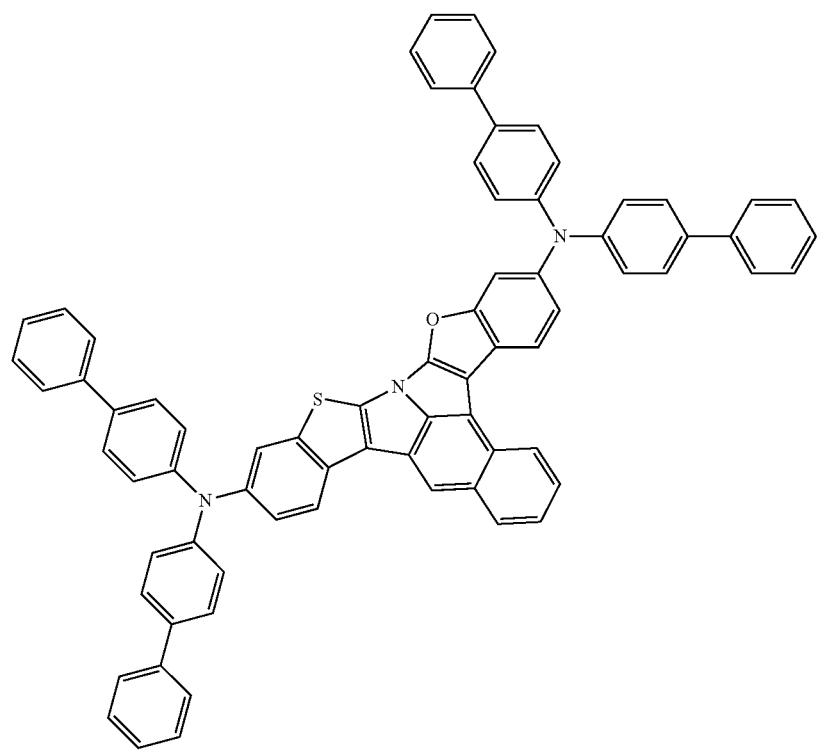

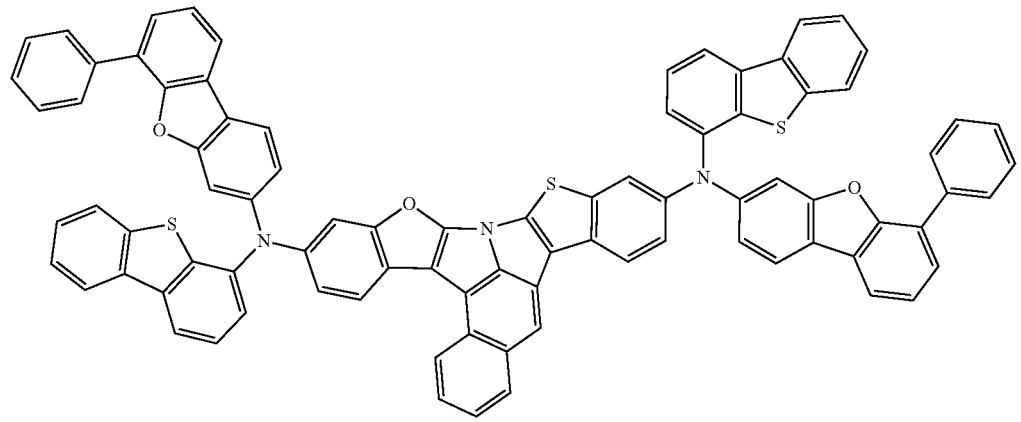
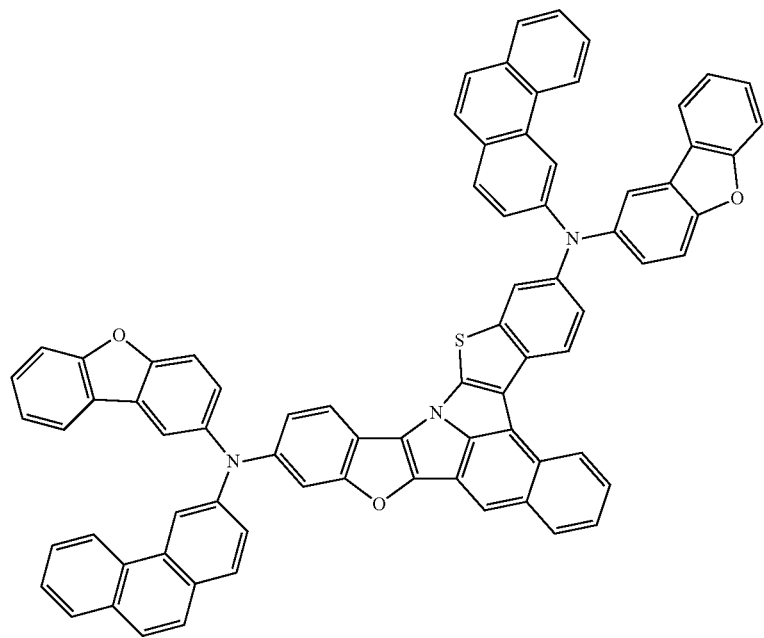
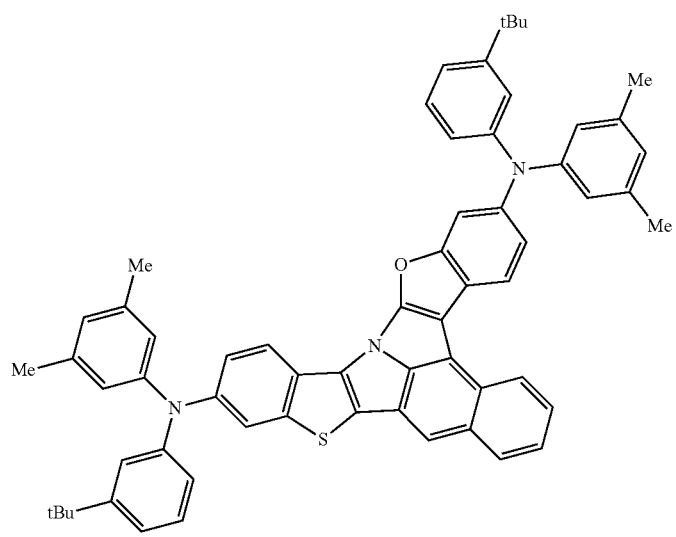

-continued
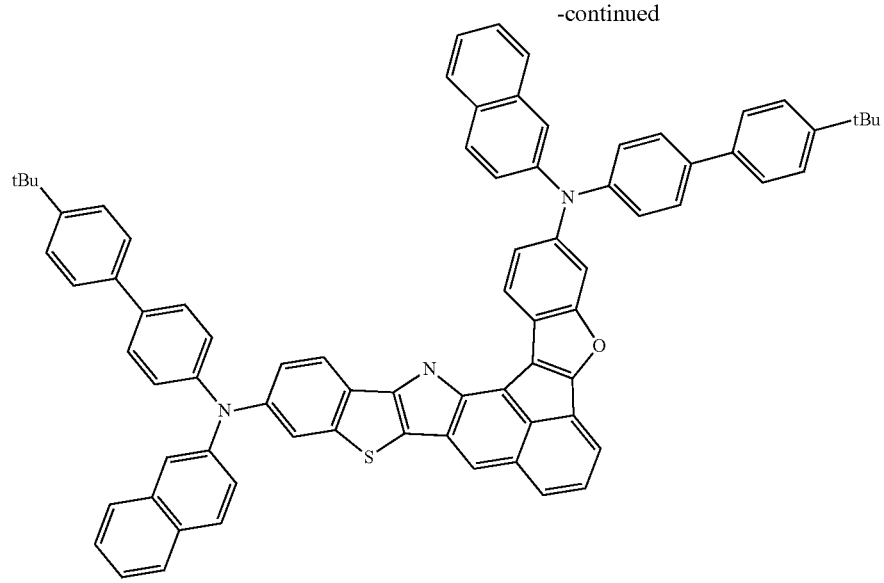
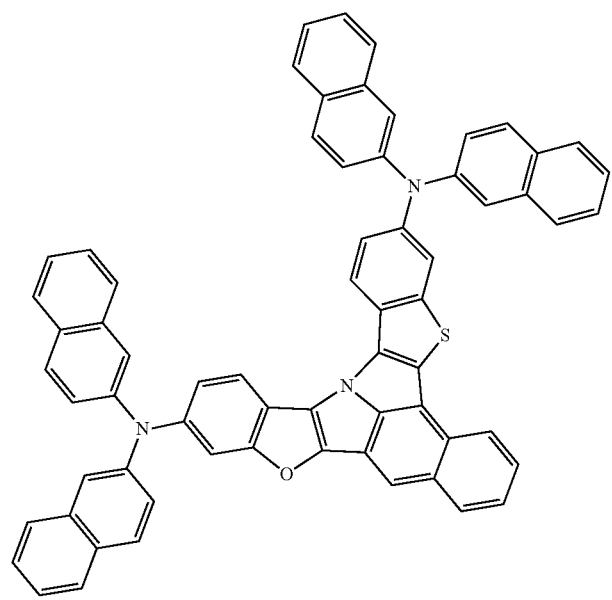

-continued
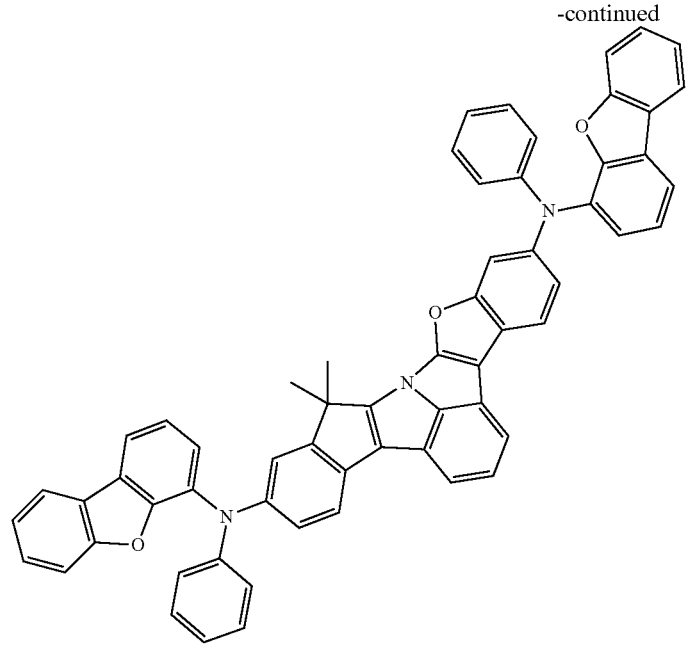
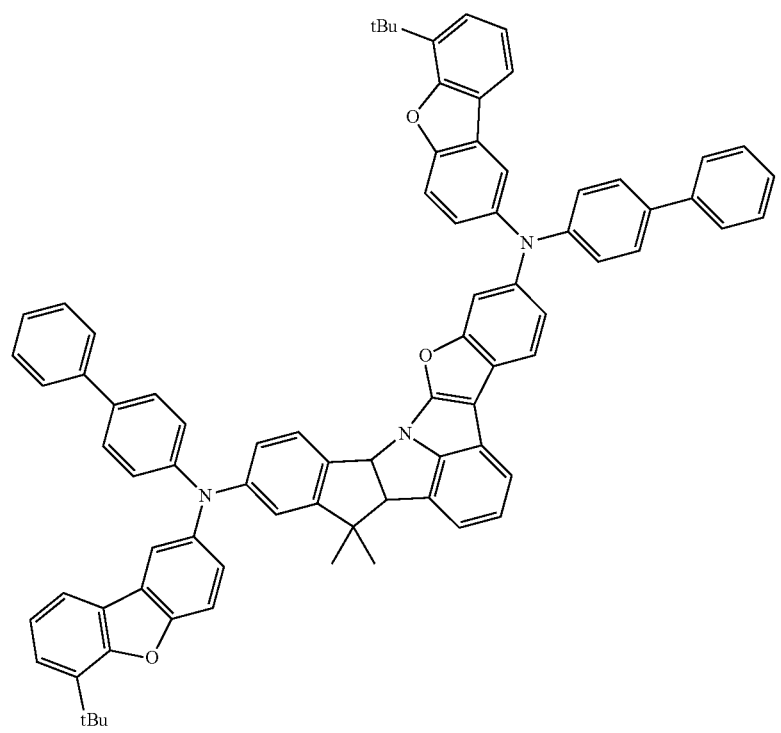

-continued
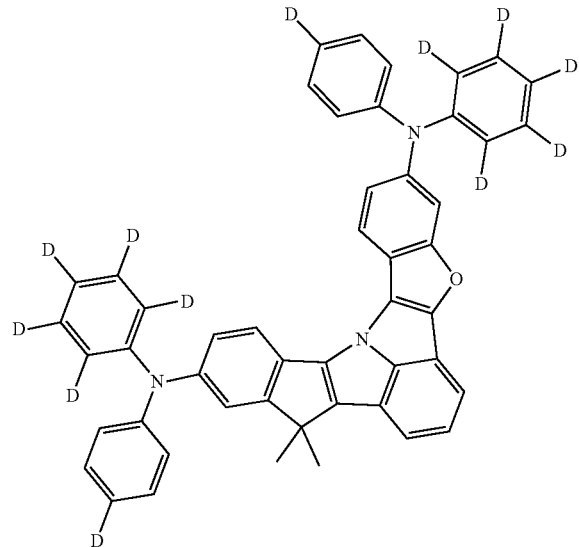
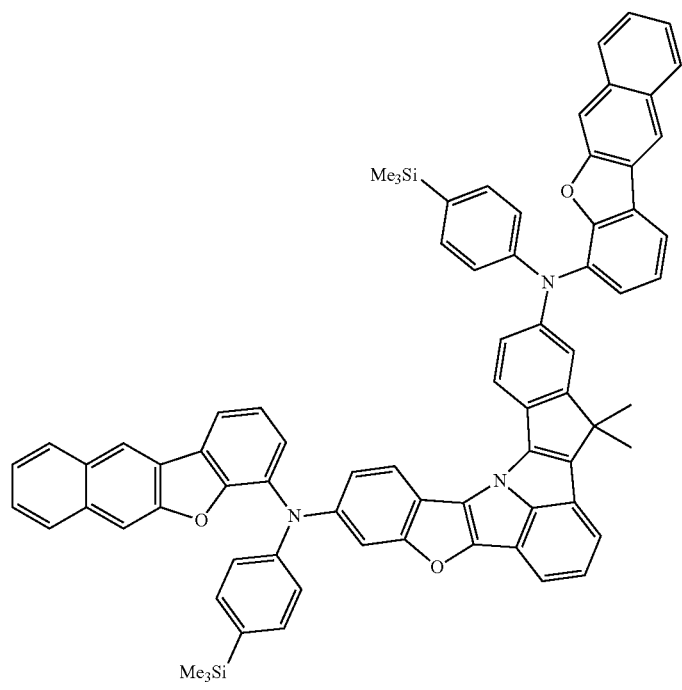

-continued
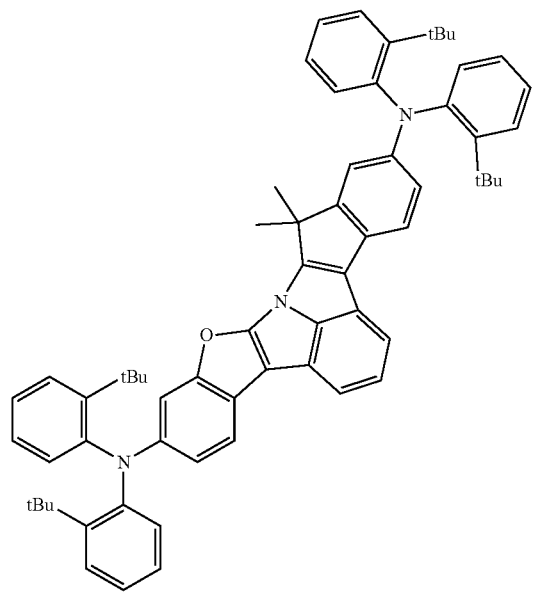
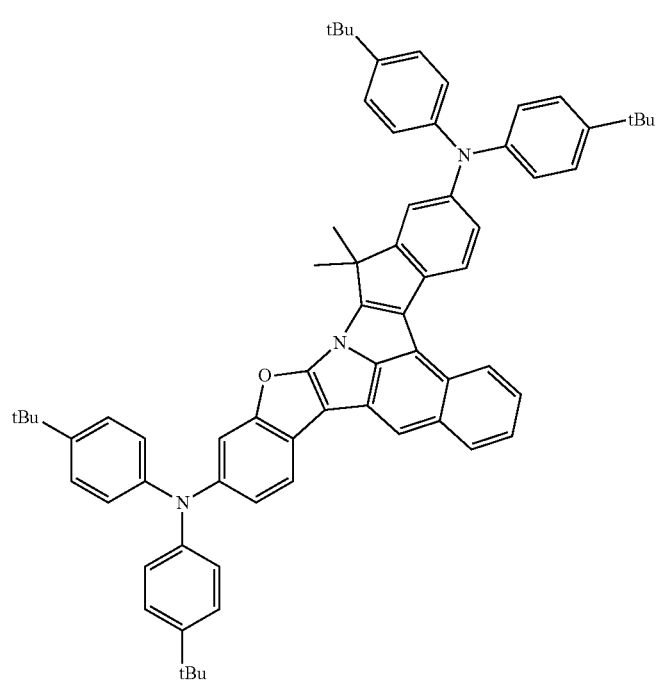 [SMILES: CC(C)(C)c1ccc(N(c2ccc(C(C)(C)C)cc2)c2ccc3c(c2)C(C)(C)c2c-3c3c4ccccc4cc4c5c6ccc(N(c7ccc(C(C)(C)C)cc7)c7ccc(C(C)(C)C)cc7)cc6oc5n2c43)cc1]

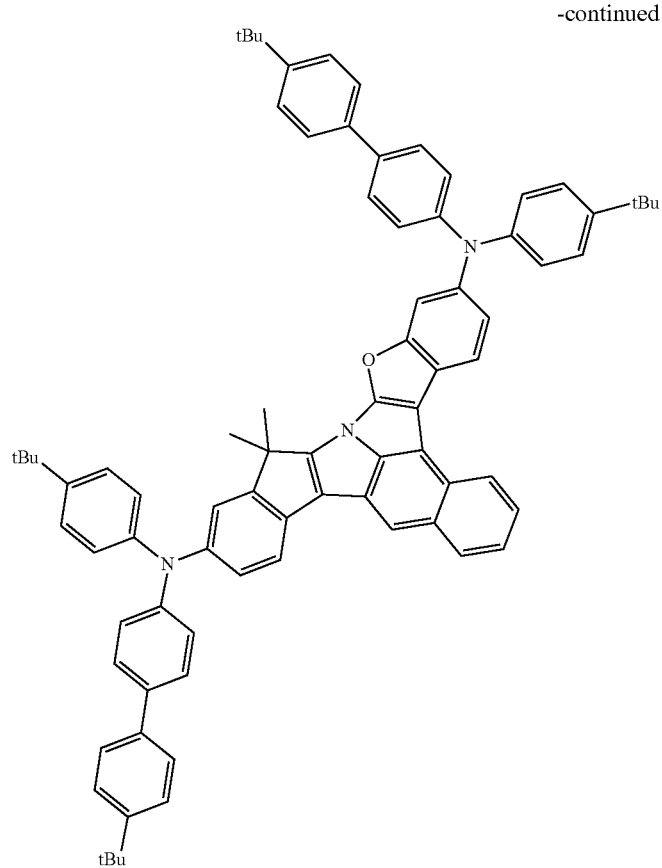
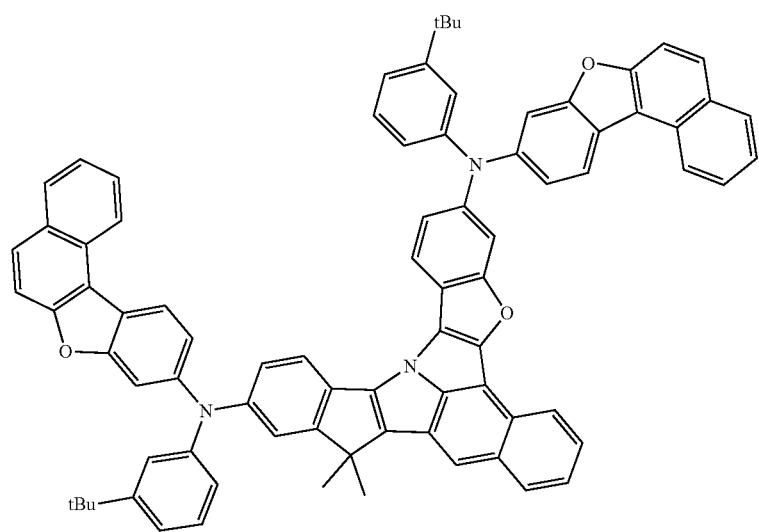

-continued
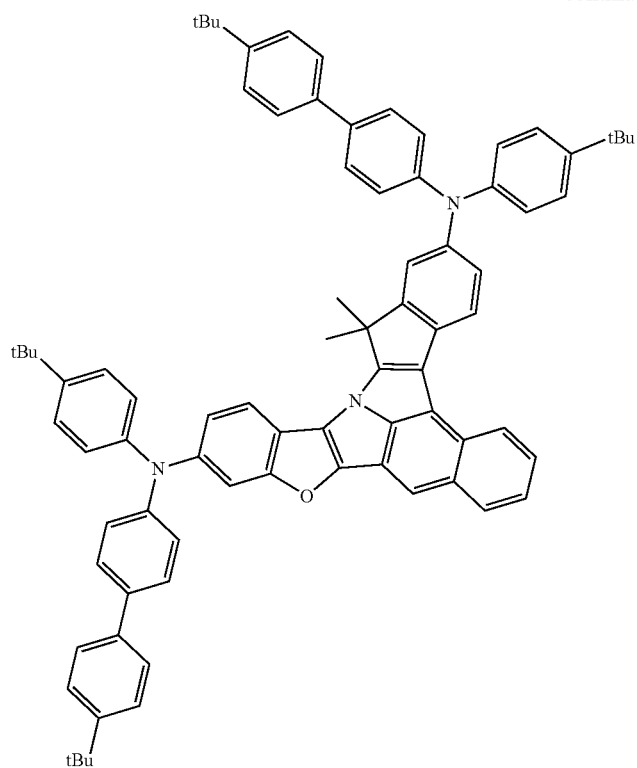
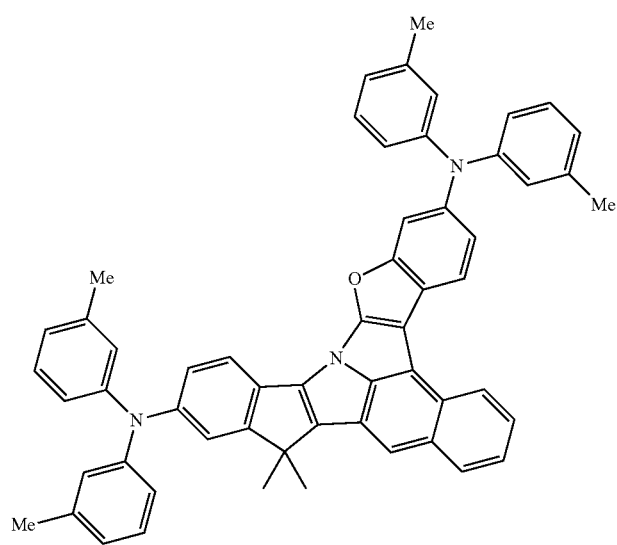

-continued
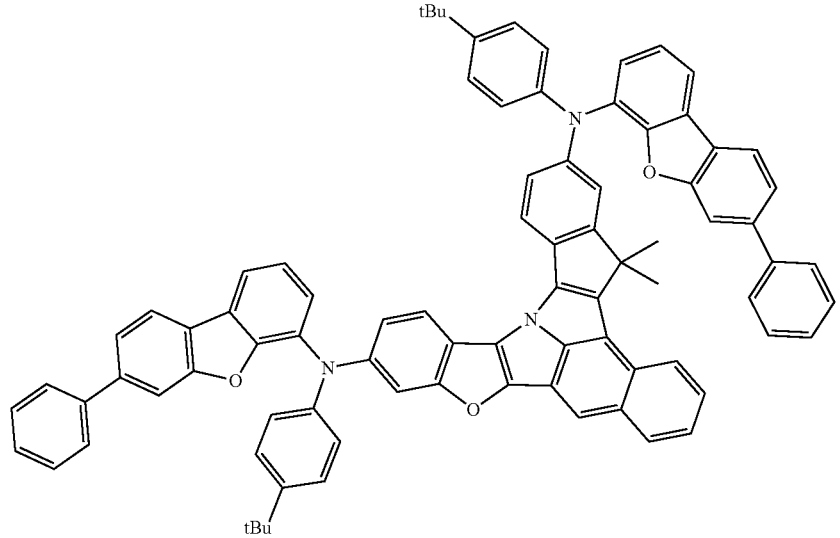
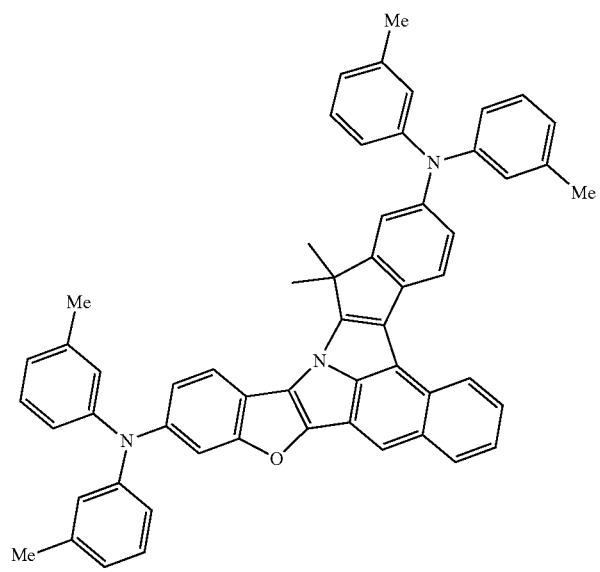
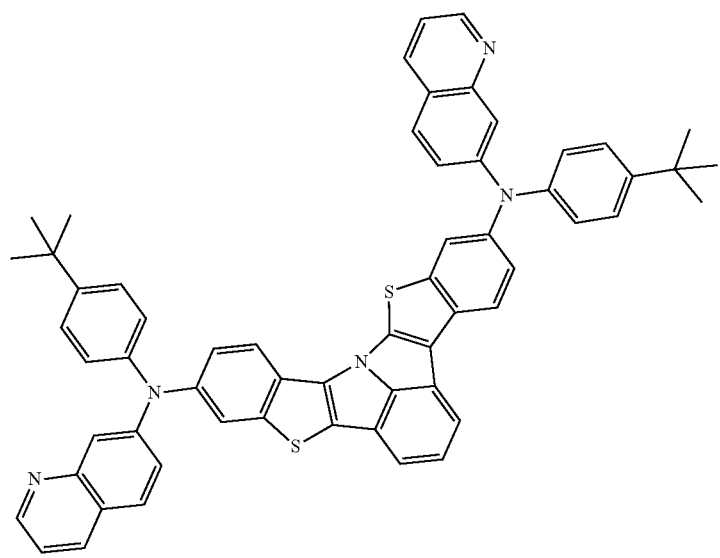

-continued
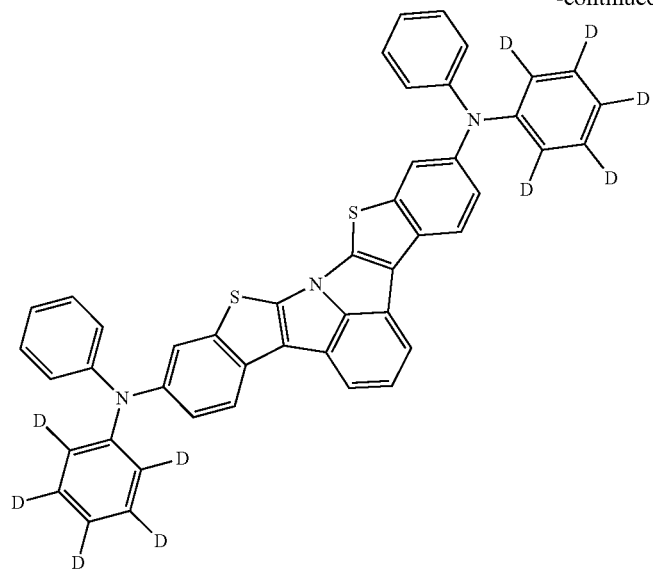
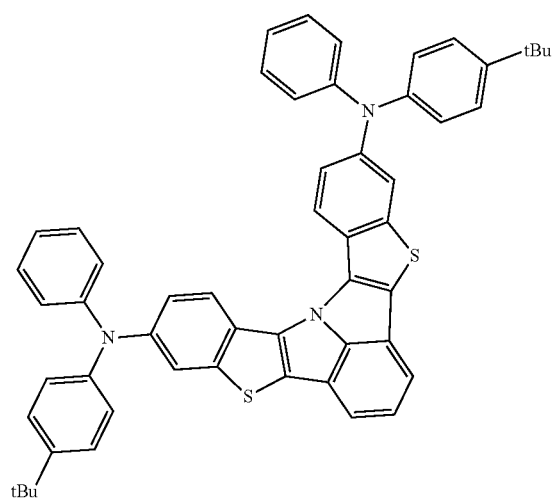

-continued
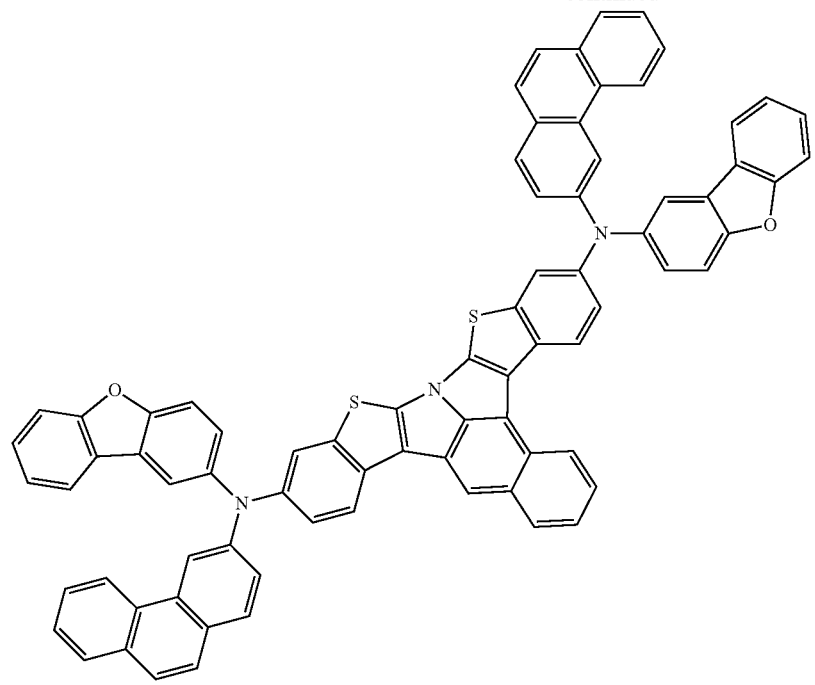
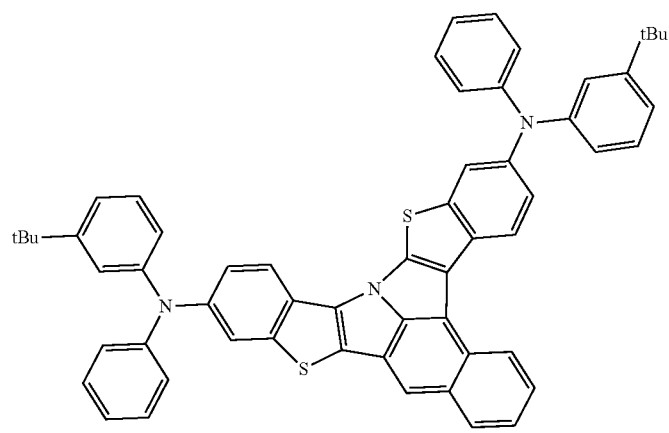
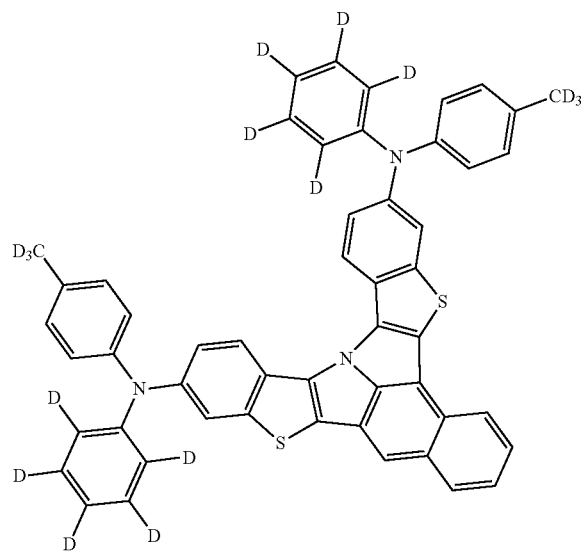

-continued
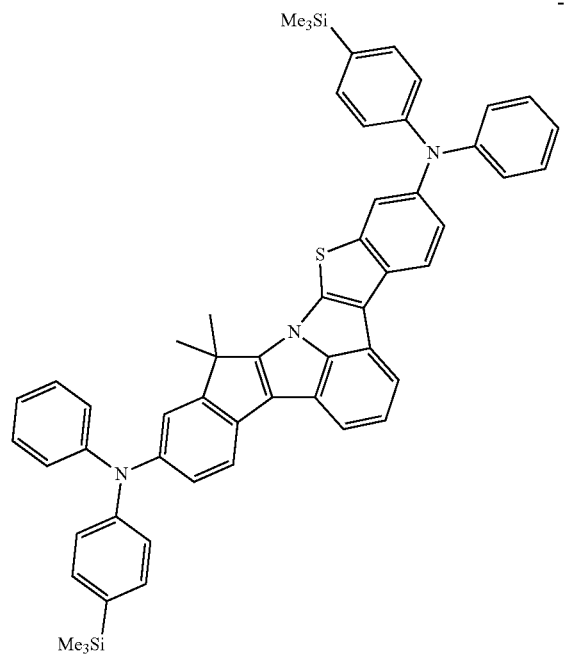
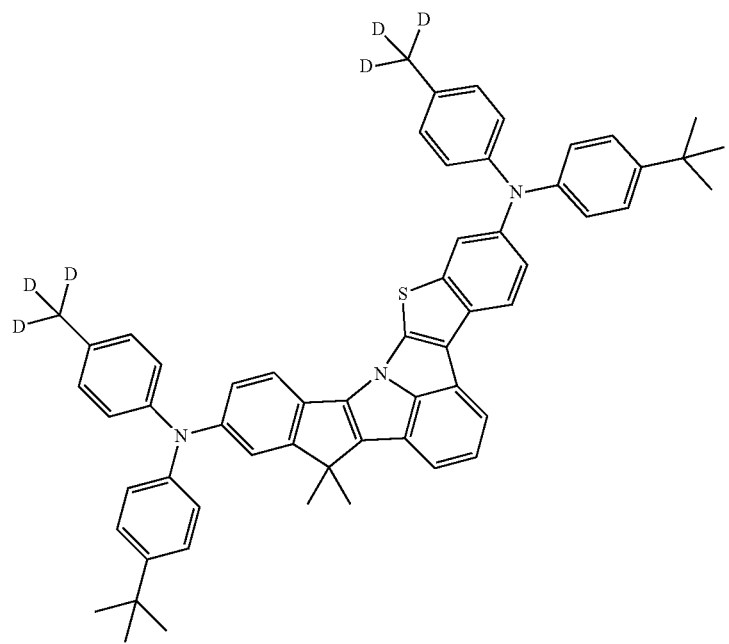

-continued
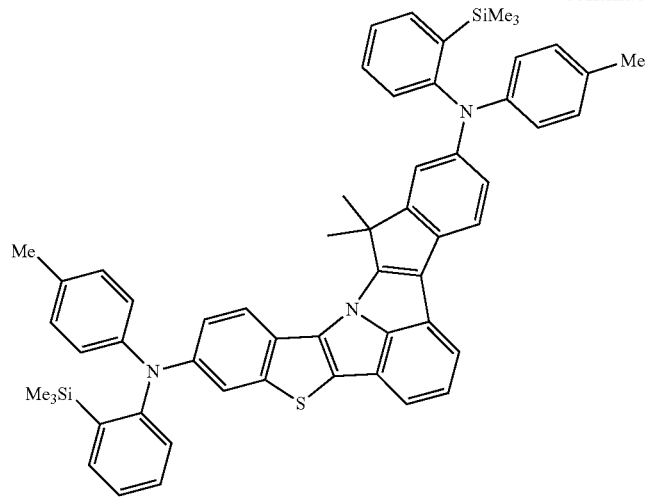
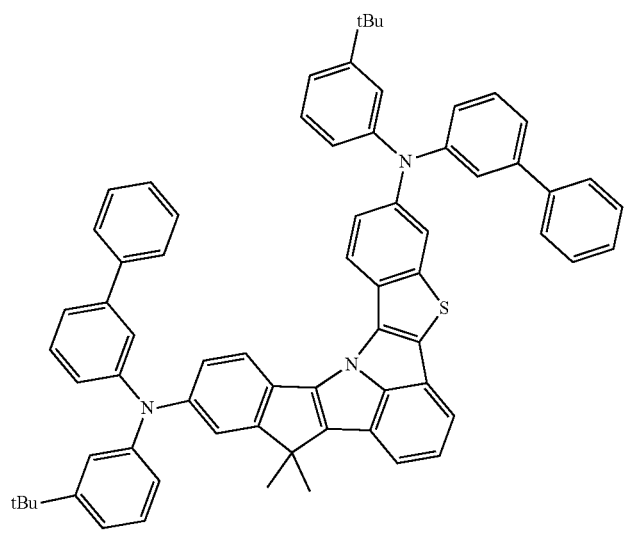
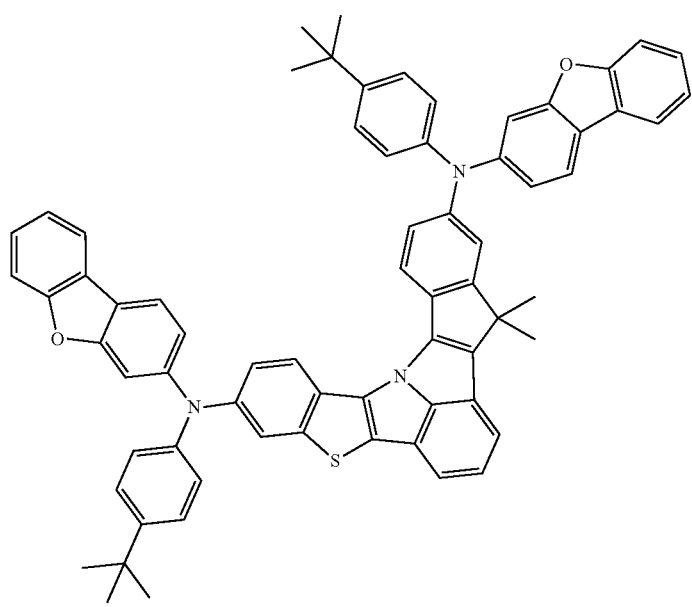

-continued
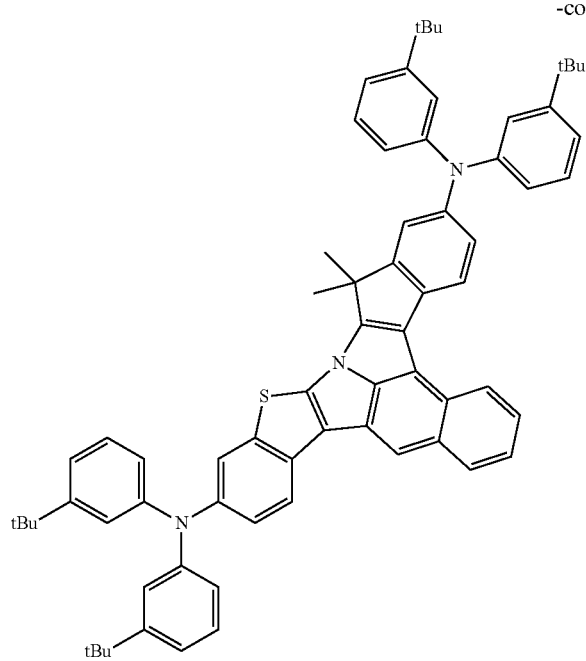
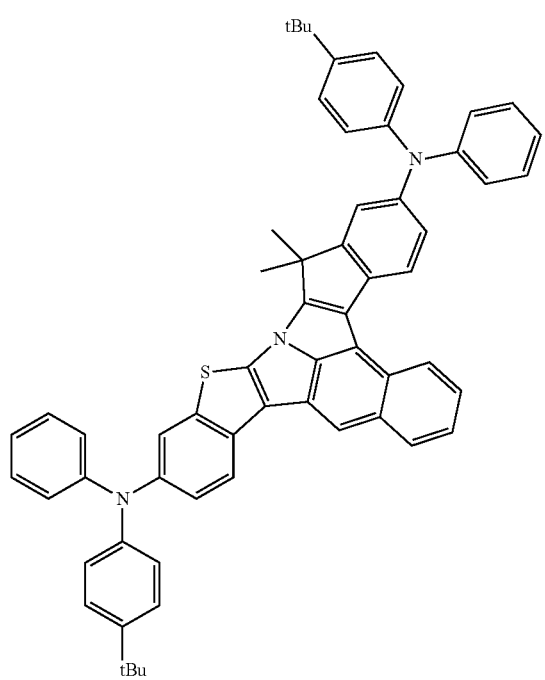

-continued
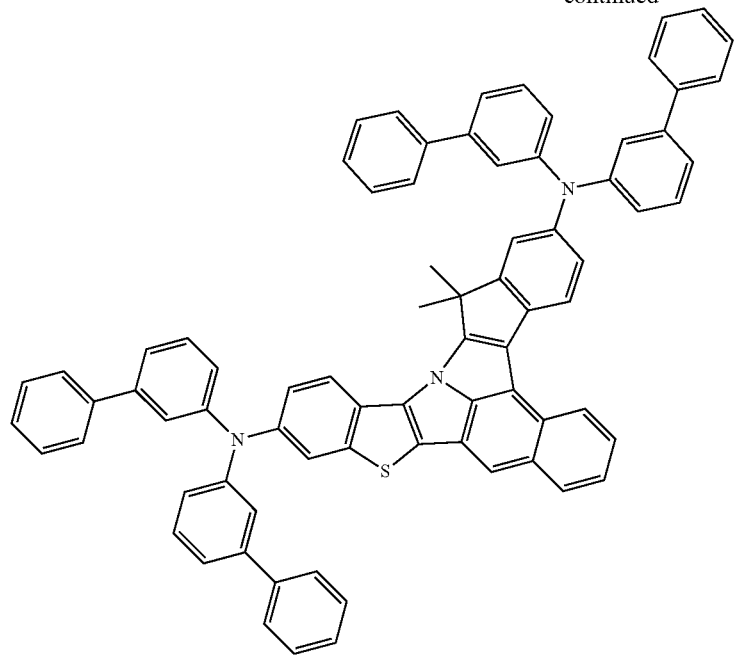
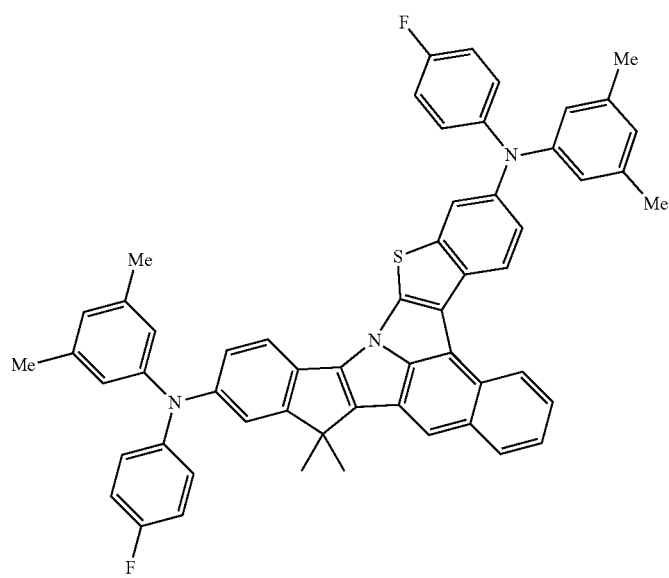

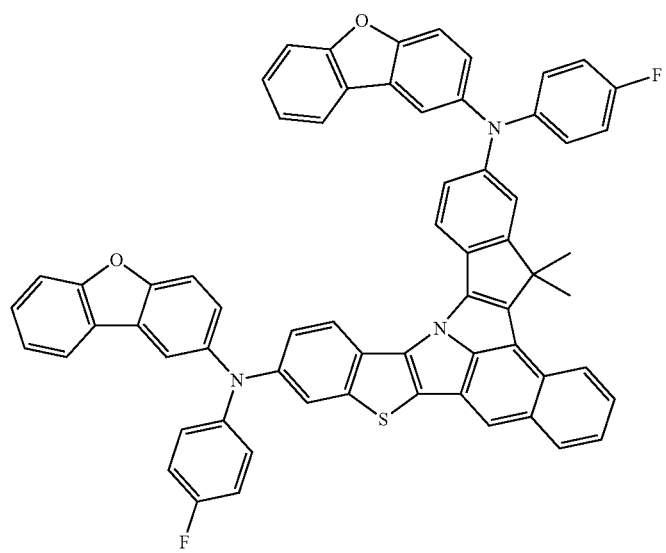
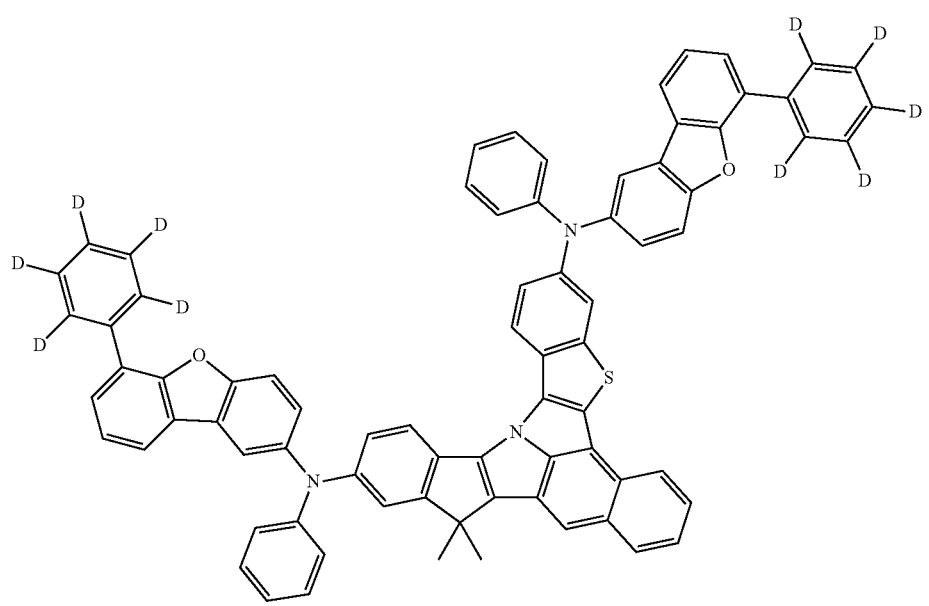

-continued
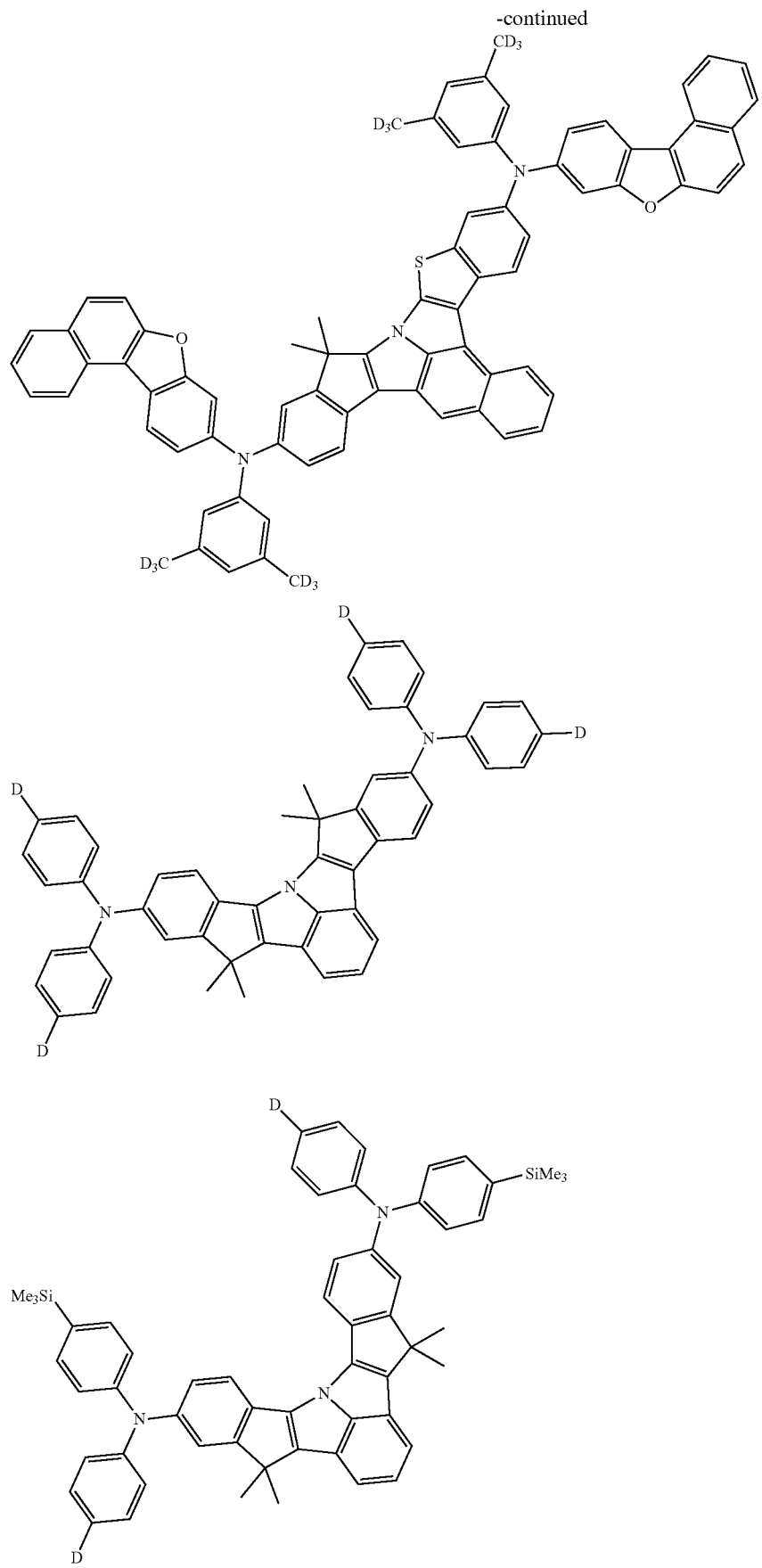

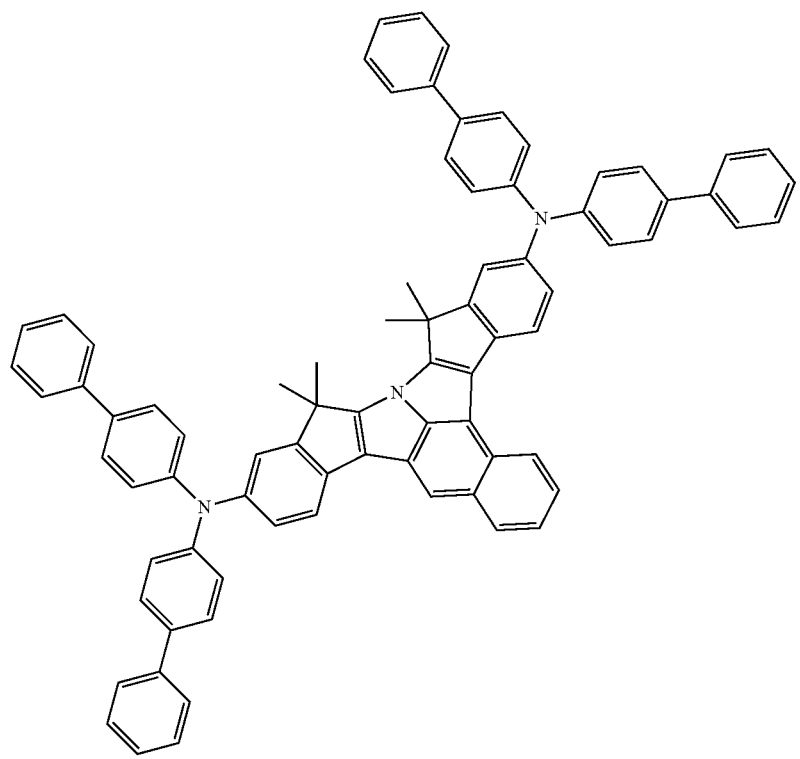
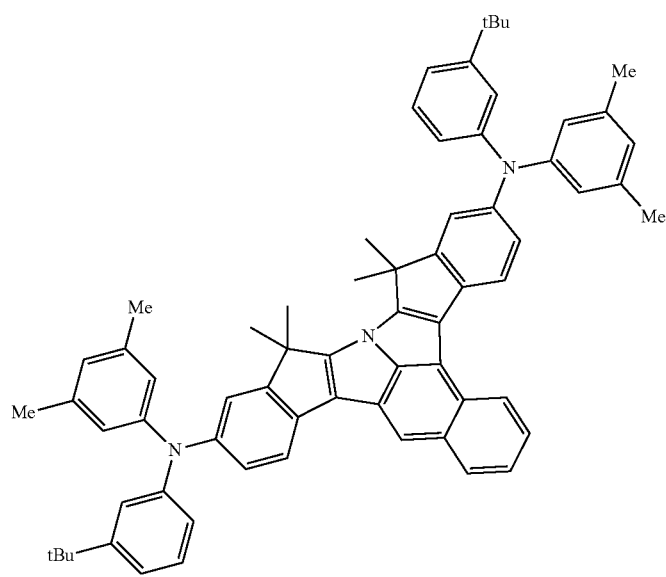

-continued
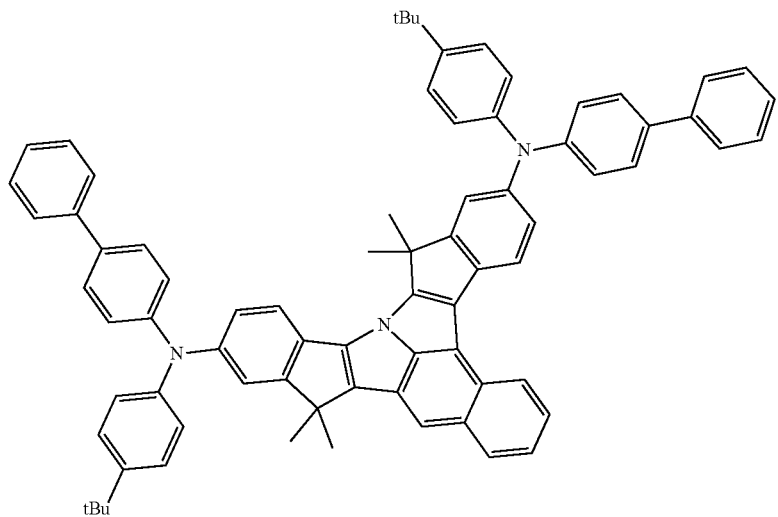
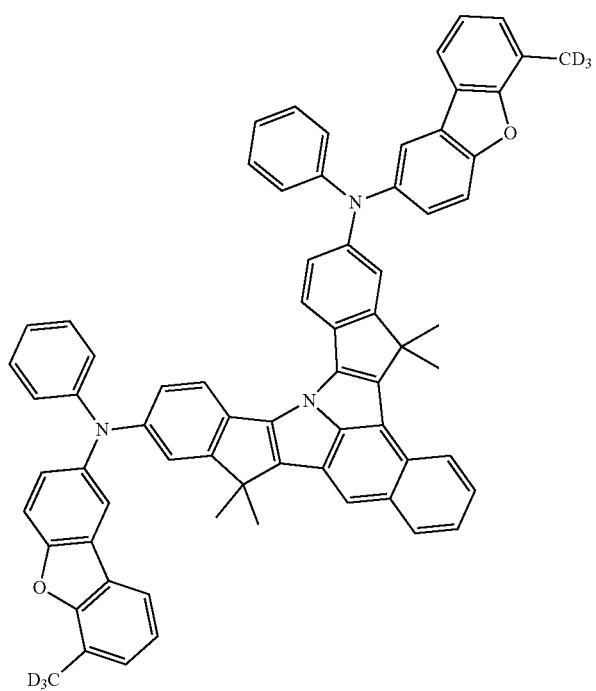

-continued
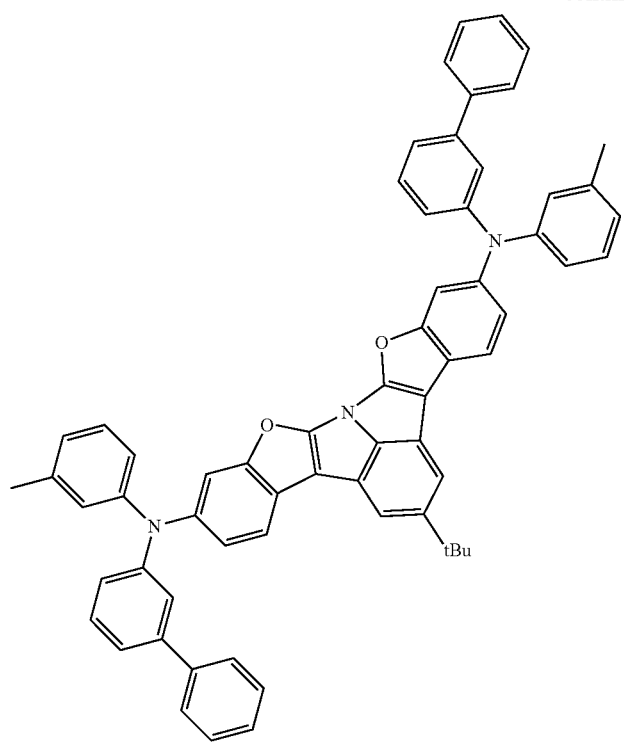
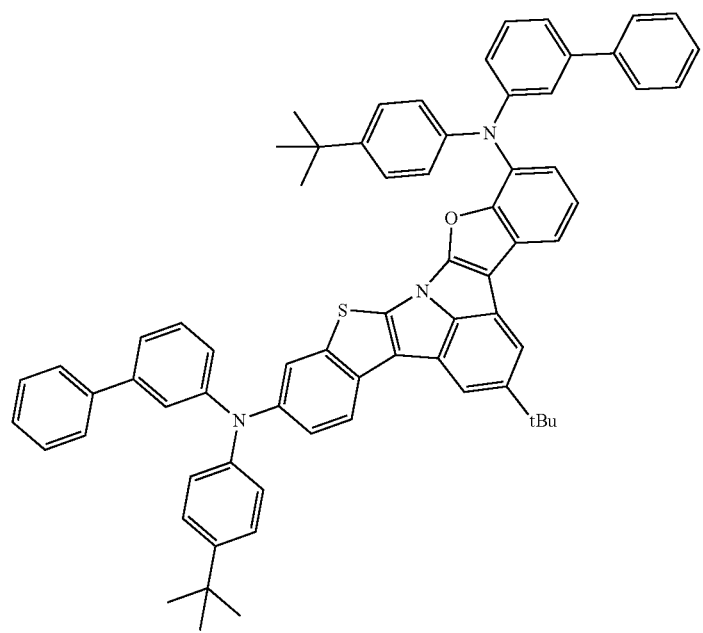

-continued
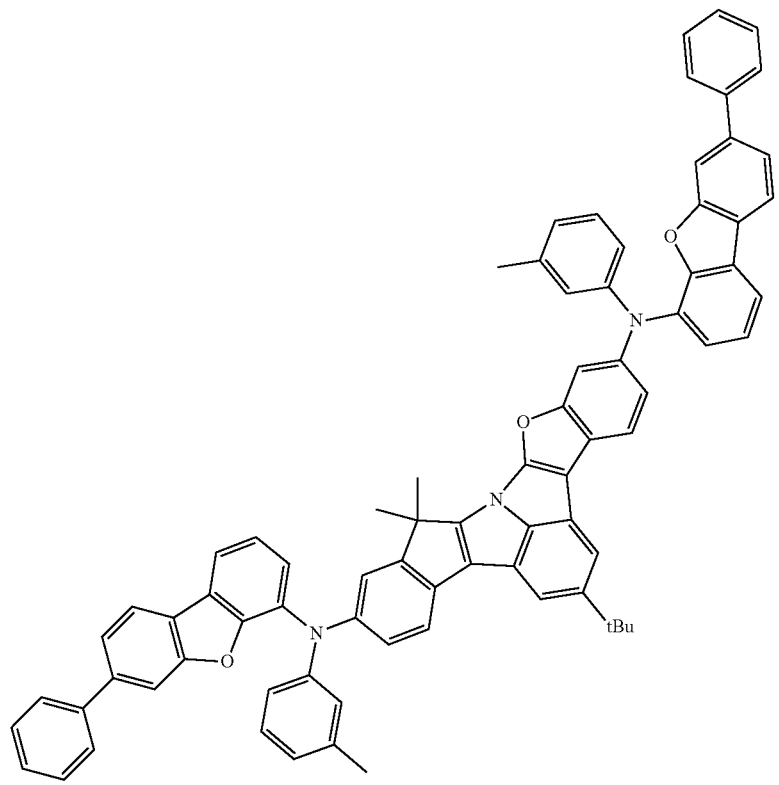
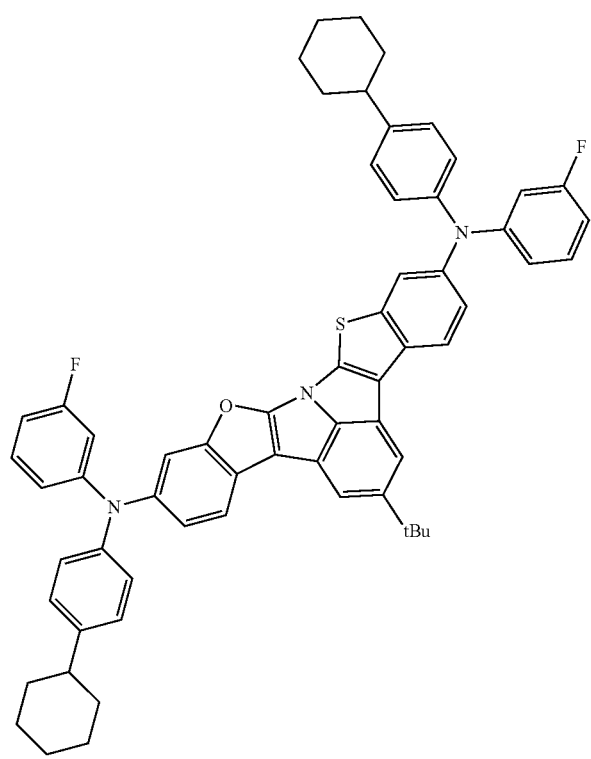

403
-continued
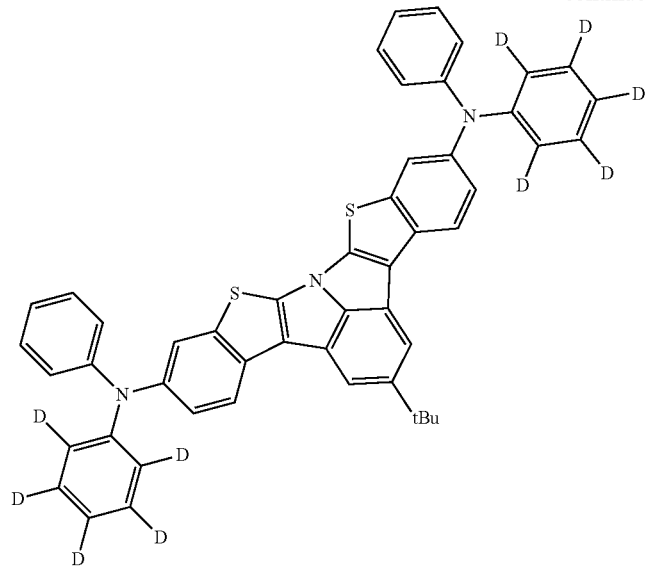
404
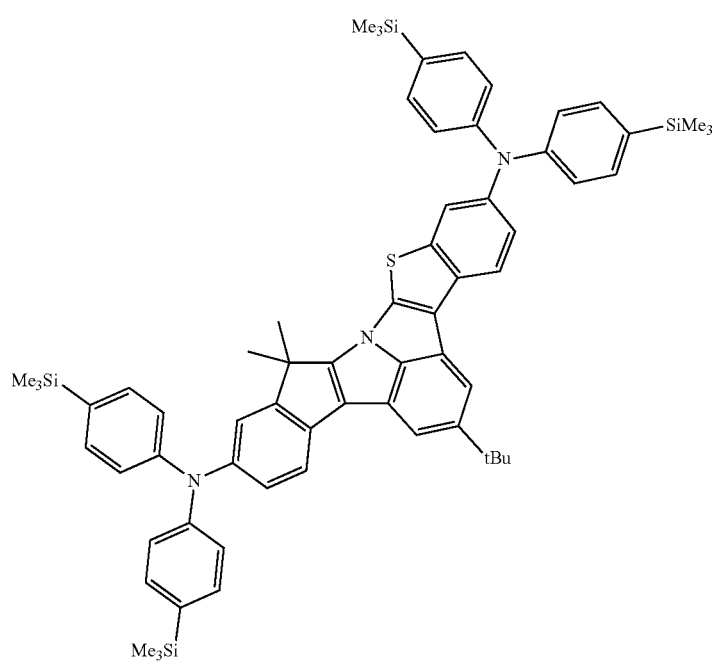

-continued
405
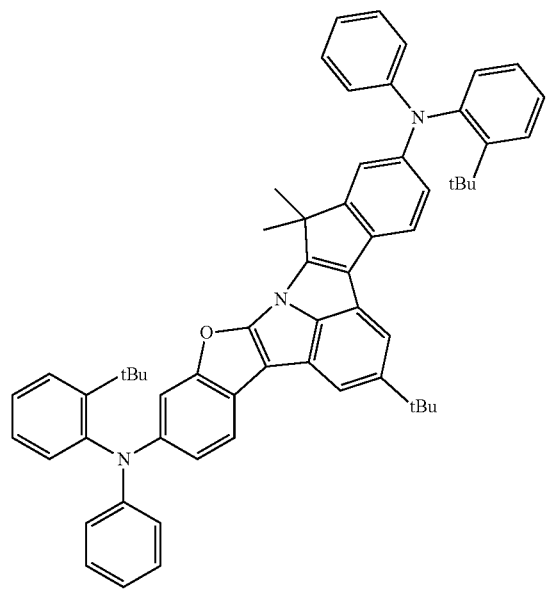
406
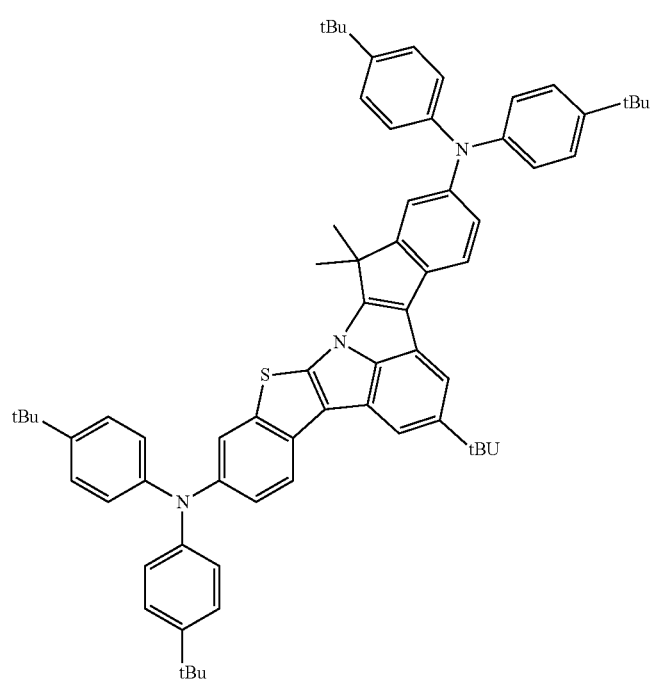

-continued
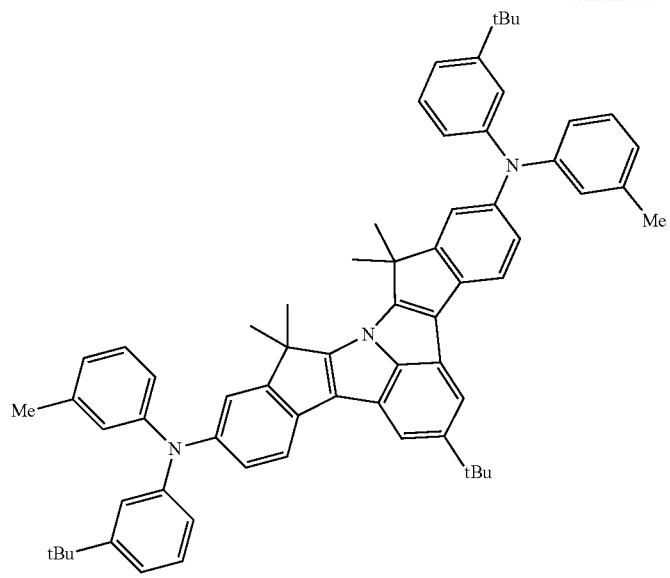
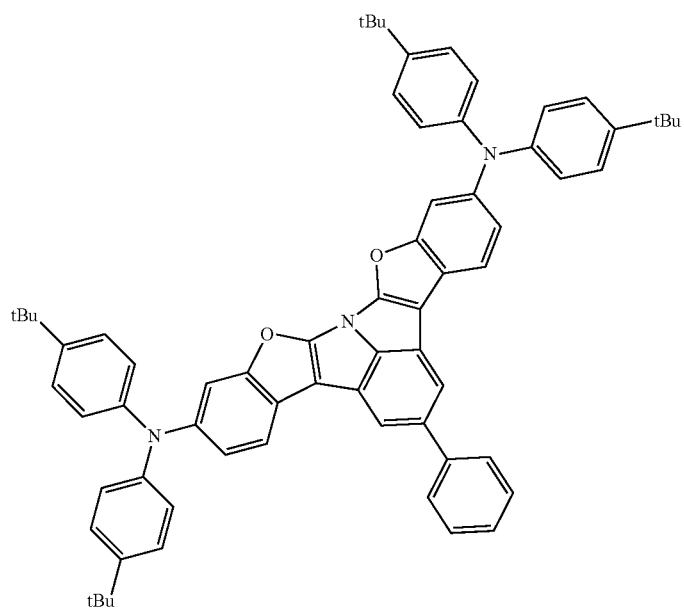

-continued
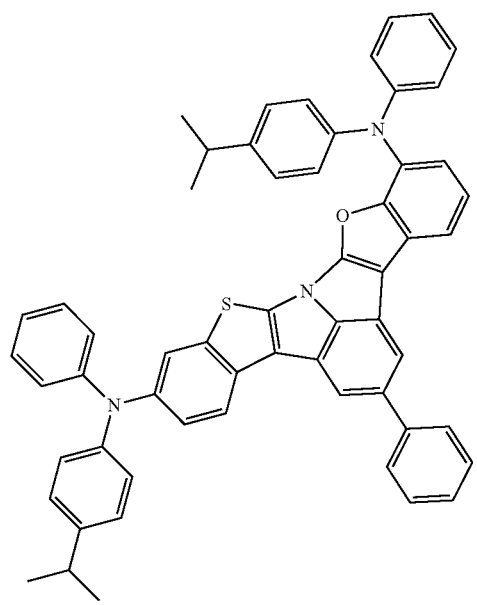
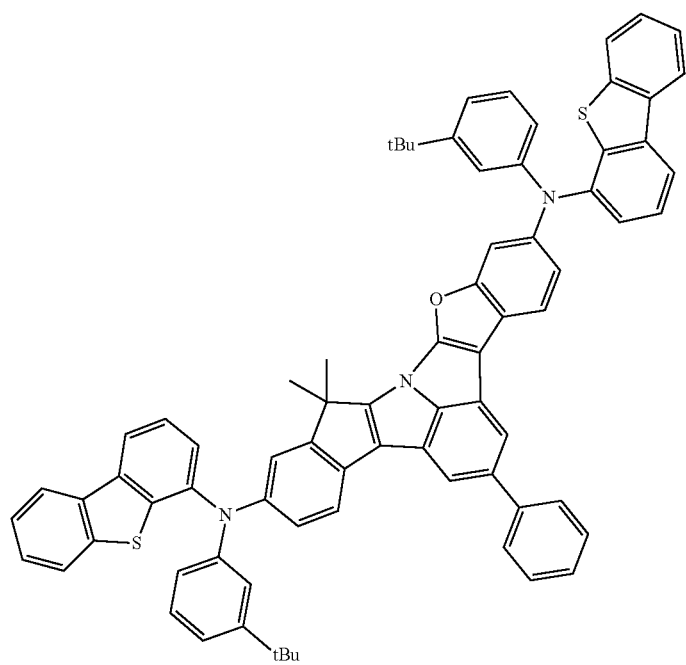

-continued
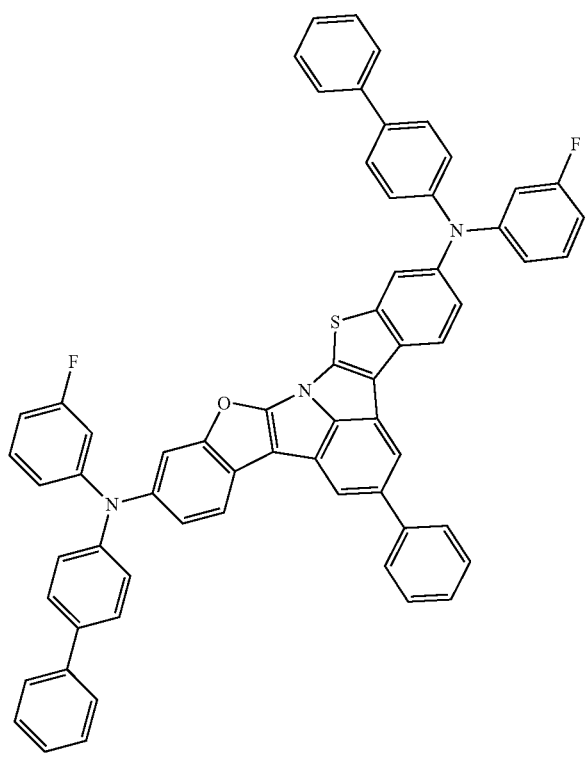
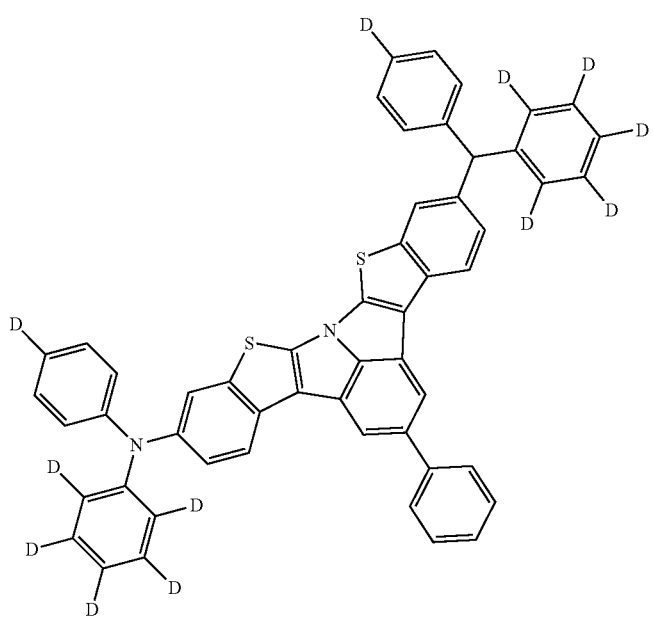

-continued
413
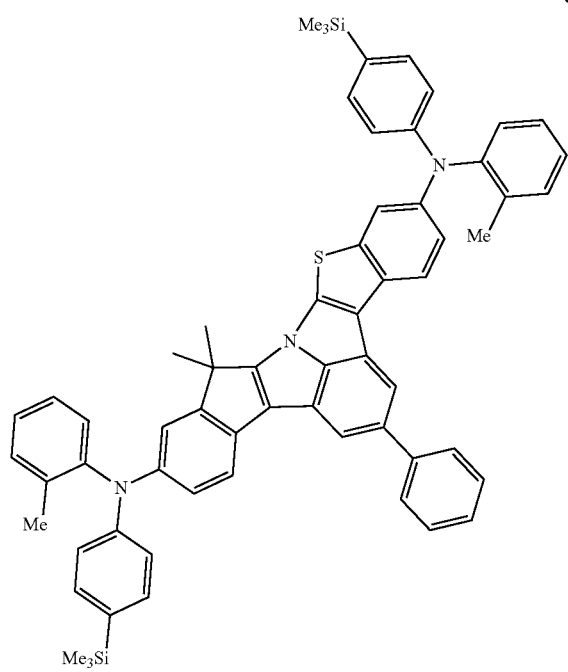
414
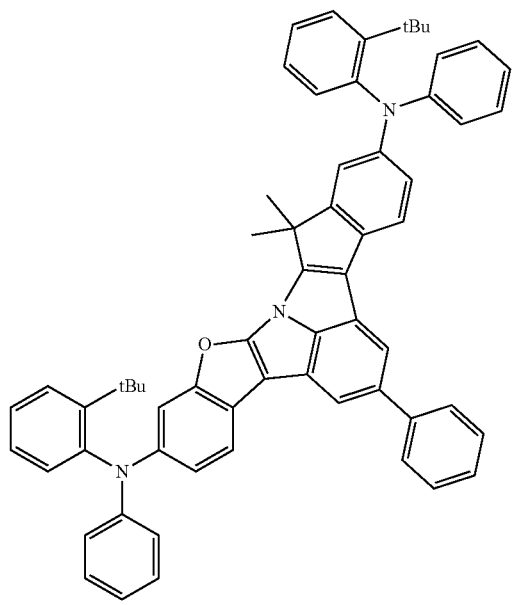
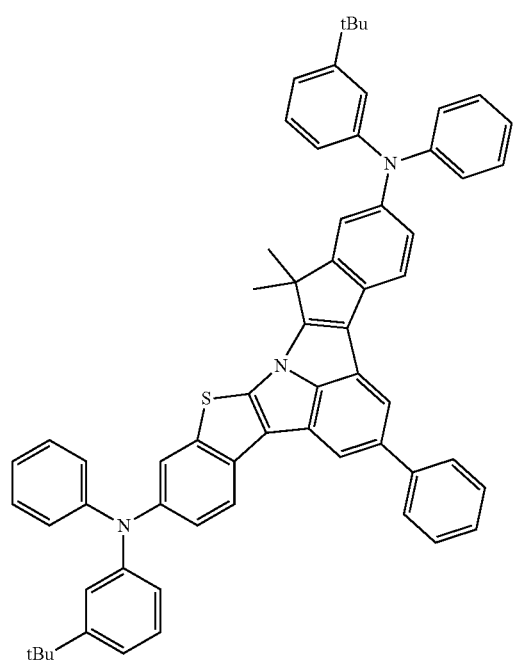

-continued
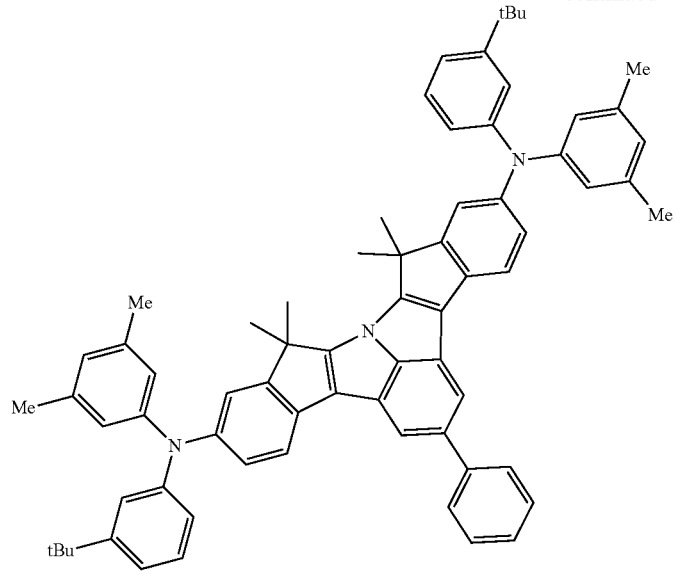 [SMILES: Cc1cc(C)cc(N(c2cccc(C(C)(C)C)c2)c2ccc3c(c2)C(C)(C)c2c-3c3cc(-c4ccccc4)cc4c5c(n2c34)C(C)(C)c2cc(N(c3cc(C)cc(C)c3)c3cccc(C(C)(C)C)c3)ccc2-5)c1]
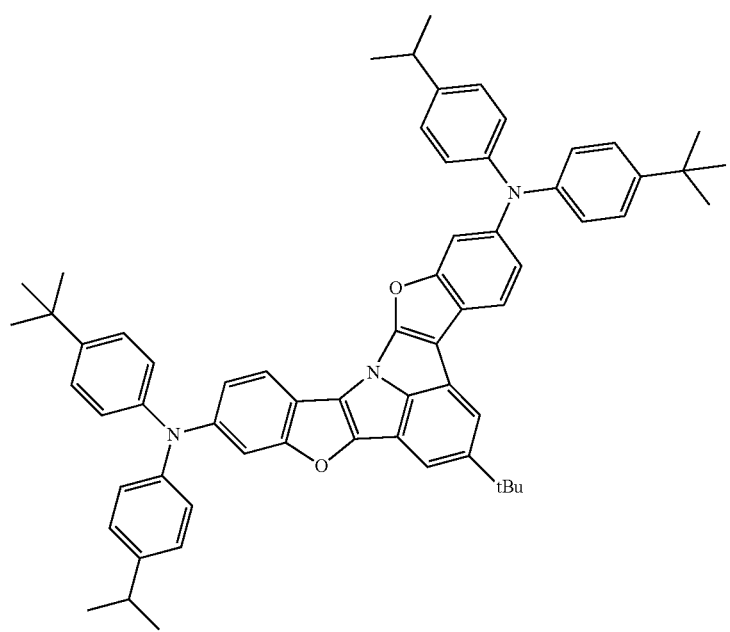

-continued
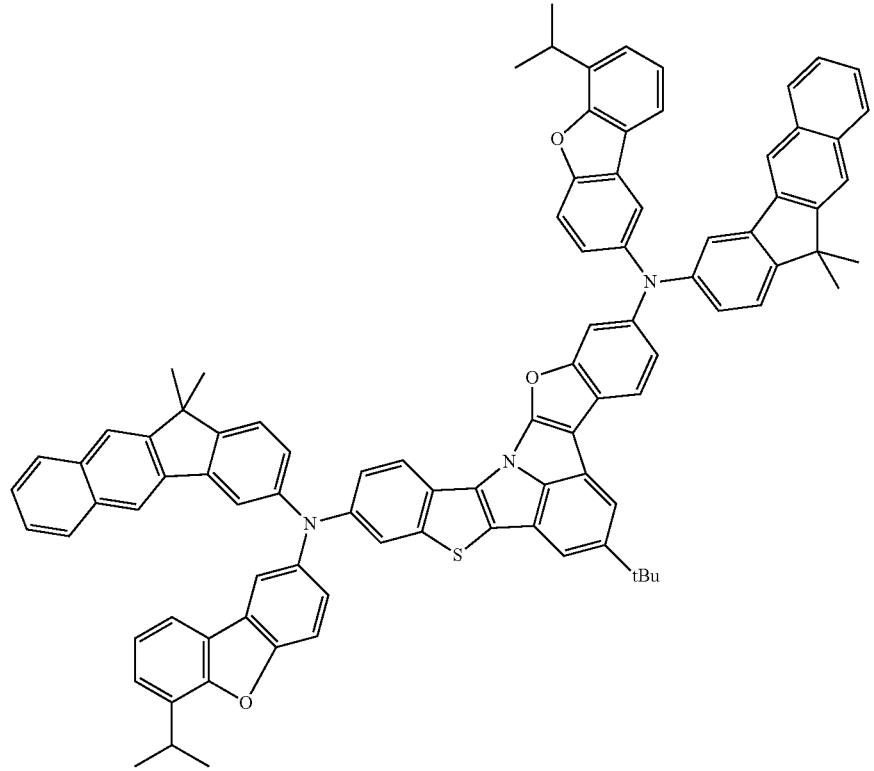
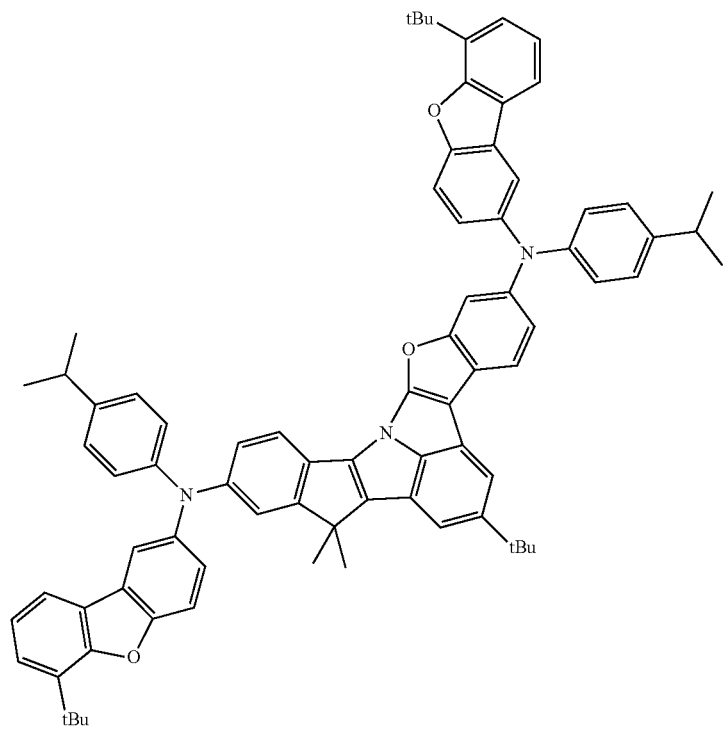

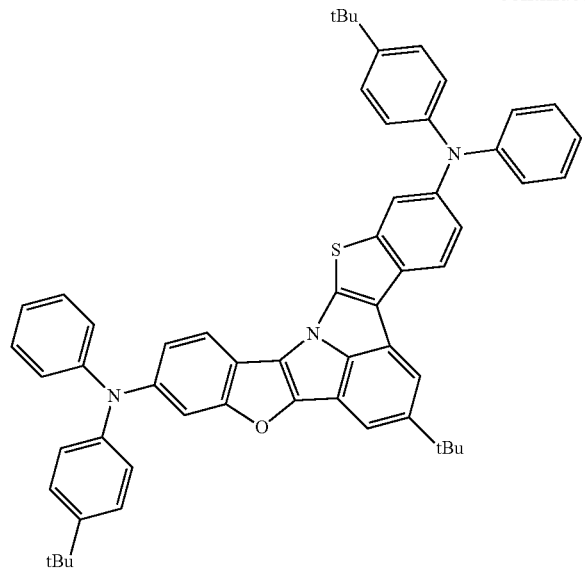
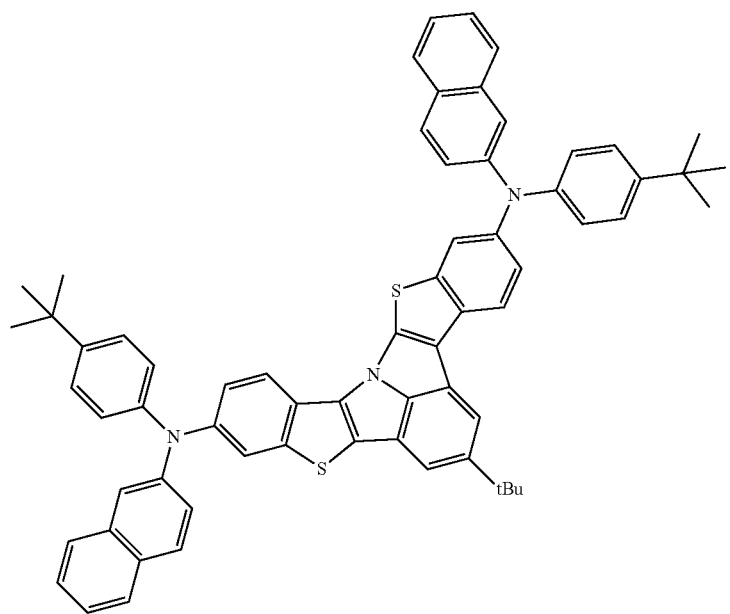

-continued
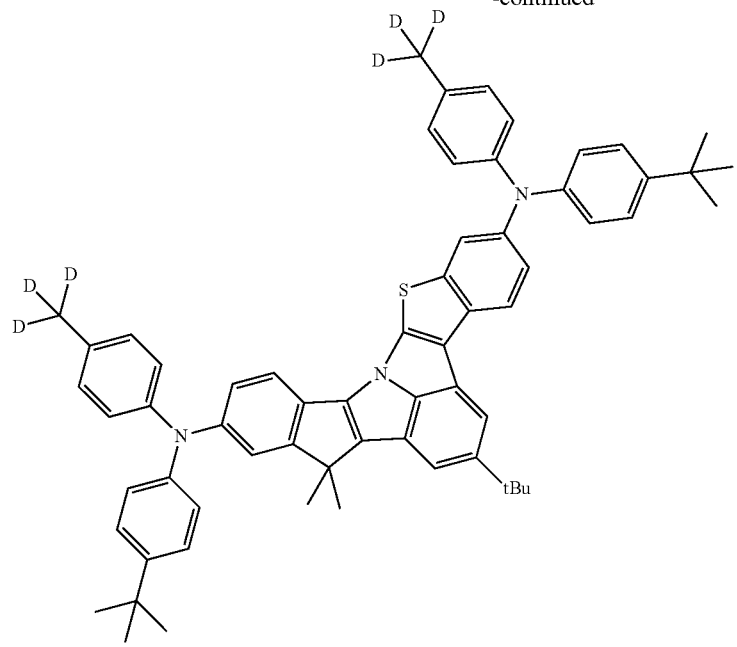
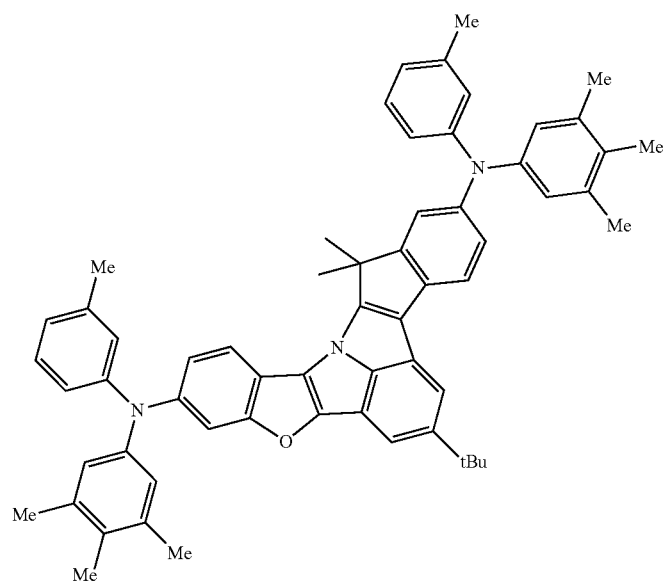

-continued
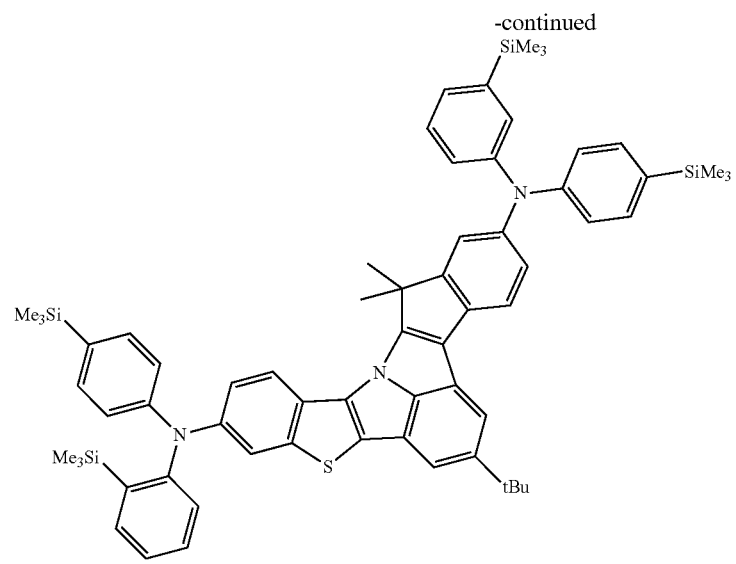
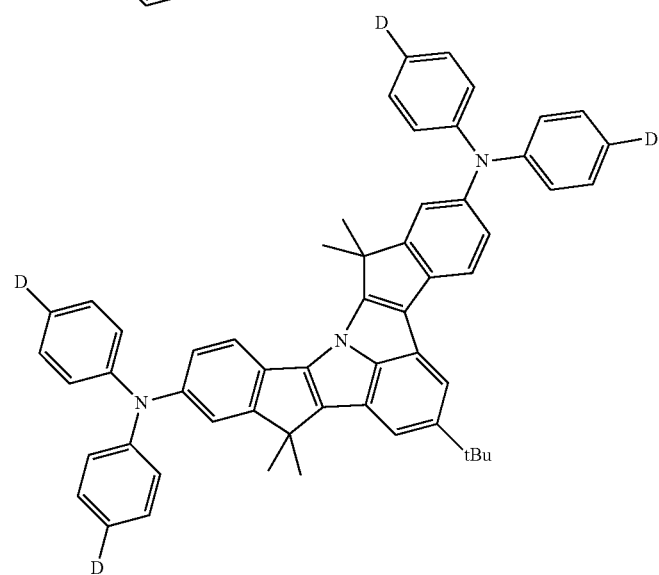
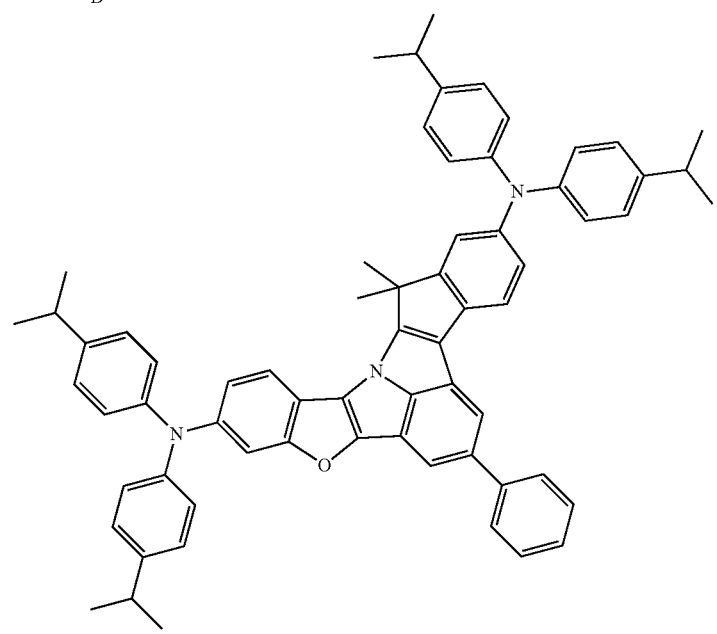

-continued
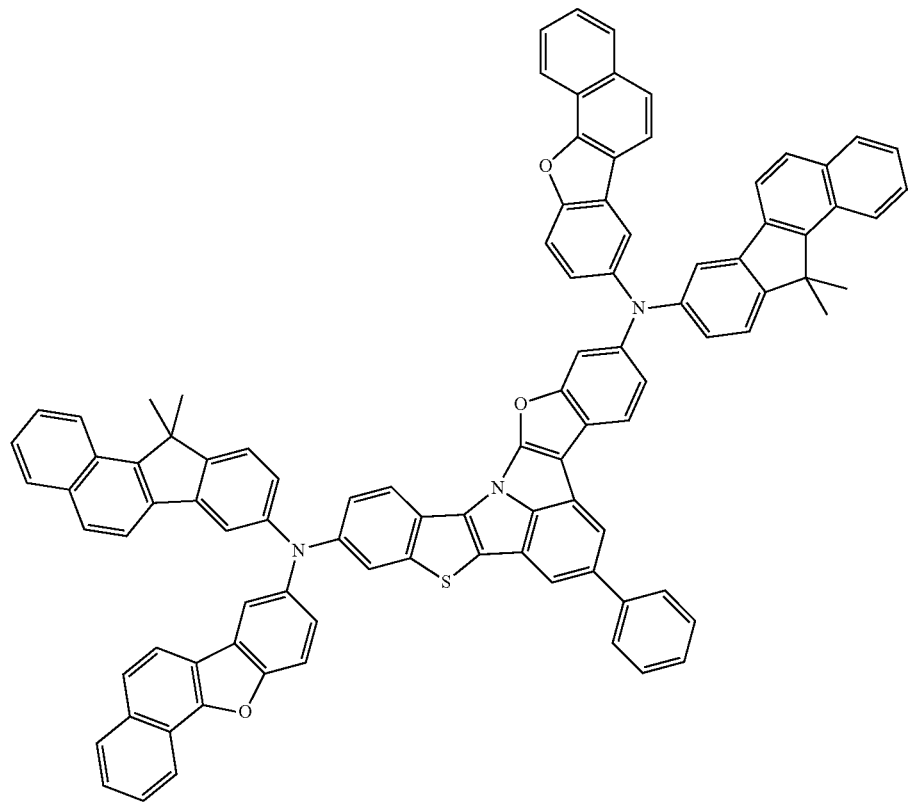
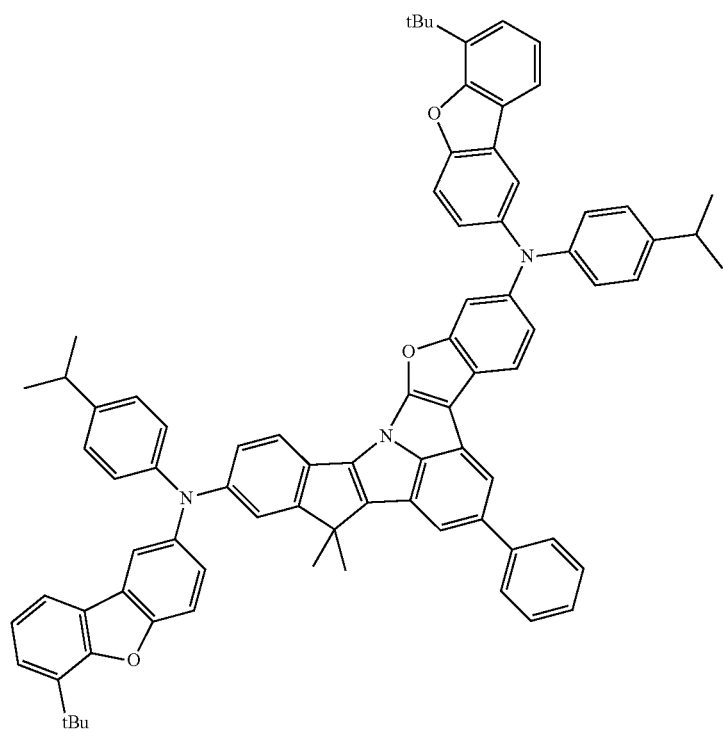

-continued
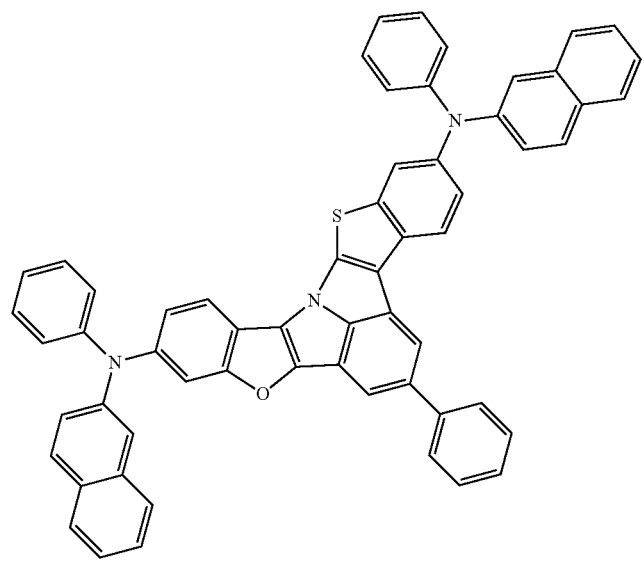
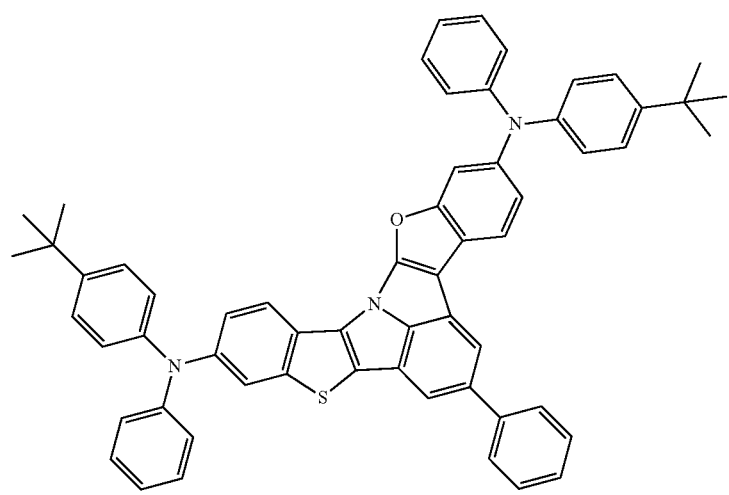
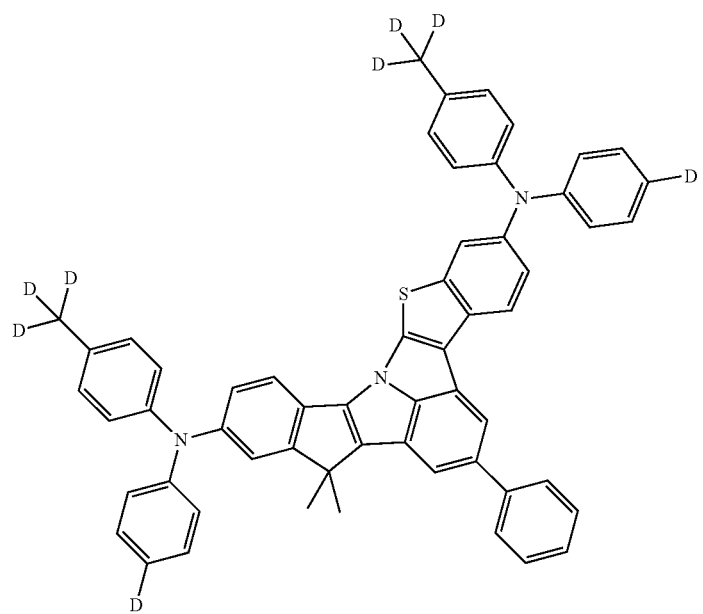

-continued
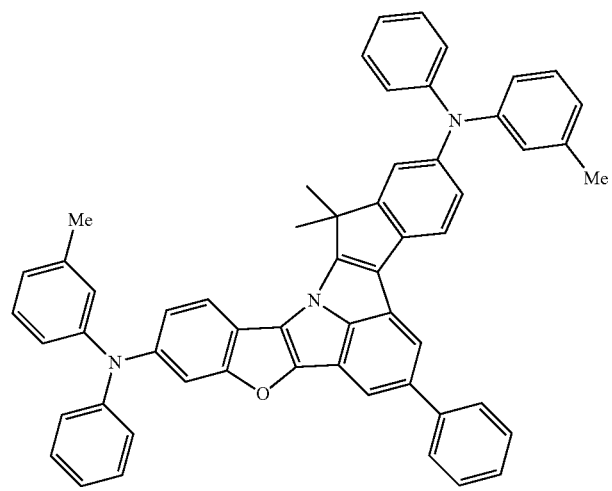
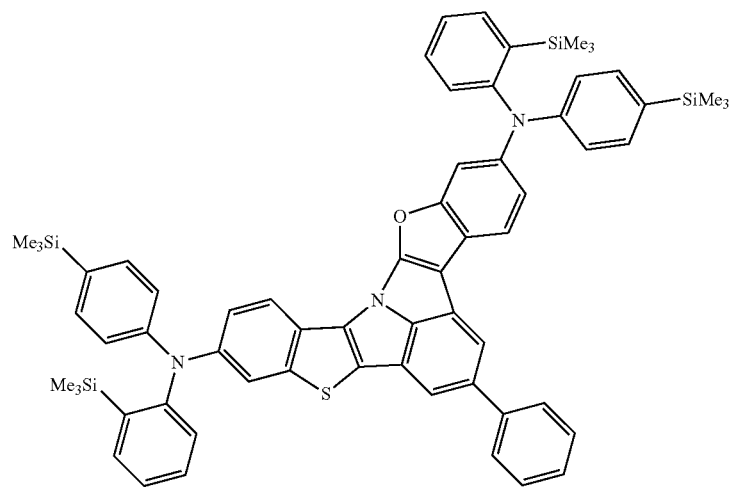
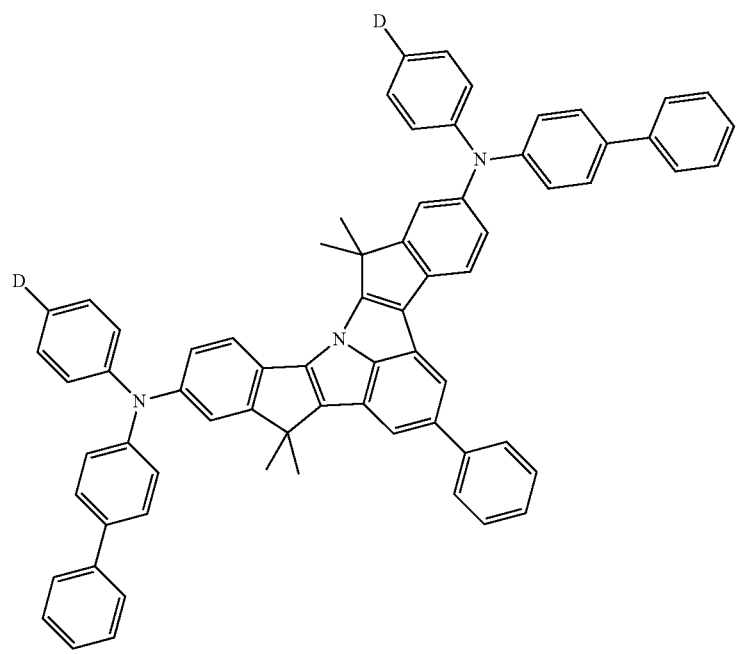

-continued
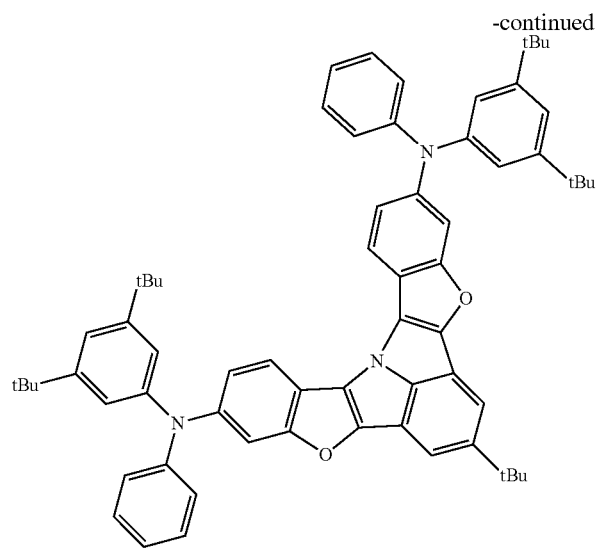
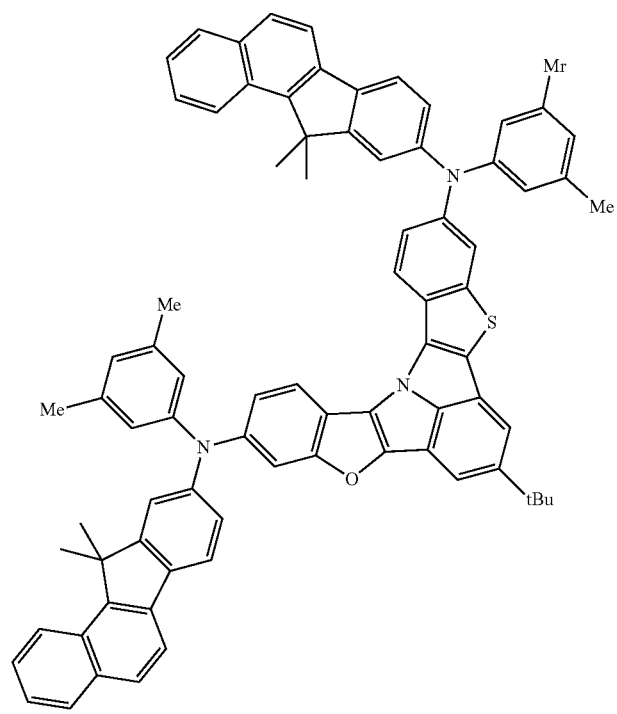

-continued
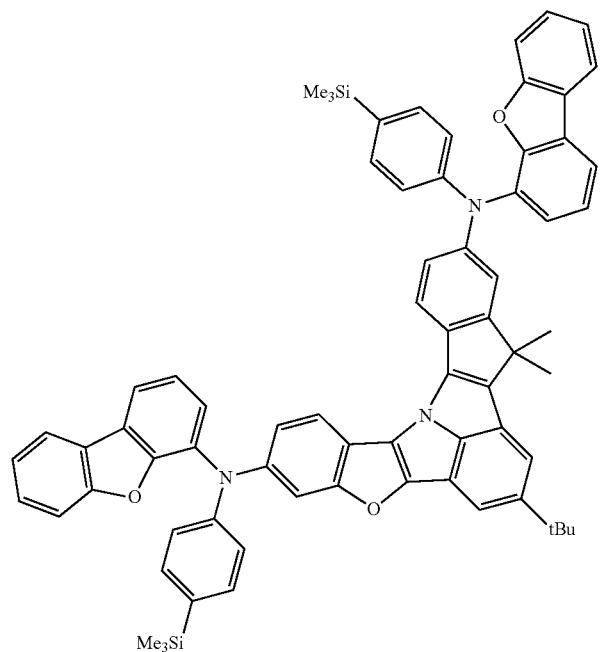
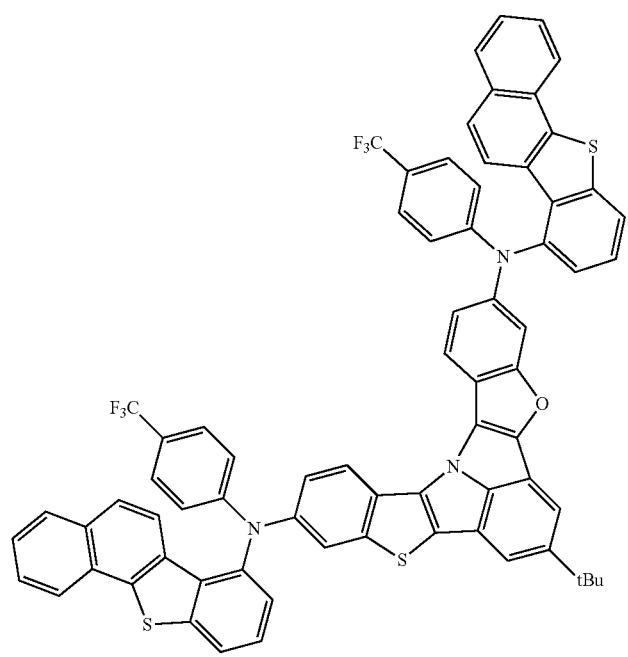

-continued
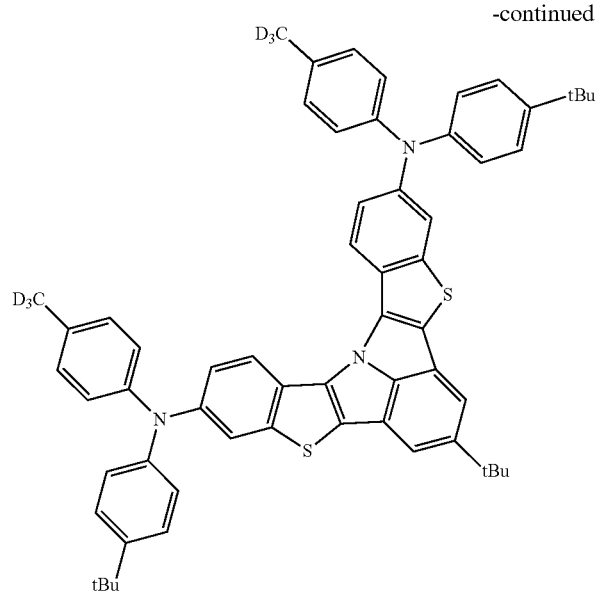
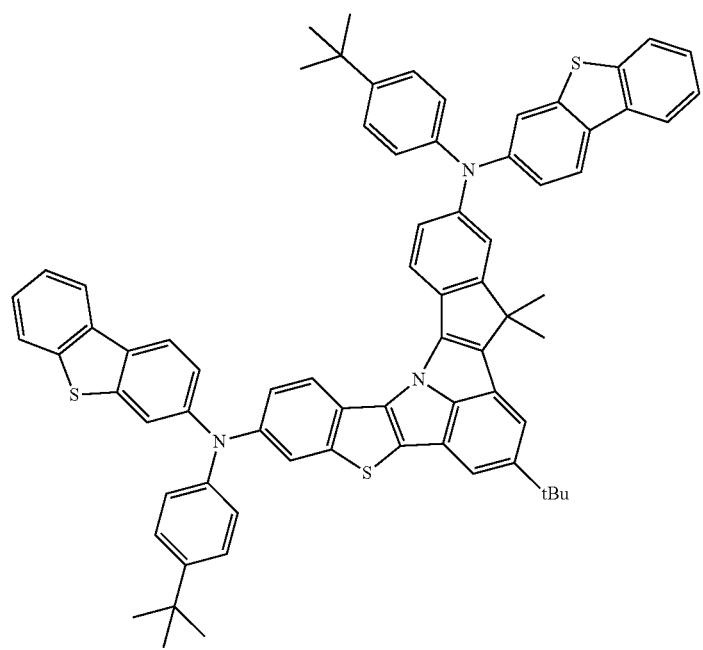

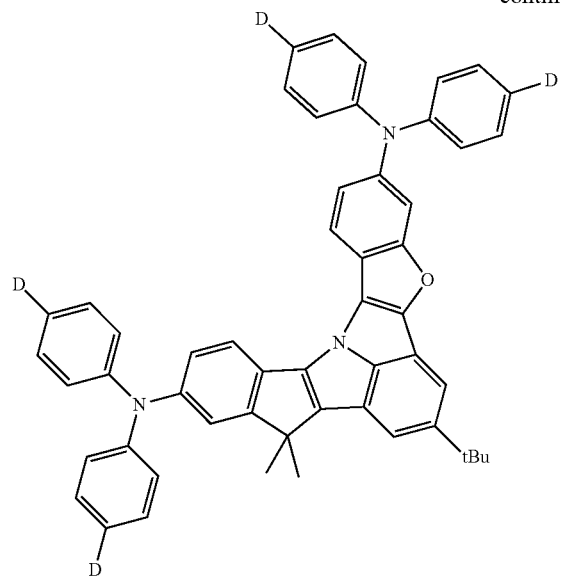
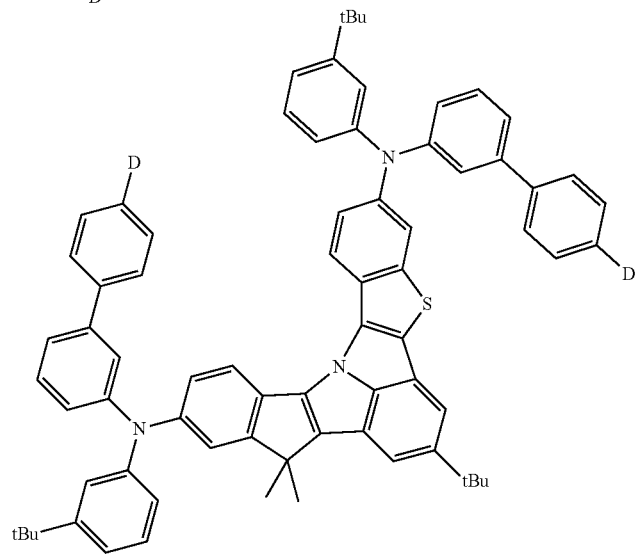
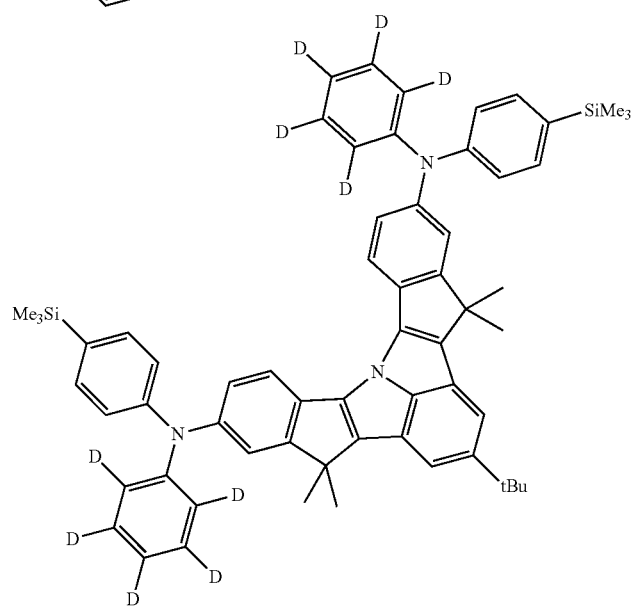

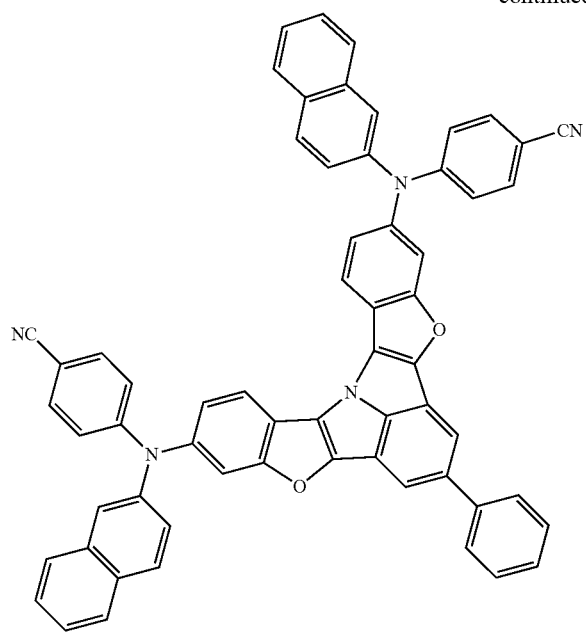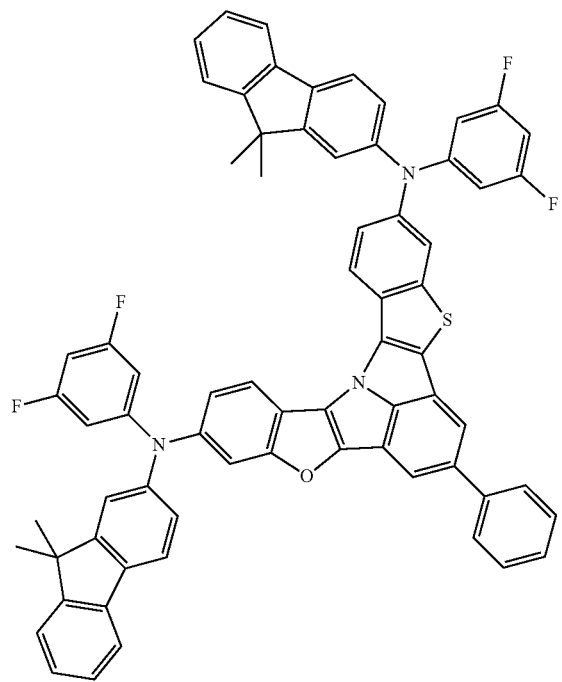

-continued
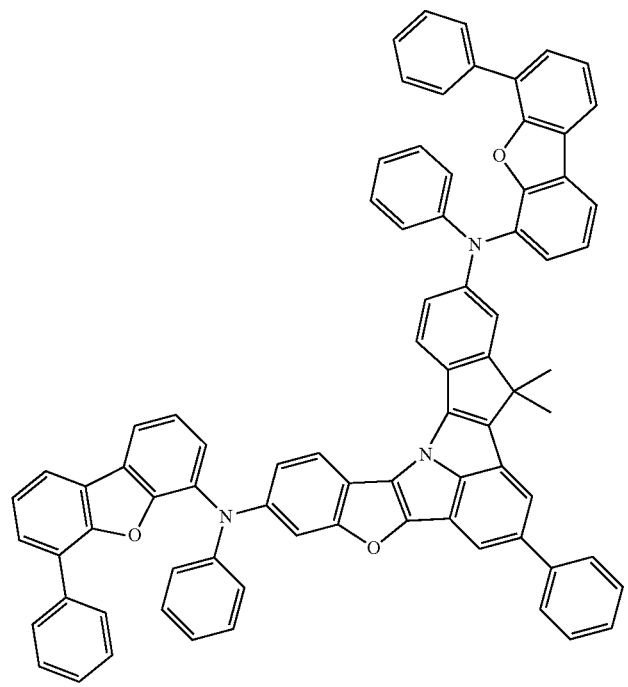
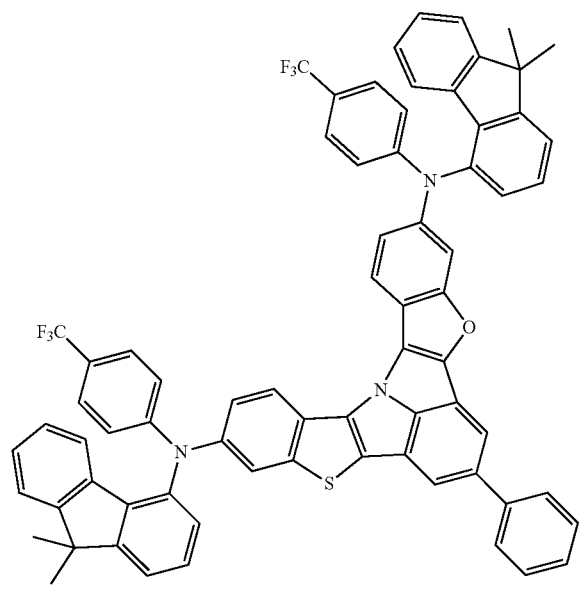

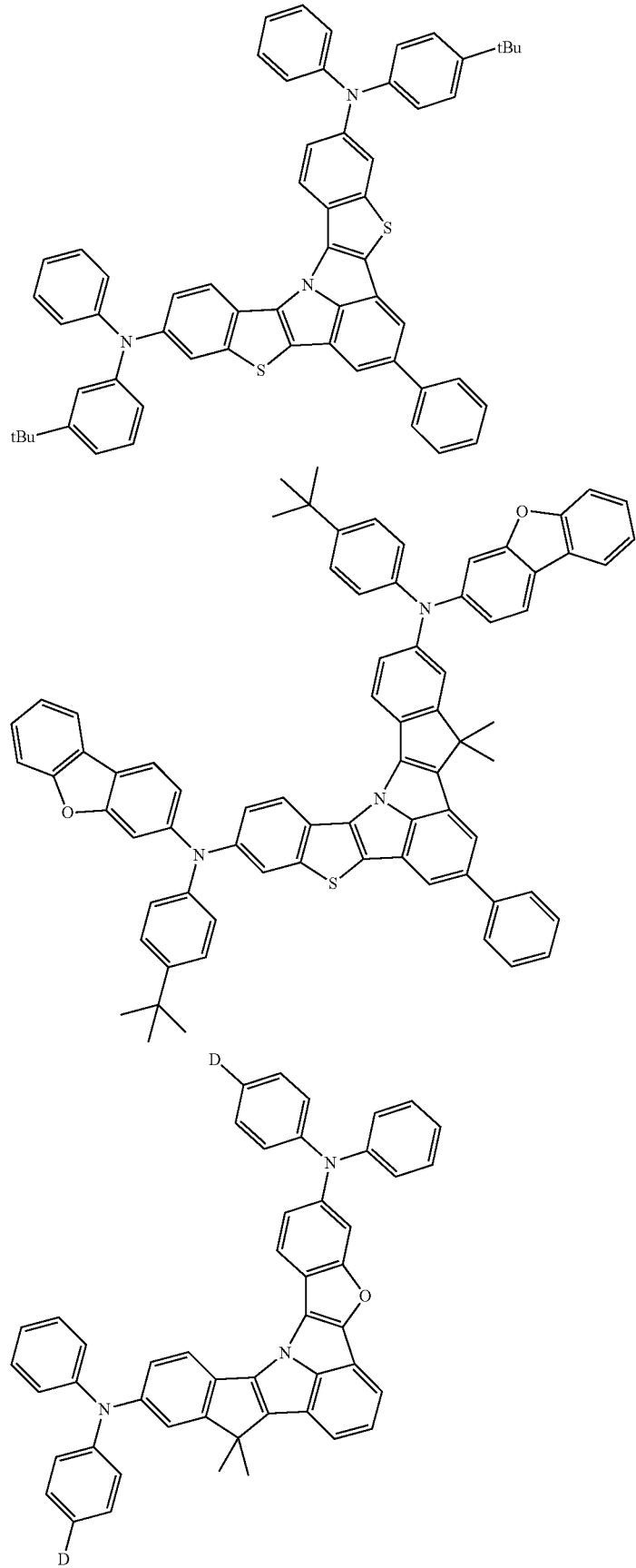

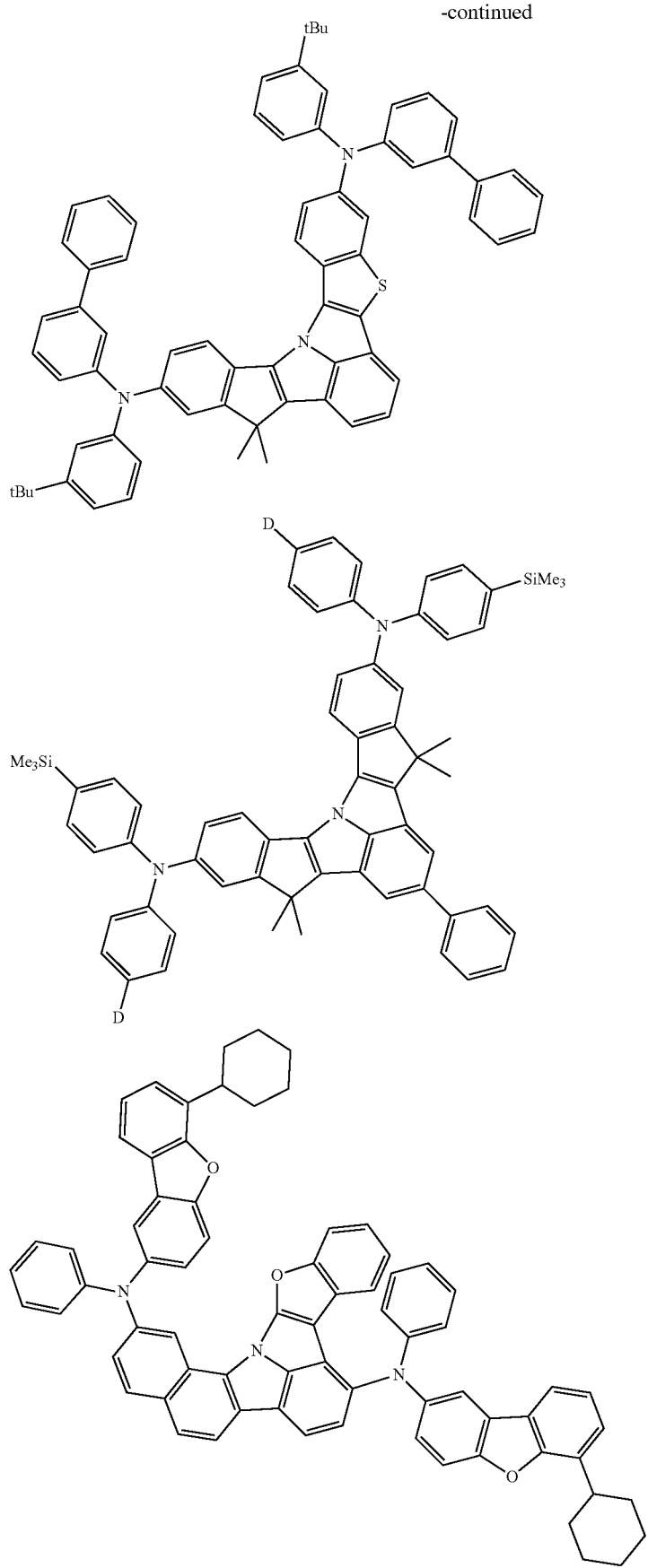

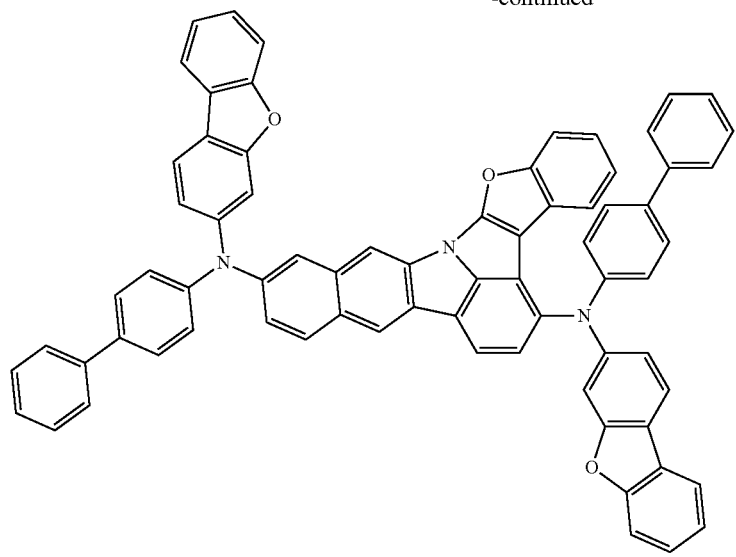
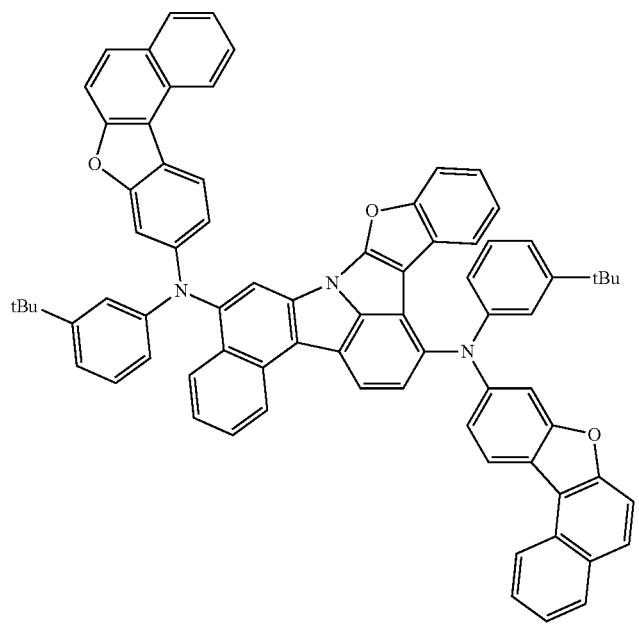
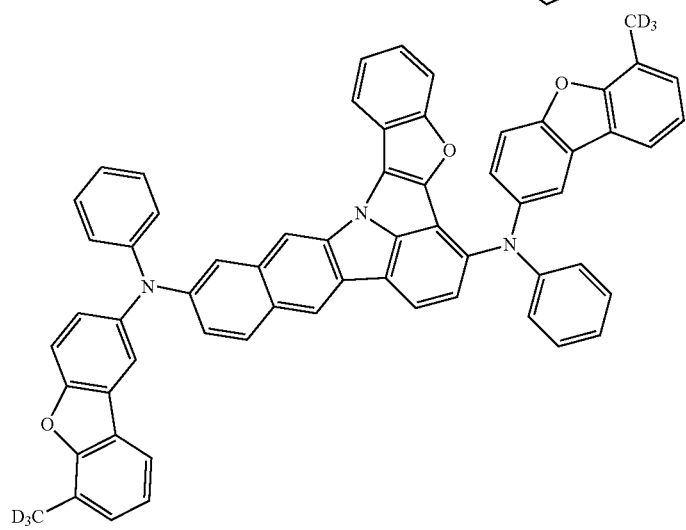

-continued
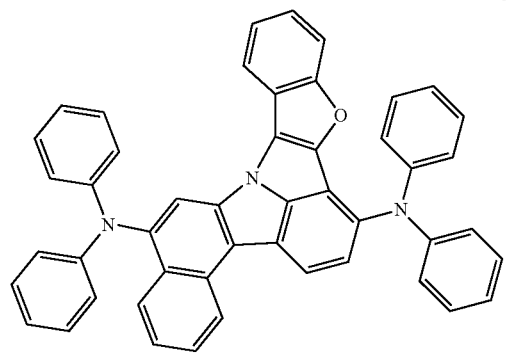
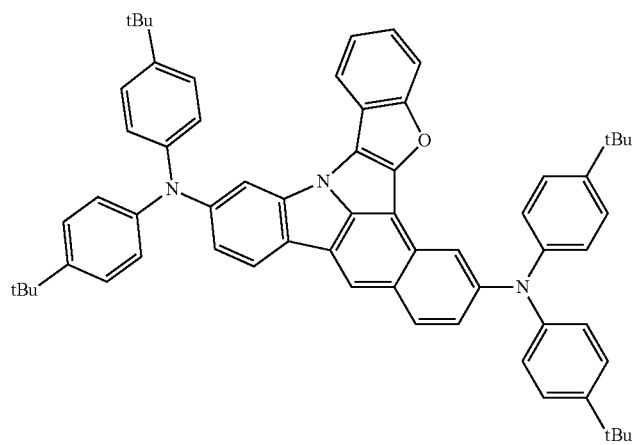
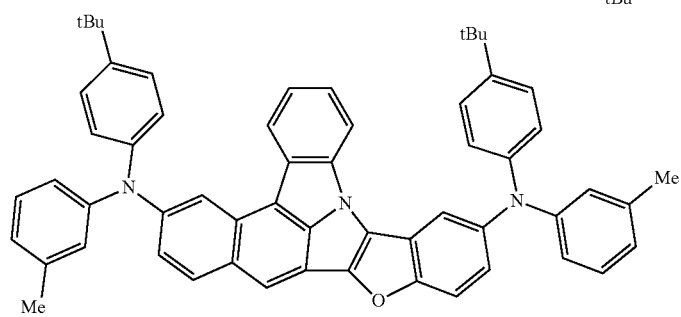
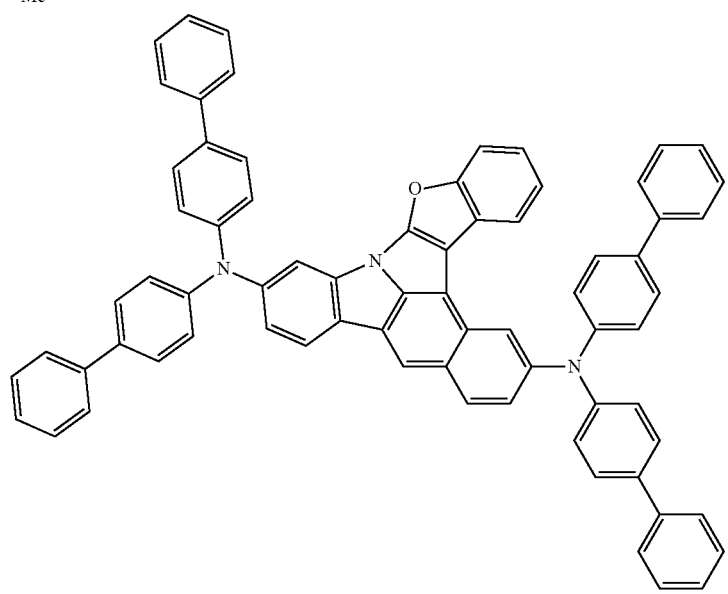

-continued
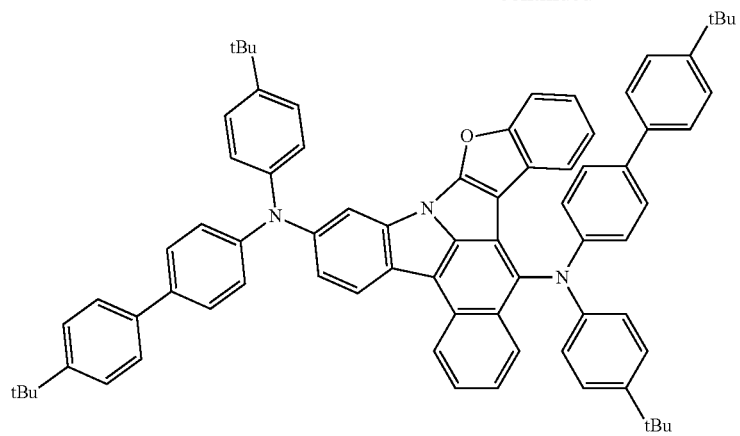
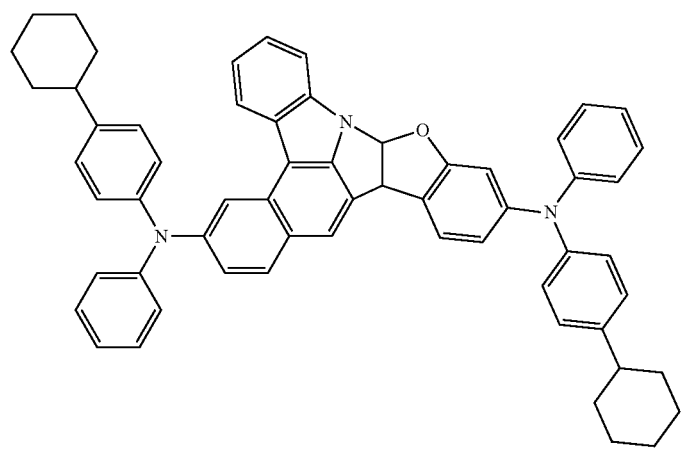
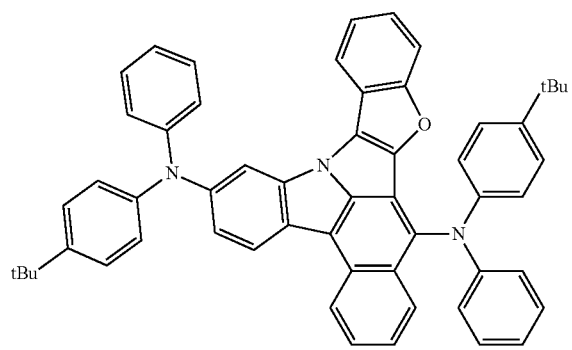
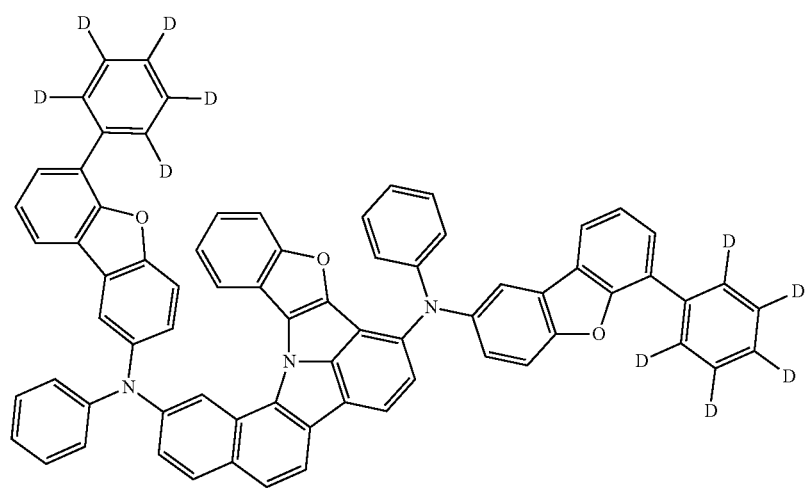

-continued
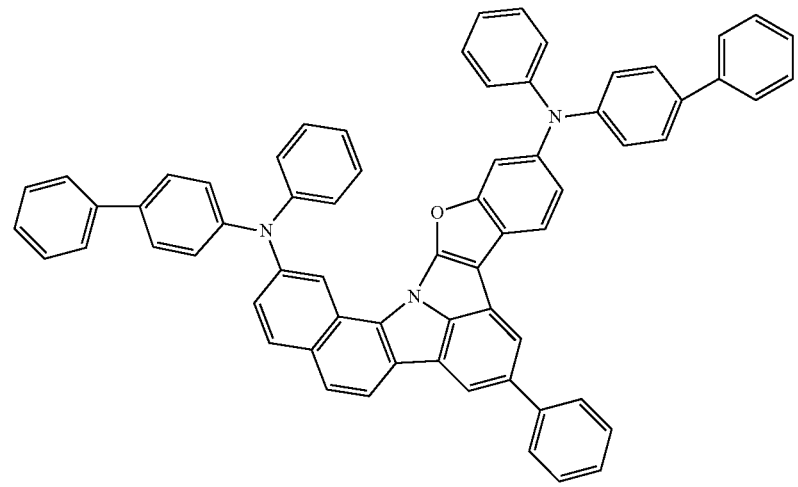
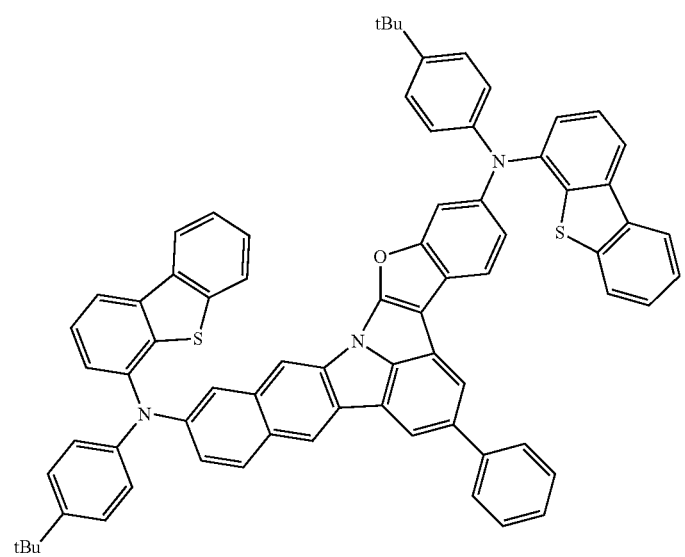
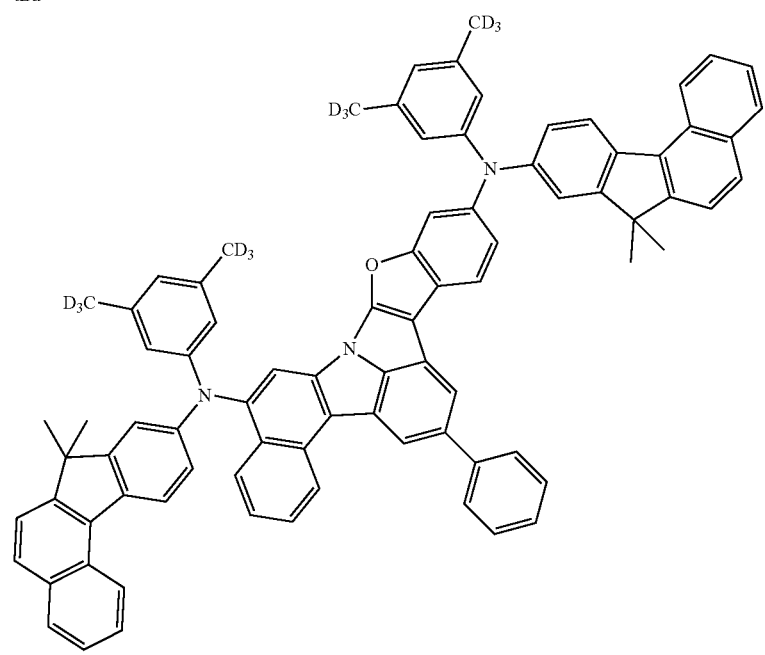

-continued
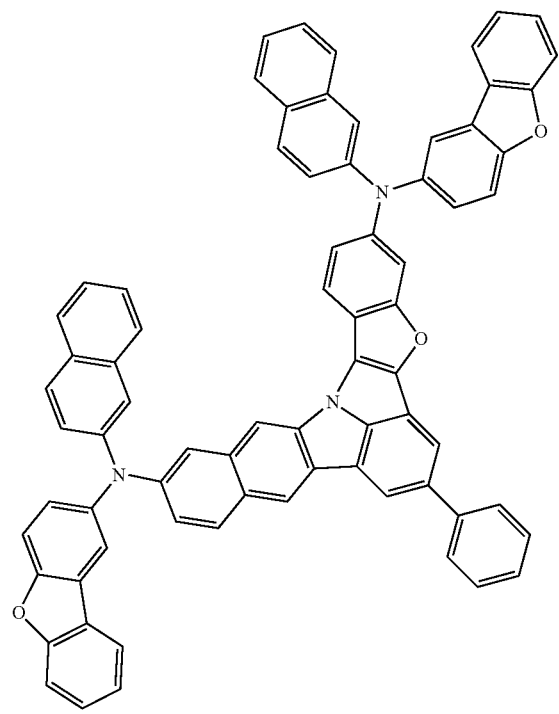
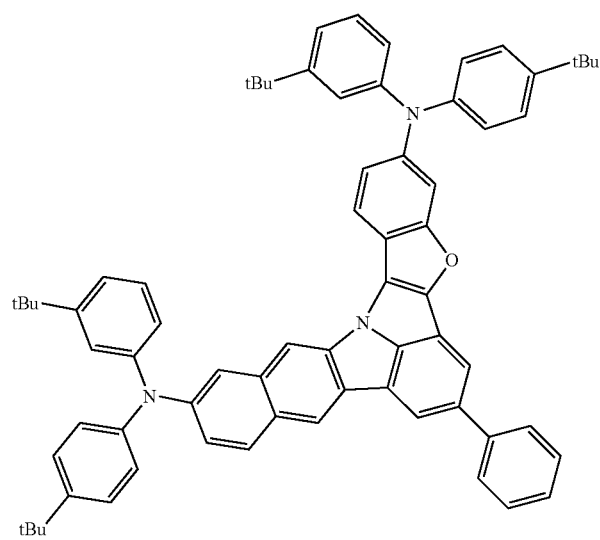

-continued
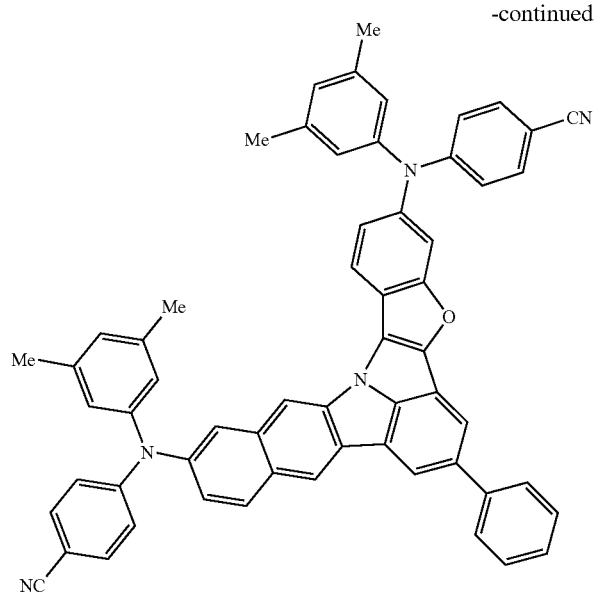
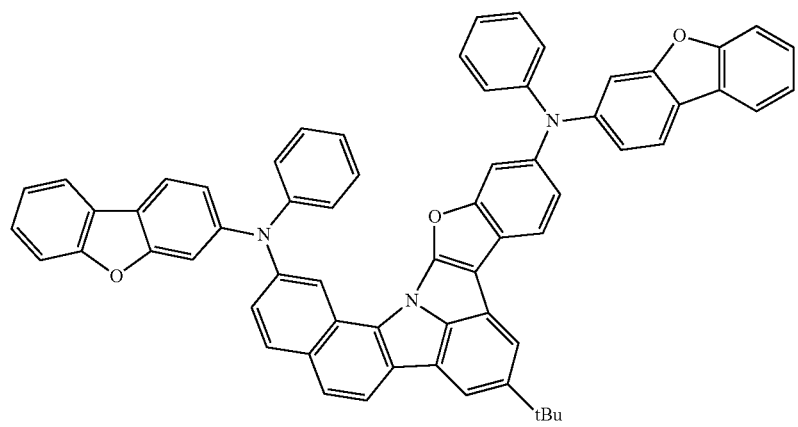
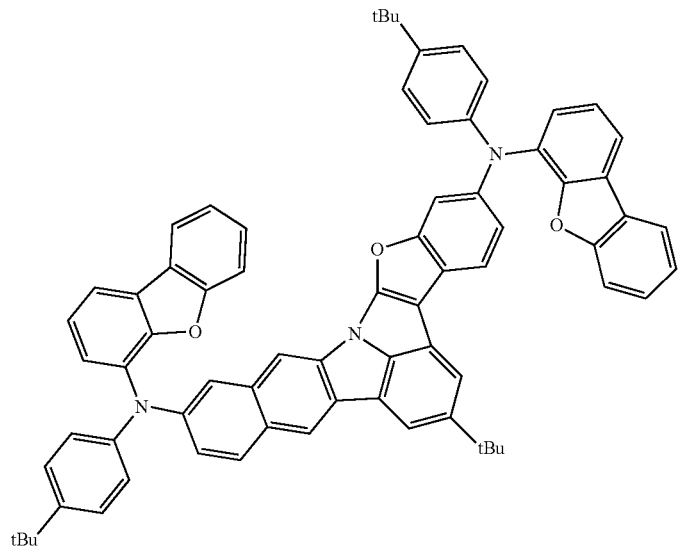

-continued
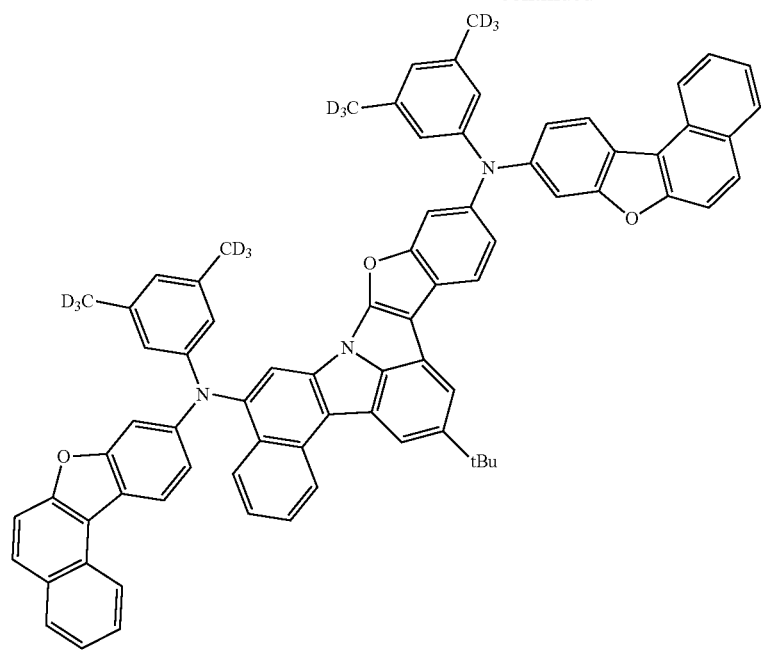
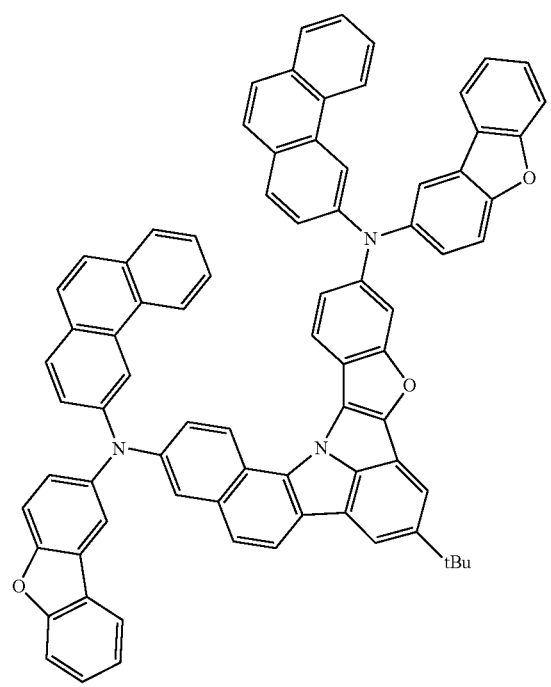

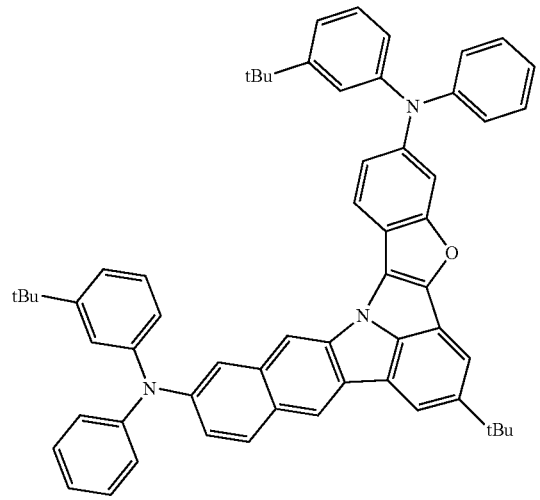
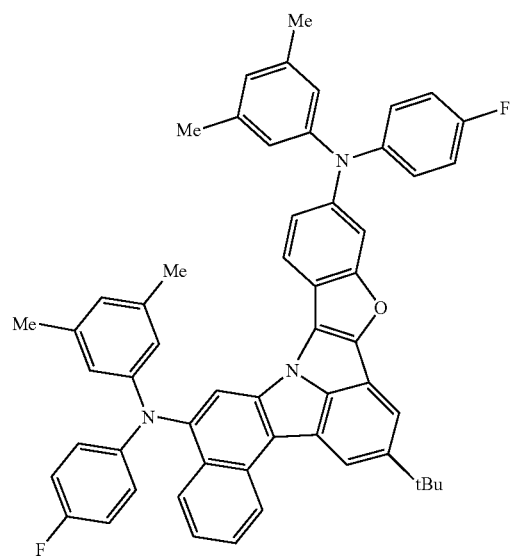
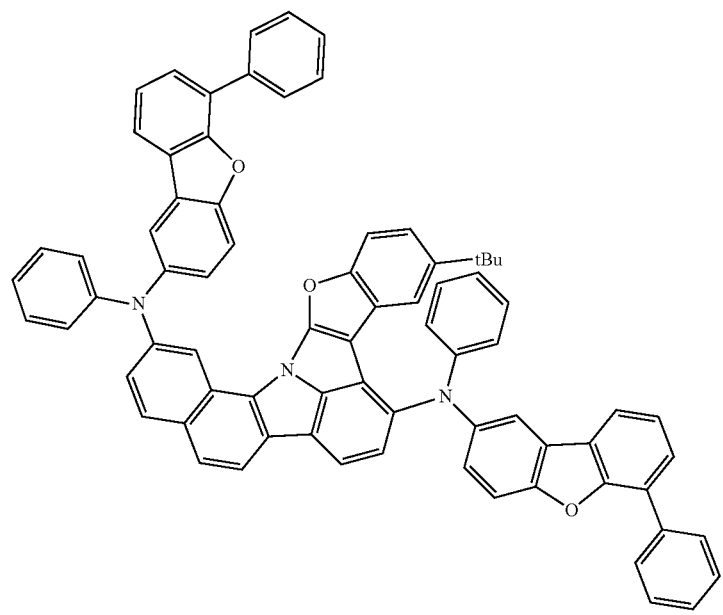

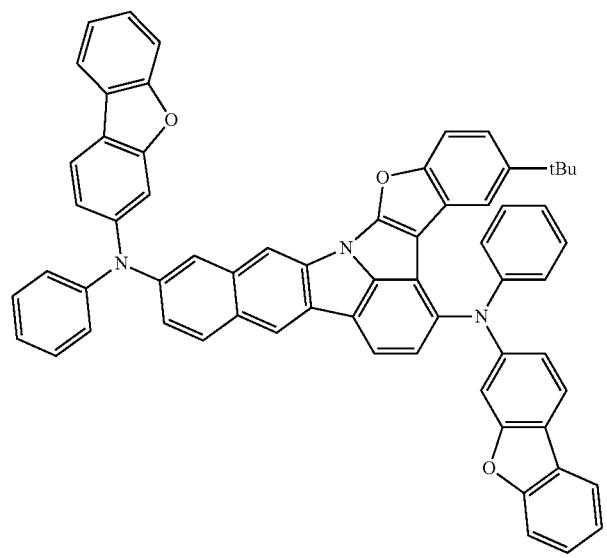
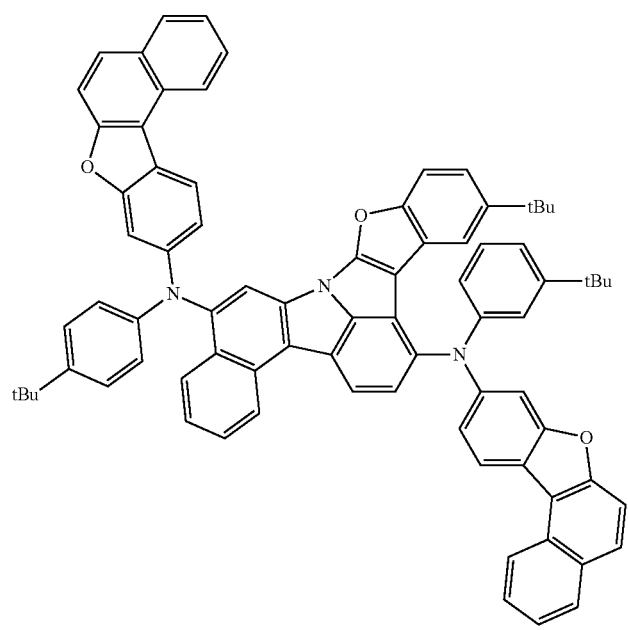

-continued
465
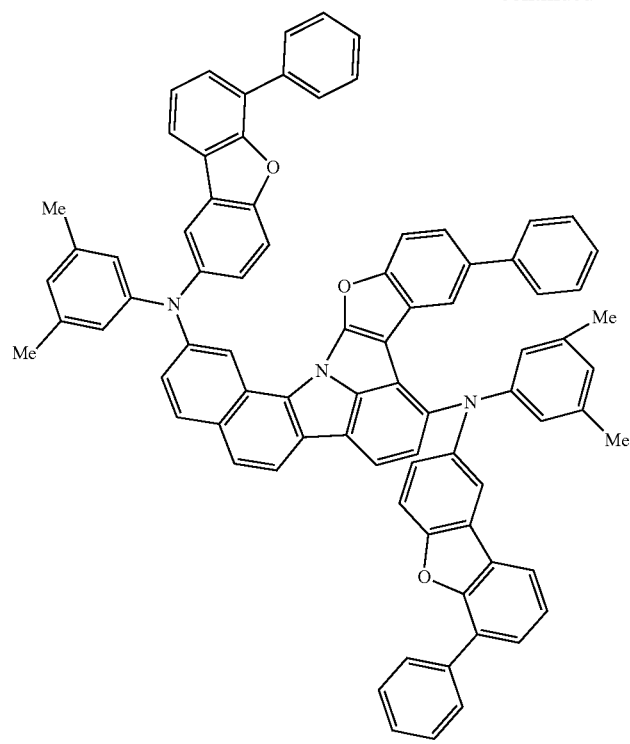
466
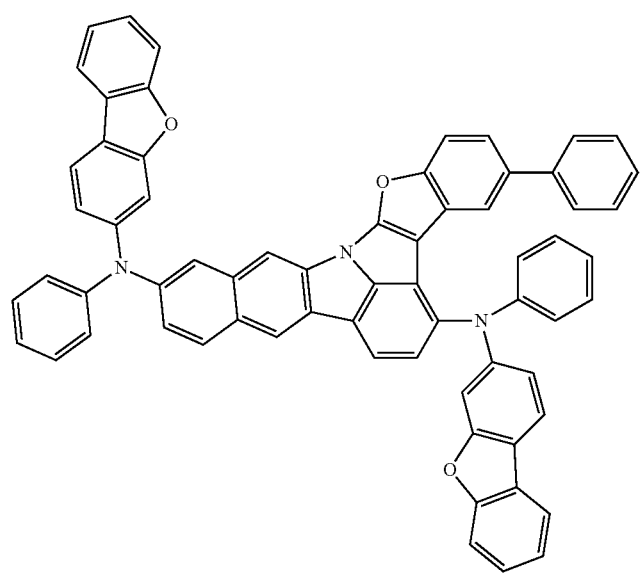

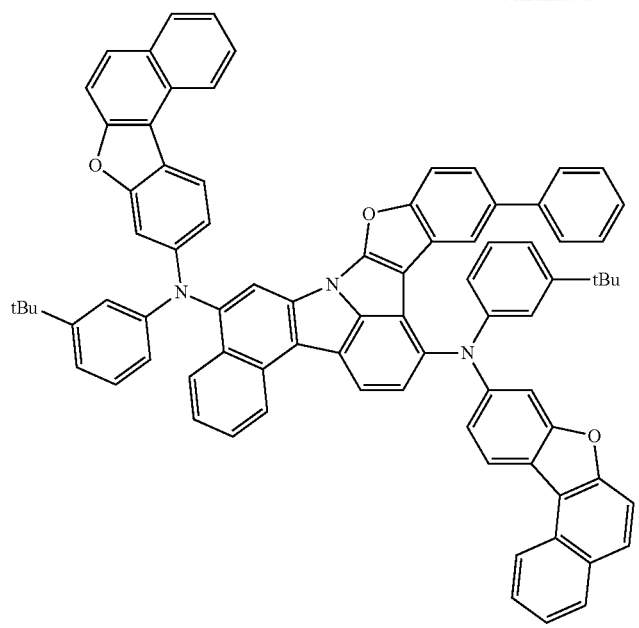
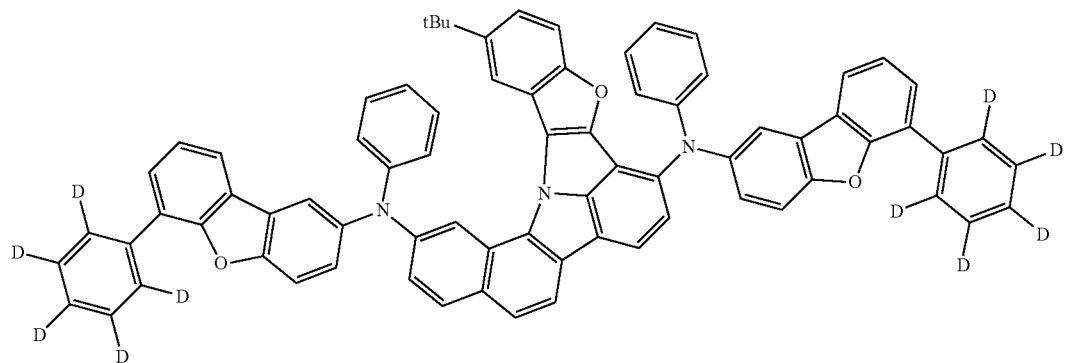
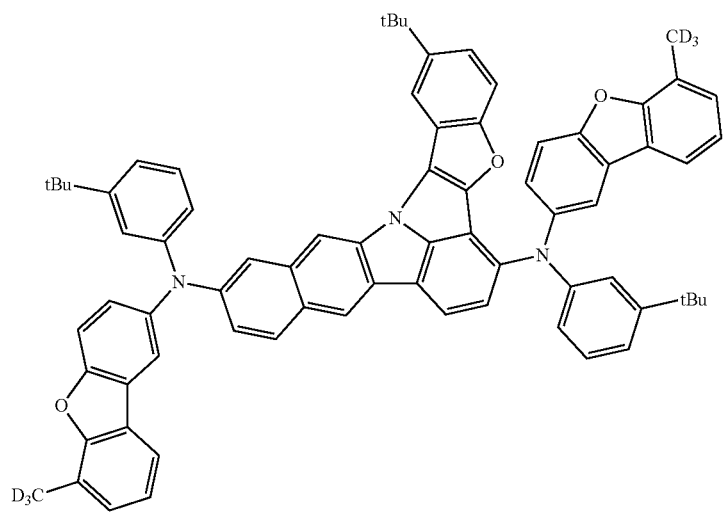

-continued
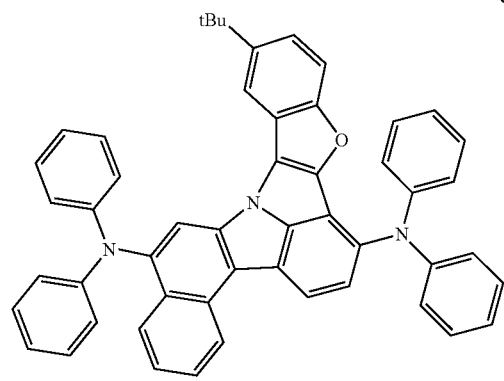
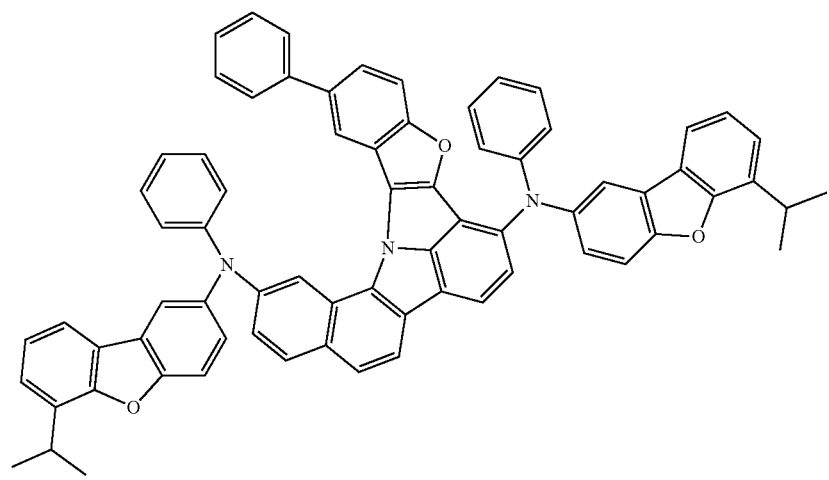 [SMILES: CC(C)c1cccc2c1oc1ccc(N(c3ccccc3)c3ccc4ccc5c6ccc(N(c7ccccc7)c7ccc8oc9c(C(C)C)cccc9c8c7)c7c8oc9ccc(-c%10ccccc%10)cc9c8n(c5c4c3)c67)cc12]
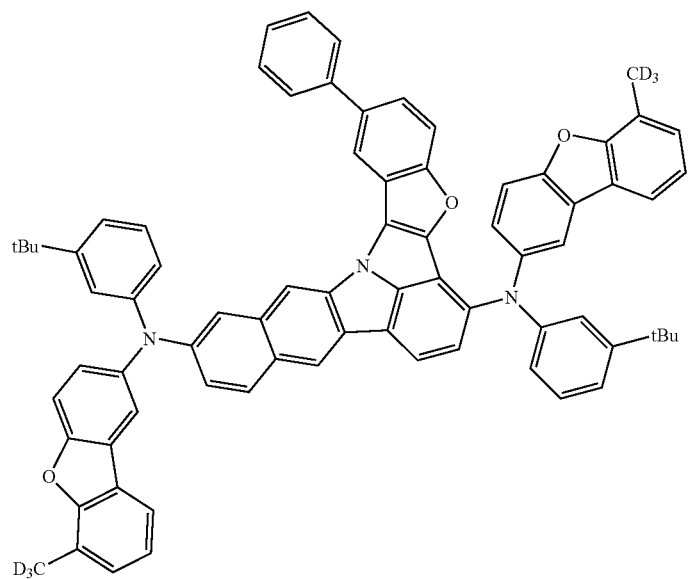

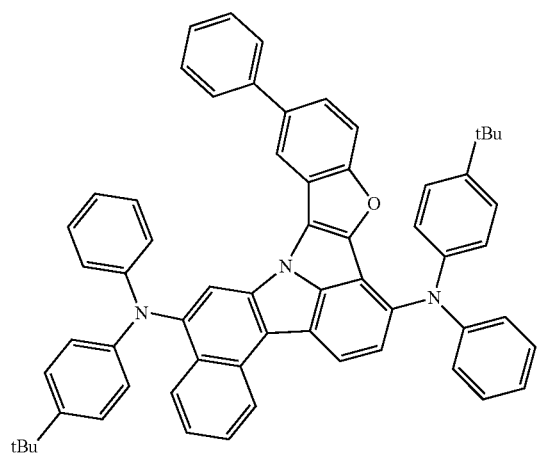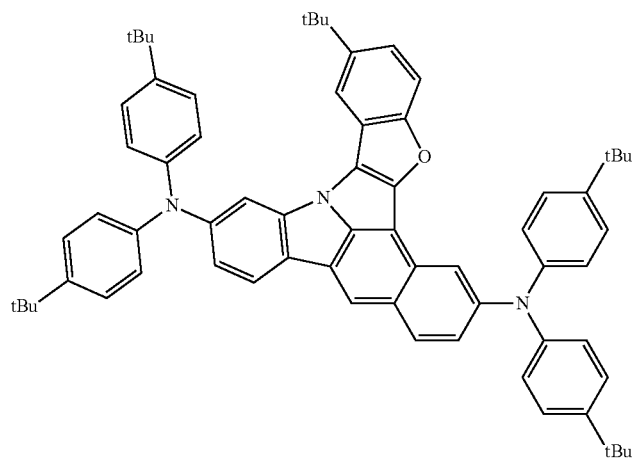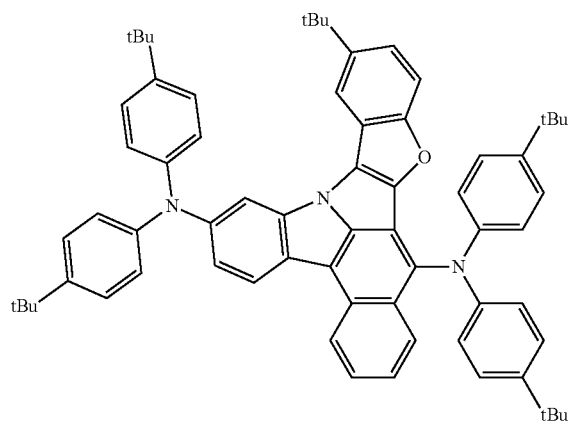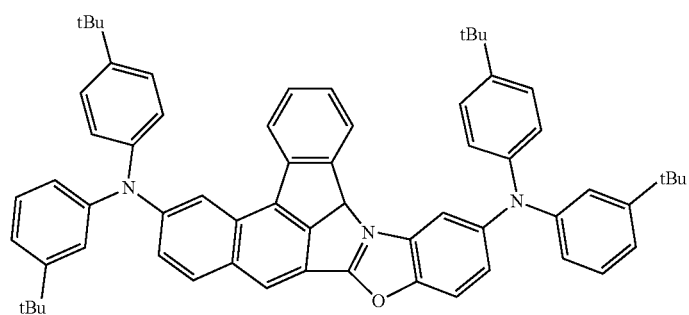

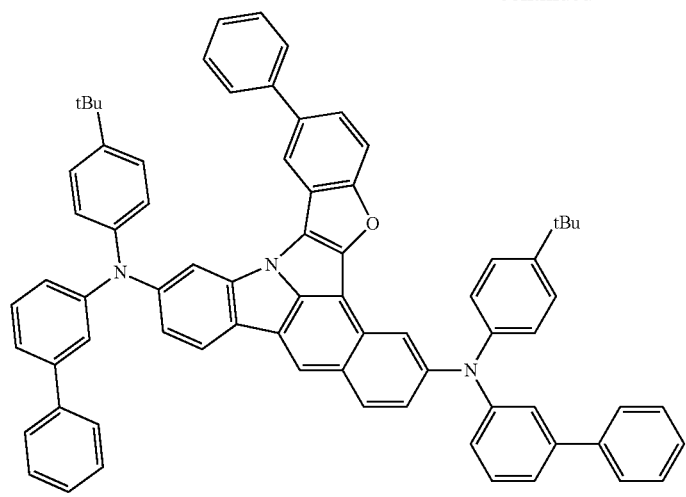
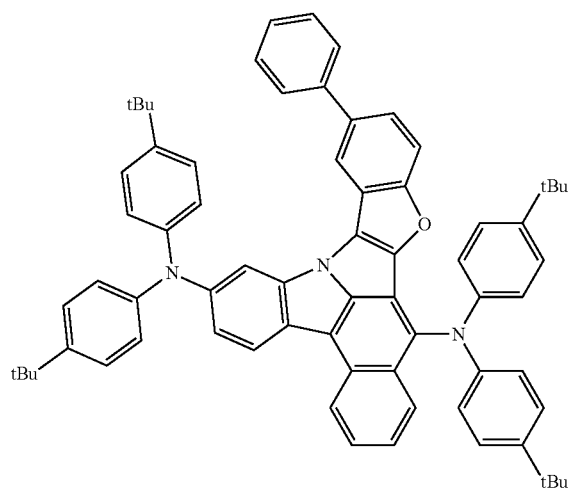
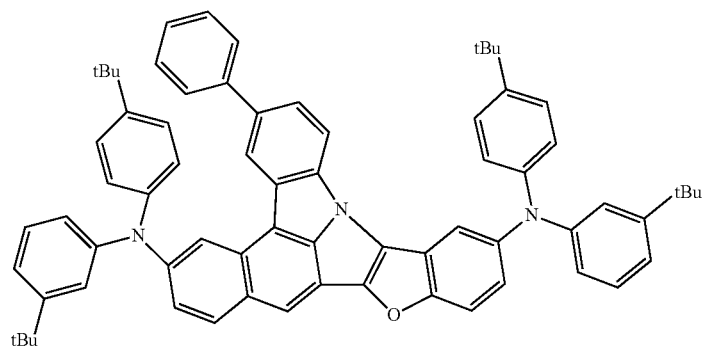

-continued
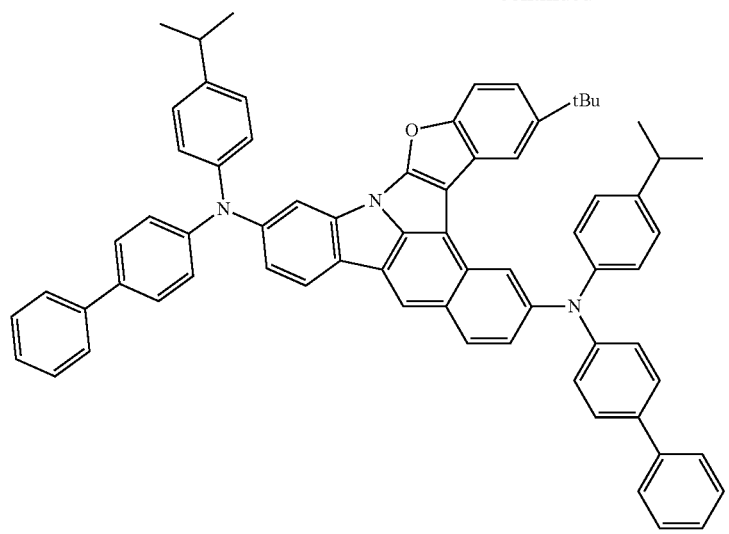
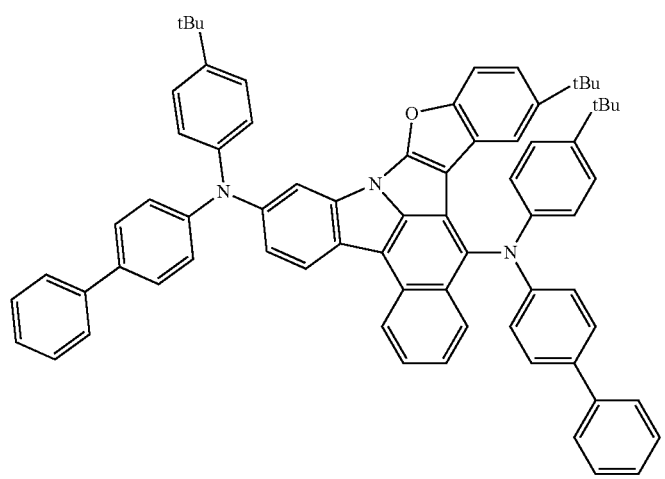
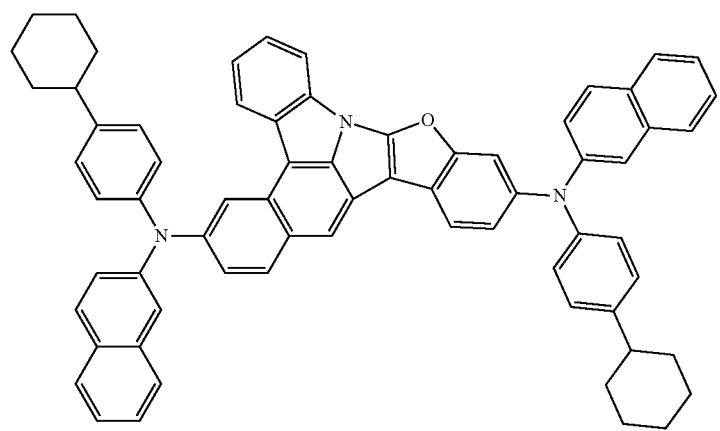

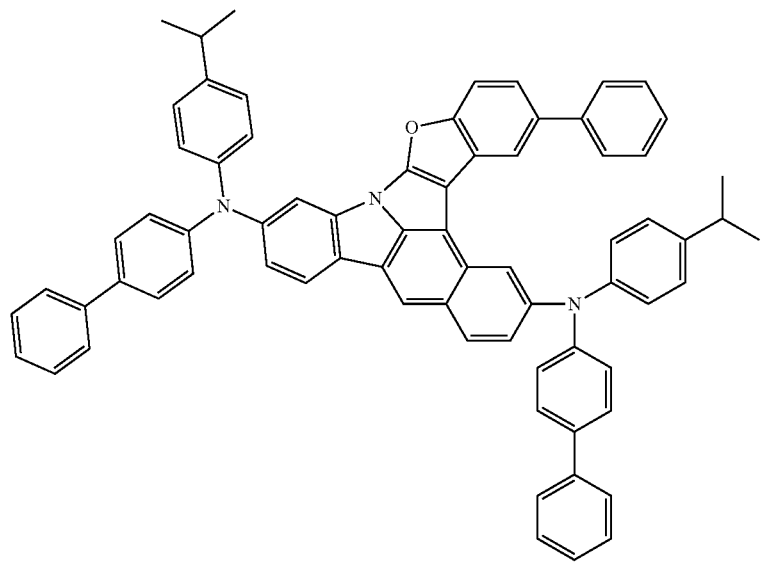
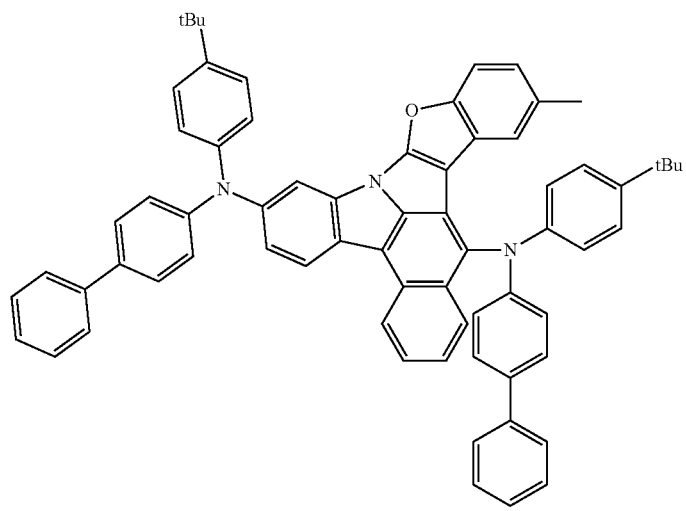
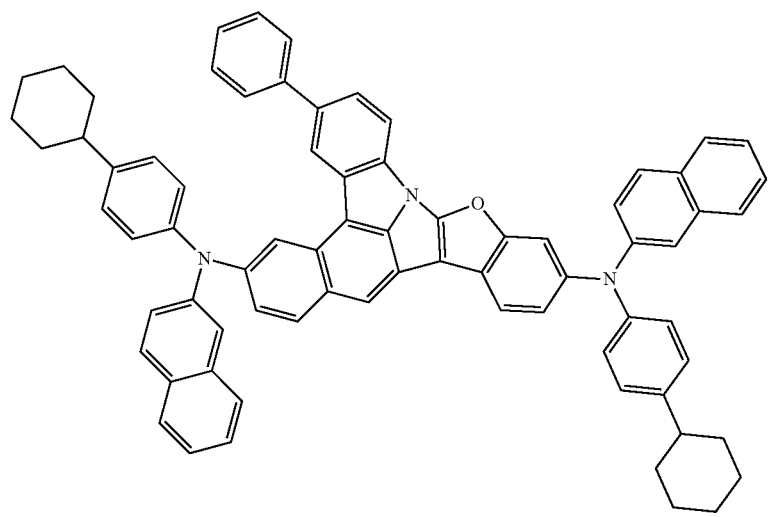

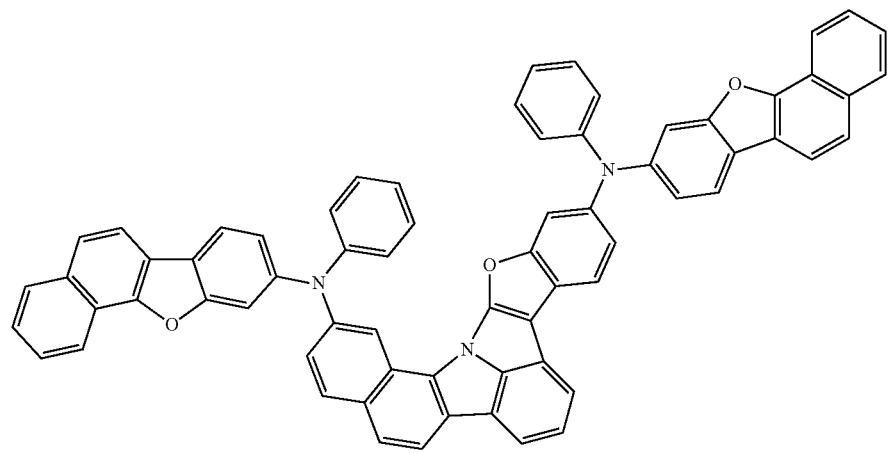
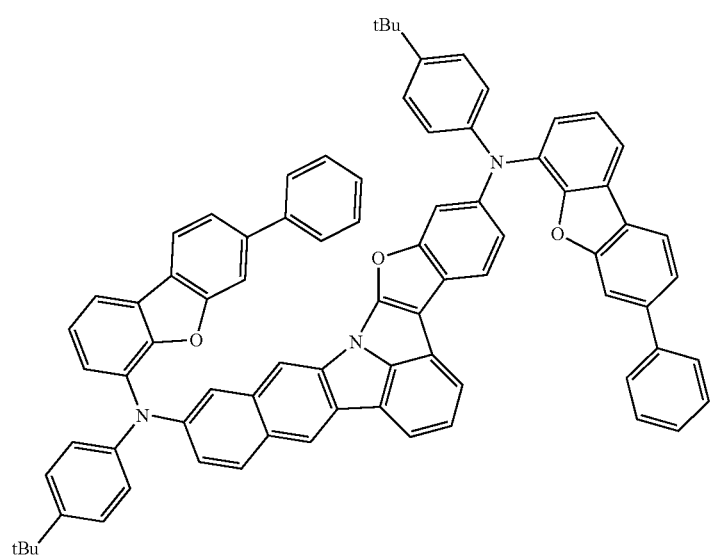
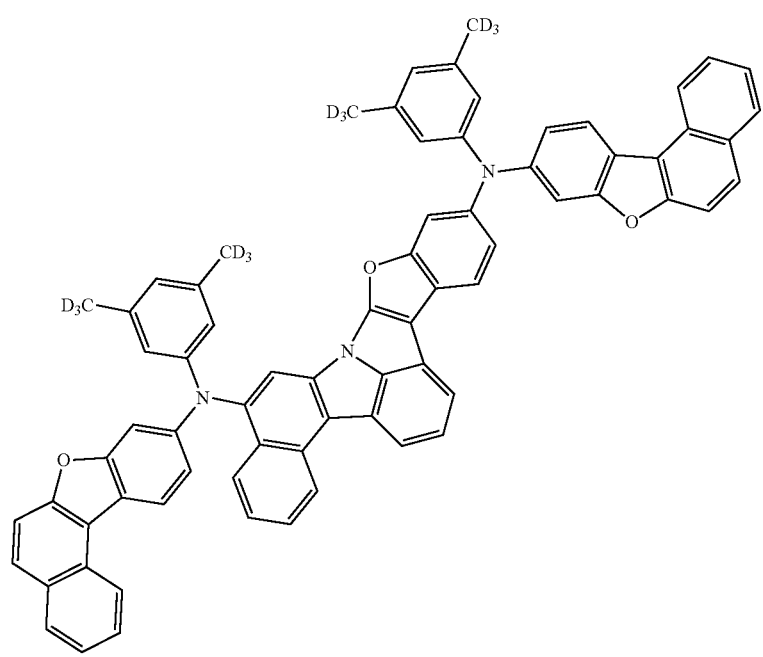

-continued
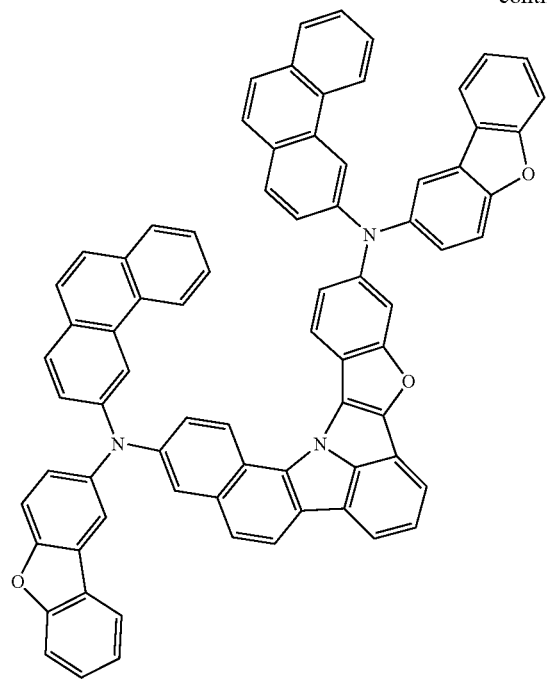
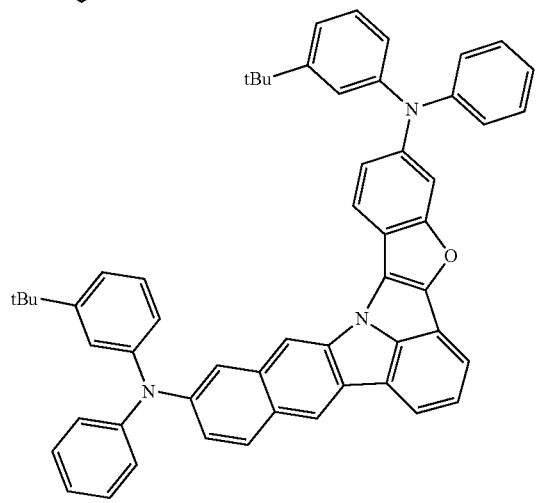
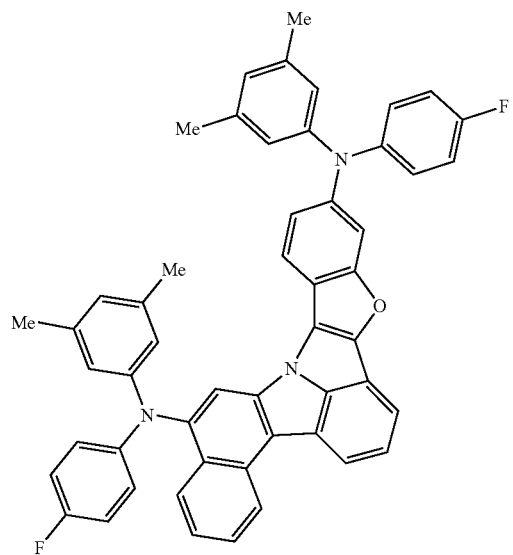

-continued
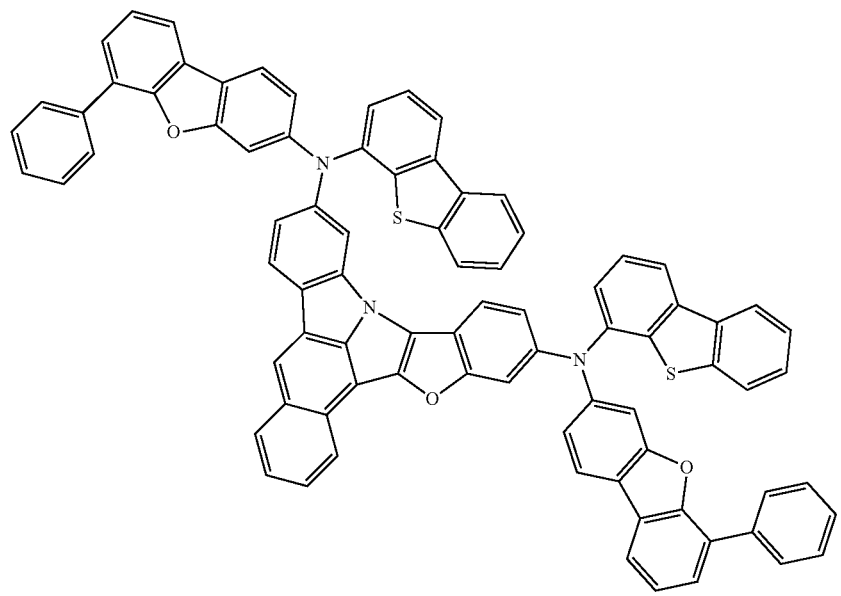
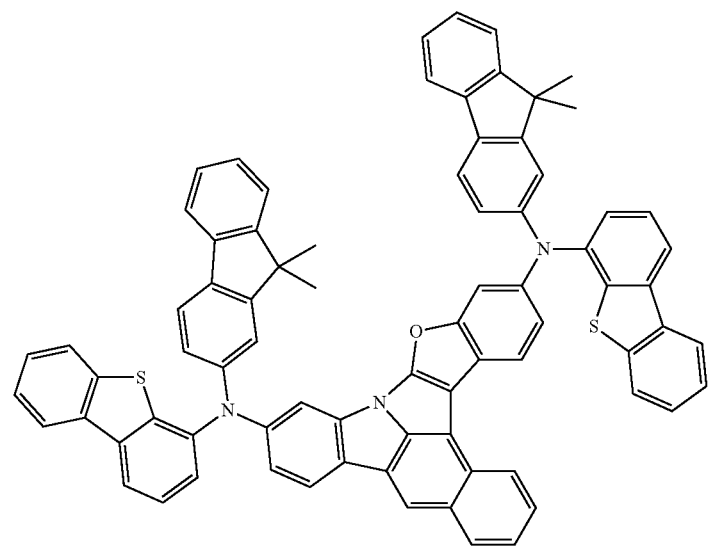

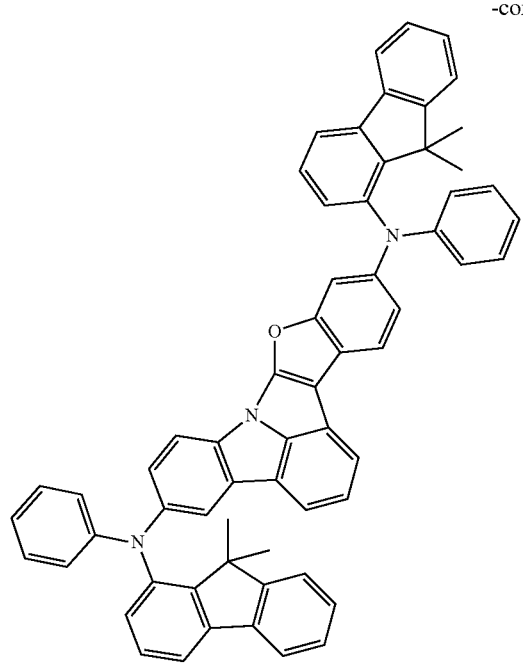
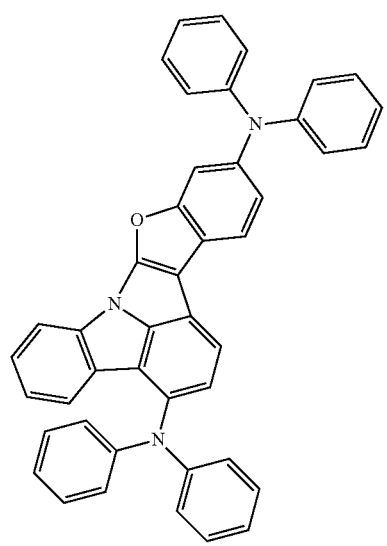

-continued
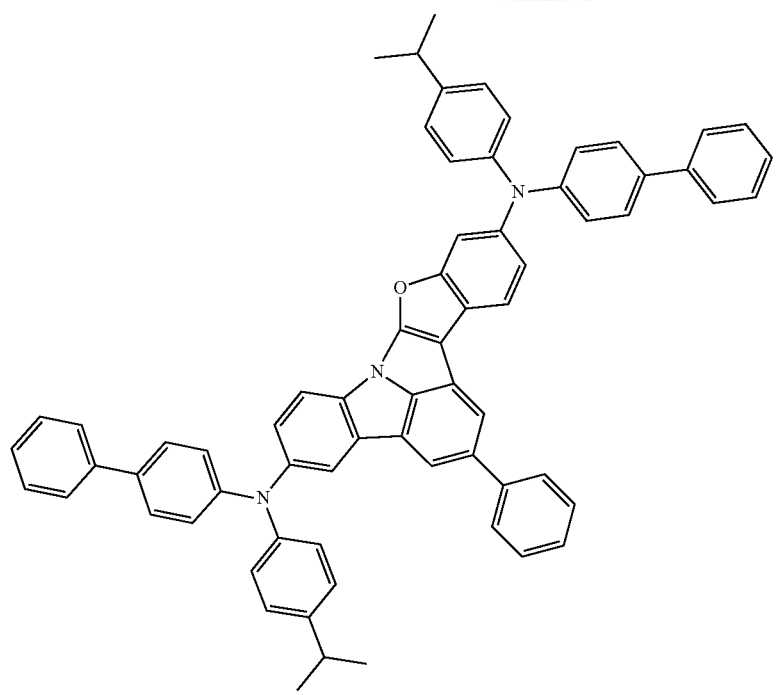
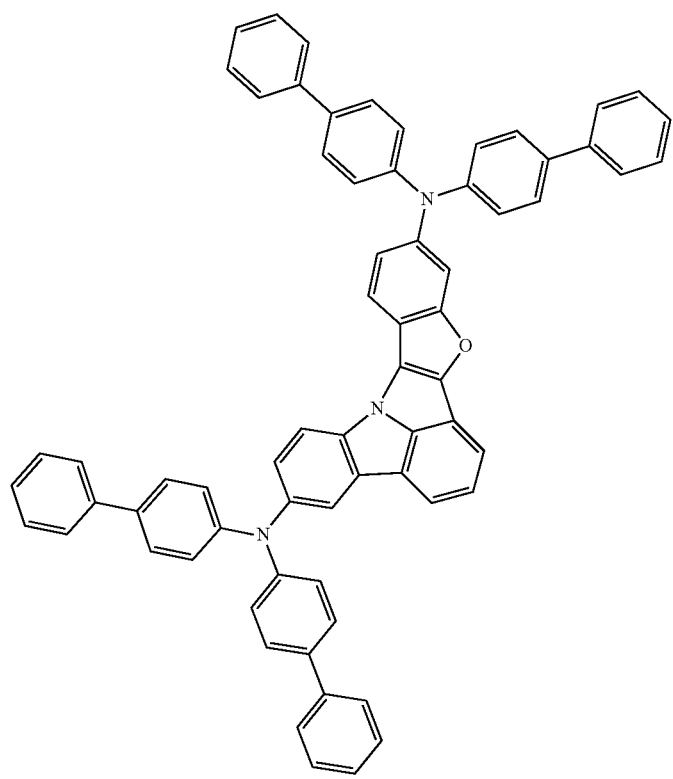

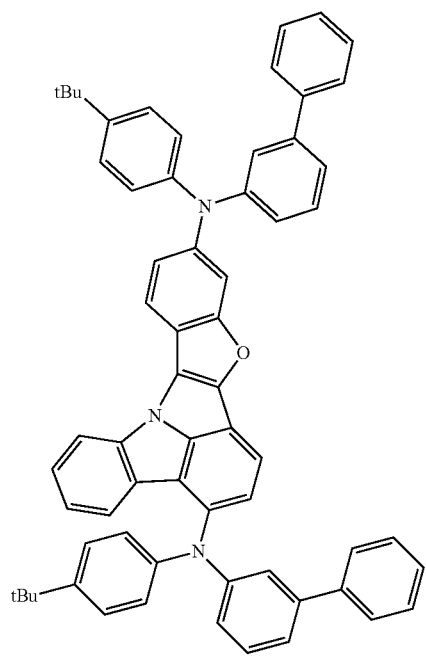
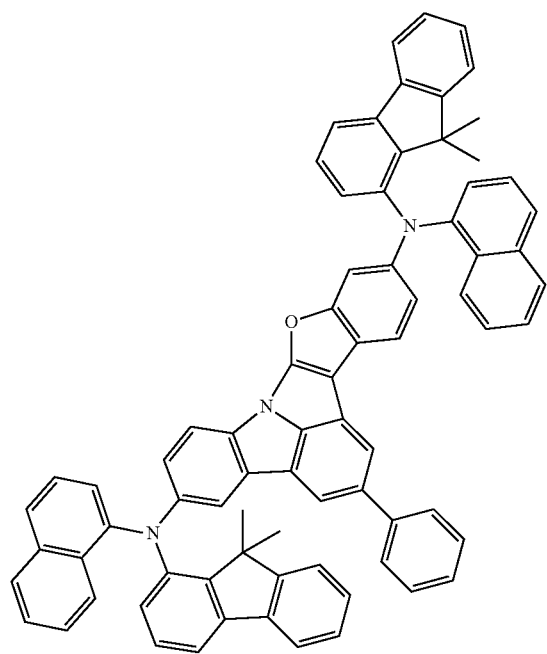

-continued
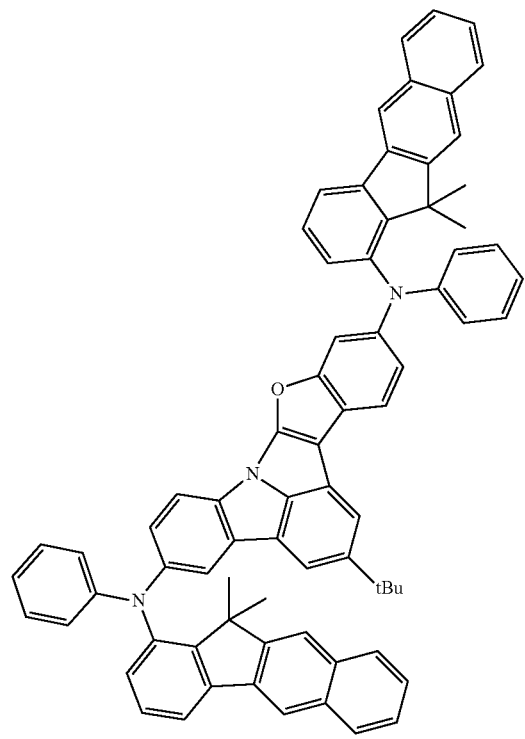
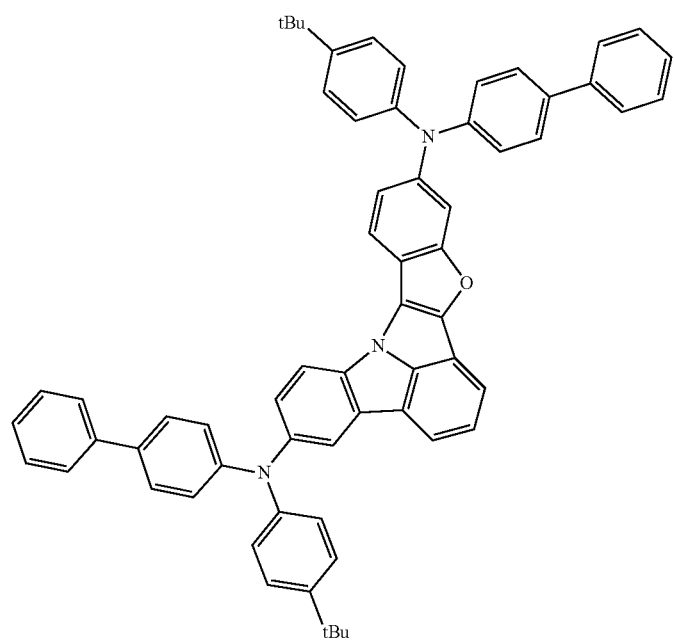 [SMILES: CC(C)(C)c1ccc(N(c2ccc(-c3ccccc3)cc2)c2ccc3c(c2)oc2c4cccc5c6cc(N(c7ccc(-c8ccccc8)cc7)c7ccc(C(C)(C)C)cc7)ccc6n(c54)c32)cc1]

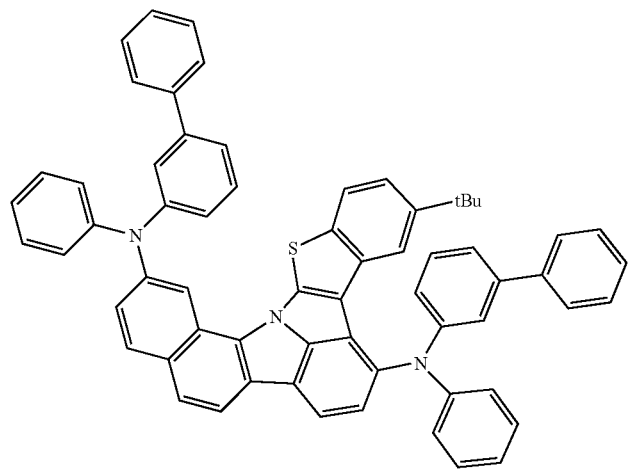
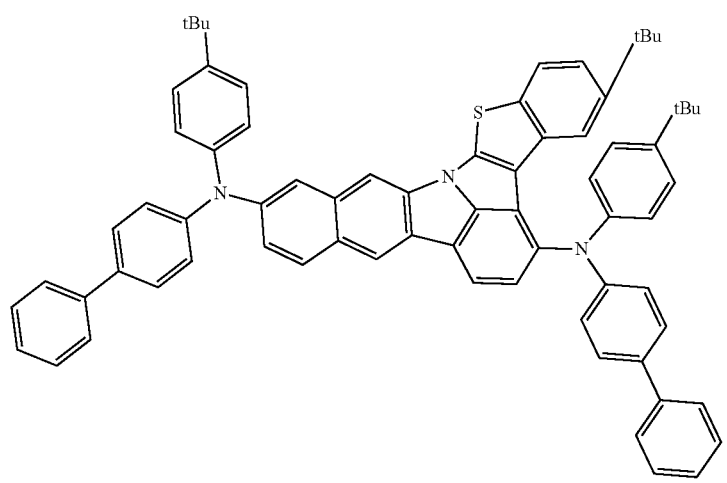
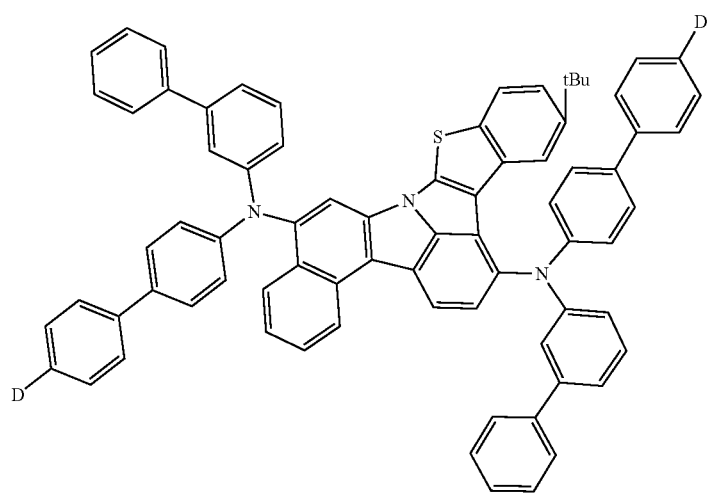

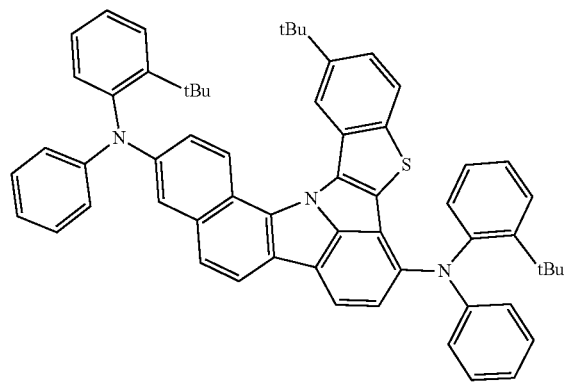
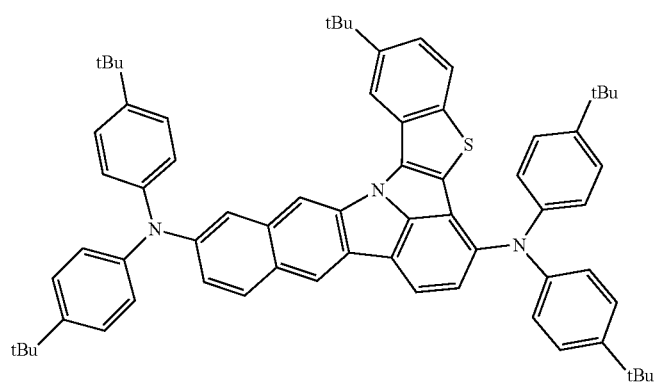
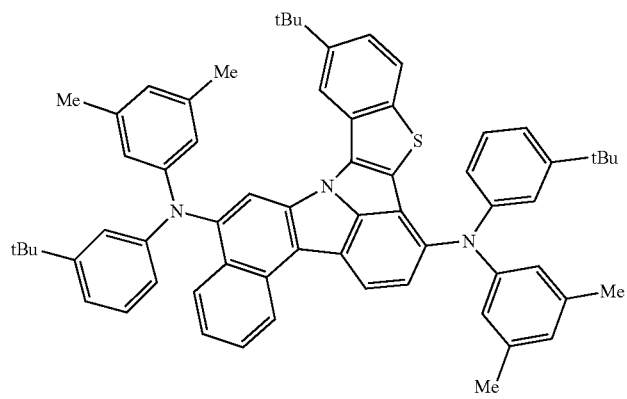
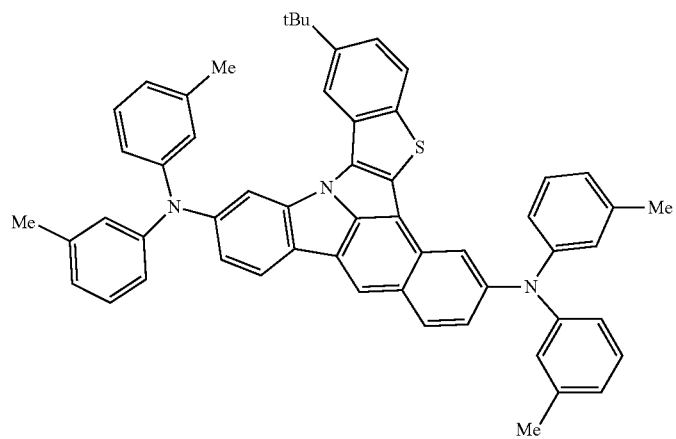

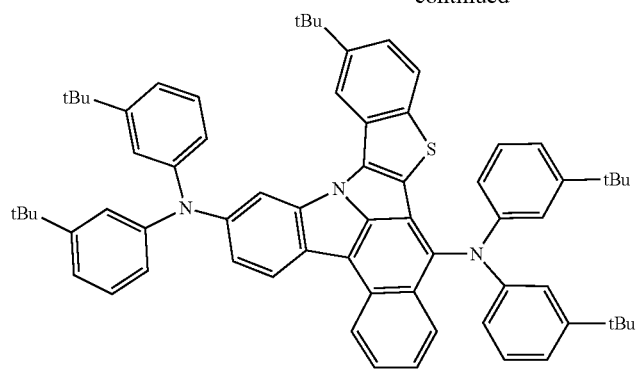
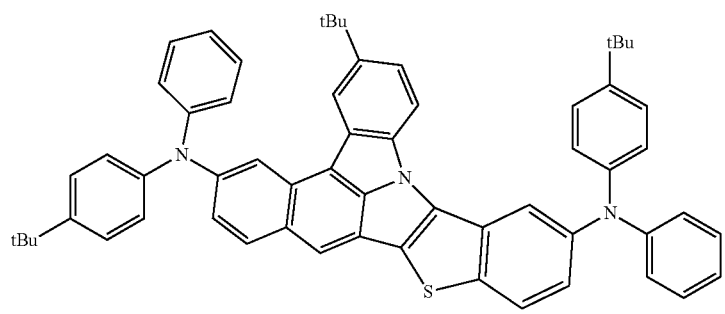
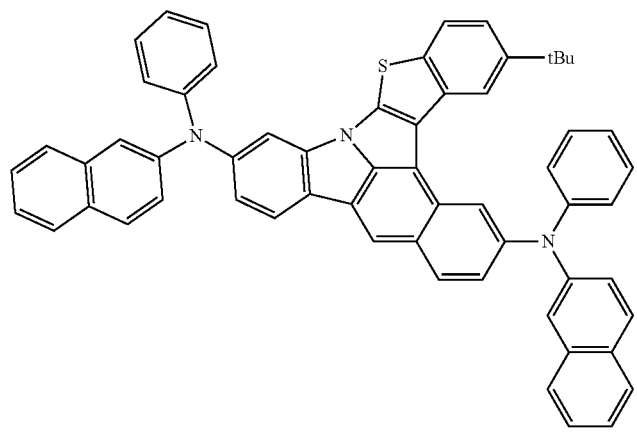
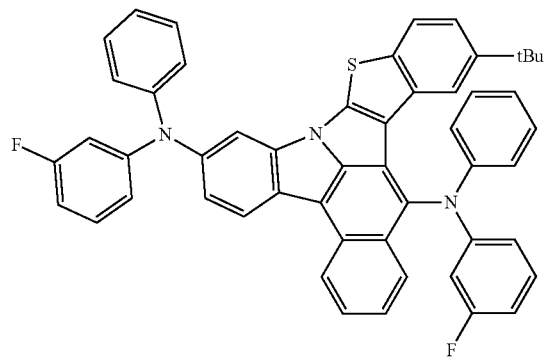

-continued
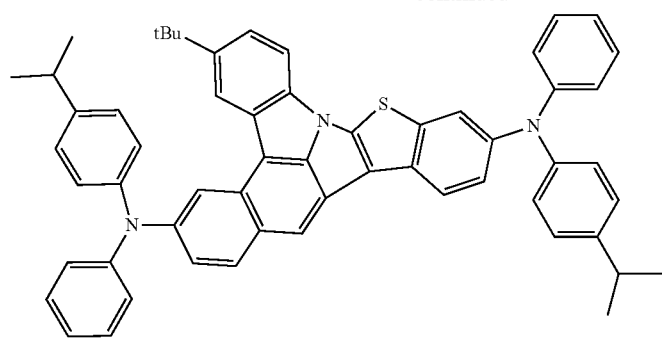
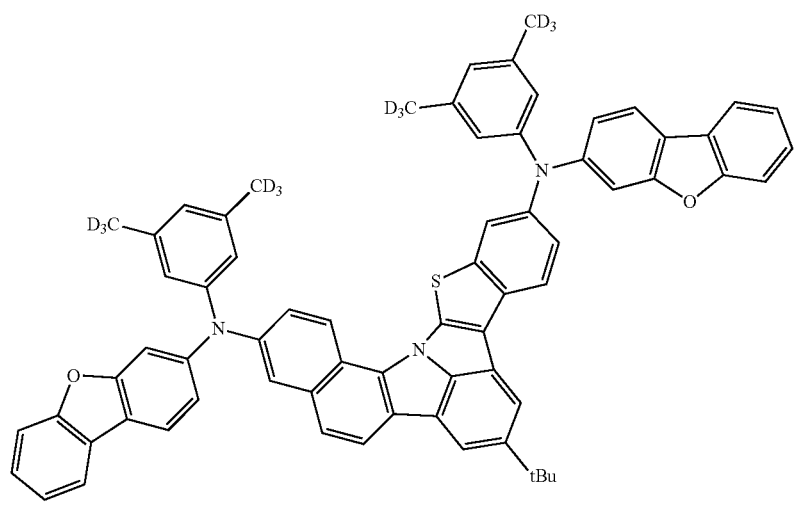
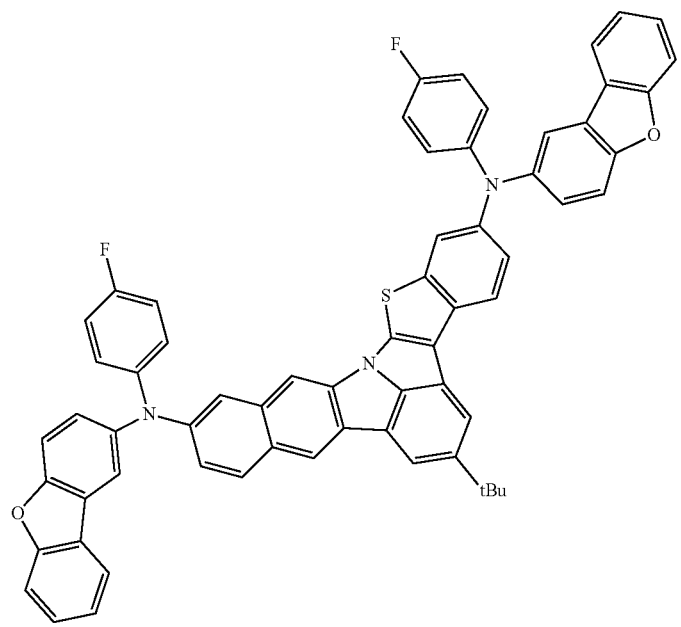

-continued
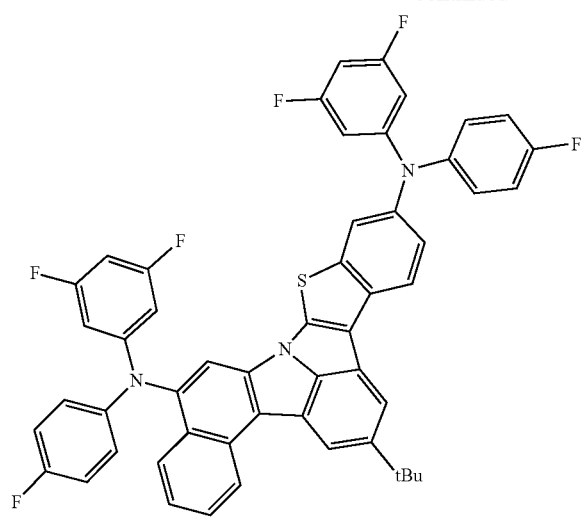
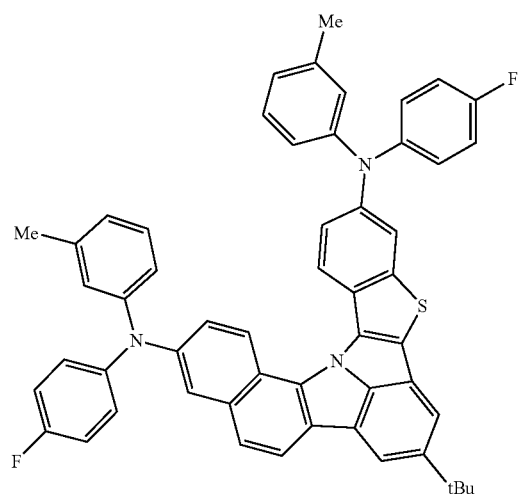
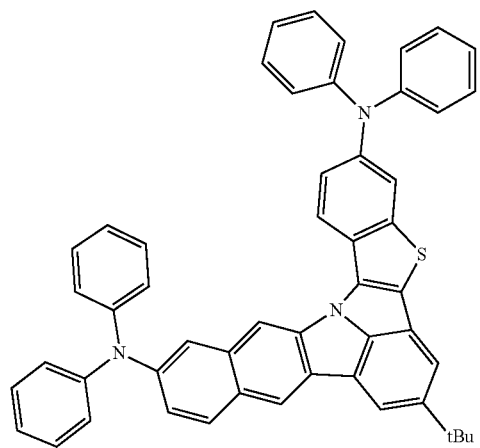

-continued
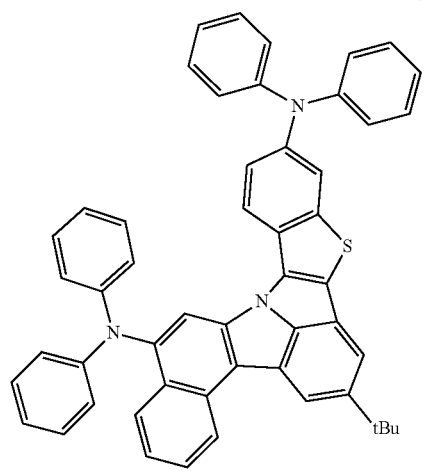
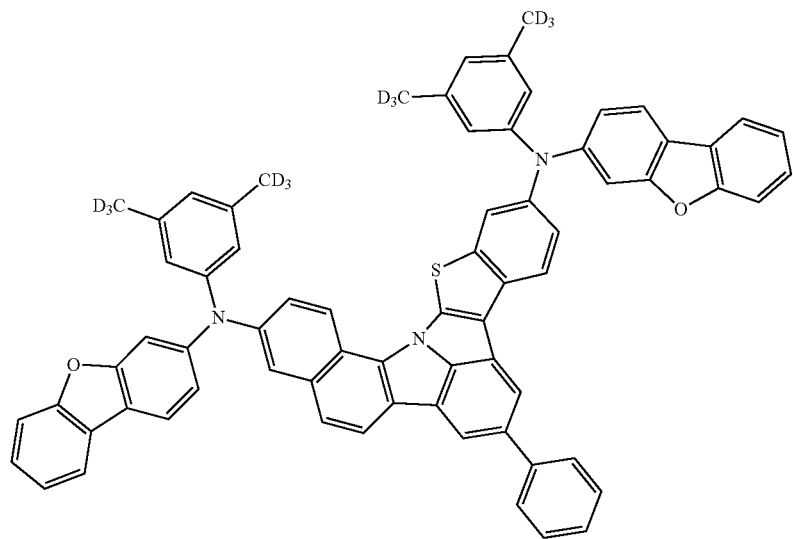
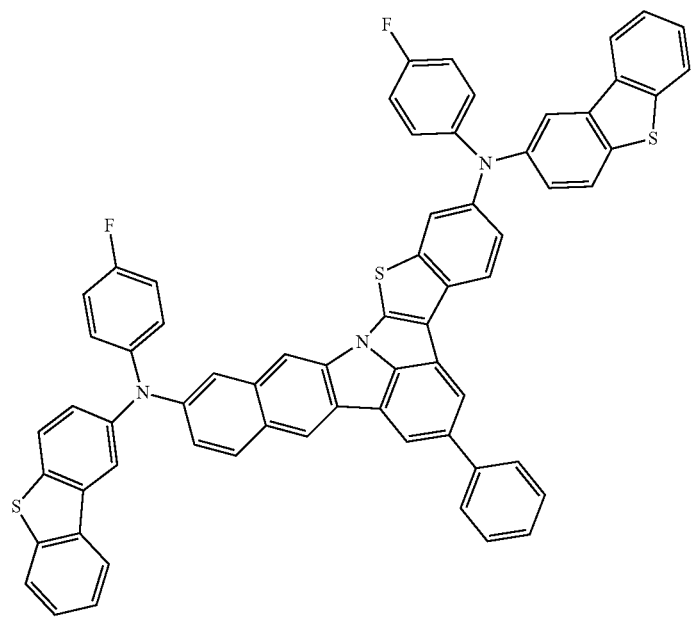

-continued
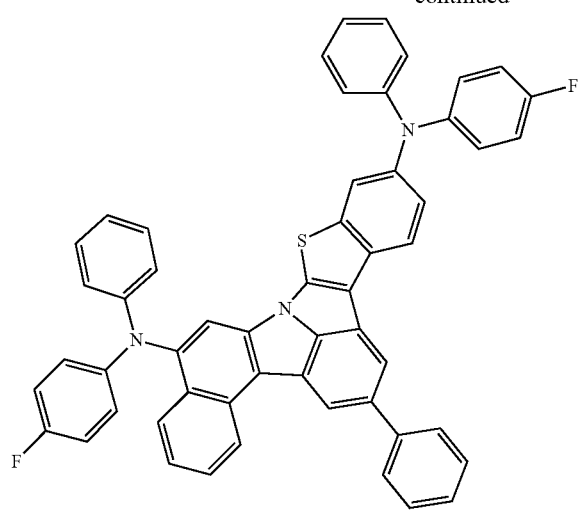
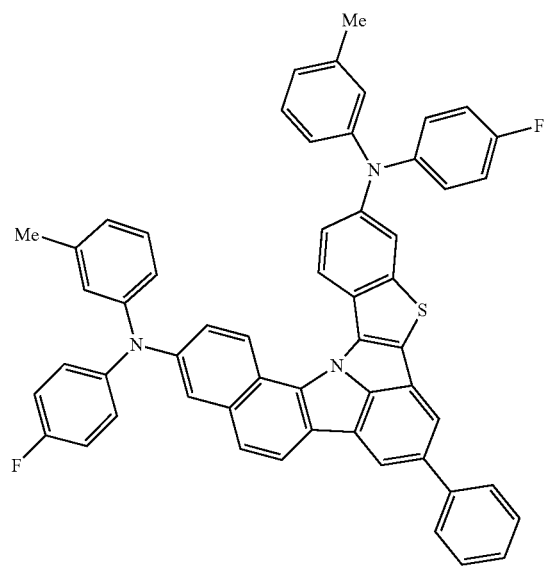
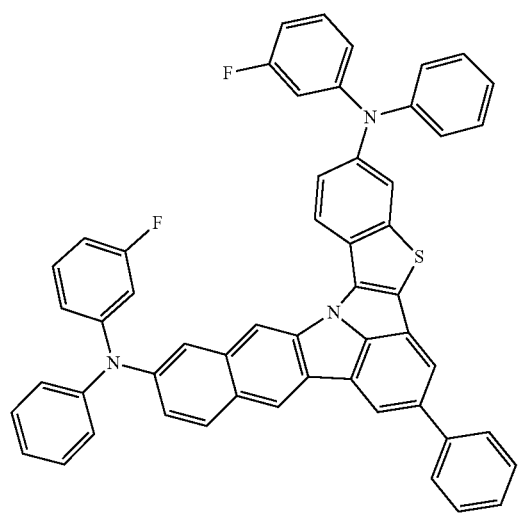

-continued
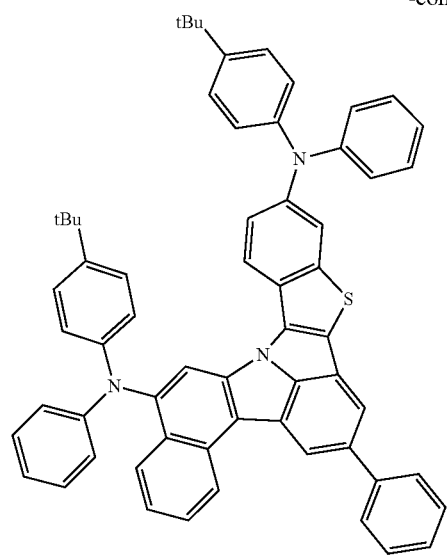
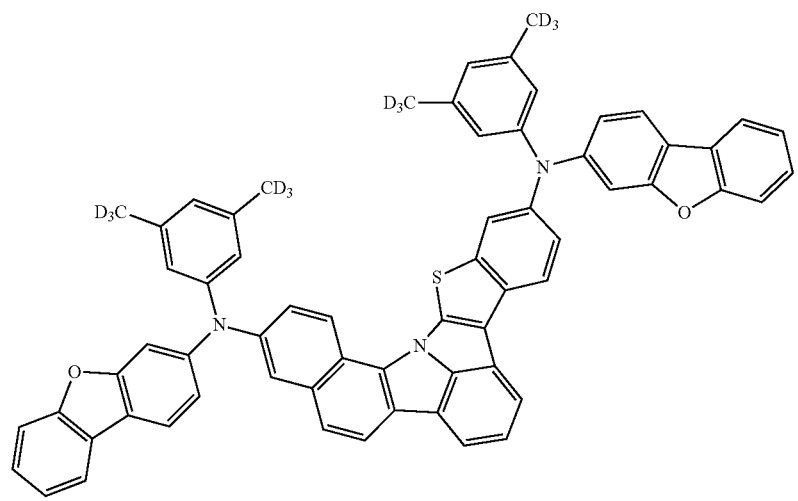
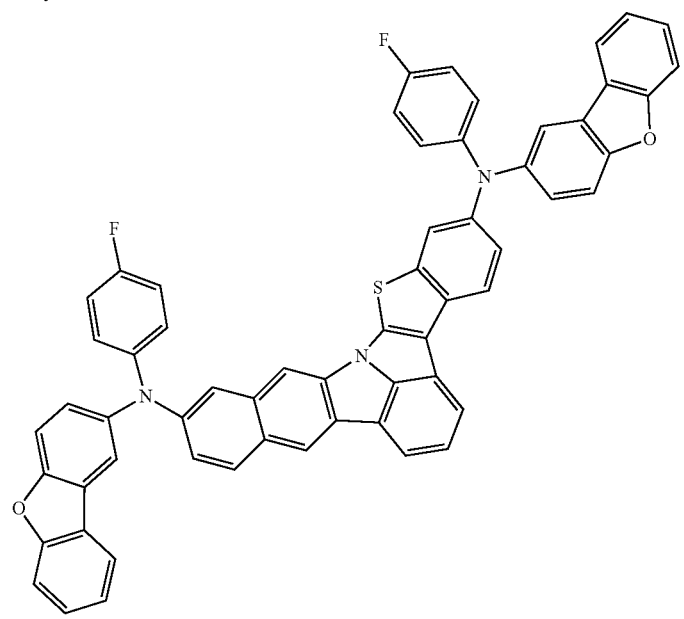

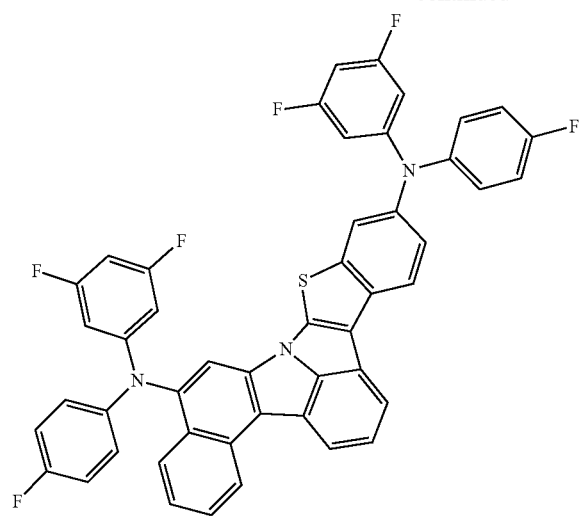
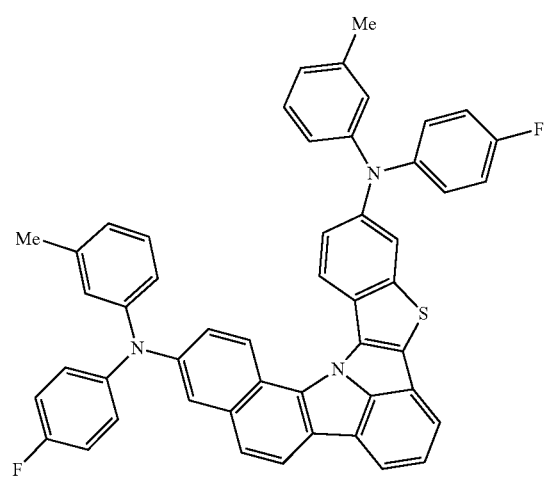
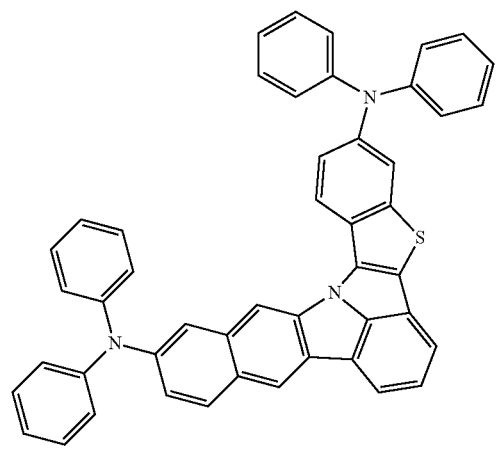

-continued
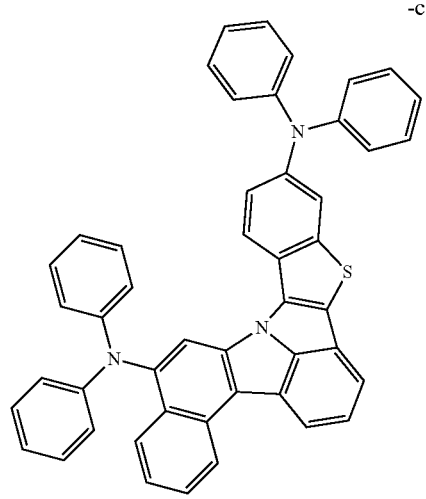
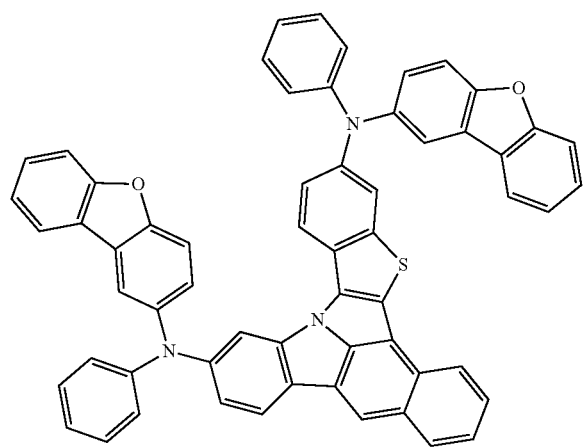
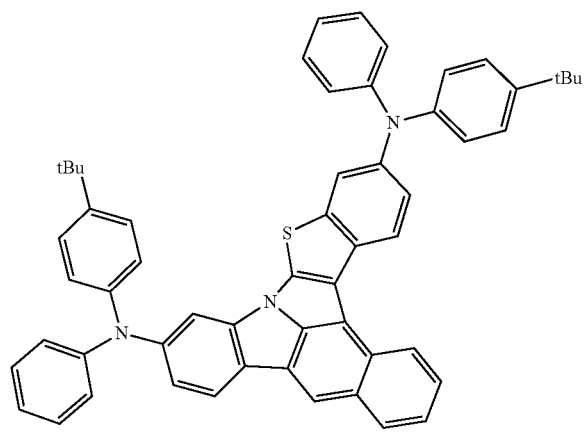

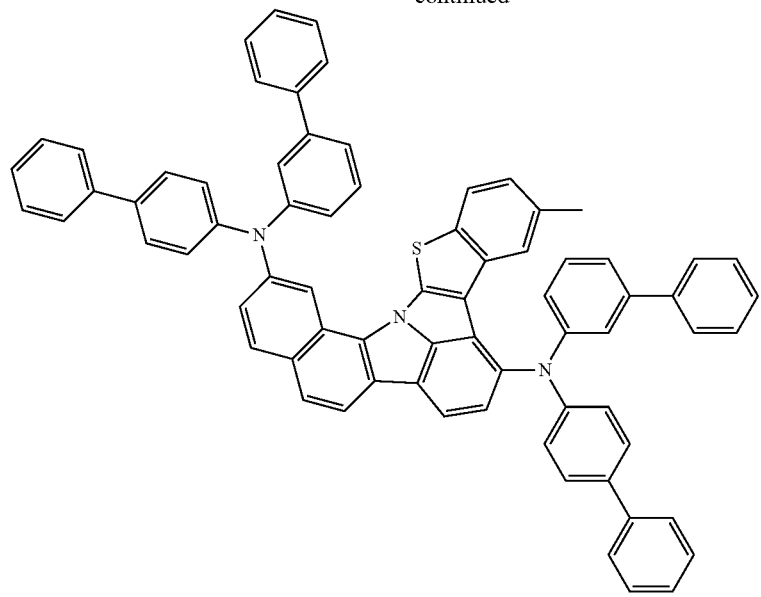
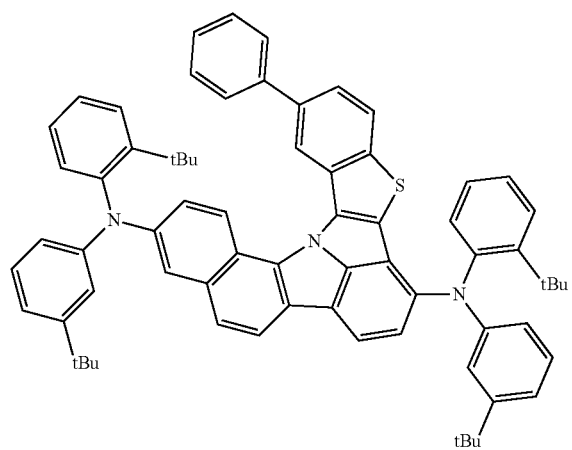
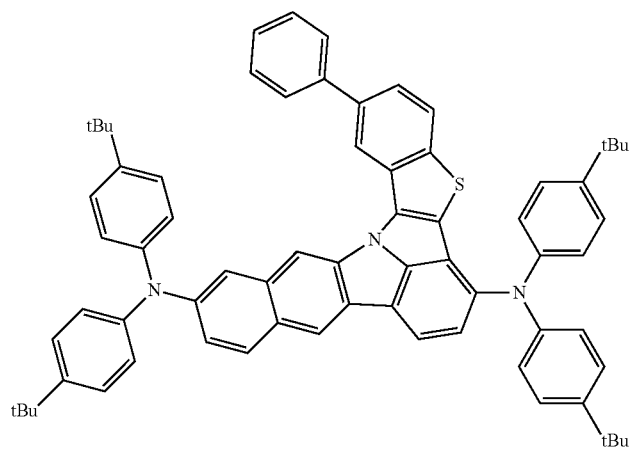

-continued
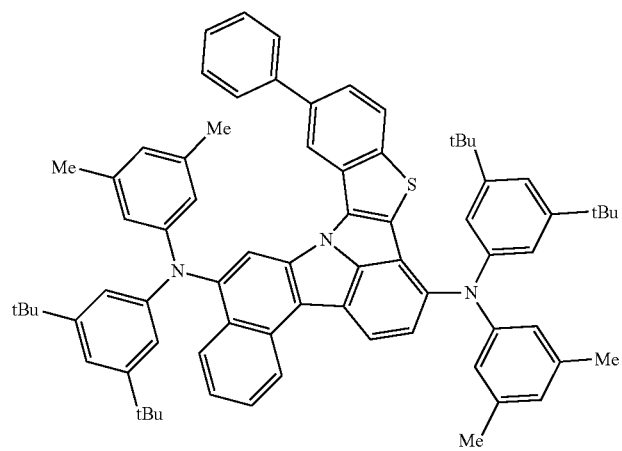
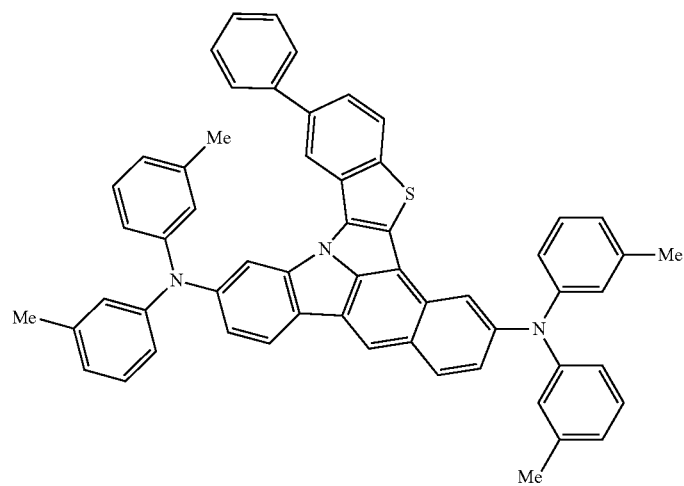
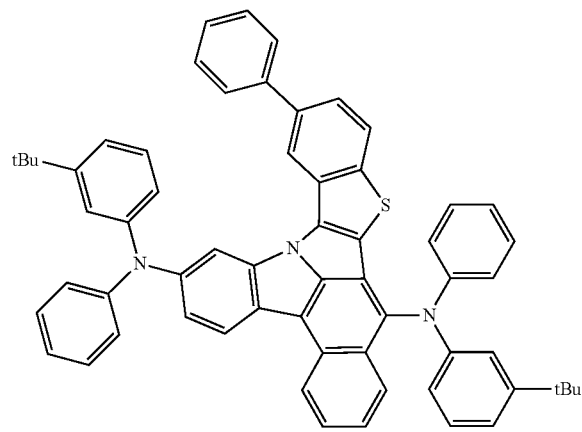
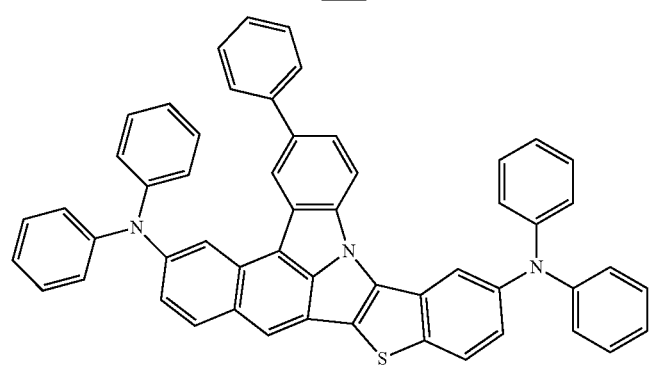

-continued
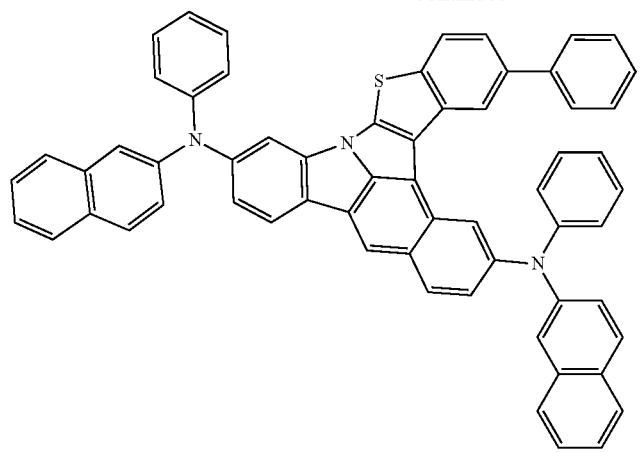
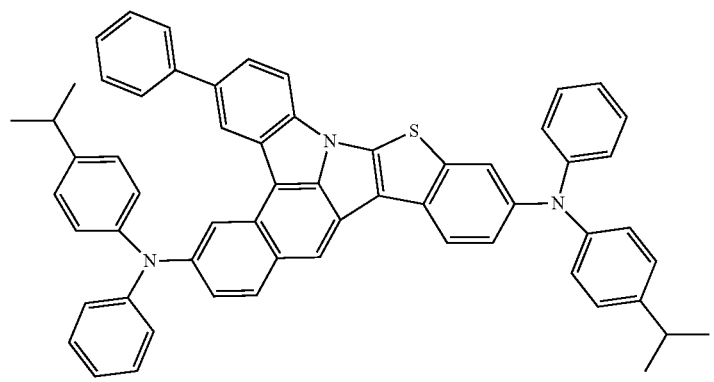
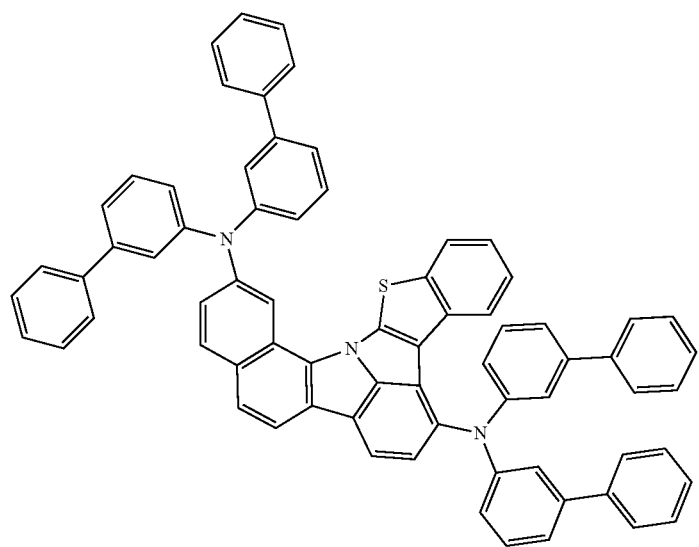

-continued
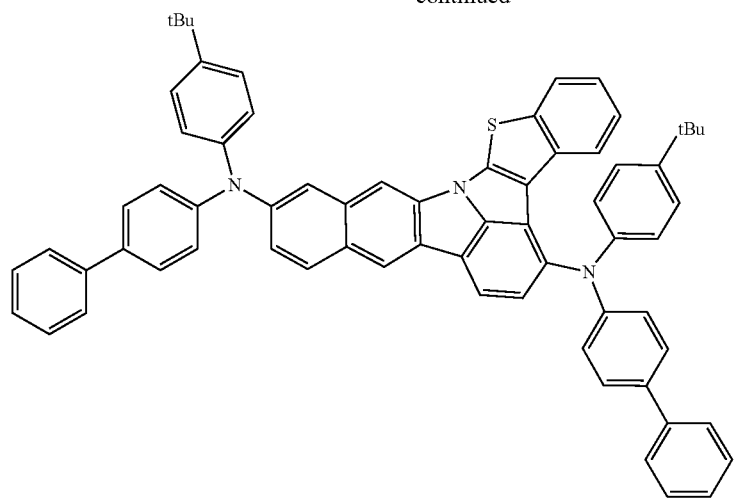
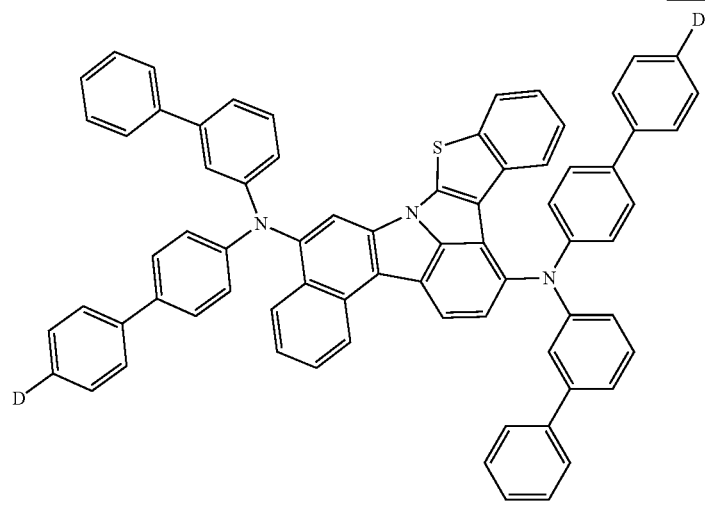
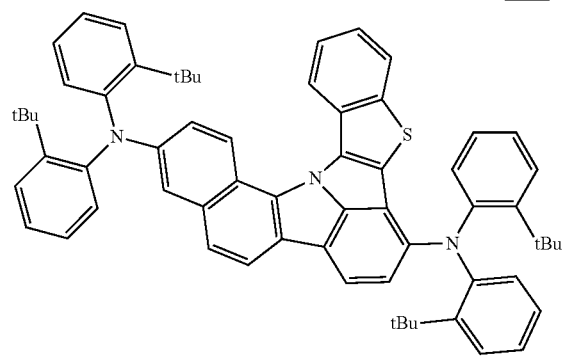
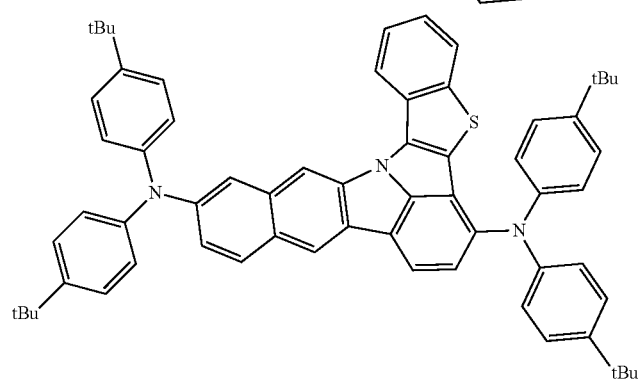

-continued
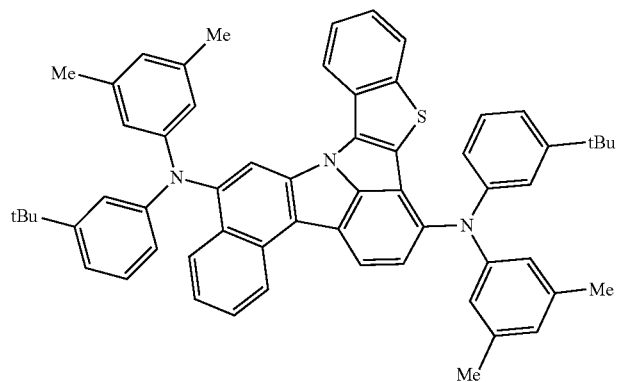
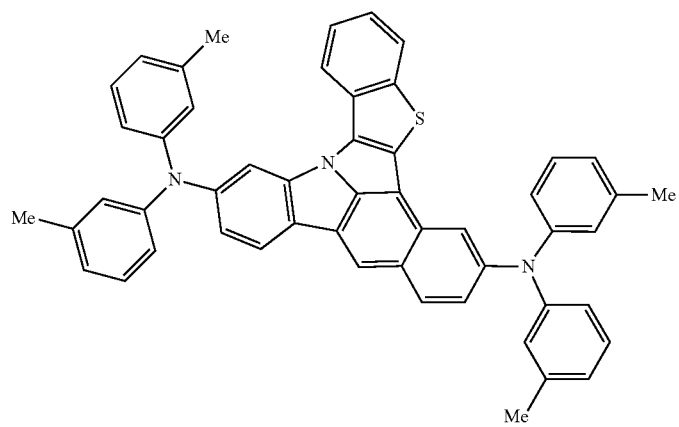
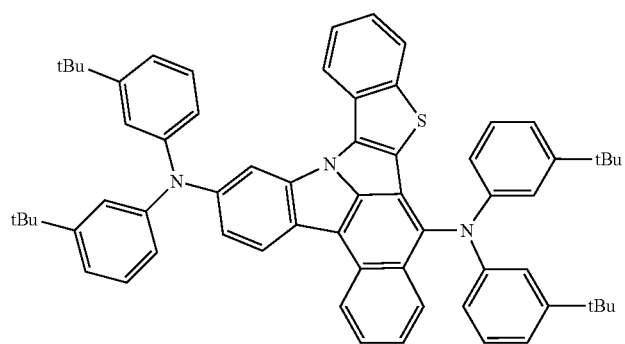
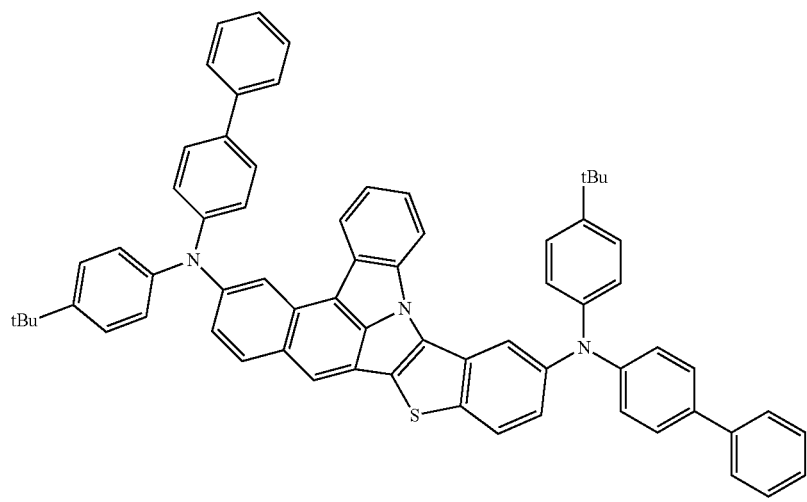

-continued
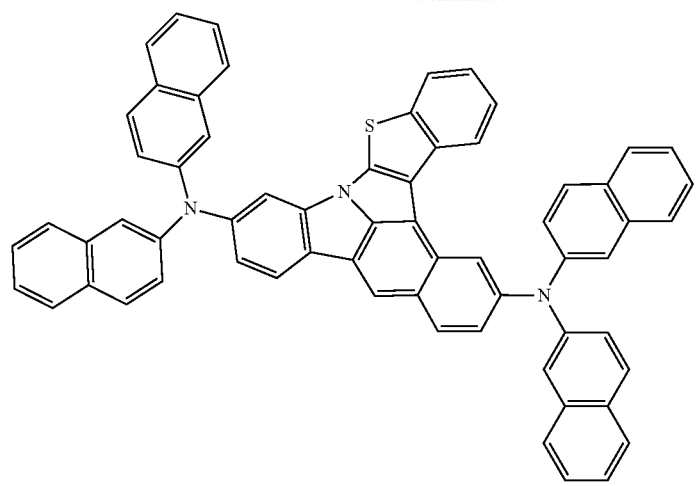
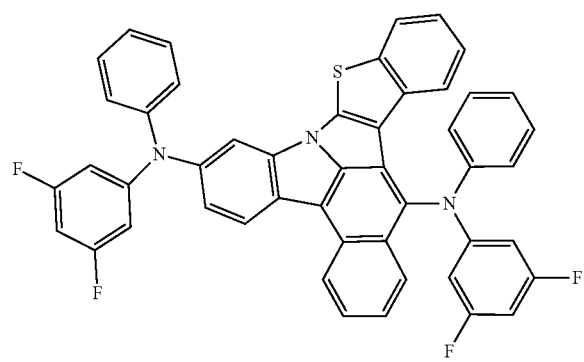
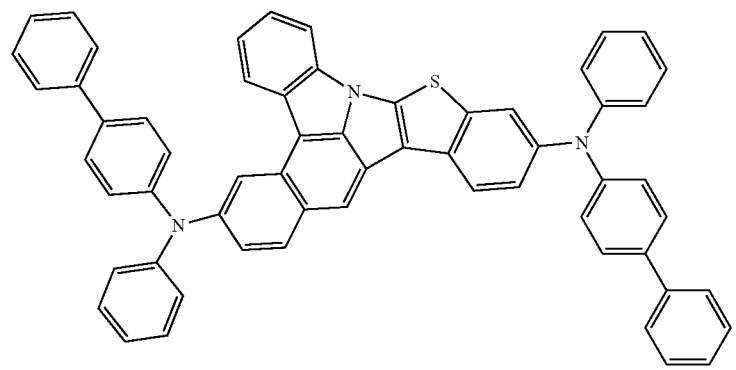

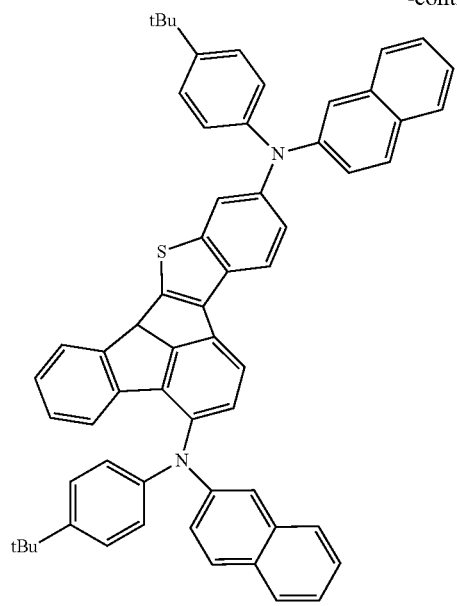
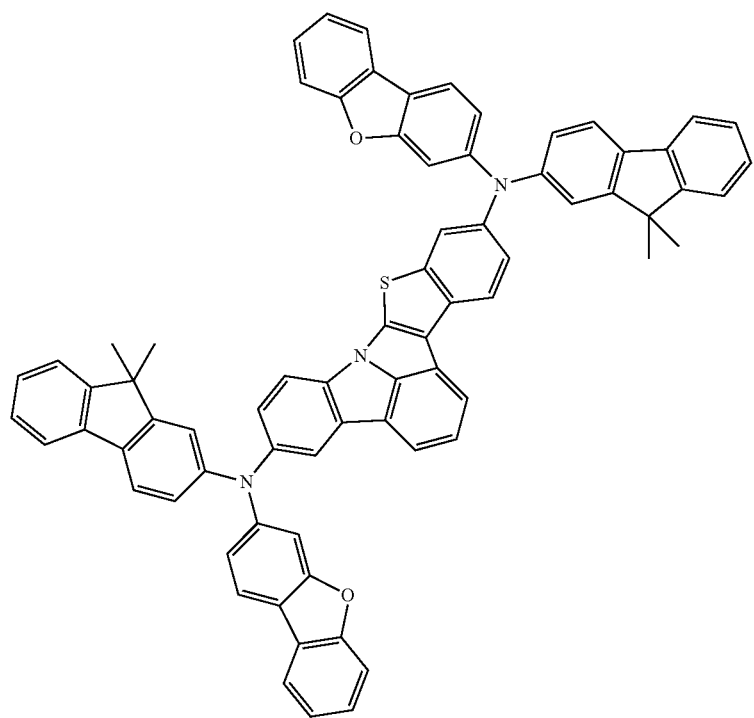

-continued
527
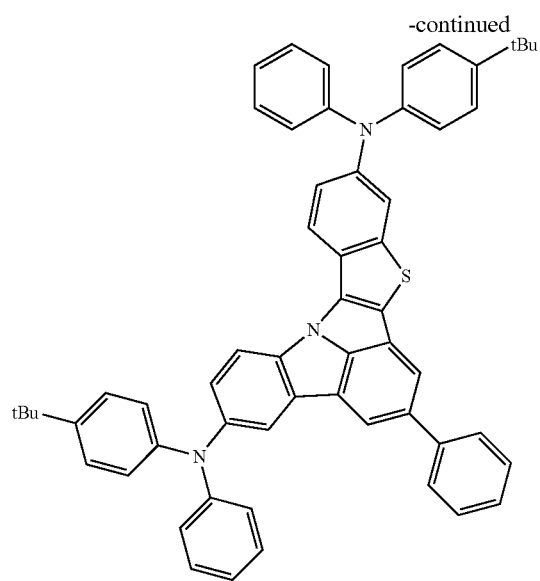
528
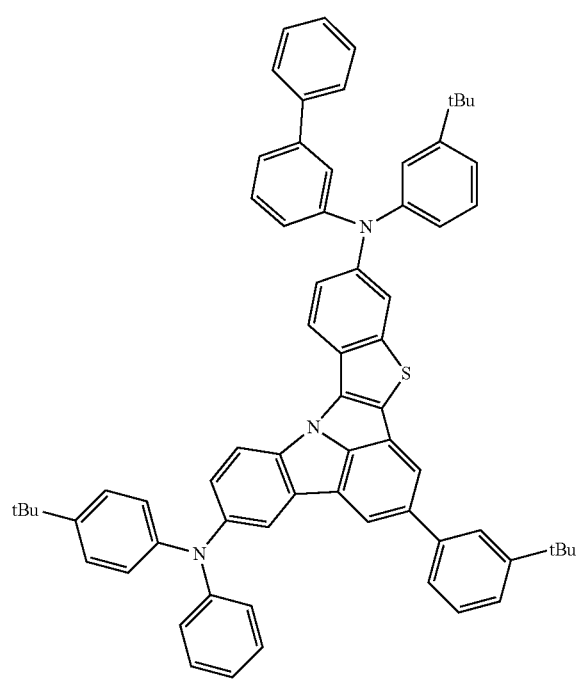

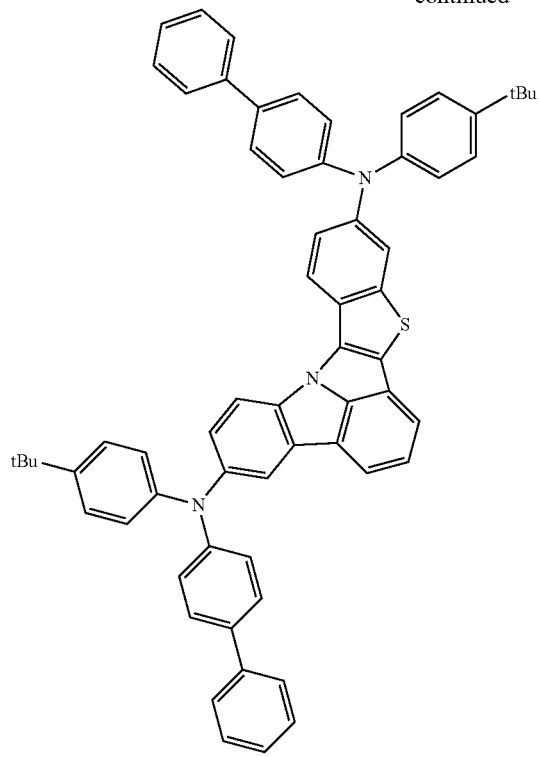
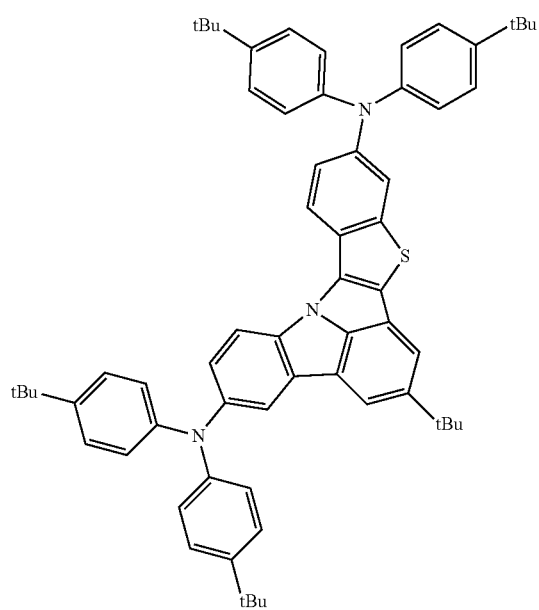

-continued
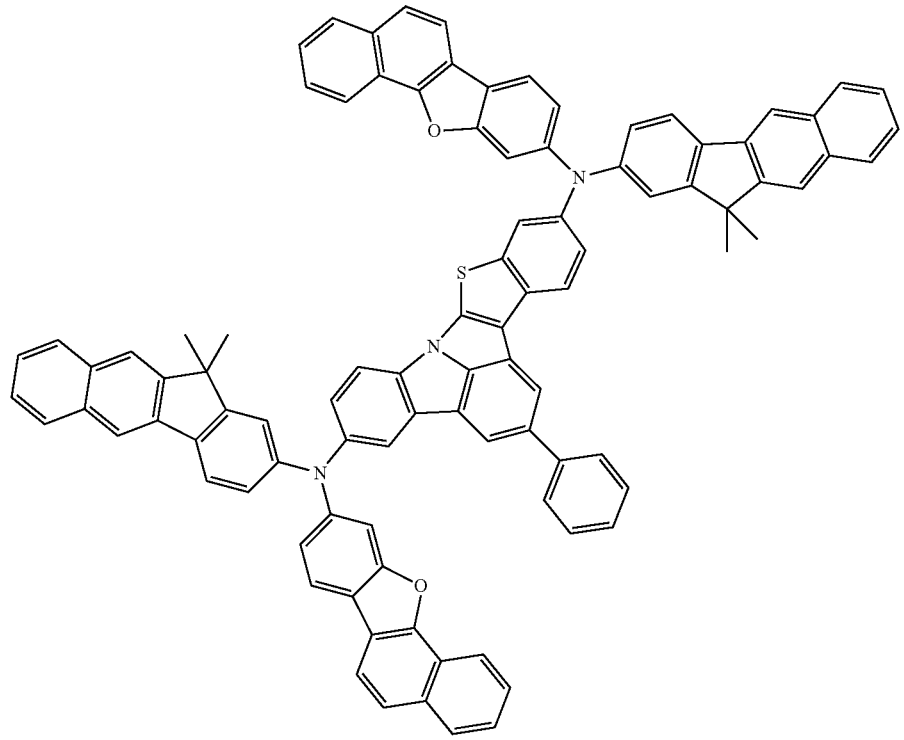
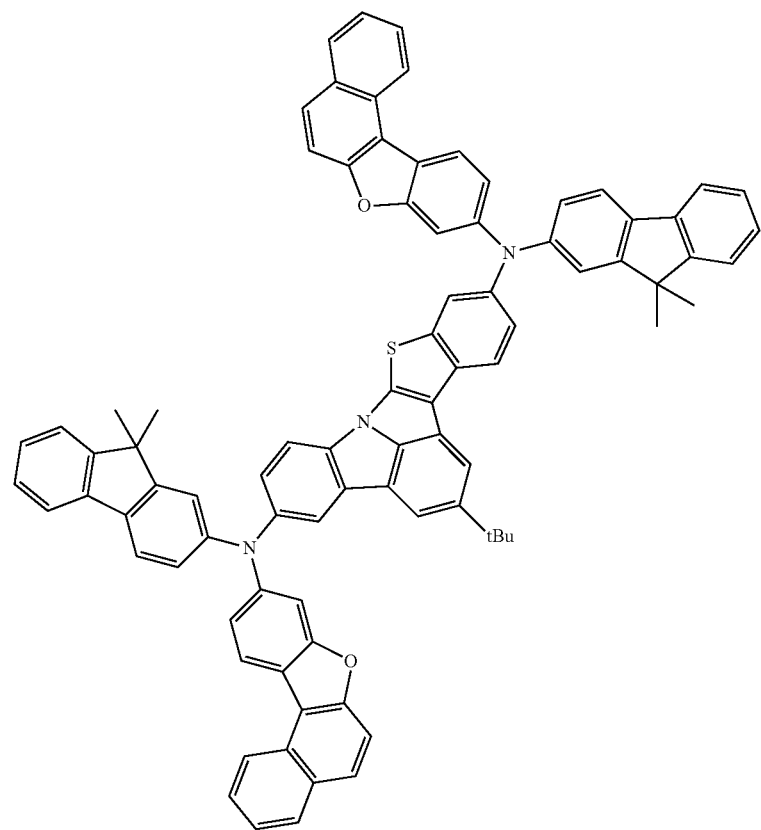

-continued
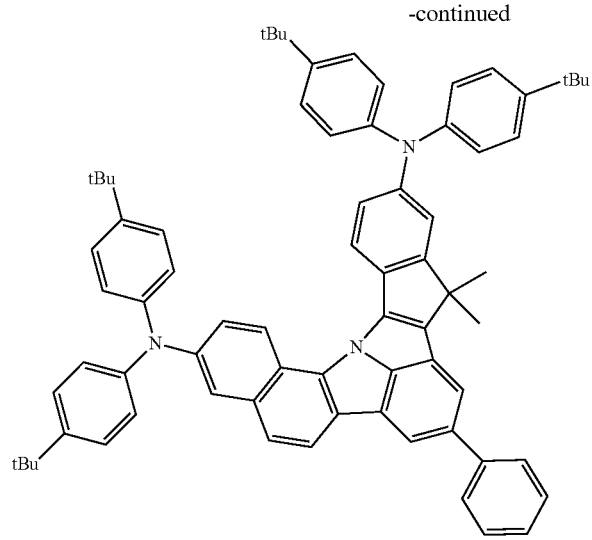
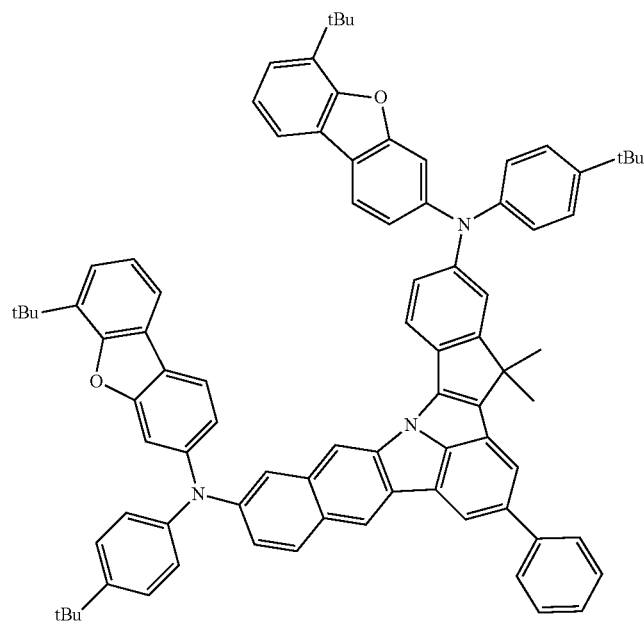
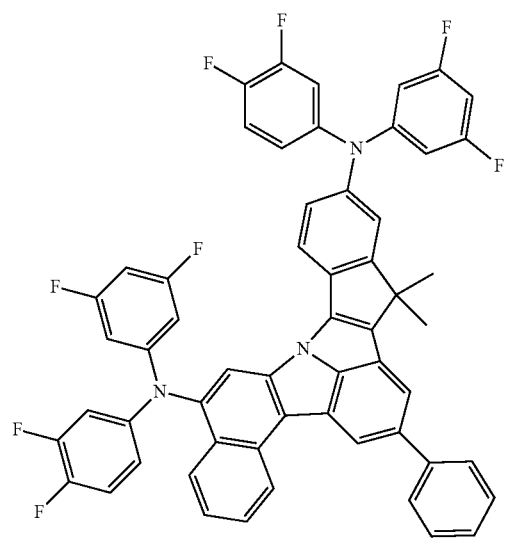

-continued
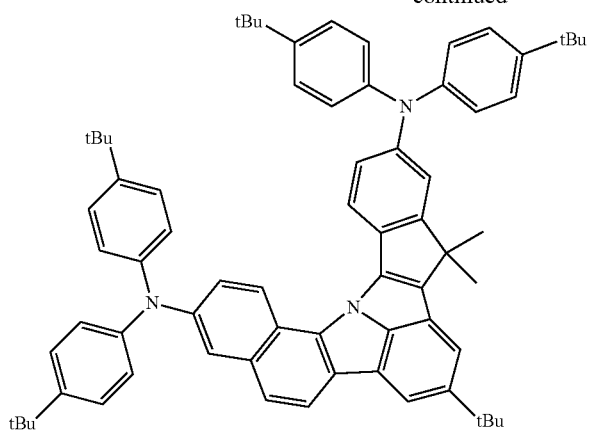
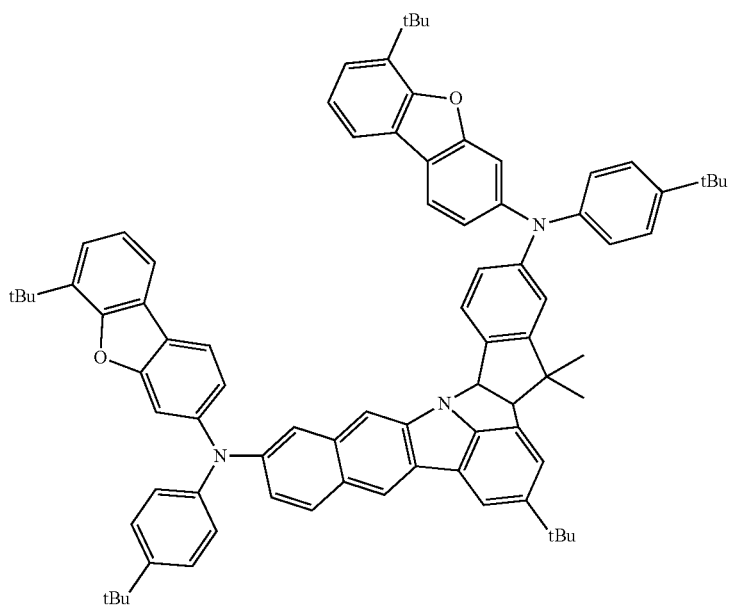
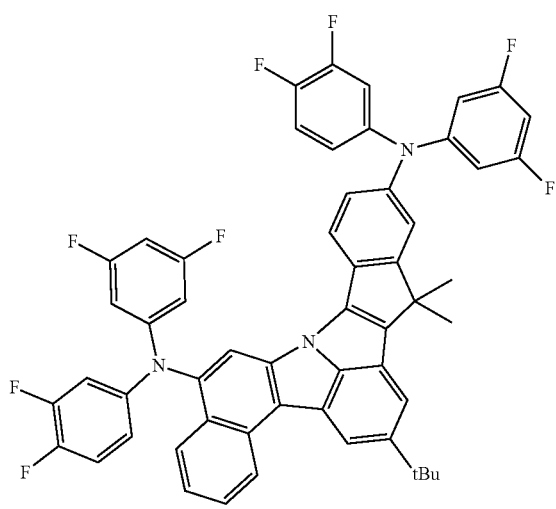

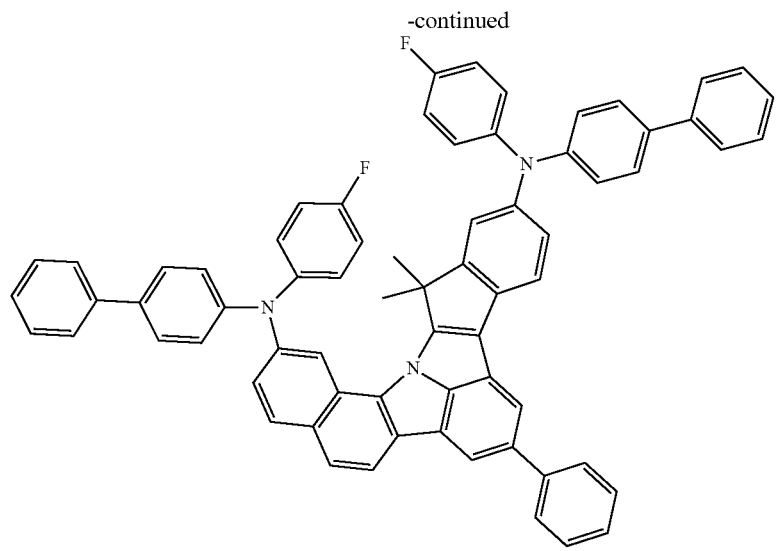
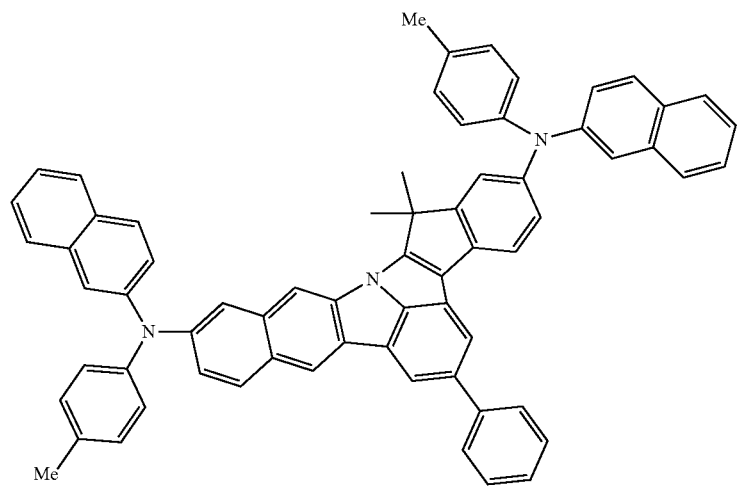
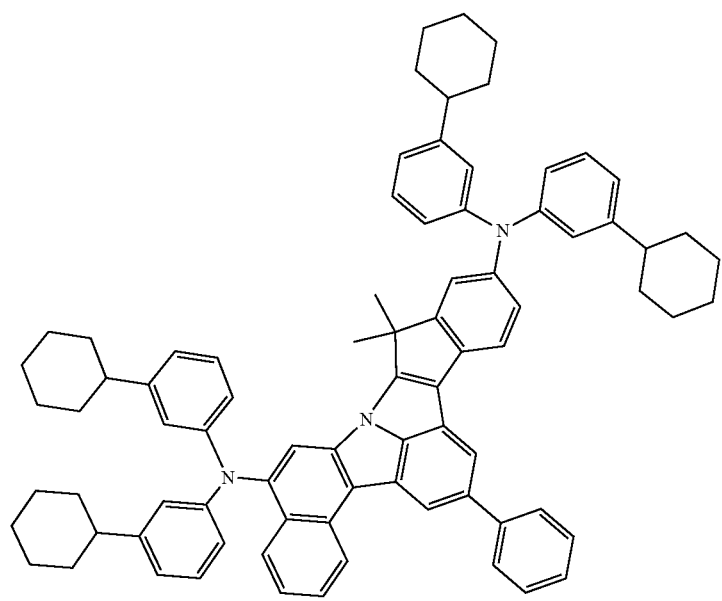

-continued
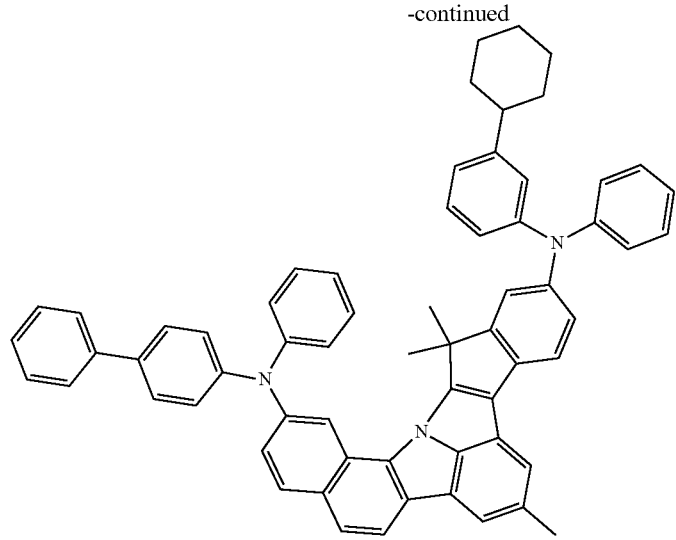
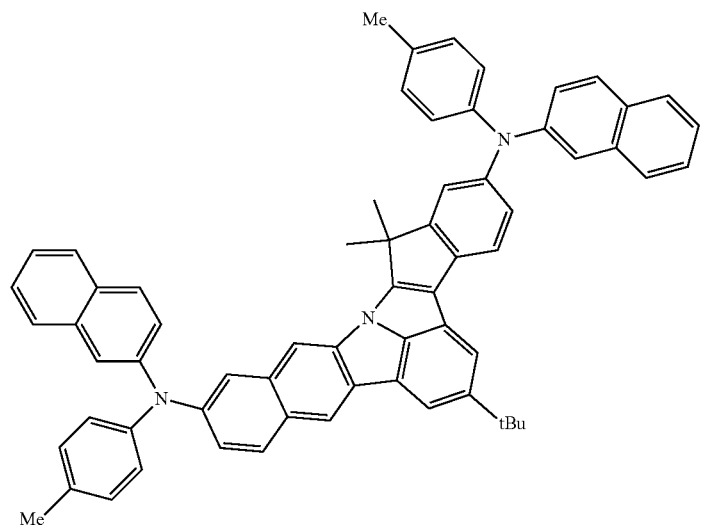
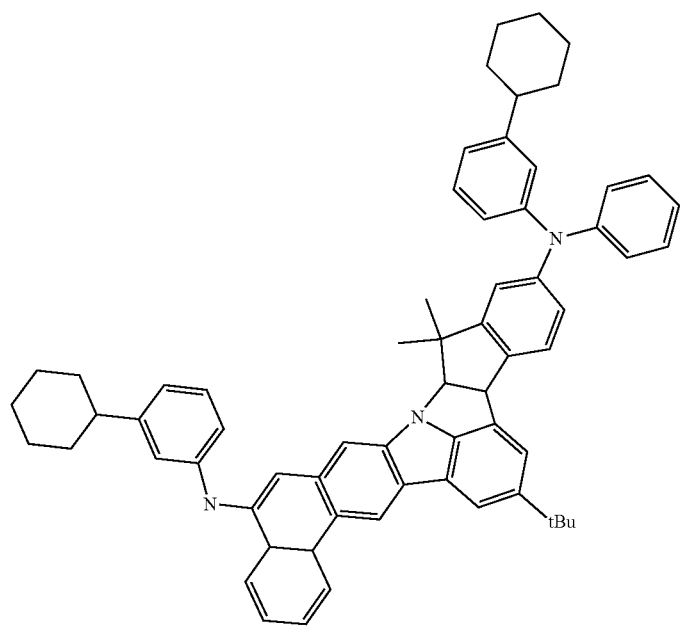

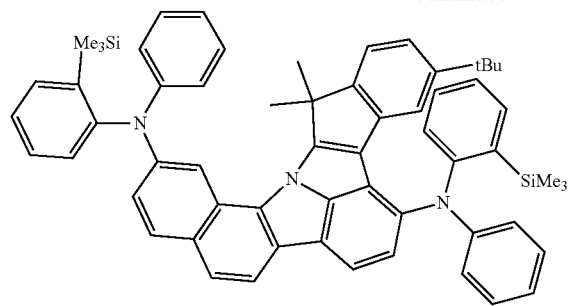
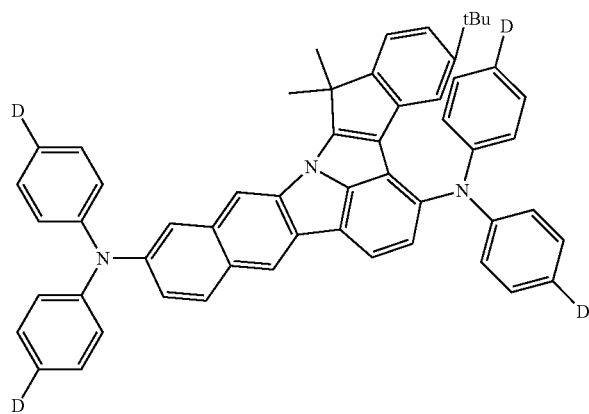
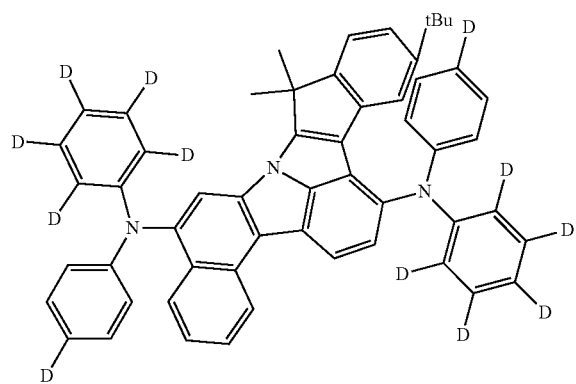
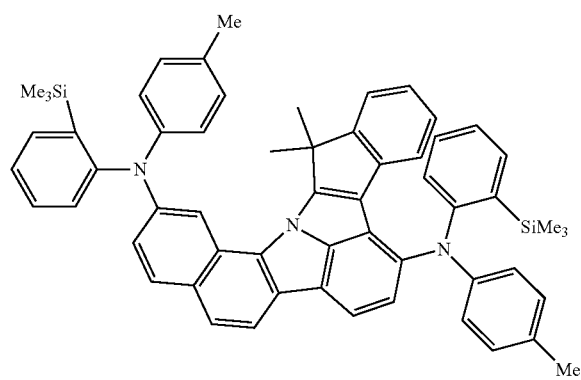

-continued
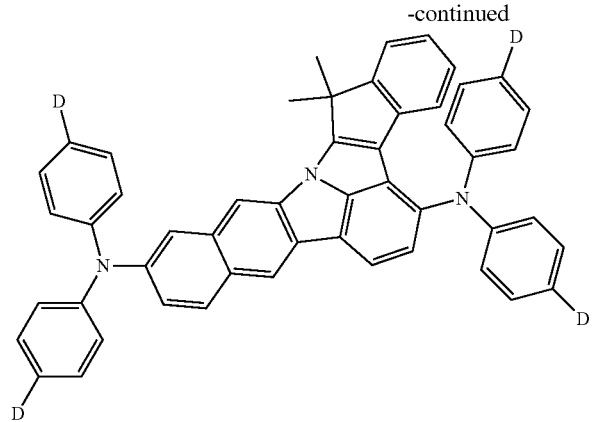
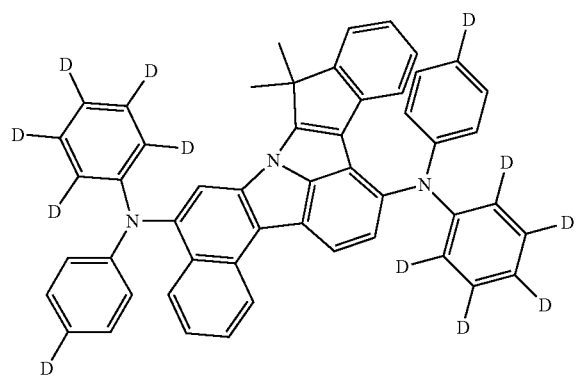
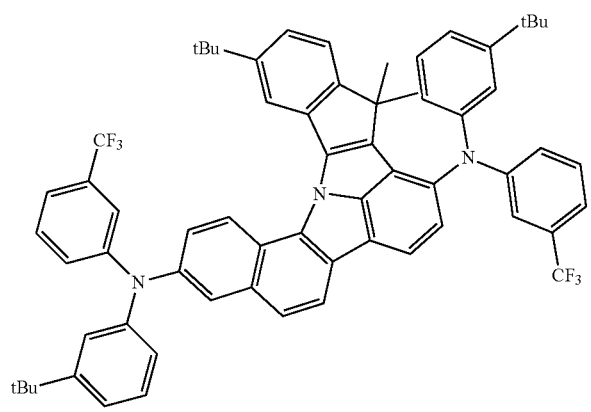
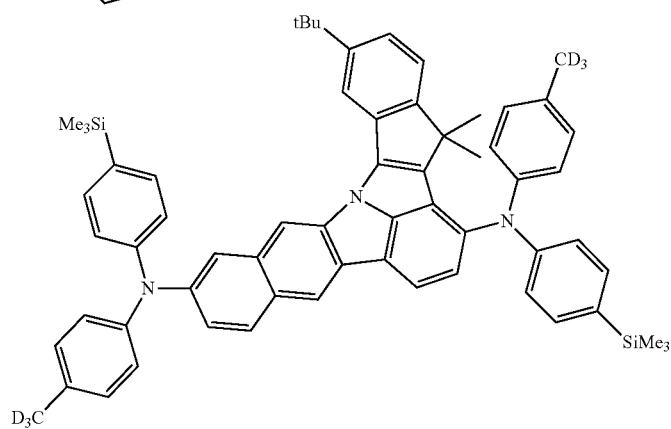

-continued
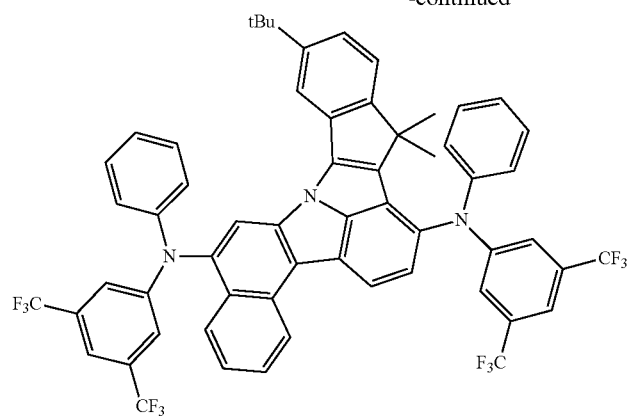
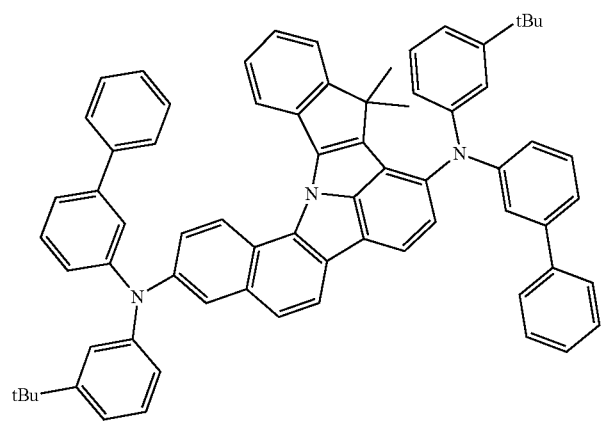
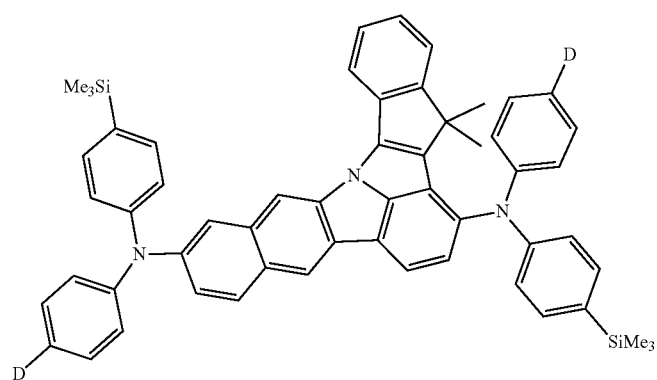
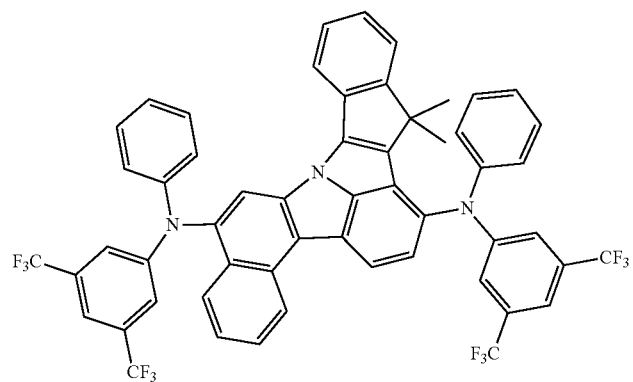

-continued
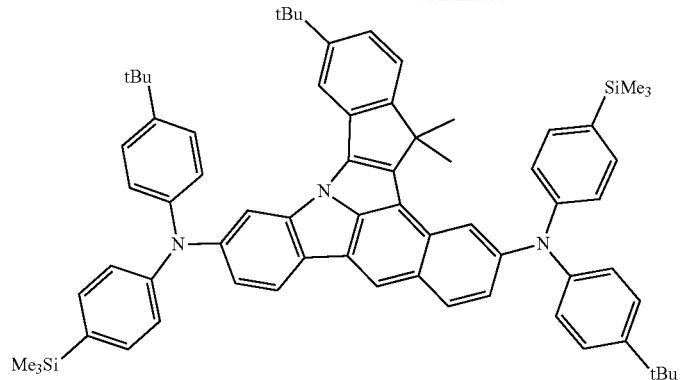
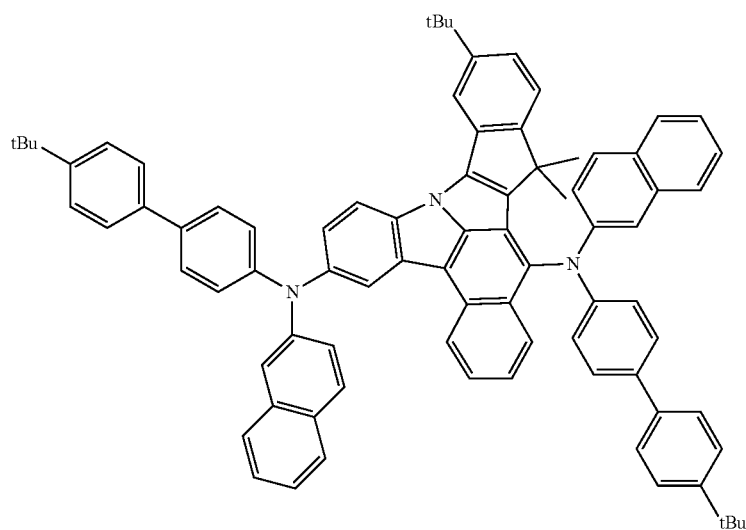
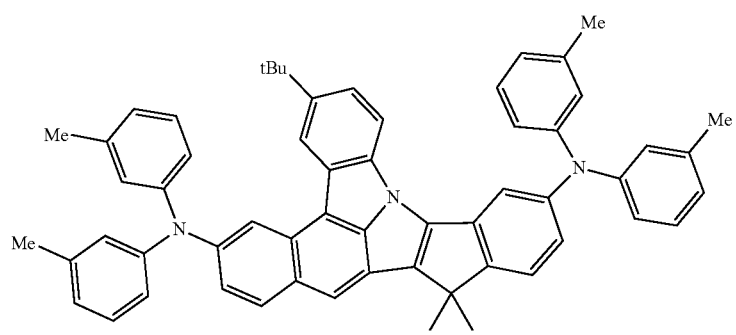
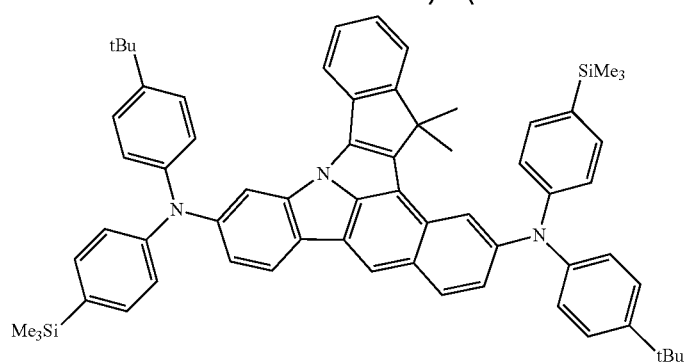

-continued
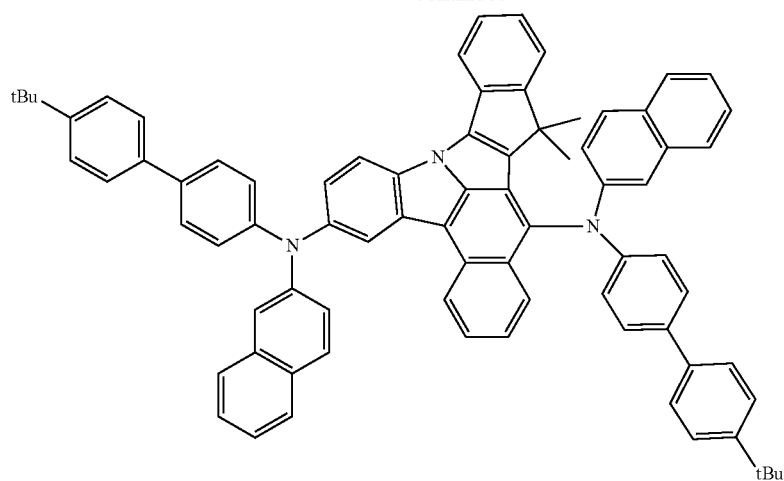
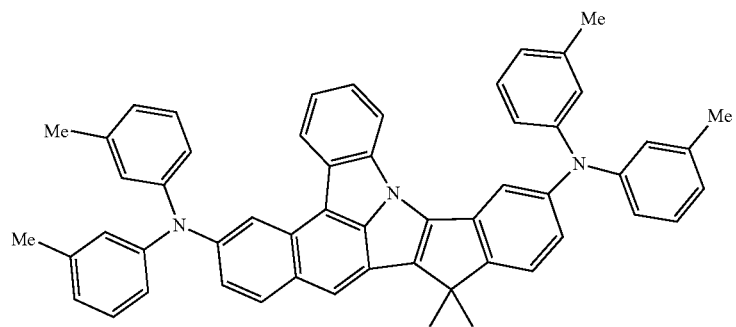
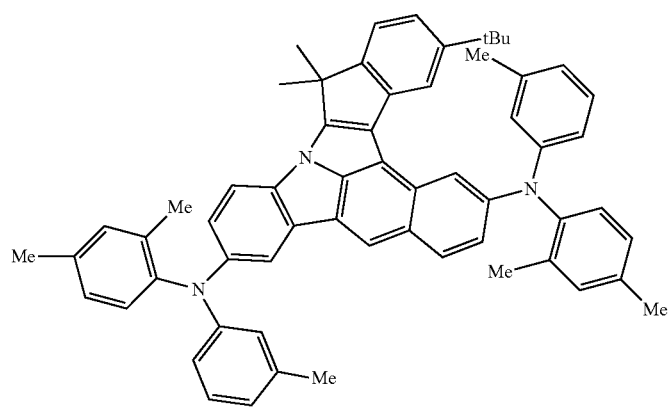
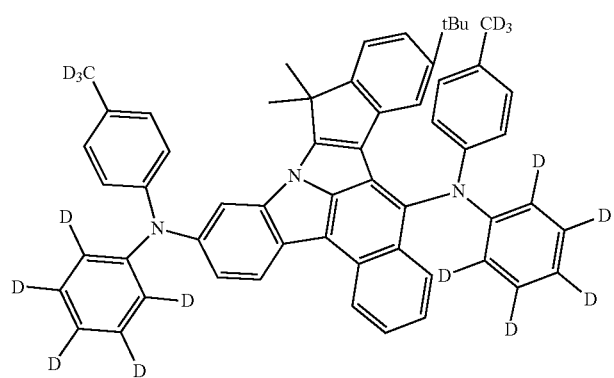

-continued
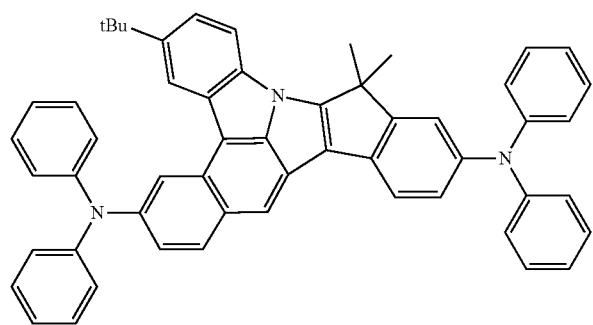
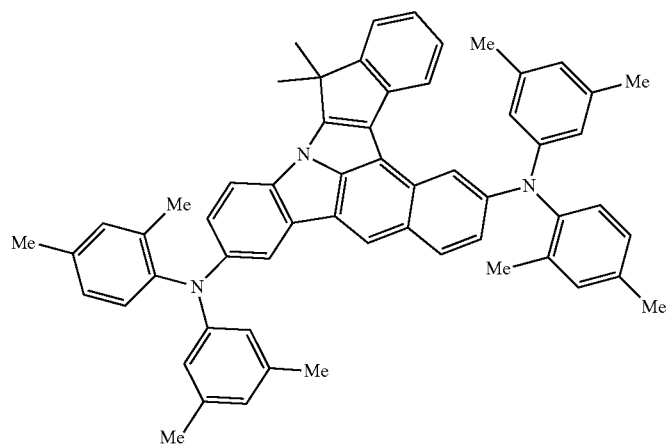
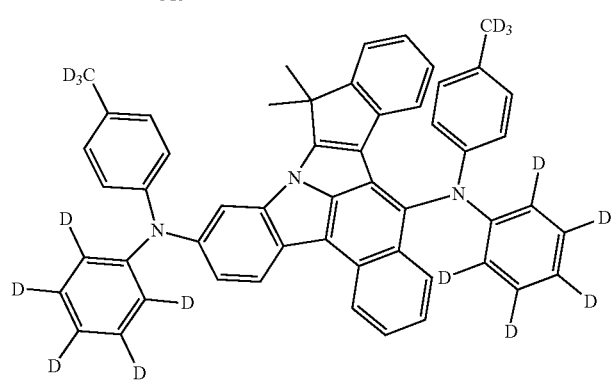
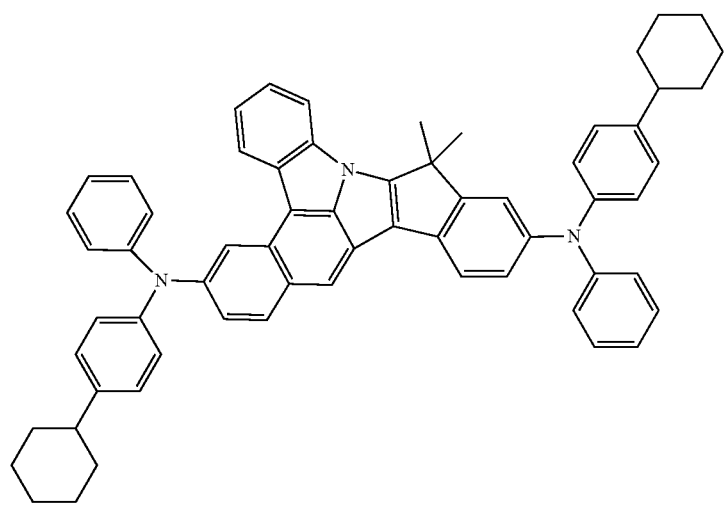

-continued
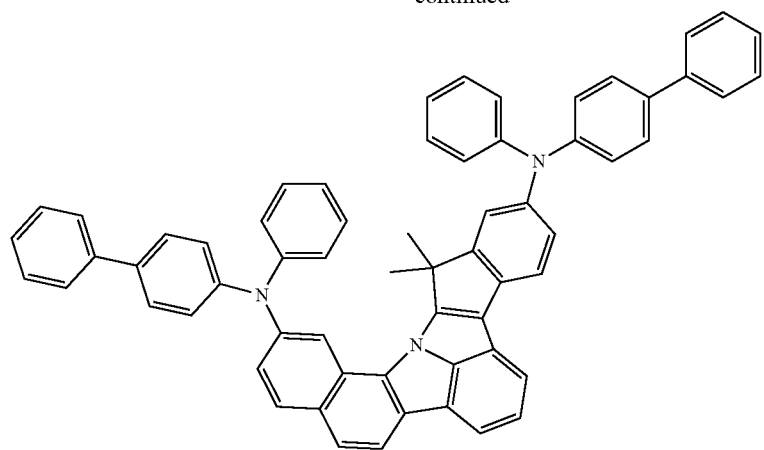
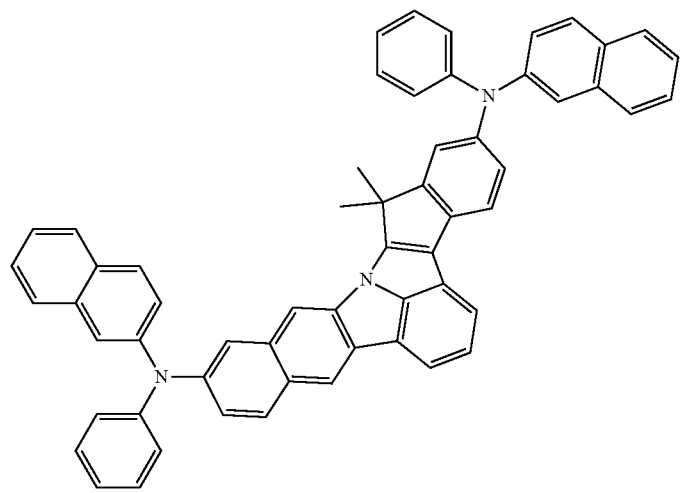
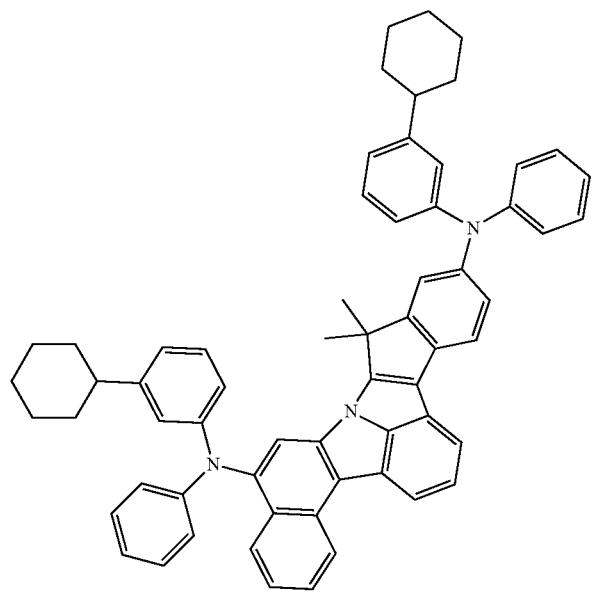

-continued
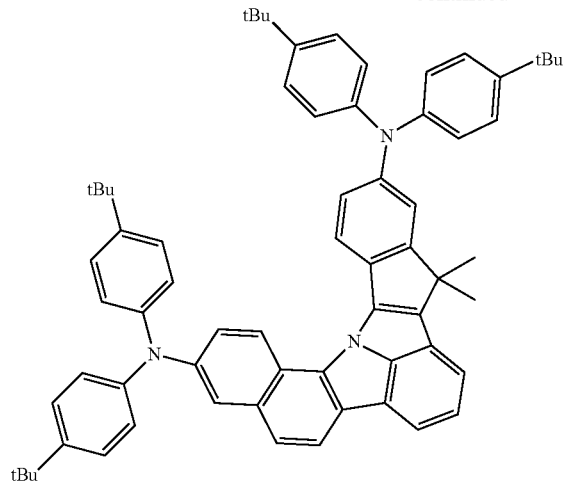
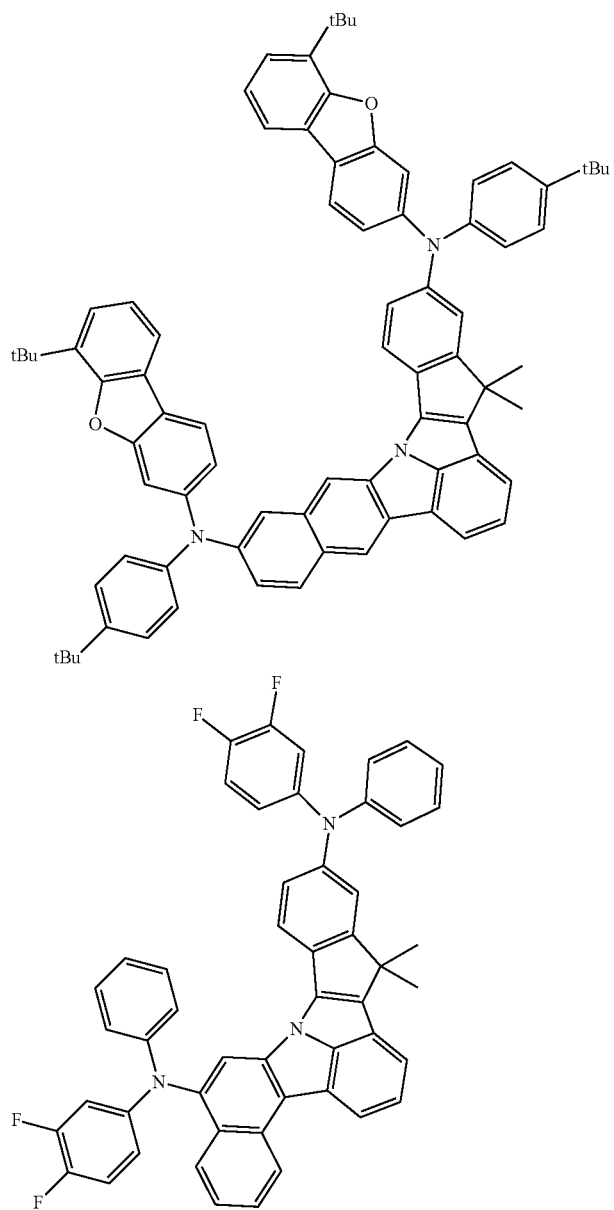

-continued
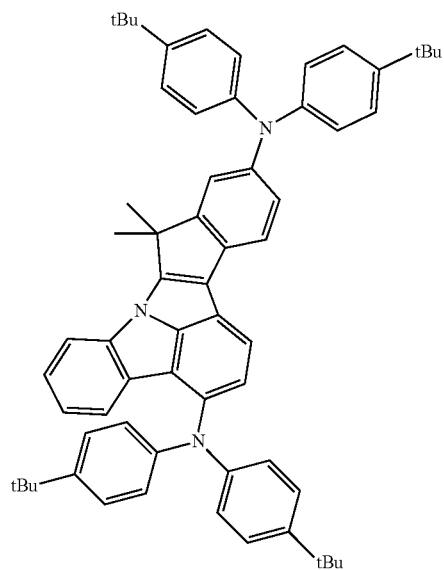
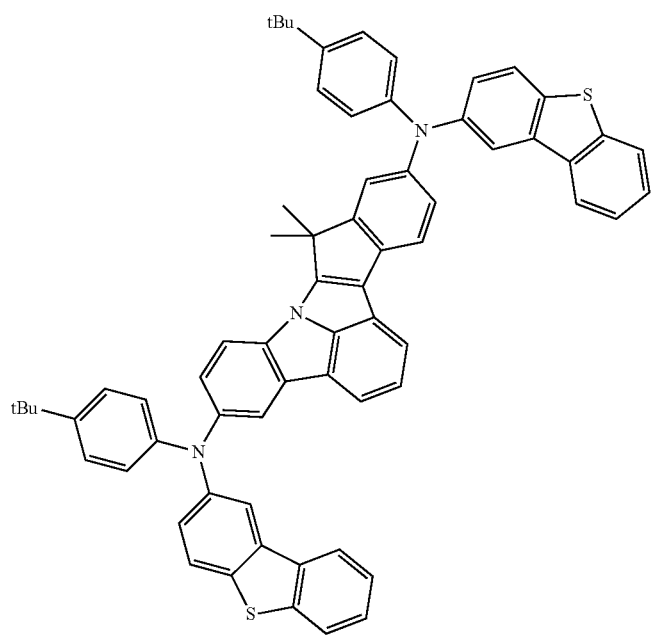

-continued
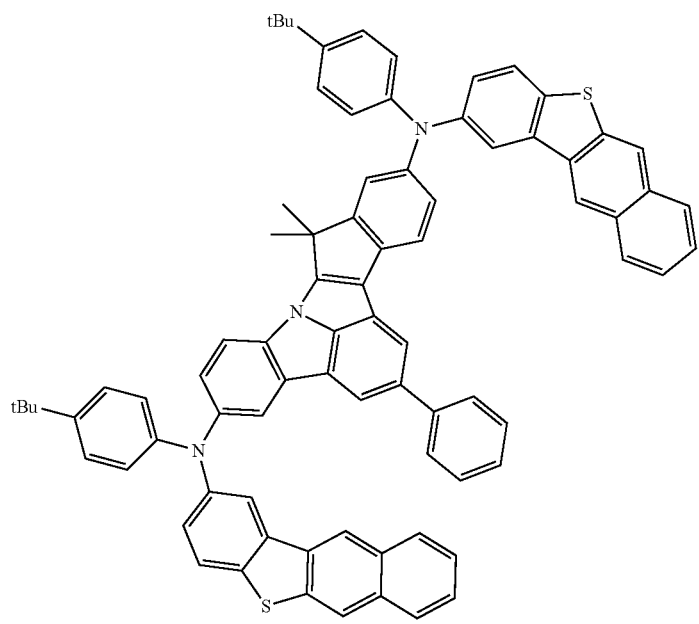
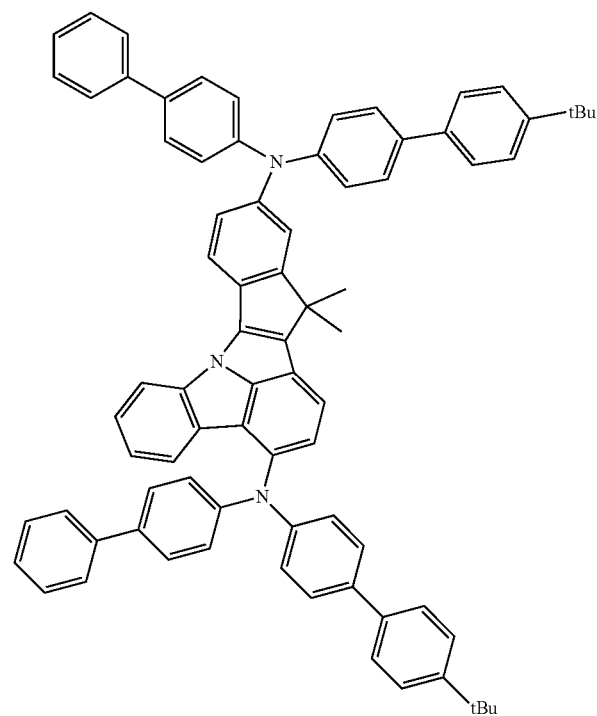

-continued
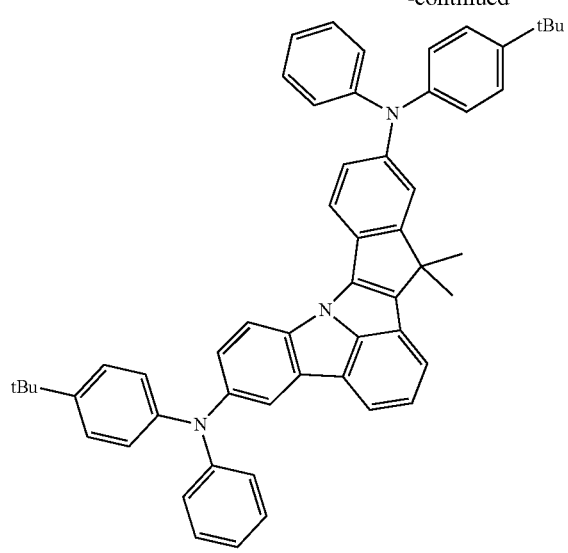
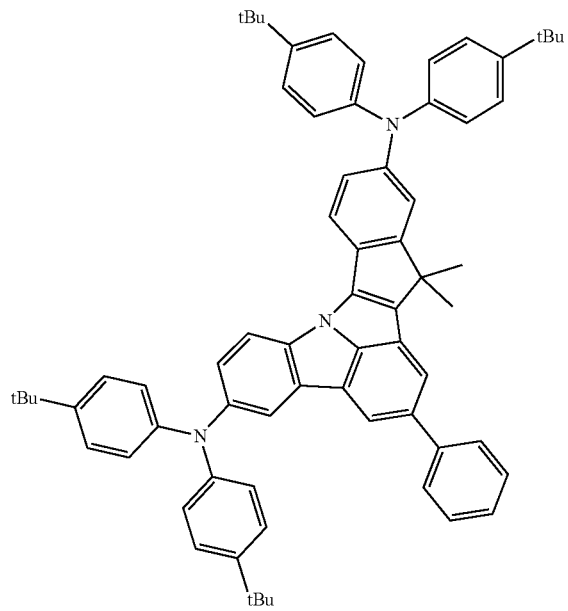
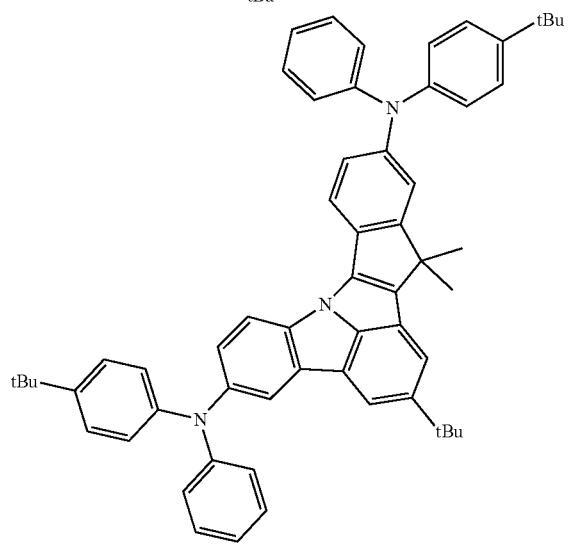

-continued

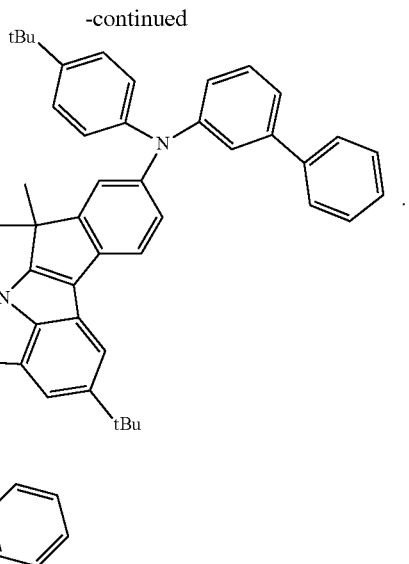

9. An organic light emitting device comprising:
a first electrode;
a second electrode provided to face the first electrode; and
an organic material layer having one or more layers provided between the first electrode and the second electrode,
wherein one or more layers of the organic material layer comprise the compound of claim 1.

10. The organic light emitting device of claim 9, wherein the organic material layer comprises a light emitting layer comprising the compound.

11. The organic light emitting device of claim 10, wherein the light emitting layer comprises a host and a dopant comprising the compound.

12. The organic light emitting device of claim 11, wherein the host comprises a compound of Formula 5:

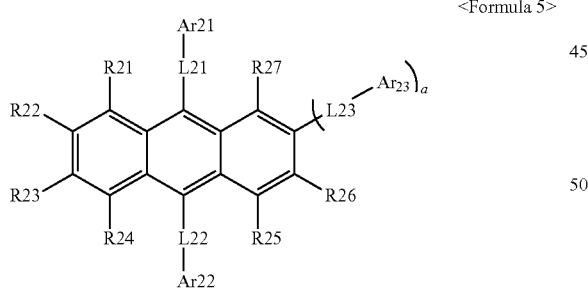

<Formula 5> wherein in Formula 5:
L21 to L23 are the same as or different from each other, and are each independently a direct bond, a substituted or unsubstituted arylene group, or a substituted or unsubstituted heteroarylene group;
R21 to R27 are the same as or different from each other, and are each independently hydrogen, deuterium, a substituted or unsubstituted alkyl group, a substituted or unsubstituted cycloalkyl group, a substituted or unsubstituted silyl group, a substituted or unsubstituted aryl group, or a substituted or unsubstituted heteroaryl group;

Ar21 to Ar23 are the same as or different from each other, and are each independently a substituted or unsubstituted aryl group or a substituted or unsubstituted heteroaryl group; and
a is 0 or 1.

13. The organic light emitting device of claim 11, wherein the host comprises a compound selected from among the following compounds:

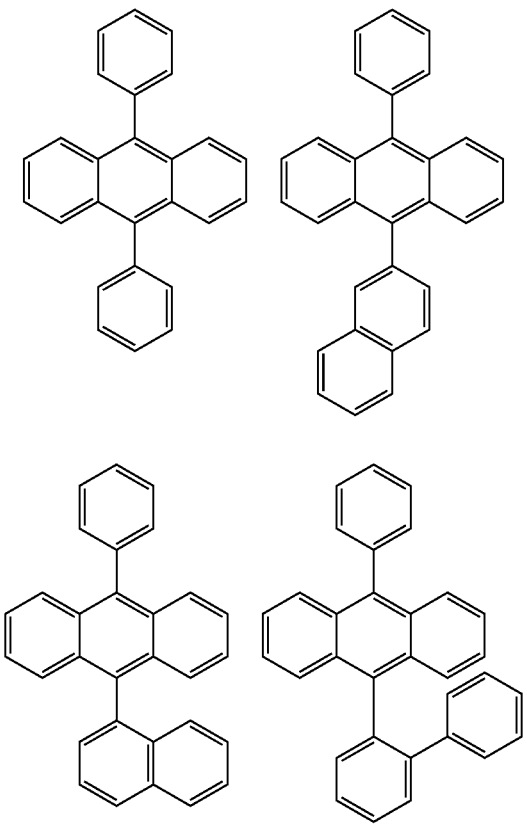

565
-continued
566
-continued
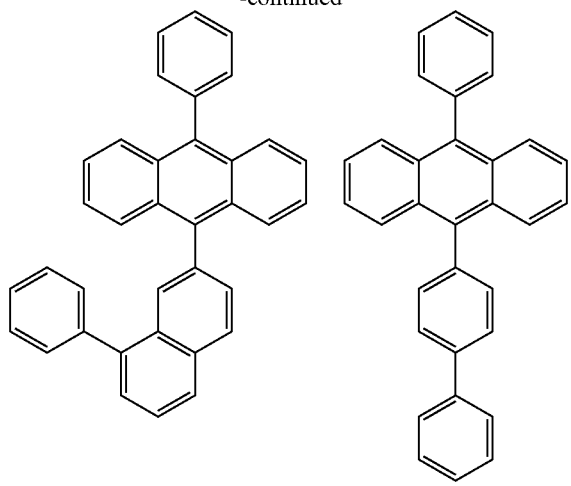
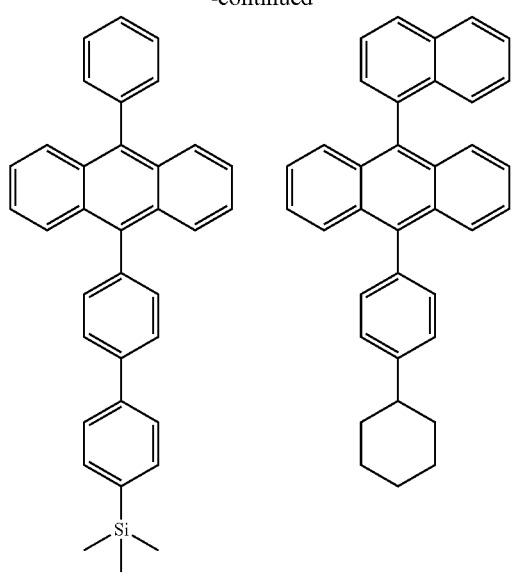
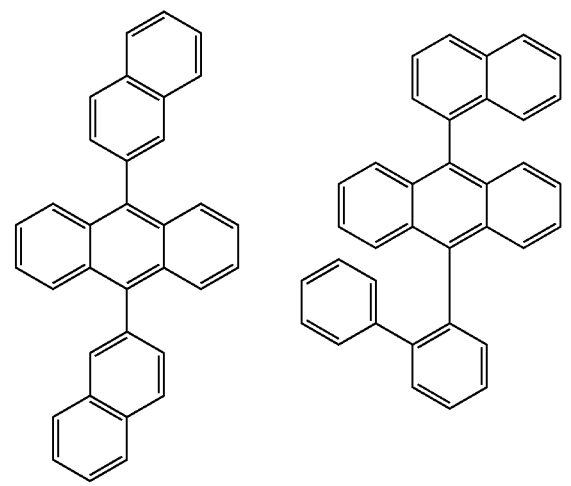
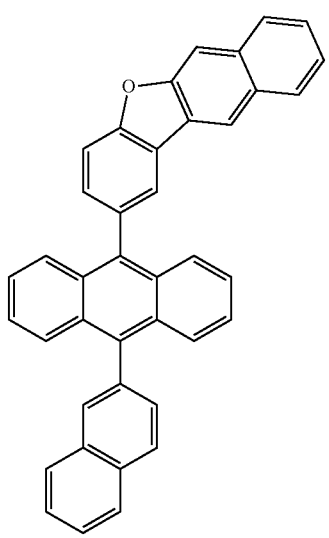
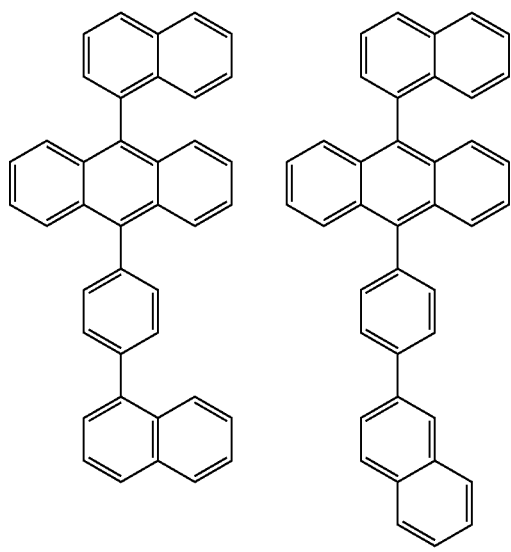
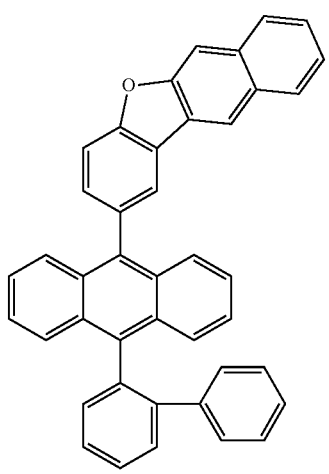

567
-continued
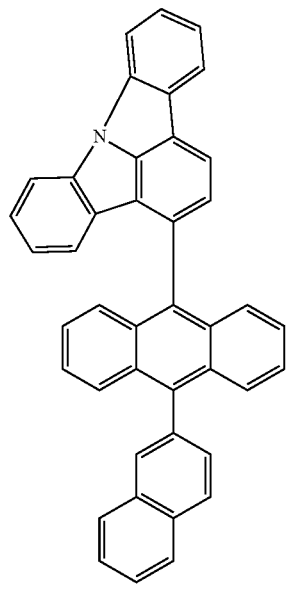
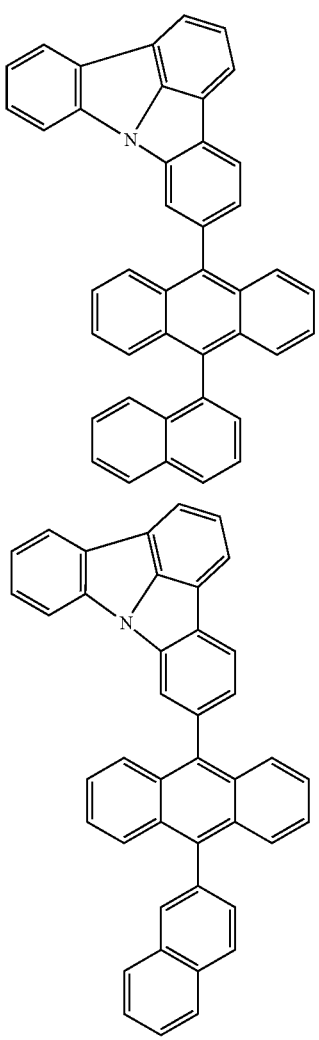
568
-continued
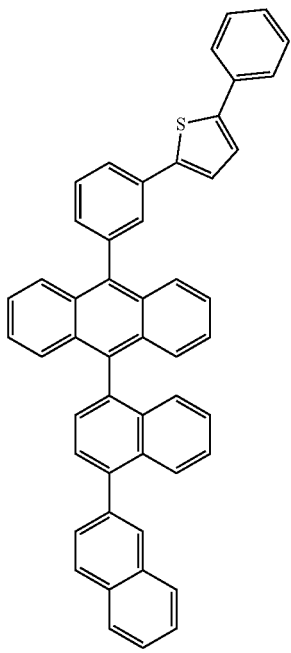
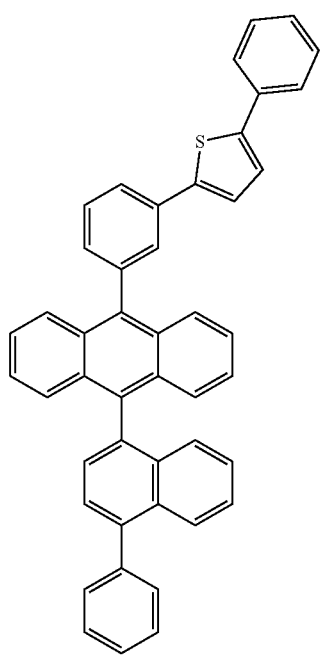

569
-continued
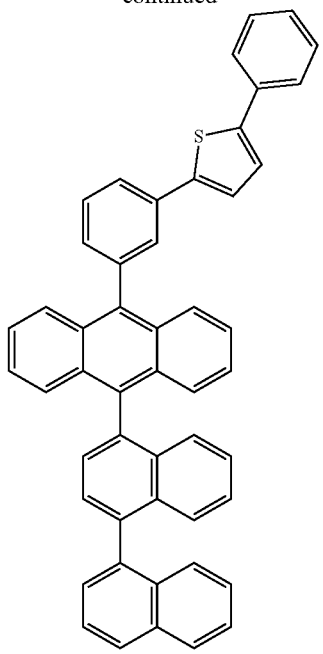
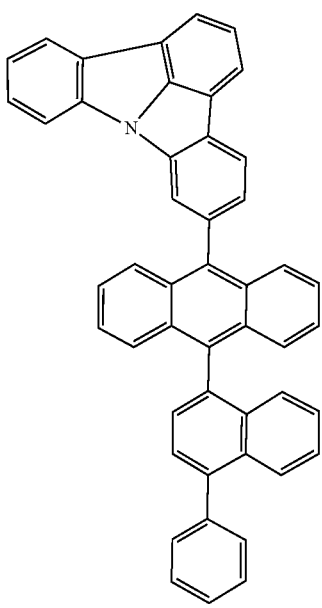
570
-continued
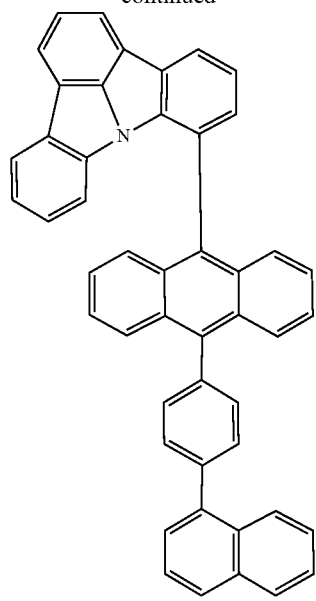
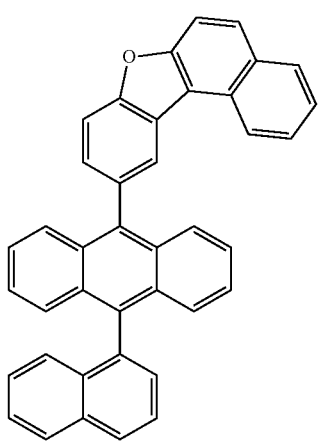
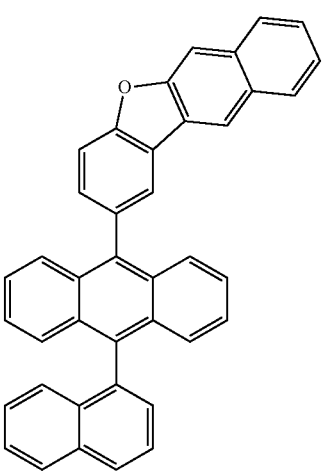

571
-continued
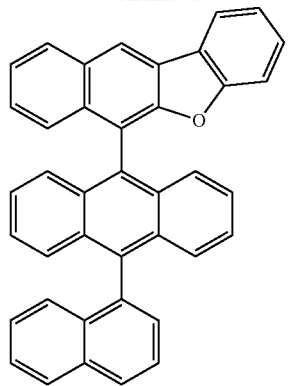
572
-continued
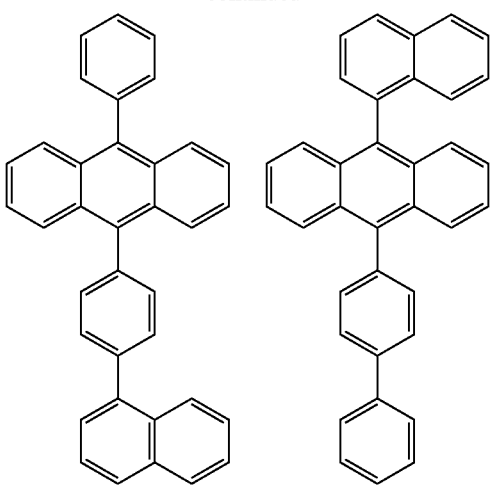
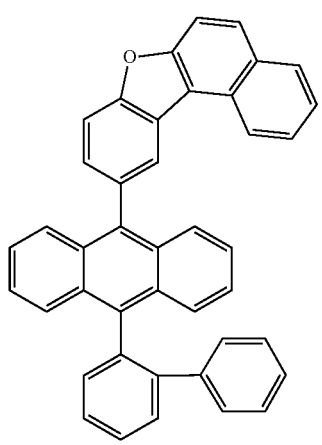
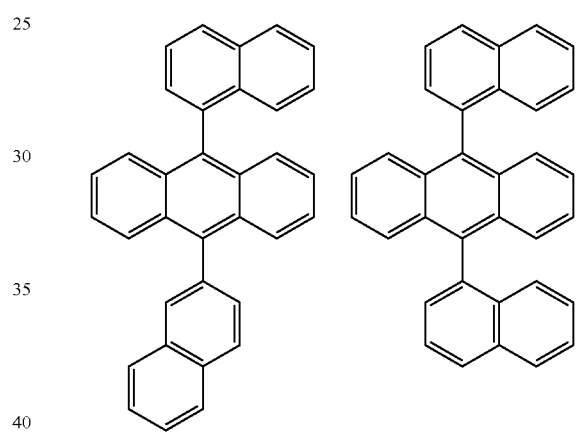
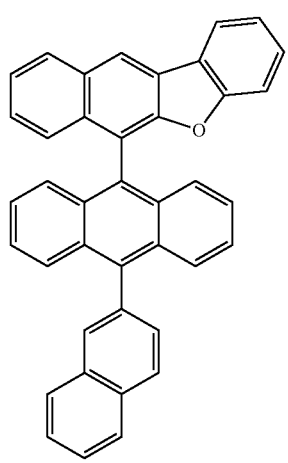
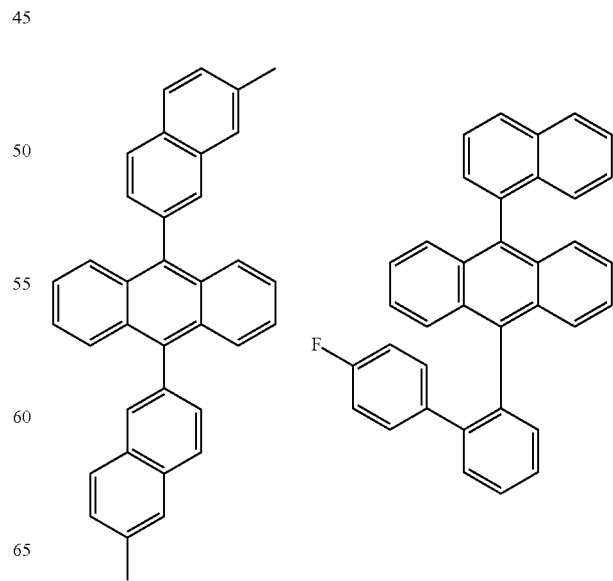

573
-continued
574
-continued
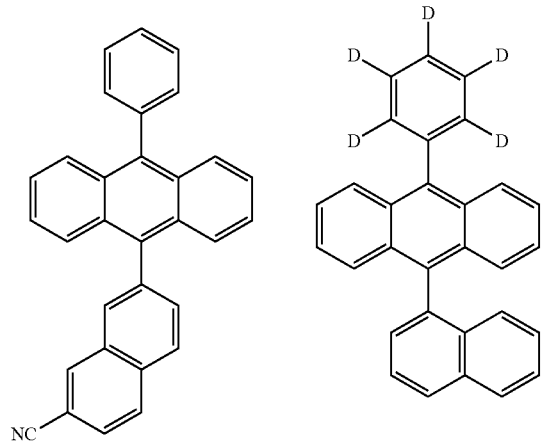
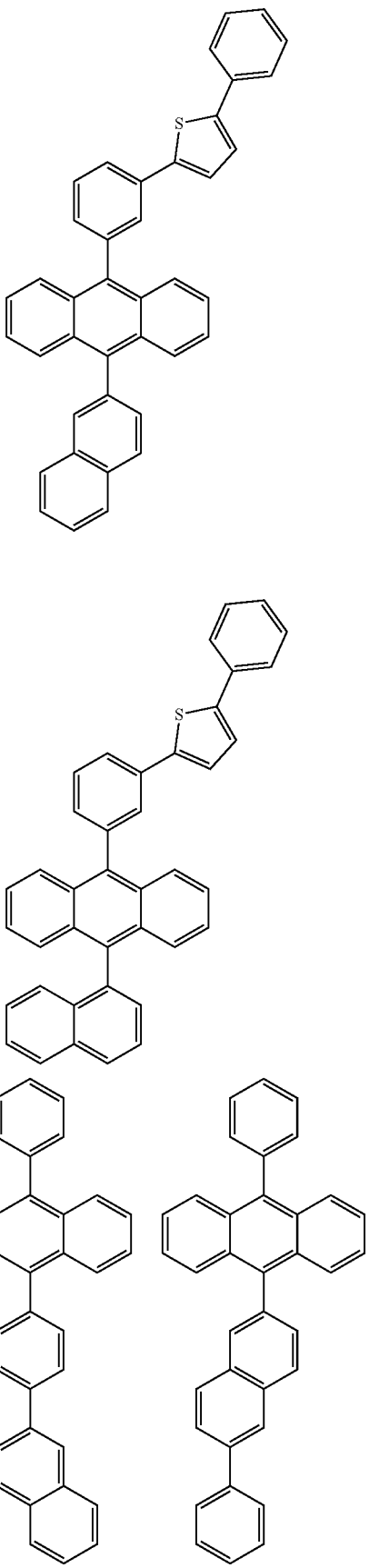

575
-continued
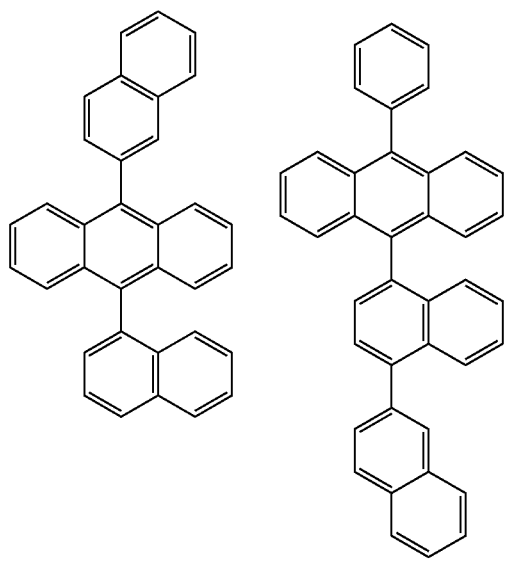
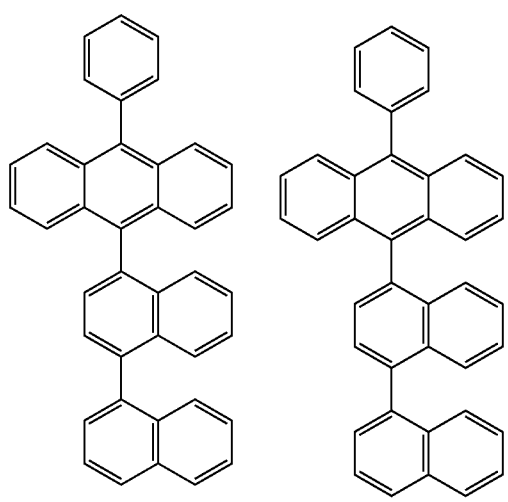
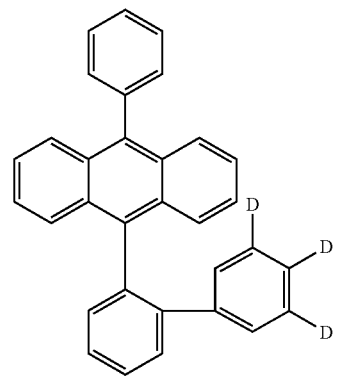
576
-continued
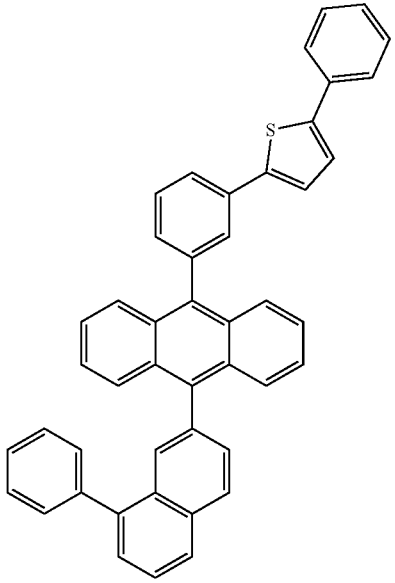
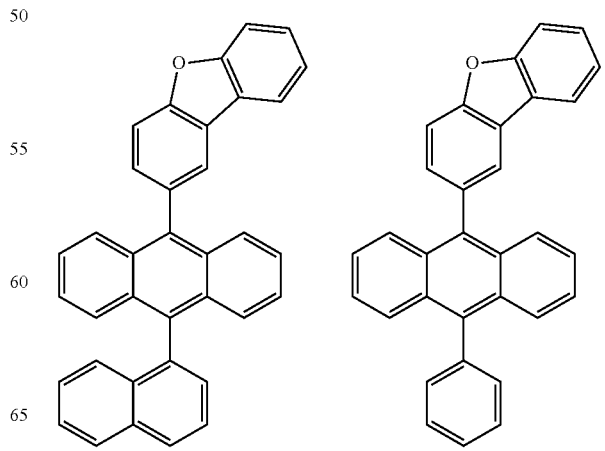
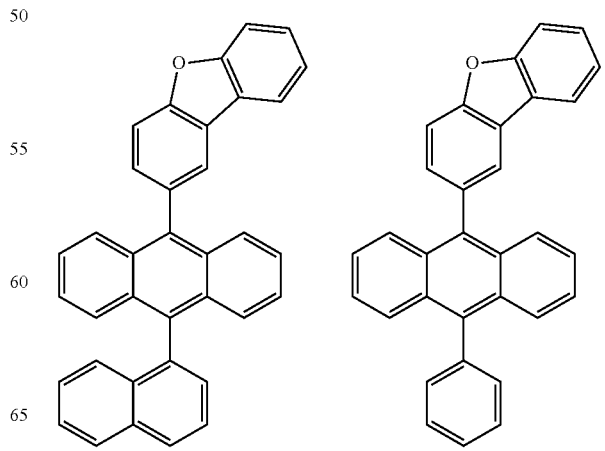

577
-continued
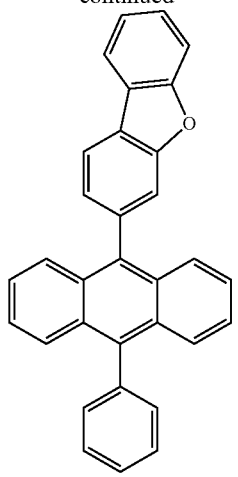
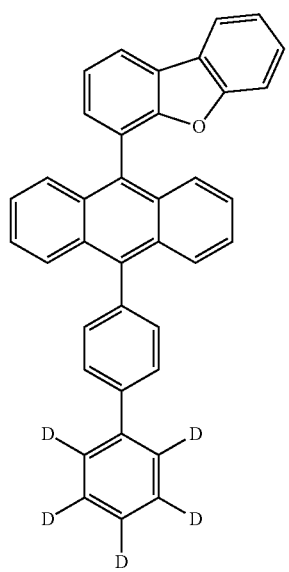
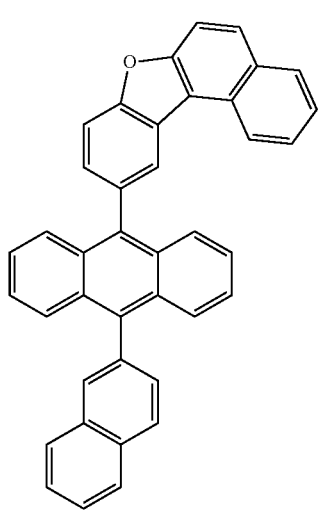
578
-continued
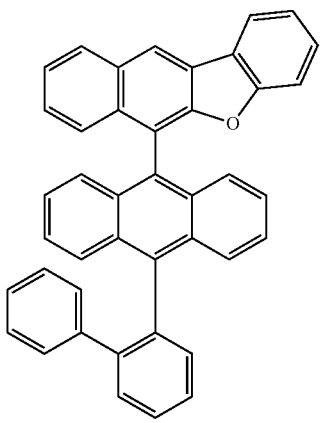
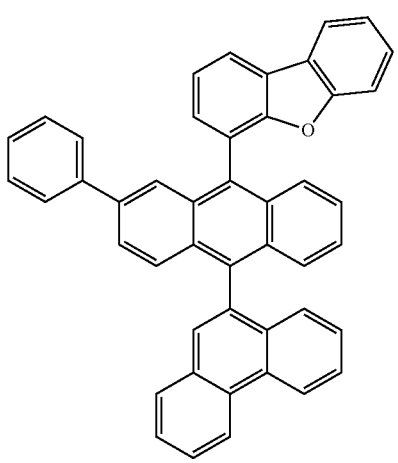
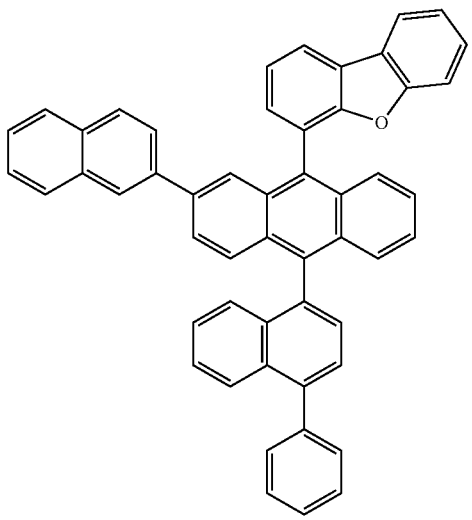

579
-continued
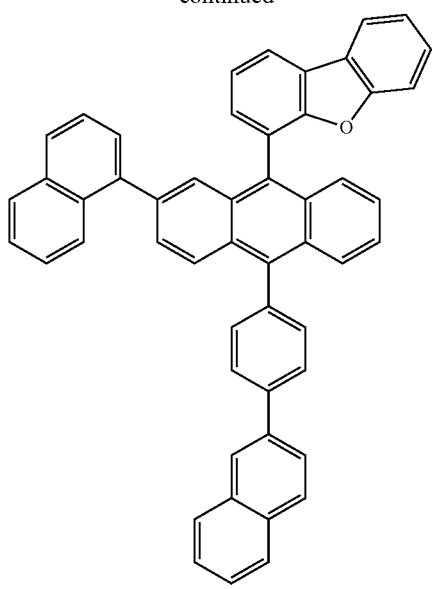
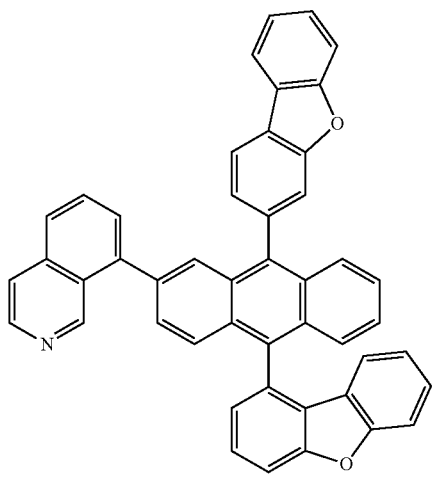
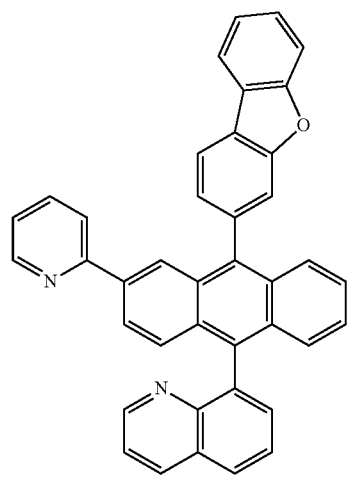
580
-continued
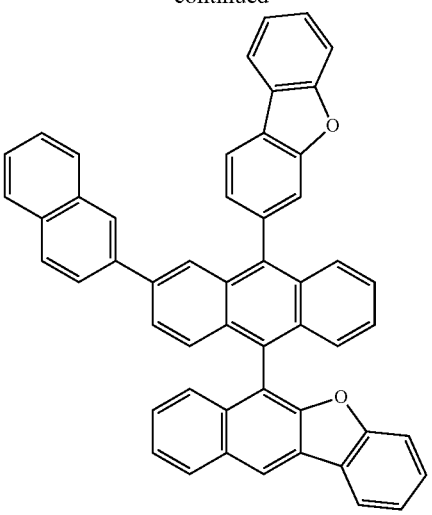
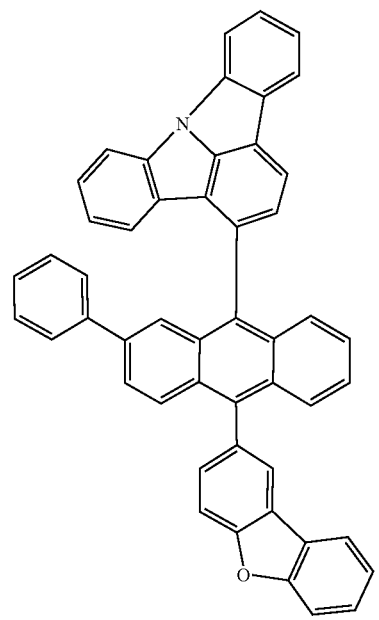
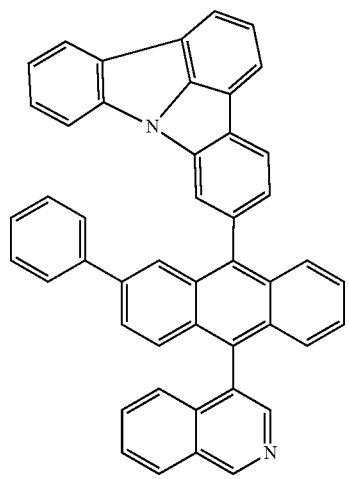

581
-continued
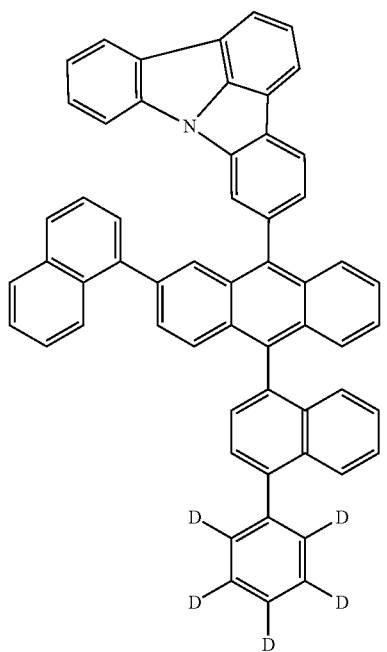
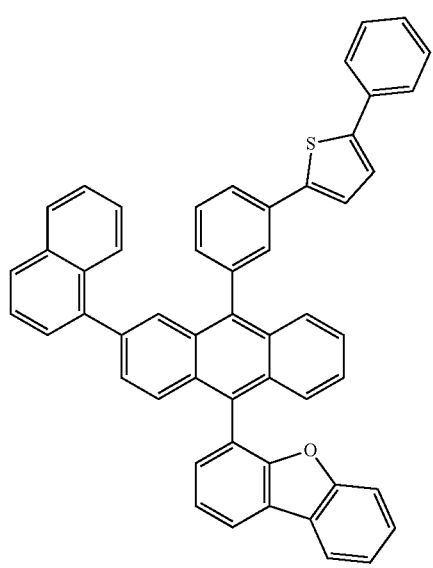
582
-continued
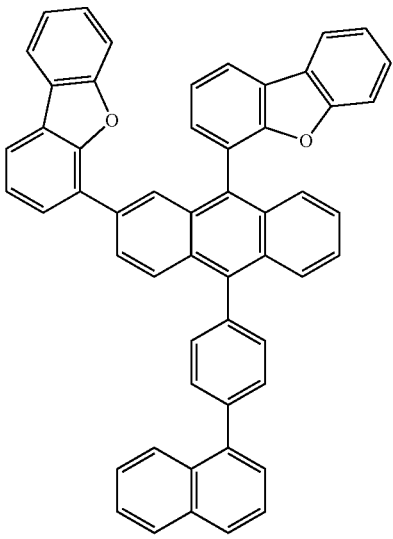
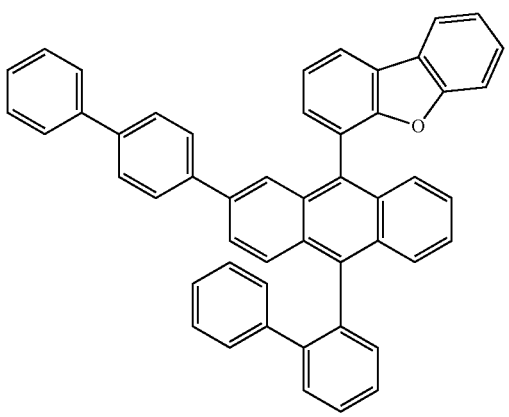

583
-continued
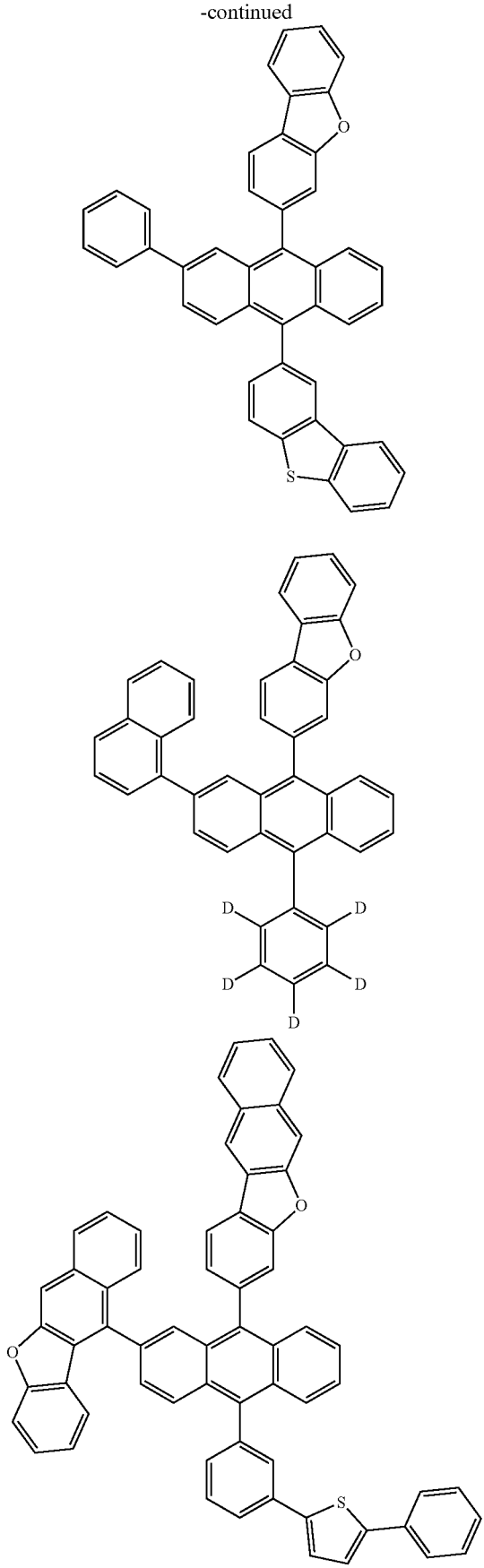
584
-continued
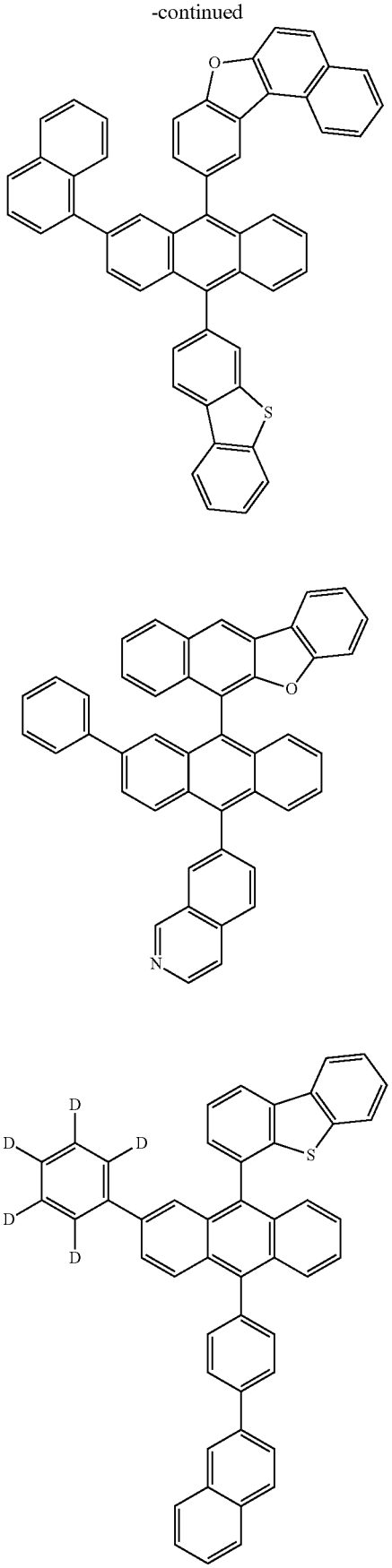

585
-continued
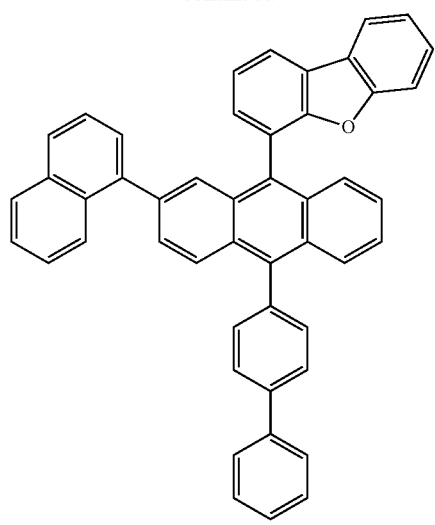
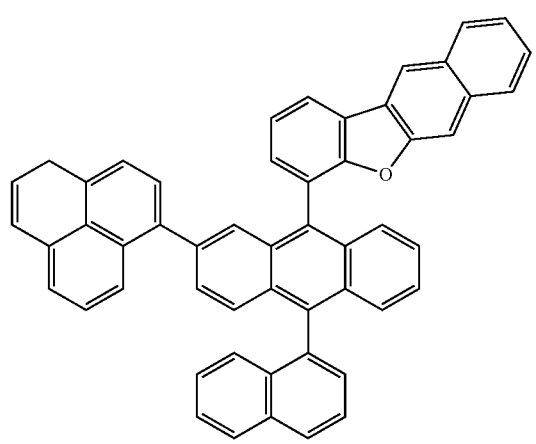
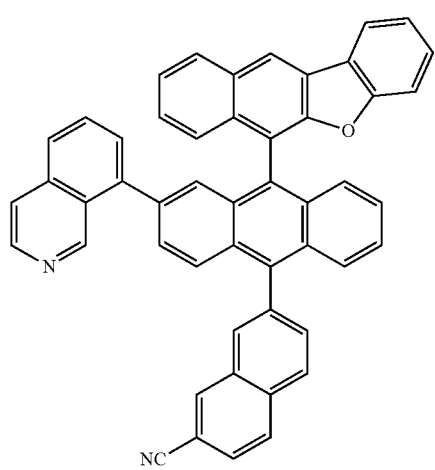
586
-continued
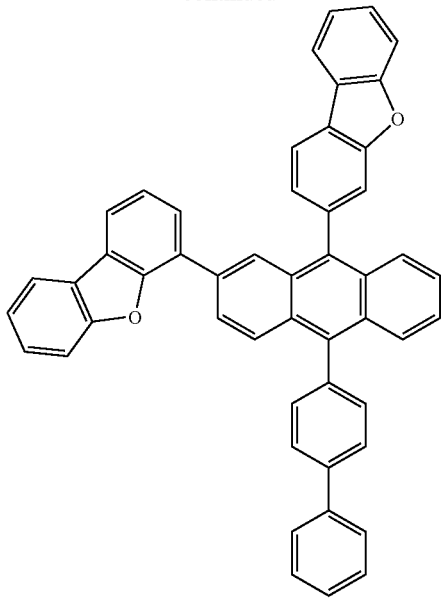
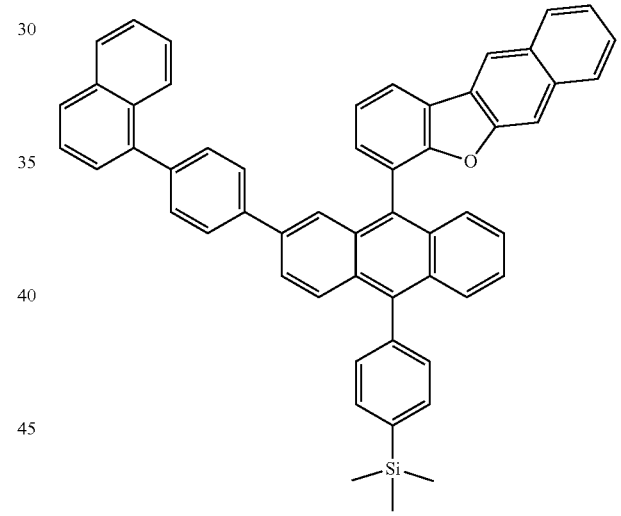
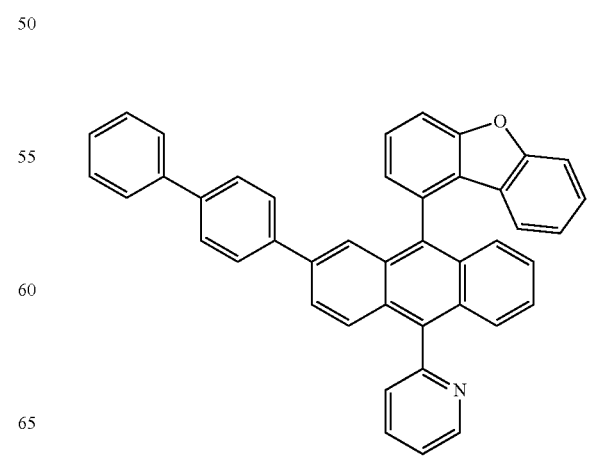

587
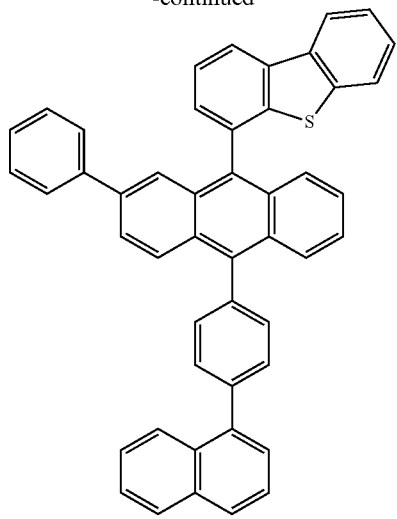
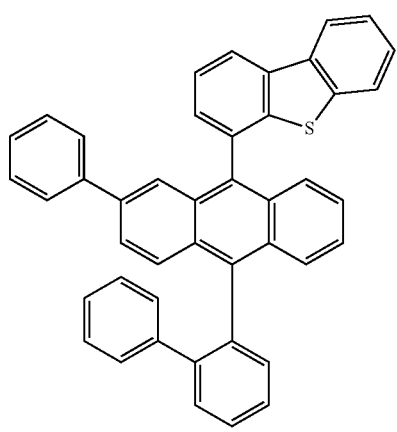
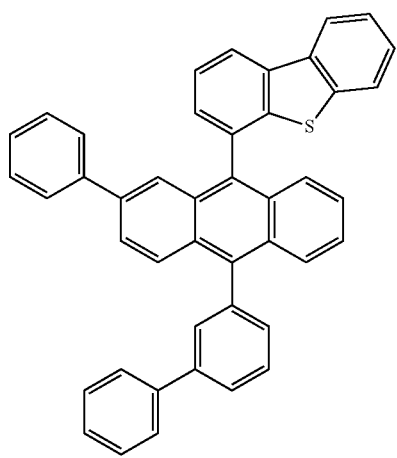
588
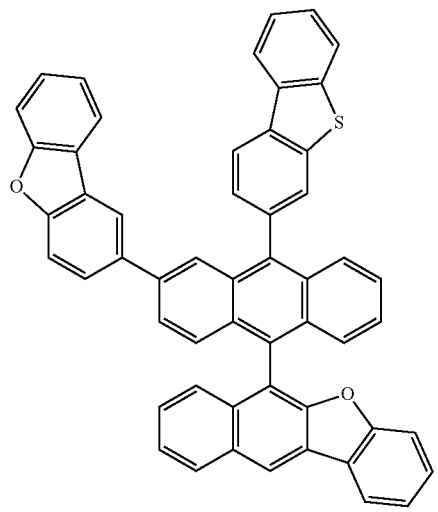
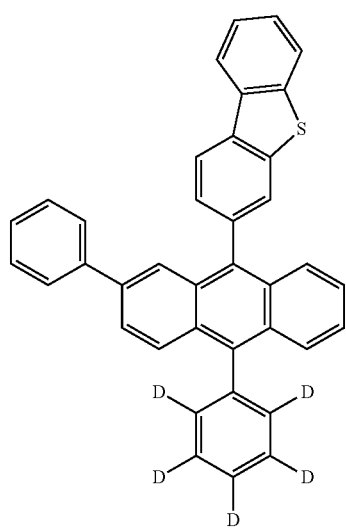
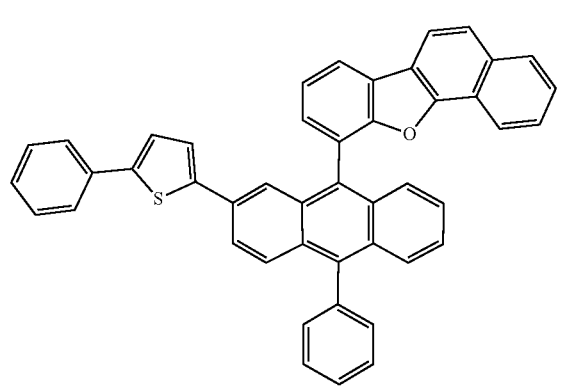

589
-continued
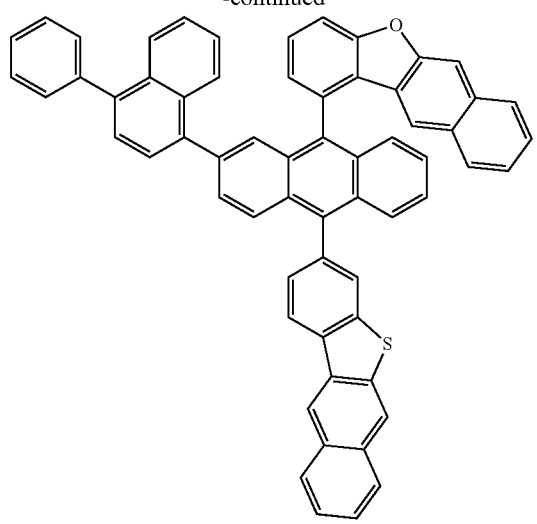
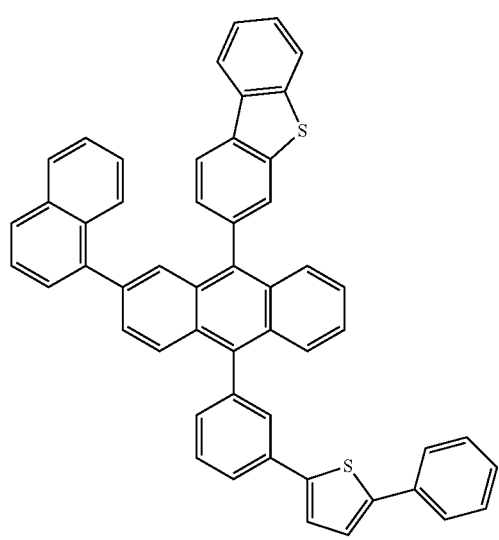
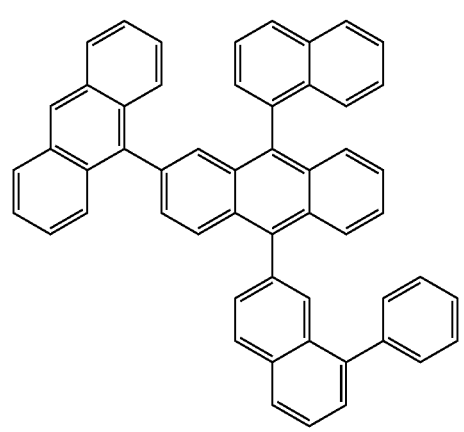
590
-continued
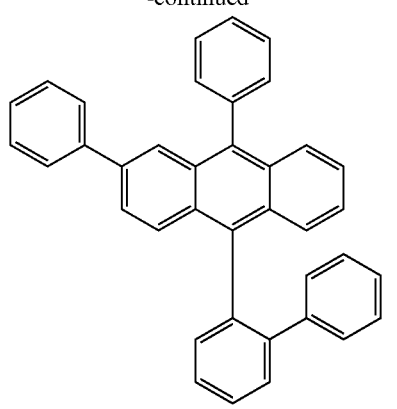
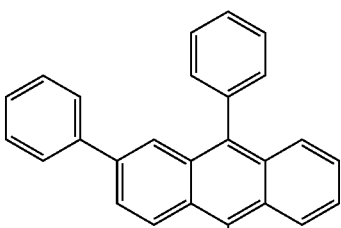
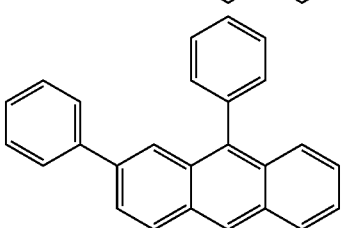
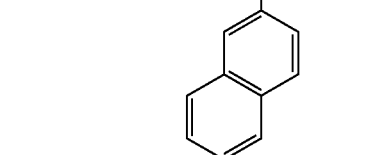
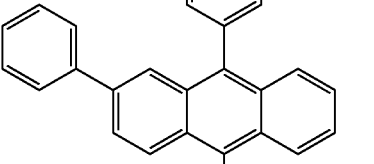

591
-continued
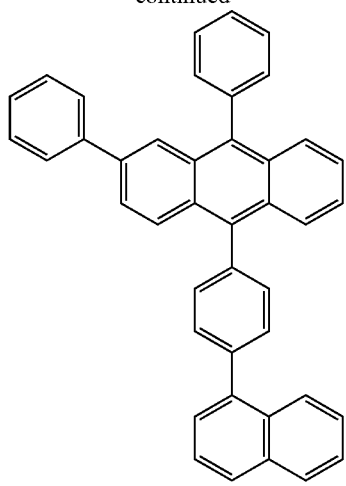
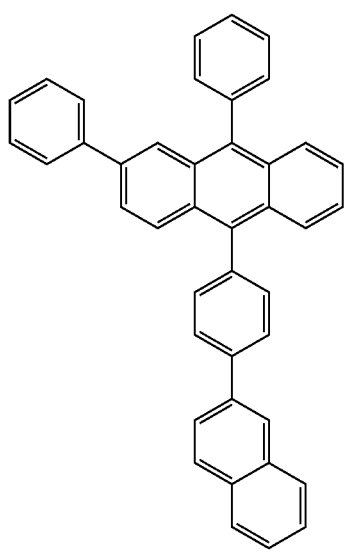
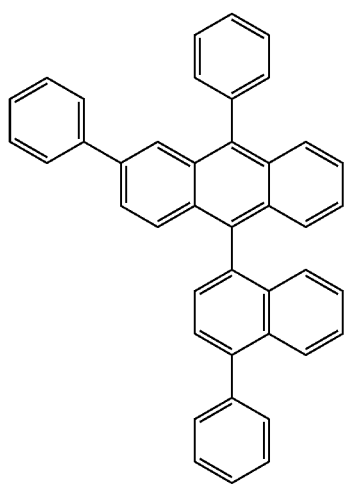
592
-continued
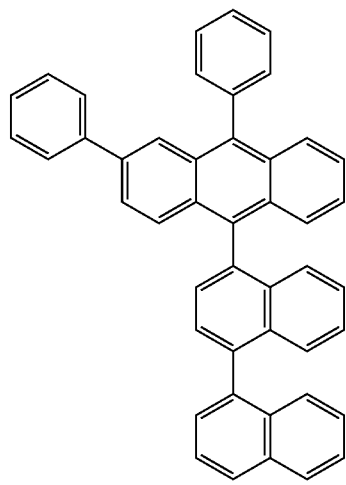
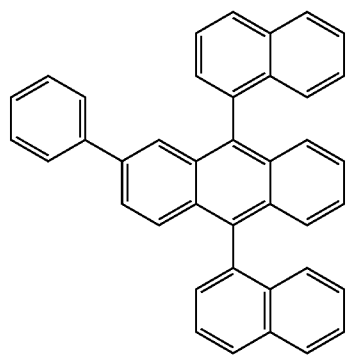
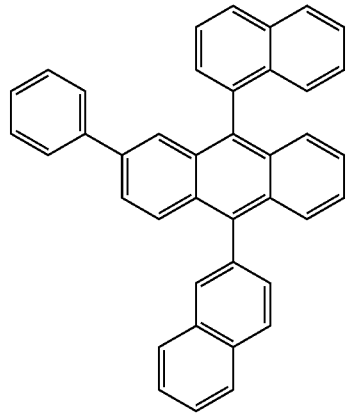
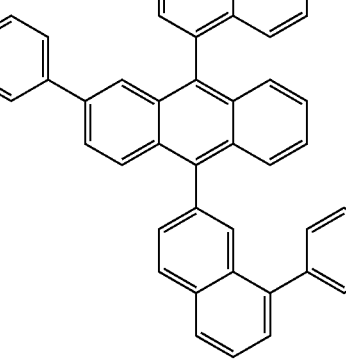

593
-continued
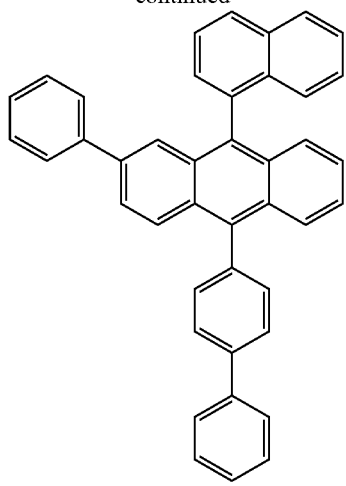
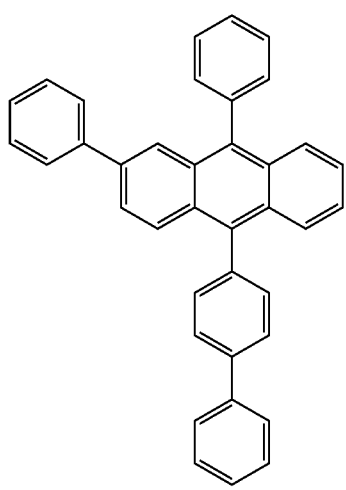
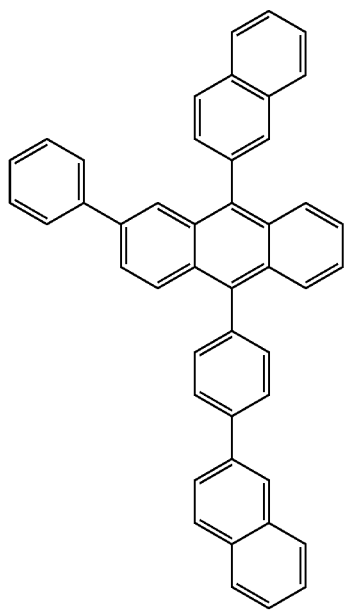
594
-continued
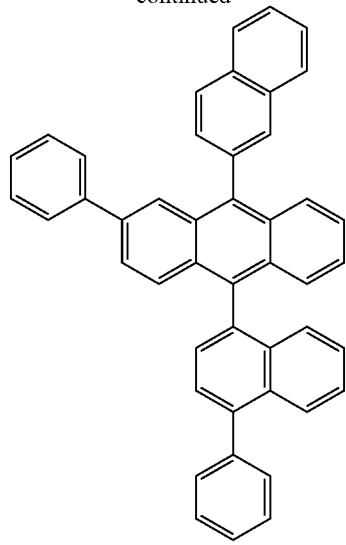
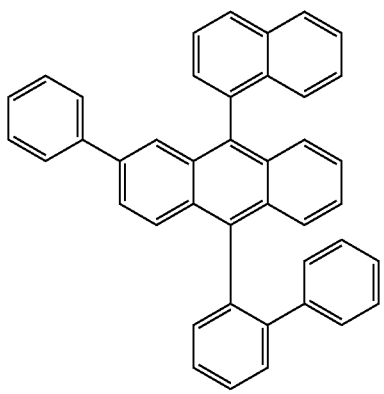
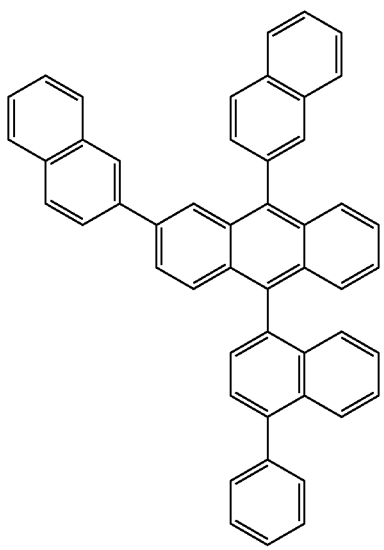

595 -continued
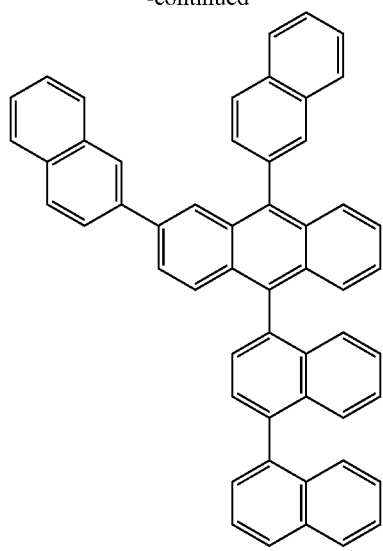
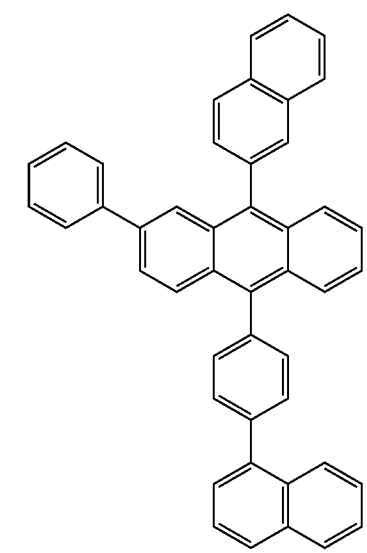
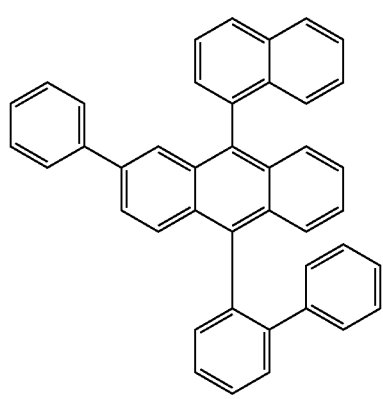
596 -continued
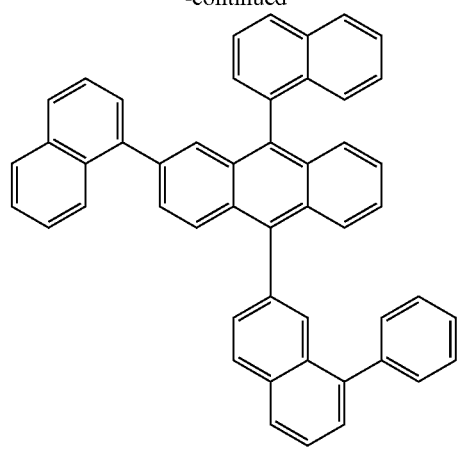
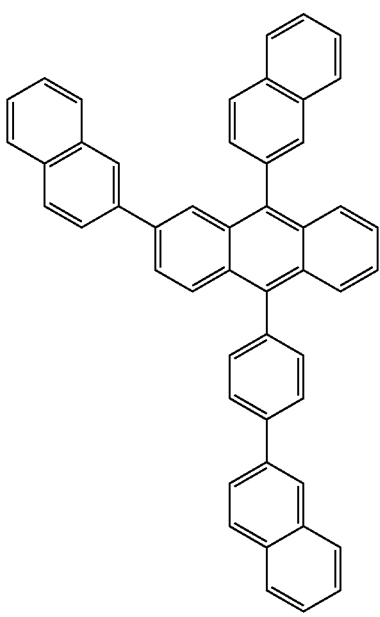
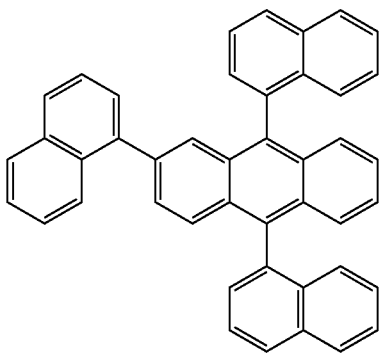

597
-continued
598
-continued
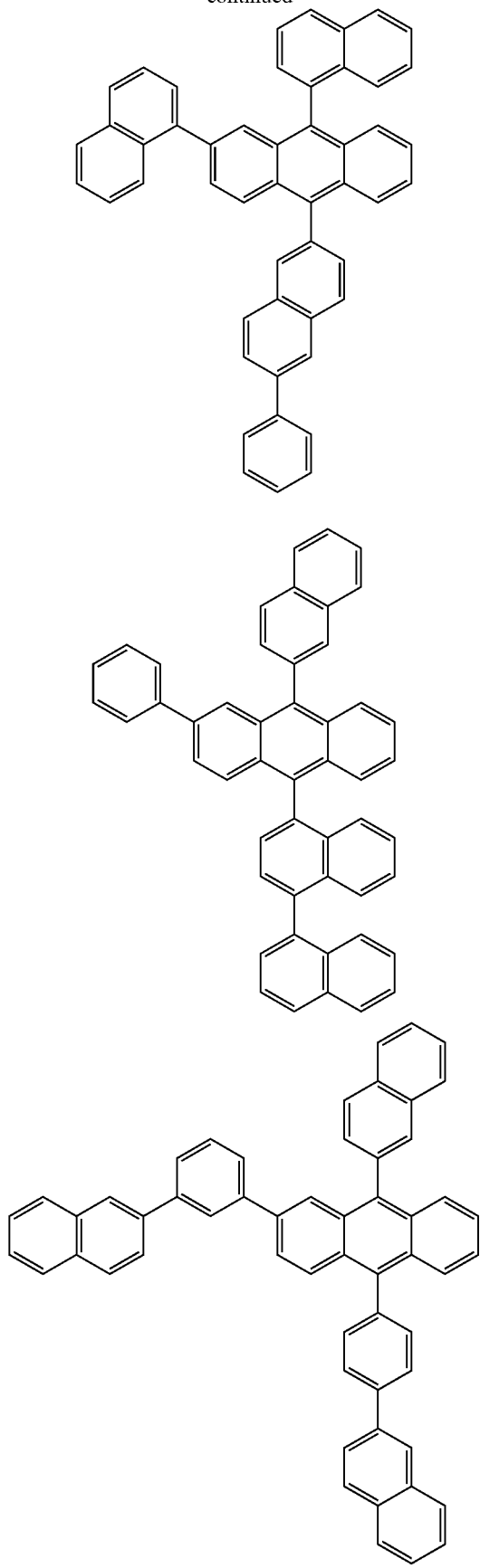
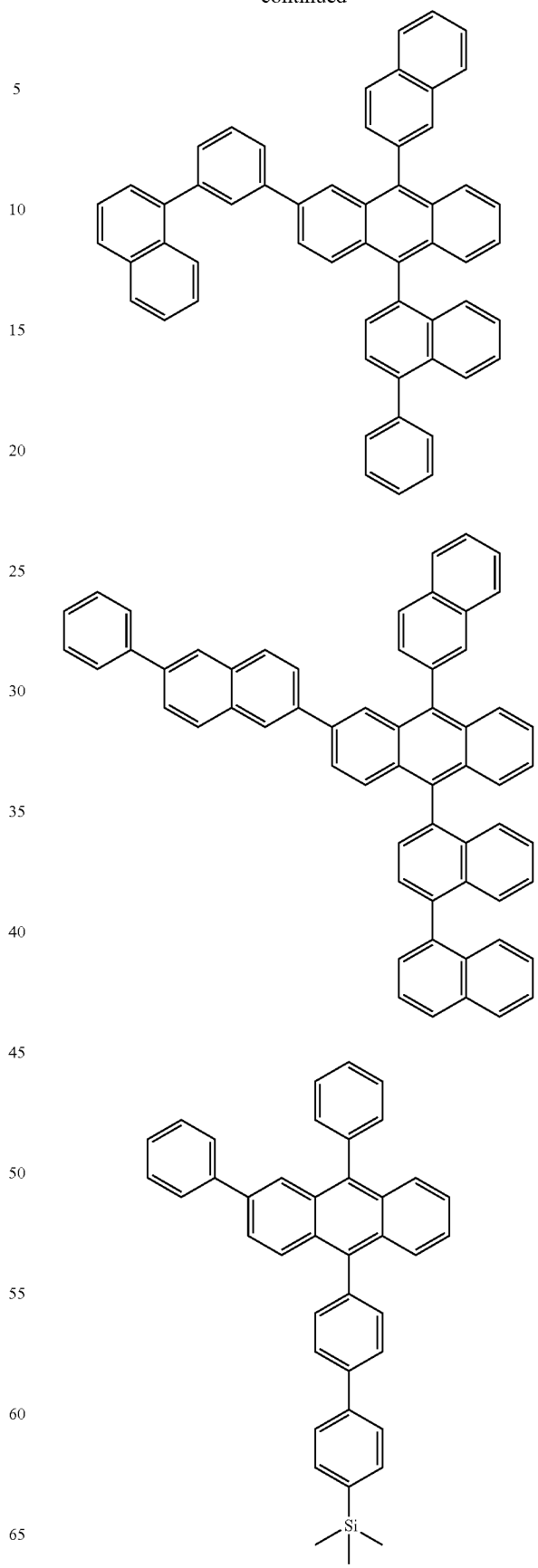

599
-continued
600
-continued
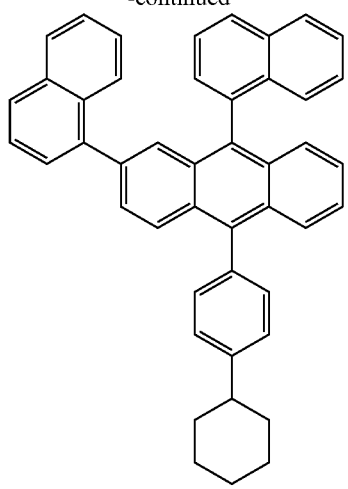
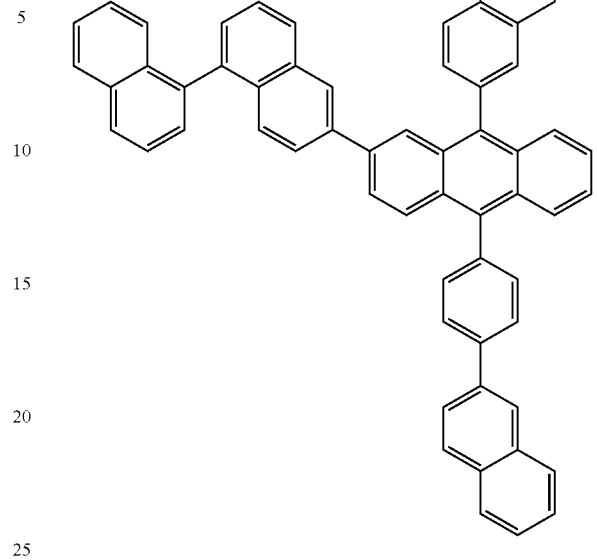
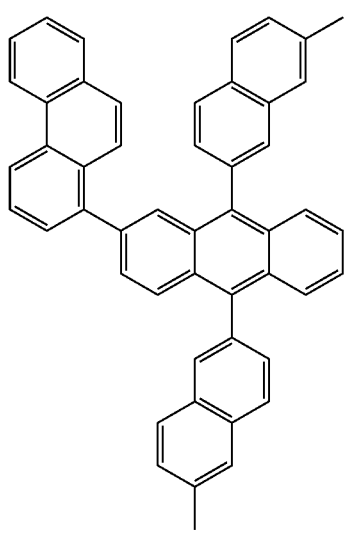
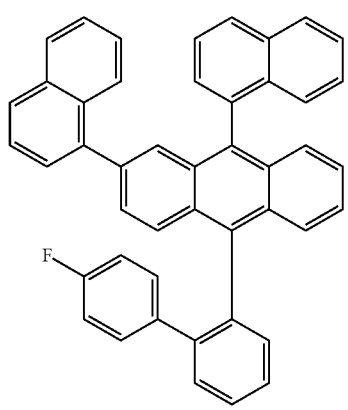

601
-continued
602
-continued
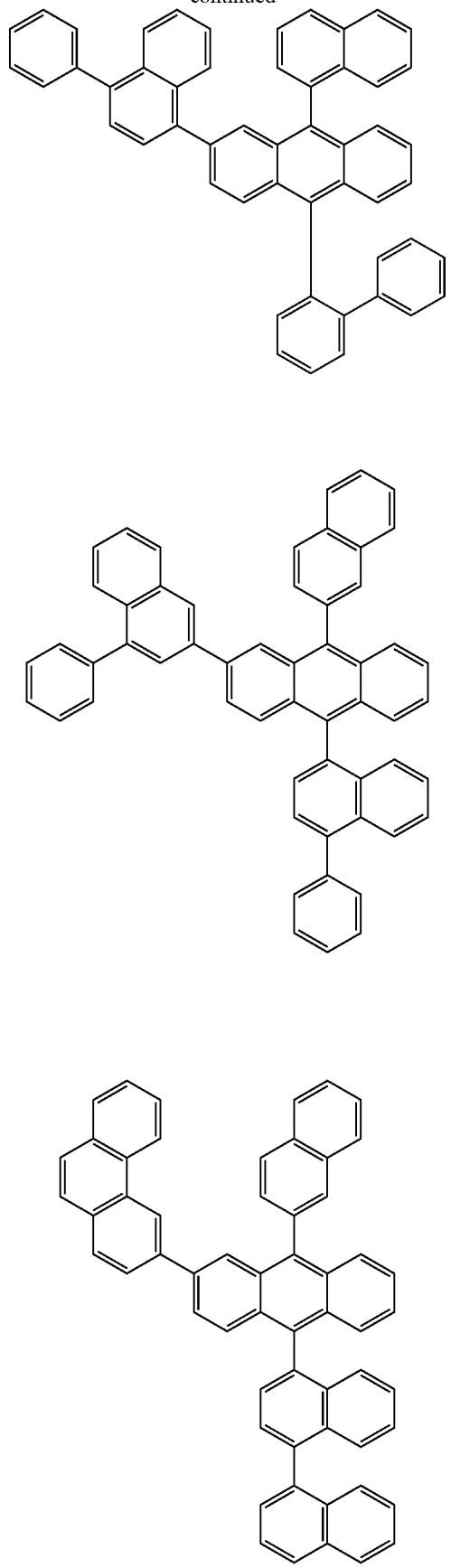
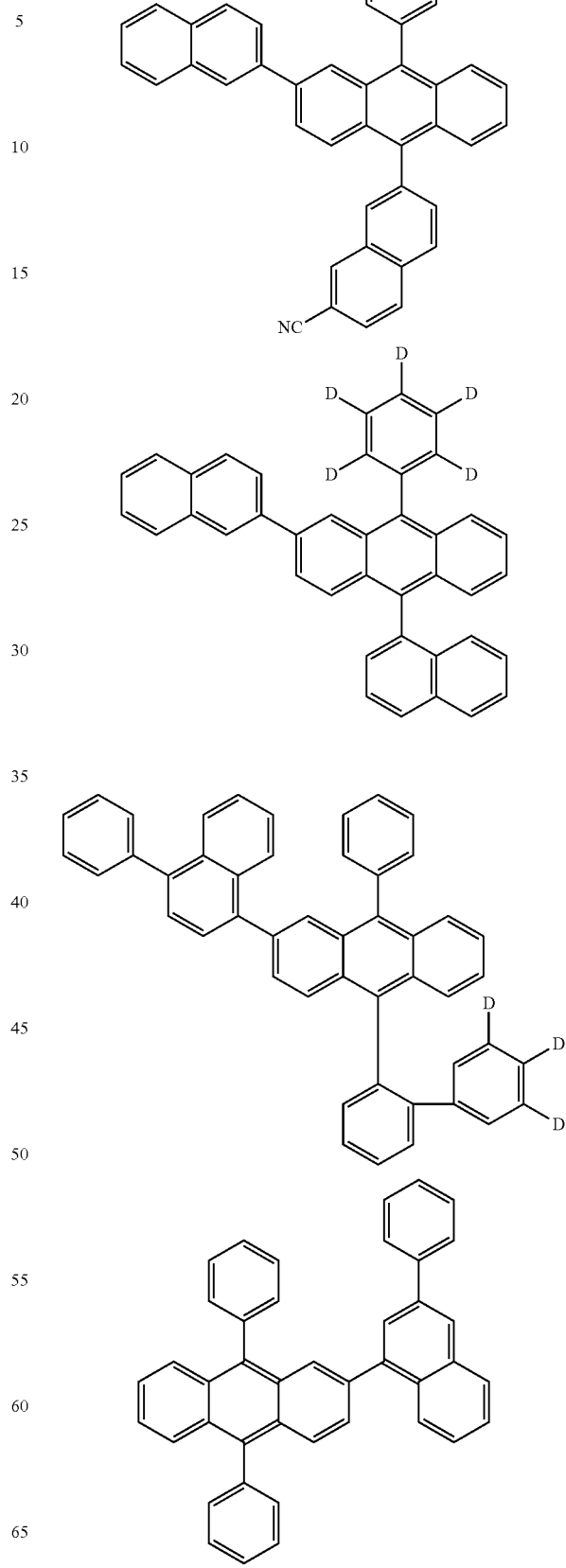

603
-continued
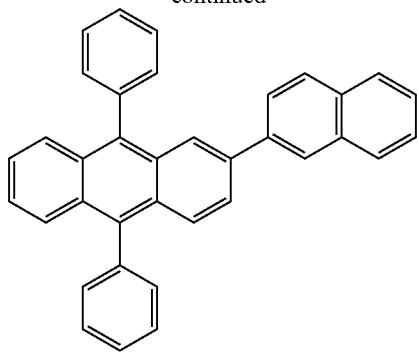
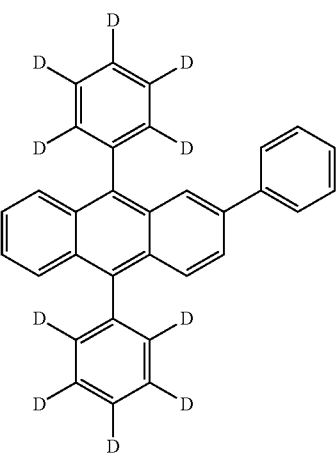
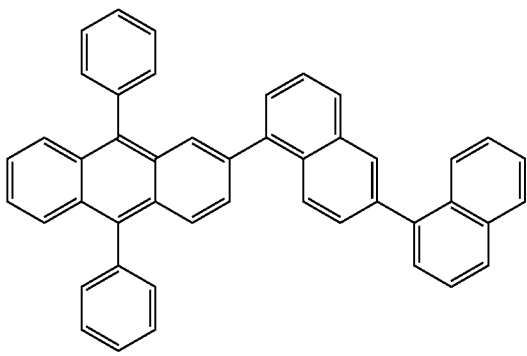
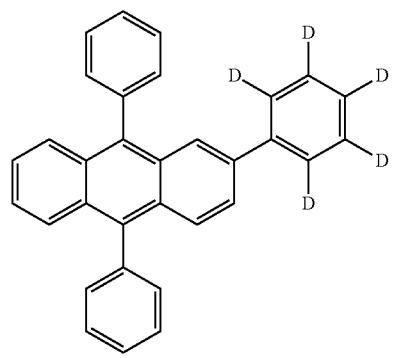
604
-continued
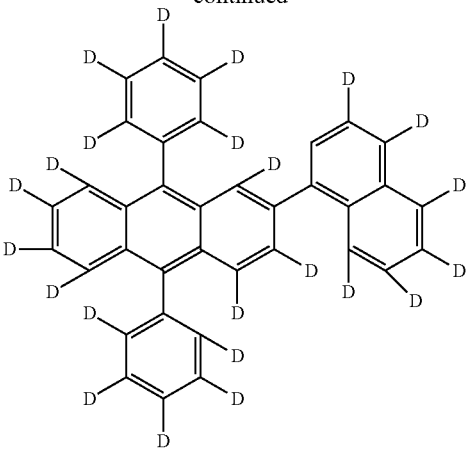
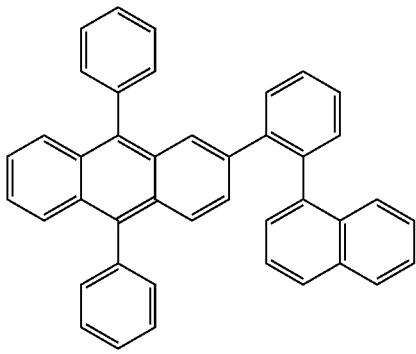
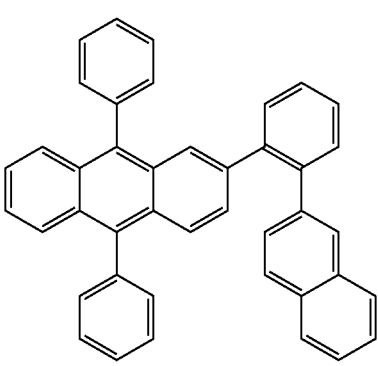
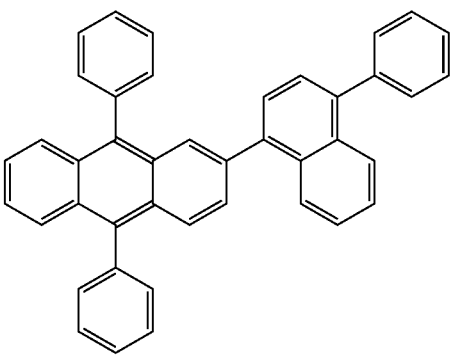

605
-continued
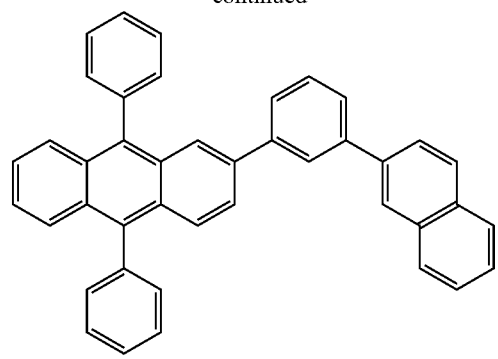
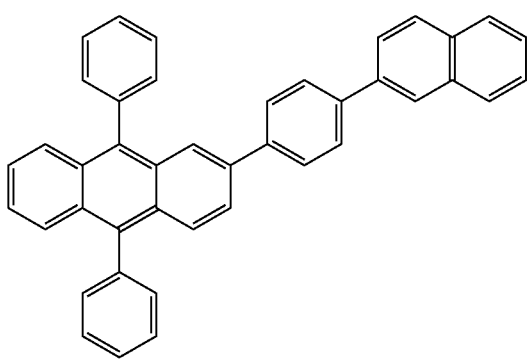
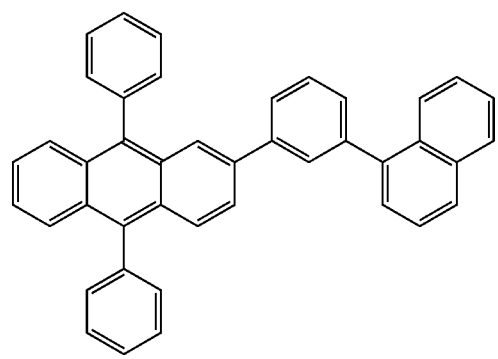
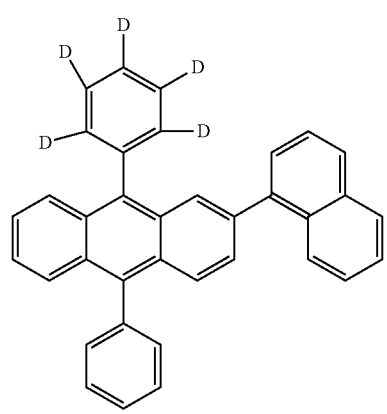
606
-continued
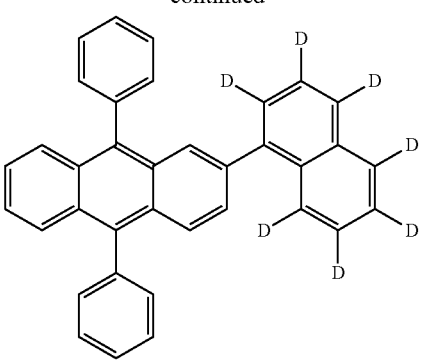
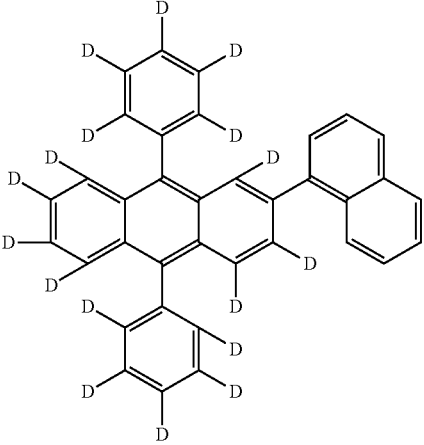
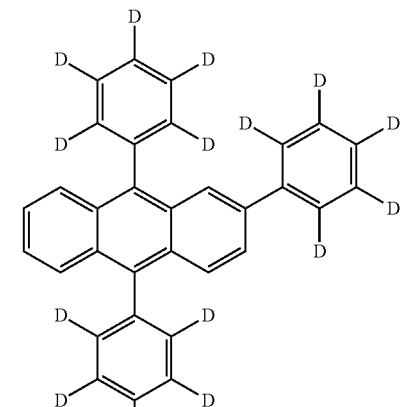
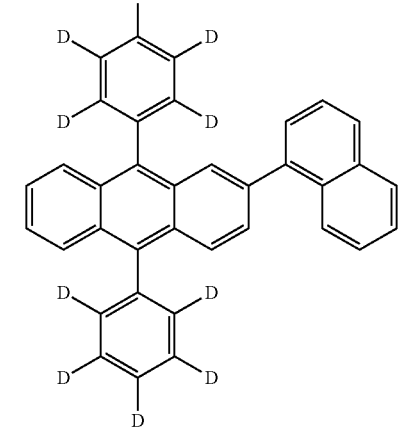

607
-continued
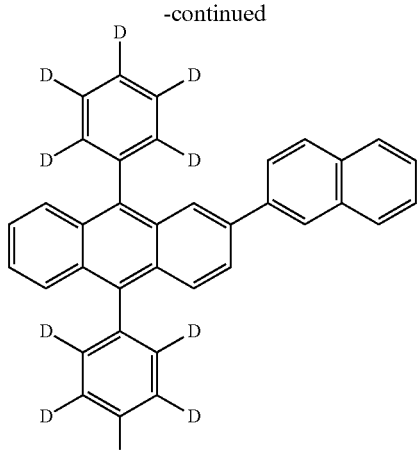
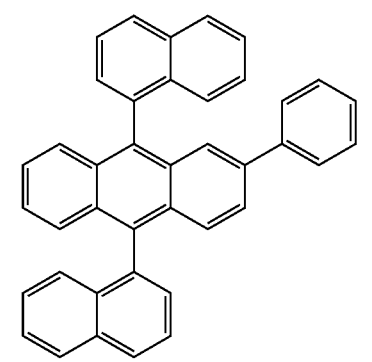
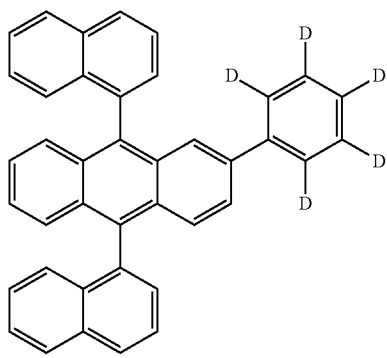
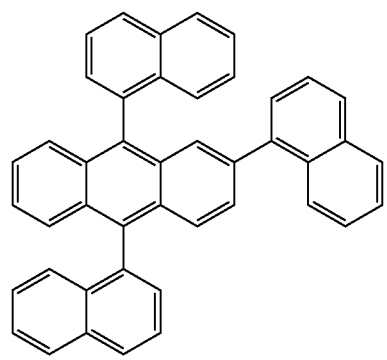
608
-continued
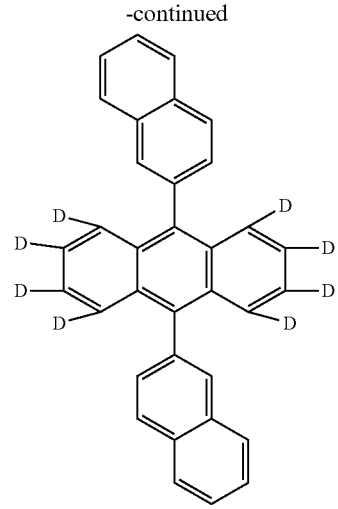
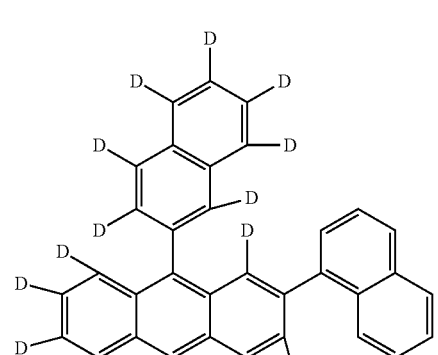
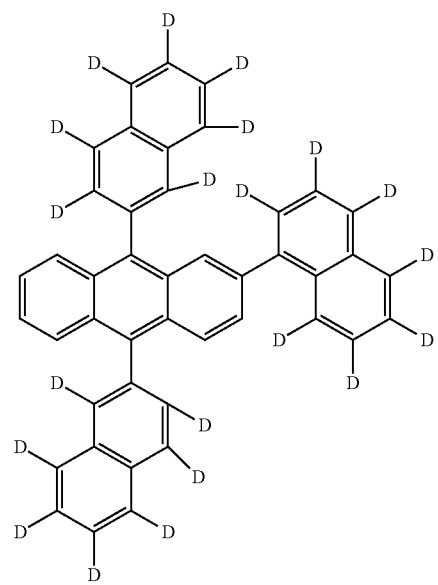

609
-continued
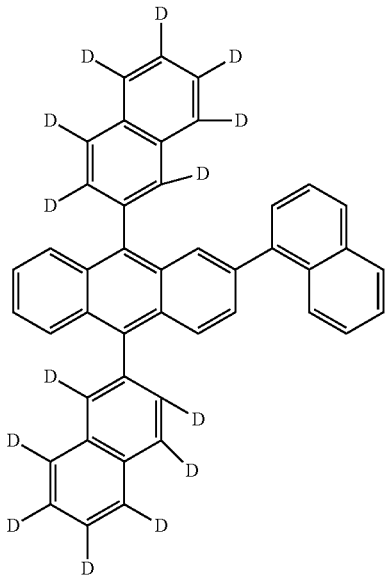
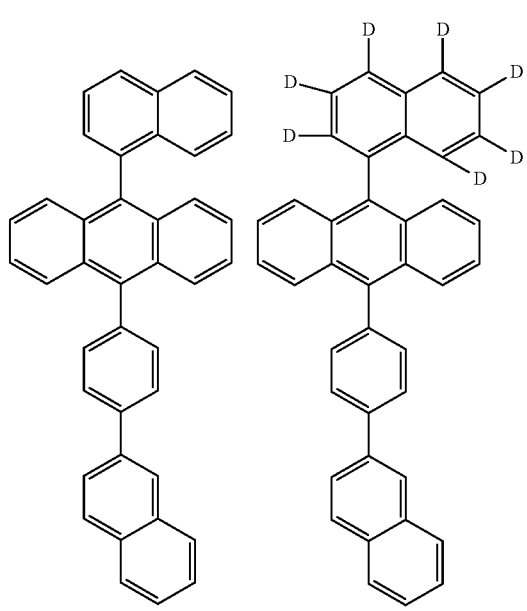
610
-continued
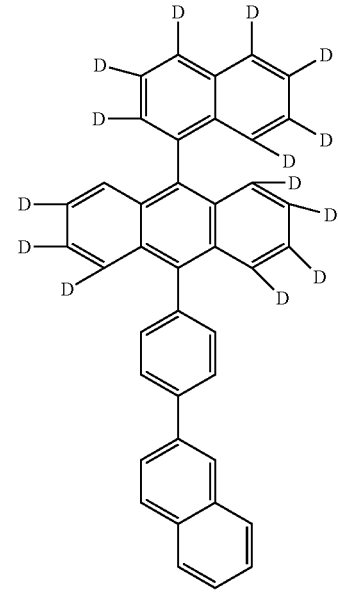
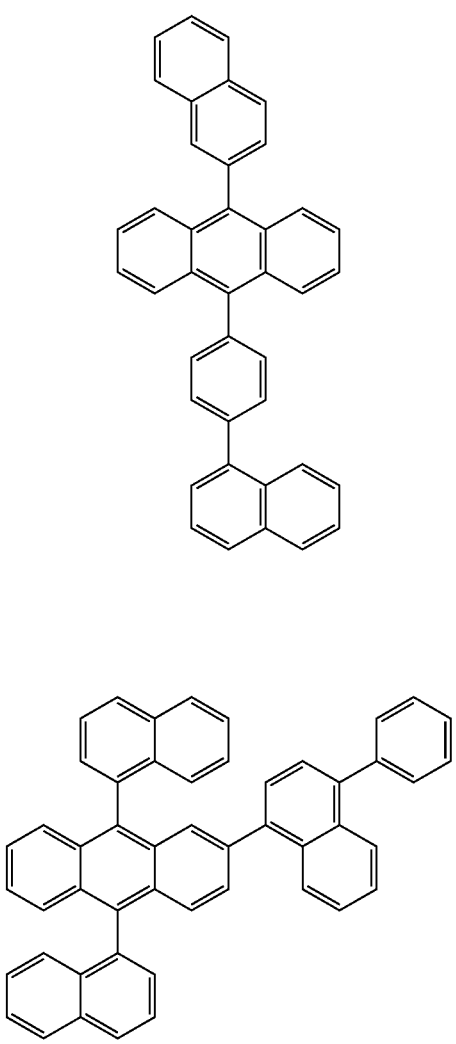

611
-continued
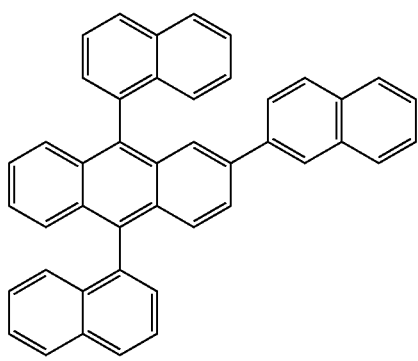
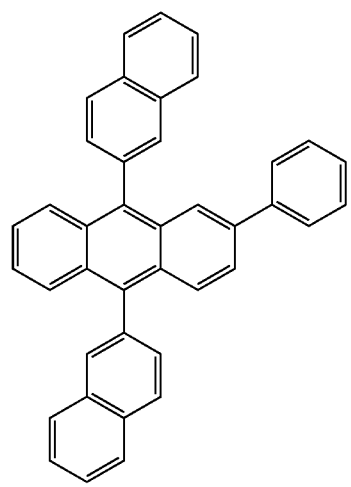
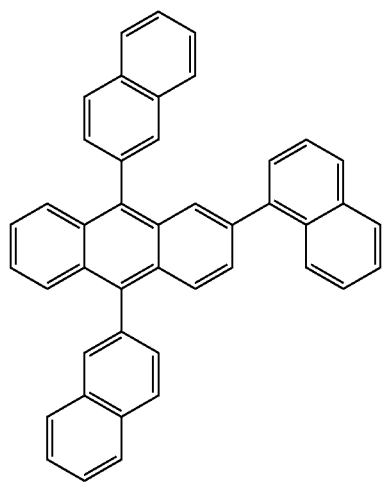
612
-continued
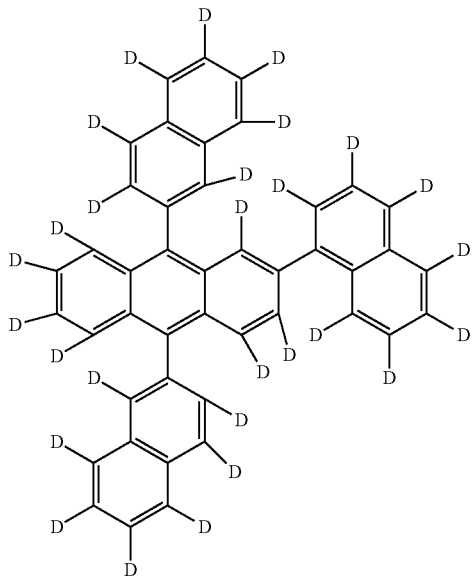
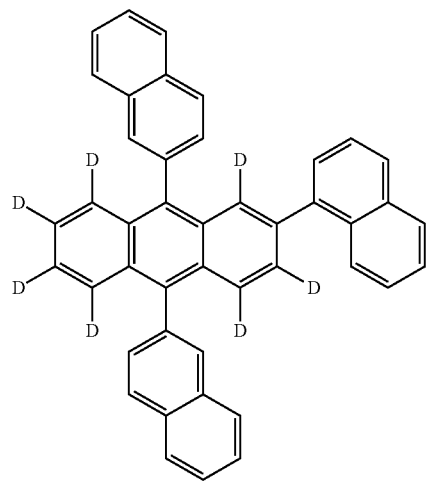
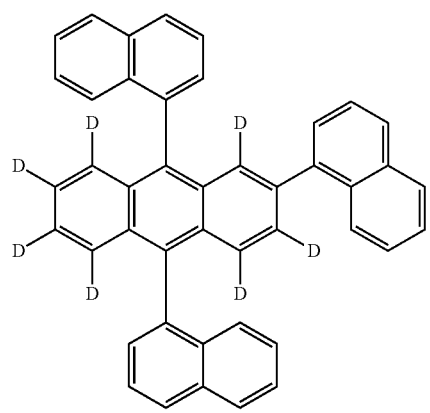

613
-continued
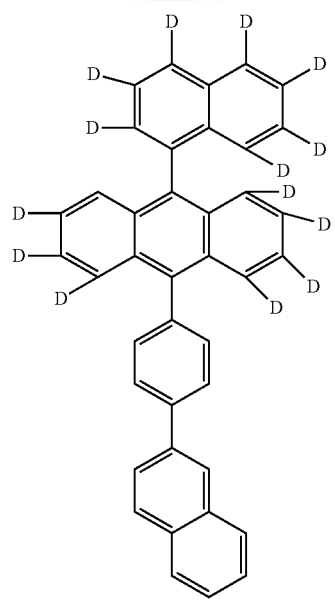
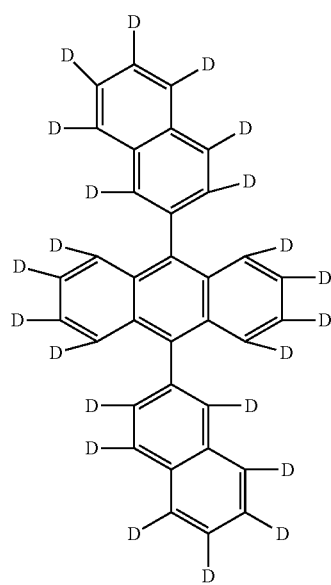
614
-continued
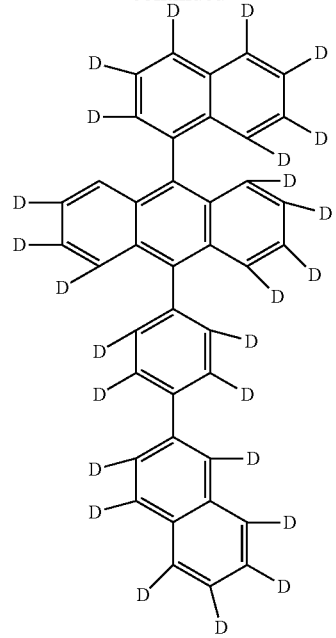
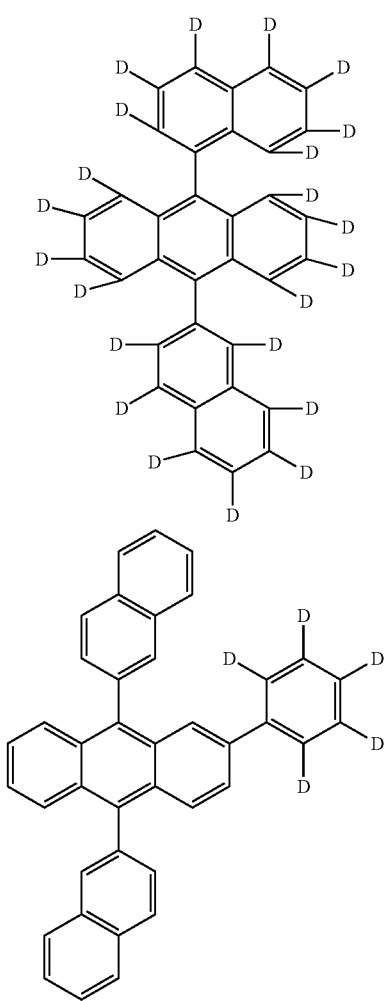

615
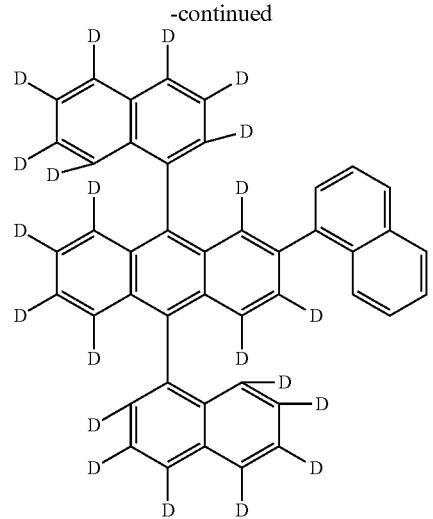
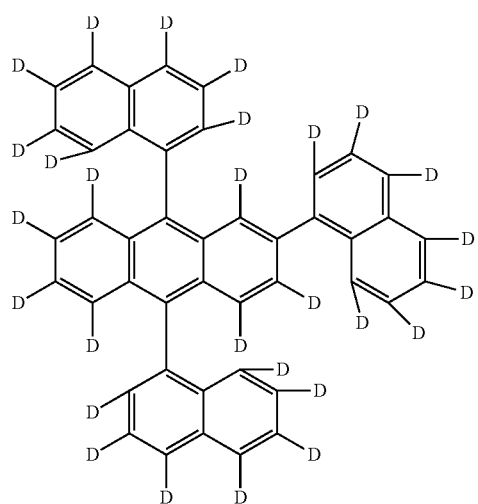
616
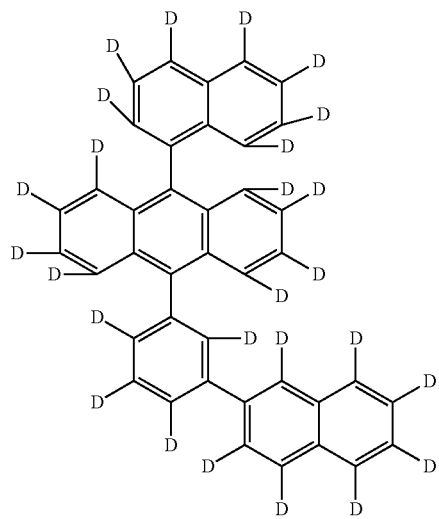
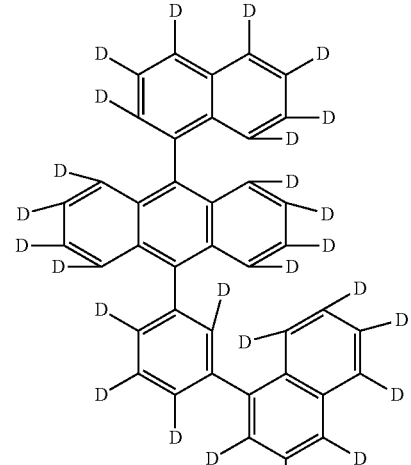
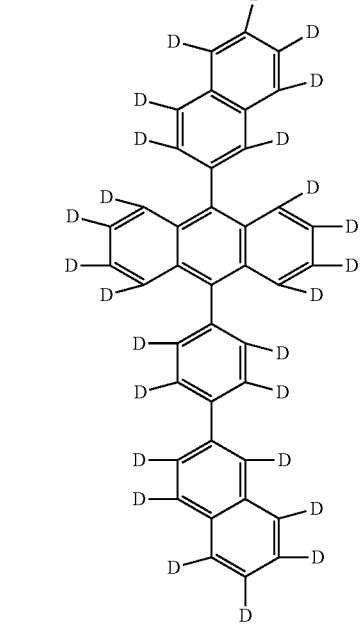

617
-continued
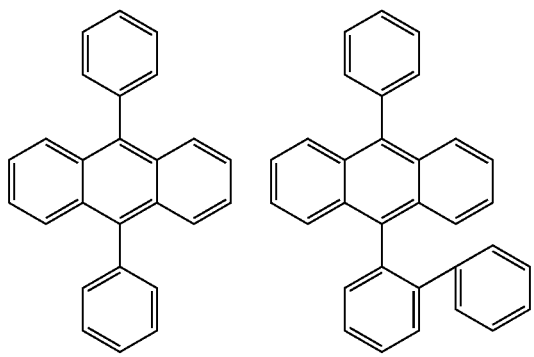
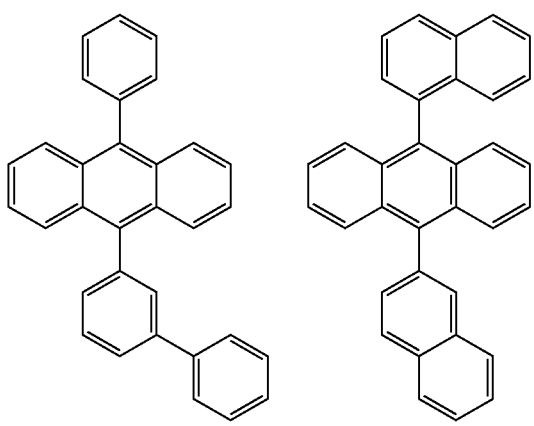
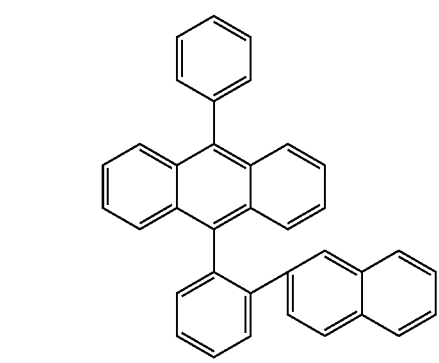
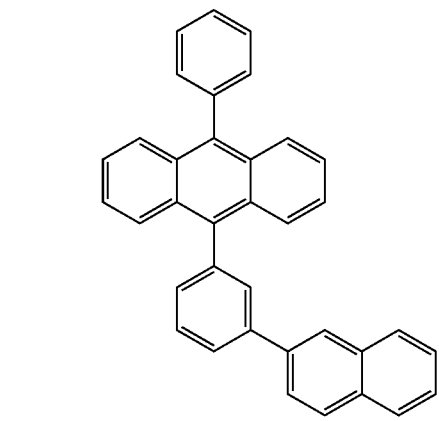
618
-continued
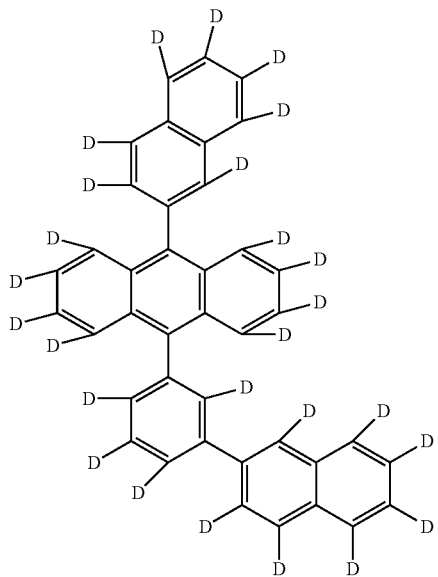
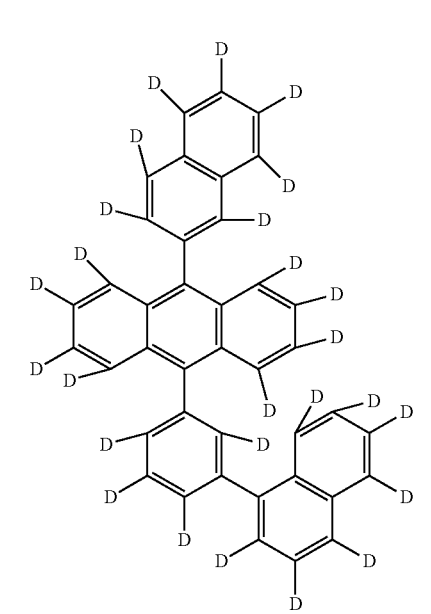
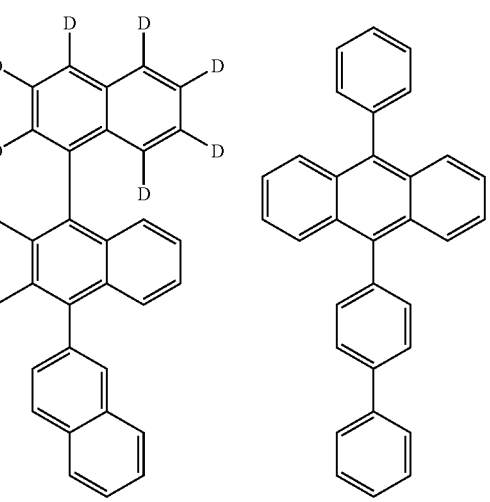

619
-continued
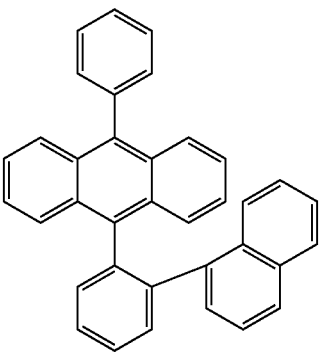
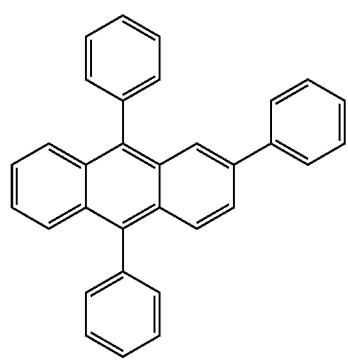
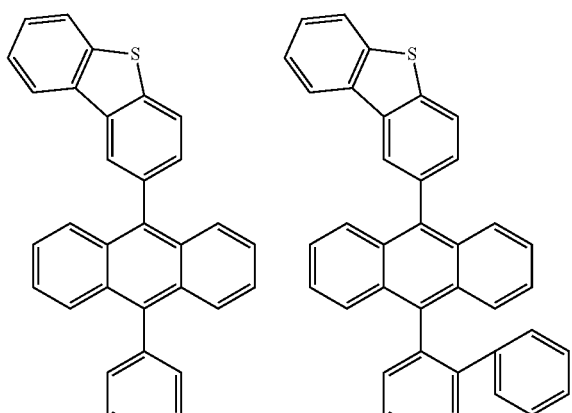
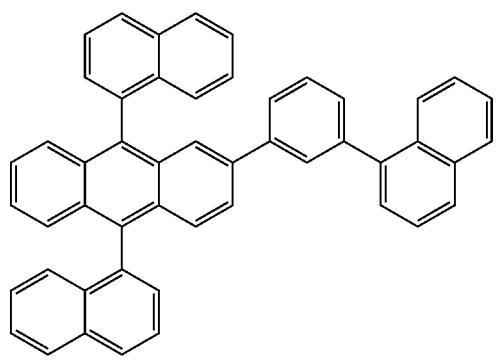
620
-continued
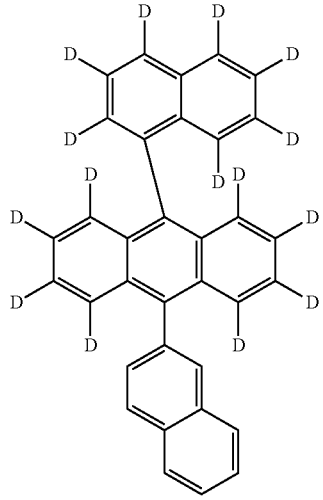
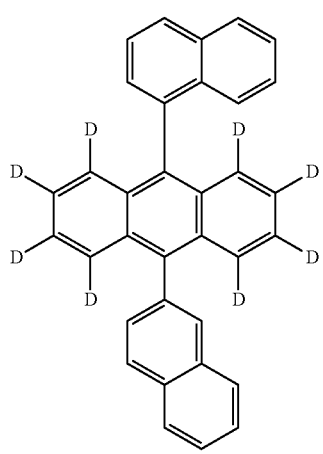
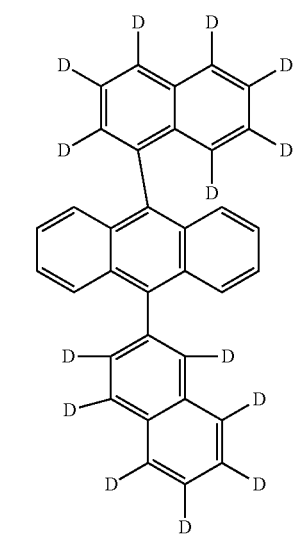

621
-continued
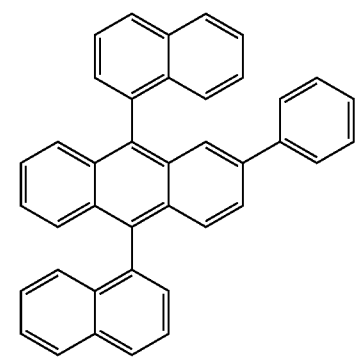
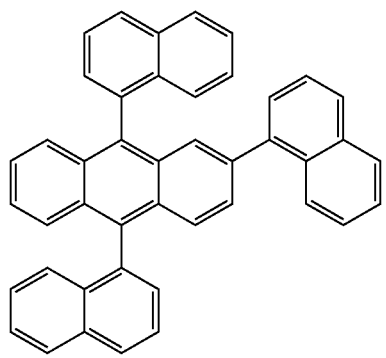
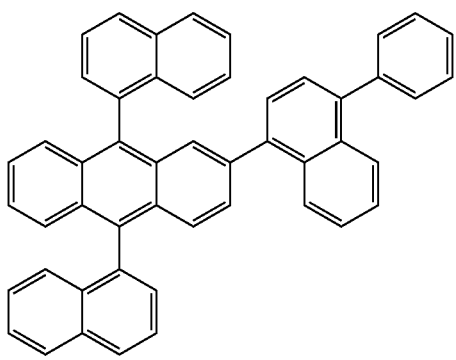
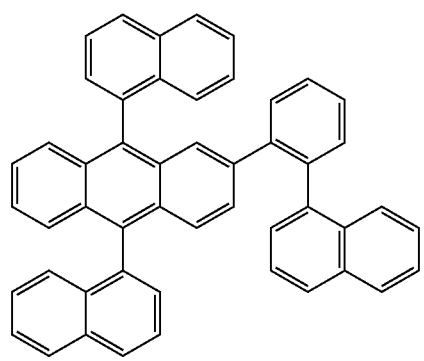
622
-continued
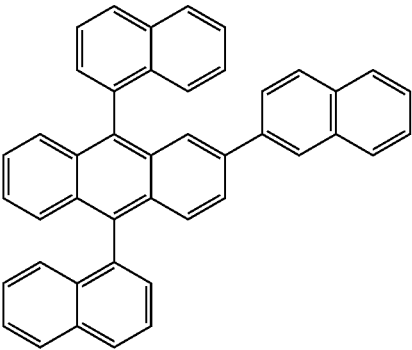
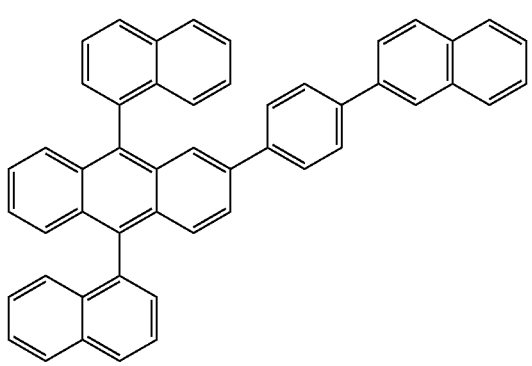
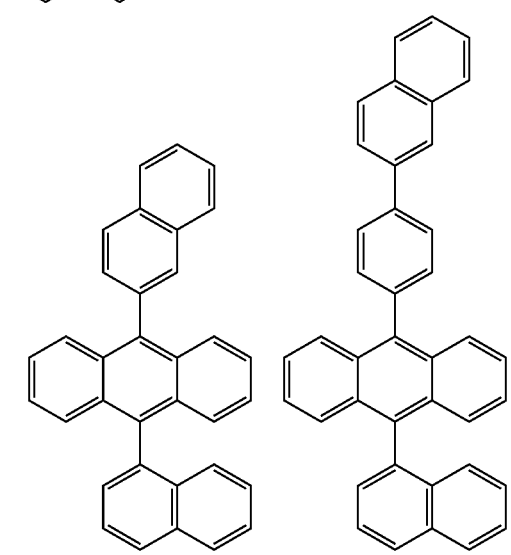
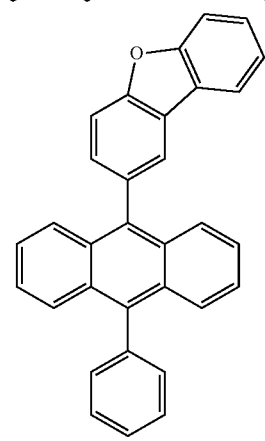

623
-continued
624
-continued
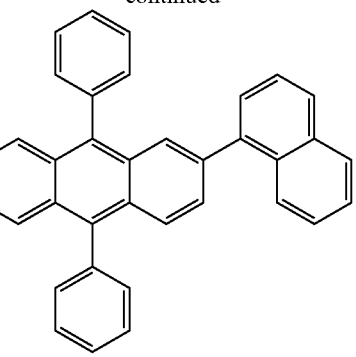
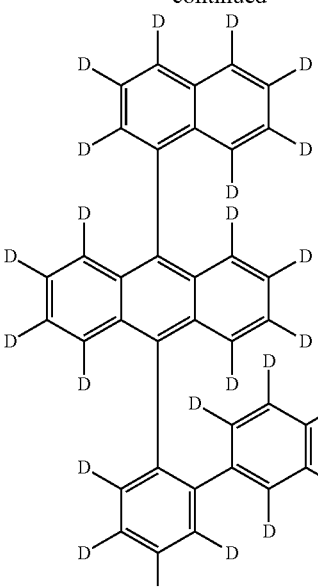
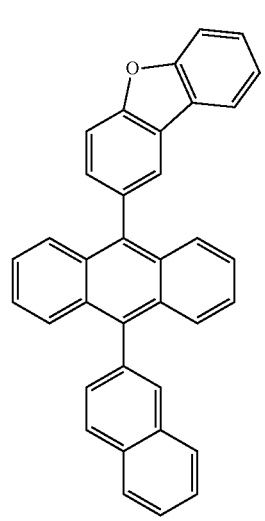
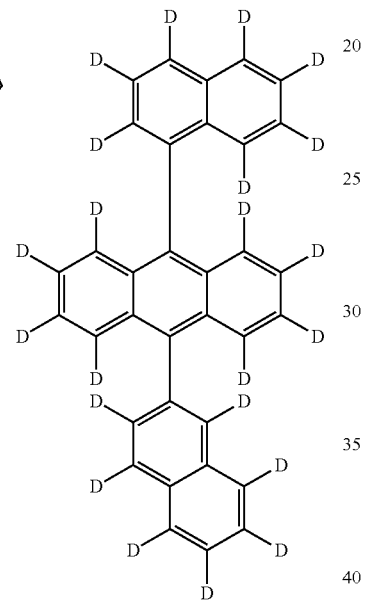
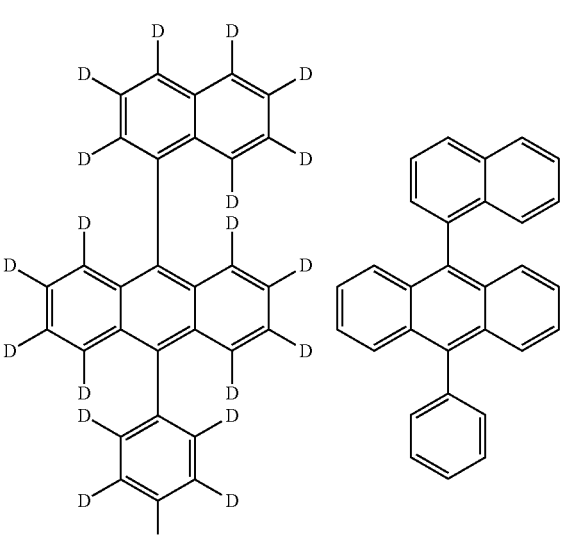
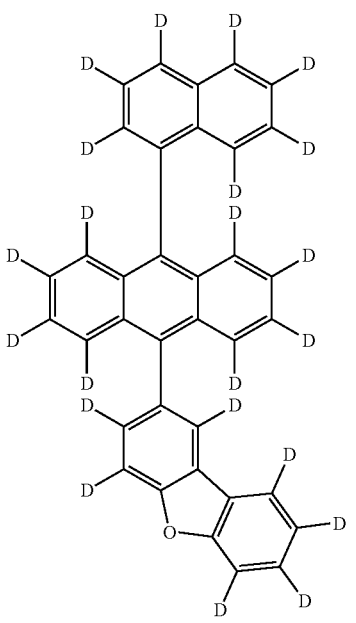
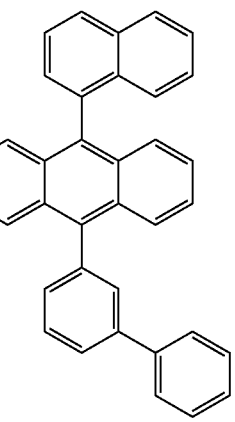

625
-continued
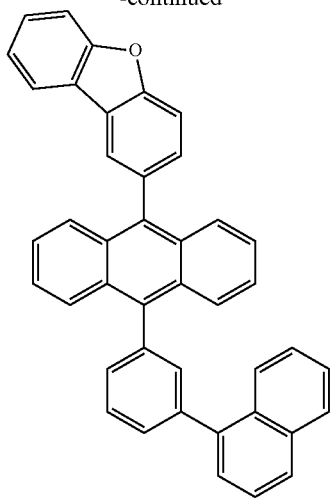
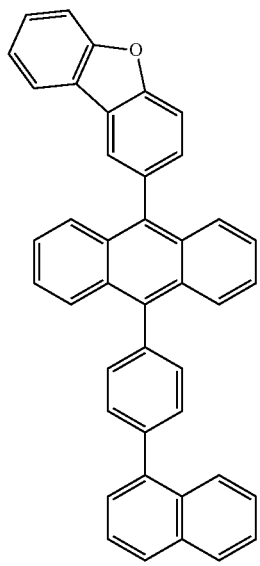
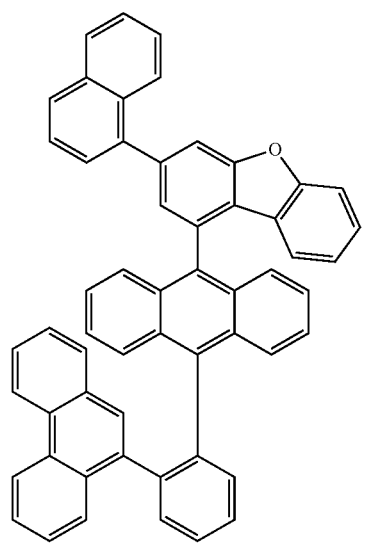
626
-continued
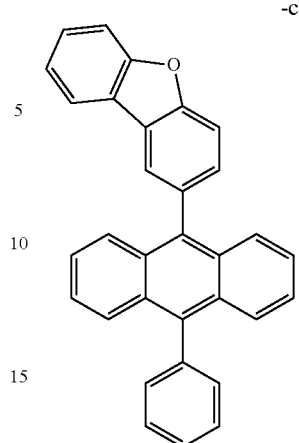 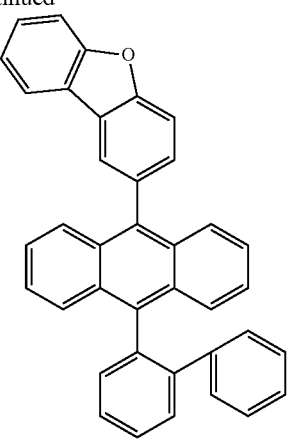
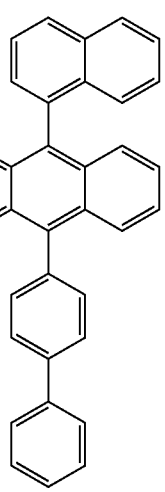
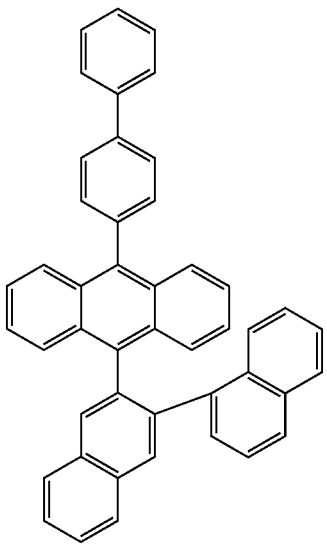

627
-continued
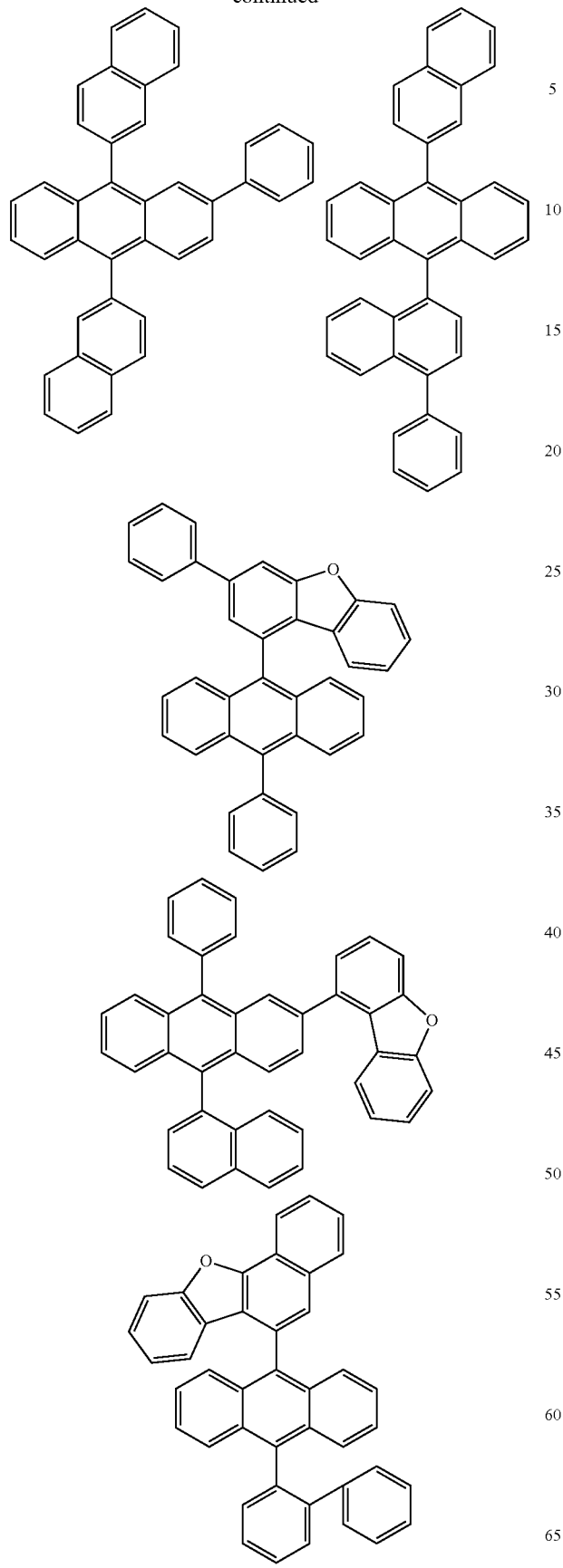
628
-continued
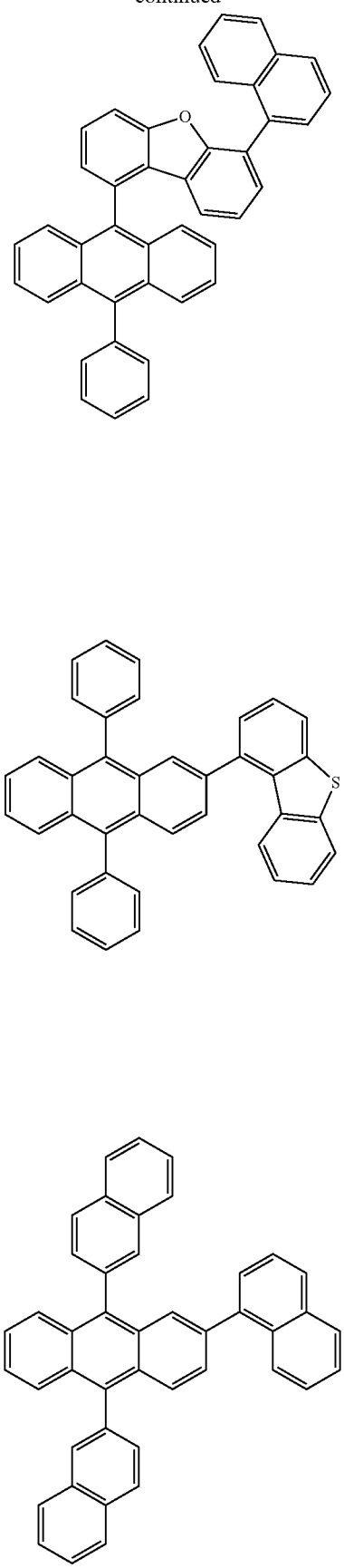

629
-continued
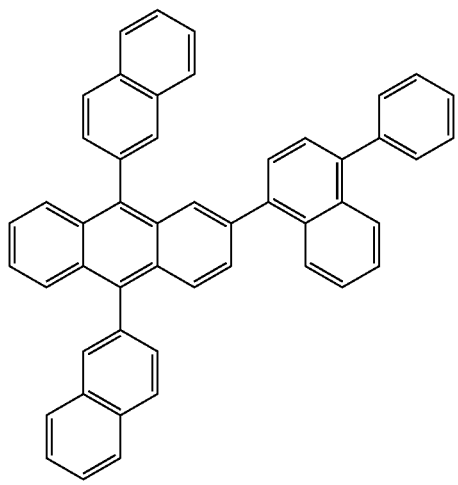
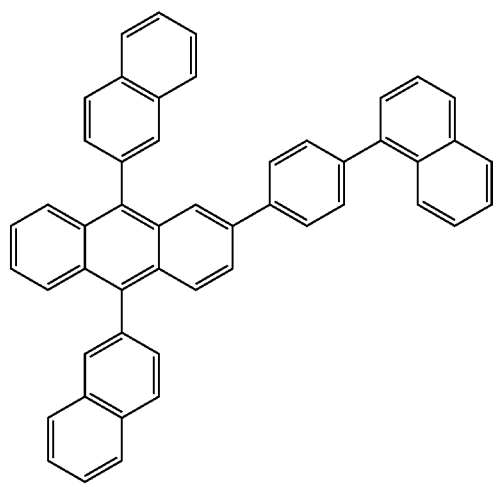
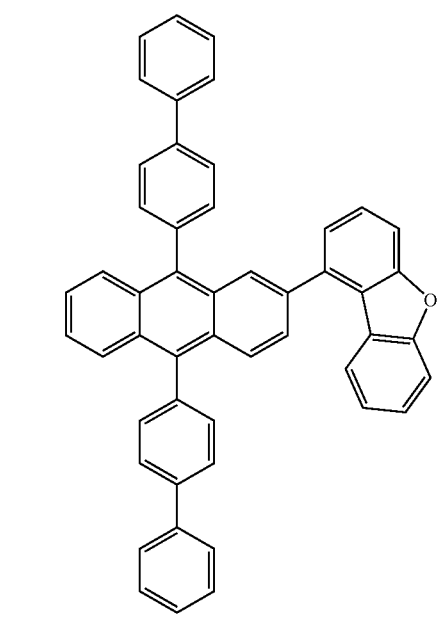
630
-continued
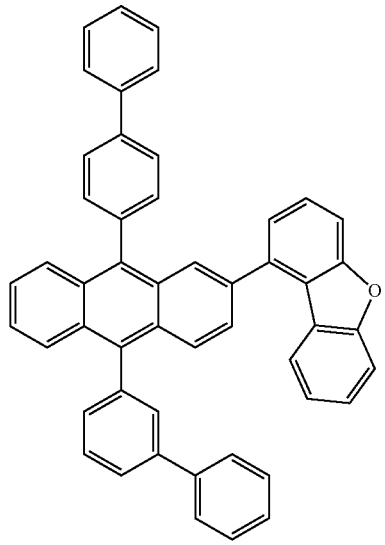
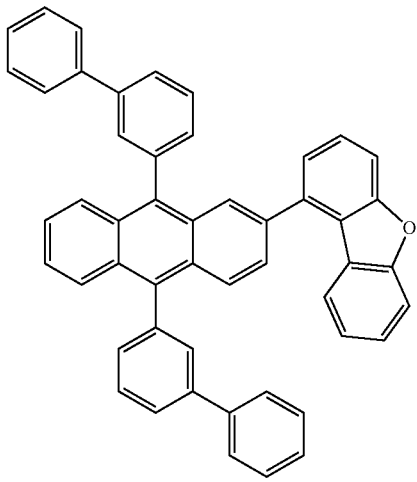
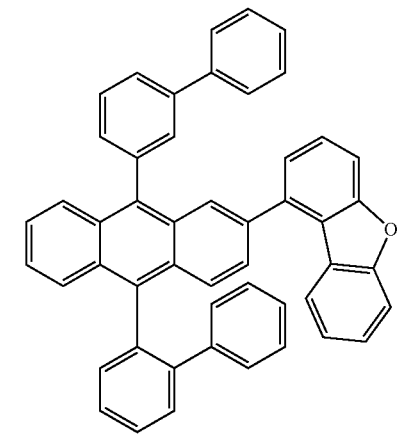

-continued
631
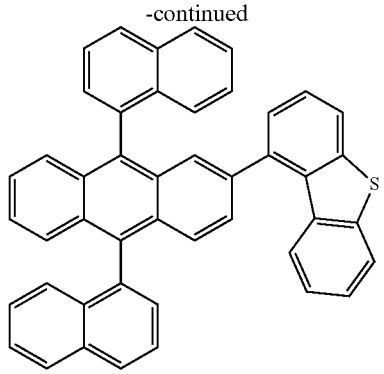
632
-continued
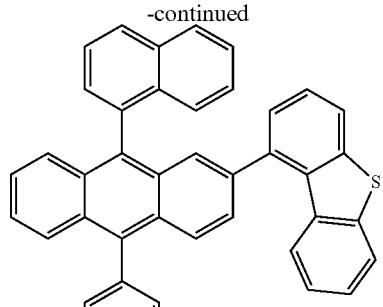
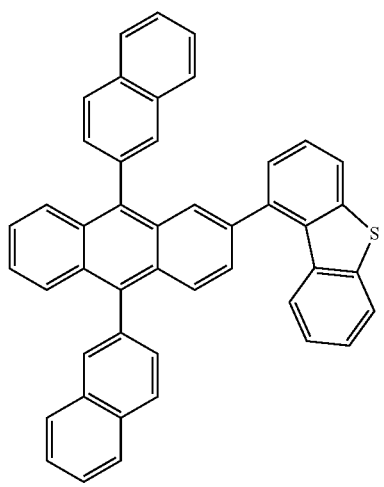
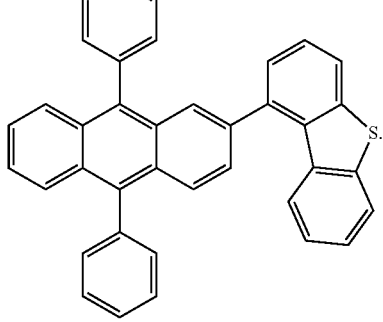
14. The organic light emitting device of claim 10, wherein the organic material layer further comprises one or two or more layers selected from the group consisting of a hole injection layer, a hole transport layer, an electron transport layer, an electron injection layer, an electron blocking layer, and a hole blocking layer.
* * * * *

UNITED STATES PATENT AND TRADEMARK OFFICE
CERTIFICATE OF CORRECTION

PATENT NO. : 12,209,095 B2  
APPLICATION NO. : 17/620255  
DATED : January 28, 2025  
INVENTOR(S) : Kim et al.

Page 1 of 8

It is certified that error appears in the above-identified patent and that said Letters Patent is hereby corrected as shown below:

In the Specification

At Column 279, Lines 1-18, the structure of Compound 6 should be as follows:

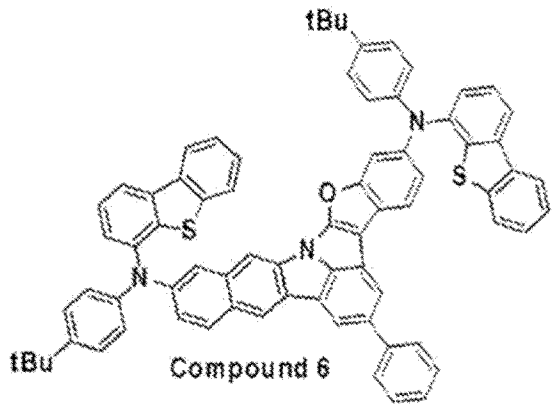

At Column 307, Lines 30-34, the structure of Compound A-4 should be as follows:

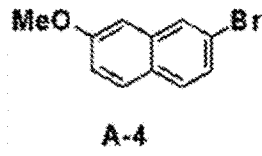

At Column 342, Lines 31-46, the structure of Compound BD-B should be as follows:

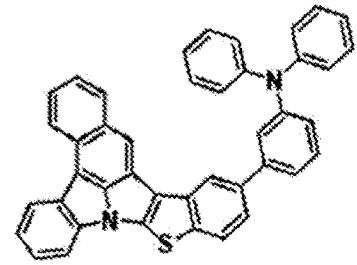

Signed and Sealed this  
Fourth Day of March, 2025

Coke Morgan Stewart  
*Acting Director of the United States Patent and Trademark Office*

CERTIFICATE OF CORRECTION (continued)

In the Claims

In Claim 8, at Column 365, the structure of the first compound should be as follows:

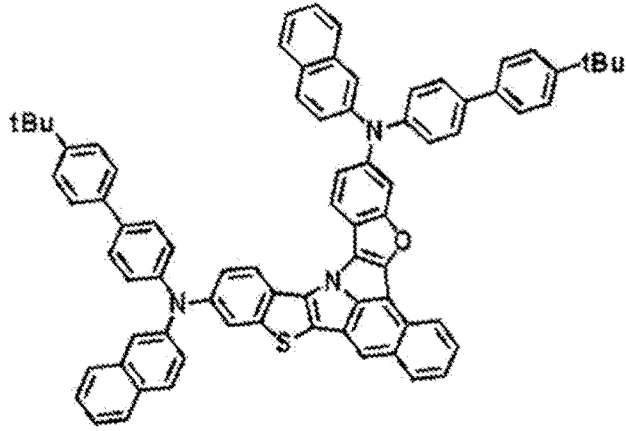

In Claim 8, at Column 405, the structure of the second compound should be as follows:

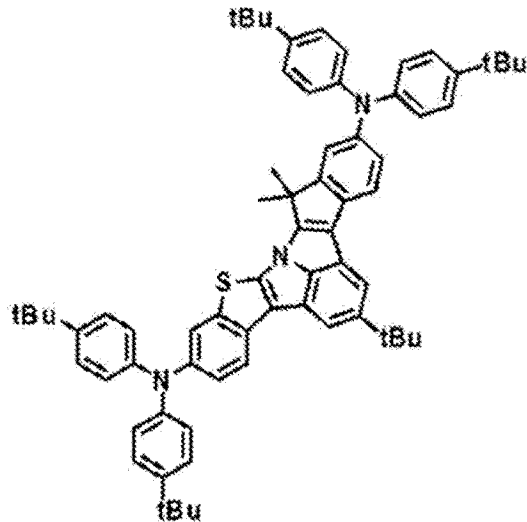

In Claim 8, at Column 423, the structure of the last compound should be as follows:

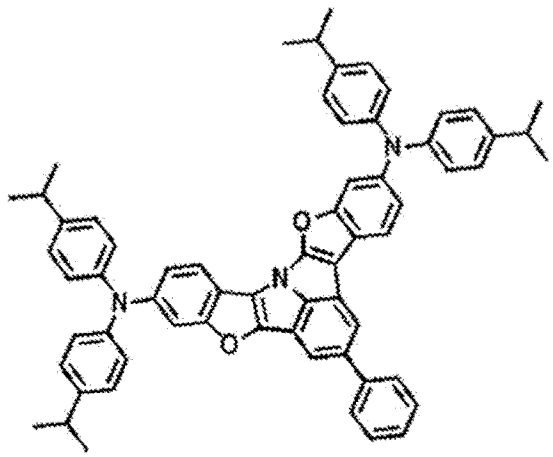

CERTIFICATE OF CORRECTION (continued)

U.S. Pat. No. 12,209,095 B2

In Claim 8, at Column 427, the structure of the second compound should be as follows:

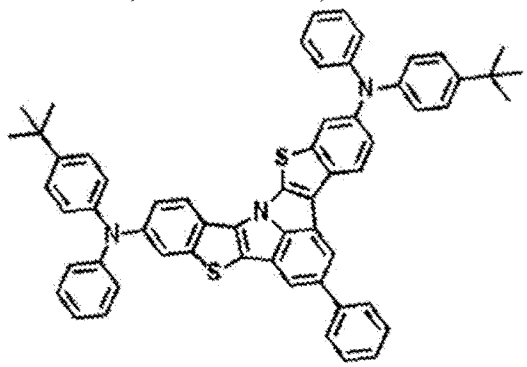

In Claim 8, at Column 429, the structure of the second compound should be as follows:

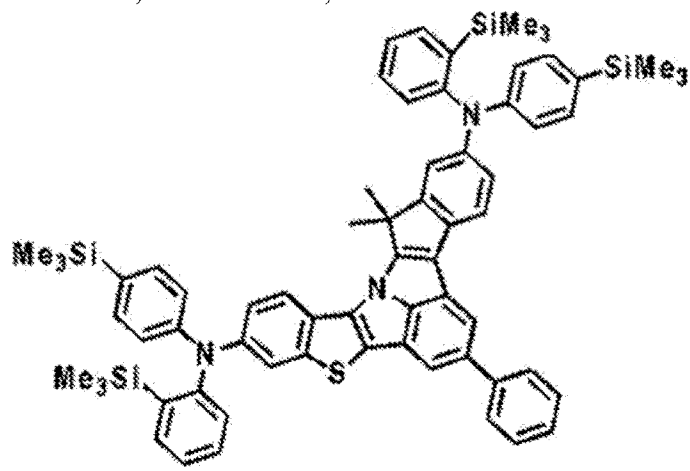

In Claim 8, at Column 443, the structure of the last compound should be as follows:

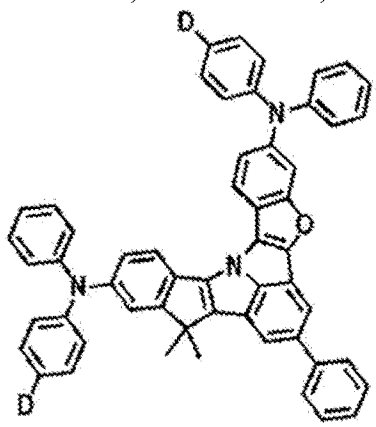

CERTIFICATE OF CORRECTION (continued)
U.S. Pat. No. 12,209,095 B2

Page 4 of 8

In Claim 8, at Column 445, the structure of the first compound should be as follows:

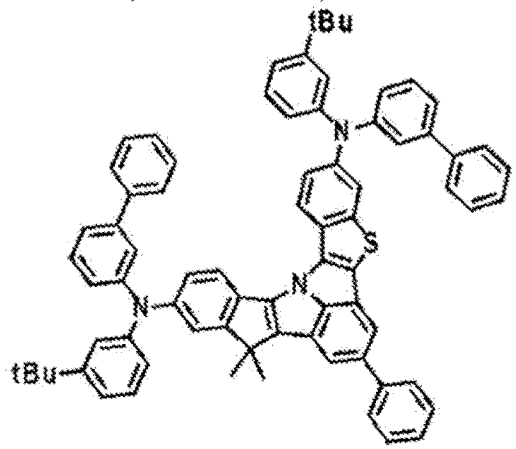

In Claim 8, at Column 455, the structure of the first compound should be as follows:

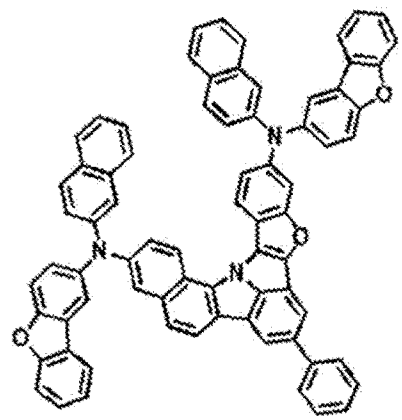

In Claim 8, at Column 457, the structure of the first compound should be as follows:

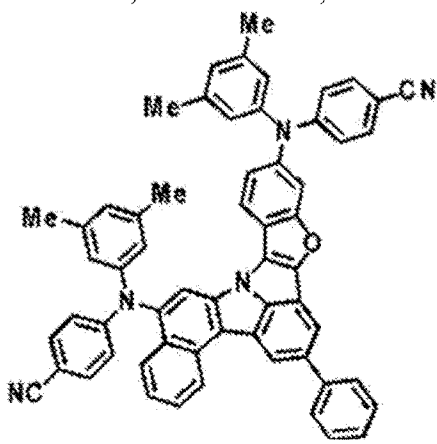

In Claim 8, at Column 463, the structure of the last compound should be as follows:
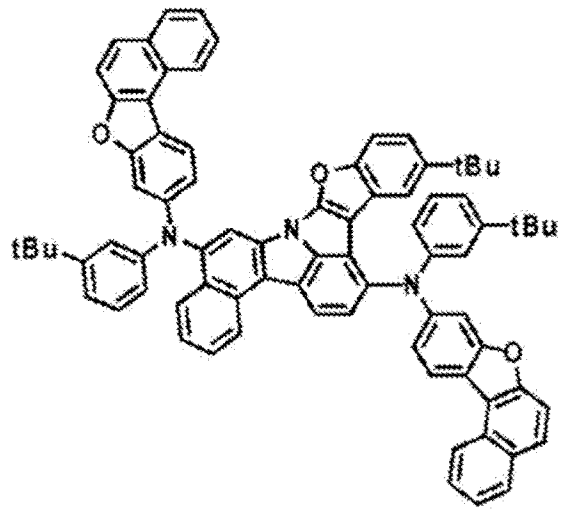
In Claim 8, at Column 471, the structure of the last compound should be as follows:
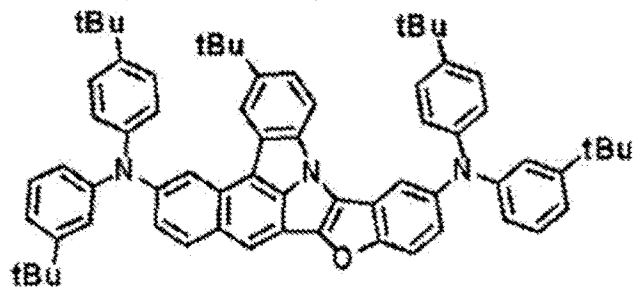
In Claim 8, at Column 487, the structure of the first compound should be as follows:
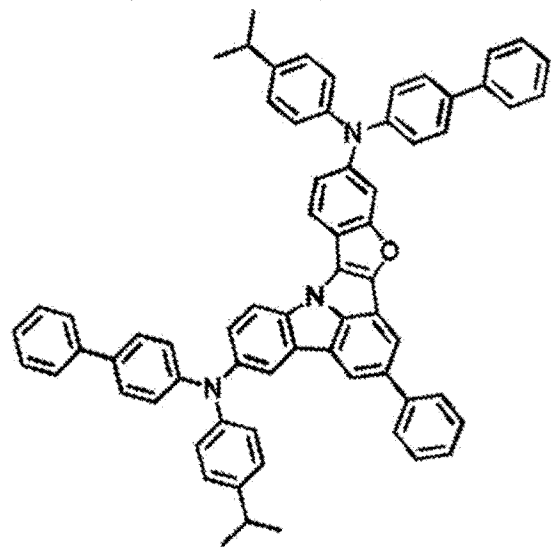

CERTIFICATE OF CORRECTION (continued)
U.S. Pat. No. 12,209,095 B2

In Claim 8, at Column 491, the structure of the last compound should be as follows:

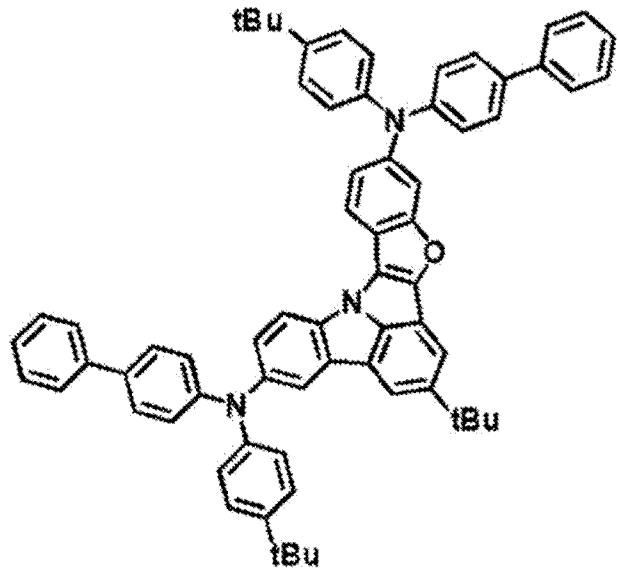

In Claim 8, at Column 525, the structure of the first compound should be as follows:

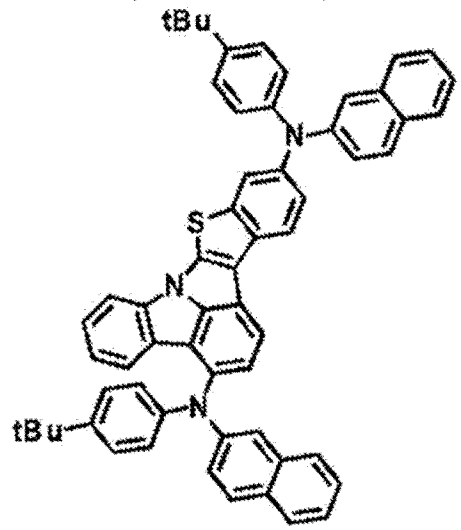

In Claim 8, at Column 527, the structure of the second compound should be as follows:
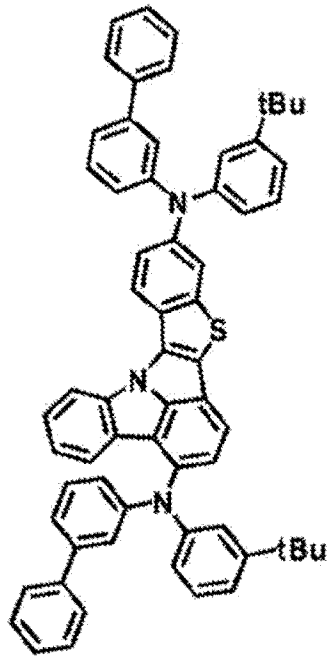
In Claim 8, at Column 535, the structure of the second compound should be as follows:
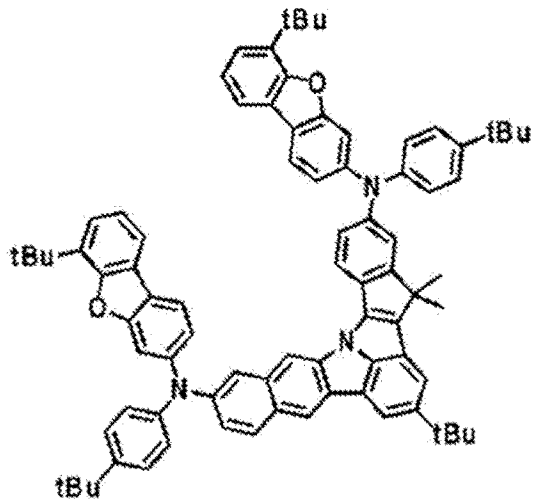
In Claim 8, at Column 539, the structure of the first compound should be as follows:
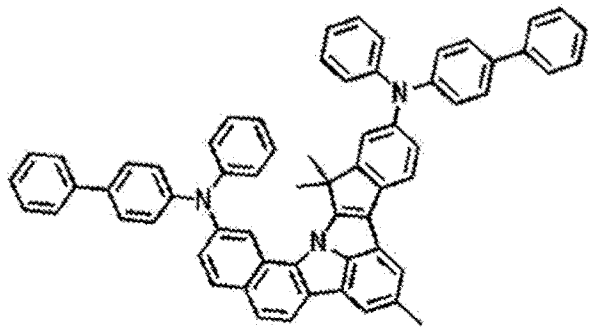

CERTIFICATE OF CORRECTION (continued)
U.S. Pat. No. 12,209,095 B2

In Claim 8, at Column 539, the structure of the last compound should be as follows:

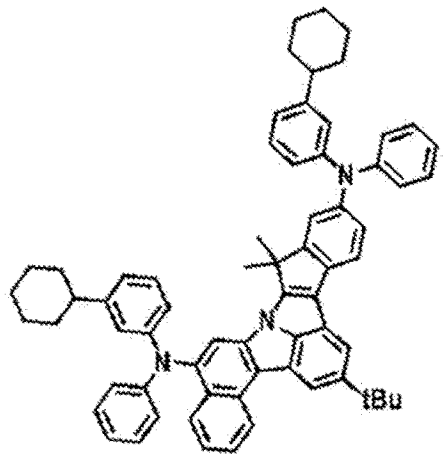

In Claim 13, at Column 575, Lines 27-47, the structure of the first compound should be as follows: